(12) United States Patent
Leblond et al.

(10) Patent No.: US 9,670,181 B2
(45) Date of Patent: *Jun. 6, 2017

(54) SUBSTITUTED 6,7-DIALKOXY-3-ISOQUINOLINOL DERIVATIVES AS INHIBITORS OF PHOSPHODIESTERASE 10 (PDE 10A)

(71) Applicant: Allergan, Inc., Irvine, CA (US)

(72) Inventors: Bertrand Leblond, Paris (FR); Cedric Chauvignac, Nogent sur Marne (FR); Thierry Taverne, St. Martin les Boulogne sur Mer (FR); Eric Beausoleil, Paris (FR); Anne-Sophie Casagrande, Draveli (FR); Laurent Desire, Paris (FR); Matthew P. Pando, Paris (FR); John E. Donello, Dana Point, CA (US); Rong Yang, Mission Viejo, CA (US)

(73) Assignees: ALLERGAN, INC., Irvine, CA (US); EXONHIT THERAPEUTICS SA, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/314,930

(22) Filed: Jun. 25, 2014

(65) Prior Publication Data

US 2014/0309253 A1    Oct. 16, 2014

Related U.S. Application Data

(63) Continuation of application No. 13/399,351, filed on Feb. 17, 2012, now Pat. No. 8,772,316.

(60) Provisional application No. 61/444,566, filed on Feb. 18, 2011.

(51) Int. Cl.
| | | |
|---|---|---|
| *C07D 491/056* | (2006.01) | |
| *C07D 401/14* | (2006.01) | |
| *C07D 217/24* | (2006.01) | |
| *C07D 401/06* | (2006.01) | |
| *C07D 405/06* | (2006.01) | |

(52) U.S. Cl.
CPC ......... *C07D 401/14* (2013.01); *C07D 217/24* (2013.01); *C07D 401/06* (2013.01); *C07D 405/06* (2013.01); *C07D 491/056* (2013.01)

(58) Field of Classification Search
None
See application file for complete search history.

(56) References Cited

U.S. PATENT DOCUMENTS 8,772,316 B2 *  7/2014  Leblond ............... C07D 217/24
                                                514/308
9,200,016 B2 * 12/2015  Leblond ................... C07F 9/62

| | | |
|---|---|---|
| 2003/0032579 A1 | 2/2003 | Lebel |
| 2008/0300240 A1 | 12/2008 | Bergmann |
| 2010/0016303 A1 | 1/2010 | Ritzen |

FOREIGN PATENT DOCUMENTS

| | | |
|---|---|---|
| JP | 2011-201873 | 10/2011 |
| WO | 01-41807 | 6/2001 |
| WO | 03-000693 | 1/2003 |
| WO | 03-014116 | 2/2003 |
| WO | 2004-002484 | 1/2004 |
| WO | 2004-005290 | 1/2004 |
| WO | 2004-005291 | 1/2004 |
| WO | 2005-002579 | 1/2005 |
| WO | 2005-003129 | 1/2005 |
| WO | 2005-012485 | 2/2005 |
| WO | 2005-082883 | 9/2005 |
| WO | 2005-120514 | 12/2005 |
| WO | 2006-011040 | 2/2006 |
| WO | 2006-028957 | 3/2006 |
| WO | 2006-034491 | 3/2006 |
| WO | 2006-034512 | 3/2006 |
| WO | 2006-070284 | 7/2006 |
| WO | 2006-071988 | 7/2006 |
| WO | 2006-072828 | 7/2006 |

(Continued)

OTHER PUBLICATIONS

Berge, Stephen M., Pharmaceutical Salts, Journal of Pharmaceutical Sciences, Jan. 1977, 1-19, 66 (1), US.

(Continued)

*Primary Examiner* — Kortney L Klinkel
*Assistant Examiner* — William Lee
(74) *Attorney, Agent, or Firm* — Jonathan Bass

(57) ABSTRACT

The invention relates to compounds of the formula wherein R', $R_1$ through $R_7$ and Ar are as defined herein. These compounds are useful as inhibitors of phosphodiesterase 10 (PDE10A) which are useful in treating central nervous system diseases such as psychosis and also in treating, for example, obesity, type II diabetes, metabolic syndrome, glucose intolerance, pain and ophthalmic diseases.

10 Claims, No Drawings

(56) References Cited

FOREIGN PATENT DOCUMENTS

| | | |
|---|---|---|
| WO | 2006-075012 | 7/2006 |
| WO | 2006-089815 | 8/2006 |
| WO | 2007-022280 | 2/2007 |
| WO | 2007-085954 | 8/2007 |
| WO | 2007-096743 | 8/2007 |
| WO | 2007-098169 | 8/2007 |
| WO | 2007-098214 | 8/2007 |
| WO | 2007-100880 | 9/2007 |
| WO | 2007-103260 | 9/2007 |
| WO | 2007-103370 | 9/2007 |
| WO | 2007-103554 | 9/2007 |
| WO | 2007-137819 | 12/2007 |
| WO | 2007-137820 | 12/2007 |
| WO | 2008-004117 | 1/2008 |
| WO | 2008-006372 | 1/2008 |
| WO | 2008-020302 | 2/2008 |
| WO | 2008-032171 | 3/2008 |
| WO | 2008-046342 | 4/2008 |
| WO | 2009-025823 | 2/2009 |
| WO | 2009-025839 | 2/2009 |
| WO | 2009-029214 | 3/2009 |
| WO | 2009-036766 | 3/2009 |
| WO | 2009-068320 | 6/2009 |
| WO | 2009-070583 | 6/2009 |
| WO | 2009-070584 | 6/2009 |
| WO | 2009-143178 | 11/2009 |
| WO | 2009-152825 | 12/2009 |
| WO | 2009-158393 | 12/2009 |
| WO | 2009-158467 | 12/2009 |
| WO | 2009-158473 | 12/2009 |
| WO | 2010-006130 | 1/2010 |
| WO | 2010-017236 | 2/2010 |
| WO | 2010-027097 | 3/2010 |
| WO | 2010-054253 | 5/2010 |
| WO | 2010-054260 | 5/2010 |
| WO | 2010-057126 | 5/2010 |
| WO | 2010-062559 | 6/2010 |
| WO | 2010-063610 | 6/2010 |
| WO | 2010-077992 | 7/2010 |
| WO | 2010-090737 | 8/2010 |
| WO | 2010-094762 | 8/2010 |
| WO | 2010-097367 | 9/2010 |
| WO | 2010-117926 | 10/2010 |
| WO | 2010-128995 | 11/2010 |
| WO | 2010-138430 | 12/2010 |
| WO | 2010-138577 | 12/2010 |
| WO | 2010-138585 | 12/2010 |
| WO | 2010-138833 | 12/2010 |
| WO | 2010-145668 | 12/2010 |
| WO | 2011-022213 | 2/2011 |
| WO | 2011-036127 | 3/2011 |
| WO | 2011-051324 | 5/2011 |
| WO | 2011-051342 | 5/2011 |
| WO | 2011-053559 | 5/2011 |
| WO | 2011-072694 | 6/2011 |
| WO | 2011-072695 | 6/2011 |
| WO | 2011-072696 | 6/2011 |
| WO | 2011-072697 | 6/2011 |
| WO | 2011-089132 | 7/2011 |
| WO | 2011-105628 | 9/2011 |
| WO | 2011-110545 | 9/2011 |
| WO | 2011-112828 | 9/2011 |
| WO | 2011-117264 | 9/2011 |
| WO | 2011-132048 | 10/2011 |
| WO | 2011-132051 | 10/2011 |
| WO | 2011-138657 | 11/2011 |
| WO | 2011-143365 | 11/2011 |
| WO | 2011-143366 | 11/2011 |
| WO | 2011-143495 | 11/2011 |
| WO | 2011-150156 | 12/2011 |
| WO | 2011-154327 | 12/2011 |
| WO | 2011-163355 | 12/2011 |
| WO | 2012-000519 | 1/2012 |
| WO | 2012-007006 | 1/2012 |
| WO | 2012-112946 | 8/2012 |

OTHER PUBLICATIONS

Cantin, Louis-David et al, PDE-10A Inhibitors as Insulin Secretagogues, Bioorganic & Medicinal Chemistry Letters, 2007, 2869-2873, 17.

Fujishige, Kotomi et al, Cloning and Characterization of a Novel Human Phosphodiesterase That Hydrolyzes Both cAMP and cGMP (PDE10A), Journal of Biological Chemistry, Jun. 25, 1999, 18438-18445, 274 (26).

Fujishige, Kotomi et al, Striatum- and Testis-Specific Phosphodiesterase PDE10A, Eur. J. Biochem., 1999, 1118-1127, 266.

Kehler, Jan et al, The Potential Therapeutic Use of Phosphodiesterase 10 Inhibitors, Expert Opin. Ther. Patents, 2007, 147-158, 17 (2).

Kotera, Jun et al, Characterization and Phosphorylation of PDE10A2, a Novel Alternative Splice Variant of Human Phosphodiesterase That Hydrolyzes cAMP and cGMP, Biochemical and Biophysical Research Communications, 1999, 551-557, 261.

Loughney, K. et al, Isolation and Characterization of PDE10A, a Novel Human 3', 5'-Cyclic Nucleotide Phosphodiesterase, Gene, 1999, 109-117, 234.

Menniti, Frank et al, Immunohistochemical Localization of PDE10A in the Rat Brain, Brain Research, 2003, 113-126, 985.

Ramesh Kanojia et al, Cardiotonic Agents. Synthesis and Inotropic Activity of a Series of Isoquinolin-3-ol Derivatives, J. Med. Chem., 1988, 1363-1368, 31.

Remingtons, Remingtons_16th, Pharmaceutical Sciences, 1980, 1-10, 16, Remingtons_16th.

Seeger, T.F., PDE10A mRNA in situ Hybridization Mapping in the Rodent Brian: Apparent Co-Localization With Dopaminoceptive Neurons, Neuroscience, 2000, 345.10, 26.

Soderling, Scott et al, Isolation and Characterization of a Dual-Substrate Phosphodiesterase Gene Family: PDE10A, Proc. Natl. Acad. Sci., Jun. 1999, 7071-7076, 96.

Wolloscheck, Tanja et al, Phosphodiesterase10A: Abundance and Circadian Regulation in the Retina and Photoreceptor of the Rat, Brian Research, 2011, 42-50, 1376.

* cited by examiner

SUBSTITUTED 6,7-DIALKOXY-3-ISOQUINOLINOL DERIVATIVES AS INHIBITORS OF PHOSPHODIESTERASE 10 (PDE 10A)

CROSS REFERENCE TO RELATED APPLICATION

This application is a continuation application of U.S. Ser. No. 13/399,351 filed Feb. 17, 2012 which claims the benefit of U.S. Provisional Application Ser. No. 61/444,566 filed Feb. 18, 2011, which is incorporated by reference herein in its entirety.

BACKGROUND OF THE INVENTION

Phosphodiesterases (PDEs) are a class of intracellular enzymes involved in the hydrolysis of the nucleotides cyclic adenosine monophosphate (cAMP) and cyclic guanosine monophosphates (cGMP) into their respective nucleotide monophosphates. The cyclic nucleotides cAMP and cGMP are synthesized by adenylyl and guanylyl cyclases, respectively.

The cAMP and cGMP function as intracellular second messengers regulating a vast array of intracellular processes particularly in neurons of the central nervous system. In neurons, this includes the activation of cAMP and cGMP-dependent kinases and subsequent phosphorylation of proteins involved in acute regulation of synaptic transmission as well as in neuronal differentiation and survival. The complexity of cyclic nucleotide signaling is indicated by the molecular diversity of the enzymes involved in the synthesis and degradation of cAMP and cGMP.

There are at least ten families of adenylyl cyclases, two of guanylyl cyclases, and eleven of phosphodiesterases. Furthermore, different types of neurons are known to express multiple isozymes of each of these classes, and there is good evidence for compartmentalization and specificity of function for different isozymes within a given neuron.

A principal mechanism for regulating cyclic nucleotide signaling is by phosphodiesterase-catalyzed cyclic nucleotide catabolism. There are 11 known families of PDEs encoded by 21 different genes. Each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE families or isozymes may offer particular therapeutic effects, fewer side effects, or both.

PDE10 is identified as a unique family based on primary amino acid sequence and distinct enzymatic activity. Homology screening of EST databases revealed human PDE10A as the first member of the PDE10 family of PDEs (Fujishige et al., *J. Biol. Chem.*, 274, 18438-18445, 1999; Loughney, K. et al., *Gene*, 234, 109-117, 1999). The murine homologue has also been cloned (Soderling, S. et al., *Proc. Natl. Acad. Sci. USA*, 96, 7071-7076, 1999) and N-terminal splice variants of both the rat and human genes have been identified (Kotera, J. et al., *Biochem. Biophys. Res. Comm.*, 261, 551-557, 1999; Fujishige, K. et al., *Eur. J. Biochem.*, 266, 1118-1127, 1999). There is a high degree of homology across species. The mouse PDE10A1 is a 779 amino acid protein that hydrolyzes both cAMP and cGMP to AMP and GMP, respectively. The affinity of PDE10 for cAMP ($K_m$=0.05 μM) is higher than for cGMP ($K_m$=3 μM). However, the approximately 5-fold greater Vmax for cGMP over cAMP has lead to the suggestion that PDE10 is a unique cAMP-inhibited cGMPase (Fujishige et al., *J. Biol. Chem.*, 274, 18438-18445, 1999).

PDE10A also is uniquely localized in mammals relative to other PDE families. mRNA for PDE10 is highly expressed only in testis and brain (Fujishige, K. et al., *Eur J Biochem.*, 266, 1118-1127, 1999; Soderling, S. et al., *Proc. Natl. Acad. Sci.*, 96, 7071-7076, 1999; Loughney, K. et al., *Gene*, 234, 109-117, 1999).

These initial studies indicated that within the brain PDE10A expression is highest in the striatum (caudate and putamen), n. accumbens, and olfactory tubercle. More recently, a detailed analysis has been made of the expression pattern in rodent brain of PDE10 mRNA (Seeger, T. F. et al., *Abst. Soc. Neurosci.*, 26, 345.10, 2000) and PDE10 protein (Menniti, F. S., Stick, $CA_1$ Seeger, T. F., and Ryan, A. M., Immunohistochemical localization of PDE10 in the rat brain, William Harvey Research Conference 'Phosphodiesterase in Health and Disease', Porto, Portugal, Dec. 5-7, 2001).

PDE10A was shown to be highly expressed in retinal neurons including photoreceptors. The levels of PDE10A transcript and protein display daily rhythms which could be seen in preparations of the whole retina (Wollscheck T. et al, *Brain Res.*, 2011, 1376, 42-50. Epub 2010 Dec. 29). These findings place PDE10A in the context of the visual system and suggest an important role of PDE10A in the adaptation of cyclic nucleotide signalling to daily changes in light intensity in retinal neurons including photoreceptors.

The tissue distribution of PDE10A indicates that PDE10A inhibitors can be used to raise levels of cAMP and/or cGMP within cells that express the PDE10 enzyme, especially neurons that comprise the basal ganglia, and the PDE10A inhibitors of the present invention would therefore be useful in treating a variety of associated neuropsychiatric conditions involving the basal ganglia such as neurological and psychiatric disorders, schizophrenia, bipolar disorder, obsessive compulsive disorder, and the like, and may have the benefit of not possessing unwanted side effects, which are associated with the current therapies on the market.

US 2003/0032579 discloses a method for treating certain neurologic and psychiatric disorders with the PDE10A inhibitor papaverine. In particular, the method relates to psychotic disorders such as schizophrenia, delusional disorders and drug-induced psychosis; to anxiety disorders such as panic and obsessive-compulsive disorder; and to movement disorders including Parkinson's disease and Huntington's disease. Other indications which may be treated using a PDE10A inhibitor are described in WO 20055120514.

A variety of therapeutic uses for PDE inhibitors has been reported including obtrusive lung disease, allergies, hypertension, angina, congestive heart failure, depression and erectile dysfunction (WO 2001041807, incorporated herein by reference). Furthermore, publications (WO 2005120514, WO 2005012485, Cantin et al., *Bioorg. & Med. Chem. Lett.*, 17, 2869-2873, 2007) suggest that PDE10A inhibitors may be useful for treatment of obesity and non-insulin dependent diabetes.

WO 2011110545, WO 2011051342 (Janssen Pharmaceutica NV) disclose respectively imidazo[1,2-a]pyrazine derivatives, imidazo[1,2-b]pyridazine derivatives PDE10A inhibitors useful for the treatment or prevention of neurological, psychiatric and metabolic disorders in which the PDE10 enzyme is involved.

WO 2012007006, WO 2012000519, WO 2011072695, WO 2011072697, WO 2011072694, WO 2011072696, WO 2010145668 (H. Lundbeck A/S) disclose respectively triazolo- and pyrazoloquinazoline derivatives, aryl- and heteroarylamid derivatives, phenylimidazole derivatives comprising an ethynylene linker, heteroaromatic aryl triazole derivatives, heteroaromatic phenylimidazole derivatives, 2-arylimidazole derivatives, novel phenylimidazole derivatives as PDE10A inhibitors reported to be useful for the treatment of psychiatric and neurodegenerative disorders including schizophrenia as well as bipolar disorders, anxiety, stress disorders and Alzheimer's, Parkinson's and Huntington's disease, dementia and attention deficit/hyperactivity disorder.

WO 2011150156 (Sunovion Pharmaceuticals Inc.) discloses heteroaryl compounds as PDE10A inhibitors useful for the treatment, prevention, and/or management of various disorders, such as CNS disorders and metabolic disorders, including, but not limited to, e.g., neurological disorders, psychosis, schizophrenia, obesity, and diabetes.

WO 2010138833 (Biotie Therapies GmbH—Wyeth) discloses substituted imidazo[1,5-a]quinoxalines as PDE10A inhibitors useful in treating central nervous system diseases such as psychosis and also in treating, for example, obesity, type 2 diabetes, metabolic syndrome, glucose intolerance, and pain.

WO 2011053559 or WO 2011022213 or WO 2010138430 and WO 2010138585 or WO 2010138430 (Merck & Co., Inc.) disclose respectively aryl or amino or alkoxy tetrahydro-pyridopyrimidine derivatives or pyrimidinones as PDE10A inhibitors useful for the treatment of neurological and psychiatric disorders including schizophrenia, delusional disorders, drug induced psychosis, anxiety, movement, mood and neurodegenerative disorders.

WO 2010138577 (Merck & Co., Inc.) discloses radiolabeled pyrimidinone compounds which are useful as radiotracers for quantitative imaging of PDE10A in mammals.

WO 2011138657, WO 2011132051, and WO 2011132048 (Glenmark Pharmaceuticals SA) disclose respectively aryl substituted olefinic compounds, tricyclic compounds, and heteroaryl compounds as PDE10A inhibitors reported to be useful for the treatment of schizophrenia.

WO 2011163355 & WO 2010090737 (Takeda Pharmaceutical Co., Ltd.) disclose respectively fused heterocyclic compounds and pyridazinone compounds as PDE10A inhibitors useful for the treatment of schizophrenia.

WO 2010128995 (EnVivo Pharmaceuticals, Inc.) discloses phenoxymethyl heterocyclic compounds as PDE10A inhibitors useful for the treatment of schizophrenia, bipolar disorder, Huntington's disease, obesity and metabolic syndrome, among other disorders.

WO 2010117926 (Schering Corp.) discloses substituted triazolopyridines and analogs thereof as PDE10A inhibitors reported to be useful for the treatment of schizophrenia, psychosis, Alzheimer's disease, bipolar disorder, depression, obesity, diabetes and metabolic syndrome.

WO 2011051324 and WO 2010097367 (Janssen Pharmaceutica NV) disclose radiolabeled fluorinated azole PDE10A ligands reported to be useful in positron emission tomography imaging and quantification of PDE10A enzymes.

WO 2011117264, WO 2011089132 & WO 2011154327, WO 2011036127, and WO 2010094762 & WO 2010063610 (F. Hoffmann-La Roche AG) disclose respectively N-(imidazopyrimidin-7-yl)-heteroarylamide derivatives, nitrogen-containing heteroaryl derivatives, novel imidazopyridines, and heteroaryl substituted pyridazinone derivatives as PDE10A inhibitors reported to be useful for the treatment of schizophrenia, cognitive disorders, anxiety, substance abuse and dependence, Parkinson's disease, mood disorders, neurodegenerative disorders, stroke, diabetes and cancer, among other disorders.

WO 2011143366, WO 2011143365, WO 2011143495, WO 2010077992, and WO 2010057126 (Amgen Inc.) disclose respectively heteroaryloxycarbocyclyl compounds, nitrogen heterocyclic compounds, heteroaryloxyheterocyclyl compounds, aminopyridine and carboxypyridine compounds, and pyridine and pyrimidine derivatives as PDE10A inhibitors that are considered to have potential in the treatment of psychiatric disorders such as schizophrenia, bipolar disorder, obsessive-compulsive disorder, obesity, non-insulin dependent diabetes.

WO 2010062559 (Schering Corp.) discloses substituted pyrazoloquinolines and derivatives thereof as PDE10A inhibitors for the treatment of PDE10-modulated disorders.

WO 2010138833, WO 2010054253 & WO 2010054260 (Biotie Therapies GmbH—Wyeth) disclose respectively substituted imidazo[1,5-a]quinoxalines and triazine derivatives as inhibitors of phosphodiesterases, particularly PDE10A and PDE2A, described as useful for the treatment of pain, cognitive disorders, diabetes, obesity, extrapyramidal disorders, epilepsy and psychiatric disorders such as depression, anxiety, schizophrenia and attention deficit/hyperactivity disorders.

JP 2011201873, WO 2011105628, and WO 2010027097 (Mitsubishi Tanabe Pharma Corp.) disclose respectively trisubstituted pyrimidine compounds, pyrazolopyrimidine compounds, and tri-substituted pyrimidine compounds and their use as PDE10A inhibitors reported to be useful for the treatment of schizophrenia, anxiety, drug addiction, cognitive and mood disorders.

WO 2011112828 and WO 2010017236 (Omeros Corp.) disclose PDE10A inhibitors described as useful for the treatment of neurological and psychiatric disorders such as schizophrenia and post-traumatic stress disorder as well as Parkinson's disease, Huntington's disease, Alzheimer's disease, encephalitis, phobias, epilepsy, pain, sleep disorders, bipolar disorder and multiple sclerosis.

US 2010016303 & WO 2009152825 (H. Lundbeck NS) disclose novel phenylimidazole derivatives as PDE10A enzyme inhibitors to be useful in the treatment of psychiatric and neurological disorders such as schizophrenia, cognition deficits, Parkinson's disease, Alzheimer's disease, Huntington's disease and substance abuse, among others.

WO 2010006130 (EnVivo Pharmaceuticals, Inc.) discloses vicinal substituted cyclopropyl compounds as PDE10A inhibitors.

WO 2009158473, WO 2009158467 & WO 2009158393 (EnVivo Pharmaceuticals, Inc.) disclose respectively 5- and 6 membered heterocyclic compounds, disubstituted phenyls compounds and 1,2-disubstituted heterocyclic compounds as PDE10A inhibitors described as useful for the treatment of schizophrenia, Huntington's disease, obesity and metabolic syndrome.

WO 2009070583 (Wyeth) discloses pyrido(3,2-e)pyrazines as inhibitors of PDE10A that are considered to have potential in the treatment of psychosis, mood diseases, anxiety, neurodegenerative disorders, obesity, diabetes, metabolic diseases, pain.

WO 2009068320 & WO 2009070584 (Biotie Therapies GmbH) disclose aryl and heteroaryl fused imidazo(1,5-a)pyrazines as inhibitors of PDE10A that are active compounds for treating central nervous system diseases of mammals, including humans.

WO 2009152825 & WO 2009036766 (H. Lundbeck NS) disclose respectively novel phenylimidazole derivatives and cyanoisoquinoline derivatives as PDE10A inhibitors.

WO 2009143178, WO 2008064342 & US 2008300240 (Omeros Corp.) disclose quinoline derivatives as PDE10A inhibitors active in psychotic, anxiety, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette syndrome, schizophrenia, delusional disorders, drug-induced psychosis and panic and obsessive-compulsive disorders.

WO 2009025839 & WO 2009025823 (Amgen Inc.) disclose cinnoline derivatives as PDE10A inhibitors that are considered to have potential in the treatment of psychiatric disorders such as schizophrenia, bipolar disorder and obsessive-compulsive disorder.

WO 2009029214 (Amgen Inc.—Memory Pharmaceuticals Corp.) discloses isoquinolone derivatives as PDE10A inhibitors that are considered to have potential in the treatment of schizophrenia, bipolar disorder, obsessive-compulsive disorder, obesity and diabetes.

WO 2008032171 (Matrix Laboratories Ltd.) discloses dibenzofuran as inhibitors of PDE4 and PDE10A with potential utility in the treatment of asthma, chronic obstructive pulmonary disease, allergic rhinitis, atopic dermatitis, multiple sclerosis, Huntington disease, Alzheimer's disease, Parkinson's disease, schizophrenia and depression, among other disorders.

WO 2008020302 (Pfizer Products Inc.) discloses heteroaromatic quinoline-based compounds as selective PDE10A inhibitors.

WO 2008006372 (H. Lundbeck NS) discloses 6,7-dialkoxyquinazoline and 6,7-dialkoxyisoquinoline derivatives as PDE10A inhibitors that are considered to have potential in the treatment of psychiatric and neurological disorders such as schizophrenia, cognition deficits, Parkinson's disease, Alzheimer's disease, dementia, epilepsy, multiple sclerosis and Huntington's diseases.

WO 2008004117 & WO 2006072828 (Pfizer Products Inc.) disclose respectively selective azole compounds and heteroaromatic quinoline compounds as PDE10A inhibitors that are considered to have potential in the treatment of psychotic, anxiety, movement, mood and neurodegenerative disorders and obesity.

WO 2007137819 & WO 2007137820 (Biotie Therapies GmbH) disclose respectively 4-amino-pyrido(3,2-e)pyrazines and pyrido(3,2-e)pyrazines as PDE10A inhibitors. More particularly, the inventions relate to the treatment of neurologic and psychiatric disorders, for example psychosis and disorders comprising cognitive deficits as symptoms.

WO 2007103370, WO 2007103260, WO 2007100880 & WO 2007022280 (Amgen Inc.—Memory Pharmaceuticals Corp.) disclose quinazoline derivatives as PDE10A inhibitors that are considered to have potential in the treatment of schizophrenia, bipolar disorder and obsessive-compulsive disorder. Further applications include obesity and non-insulin diabetes.

WO 2007103554, WO 2007098214 & WO 2007098169 (Amgen Inc.—Memory Pharmaceuticals Corp.) disclose cinnoline derivatives as PDE10A inhibitors that are considered to have potential in the treatment psychiatric disorders such as schizophrenia, bipolar disorders and obsessive-compulsive disorder.

WO 2007096743 & WO 2007085954 (Pfizer Products Inc.) disclose respectively substituted quinazolines and aminophthalazine compounds as PDE10A inhibitors that are considered to have potential in the treatment of psychotic disorders, anxiety disorders, movement disorders such as Parkinson and Huntington diseases, mood disorders, obesity and drug addiction.

WO 2006089815 & WO 2006075012 (Nycomed GmbH) disclose novel pyrrolodihydroisoquinolines as PDE10A inhibitors with potential utility in the treatment of neurological and psychiatric disorders, in diabetes therapy and in the regulation of fertility.

WO 2006071988 & WO 2006028957 (Memory Pharmaceuticals Corp.) disclose respectively thienopyrimidine derivatives and 4-substituted-4,6-dialkoxy-cinnoline derivatives as PDE10A inhibitors that are considered to have potential in the treatment of psychosis, including schizophrenia, bipolar disorder and obsessive-compulsive disorder, Alzheimer's disease and movement disorders such as Parkinson's disease. Other conditions include epilepsy, multiple sclerosis, Huntington's disease, disorders relating to the basal ganglia, diabetes and obesity.

WO 2006070284 & WO 2006011040 (Pfizer Products Inc.) disclose respectively pyrrolidyl derivatives of heteroaromatic compounds, and quinazolin-4-yl-piperidine and cinnolin-4-yl derivatives as PDE10A inhibitors that are considered to have potential in the treatment of CNS disorders, including schizophrenia, delusional disorders, drug-induced psychosis, anxiety, mood and movement disorders, neurodegenerative disorders and drug addiction.

WO 2005082883 (Pfizer Products Inc.) discloses tetrahydroisoquinolinyl derivatives of quinazoline and isoquinoline as PDE10A inhibitors that are claimed for use in the treatment of psychotic disorders, anxiety and movement disorders including Parkinson's disease and Huntington's disease, among other conditions.

WO 2006034512 & WO 2006034491 (Bayer Pharmaceuticals Corp.) disclose PDE10A inhibitors described as useful for the treatment of diabetes and related disorders. Pyrrolodihydroisoquinolines and variants thereof are disclosed as inhibitors of PDE10A in WO 2005003129 and WO 2005002579 (Nycomed GmbH).

WO 2004005291 & WO 2004005290 (Bayer Healthcare AG) disclose hetero-cyclically substituted imidazotriazines as PDE10A inhibitors described as useful for the treatment of neurodegenerative conditions, particularly Parkinson's disease and schizophrenia, and cancer.

WO 2004002484 (Kyowa Hakko Kirin Co., Ltd.) discloses quinoline derivatives as PDE10A inhibitors with potential in the treatment of Parkinson's disease, dyskinesia, anxiety, stress, mood and cognitive disorders, drug abuse, schizophrenia, cerebrovascular disorders, erectile dysfunction, diabetes, ischemic cardiopathies, renal disorders, peripheral vascular disease, hypertension, urinary incontinence, autoimmune diseases, respiratory disorders, allergies, pain, osteoporosis, cancer.

WO 2003014116 (Bayer Healthcare AG) discloses pyrrolo[2.1-a]isoquinoline derivatives as PDE10A inhibitors with potential in the treatment of cancer. WO 2003000693 (Bayer Healthcare AG) discloses imidazotriazines for use as PDE10A inhibitors considered to have potential in the treatment of Parkinson's disease.

All the above-mentioned publications are incorporated herein by reference.

However, these disclosures do not pertain to the compounds of the invention, which are structurally unrelated to any of the known PDE10A inhibitors (Kehler, J. et al., *Expert Opin. Ther. Patents*, 17, 147-158, 2007 and above cited patent literature), and which have now been found by the inventors to be highly active and selective PDE10A enzyme inhibitors.

The compounds of the invention offer alternatives to current marketed treatments for neurodegenerative and/or psychiatric disorders, which are not efficacious in all patients.

SUMMARY OF THE INVENTION

The present invention provides compounds that are PDE10A enzyme inhibitors, in particular selective PDE10A enzyme inhibitors. The present invention further provides compounds which have such activity. The invention also provides an effective treatment, in particular long-term treatment, of a human patient, without causing the side effects typically associated with current therapies for neurological and psychiatric disorders. Further aspects of the invention will become apparent upon reading the present specification.

In one aspect the present invention relates to compounds of formula (I):

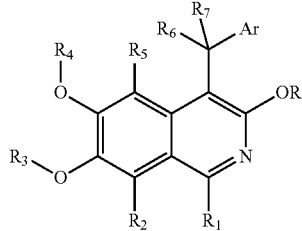

(I)

wherein
$R_1$ is a $(C_1-C_4)$alkyl group which can optionally be substituted with a $R_a$NH group, $R_a$ being selected from the group consisting of $(C_1-C_4)$alkyl-CO and $(C_1-C_4)$alkyl-SO$_2$;
$R_2$ is a hydrogen atom;
$R_3$ and $R_4$ independently represent a $(C_1-C_3)$alkyl group;
$R_5$ is a hydrogen atom;
$R_6$ and $R_7$ independently represent a hydrogen atom or a halogen atom, in particular fluorine, or $R_6$ and $R_7$ form together a =O group;
Ar is an aryl or heteroaryl group which can optionally be substituted with one to four substituents independently selected from the group consisting of hydroxy, $(C_1-C_4)$alkyl, $(C_1-C_4)$alkoxy, aryl, $(C_1-C_4)$alkyl-aryl, amino-substituted aryl, aryloxy, heteroaryl, $(C_1-C_4)$alkyl-heteroaryl and $R_bR_cN$, or wherein two substituents at adjacent positions of the aryl or heteroaryl are bound together to form a heterocyclic ring;
$R_b$ and $R_c$ being independently selected from the group consisting of hydrogen, $(C_1-C_4)$alkyl, halogeno$(C_1-C_4)$alkyl, aryl$(C_1-C_4)$alkyl and acetylamino$(C_1-C_4)$alkyl; and R is a hydrogen atom, a $(C_1-C_3)$alkyl group or a $(C_1-C_3)$alkyl-CO group;
and pharmaceutically acceptable salts, tautomer forms, solvates and esters thereof.

In another aspect the present invention relates to compounds of Formula (I):

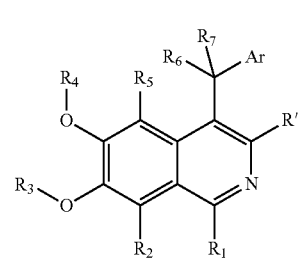

Formula (I)

or a pharmaceutically acceptable salt, tautomer form, solvate or ester thereof;
wherein:
$R_1$ is a $(C_1-C_4)$alkyl group which can optionally be substituted with a —$(C_1-C_4)$alkoxy or a $R_a$NH group, $R_a$ being selected from the group consisting of, $(C_1-C_4)$alkyl-C(=O)— and $(C_1-C_4)$alkyl-S(=O)$_2$—;
$R_2$ is a hydrogen atom;
$R_3$ and $R_4$ independently represent a $(C_1-C_3)$alkyl group;
$R_5$ is a hydrogen atom;
$R_6$ and $R_7$ independently represent a hydrogen atom, a halogen atom, or $R_6$ and $R_7$ together with the carbon atom to which they are shown attached form a —C(=O)— group;
R' is —NH$_2$ or —OR, wherein R is a hydrogen atom, a $(C_1-C_3)$alkyl group or a $(C_1-C_3)$alkyl-C(=O)— group
Ar is an aryl or heteroaryl group which can optionally be substituted with one to four substituents independently selected from the group consisting of halogen, azido, hydroxy, $(C_1-C_4)$alkyl, $(C_1-C_4)$alkoxy, —O—$(C_1-C_4)$alkyl-$(C_1-C_6)$cycloalkyl, aryl, $(C_1-C_4)$alkyl-aryl-, $(C_1-C_4)$alkoxy-aryl-, amino-substituted aryl, N($(C_1-C_4)$alkyl)$_2$-substituted aryl, aryloxy, heteroaryl, $(C_1-C_4)$alkyl-heteroaryl-, and $R_bR_cN$, or wherein two substituents at adjacent positions of the aryl or heteroaryl together with the atoms to which they are attached form a heterocyclic ring; and
$R_b$ and $R_c$ are independently selected from the group consisting of hydrogen, $(C_1-C_4)$alkyl, halogeno$(C_1-C_4)$alkyl-, $(C_1-C_4)$alkoxy$(C_1-C_4)$alkyl-, aryl$(C_1-C_4)$alkyl- and acetylamino$(C_1-C_4)$alkyl-.

DETAILED DESCRIPTION OF THE INVENTION

Within the context of the present application, the term "alkyl", alone or in combination with other groups, denotes linear or branched saturated hydrocarbon radical containing preferably from 1 to 10 carbon atoms, in particular from 1 to 6 carbon atoms, more particularly from 1 to 4 carbon atoms, unless otherwise indicated. Examples of alkyl groups having from 1 to 6 carbon atoms inclusive are methyl, ethyl, propyl (e.g., n-propyl, iso-propyl), butyl (e.g., tert-butyl, sec-butyl, n-butyl), pentyl (e.g., neo-pentyl), hexyl (e.g., n-hexyl), 2-methylbutyl, 2-methylpentyl and the other isomeric forms thereof. In the present invention, the alkyl groups can be halogenated or not. The term "halogenoalkyl" denotes such alkyl group substituted by one or more halogens up to the maximum valency of the alkyl group. Representative halogenoalkyl groups include trifluoromethyl (CF$_3$), difluoromethyl (CF$_2$H) and CF$_3$CH$_2$.

The term "halogen" denotes a chlorine, bromine, iodine or fluorine atom.

The term "acetylaminoalkyl" denotes a CH₃CONH-alkyl group.

The term "alkoxy" denotes an alkyl-O— group, with alkyl as defined above. Examples of alkoxy groups are methoxy, ethoxy, n-propyloxy, isopropyloxy and sec-butyloxy.

The term "aryl" refers to monocyclic or polycyclic (e.g. having 2, 3 or 4 fused rings) aromatic hydrocarbons such as, for example, phenyl, naphthyl, antracenyl, phenanthrenyl and the like. In some embodiments, an aryl group has from 5 to 20 carbons, in particular from 6 to 14 carbon atoms. Most preferred aryl groups are mono- or bi-cyclic and comprises from 6 to 14 carbon atoms, such as phenyl, α-naphthyl, β-naphthyl, antracenyl.

The term "aryloxy" denotes an aryl-O— group, with aryl as defined above.

The term "heteroaryl" denotes an aryl group interrupted by one or several heteroatoms selected from N, O, S or P. Heteroaryl groups include mono- or polycyclic groups (e.g. having 2, 3 or 4 fused rings). Representative heteroaryl groups include pyridinyl, quinolinyl, isoquinolinyl and dibenzofuran groups.

It will be understood that aryl and heteroaryl groups as substituents on the compound according to the invention can be branched to the remainder of the compound via any of the carbon atoms contained in said aryl and heteroaryl group.

In particular embodiments, compounds of the invention have one or more of the following features:
  $R_1$ is a substituted or unsubstituted $(C_1-C_4)$alkyl group preferably selected in the group consisting of methyl, ethyl, n-propyl, isopropyl, $CH_3CONHCH_2$ and $CH_3SO_2NHCH_2$; and/or
  $R_2$, $R_5$, $R_6$, $R_7$ are hydrogen; and/or
  $R_3$ and $R_4$ both represent a methyl group; and/or
  R' is selected from the group consisting of —NH₂, —OH, —OCH₃, and —OC(=O)CH₃; and/or
  Ar represents a pyridinyl, phenyl, naphthyl, quinolinyl, isoquinolinyl, [1,3]dioxolo[4,5-g]quinolyn, or dibenzofuran group, said Ar group being optionally substituted with one or more (e.g. two or three) substituents independently selected from the group consisting of $(C_1-C_4)$alkyl, aryl, $(C_1-C_4)$alkylaryl, heteroaryl, $(C_1-C_4)$heteroaryl, $(C_1-C_4)$alkyloxy, aryloxy, $(C_1-C_4)$ alkoxy-aryl-, aminoaryl (i.e, H₂N-aryl), and $R_bR_cN$.

In a particular embodiment, Ar represents:
  a pyridinyl group optionally substituted with one or two substituents independently selected from the group consisting of aryl, $(C_1-C_4)$alkylaryl, heteroaryl, $(C_1-C_4)$heteroaryl and $(C_1-C_4)$alkoxy-aryl-;
  a phenyl group optionally substituted with one or two substituents selected from the group consisting of $(C_1-C_4)$alkyloxy, aryloxy, $(C_1-C_4)$alkoxy-aryl-, and aminoaryl;
  a naphthyl group optionally substituted with one or two substituents selected from the group consisting of $(C_1-C_4)$alkyloxy, aryloxy, $(C_1-C_4)$alkoxy-aryl and aminoaryl;
  a quinolinyl group optionally substituted with one or more substituents, in particular one or two substituents, selected from the group consisting of $(C_1-C_4)$alkyl, $(C_1-C_4)$alkyloxy and $R_bR_cN$;
  [1,3]dioxolo[4,5-g]quinolyn group, optionally substituted with a $R_bR_cN$-substituent (i.e., a compound of the structure:

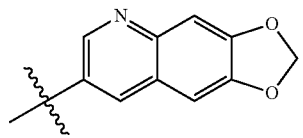 [SMILES: *c1cnc2cc3c(cc2c1)OCO3]

which is optionally substituted with a $R_bR_cN$— substituent);
  an isoquinolinyl group; or
  a dibenzofuran group.

Specific representative, and non-limiting, substituents of the Ar group include fluoro, azido, hydroxyl, methyl, ethyl, hydroxy, methoxy, ethoxy, cyclopropylmethoxy (i.e., —O—CH₂-cyclopropyl), phenyl, methoxyphenyl, aminophenyl, phenoxy, pyridinyl, methylamino, ethylamino, N,N-dimethylamino, ethylamino, n-propylamino, n-butylamino, isopropylamino, trifluoromethyl, 2,2,2-trifluoroethylamino, benzylamino, and acetyl-2-aminoethylamino groups.

In a particular embodiment, the compound of the invention is a compound of formula (I) wherein:
  $R_1$ is an unsubstituted $(C_1-C_3)$alkyl group, preferably selected in the group consisting of methyl, ethyl and n-propyl
  $R_2$, $R_5$, $R_6$, $R_7$ are hydrogen;
  $R_3$ and $R_4$ both represent a methyl group;
  R is hydrogen; and
  Ar is selected in the group consisting of:
    a phenyl group optionally substituted with one or two substituents selected from the group consisting of $(C_1-C_4)$alkyloxy, aryloxy, $(C_1-C_4)$alkoxy-aryl-, and aminoaryl;
    an unsubstituted naphthyl group, in particular the following naphthyl group

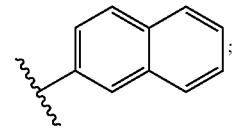 [SMILES: *c1ccc2ccccc2c1]

a dibenzoburan group of the formula

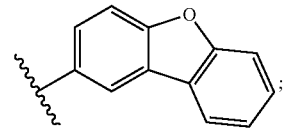 [SMILES: *c1ccc2oc3ccccc3c2c1]

and
    a quinolinyl group selected from the group consisting of:

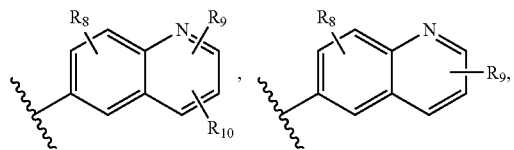

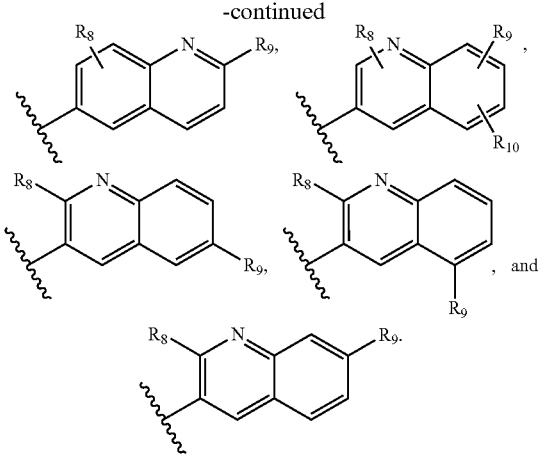

wherein:
R$_8$ is selected in the group consisting of hydrogen, halogenoalkyl, azido, (C$_1$-C$_4$)alkyl, and R$_b$R$_c$N (such as (C$_1$-C$_4$)alkylNH, (C$_1$-C$_4$)halogenoalkylNH or benzylNH, more specifically from methylamino, dimethylamino, ethylamino, n-propylamino, isopropylamino, 2,2,2-trifluoroethylamino, benzylamino, 2-methoxyethylamino, and acetyl-2-aminoethylamino groups;

R$_9$ and R$_{10}$ are independently selected from the group consisting of hydrogen, halogen, hydroxyl, (C$_1$-C$_3$) alkoxy, and —O—(C$_1$-C$_4$)alkyl-(C$_1$-C$_6$)cycloalkyl;

or R$_9$ and R$_{10}$, together with the carbon atoms to which they are attached on the quinolinyl group, form 5- or 6-membered heterocyclic ring, for example as in the following structure:

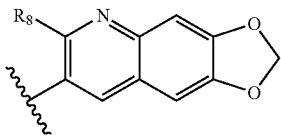

In one embodiment, R$_9$ is a methyl group or a (C$_1$-C$_3$) alkoxy group, in particular methoxy or ethoxy, and R$_{10}$ is a hydrogen.

In another embodiment, both R$_9$ and R$_{10}$ are hydroxyl groups.

Specific compounds of formula (I) which fall within the scope of the present invention include each of compounds 1 to 88 presented in the following "Examples" part. The invention thus relates to a compound of formula (I), selected in the group consisting of compounds 1 to 88 or a pharmaceutically acceptable salt thereof:

4-benzyl-6,7-dimethoxy-1-methylisoquinolin-3-ol hydrochloride 1,
4-(3,4-dimethoxybenzyl)-6,7-dimethoxy-1-methylisoquinolin-3-ol hydrochloride 2,
4-(3,4-dimethoxybenzyl)-3,6,7-trimethoxy-1-methylisoquinoline hydrochloride 3,
6,7-dimethoxy-1-methyl-4-(3-phenoxybenzyl)isoquinolin-3-ol hydrochloride 4,
6,7-dimethoxy-1-methyl-4-(4-phenoxybenzyl)isoquinolin-3-ol hydrochloride 5,
4-(dibenzo[b,d]furan-2-ylmethyl)-1-ethyl-6,7-dimethoxyisoquinolin-3-ol hydrochloride 6,
4-(dibenzo[b,d]furan-2-ylmethyl)-6,7-dimethoxy-1-propylisoquinolin-3-ol hydrochloride 7,
4-([1,1'-biphenyl]-3-ylmethyl)-1-ethyl-6,7-dimethoxyisoquinolin-3-ol hydrochloride 8,
1-ethyl-6,7-dimethoxy-4-((4'-methoxy-[1,1'-biphenyl]-3-yl)methyl)isoquinolin-3-ol hydrochloride 9,
4-((3'-amino-[1,1'-biphenyl]-3-yl)methyl)-1-ethyl-6,7-dimethoxyisoquinolin-3-ol dihydrochloride 10,
6,7-dimethoxy-1-methyl-4-(pyridin-4-ylmethyl)isoquinolin-3-ol hydrochloride 11,
6,7-dimethoxy-1-methyl-4-((6-phenylpyridin-2-yl)methyl)isoquinolin-3-ol dihydrochloride 12,
6,7-dimethoxy-4-((6-(4-methoxyphenyl)pyridin-2-yl)methyl)-1-methylisoquinolin-3-ol dihydrochloride 13,
4-([2,4'-bipyridin]-6-ylmethyl)-6,7-dimethoxy-1-methylisoquinolin-3-ol trihydrochloride 14,
6,7-dimethoxy-1-methyl-4-((5-phenylpyridin-3-yl)methyl)isoquinolin-3-ol dihydrochloride 15,
6,7-dimethoxy-4-((5-(4-methoxyphenyl)pyridin-3-yl)methyl)-1-methylisoquinolin-3-ol dihydrochloride 16,
6,7-dimethoxy-1-methyl-4-(naphthalen-2-ylmethyl)isoquinolin-3-ol hydrochloride 17,
3,6,7-trimethoxy-1-methyl-4-(naphthalen-2-ylmethyl)isoquinoline hydrochloride 18,
1-ethyl-6,7-dimethoxy-4-(naphthalen-2-ylmethyl)isoquinolin-3-ol hydrochloride 19,
6,7-dimethoxy-4-(naphthalen-2-ylmethyl)-1-propylisoquinolin-3-ol hydrochloride 20,
4-(isoquinolin-6-ylmethyl)-6,7-dimethoxy-1-methylisoquinolin-3-ol dihydrochloride 21,
4-(isoquinolin-5-ylmethyl)-6,7-dimethoxy-1-methylisoquinolin-3-ol 22,
6,7-dimethoxy-1-methyl-4-(quinolin-2-ylmethyl)isoquinolin-3-ol dihydrochloride 23,
6,7-dimethoxy-1-methyl-4-(quinolin-6-ylmethyl)isoquinolin-3-ol dihydrochloride 24,
6,7-dimethoxy-1-methyl-4-(quinolin-4-ylmethyl)isoquinolin-3-ol dihydrochloride 25,
6,7-dimethoxy-1-methyl-4-(quinolin-3-ylmethyl)isoquinolin-3-ol dihydrochloride 26,
6,7-dimethoxy-4-((5-methoxyquinolin-3-yl)methyl)-1-methylisoquinolin-3-ol dihydrochloride 27,
4-((5-ethoxyquinolin-3-yl)methyl)-6,7-dimethoxy-1-methylisoquinolin-3-ol dihydrochloride 28,
6,7-dimethoxy-4-((7-methoxyquinolin-3-yl)methyl)-1-methylisoquinolin-3-ol dihydrochloride 29,
4-((7-ethoxyquinolin-3-yl)methyl)-6,7-dimethoxy-1-methylisoquinolin-3-ol dihydrochloride 30,
1-ethyl-6,7-dimethoxy-4-((7-methoxyquinolin-3-yl)methyl)isoquinolin-3-ol dihydrochloride 31,
6,7-dimethoxy-4-((7-methoxyquinolin-3-yl)methyl)-1-propylisoquinolin-3-ol dihydrochloride 32,
6,7-dimethoxy-1-methyl-4-((6-methyl-2-(methylamino)quinolin-3-yl)methyl)isoquinolin-3-ol dihydrochloride 33,
6,7-dimethoxy-4-((6-methyl-2-(methylamino)quinolin-3-yl)methyl)-1-propylisoquinolin-3-ol dihydrochloride 34,
4-((2-(ethylamino)-6-methylquinolin-3-yl)methyl)-6,7-dimethoxy-1-propylisoquinolin-3-ol dihydrochloride 35,
4-((2-(dimethylamino)-6-methylquinolin-3-yl)methyl)-6,7-dimethoxy-1-propylisoquinolin-3-ol dihydrochloride 36,
6,7-dimethoxy-4-((6-methoxy-2-(methylamino)quinolin-3-yl)methyl)-1-methyl-isoquinolin-3-ol dihydrochloride 37,
6,7-dimethoxy-4-((6-methoxy-2-(propylamino)quinolin-3-yl)methyl)-1-propylisoquinolin-3-ol dihydrochloride 38,
1-ethyl-6,7-dimethoxy-4-((6-methoxy-2-(methylamino)quinolin-3-yl)methyl)isoquinolin-3-ol 39, 1-ethyl-6,7-dimethoxy-4-((6-methoxy-2-(ethylamino)quinolin-3-yl)methyl)isoquinolin-3-ol dihydrochloride 40,
1-ethyl-6,7-dimethoxy-4-((6-ethoxy-2-(ethylamino)quinolin-3-yl)methyl)isoquinolin-3-ol dihydrochloride 41,
1-ethyl-6,7-dimethoxy-4-((6-methoxy-2-(propylamino)quinolin-3-yl)methyl)isoquinolin-3-ol dihydrochloride 42,
1-ethyl-4-((2-(isopropylamino)-6-methoxyquinolin-3-yl)methyl)-6,7-dimethoxyisoquinolin-3-ol dihydrochloride 43,
4-((2-(benzylamino)-6-methoxyquinolin-3-yl)methyl)-1-ethyl-6,7-dimethoxyisoquinolin-3-ol dihydrochloride 44,
1-ethyl-6,7-dimethoxy-4-((6-methoxy-2-(2,2,2-trifluoroethylamino)quinolin-3-yl)methyl)isoquinolin-3-ol dihydrochloride 45,
4-((6-ethoxy-2-(ethylamino)quinolin-3-yl)methyl)-1-isopropyl-6,7-dimethoxyisoquinolin-3-ol dihydrochloride 46,
4-((2-(ethylamino)-6-methoxyquinolin-3-yl)methyl)-1-isopropyl-6,7-dimethoxyisoquinolin-3-ol dihydrochloride 47,
6,7-dimethoxy-4-((6-methoxy-2-(methylamino)quinolin-3-yl)methyl)-1-propylisoquinolin-3-ol dihydrochloride 48,
4-((6-ethoxy-2-(ethylamino)quinolin-3-yl)methyl)-6,7-dimethoxy-1-propylisoquinolin-3-ol dihydrochloride 49,
4-((2-(ethylamino)-6-methoxyquinolin-3-yl)methyl)-6,7-dimethoxy-1-propylisoquinolin-3-ol dihydrochloride 50,
1-isopropyl-6,7-dimethoxy-4-((6-methoxy-2-(2,2,2-trifluoroethylamino)quinolin-3-yl)methyl)isoquinolin-3-ol dihydrochloride 51,
6,7-dimethoxy-4-((6-methoxy-2-(propylamino)quinolin-3-yl)methyl)-1-propylisoquinolin-3-ol dihydrochloride 52,
4-((2-(isopropylamino)-6-methoxyquinolin-3-yl)methyl)-6,7-dimethoxy-1-propylisoquinolin-3-ol dihydrochloride 53,
6,7-dimethoxy-4-((6-methoxy-2-((2,2,2-trifluoroethyl)amino)quinolin-3-yl)methyl)-1-propylisoquinolin-3-ol dihydrochloride 54,
N-(2-((3-((3-hydroxy-6,7-dimethoxy-1-propylisoquinolin-4-yl)methyl)-6-methoxyquinolin-2-yl)amino)ethyl)acetamide dihydrochloride 55,
1-(acetamidomethyl)-4-((2-(ethylamino)-6-methoxyquinolin-3-yl)methyl)-6,7-dimethoxyisoquinolin-3-yl acetate 56,
N-((4-((2-(ethylamino)-6-methoxyquinolin-3-yl)methyl)-3-hydroxy-6,7-dimethoxyisoquinolin-1-yl)methyl)acetamide dihydrochloride 57,
N-((4-((2-(ethylamino)-6-methoxyquinolin-3-yl)methyl)-3-hydroxy-6,7-dimethoxyisoquinolin-1-yl)methyl)methanesulfonamide dihydrochloride 58,
3-((3-hydroxy-6,7-dimethoxy-1-methylisoquinolin-4-yl)methyl)-2-(methylamino)quinoline-6,7-diol dihydrochloride 59,
6,7-dimethoxy-1-methyl-4-((6-(methylamino)-[1,3]dioxolo[4,5-g]quinolin-7-yl)methyl)isoquinolin-3-ol dihydrochloride 60,
1-ethyl-6,7-dimethoxy-4-((6-(methylamino)-[1,3]dioxolo[4,5-g]quinolin-7-yl)methyl)isoquinolin-3-ol dihydrochloride 61,
6,7-dimethoxy-4-((6-(methylamino)-[1,3]dioxolo[4,5-g]quinolin-7-yl)methyl)-1-propylisoquinolin-3-ol dihydrochloride 62,
4-((6-(dimethylamino)-[1,3]dioxolo[4,5-g]quinolin-7-yl)methyl)-6,7-dimethoxy-1-propylisoquinolin-3-ol dihydrochloride 63,
4-((6-(ethylamino)-[1,3]dioxolo[4,5-g]quinolin-7-yl)methyl)-6,7-dimethoxy-1-propylisoquinolin-3-ol dihydrochloride 64,
4-(dibenzo[b,d]furan-2-ylmethyl)-6,7-dimethoxy-1-propylisoquinolin-3-amine hydrochloride 65,
4-((2-ethyl-6-methoxyquinolin-3-yl)methyl)-6,7-dimethoxy-1-propylisoquinolin-3-ol dihydrochloride 66,
4-((2-(ethylamino)-6-methoxyquinolin-3-yl)methyl)-6,7-dimethoxy-1-(methoxymethyl)isoquinolin-3-ol dihydrochloride 67,
4-((2-azido-6-methoxyquinolin-3-yl)methyl)-1-ethyl-6,7-dimethoxyisoquinolin-3-ol dihydrochloride 68,
N-(2-((3-((1-ethyl-3-hydroxy-6,7-dimethoxyisoquinolin-4-yl)methyl)-6-methoxyquinolin-2-yl)amino)ethyl)acetamide dihydrochloride 69,
4-((2-(ethylamino)-7-fluoro-6-methoxyquinolin-3-yl)methyl)-6,7-dimethoxy-1-propylisoquinolin-3-ol dihydrochloride 70,
4-((2-butyl-6-methoxyquinolin-3-yl)methyl)-6,7-dimethoxy-1-propylisoquinolin-3-ol dihydrochloride 71,
6,7-dimethoxy-4-((6-methoxy-2-(trifluoromethyl)quinolin-3-yl)methyl)-1-propylisoquinolin-3-ol hydrochloride 72,
N-(2-((3-((3-hydroxy-6,7-dimethoxy-1-methylisoquinolin-4-yl)methyl)-6-methoxyquinolin-2-yl)amino)ethyl)acetamide dihydrochloride 73,
6,7-dimethoxy-1-propyl-4-(quinolin-3-ylmethyl)isoquinolin-3-ol dihydrochloride 74,
(2-(ethylamino)-6-methoxyquinolin-3-yl)(3-hydroxy-6,7-dimethoxy-1-methylisoquinolin-4-yl)methanone dihydrochloride 75,
6,7-dimethoxy-4-((6-methoxy-2-((2-methoxyethyl)amino)quinolin-3-yl)methyl)-1-propylisoquinolin-3-ol dihydrochloride 76,
1-ethyl-6,7-dimethoxy-4-((6-methoxy-2-((2-methoxyethyl)amino)quinolin-3-yl)methyl)isoquinolin-3-ol dihydrochloride 77,
1-ethyl-6,7-dimethoxy-4-(quinolin-3-ylmethyl)isoquinolin-3-ol dihydrochloride 78,
1-isopropyl-6,7-dimethoxy-4-(quinolin-3-ylmethyl)isoquinolin-3-ol dihydrochloride 79,
6,7-dimethoxy-4-((2-methylquinolin-6-yl)methyl)-1-propylisoquinolin-3-ol dihydrochloride 80,
1-ethyl-6,7-dimethoxy-4-((2-methylquinolin-6-yl)methyl)isoquinolin-3-ol dihydrochloride 81,
1-ethyl-4-((2-(ethylamino)-7-fluoro-6-methoxyquinolin-3-yl)methyl)-6,7-dimethoxyisoquinolin-3-ol dihydrochloride 82,
N-(2-(((6-(cyclopropylmethoxy)-3-((3-hydroxy-6,7-dimethoxy-1-propylisoquinolin-4-yl)methyl)quinolin-2-yl)amino)ethyl)acetamide dihydrochloride 83,
6,7-dimethoxy-4-((6-methoxyquinolin-3-yl)methyl)-1-propylisoquinolin-3-ol dihydrochloride 84,
1-ethyl-6,7-dimethoxy-4-((6-methoxyquinolin-3-yl)methyl)isoquinolin-3-ol dihydrochloride 85,
4-((6-ethoxy-2-(ethylamino)-7-fluoroquinolin-3-yl)methyl)-6,7-dimethoxy-1-propylisoquinolin-3-ol dihydrochloride 86,
N-(2-(((6-(cyclopropylmethoxy)-3-((1-ethyl-3-hydroxy-6,7-dimethoxyisoquinolin-4-yl)methyl)quinolin-2-yl)amino)ethyl)acetamide dihydrochloride 87, and
N-(2-(((6-ethoxy-3-((3-hydroxy-6,7-dimethoxy-1-propylisoquinolin-4-yl)methyl)quinolin-2-yl)amino)ethyl)acetamide dihydrochloride 88.

Included within the scope of the invention are all stereoisomers, tautomeric forms, salts and solvates of the compound of formula (I).

The compounds according to the invention can be in the form of salts, particularly acid or base salts, preferably compatible with pharmaceutical use (i.e. pharmaceutically acceptable salts of the compounds of the invention). It will be appreciated by those skilled in the art that non-pharmaceutically acceptable salts of compounds of formula (I) are also part of the present invention, since such non-pharmaceutically acceptable salts can be useful as intermediates in the preparation of pharmaceutically acceptable salts.

Salts of compounds of the invention include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in *J. Pharm. Sci.*, 66, 2, 1977 which is incorporated herein by reference. Examples of metal salts include lithium, sodium, potassium, magnesium salts and the like. Base salts include, but are not limited to, those formed with pharmaceutically acceptable cations, such as sodium, potassium, lithium, calcium, magnesium, ammonium and alkylammonium. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Other examples of organic bases include lysine, arginine, guanidine, diethanolamine, choline and the like.

The pharmaceutically acceptable salts can in particular be prepared by reacting the compound of formula (I) with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents may also be used.

Compounds of Formula (I) may have optical centers and therefore may occur in different enantiomeric and diastereomeric configurations. The present invention includes all enantiomers, diastereomers, and other stereoisomers of such compounds of Formula (I), as well as racemic compounds and racemic mixtures and other mixtures of stereoisomers thereof.

Where structural isomers are interconvertible via a low energy barrier, tautomeric isomerism can occur. The compounds having structures that correspond to the formula (I) are also capable of existing as the corresponding 3-keto tautomeric forms. It follows that a single compound may exhibit more than one type of isomerism.

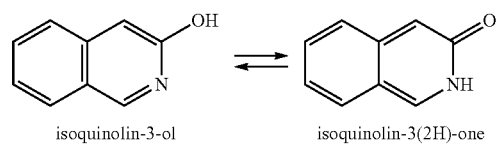 [SMILES: Oc1cc2ccccc2cn1 ; O=c1cc2ccccc2c[nH]1]

isoquinolin-3-ol      isoquinolin-3(2H)-one

The compounds according to the present invention may be prepared by various methods known to those skilled in the art. General and specific methods for the preparation of compounds of formula (I) are described herein below.

The intermediary 6,7-dimethoxy-1-alkylisoquinolin-3-ols CCH 18060, SLA 28136, SIL 32164, RBO 35142 and SMA 44012 were prepared in 2-82% yields (Reaction scheme 1) following a method described by Kanojia, R M et al. starting from the methyl ester SLA 28134 (Kanojia, R M et al., *J. Med. Chem.*, 1988, 31, 7, 1363). The phthalimide derivative SIL 32166 was prepared in three steps from 6,7-dimethoxy-1-methylisoquinolin-3-ol CCH 18060: O-acylation of CCH 18060 with acetic anhydride in presence of diisopropylethylamine and DMAP overnight at RT led to the acetate SIL 32158 in 88% yield. Bromination of acetate SIL 32158 with N-bromosuccinimide in carbon tetrachloride for 15 min at 130° C. under microwave irradiation afforded to the bromomethyl derivative SIL 32162 in 41% yield. Finally SIL 32162 was treated with potassium phthalimide in DMF overnight at room temperature to give the phthalimide derivative SIL 32162 in 68% yield (Reaction scheme 1).

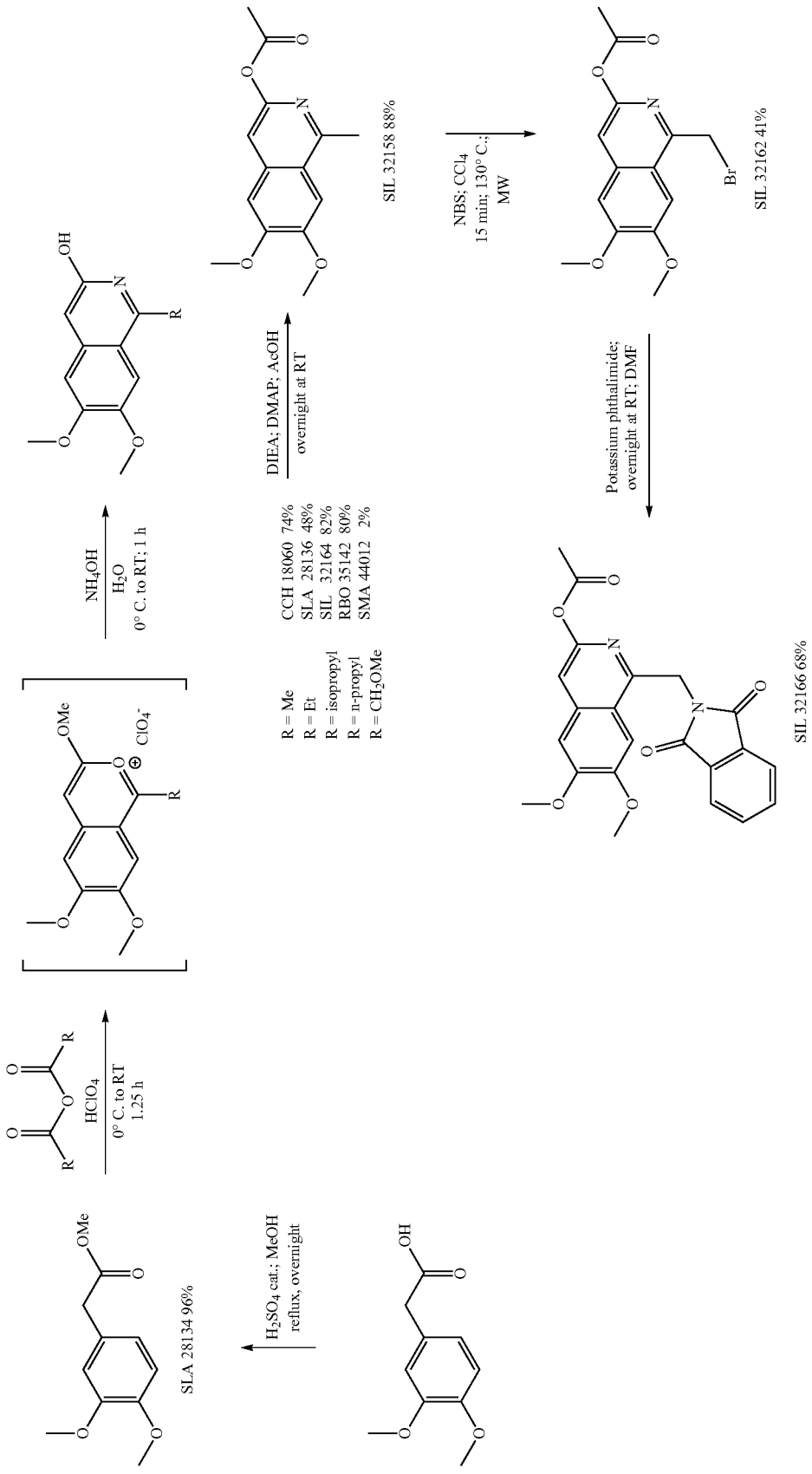

The compounds 1, 2, 4-7, 11, 17, 19-26, 28-55, 60-64, 66-70, 73, 76-88 of the invention (Reaction Scheme 2) were prepared by C-alkylation of 6,7-dimethoxy-1-alkylisoquinolin-3-ols CCH 18060, SLA 28136, SIL 32164, RBO 35142 or SMA 44012 preferably in toluene or THF at 110-160° C. under microwave irradiation for 15-120 min by a halogenomethyl-aryl or a halogenomethyl-heteroaryl derivative in presence of a 2 N aqueous KOH or LiOH solution as base.

Reaction Scheme 2: Synthetic routes followed to prepare final compounds

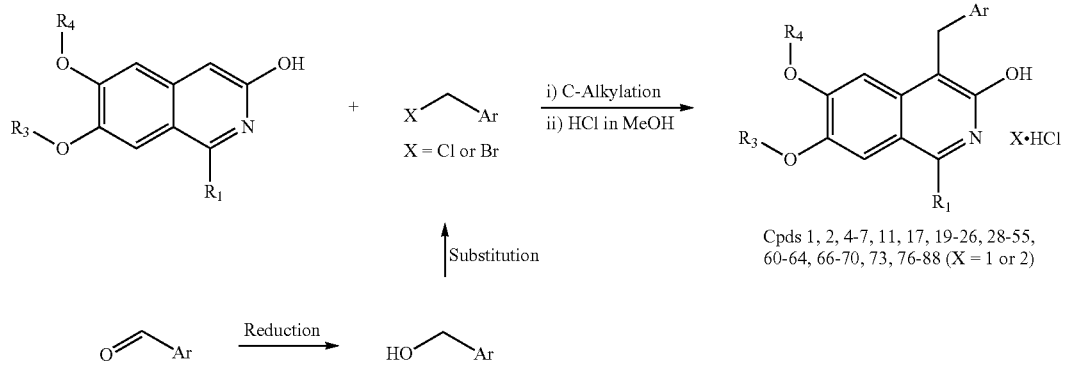

Compound 52 was prepared with the same type of microwave-assisted C-alkylation at 150° C. for 90 min using THF as solvent and a 1.6 M solution of n-BuLi in hexane as base. The chloro or bromo-alkylating reagents (halogenomethyl-aryl or halogenomethyl-heteroaryl derivatives) were commercially available or prepared from the corresponding primary alcohols by substitution of the hydroxyl function by a chlorine or a bromine atom using respectively thionyl chloride or triphenylphosphine and bromine in dichloromethane. The primary alcohols were prepared by reduction of the corresponding aldehydes using sodium borohydride (Reaction scheme 2).

In some cases the products obtained by following the reaction Scheme 2 may be further modified, for example, by manipulation of substituents.

For example compound 3 was obtained from compound 2 free base by microwave-assisted O-methylation using methyl iodide in presence of cesium carbonate in dimethylformamide (reaction scheme 3).

Reaction Scheme 3: Preparation of compounds 3 and 18

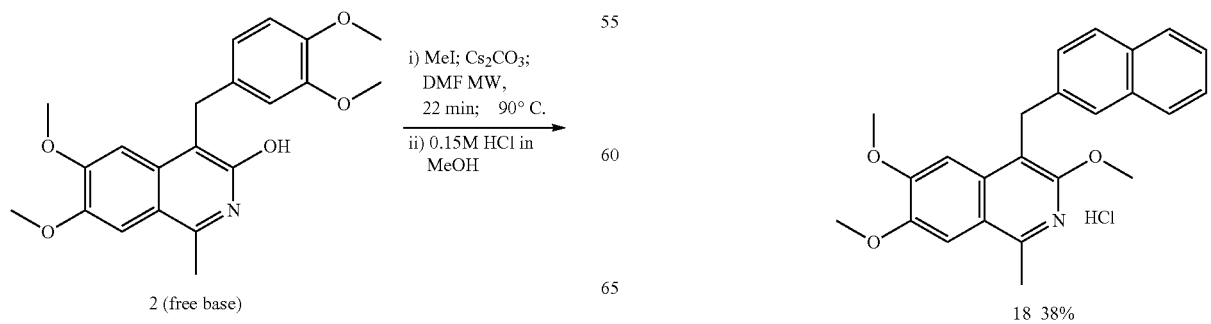

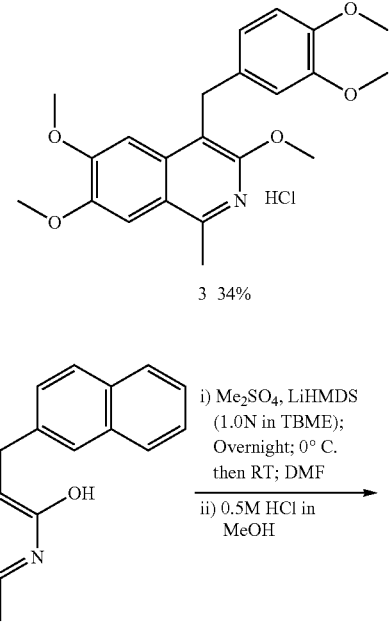

Compound 18 was obtained from compound 17 by O-methylation using dimethylsulfate with lithium hexamethyldisilazide (LiHMDS) as base and in dimethylformamide (Reaction scheme 3)

For example microwave-assisted Suzuki cross coupling reaction between the bromo derivatives SLA 28138, CCH 34150 and CCH 34166 and different substituted phenylboronic acids afforded direct access to compounds 8-10 and 12-14 in 30-91% yields (Reaction Scheme 4).

Reaction Scheme 4: Synthetic routes followed to prepare compounds 8-10 & 12-14

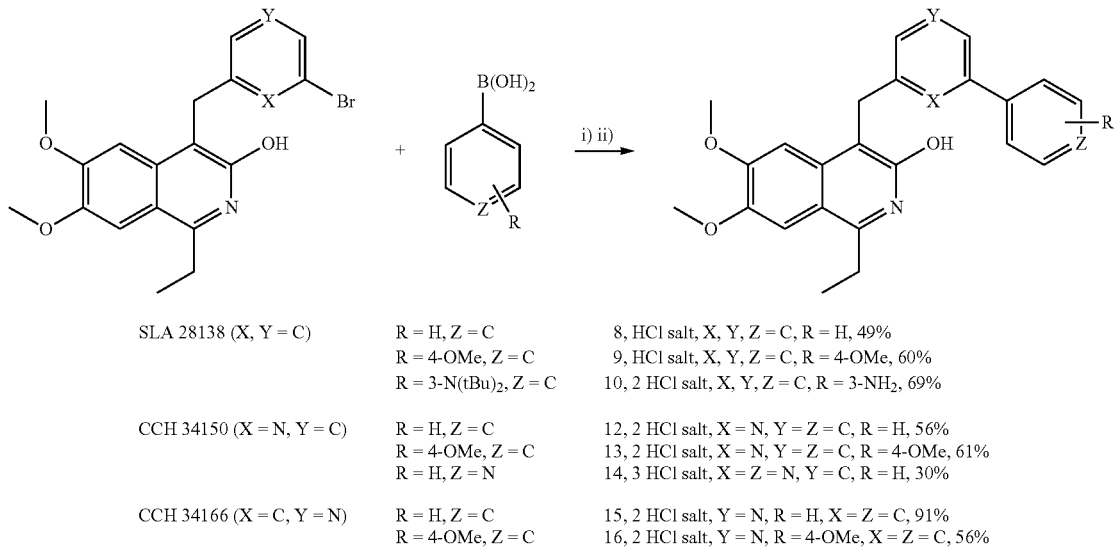

| | | |
|---|---|---|
| SLA 28138 (X, Y = C) | R = H, Z = C | 8, HCl salt, X, Y, Z = C, R = H, 49% |
| | R = 4-OMe, Z = C | 9, HCl salt, X, Y, Z = C, R = 4-OMe, 60% |
| | R = 3-N(tBu)$_2$, Z = C | 10, 2 HCl salt, X, Y, Z = C, R = 3-NH$_2$, 69% |
| CCH 34150 (X = N, Y = C) | R = H, Z = C | 12, 2 HCl salt, X = N, Y = Z = C, R = H, 56% |
| | R = 4-OMe, Z = C | 13, 2 HCl salt, X = N, Y = Z = C, R = 4-OMe, 61% |
| | R = H, Z = N | 14, 3 HCl salt, X = Z = N, Y = C, R = H, 30% |
| CCH 34166 (X = C, Y = N) | R = H, Z = C | 15, 2 HCl salt, Y = N, R = H, X = Z = C, 91% |
| | R = 4-OMe, Z = C | 16, 2 HCl salt, Y = N, R = 4-OMe, X = Z = C, 56% | i) Pd(PPh$_3$)$_2$Cl$_2$; Na$_2$CO$_3$; DME; MW; 140° C.
ii) 0.49M HCl in MeOH

The compound 27 was obtained from a different synthetic route (Reaction scheme 5). The methyl ester SLA 28134 was deprotonated by LiHMDS followed by treatment with the chloro derivative CCH 34144B to obtain the methyl ester CCH 34144-5 in 35% yield. The methyl ester CCH 34144-5 was treated with acetic anhydride in presence of perchloric acid to give the corresponding acetyl derivative CCH 34154 in 59% yield. Finally microwave-assisted treatment of CCH 34154 by ammonium acetate at 160° C. for 7 minutes followed by a subsequent treatment at room temperature by a 0.09 M HCl solution in methanol afforded compound 27 as a dihydrochloride salt in 76% yield (scheme 5).

Reaction Scheme 5: Synthetic route followed to prepare the compound 27

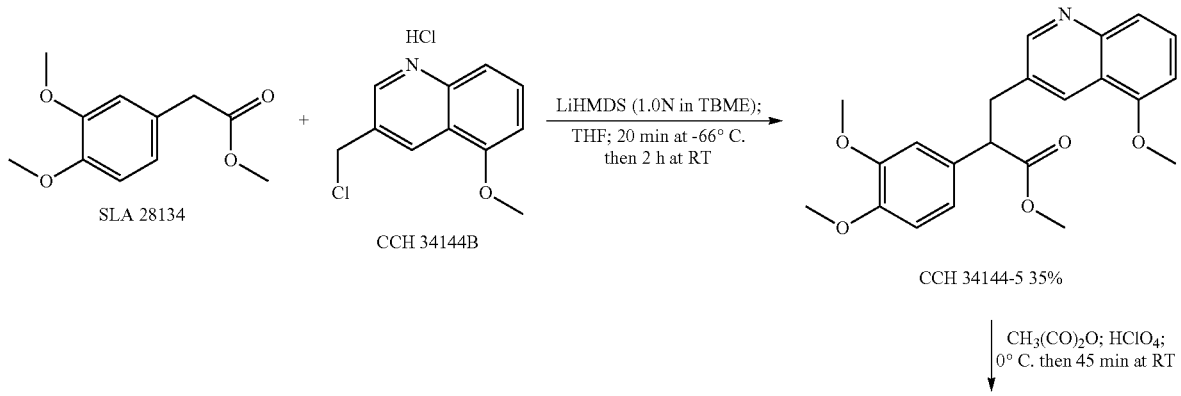

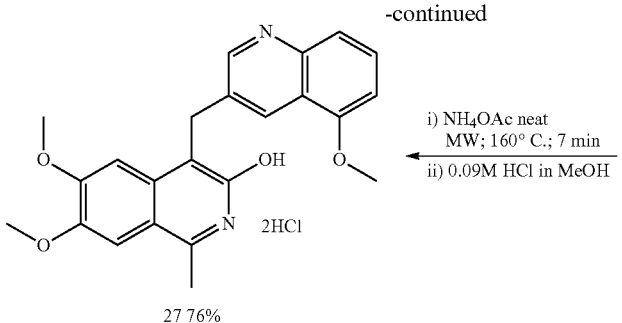

27 76% i) NH₄OAc neat
MW; 160° C.; 7 min
ii) 0.09M HCl in MeOH

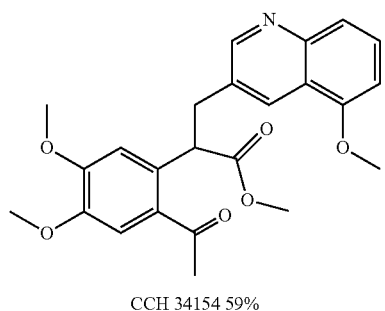

CCH 34154 59%

The compounds 56-58 were prepared following the synthetic routes described in scheme 6. The acetate SIL 32166 was first deprotected to its corresponding hydroxy derivative by a 7N $NH_3$ solution in methanol for 4 hours at room temperature.
The intermediary hydroxy compound was then C-alkylated in THF with SLA 28166 free base at 150° C. for 1.5 hours in presence of a 2 N aqueous LiOH solution as base and under microwave irradiation. The obtained phthalimide CCH 42006-1 was then deprotected to its corresponding amino derivative by treatment with hydrazine hydrate in ethanol for 10 min at 130° C. under microwave irradiation. The amino derivative was treated by acetic anhydride in presence of diisopropylaminomethyl-polystyrene resin and DMAP for 20 min at 100° C. under microwave irradiation to obtain the bis-acetylated derivative 56 in 72% yield. Compound 56 was deprotected to its corresponding hydroxy derivative by a 7 N $NH_3$ solution in methanol overnight at room temperature to obtain, after treatment at RT with a 0.4 M HCl solution in MeOH, compound 57 as a dihydrochloride salt in 79% yield. The intermediary amino derivative was also treated by methanesulfonyl chloride, in presence of diisopropylaminomethyl-polystyrene resin, and DMAP for 20 min at 100° C. under microwave irradiation to obtain, after purification and treatment for 5 min at RT with a 0.4 M HCl solution in MeOH, compound 58 as a hydrochloride salt in 31% yield (reaction scheme 6).

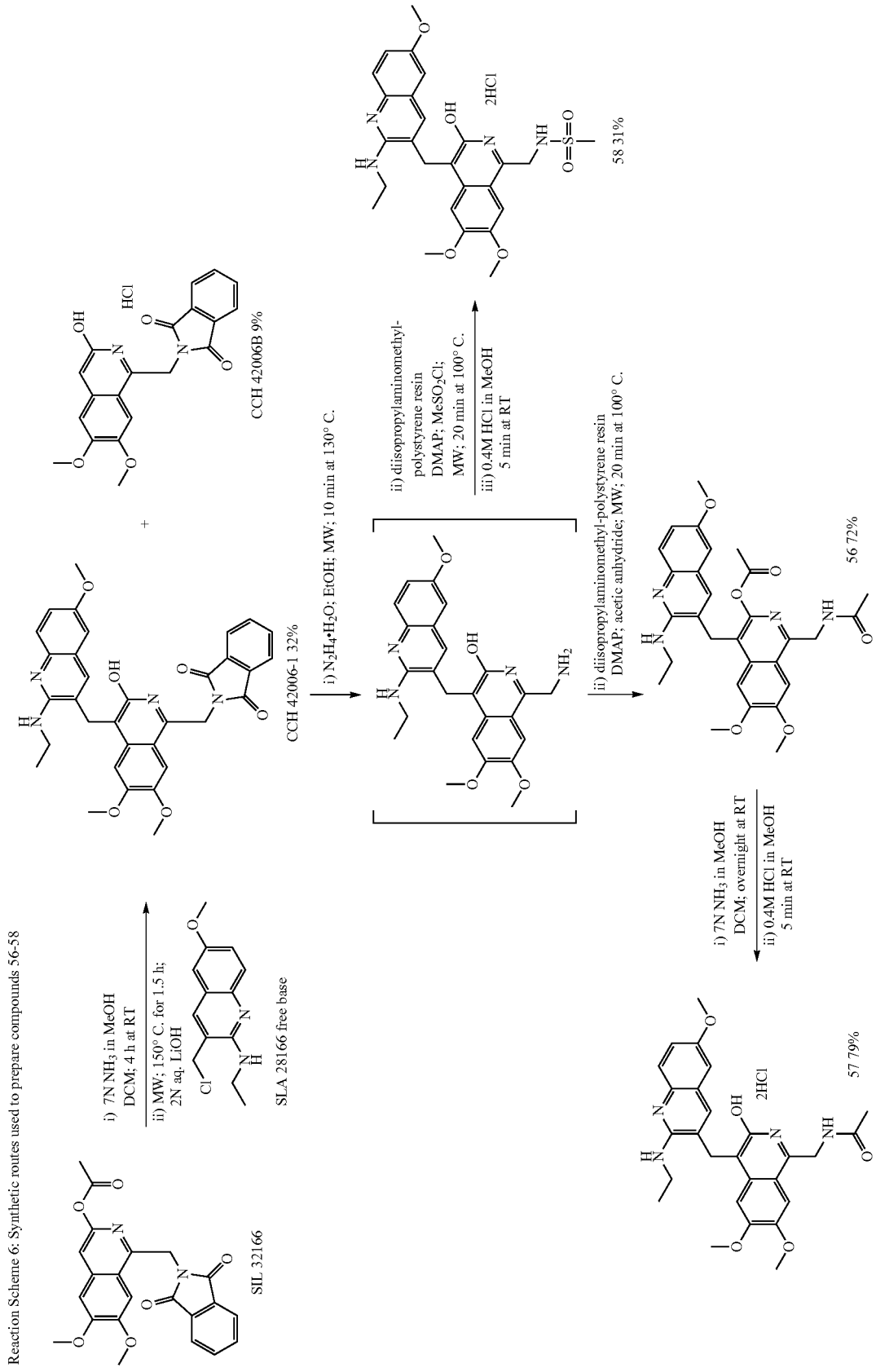
Reaction Scheme 6: Synthetic routes used to prepare compounds 56-58

The compound 59 was prepared from compound 60 following the reaction described in scheme 7. Compound 60 freebase in dichloromethane was treated at 0° C. by a 1.0 N solution of BCl₃ in dichloromethane and the reaction mixture was stirred overnight at RT. After purification and treatment with a 0.19 N HCl solution in methanol at RT, compound 59 was obtained as a dihydrochloride salt in 31% yield.

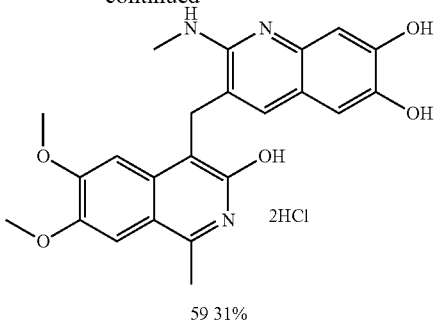

59 31%

The compound 65 was prepared from compound 7 following the reaction described in scheme 8. The compound 7 was treated, for 5 hours at room temperature then for 1 hour at 65° C., by N-phenyl-bis(trifluoromethanesulfonimide) in dimethylformamide in presence of triethylamine as a base to obtain the triflate CCH 42040-1 in 72% yield. Buchwald-Hartwig cross coupling reaction, preferentially for 45 minutes in THF and at 140° C. under microwave irradiation, between triflate CCH 42040-1 and t-butylcarbamate using tris(dibenzylideneacetone)dipalladium(0) as catalyst, xantphos (4,5-bis(diphenylphosphino)-9,9-dimethylxanthene) as ligand and cesium carbonate as a base led, after subsequent trifluoroacetic acid treatment overnight at room temperature followed by a final treatment of the obtained free base in methanol for 5 min at RT with a 0.49 M HCl solution in MeOH, to the compound 59 as a dihydrochloride salt in 31% overall yield (reaction scheme 8).

Reaction Scheme 7: Synthetic route followed to prepare the compounds 59

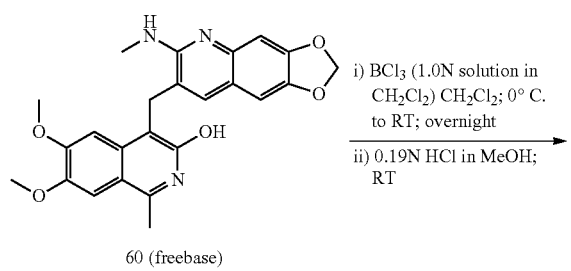

i) BCl₃ (1.0N solution in CH₂Cl₂) CH₂Cl₂; 0° C. to RT; overnight ii) 0.19N HCl in MeOH; RT 60 (freebase)

Reaction Scheme 8: Synthetic route to prepare the compound 65

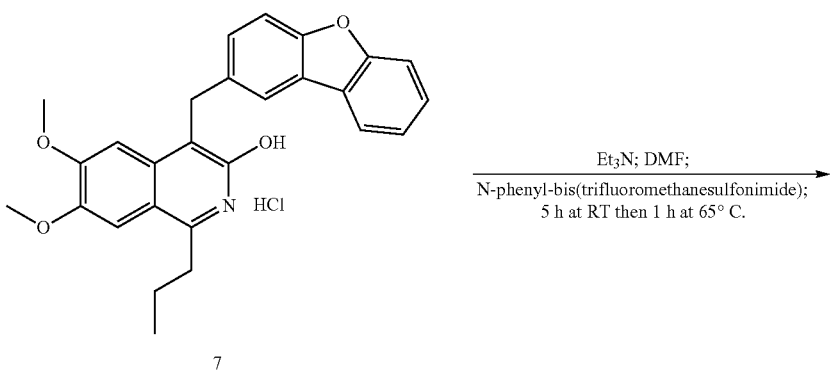

Et₃N; DMF;
N-phenyl-bis(trifluoromethanesulfonimide);
5 h at RT then 1 h at 65° C.

7

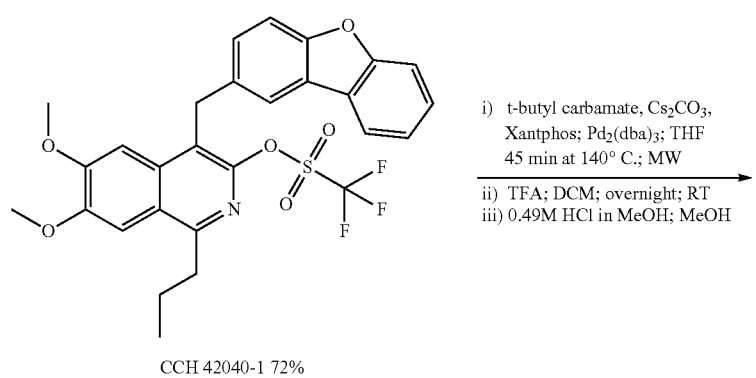

i) t-butyl carbamate, Cs₂CO₃, Xantphos; Pd₂(dba)₃; THF
45 min at 140° C.; MW ii) TFA; DCM; overnight; RT iii) 0.49M HCl in MeOH; MeOH

CCH 42040-1 72%

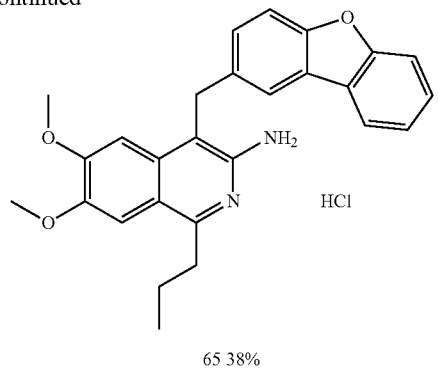

65 38%

Another method to prepare the compounds of the invention is the route followed to synthesize the compounds 71, 72 & 74 that is described in scheme 9. The key step is a halogen-metal exchange reaction, preferentially performed at −105° C. in presence of anhydrous THF as solvent, between the iodo derivative CCH 42098-2 and a 1.6 M solution of n-butyl lithium in hexanes followed by a subsequent quench with the aldehyde SMA 44044 to obtain an intermediary secondary alcohol derivative that can be purified by column chromatography. The secondary alcohol derivative can then be reduced, preferentially by using triethylsilane in presence of TFA in dichloromethane overnight at RT. After neutralization of the obtained residue by a $NaHCO_3$ aqueous solution, the free base of the reduced compound was obtained after purification by column chromatography. The subsequent treatment of the obtained free base in dichloromethane for 5 min at RT with a 0.49 M HCl solution in MeOH led to the compound 71 as a dihydrochloride salt in 24% overall yield. The compounds 72 and 74 were obtained by this method using respectively 6-methoxy-2-(trifluoromethyl)quinoline-3-carbaldehyde SLA 47010 and 3-quinolinecarboxaldehyde instead of 2-butyl-6-methoxyquinoline-3-carbaldehyde SMA 44044 (reaction scheme 9).

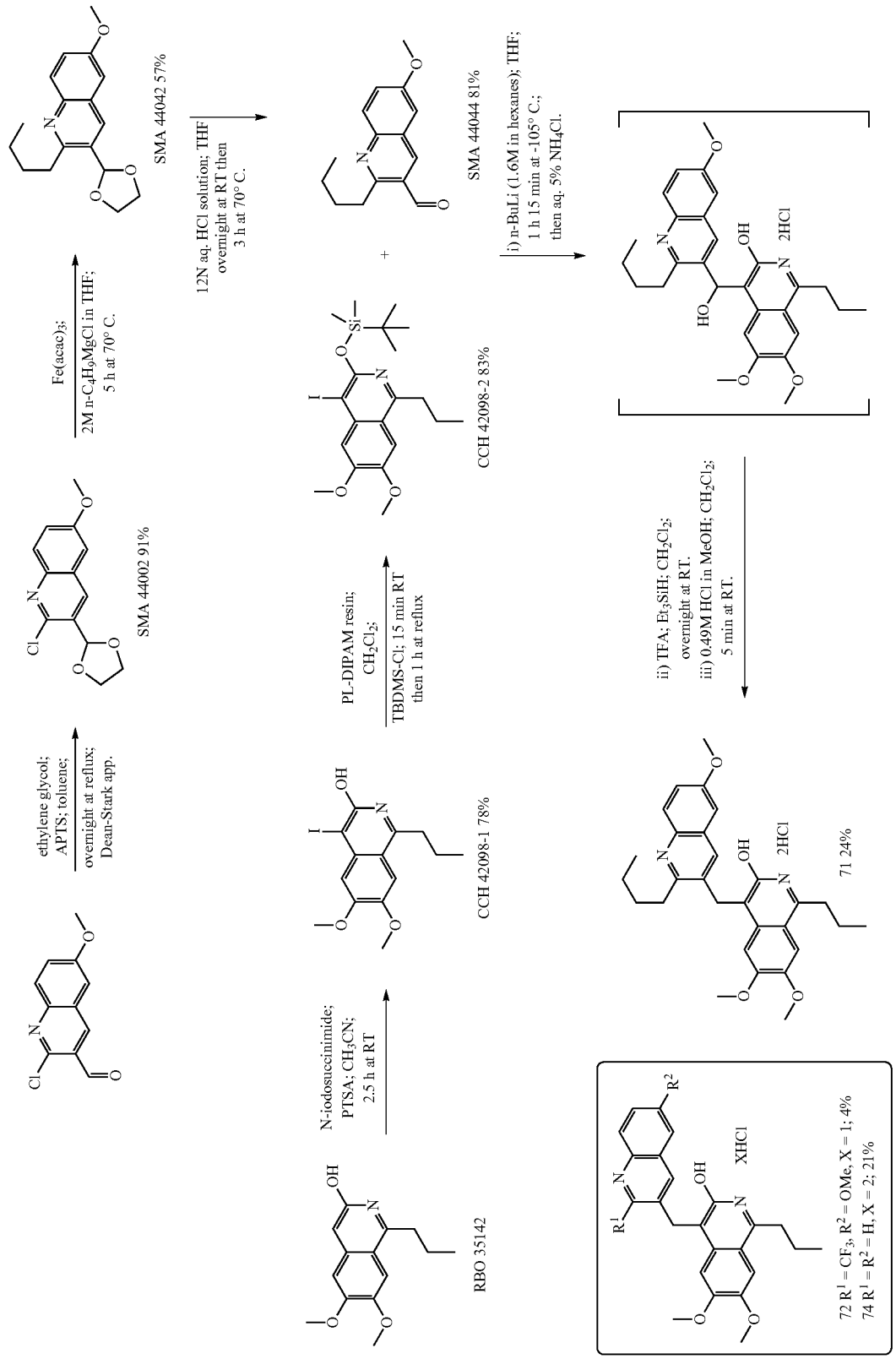
Reaction Scheme 9: Synthetic route followed to prepare compounds 71, 72 & 74

The compound 75 was prepared from compound CCH 18060 following the reaction described in scheme 10. The key step is a halogen-metal exchange reaction, performed preferentially at −105° C. in presence of anhydrous THF as solvent, between the bromo derivative SMA 44070 and a 1.6 M solution of n-butyl lithium in hexanes followed by a subsequent quench with 2-chloro-6-methoxyquinoline-3-carbaldehyde to obtain an intermediary secondary alcohol derivative that can be purified by column chromatography. The secondary alcohol derivative can then be oxidized in ketone preferentially using Dess-Martin periodinane in dichloromethane from 0° C. to RT for 2 hours. The oxidized chloro compound was purified by column chromatography and then the chloro aromatic substituent was substituted in tetrahydrofuran by ethylamine preferentially by using a 2.0 M ethylamine solution in THF for 30 min at 160° C. under microwave irradiation. The subsequent treatment of the obtained ethylamine free base derivative in dichloromethane for 5 min at RT with a 0.49 M HCl solution in MeOH led to the compound 75 as a dihydrochloride salt in 2% overall yield (reaction scheme 10).

Mack Publishing), in either single or multiple doses. The invention thus also includes a pharmaceutical composition comprising, in a pharmaceutically acceptable carrier, a compound of formula (I).

Suitable pharmaceutical carriers include inert solid diluents or fillers, sterile aqueous solutions and various organic solvents. The pharmaceutical compositions formed thereby can then be readily administered in a variety of dosage forms such as tablets, powders, lozenges, liquid preparations, syrups, injectable solutions and the like. These pharmaceutical compositions can optionally contain additional ingredients such as flavorings, binders, excipients and the like. Thus, the compound of the invention may be formulated for oral, ocular, buccal, intranasal, parenteral (e.g. intravenous, intramuscular or subcutaneous), transdermal (e.g. patch) or rectal administration, or in a form suitable for administration by inhalation or insufflation. The pharmaceutical compositions of the invention can be formulated either as solid or liquid compositions.

For oral administration, the pharmaceutical compositions may take the form of, for example, tablets or capsules Reaction Scheme 10: Synthetic route used to prepare the compound 75

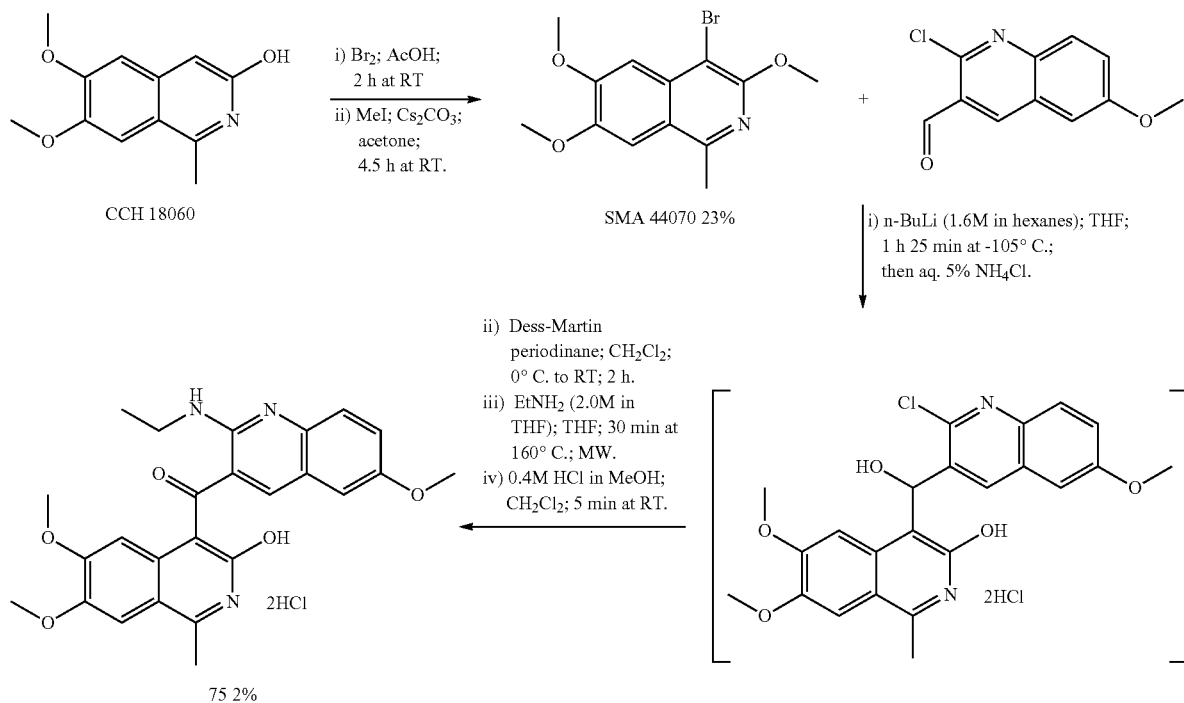

It should be understood that other ways of producing these compounds may be designed by the skilled person, based on common general knowledge and following guidance contained in this application.

Another object of the present invention is the intermediate compounds used for the preparation of compounds of formula (I). In particular, the present invention relates to the intermediate compounds herein below mentioned in the examples.

The compounds of the invention can be administered alone, but are generally administered with a pharmaceutical carrier, with respect to standard pharmaceutical practice (such as described in Remington's Pharmaceutical Sciences, prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration, the composition may take the form of tablets or lozenges formulated in conventional manner.

The compounds of the invention may be formulated for parenteral administration by injection, including using conventional catheterization techniques or infusion. Formulations for injection may be presented in unit dosage form, e.g. in ampoules or in multi-dose containers, with an added preservative. They may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use. When a product solution is required, it can be made by dissolving the isolated inclusion complex in water (or other aqueous medium) in an amount sufficient to generate a solution of the required strength for oral or parenteral administration to patients. The compounds may be formulated for fast dispersing dosage forms, which are designed to release the active ingredient in the oral cavity. These have often been formulated using rapidly soluble gelatin-based matrices. These dosage forms are well known and can be used to deliver a wide range of drugs. Most fast dispersing dosage forms utilize gelatin as a carrier or structure-forming agent. Typically, gelatin is used to give sufficient strength to the dosage form to prevent breakage during removal from packaging, but once placed in the mouth, the gelatin allows immediate dissolution of the dosage form. Alternatively, various starches are used to the same effect. The compounds of the invention may also be formulated in rectal compositions such as suppositories or retention enemas, e.g. containing conventional suppository bases such as cocoa butter or other glycerides.

The dosages and dosage regimen in which the compounds of formula (I) are administered will vary according to the pharmacodynamic characteristics of the particular agent and its mode and route of administration; the age, health and weight of the recipient; the nature and extent of the symptoms; the kind of concurrent treatment; the frequency of treatment; and the effect desired. Accordingly, optimal therapeutic concentrations will be best determined at the time and place through routine experimentation.

The compounds according to the invention can be used enterally or parenterally. Orally, the compounds according to the invention are suitably administered in the amount from about 0.1 mg per day to 1,000 mg per day. For parenteral, sublingual, intranasal, or intrathecal administration, the compounds according to the invention are suitably used in the amount from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg. In a preferred aspect, the therapeutically effective amounts for oral administration is from about 1 mg/day to about 100 mg/day; and for parenteral administration from about 5 to about 50 mg daily. In a more preferred aspect, the therapeutically effective amounts for oral administration are from about 5 mg/day to about 50 mg/day.

The daily dose may be administered as single dose or in divided doses and, in addition, the upper limit can also be exceeded when this is found to be indicated.

The present invention also relates to a compound of formula (I), or a composition comprising a compound of formula (I), for use as a medicament. Indeed, the compounds according to the invention have been found to have pharmacologically important properties which can be used therapeutically. The compounds of the invention can be used alone, in combination with each other or in combination with other active compounds.

The compounds of the invention are inhibitors selective for PDE10A. The invention thus also relates to a compound of formula (I) or a pharmaceutical composition comprising the same, for use in a method for the treatment of a disease selected in the group consisting of the diseases or groups of diseases described below, where inhibition of PDE10 would be efficient in the treatment of said diseases.

The present invention also pertains to a pharmaceutical composition for use in the treatment of certain psychotic disorders and conditions such as schizophrenia, delusional disorders and drug induced psychosis; to anxiety disorders such as panic and obsessive-compulsive disorder; and to movement disorders including Parkinson's disease and Huntington's disease, comprising an amount of a compound of formula (I) effective in inhibiting PDE10A.

In another embodiment, the invention relates to a pharmaceutical composition for treating psychotic disorders and condition such as schizophrenia, delusional disorders and drug induced psychosis; anxiety disorders such as panic and obsessive-compulsive disorder; and movement disorders including Parkinson's disease and Huntington's disease, comprising an amount of a compound of formula (I) effective in treating said disorder or condition.

The invention also relates to a compound of formula (I), for use in the treatment of certain psychotic disorders and conditions such as schizophrenia, delusional disorders and drug induced psychosis; to anxiety disorders such as panic and obsessive-compulsive disorder; and to movement disorders including Parkinson's disease and Huntington's disease.

Examples of psychotic disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type. Examples of movement disorders that can be treated according to the present invention include but are not limited to Huntington's disease and dyskinesia associated with dopamine agonist therapy, Parkinson's disease, restless leg syndrome, and essential tremor.

Other disorders that can be treated according to the present invention are obsessive/compulsive disorders, Tourette's syndrome and other tic disorders.

In another embodiment, the invention relates to a method for treating an anxiety disorder or condition in a mammal which method comprises administering to said mammal an amount of a compound of formula (I) effective in inhibiting PDE10A.

The invention also provides a method for treating an anxiety disorder or condition in a mammal which method comprises administering to said mammal an amount of a compound of formula (I) effective in treating said disorder or condition.

The invention also relates to a compound of formula (I), for use in the treatment of an anxiety disorder or condition in a mammal.

Examples of anxiety disorders that can be treated according to the present invention include, but are not limited to, panic disorder; agoraphobia; a specific phobia; social phobia; obsessive-compulsive disorder; post-traumatic stress disorder; acute stress disorder; and generalized anxiety disorder.

The invention further provides a method of treating a drug addiction, for example an alcohol, amphetamine, cocaine, or opiate addiction, in a mammal, including a human, which method comprises administering to said mammal an amount of a compound of formula (I) effective in treating drug addiction. The invention also provides a method of treating a drug addiction, for example an alcohol, amphetamine, cocaine, or opiate addiction, in a mammal, including a human, which method comprises administering to said mammal an amount of a compound of formula (I) effective in inhibiting PDE10A.

The invention also relates to a compound of formula (I), for use in the treatment of a drug addiction, for example an alcohol, amphetamine, cocaine, or opiate addiction, in a mammal, including a human.

A "drug addiction", as used herein, means an abnormal desire for a drug and is generally characterized by motivational disturbances such a compulsion to take the desired drug and episodes of intense drug craving.

The invention further provides a method of treating a disorder comprising as a symptom a deficiency in attention and/or cognition in a mammal, including a human, which method comprises administering to said mammal an amount of a compound of formula (I) effective in treating said disorder. The invention also provides a method of treating a disorder or condition comprising as a symptom a deficiency in attention and/or cognition in a mammal, including a human, which method comprises administering to said mammal an amount of a compound of formula (I) effective in inhibiting PDE10A.

The invention also provides a method of treating a disorder or condition comprising as a symptom a deficiency in attention and/or cognition in a mammal, including a human, which method comprises administering to said mammal an amount of a compound of formula (I) effective in treating said disorder or condition.

The invention also relates to a compound of formula (I), for use in the treatment of a disorder or condition comprising as a symptom a deficiency in attention and/or cognition in a mammal, including a human.

The phrase "deficiency in attention and/or cognition" as used herein in "disorder comprising as a symptom a deficiency in attention and/or cognition" refers to a subnormal functioning in one or more cognitive aspects such as memory, intellect, or learning and logic ability, in a particular individual relative to other individuals within the same general age population. "Deficiency in attention and/or cognition" also refers to a reduction in any particular individual's functioning in one or more cognitive aspects, for example as it occurs in age-related cognitive decline. Examples of disorders that comprise as a symptom a deficiency in attention and/or cognition that can be treated according to the present invention are dementia, for example Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

The invention also provides a method of treating a mood disorder or mood episode in a mammal, including a human, comprising administering to said mammal an amount of a compound of formula (I) effective in treating said disorder or episode.

The invention also provides a method of treating a mood disorder or mood episode in a mammal, including a human, comprising administering to said mammal an amount of a compound of formula (I) effective in inhibiting PDE10A.

The invention also relates to a compound of formula (I), for use in the treatment of a mood disorder or mood episode in a mammal, including a human Examples of mood disorders and mood episodes that can be treated according to the present invention include, but are not limited to, major depressive episode of the mild, moderate or severe type, a manic or mixed mood episode, a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder.

The invention further provides a method of treating a neurodegenerative disorder or condition in a mammal, including a human, which method comprises administering to said mammal an amount of a compound of formula (I) effective in treating said disorder or condition. The invention further provides a method of treating a neurodegenerative disorder or condition in a mammal, including a human, which method comprises administering to said mammal an amount of a compound of formula (I) effective in inhibiting PDE10A. The invention also provides to a compound of formula (I), for use in the treatment of a neurodegenerative disorder or condition in a mammal, including a human.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temperal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the invention, the neurodegenerative disorder is Parkinson's disease or Alzheimer's disease.

In one embodiment of the present invention, the neurodegenerative disorder or condition comprises neurodegeneration of striatal medium spiny neurons in a mammal, including a human.

In a further embodiment of the present invention, the neurodegenerative disorder or condition is Huntington's disease.

The invention also provides a pharmaceutical composition for treating psychotic disorders, delusional disorders and drug induced psychosis; anxiety disorders, movement disorders, mood disorders, neurodegenerative disorders, obesity, and drug addiction, comprising an amount of a compound of formula (I) effective in treating said disorder or condition.

The invention also provides a method of treating a disorder selected from psychotic disorders, delusional disorders and drug induced psychosis; anxiety disorders, movement disorders, obesity, mood disorders, and neurodegenerative disorders, which method comprises administering an amount of a compound of formula (I) effective in treating said disorder.

The invention also provides to a compound of formula (I), for use in the treatment of a disorder selected from psychotic disorders, delusional disorders and drug induced psychosis; anxiety disorders, movement disorders, obesity, mood disorders, and neurodegenerative disorders.

The invention also provides a method of treating disorders selected from the group consisting of: dementia, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; age-related cognitive decline, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder comprising a delusional disorder or schizophrenia; a bipolar disorder comprising bipolar I disorder, bipolar II disorder, cyclothymic disorder, Parkinson's disease; Huntington's disease; Fronto temperal Dementia; neurodegeneration associated with cerebral trauma; neurodegeneration associated with stroke; neurodegeneration associated with cerebral infarct; hypoglycemia-induced neurodegeneration; neurodegeneration associated with epileptic seizure; neurodegeneration associated with neurotoxin poisoning; multi-system atrophy, paranoid, disorganized, catatonic, undifferentiated or residual type; schizophreniform disorder; schizoaffective disorder of the delusional type or the depressive type; delusional disorder; substance-induced psychotic disorder, psychosis induced by alcohol, amphetamine, cannabis, cocaine, hallucinogens, obesity, inhalants, opioids, or phencyclidine; personality disorder of the paranoid type; and personality disorder of the schizoid type, which method comprises administering an amount of a compound of Formula (I) effective in treating said disorders. The invention thus also provides a compound of formula (I), for use in the treatment of the diseases mentioned in the previous sentence.

The invention also provides a method for the treatment of psychotic disorders, delusional disorders and drug induced psychosis; anxiety disorders, movement disorders, mood disorders, neurodegenerative disorders, obesity, and drug addiction which method comprises administering an amount of a compound of formula (I) effective in inhibiting PDE10A.

The invention also provides a method for the treatment of diseases of the retina, which method comprises administering an amount of a compound of formula (I) effective in inhibiting PDE10A. By "diseases of the retina," the applicants mean any condition of the retina which impairs the normal functioning of the retina, its surrounding tissues, or the eye. These include macular degeneration, myopic retinal degeneration, diabetic retinopathy, choroidal neovascularization, macular edema (also referred to as cystoid macular edema and macular swelling), epiretinal membrane (macular pucker), macular hole, retinitis (such as retinitis pigmentosa), macular dystrophies (such as Stargardt's juvenile macular degeneration, Best's vitelliform dystrophy, cone dystrophies, and pattern dystrophy of the retinal pigmented epithelium), retinal detachment, retinal trauma, retinal tumors and retinal diseases associated with them, congenital hypertrophy of the retinal pigmented epithelium, acute posterior multifocal placoid pigment epitheliopathy, acute retinal pigment epithelitis, and uveitis (including iritis, pars planitis, choroiditis, retinitis, and chorioretinitis).

According to a particular aspect, the invention relates to a compound of formula (I) or a composition comprising a compound of formula (I), for use in a method for the treatment of type I or type II diabetes, impaired glucose tolerance, impaired fasting glucose, metabolic syndrome, metabolism related disorders including excess of body weight or excess of body fat in obese patients, psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, pain, ophthalmic diseases such as macular degeneration/retinal degeneration, including wet Age Related Macular Degeneration (ARMD), dry ARMD, retinitis pigmentosa, choroidal neovascularization, vascular diseases/exudative diseases, retinopathy, including diabetic retinopathy, uveitis/retinitis/choroiditis, Stargard's disease, macular edema, retinal detachment, trauma, systemic disorders with associated retinal dystrophies, cone dystrophies, dystrophy of the retinal pigmented epithelium, myopic retinal degeneration, acute retinal pigment epithelitis, retinal tumors, retinal disease associated with tumors.

The invention further relates to a method for the treatment of type I or type II diabetes, impaired glucose tolerance, impaired fasting glucose, metabolic syndrome, metabolism related disorders including excess of body weight or excess of body fat in obese patients, psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, pain, ophthalmic diseases such as macular degeneration/retinal degeneration, including wet Age Related Macular Degeneration, dry ARMD, retinitis pigmentosa, choroidal neovascularization, vascular diseases/exudative diseases, retinopathy, including diabetic retinopathy, uveitis/retinitis/choroiditis, Stargard's disease, macular edema, retinal detachment, trauma, systemic disorders with associated retinal dystrophies, cone dystrophies, dystrophy of the retinal pigmented epithelium, myopic retinal degeneration, acute retinal pigment epithelitis, retinal tumors, retinal disease associated with tumors, which method comprises administering an amount of a compound of formula (I) effective in inhibiting PDE10A.

The invention further relates to a method for the treatment of type I or type II diabetes, impaired glucose tolerance, impaired fasting glucose, metabolic syndrome, metabolism related disorders including excess of body weight or excess of body fat in obese patients, psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, pain, ophthalmic diseases such as macular degeneration/retinal degeneration, including wet Age Related Macular Degeneration, dry ARMD, retinitis pigmentosa, choroidal neovascularization, vascular diseases/exudative diseases, retinopathy, including diabetic retinopathy, uveitis/retinitis/choroiditis, Stargard's disease, macular edema, retinal detachment, trauma, systemic disorders with associated retinal dystrophies, cone dystrophies, dystrophy of the retinal pigmented epithelium, myopic retinal degeneration, acute retinal pigment epithelitis, retinal tumors, retinal disease associated with tumors, which method comprises administering an amount of a compound of Formula (I) effective in treating said disorders.

The term "treating", as in "a method of treating a disorder", refers to reversing, alleviating, or inhibiting the progress of the disorder to which such term applies, or one or more symptoms of the disorder. As used herein, the term also encompasses, depending on the condition of the patient, preventing the disorder, including preventing onset of the disorder or of any symptoms associated therewith, as well as reducing the severity of the disorder or any of its symptoms prior to onset. "Treating" as used herein refers also to preventing a recurrence of a disorder.

The following examples illustrate the invention. However, it is to be understood that the invention is not limited to the details provided in these examples.

EXAMPLES

Example 1

Preparation of Compounds According to the Invention

General $^1$H-NMR and $^{13}$C-NMR spectra were recorded at ambient temperature with an Advance 300 (Bruker) spectrometer.

The compounds were analyzed by reverse phase high performance liquid chromatography (HPLC) using a Waters Autopurification System equipped with a Waters 2525 Pump, a Waters 2696 photodiode array detector. The Method A (10 min) was performed with an XTerra™ column (5 μm, C18, 4.5×50 mm, Model #186000482) and the Method B was performed with an XBridge™ column (5 μm, C18, 4.5×50 mm, Model #186003113). Solvent A was H$_2$O with 0.05% TFA and solvent B was CH$_3$CN with 0.05% TFA. The 10 min gradient run was realized using 1.0 mL min$^{-1}$ with 5% B in A (0.0-1.0 min), 5% to 100% B in A (1.0-7.0 min), 100% to 5% B in A (7.0-7.5 min), 5 B in A (7.5-10.0 min). The 5 min gradient run was realized using 1.0 mL min$^{-1}$ with 5% B in A (0.0-0.25 min), 5% to 100% B in A (0.25-3.0 min), 100% to 5% B in A (3.0-4.0 min), 5% B in A (4.0-5.0 min).

Melting points were measured with a Büchi B-545 melting point apparatus and were uncorrected. Microwave reactions were performed in a Biotage Initiator 60 EXP microwave reactor.

To isolate reaction products the solvent were removed by evaporation using a vacuum rotatory evaporator, unless otherwise indicated, the water bath temperature did not exceed 40° C.

Preparation of
4-benzyl-6,7-dimethoxy-1-methylisoquinolin-3-ol
hydrochloride 1

Methyl 2-(3,4-dimethoxyphenyl)acetate SLA 28134

To a solution of 2-(3,4-dimethoxyphenyl)acetic acid (25.0 g, 127.4 mmol) in MeOH (100 mL) in a 500 mL round-bottomed flask equipped with a magnetic stirrer was added a catalytic amount of sulfuric acid (around 10 drops) and the mixture was stirred overnight under reflux. After cooling to RT, MeOH was removed at 40° C. under vacuum and the product was taken up in CH$_2$Cl$_2$ (250 mL), washed with water (5×20 mL), brine (20 mL), dried over Na$_2$SO$_4$, filtered, and concentrated under vacuum to give methyl 2-(3,4-dimethoxyphenyl)acetate SLA 28134 as an orange oil (25.77 g, 96% yield).

SLA 28134

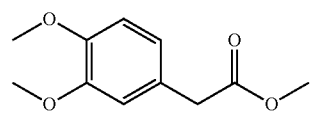

MW: 210.23; Yield: 96%; Orange oil.

R$_f$: 0.25 (cyclohexane:EtOAc=3:1).

$^1$H-NMR (CDCl$_3$, δ): 3.56 (s, 2H, CH$_2$), 3.70 (s, 3H, CH$_3$), 3.87 (s, 3H, OCH$_3$), 3.88 (s, 3H, OCH$_3$), 6.82-6.83 (m, 3H, 3×ArH).

$^{13}$C-NMR (CDCl$_3$, δ): 40.6, 51.9, 55.8 (2×C), 111.2, 112.4, 121.4, 126.4, 148.2, 148.9, 172.2.

MS-ESI m/z (% rel. Int.): 233.2 ([M+Na]$^+$, 3), 151.1 (100).

HPLC: Method B (10 min), XBridge™ column (5 μm, C18, 4.5×50 mm, Model #186003113), detection UV 254 nm, RT=4.78 min.

6,7-Dimethoxy-1-methylisoquinolin-3-ol CCH 18060

To a solution of methyl 2-(3,4-dimethoxyphenyl)acetate SLA 28134 (23.82 g, 113.30 mmol) in acetic anhydride (57 mL) at 0° C. in a 1 L round-bottomed flask equipped with a magnetic stirrer under N$_2$ was added perchloric acid (70% solution in water, 11.3 mL) over a period of 30 min. The reaction mixture was then allowed to warm up to RT, stirred for a further 45 min and diluted with Et$_2$O (450 mL). The solid was then filtered and washed several times with Et$_2$O (6×15 mL) to give after drying under vacuum a dark yellow solid (27.97 g, 74% yield).

To a suspension of the above solid (11.09 g, 34.58 mmol) in H$_2$O (60 mL) in a 500 mL 3-neck round-bottomed flask equipped with a dropping funnel and a magnetic stirrer in an ice bath was added dropwise conc. NH$_4$OH (90 mL) and the reaction mixture was stirred at RT for 1 h, after which the solid was filtered and washed with cold water (4×15 mL). After drying under high vacuum, 6,7-dimethoxy-1-methylisoquinolin-3-ol CCH 18060 was isolated as a yellow solid (7.53 g, 99% yield).

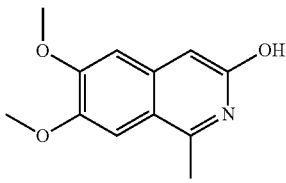 [SMILES: COc1cc2cc(O)nc(C)c2cc1OC]

MW: 219.24; Yield: 74%; Yellow solid; Mp (° C.): 283 (dec.).

R$_f$: 0.2 (cyclohexane:EtOAc=2:1).

$^1$H-NMR (DMSO d$_6$, δ): 2.68 (s, 3H, CH$_3$), 3.85 (s, 3H, OCH$_3$), 3.86 (s, 3H, OCH$_3$), 6.51 (s, 1H, ArH), 6.97 (s, 1H, ArH), 7.12 (s, 1H, ArH), 10.69 (broad s, 1H, OH).

$^{13}$C-NMR (DMSO d$_6$, δ): 20.3, 55.6, 55.7, 99.5, 103.6, 103.8, 116.2, 138.0, 147.1, 152.0, 153.3, 159.0.

MS-ESI m/z (rel. int.): 220 ([M+H]$^+$, 100).

HPLC: Method A (10 min), XTerra™ column (5 μm, C18, 4.5×50 mm, Model #186000482), detection UV 254 nm, RT=3.83 min.

4-Benzyl-6,7-dimethoxy-1-methylisoquinolin-3-ol hydrochloride 1

To a solution of 6,7-dimethoxy-1-methylisoquinolin-3-ol CCH 18060 (51 mg, 233 μmol) in toluene (1 mL) in a 2 mL microwave vial equipped with a magnetic stirrer was added a 2 N aq. KOH solution (0.12 mL, 0.24 mmol) at RT followed by benzyl bromide (30 mg, 251 μmol) and the mixture was stirred at 110° C. for 15 min under microwave irradiation. After cooling to RT, the mixture was diluted with H$_2$O (5 mL) before extraction with CH$_2$Cl$_2$ (20 mL). The organic phase was isolated and the aqueous phase was acidified with AcOH (5 drops) and then further extracted with CH$_2$Cl$_2$. The organic phase was combined, washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 95:5) gave, after evaporation and drying, 4-benzyl-6,7-dimethoxy-1-methylisoquinolin-3-ol. This free base was dissolved in MeOH (2 mL) in a 10 mL round-bottomed flask equipped with a magnetic stirrer before addition of a 0.2 M HCl solution in MeOH (1 mL). The reaction mixture was stirred for 5 min at RT and concentrated at 40° C. under vacuum to afford 4-benzyl-6,7-dimethoxy-1-methylisoquinolin-3-ol hydrochloride 1 as a pale brown solid (31 mg, 38% yield).

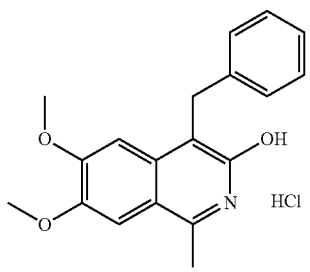

MW: 345.82; Yield: 38%; Pale brown solid; Mp (° C.): 189.1 (dec.).

R$_f$ (free base): 0.2 (CH$_2$Cl$_2$:MeOH=95:5).

$^1$H-NMR (CD$_3$OD, δ): 3.02 (s, 3H, CH$_3$), 3.95 (s, 3H, OCH$_3$), 3.98 (s, 3H, OCH$_3$), 4.46 (s, 2H, CH$_2$), 7.13-7.30 (m, 6H, 6×ArH), 7.42 (s, 1H, ArH).

$^{13}$C-NMR (CD$_3$OD, δ): 15.7, 29.7, 56.8, 56.9, 103.7, 105.8, 114.9, 120.0, 127.7, 129.3 (2×C), 129.8 (2×C), 139.8, 140.5, 150.4, 151.2, 151.8, 158.9.

MS-ESI m/z (rel.int.): 310 ([MH]$^+$, 100).

HPLC: Method A (10 min), XTerra™ column (5 μm, C18, 4.5×50 mm, Model #186000482), detection UV 254 nm, RT=4.74 min, peak area 98.9%.

Preparation of 4-(3,4-dimethoxybenzyl)-6,7-dimethoxy-1-methylisoquinolin-3-ol hydrochloride 2

To a solution of triphenylphosphine (950 mg, 3.62 mmol) in dry CH$_2$Cl$_2$ (15 mL) at 0° C. in a 50 mL round-bottomed flask equipped with a magnetic stirrer is added bromine (150 μL, 2.93 mmol) and the solution is stirred at 0° C. for 15 min, after which 3,4-dimethoxybenzyl alcohol (0.50 mL, 3.42 mmol) is added. The reaction mixture is stirred at RT for 2.5 h then concentrated under vacuum.

To a solution of the freshly prepared bromide in toluene (8 mL) in a 20 mL microwave vial equipped with a magnetic stirrer was added 6,7-dimethoxy-1-methylisoquinolin-3-ol CCH 18060 (495 mg, 2.26 mmol) at RT followed by a 2 N aq. KOH solution (1.70 mL, 3.40 mmol) and the mixture was stirred at 110° C. for 15 min under microwave irradiation. After cooling to RT, the mixture was diluted with H$_2$O (10 mL) before extraction with CH$_2$Cl$_2$ (50 mL). The organic phase was isolated and washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 95:4.5) gave 4-(3,4-dimethoxybenzyl)-6,7-dimethoxy-1-methylisoquinolin-3-ol as a yellow solid (286 mg, 34% yield). A portion of the free base (43 mg) was dissolved in MeOH (2 mL) in a 10 mL round-bottomed flask equipped with a magnetic stirrer before addition of a 0.15 M HCl solution in MeOH (2 mL). The reaction mixture was stirred for 5 min at RT and concentrated at 40° C. under vacuum. The solid was then washed with cold MeOH to afford, after drying, 4-(3,4-dimethoxybenzyl)-6,7-dimethoxy-1-methylisoquinolin-3-ol hydrochloride 2 as a yellow solid (22 mg, 47% yield).

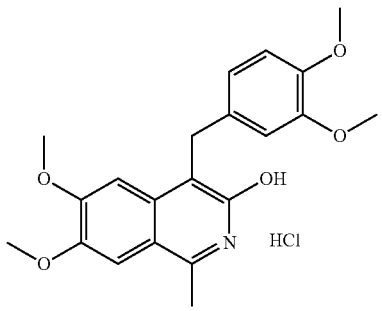

2

MW: 405.87; Yield: 16%; Yellow solid; Mp (° C.): 211.9 (dec.).

R$_f$ (free base): 0.2 (CH$_2$Cl$_2$:MeOH=95:4.5).

$^1$H-NMR (CD$_3$OD, δ): 3.01 (s, 3H, CH$_3$), 3.80 (s, 3H, OCH$_3$), 3.82 (s, 3H, OCH$_3$), 3.96 (s, 3H, OCH$_3$), 4.01 (s, 3H, OCH$_3$), 4.27 (s, 2H, CH$_2$), 6.74-6.81 (m, 3H, 3×ArH), 7.08 (s, 1H, ArH), 7.13 (s, 1H, ArH).

$^{13}$C-NMR (CD$_3$OD, δ): 17.2, 30.6, 56.2, 56.3, 56.6, 56.8, 102.9, 104.6, 112.1, 112.3, 114.8, 119.1, 120.7, 131.4, 140.1, 148.4, 149.8, 150.8, 150.9, 157.9, (1×C not observed).

MS-ESI m/z (rel.int.): 370 ([MH]$^+$, 100).

HPLC Method A (10 min), XTerra™ column (5 μm, C18, 4.5×50 mm, Model #186000482), detection UV 254 nm, RT=4.41 min, peak area 97.0%.

Preparation of 4-(3,4-dimethoxybenzyl)-3,6,7-trimethoxy-1-methylisoquinoline hydrochloride 3

A mixture of 4-(3,4-dimethoxybenzyl)-6,7-dimethoxy-1-methylisoquinolin-3-ol (compound 2 free base, 60 mg, 162 μmol), cesium carbonate (70 mg, 215 μmol) and iodomethane (13 μL, 208 μmol) in dry DMF (2 mL) in a 5 mL microwave vial equipped with a magnetic stirrer was stirred at 90° C. for 22 min under microwave irradiation. After cooling to RT, the mixture was diluted with Et$_2$O (50 mL) before washing with water (10 mL) then with brine (10 mL), drying over Na$_2$SO$_4$, filtration and concentration at 40° C. under vacuum. Purification by column chromatography (SiO$_2$, eluent cyclohexane:EtOAc=100:0 to 75:25) gave 4-(3,4-dimethoxybenzyl)-3,6,7-trimethoxy-1-methylisoquinoline as a colorless oil (33 mg). This free base was dissolved in MeOH (2 mL) in a 10 mL round-bottomed flask equipped with a magnetic stirrer before addition of a 0.15 M HCl solution in MeOH (1.5 mL). The reaction mixture was stirred for 5 min at RT and concentrated at 40° C. under vacuum. The solid was then washed with Et$_2$O to afford, after drying, 4-(3,4-dimethoxybenzyl)-3,6,7-trimethoxy-1-methylisoquinoline hydrochloride 3 as a pale brown solid (23 mg, 34% yield).

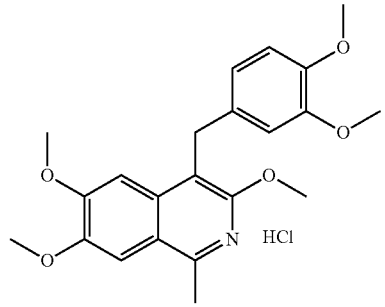

3

MW: 419.90; Yield: 34%; Yellow solid; Mp (° C.): 182.2 (dec.).

R$_f$ (free base): 0.2 (cyclohexane:EtOAc=75:25).

$^1$H-NMR (CD$_3$OD, δ): 2.94 (s, 3H, CH$_3$), 3.73 (s, 3H, OCH$_3$), 3.75 (s, 3H, OCH$_3$), 3.87 (s, 3H, OCH$_3$), 3.98 (s, 3H, OCH$_3$), 4.10 (s, 3H, OCH$_3$), 4.32 (s, 2H, CH$_2$), 6.69 (d, 1H, J=8.0 Hz, ArH), 6.80 (d, 1H, J=8.0 Hz, ArH), 6.87 (s, 1H, ArH), 7.21 (s, 1H, ArH), 7.39 (s, 1H, ArH).

$^{13}$C-NMR (CD$_3$OD, δ): 17.6, 30.9, 56.5, 56.6, 57.0, 57.2, 63.8, 104.6, 106.4, 113.2, 113.5, 120.9, 121.6, 121.7, 132.7, 140.0, 149.4, 150.8, 151.9, 152.5, 152.8, 159.1.

MS-ESI m/z (rel.int.): 384 ([MH]$^+$, 100).

HPLC: Method A (10 min), XTerra™ column (5 μm, C18, 4.5×50 mm, Model #186000482), detection UV 254 nm, RT=5.23 min, peak area 96.2%.

Preparation of 6,7-dimethoxy-1-methyl-4-(3-phenoxybenzyl)isoquinolin-3-ol hydrochloride 4

To a solution of 6,7-dimethoxy-1-methylisoquinolin-3-ol CCH 18060 (152 mg, 693 μmol) in toluene (15 mL) in a 20 mL microwave vial equipped with a magnetic stirrer was added a 2 N aq. KOH solution (0.38 mL, 0.76 mmol) at RT followed by 1-(bromomethyl)-3-phenoxybenzene (191 mg, 726 μmol) and the mixture was stirred at 130° C. for 45 min under microwave irradiation. After cooling to RT, the mixture was diluted with H$_2$O (10 mL) before extraction with EtOAc (50 mL). The organic phase was isolated and the aqueous phase was further extracted with CH$_2$Cl$_2$ (50 mL). Both organic phases were washed with brine (10 mL), combined, dried over Na$_2$SO$_4$, filtered and concentrated at 40° C. under vacuum. Purification by column chromatography (SiO$_2$, eluent CH$_2$Cl$_2$:MeOH=100:0 to 95:3) gave 28 mg of 6,7-dimethoxy-1-methyl-4-(3-phenoxybenzyl)isoquinolin-3-ol. This free base was dissolved in MeOH (2 mL) in a 10 mL round-bottomed flask equipped with a magnetic stirrer before addition of a 0.09 M HCl solution in MeOH (2 mL). The reaction mixture was stirred for 5 min at RT and concentrated at 40° C. under vacuum to afford 6,7-dimethoxy-1-methyl-4-(3-phenoxybenzyl)isoquinolin-3-ol hydrochloride 4 as a brown solid (31 mg, 10% yield).

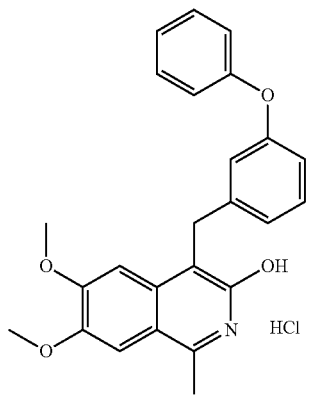

MW: 437.92; Yield: 10%; Brown solid; Mp (° C.): 95.1 (dec.).

$R_f$ (free base): 0.2 ($CH_2Cl_2$:MeOH=95:3).

$^1$H-NMR ($CD_3OD$, δ): 3.00 (s, 3H, $CH_3$), 3.85 (s, 3H, $OCH_3$), 4.01 (s, 3H, $OCH_3$), 4.44 (s, 2H, $CH_2$), 6.81-6.87 (m, 4H, 4×ArH), 6.99-7.12 (m, 3H, 3×ArH), 7.23-7.29 (m, 3H, 3×ArH), 7.43 (s, 1H, ArH).

$^{13}$C-NMR ($CD_3OD$, δ): 17.3, 31.1, 56.9, 57.0, 103.6, 105.9, 114.6, 118.0, 119.5, 119.9 (2×C), 120.0, 124.2, 124.5, 130.8 (2×C), 131.2, 140.5, 142.0, 150.6, 151.2, 151.9, 158.4, 159.0, 159.2.

MS-ESI m/z (rel.int.): 402 ([MH]$^+$, 100).

HPLC: Method A (10 min), XTerra™ column (5 μm, C18, 4.5×50 mm, Model #186000482), detection UV 254 nm, RT=5.78 min, peak area 97.7%.

Preparation of 6,7-dimethoxy-1-methyl-4-(4-phenoxybenzyl)isoquinolin-3-ol hydrochloride 5

To a solution of 6,7-dimethoxy-1-methylisoquinolin-3-ol CCH 18060 (152 mg, 693 μmol) in toluene (15 mL) in a 20 mL microwave vial equipped with a magnetic stirrer was added a 2 N aq. KOH solution (0.38 mL, 0.76 mmol) at RT followed by 1-(bromomethyl)-4-phenoxybenzene (191 mg, 726 μmol) and the mixture was stirred at 140° C. for 50 min under microwave irradiation then at 160° C. for 50 min under microwave irradiation. After cooling to RT, the mixture was diluted with $H_2O$ (10 mL) before extraction with EtOAc (50 mL). The organic phase was isolated and the aqueous phase was further extracted with $CH_2Cl_2$ (50 mL). Both organic phases were washed with brine (10 mL), combined, dried over $Na_2SO_4$, filtered and concentrated at 40° C. under vacuum. Purification by column chromatography ($SiO_2$, eluent $CH_2Cl_2$:MeOH=100:0 to 95:3) gave 43 mg of 6,7-dimethoxy-1-methyl-4-(4-phenoxybenzyl)isoquinolin-3-ol. This free base was dissolved in MeOH (2 mL) in a 10 mL round-bottomed flask equipped with a magnetic stirrer before addition of a 0.09 M HCl solution in MeOH (3 mL). The reaction mixture was stirred for 5 min at RT and concentrated at 40° C. under vacuum to afford 6,7-dimethoxy-1-methyl-4-(4-phenoxybenzyl)isoquinolin-3-ol hydrochloride 5 as a brown solid (47 mg, 15% yield).

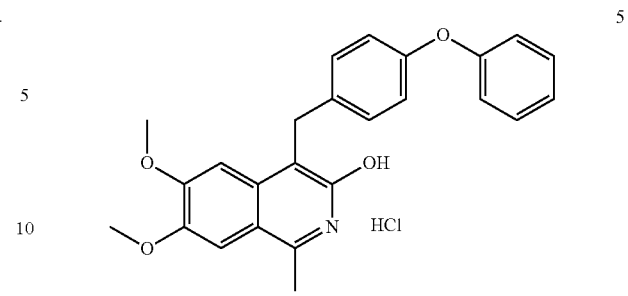

MW: 437.92; Yield: 15%; Brown solid; Mp (° C.): 98.0 (dec.).

$R_f$ (free base): 0.2 ($CH_2Cl_2$:MeOH=95:3).

$^1$H-NMR ($CD_3OD$, δ): 3.02 (s, 3H, $CH_3$), 3.90 (s, 3H, $OCH_3$), 4.00 (s, 3H, $OCH_3$), 4.44 (s, 2H, $CH_2$), 6.87-6.90 (m, 4H, 4×ArH), 7.03-7.08 (m, 1H, ArH), 7.18-7.28 (m, 5H, 5×ArH), 7.43-7.45 (m, 1H, ArH).

$^{13}$C-NMR ($CD_3OD$, δ): 17.3, 30.6, 56.8, 57.1, 103.7, 105.9, 115.0, 119.7 (2×C), 120.1 (2×C), 120.1, 124.4, 130.7 (2×C), 130.9 (2×C), 134.7, 140.5, 150.5, 151.1, 151.9, 157.5, 158.6, 159.0.

MS-ESI m/z (rel.int.): 402 ([MH]$^+$, 100).

HPLC: Method A (10 min), XTerra™ column (5 μm, C18, 4.5×50 mm, Model #186000482), detection UV 254 nm, RT=5.89 min, peak area 97.8%.

Preparation of 4-(dibenzo[b,d]furan-2-ylmethyl)-1-ethyl-6,7-dimethoxyisoquinolin-3-ol hydrochloride 6

Dibenzo[b,d]furan-2-ylmethanol CCH 34116

To a solution of dibenzo[b,d]furan-2-carbaldehyde (191 mg, 973 μmol) in THF (10 mL) in a 50 mL round-bottomed flask equipped with a magnetic stirrer was added $NaBH_4$ (37 mg, 0.978 mmol) and the mixture was stirred for 2 h at RT and quenched by adding 10 mL of a 1 N aq. HCl solution. The reaction mixture was stirred at RT for 20 min and extracted with $CH_2Cl_2$ (2×50 mL). The organic phase was washed with water (10 mL), brine (10 mL), dried over $Na_2SO_4$, filtered and concentrated at 40° C. under vacuum to afford dibenzo[b,d]furan-2-ylmethanol CCH 34116 as an off-white solid (192 mg, 100% yield).

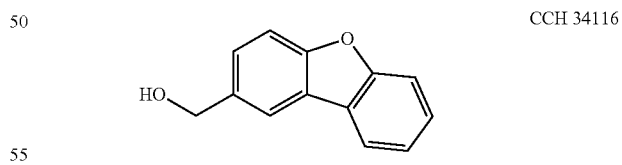

MW: 198.22; Yield: 100%; Off-white solid.

$R_f$: 0.45 (cyclohexane:EtOAc=1:1).

MS-ESI m/z (% rel. Int.): 181.1 ([M−OH]$^+$, 100).

HPLC: Method A (10 min), XTerra™ column (5 μm, C18, 4.5×50 mm, Model #186000482), detection UV 254 nm, RT=5.74 min.

2-(Chloromethyl)dibenzo[b,d]furan CCH 34116-2

Dibenzo[b,d]furan-2-ylmethanol CCH 34116 (174 mg, 878 μmol) was immediately dissolved in dry $CH_2Cl_2$ (10 mL) in a 20 mL microwave vial equipped with a magnetic stirrer before slow addition of SOCl$_2$ (1.0 mL, 13.78 mmol) and the reaction mixture was stirred for 20 min at 80° C. under microwave irradiation. After cooling to RT, the volatiles were removed at 40° C. under vacuum. The residue was taken up in CH$_2$Cl$_2$ (20 mL) before concentration back to dryness at 40° C. under vacuum (done 3 times) to give 2-(chloromethyl)dibenzo[b,d]furan CCH 34116-2 as a grey solid (189 mg, 99% yield).

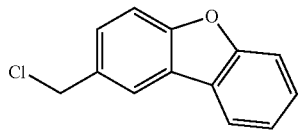

CCH 34116-2

MW: 216.66; Yield: 99%; Grey solid.

$^1$H-NMR (CDCl$_3$, δ): 4.76 (s, 2H, CH$_2$), 7.32-7.37 (m, 1H, ArH), 7.44-7.58 (m, 4H, 4×ArH), 7.92-7.97 (m, 2H, 2×ArH).

$^{13}$C-NMR (CDCl$_3$, δ): 46.6, 111.8, 111.9, 120.8, 121.0, 122.9, 123.8, 124.6, 127.5, 127.9, 132.2, 156.0, 156.7.

MS-ESI m/z (% rel. Int.): 181.1 ([M−Cl]$^+$, 100).

HPLC: Method A (10 min), XTerra™ column (5 μm, C18, 4.5×50 mm, Model #186000482), detection UV 254 nm, RT=6.61 min.

1-Ethyl-6,7-dimethoxyisoquinolin-3-ol SLA 28136

To a solution of methyl 2-(3,4-dimethoxyphenyl)acetate SLA 28134 (10.01 g, 47.6 mmol) in propionic anhydride (24.0 mL, 187.2 mmol) at 0° C. in a 500 mL round-bottomed flask equipped with a magnetic stirrer was added HClO$_4$ (ca. 70% solution in water, 4.89 mL, 56.6 mmol) over a period of 30 min. The reaction mixture was then allowed to warm up to RT, stirred for 45 min and diluted with Et$_2$O (450 mL). The solid was filtered and washed several times with Et$_2$O giving 10.5 g of a brown solid. To a suspension of this solid (9.98 g, 29.8 mmol) in H$_2$O (54 mL) in a 500 mL round-bottomed flask equipped with a magnetic stirrer and cooled in an ice bath was added dropwise concentrated NH$_4$OH (81 mL). After complete addition, the ice bath was removed and the reaction mixture was stirred at RT for 1 h, after which the solid was filtered and washed with plenty of water until neutral pH of the filtrate. The solid was dried under vacuum in presence of P$_2$O$_5$ to give 1-ethyl-6,7-dimethoxyisoquinolin-3-ol SLA 28136 as a yellow solid (5.30 g, 48% yield).

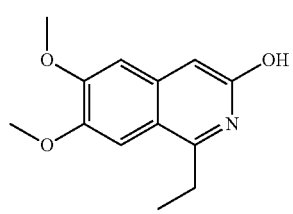

SLA 28136

MW: 233.26; Yield: 48%; Yellow solid; Mp (° C.): 219.7

$^1$H-NMR (CDCl$_3$:CD$_3$OD=1:1, δ): 1.42 (t, 3H, J=7.6 Hz, CH$_3$), 3.11 (q, 2H, J=7.6 Hz, CH$_2$), 3.97 (s, 3H, OCH$_3$), 3.99 (s, 3H, OCH$_3$), 6.56 (s, 1H, ArH), 6.74 (s, 1H, ArH), 6.92 (s, 1H, ArH).

$^{13}$C-NMR (CDCl$_3$:CD$_3$OD=1:1, δ): 17.6, 28.0, 59.5, 59.7, 105.6, 106.6, 108.8, 116.4, 146.7, 152.0, 154.7, 159.3, 165.0.

MS-ESI m/z (% rel. Int.): 234.1 ([MH]$^+$, 100).

HPLC: Method B (10 min), XBridge™ column (5 μm, C18, 4.5×50 mm, Model #186003113), detection UV 214 nm, RT=3.47 min.

4-(Dibenzo[b,d]furan-2-ylmethyl)-1-ethyl-6,7-dimethoxyisoquinolin-3-ol hydrochloride 6

To a solution of 1-ethyl-6,7-dimethoxyisoquinolin-3-ol SLA 28136 (50 mg, 214 μmol) in toluene (10 mL) in a 20 mL microwave vial equipped with a magnetic stirrer was added a 2 N aq. KOH solution (0.11 mL, 0.22 mmol) at RT followed by 2-(chloromethyl)dibenzo[b,d]furan CCH 34116-2 (47 mg, 217 μmol) and the mixture was stirred at 150° C. for 1.5 h under microwave irradiation. After cooling to RT, the mixture was diluted with a mixture CH$_2$Cl$_2$:MeOH=9:1 (50 mL), washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 96:4) gave 4-(dibenzo[b,d]furan-2-ylmethyl)-1-ethyl-6,7-dimethoxyisoquinolin-3-ol (10 mg, 11%). This free base was dissolved in MeOH (2 mL) in a 10 mL round-bottomed flask equipped with a magnetic stirrer before addition of a 0.2 M HCl solution in MeOH (0.25 mL). The reaction mixture was stirred for 5 min at RT and concentrated at 40° C. under vacuum to afford 4-(dibenzo[b,d]furan-2-ylmethyl)-1-ethyl-6,7-dimethoxyisoquinolin-3-ol hydrochloride 6 as a pale brown solid (11 mg, 11% yield).

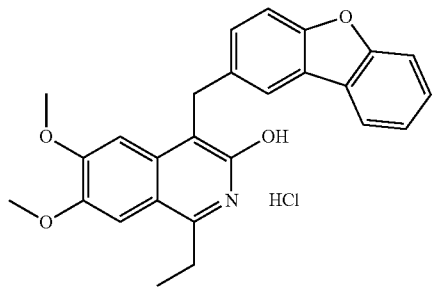

6

MW: 449.93; Yield: 11%; Pale brown solid; Mp (° C.): 225.6 (dec.).

R$_f$ (free base): 0.3 (CH$_2$Cl$_2$:MeOH=95:5).

$^1$H-NMR (CD$_3$OD, δ): 1.49 (t, 3H, J=7.5 Hz, CH$_2$CH$_3$), 3.33-3.43 (m, 2H, CH$_2$CH$_3$), 3.83 (s, 3H, OCH$_3$), 3.97 (s, 3H, OCH$_3$), 4.61 (s, 2H, CH$_2$), 7.23-7.53 (m, 7H, 7×ArH), 7.90-7.92 (m, 2H, 2×ArH).

$^{13}$C-NMR (CD$_3$OD, δ): 14.7, 25.3, 31.3, 56.8, 56.9, 103.8, 105.3, 112.6, 112.7, 115.2, 119.0, 121.2, 121.7, 124.0, 125.0, 125.8, 128.5, 128.6, 134.6, 141.3, 151.7, 152.0, 155.2, 156.3, 157.9, 159.0.

MS-ESI m/z (rel. int.): 414.3 ([M+H]$^+$, 100).

HPLC: Method A (10 min), XTerra™ column (5 μm, C18, 4.5×50 mm, Model #186000482), detection UV 254 nm, RT=6.14 min, peak area 95.0%.

Preparation of 4-(dibenzo[b,d]furan-2-ylmethyl)-6,
7-dimethoxy-1-propylisoquinolin-3-ol hydrochloride
7

6,7-Dimethoxy-1-propylisoquinolin-3-ol RBO
35142

To a solution of 3,4-dimethoxy-phenyl)-acetic acid methyl ester SLA 28134 (15.0 g, 71 mmol) in butyric anhydride (150 mL) in a round-bottomed flask equipped with a magnetic stirrer was added perchloric acid (10 mL) dropwise at 0° C. The mixture was stirred overnight at RT to obtain a black and viscous mixture that was diluted in Et$_2$O (600 mL). The precipitate formed was filtered, washed with Et$_2$O (3×150 mL) and dried under high vacuum to give a yellow solid (23.34 g). The solid was suspended in 300 mL of water and ammonia (25% aq. solution, 90 mL) was added dropwise at 0° C. The mixture was stirred at RT for 2 h, filtered and dried under high vacuum to obtain 6,7-dimethoxy-1-propylisoquinolin-3-ol RBO 35142 as yellow solid (14.12 g, 80% yield).

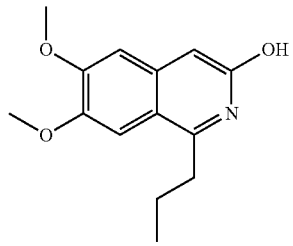

RBO 35142

MW: 247.30; Yield: 80%; Yellow solid; Mp (° C.): 227.2° C.

$^1$H-NMR (CDCl$_3$, δ): 1.01 (t, 3H J=9 Hz, CH$_3$), 1.89 (m, 2H, CH$_2$), 3.13 (t, 2H J=6 Hz, CH$_2$), 3.93 (s, 3H, OCH$_3$), 3.97 (s, 3H, OCH$_3$), 6.58 (s, 1H, ArH), 6.62 (s, 1H, ArH), 6.87 (s, 1H, ArH), OH not seen.

$^1$H-NMR (CDCl$_3$, δ): 13.8, 22.9, 32.7, 55.8, 56.2, 102.3, 102.7, 104.7, 112.7, 141.9, 148.3, 150.5, 154.7, 162.0.

MS-ESI m/z (rel.int.): 248 ([MH]$^+$, 100).

HPLC: Method A (10 min), XTerra™ column (5 µm, C18, 4.5×50 mm, Model #186000482), detection UV 254 nm, RT=3.56 min, peak area 99.9%.

4-(Dibenzo[b,d]furan-2-ylmethyl)-6,7-dimethoxy-1-
propylisoquinolin-3-ol hydrochloride 7

To a solution of 6,7-dimethoxy-1-propylisoquinolin-3-ol RBO 35142 (75 mg, 303 µmol) in toluene (10 mL) in a 20 mL microwave vial equipped with a magnetic stirrer was added a 2 N aq. KOH solution (0.15 mL, 0.30 mmol) at RT followed by 2-(chloromethyl)dibenzo[b,d]furan CCH 34116-2 (70 mg, 323 µmol) and the mixture was stirred at 150° C. for 1.5 h under microwave irradiation. After cooling to RT, the mixture was diluted with CH$_2$Cl$_2$:MeOH=9:1 (50 mL), washed with brine (10 mL), dried over Na$_2$SO$_4$, filtered, and concentrated at 40° C. under vacuum. Purification by column chromatography (SiO$_2$, eluent CH$_2$Cl$_2$:MeOH=100:0 to 96:4) gave, after evaporation and drying, 4-(dibenzo[b,d]furan-2-ylmethyl)-6,7-dimethoxy-1-propylisoquinolin-3-ol (11 mg, 8% yield). This free base was dissolved in MeOH (2 mL) in a 10 mL round-bottomed flask equipped with a magnetic stirrer before addition of a 0.20 M HCl solution in MeOH (0.25 mL). The reaction mixture was stirred for 5 min at RT and concentrated at 40° C. under vacuum to afford 4-(dibenzo[b,d]furan-2-ylmethyl)-6,7-dimethoxy-1-propylisoquinolin-3-ol hydrochloride 7 as a pale brown solid (11 mg, 8% yield).

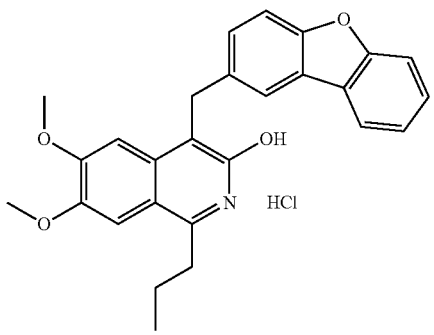

7

MW: 463.95; Yield: 8%; Pale brown solid; Mp (° C.): 212.7 (dec.)

R$_f$ (free base): 0.32 (CH$_2$Cl$_2$:MeOH=95.5:4.5).

$^1$H-NMR (CD$_3$OD, δ): 1.11 (t, 3H, J=7.4 Hz, CH$_2$CH$_3$), 1.93 (sextuplet, 2H, J=7.4 Hz, CH$_2$CH$_3$), 3.32-3.37 (m, 2H, CH$_2$CH$_2$), 3.83 (s, 3H, OCH$_3$), 3.96 (s, 3H, OCH$_3$), 4.60 (s, 2H, CH$_2$), 7.21 (s, 1H, ArH), 7.26-7.49 (m, 6H, 6×ArH), 7.89-7.91 (m, 2H, 2×ArH).

$^{13}$C-NMR (CD$_3$OD, δ): 14.2, 24.7, 31.3, 33.4, 56.8, 57.0, 103.8, 105.6, 112.5, 112.8, 115.4, 119.5, 121.2, 121.7, 124.0, 125.0, 125.8, 128.6 (2×C), 134.7, 141.1, 151.5, 151.9, 153.9, 156.3, 157.9, 159.0.

MS-ESI m/z (rel. int.): 428.3 ([M+H]$^+$, 100).

HPLC: Method A (10 min), XTerra™ column (5 µm, C18, 4.5×50 mm, Model #186000482), detection UV 254 nm, RT=6.38 min, peak area 96.9%.

Preparation of 4-([1,1'-biphenyl]-3-ylmethyl)-1-
ethyl-6,7-dimethoxyisoquinolin-3-ol hydrochloride
8

4-(3-Bromobenzyl)-1-ethyl-6,7-dimethoxyisoquino-
lin-3-ol SLA 28138

To a stirred solution of 1-ethyl-6,7-dimethoxyisoquinolin-3-ol SLA 28136 (1.00 g, 4.29 mmol) in toluene (15 mL) in a 20 mL microwave vial equipped with a magnetic stirrer was added 1-bromo-3-(bromomethyl)benzene (1.07 g, 4.29 mmol) at RT followed by a 2 N aq. LiOH solution (1.07 mL, 2.14 mmol) and the mixture was stirred at 150° C. for 1.5 h. After cooling to RT, the mixture was diluted with CH$_2$Cl$_2$:MeOH=9:1 (150 mL) and washed with brine (50 mL), dried over Na$_2$SO$_4$, filtered, and concentrated at 40° C. under vacuum. Purification by column chromatography (SiO$_2$, eluent CH$_2$Cl$_2$:MeOH=100:0 to 92:8) gave, after evaporation and drying, 4-(3-bromobenzyl)-1-ethyl-6,7-dimethoxyisoquinolin-3-ol SLA 28138 as a brown solid (0.403 mg, 23% yield).

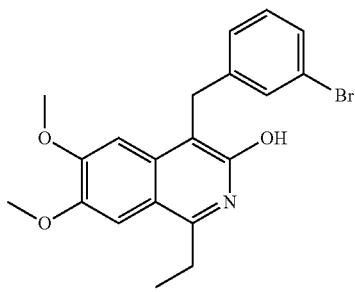

SLA 28138

MW: 402.28; Yield: 23%; Brown solid; Mp (° C.): 251.4
$^1$H-NMR (CDCl$_3$, δ): 1.41 (t, 3H, J=7.6 Hz, CH$_3$), 3.12 (q, 2H, J=7.6 Hz, CH$_2$), 3.90 (s, 3H, OCH$_3$), 3.93 (s, 3H, OCH$_3$), 4.28 (s, 2H, CH$_2$), 6.74 (s, 1H, ArH), 6.89 (s, 1H, ArH), 7.07-7.13 (m, 1H, ArH), 7.26-7.29 (m, 2H, 2×ArH), 7.53-7.54 (m, 1H, ArH).
$^{13}$C-NMR (CDCl$_3$, δ): 14.2, 24.6, 31.1, 55.8, 55.8, 100.2, 102.8, 112.4, 113.4, 122.4, 127.1, 128.9, 129.8, 131.6, 139.0, 144.0, 146.9, 150.0, 154.6, 160.9.

4-([1,1'-Biphenyl]-3-ylmethyl)-1-ethyl-6,7-dimethoxyisoquinolin-3-ol hydrochloride 8

To a stirred solution of 4-(3-bromobenzyl)-1-ethyl-6,7-dimethoxyisoquinolin-3-ol SLA 28138 (79 mg, 0.196 mmol) in EtOH (0.9 mL) in a 20 mL microwave vial equipped with a magnetic stirrer were added phenylboronic acid (48 mg, 0.393 mmol), Pd(PPh$_3$)$_2$Cl$_2$ (10.0 mg), a 2 N aq. Na$_2$CO$_3$ solution (0.30 mL, 0.60 mmol), H$_2$O (2.7 mL), dimethoxyethane (3.5 mL) and the resulting mixture was stirred at 140° C. for 25 min. After cooling to RT, the mixture was diluted with EtOAc (30 mL) and the organic solution was passed through a celite plug and washed with brine (10 mL). The celite plug was then further washed with CH$_2$Cl$_2$ (50 mL) and the organic layer was washed with brine (20 mL). The combined organic layers were dried over Na$_2$SO$_4$, filtered, and concentrated at 40° C. under vacuum. Purification by column chromatography (SiO$_2$, eluent CH$_2$Cl$_2$:MeOH=100:0 to 98:2) gave, after evaporation and drying, 4-([1,1'-biphenyl]-3-ylmethyl)-1-ethyl-6,7-dimethoxyisoquinolin-3-ol. This free base was dissolved in CH$_2$Cl$_2$ (2 mL) in a 10 mL round-bottomed flask before addition of a 0.49 M HCl solution in MeOH (3 mL). The reaction mixture was stirred for 5 min at RT and concentrated at 40° C. under vacuum to give 4-([1,1'-biphenyl]-3-ylmethyl)-1-ethyl-6,7-dimethoxyisoquinolin-3-ol hydrochloride 8 as a yellow solid (42 mg, 49% yield).

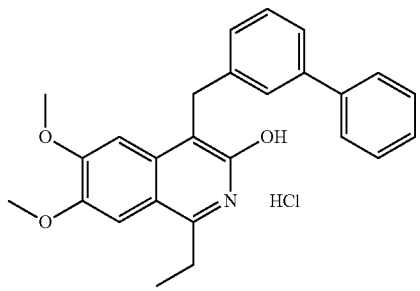

8

MW: 435.94; Yield: 49%; Yellow solid; Mp (° C.): 159.5
$^1$H-NMR (CD$_3$OD, δ): 1.47 (t, 3H, J=7.6 Hz, CH$_3$), 3.39 (q, 2H, J=7.6 Hz, CH$_2$), 3.84 (s, 3H, OCH$_3$), 3.99 (s, 3H, OCH$_3$), 4.53 (s, 2H, CH$_2$), 7.166 (d, 1H, J=7.5 Hz, ArH), 7.23 (s, 1H, ArH), 7.30-7.54 (m, 9H, 9×ArH).
$^{13}$C-NMR (CD$_3$OD, δ): 13.1, 23.8, 29.9, 55.3, 55.4, 102.4, 103.9, 113.5, 117.5, 124.9, 126.4, 126.5, 126.6, 126.6, 127.0, 128.4, 128.4, 128.8, 138.9, 139.7, 140.6, 141.6, 150.0, 150.5, 153.8, 157.5.
MS-ESI m/z (% rel. Int.): 400 ([MH]$^+$, 100).
HPLC: Method B (10 min), XBridge™ column (5 μm, C18, 4.5×50 mm, Model #186003113), detection UV 214 nm, RT=5.45 min, peak area 98.2%.

Preparation of 1-ethyl-6,7-dimethoxy-4-((4'-methoxy-[1,1'-biphenyl]-3-yl)methyl)isoquinolin-3-ol hydrochloride 9

To a stirred solution of 4-(3-bromobenzyl)-1-ethyl-6,7-dimethoxyisoquinolin-3-ol SLA 28138 (79 mg, 0.196 mmol) in EtOH (0.9 mL) in a 20 mL microwave vial equipped with a magnetic stirrer were added 4-methoxyphenylboronic acid (60 mg, 0.393 mmol), Pd(PPh$_3$)$_2$Cl$_2$ (10.0 mg), a 2 N aq. Na$_2$CO$_3$ solution (0.3 mL), H$_2$O (2.7 mL) and dimethoxyethane (3.5 mL) and the resulting mixture was stirred at 140° C. for 25 min. After cooling to RT, the mixture was diluted with EtOAc (30 mL) and the organic solution was passed through a celite plug, then washed with brine (10 mL). The celite plug was then further washed with CH$_2$Cl$_2$ (50 mL) and the organic layer was washed with brine (20 mL). The combined organic layers were dried over Na$_2$SO$_4$, filtered, and concentrated at 40° C. under vacuum. Purification by column chromatography (SiO$_2$, eluent CH$_2$Cl$_2$:MeOH=100:0 to 98:2) gave 1-ethyl-6,7-dimethoxy-4-((4'-methoxy-[1,1'-biphenyl]-3-yl)methyl)isoquinolin-3-ol. This free base was dissolved in CH$_2$Cl$_2$ (2 mL) in a 10 mL round-bottomed flask equipped with a magnetic stirrer before addition of a 0.49 M HCl solution in MeOH (3 mL). The reaction mixture was stirred for 5 min at RT and concentrated at 40° C. under vacuum to afford 1-ethyl-6,7-dimethoxy-4-((4'-methoxy-[1,1'-biphenyl]-3-yl)methyl)isoquinolin-3-ol hydrochloride 9 as a yellow solid (55 mg, 60% yield).

9

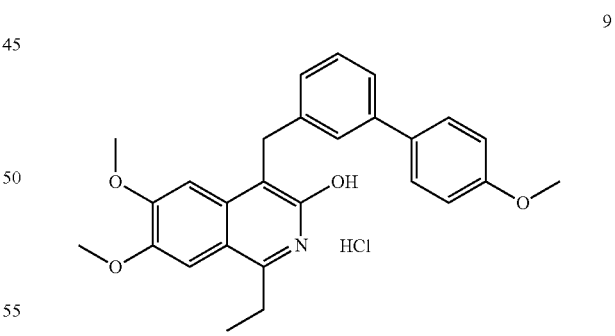

MW: 465.17; Yield: 60%; Yellow solid; Mp (° C.): 130.7
$^1$H-NMR (CD$_3$OD, δ): 1.44-1.47 (m, 3H, CH$_3$), 3.34-3.39 (m, 2H, CH$_2$), 3.78 (s, 3H, OCH$_3$), 3.82 (s, 3H, OCH$_3$), 3.98 (s, 3H, OCH$_3$), 4.50 (s, 2H, CH$_2$), 6.90-6.94 (m, 2H 2×ArH), 7.10-7.45 (m, 8H, 8×ArH).
$^{13}$C-NMR (CD$_3$OD, δ): 13.1, 23.8, 30.0, 54.2, 55.3, 55.5, 102.4, 103.9, 113.8 (2×C), 117.5, 124.4, 125.9, 126.1, 127.4, 128.8, 132.9, 138.9, 139.7, 141.2, 150.5, 159.3 (5×C not observed).
MS-ESI m/z (% rel. Int.): 430 ([MH]$^+$, 100).

HPLC: Method B (10 min), XBridge™ column (5 µm, C18, 4.5×50 mm, Model #186003113), detection UV 214 nm, RT=5.52 min, peak area 95.2%.

Preparation of 4-((3'-amino-[1,1'-biphenyl]-3-yl)methyl)-1-ethyl-6,7-dimethoxyisoquinolin-3-ol dihydrochloride 10

To a stirred solution of 4-(3-bromobenzyl)-1-ethyl-6,7-dimethoxyisoquinolin-3-ol SLA 28138 (79 mg, 0.196 mmol) in EtOH (0.9 mL) in a 20 mL microwave vial equipped with a magnetic stirrer were added di-tert-butyl 3-aminophenylboronate (49 mg, 0.393 mmol), Pd(PPh$_3$)$_2$Cl$_2$ (10.0 mg), a 2 N aq. Na$_2$CO$_3$ solution (0.3 mL), H$_2$O (2.7 mL) and dimethoxyethane (3.5 mL) and the resulting mixture was stirred at 140° C. for 25 min. After cooling to RT, the mixture was diluted with EtOAc (30 mL) and the organic solution was passed through a celite plug, then washed with brine (10 mL). The celite plug was then further washed with CH$_2$Cl$_2$ (50 mL) and the organic layer was washed with brine (20 mL). The combined organic layers were dried over Na$_2$SO$_4$, filtered, and concentrated at 40° C. under vacuum. Purification by column chromatography (SiO$_2$, eluent CH$_2$Cl$_2$:MeOH=100:0 to 98:2) gave 4-((3'-amino-[1,1'-biphenyl]-3-yl)methyl)-1-ethyl-6,7-dimethoxyisoquinolin-3-ol. This free base was dissolved in CH$_2$Cl$_2$ (2 mL) in a 10 mL round-bottomed flask equipped with a magnetic stirrer before addition of a 0.49 M HCl solution in MeOH (3 mL). The reaction mixture was stirred for 5 min at RT and concentrated at 40° C. under vacuum to afford 4-((3'-amino-[1,1'-biphenyl]-3-yl)methyl)-1-ethyl-6,7-dimethoxyisoquinolin-3-ol dihydrochloride 10 as a yellow solid (43 mg, 69% yield).

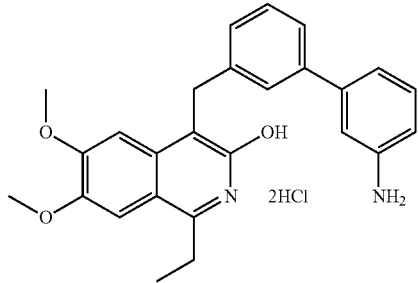

10

MW: 450.96; Yield: 49%; Yellow solid; Mp (° C.): 225.1
$^1$H-NMR (CD$_3$OD, δ): 1.46 (t, 3H, J=7.5 Hz, CH$_3$), 3.40 (q, 2H, J=7.5 Hz, CH$_2$), 3.81 (s, 3H, OCH$_3$), 3.99 (s, 3H, OCH$_3$), 4.57 (s, 2H, CH$_2$), 7.21-7.27 (m, 2H, 2×ArH), 7.37-7.44 (m, 2H, 2×ArH), 7.49-7.53 (m, 2H, 2×ArH), 7.57-7.62 (m, 3H, 3×ArH), 7.66 (d, 1H, J=7.0 Hz, ArH).
$^{13}$C-NMR (CD$_3$OD, δ): 14.6, 25.3, 31.4, 56.9, 57.1, 103.9, 105.5, 114.9, 119.1, 122.6, 123.0, 126.5, 128.1, 128.7, 129.2, 130.7, 131.8, 132.6, 141.0, 141.1, 141.2, 144.4, 151.5, 152.1, 155.4, 159.1.
MS-ESI m/z (% rel. Int.): 415 ([MH]$^+$, 100).
HPLC: Method B (10 min), XBridge™ column (5 µm, C18, 4.5×50 mm, Model #186003113), detection UV 214 nm, RT=3.97 min, peak area 97.3%.

Preparation of 6,7-dimethoxy-1-methyl-4-(pyridin-4-ylmethyl)isoquinolin-3-ol hydrochloride 11

To a solution of 6,7-dimethoxy-1-methylisoquinolin-3-ol CCH 18060 (197 mg, 899 µmol) in toluene (10 mL) in a 20 mL microwave vial equipped with a magnetic stirrer was added a 2 N aq. KOH solution (1.20 mL, 2.40 mmol) at RT followed by 4-(bromomethyl)pyridine hydrobromide (250 mg, 988 µmol) and the mixture was stirred at 110° C. for 15 min under microwave irradiation. After cooling to RT, the mixture was diluted with H$_2$O (5 mL) before extraction with CH$_2$Cl$_2$ (50 mL). The organic layer was washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 90:10) gave 70 mg of 6,7-dimethoxy-1-methyl-4-(pyridin-4-ylmethyl)isoquinolin-3-ol as a yellow solid. This free base was dissolved in MeOH (5 mL) in a 25 mL round-bottomed flask equipped with a magnetic stirrer before addition of a 0.15 M HCl solution in MeOH (7 mL). The reaction mixture was stirred for 5 min at RT and concentrated at 40° C. under vacuum to afford 6,7-dimethoxy-1-methyl-4-(pyridin-4-ylmethyl)isoquinolin-3-ol hydrochloride 11 as a yellow solid (78 mg, 25% yield).

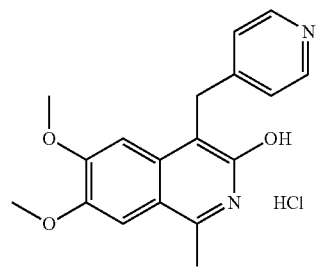

11

MW: 346.81; Yield: 25%; Yellow solid; Mp (° C.): 158.2 (dec.).
R$_f$ (free base): 0.2 (cyclohexane:EtOAc=75:25).
$^1$H-NMR (DMSO d$_6$, δ): 2.88 (s, 3H, CH$_3$), 3.89 (s, 3H, OCH$_3$), 3.91 (s, 3H, OCH$_3$), 4.75 (s, 2H, CH$_2$), 7.03 (s, 1H, ArH), 7.32 (s, 1H, ArH), 7.90 (d, 2H, J=6.4 Hz, 2×ArH), 8.77 (d, 2H, J=6.4 Hz, 2×ArH).
$^{13}$C-NMR (DMSO d$_6$, δ): 17.8, 30.5, 55.8, 56.2, 100.9, 105.0, 109.0, 116.2, 126.6 (2×C), 137.5, 140.9 (2×C), 148.0, 149.7, 154.1, 155.8, 161.2.
MS-ESI m/z (rel.int.): 311 ([MH]$^+$, 100).
HPLC Method A (10 min), XTerra™ column (5 µm, C18, 4.5×50 mm, Model #186000482), detection UV 254 nm, RT=3.60 min, peak area 99.3%.

Preparation of 6,7-dimethoxy-1-methyl-4-((6-phenylpyridin-2-yl)methyl)isoquinolin-3-ol dihydrochloride 12

4-((6-Bromopyridin-2-yl)methyl)-6,7-dimethoxy-1-methylisoquinolin-3-ol CCH 34150

To a solution of 2-bromo-6-(hydroxymethyl)pyridine (0.54 g, 2.87 mmol) in dry CH$_2$Cl$_2$ (10 mL) at 0° C. under N$_2$ in a 25 mL round-bottomed flask equipped with a magnetic stirrer was added dropwise SOCl$_2$ (4.2 mL, 57.90 mmol) and the mixture was stirred for 2 h at RT. The volatiles were then removed at 40° C. under vacuum and the residue was taken up in CHCl$_3$ (20 mL) before concentration back to dryness at 40° C. under vacuum (done twice) to give 2-bromo-6-(chloromethyl)pyridine hydrochloride CCH 34150-1 as a brown solid (0.65 g, 93% yield).

The solid CCH 34150-1 (300 mg, 1.23 mmol) was added to a mixture of 6,7-dimethoxy-1-methylisoquinolin-3-ol CCH 18060 (318 mg, 1.45 mmol) with a 2 N aq. KOH solution (0.72 mL, 1.44 mmol) and toluene (10 mL) in a 20 mL microwave vial equipped with a magnetic stirrer. This resulting mixture was stirred at 150° C. for 20 min under microwave irradiation. After cooling to RT, another portion of a 2 N aq. KOH solution (0.30 mL, 0.60 mmol) was added and the mixture was stirred at 150° C. for 1.5 h under microwave irradiation. After cooling to RT, the mixture was diluted with CH$_2$Cl$_2$:MeOH=9:1 (90 mL) and the resulting organic solution was washed with brine (15 mL), dried over Na$_2$SO$_4$, filtered and concentrated at 40° C. under vacuum. Purification by column chromatography (SiO$_2$, eluent CH$_2$Cl$_2$:MeOH=100:0 to 94:6) gave 4-((6-bromopyridin-2-yl)methyl)-6,7-dimethoxy-1-methylisoquinolin-3-ol CCH 34150 as a yellow solid (234 mg, 42% yield).

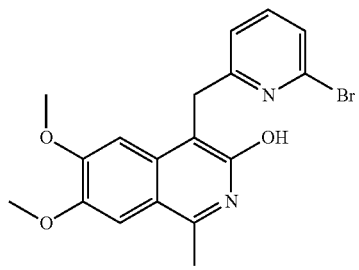

CCH 34150

MW: 389.24; Yield: 42%; Yellow solid.

R$_f$: 0.25 (CH$_2$Cl$_2$:MeOH=94:6).

$^1$H-NMR (CDCl$_3$, δ): 2.79 (s, 3H, CH$_3$), 3.93 (s, 3H, OCH$_3$), 4.04 (s, 3H, OCH$_3$), 4.47 (s, 2H, CH$_2$), 5.32 (broad s, 1H, OH), 6.81 (s, 1H, ArH), 7.17 (s, 1H, ArH), 7.26-7.41 (m, 3H, 3×ArH).

$^{13}$C-NMR (CDCl$_3$, δ): 17.1, 33.9, 55.8, 56.4, 101.1, 102.6, 112.8, 113.4, 122.1, 125.4, 139.2, 139.6, 140.5, 143.8, 147.3, 155.1, 160.1, 163.2.

MS-ESI m/z (rel.int.): 389 ([MH]$^+$, $^{79}$Br, 94), 391 ([MH]$^+$, $^{81}$Br, 100).

HPLC: Method A (10 min), XTerra™ column (5 µm, C18, 4.5×50 mm, Model #186000482), detection UV 254 nm, RT=4.34 min.

6,7-Dimethoxy-1-methyl-4-((6-phenylpyridin-2-yl)methyl)isoquinolin-3-ol dihydrochloride 12

To a stirred solution of 4-((6-bromopyridin-2-yl)methyl)-6,7-dimethoxy-1-methylisoquinolin-3-ol CCH 34150 (59 mg, 152 µmol) in absolute EtOH (0.9 mL) in a 20 mL microwave vial equipped with a magnetic stirrer were added phenylboronic acid (18 mg, 148 µmol), Pd(PPh$_3$)$_2$Cl$_2$ (10 mg, 14 µmol), a 2 N aq. Na$_2$CO$_3$ solution (0.30 mL, 0.60 mmol), H$_2$O (2.7 mL) and dimethoxyethane (3.5 mL) and the resulting mixture was stirred at 140° C. for 25 min. After cooling to RT, the mixture was diluted with EtOAc (30 mL) and the organic solution was filtered through a celite plug, then washed with brine (10 mL). The organic layer was isolated and the celite plug was then further washed with CH$_2$Cl$_2$ (50 mL) and the resulting organic layer was washed with brine (20 mL). The organic layers were combined, dried over Na$_2$SO$_4$, filtered, and concentrated at 40° C. under vacuum. Purification by column chromatography (SiO$_2$, eluent CH$_2$Cl$_2$:MeOH=100:0 to 94:6) provided 32 mg of 6,7-dimethoxy-1-methyl-4-((6-phenylpyridin-2-yl)methyl)isoquinolin-3-ol. This free base was dissolved in MeOH (2 mL) in a 10 mL round-bottomed flask equipped with a magnetic stirrer before addition of a 0.49 M HCl solution in MeOH (0.5 mL). The reaction mixture was stirred for 5 min at RT then concentrated at 40° C. under vacuum to afford 6,7-dimethoxy-1-methyl-4-((6-phenylpyridin-2-yl)methyl)isoquinolin-3-ol dihydrochloride 12 as a pale brown solid (38 mg, 56% yield).

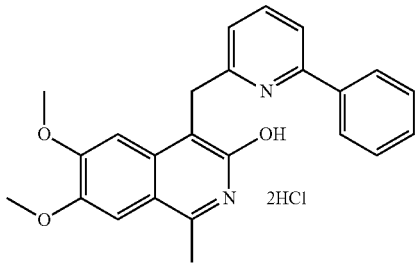

12

MW: 459.36; Yield: 56%; Pale brown solid; Mp (° C.): 208.4 (dec.).

R$_f$ (free base): 0.2 (CH$_2$Cl$_2$:MeOH=95:5).

$^1$H-NMR (CD$_3$OD, δ): 3.11 (s, 3H, CH$_3$), 4.04 (s, 3H, OCH$_3$), 4.07 (s, 3H, OCH$_3$), 5.12 (s, 2H, CH$_2$), 7.33 (s, 1H, ArH), 7.41 (d, 1H, J=7.8 Hz, ArH), 7.57 (s, 1H, ArH), 7.72-7.76 (m, 3H, 3×ArH), 8.09-8.12 (m, 2H, 2×ArH), 8.22 (d, 1H, J=8.0 Hz, ArH), 8.45 (dd, 1H, J=8.0 Hz, ArH).

$^{13}$C-NMR (CD$_3$OD, δ): 17.7, 30.1, 57.0, 57.8, 102.7, 106.4, 109.3, 120.0, 125.2, 125.6, 129.9 (2×C), 130.8 (2×C), 132.6, 133.5, 140.7, 148.3, 152.1, 152.2, 152.3, 155.0, 155.8, 160.2.

MS-ESI m/z (rel.int.): 387 ([MH]$^+$, 100).

HPLC: Method B (10 min), XBridge™ column (5 µm, C18, 4.5×50 mm, Model #186003113), detection UV 254 nm, RT=3.97 min, peak area 98.7%.

Preparation of 6,7-dimethoxy-4-((6-(4-methoxyphenyl)pyridin-2-yl)methyl)-1-methylisoquinolin-3-ol dihydrochloride 13

To a stirred solution of 4-((6-bromopyridin-2-yl)methyl)-6,7-dimethoxy-1-methylisoquinolin-3-ol CCH 34150 (59 mg, 152 µmol) in EtOH (0.9 mL) in a 20 mL microwave vial equipped with a magnetic stirrer were added 4-methoxyphenylboronic acid (23 mg, 151 µmol), Pd(PPh$_3$)$_2$Cl$_2$ (10 mg, 14 µmol), a 2 N aq. Na$_2$CO$_3$ solution (0.30 mL, 0.60 mmol), H$_2$O (2.7 mL) and dimethoxyethane (3.5 mL) and the resulting mixture was stirred at 140° C. for 25 min. After cooling to RT, the mixture was diluted with EtOAc (30 mL) and the solution was filtered through a celite plug, then washed with brine (10 mL). The organic phase was isolated and the celite plug was then further washed with CH$_2$Cl$_2$ (50 mL) and the resulting organic layer was washed with brine (20 mL). The organic layers were then combined, dried over Na$_2$SO$_4$, filtered, and concentrated at 40° C. under vacuum. Purification by column chromatography (SiO$_2$, eluent CH$_2$Cl$_2$:MeOH=100:0 to 94:6) provided 39 mg of 6,7-dimethoxy-4-((6-(4-methoxyphenyl)pyridin-2-yl)methyl)-1-methylisoquinolin-3-ol. This free base was dissolved in MeOH (2 mL) in a 10 mL round-bottomed flask equipped with a magnetic stirrer before addition of a 0.49 M HCl solution in MeOH (1.0 mL). The reaction mixture was stirred for 5 min at RT then concentrated at 40° C. under vacuum to afford 6,7-dimethoxy-4-((6-(4-methoxyphenyl)pyridin-2-yl)methyl)-1-methylisoquinolin-3-ol dihydrochloride 13 as a brown solid (45 mg, 61% yield).

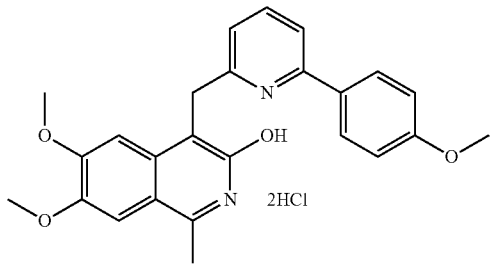

MW: 489.39; Yield: 61%; Brown solid; Mp (° C.): 190.3 (dec.).

$R_f$ (free base): 0.2 ($CH_2Cl_2$:MeOH=94:6).

$^1$H-NMR ($CD_3OD$, δ): 3.07 (s, 3H, $CH_3$), 3.96 (s, 3H, $OCH_3$), 4.05 (s, 6H, 2×$OCH_3$), 5.02 (s, 2H, $CH_2$), 7.23-7.36 (m, 4H, 4×ArH), 7.52 (s, 1H, ArH), 8.06-8.17 (m, 3H, 3×ArH), 8.33-8.39 (m, 1H, ArH).

$^{13}$C-NMR ($CD_3OD$, δ): 17.5, 30.1, 56.3, 56.9, 57.6, 102.4, 106.2, 109.5, 116.3 (2×C), 119.5, 124.0, 124.4, 124.7, 131.5 (2×C), 140.7, 147.8, 151.6, 151.9, 154.8, 155.5, 160.0, 164.9 (1×C not observed).

MS-ESI m/z (rel.int.): 417 ($[MH]^+$, 100).

HPLC: Method B (10 min), XBridge™ column (5 µm, C18, 4.5×50 mm, Model #186003113), detection UV 254 nm, RT=4.06 min, peak area 98.7%.

Preparation of 4-([2,4'-bipyridin]-6-ylmethyl)-6,7-dimethoxy-1-methylisoquinolin-3-ol trihydrochloride 14

To a stirred solution of 4-((6-bromopyridin-2-yl)methyl)-6,7-dimethoxy-1-methylisoquinolin-3-ol CCH 34150 (53 mg, 136 µmol) in EtOH (0.9 mL) in a 20 mL microwave vial equipped with a magnetic stirrer were added 4-pyridinylboronic acid (17 mg, 138 µmol), $Pd(PPh_3)_2Cl_2$ (10 mg, 14 µmol), a 2 N aq. $Na_2CO_3$ solution (0.30 mL, 0.60 mmol), $H_2O$ (2.7 mL) and dimethoxyethane (3.5 mL) and the resulting mixture was stirred at 140° C. for 25 min. After cooling to RT, the mixture was diluted with EtOAc (30 mL) and the solution was filtered through a celite plug, then washed with brine (10 mL). The organic layer was isolated and the celite plug was then further washed with $CH_2Cl_2$ (50 mL) and the organic layer was washed with brine (20 mL). The organic layers were then combined, dried over $Na_2SO_4$, filtered, and concentrated at 40° C. under vacuum. Purification by column chromatography ($SiO_2$, eluent $CH_2Cl_2$:MeOH=100:0 to 92:8) provided 16 mg of 4-(2,4'-bipyridin-6-ylmethyl)-6,7-dimethoxy-1-methylisoquinolin-3-ol. This free base was dissolved in MeOH (2 mL) in a 10 mL round-bottomed flask equipped with a magnetic stirrer before addition of a 0.49 M HCl solution in MeOH (0.5 mL). The reaction mixture was stirred for 5 min at RT then concentrated at 40° C. under vacuum to afford 4-(2,4'-bipyridin-6-ylmethyl)-6,7-dimethoxy-1-methylisoquinolin-3-ol trihydrochloride trihydrochloride 14 as a pale brown solid (20 mg, 30% yield).

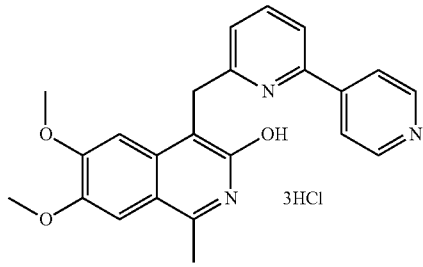

MW: 496.81; Yield: 30%; Pale brown solid; Mp (° C.)>250 (dec.).

$R_f$ (free base): 0.25 ($CH_2Cl_2$:MeOH=92:8).

$^1$H-NMR ($CD_3OD$, δ): 3.05 (s, 3H, $CH_3$), 3.92 (s, 3H, $OCH_3$), 4.00 (s, 3H, $OCH_3$), 4.80 (s, 2H, $CH_2$), 7.38 (s, 1H, ArH), 7.47 (s, 1H, ArH), 7.71 (d, 1H, J=7.8 Hz, ArH), 8.05 (dd, 1H, J=7.8 Hz, ArH), 8.23 (d, 1H, J=7.8 Hz, ArH), 8.68 (d, 2H, J=5.4 Hz, 2×ArH), 8.94 (d, 2H, J=5.4 Hz, 2×ArH).

$^{13}$C-NMR ($CD_3OD$, δ): 17.4, 34.1, 56.9, 57.2, 103.4, 106.0, 113.7, 120.1, 122.7, 125.3 (2×C), 127.2, 140.6, 140.7, 143.3 (2×C), 150.8, 151.3, 151.6, 152.0, 156.6, 159.3, 161.3.

MS-ESI m/z (rel.int.): 388 ($[MH]^+$, 100).

HPLC: Method B (10 min), XBridge™ column (5 µm, C18, 4.5×50 mm, Model #186003113), detection UV 254 nm, RT=3.31 min, peak area 98.1%.

Preparation of 6,7-dimethoxy-1-methyl-4-((5-phenylpyridin-3-yl)methylisoquinolin-3-ol dihydrochloride 15

4-((5-Bromopyridin-3-yl)methyl)-6,7-dimethoxy-1-methylisoquinolin-3-ol CCH 34166

To a mixture of 6,7-dimethoxy-1-methylisoquinolin-3-ol CCH 18060 (318 mg, 1.45 mmol) and 3-bromo-5-(chloromethyl)pyridine hydrochloride (352 mg, 1.45 mmol) in toluene (10 mL) in a 20 mL microwave vial equipped with a magnetic stirrer was added 2 N aq. KOH (1.42 mL, 2.84 mmol) and the mixture was stirred at 150° C. for 1.5 h under microwave irradiation. After cooling to RT, the mixture was diluted with $CH_2Cl_2$:MeOH=9:1 (90 mL) and the organic solution was washed with brine (15 mL), dried over $Na_2SO_4$, filtered and concentrated at 40° C. under vacuum. Purification by column chromatography ($SiO_2$, eluent $CH_2Cl_2$: 7N $NH_3$ in MeOH=100:0 to 95:5) gave, after evaporation and drying, 4-((5-bromopyridin-3-yl)methyl)-6,7-dimethoxy-1-methylisoquinolin-3-ol CCH 34166 as a yellow solid (189 mg, 33% yield).

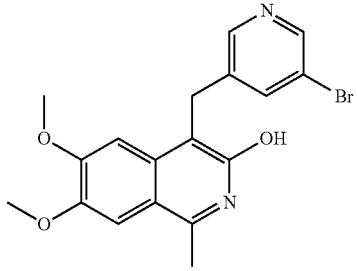

MW: 389.24; Yield: 33%; Yellow solid.

$R_f$: 0.2 ($CH_2Cl_2$: 7N $NH_3$ in MeOH=95:5).

$^1$H-NMR ($CDCl_3$, δ): 2.80 (s, 3H, $CH_3$), 3.94 (s, 6H, 2×$OCH_3$), 4.27 (s, 2H, $CH_2$), 6.72 (s, 1H, ArH), 6.86 (s, 1H, ArH), 7.82 (s, 1H, ArH), 8.46 (s, 1H, ArH), 8.59 (s, 1H, ArH), OH not seen.

$^{13}$C-NMR (CDCl$_3$, δ): 17.2, 28.3, 55.9, 55.9, 99.4, 103.3, 112.0, 113.4, 120.8, 138.6, 138.7, 138.8, 144.9, 147.0, 148.0, 148.4, 155.2, 160.8.

MS-ESI m/z (rel.int.): 389 ([MH]$^+$, $^{79}$Br, 94), 391 ([MH]$^+$, $^{81}$Br, 100).

HPLC: Method B (10 min), XBridge™ column (5 μm, C18, 4.5×50 mm, Model #186003113), detection UV 254 nm, RT=3.77 min.

6,7-Dimethoxy-1-methyl-4-((5-phenylpyridin-3-yl)methyl)isoquinolin-3-ol dihydrochloride 15

To a stirred solution of 4-((5-bromopyridin-3-yl)methyl)-6,7-dimethoxy-1-methylisoquinolin-3-ol CCH 34166 (66 mg, 170 μmol) in absolute EtOH (0.9 mL) in a 20 mL microwave vial equipped with a magnetic stirrer were added phenylboronic acid (20 mg, 164 μmol), Pd(PPh$_3$)$_2$Cl$_2$ (10 mg, 14 μmol), a 2 N aq. Na$_2$CO$_3$ solution (0.30 mL, 0.60 mmol), H$_2$O (2.7 mL) and dimethoxyethane (3.5 mL) and the resulting mixture was stirred at 140° C. for 25 min. After cooling to RT, the mixture was diluted with EtOAc (30 mL) and the solution was filtered through a celite plug, then washed with brine (10 mL). The organic layer was isolated and the celite plug was then further washed with CH$_2$Cl$_2$ (50 mL) and the organic layer was washed with brine (20 mL). The combined organic layers were dried over Na$_2$SO$_4$, filtered, and concentrated at 40° C. under vacuum. Purification by column chromatography (SiO$_2$, eluent CH$_2$Cl$_2$:MeOH=100:0 to 92:8) provided 60 mg of 6,7-dimethoxy-1-methyl-4-((5-phenylpyridin-3-yl)methyl)isoquinolin-3-ol. This free base was dissolved in MeOH (2 mL) in a 10 mL round-bottomed flask equipped with a magnetic stirrer before addition of a 0.49 M HCl solution in MeOH (1.0 mL). The reaction mixture was stirred for 5 min at RT and concentrated at 40° C. under vacuum to give 6,7-dimethoxy-1-methyl-4-((5-phenylpyridin-3-yl)methyl)isoquinolin-3-ol dihydrochloride 15 as a pale brown solid (71 mg, 91% yield).

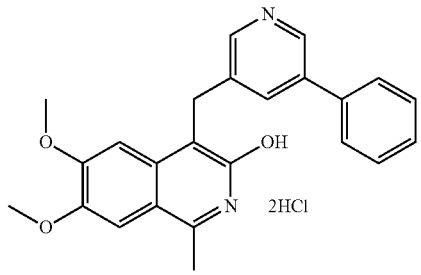

15

MW: 459.36; Yield: 91%; Pale brown solid; Mp (° C.): 89.0

R$_f$ (free base): 0.15 (CH$_2$Cl$_2$:MeOH=93:7).

$^1$H-NMR (CD$_3$OD, δ): 3.08 (s, 3H, CH$_3$), 4.01 (s, 3H, OCH$_3$), 4.04 (s, 3H, OCH$_3$), 4.86 (s, 2H, CH$_2$), 7.24 (s, 1H, ArH), 7.53-7.58 (m, 4H, 4×ArH), 7.80-7.82 (m, 2H, 2×ArH), 8.64 (s, 1H, ArH), 8.87 (s, 1H, ArH), 9.08 (s, 1H, ArH).

$^{13}$C-NMR (CD$_3$OD, δ): 17.6, 28.6, 56.9, 57.4, 102.4, 106.2, 111.6, 119.3, 128.5 (2×C), 130.7 (2×C), 131.4, 134.6, 139.0, 139.9, 140.1, 141.4, 141.5, 145.0, 151.1, 151.4, 152.7, 159.3.

MS-ESI m/z (rel.int.): 387 ([MH]$^+$, 100).

HPLC: Method B (10 min), XBridge™ column (5 μm, C18, 4.5×50 mm, Model #186003113), detection UV 254 nm, RT=3.68 min, peak area 98.5%.

Preparation of 6,7-dimethoxy-4-((5-(4-methoxyphenyl)pyridin-3-yl)methyl)-1-methylisoquinolin-3-ol dihydrochloride 16

To a stirred solution of 4-((5-bromopyridin-3-yl)methyl)-6,7-dimethoxy-1-methylisoquinolin-3-ol CCH 34166 (53 mg, 136 μmol) in absolute EtOH (0.9 mL) in a 20 mL microwave vial equipped with a magnetic stirrer were added 4-methoxyphenylboronic acid (41 mg, 270 μmol), Pd(PPh$_3$)$_2$Cl$_2$ (10 mg, 14 μmol), a 2 N aq. Na$_2$CO$_3$ solution (0.30 mL, 0.60 mmol), H$_2$O (2.7 mL) and dimethoxyethane (3.5 mL) and the resulting mixture was stirred at 140° C. for 25 min. After cooling to RT, the mixture was diluted with EtOAc (30 mL) and this solution was filtered through a celite plug, then washed with brine (10 mL). The organic phase was isolated and the celite plug was then further washed with CH$_2$Cl$_2$ (50 mL) and the organic layer was washed with brine (20 mL). The organic layers were then combined, dried over Na$_2$SO$_4$, filtered, and concentrated at 40° C. under vacuum. Purification by column chromatography (SiO$_2$, eluent CH$_2$Cl$_2$:MeOH=100:0 to 94:6) provided 32 mg of 6,7-dimethoxy-4-((5-(4-methoxyphenyl)pyridin-3-yl)methyl)-1-methylisoquinolin-3-ol. This free base was dissolved in MeOH (2 mL) in a 10 mL round-bottomed flask equipped with a magnetic stirrer before addition of a 0.49 M HCl solution in MeOH (0.5 mL). The reaction mixture was stirred for 5 min at RT and concentrated at 40° C. under vacuum to give 6,7-dimethoxy-4-((5-(4-methoxyphenyl)pyridin-3-yl)methyl)-1-methylisoquinolin-3-ol dihydrochloride 16 as a pale brown solid (37 mg, 56% yield).

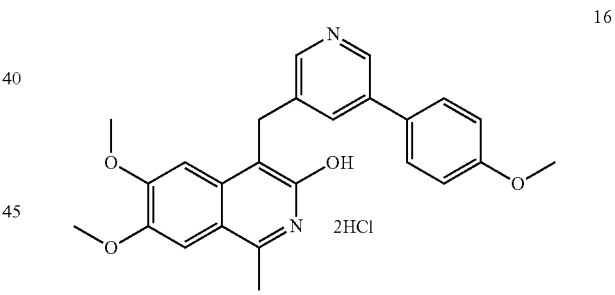

16

MW: 489.39; Yield: 56%; Pale brown solid; Mp (° C.): 195.0 (dec.)

R$_f$ (free base): 0.2 (CH$_2$Cl$_2$:MeOH=94:6).

$^1$H-NMR (CD$_3$OD, δ): 3.04 (s, 3H, CH$_3$), 3.87 (s, 3H, OCH$_3$), 4.00 (s, 3H, OCH$_3$), 4.03 (s, 3H, OCH$_3$), 4.79 (s, 2H, CH$_2$), 7.13-7.19 (m, 3H, 3×ArH), 7.48 (s, 1H, ArH), 7.75 (d, 2H, J=7.3 Hz, 2×ArH), 8.55 (s, 1H, ArH), 8.80 (s, 1H, ArH), 9.01 (s, 1H, ArH).

$^{13}$C-NMR (CD$_3$OD, δ): 17.5, 28.5, 56.0, 56.8, 57.4, 102.2, 106.0, 111.8, 116.1 (2×C), 119.3, 126.4, 129.7 (2×C), 138.2, 138.8, 140.2, 141.3, 141.5, 144.0, 150.8, 151.5, 152.8, 159.4, 162.9.

MS-ESI m/z (rel.int.): 417 ([MH]$^+$, 100).

HPLC: Method B (10 min), XBridge™ column (5 μm, C18, 4.5×50 mm, Model #186003113), detection UV 254 nm, RT=3.73 min, peak area 97.7%.

Preparation of 6,7-dimethoxy-1-methyl-4-(naphthalen-2-ylmethyl)isoquinolin-3-ol hydrochloride 17

To a solution of 6,7-dimethoxy-1-methylisoquinolin-3-ol CCH 18060 (232 mg, 1.06 mmol) in toluene (4.5 mL) in a 10 mL microwave vial equipped with a magnetic stirrer was added a 2 N aq. KOH solution (0.55 mL, 1.10 mmol) at RT followed by 2-(bromomethyl)naphthalene (252 mg, 1.14 mmol) and the mixture was stirred at 110° C. for 15 min under microwave irradiation. After cooling to RT, the mixture was diluted with $H_2O$ (5 mL) before extraction with $CH_2Cl_2$ (50 mL). The organic layer was washed with brine (10 mL), dried over $Na_2SO_4$, filtered and concentrated at 40° C. under vacuum. Purification by column chromatography ($SiO_2$, eluent $CH_2Cl_2$:MeOH=100:0 to 95:5) gave 210 mg of 6,7-dimethoxy-1-methyl-4-(naphthalen-2-ylmethyl)isoquinolin-3-ol as a yellow solid. The free base was dissolved in MeOH (10 mL) in a 25 mL round-bottomed flask equipped with a magnetic stirrer before addition of a 0.15 M HCl solution in MeOH (8 mL). The reaction mixture was stirred for 5 min at RT and concentrated at 40° C. under vacuum to afford after drying 6,7-dimethoxy-1-methyl-4-(naphthalen-2-ylmethyl)isoquinolin-3-ol hydrochloride 17 as a yellow solid (230 mg, 55% yield).

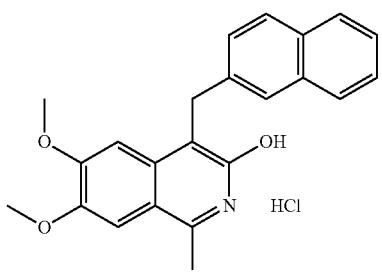

MW: 395.88; Yield: 55%; Yellow solid; Mp (° C.): 171.6 (dec.).

$R_f$ (free base): 0.3 ($CH_2Cl_2$:MeOH=95:5).

$^1$H-NMR (DMSO $d_6$, exchang. with $CD_3OD$, δ): 2.99 (s, 3H, $CH_3$), 3.86 (s, 3H, $OCH_3$), 3.93 (s, 3H, $OCH_3$), 4.66 (s, 2H, $CH_2$), 7.28 (s, 1H, ArH), 7.41-7.47 (m, 4H, 4×ArH), 7.76-7.83 (m, 4H, 4×ArH).

$^{13}$C-NMR (DMSO $d_6$, δ): 17.2, 30.0, 56.0, 56.2, 102.1, 105.1, 113.3, 117.6, 125.4, 126.1, 126.2, 127.1, 127.2, 127.4, 127.9, 131.6, 132.9, 137.2, 137.9, 148.9, 149.3, 151.0, 156.0.

MS-ESI m/z (rel.int.): 360 ([MH]$^+$, 100).

HPLC: Method A (10 min), XTerra™ column (5 μm, C18, 4.5×50 mm, Model #186000482), detection UV 254 nm, RT=5.30 min, peak area 99.6%.

Preparation of 3,6,7-trimethoxy-1-methyl-4-(naphthalen-2-ylmethyl)isoquinoline hydrochloride 18

To a solution of 6,7-dimethoxy-1-methyl-4-(naphthalen-2-ylmethyl)isoquinolin-3-ol CCH 29038 free base (58 mg, 161 μmol) in dry DMF (6 mL) at 0° C. in a 25 mL round-bottomed flask equipped with a magnetic stirrer was added LiHMDS (1.0 N in TBME, 175 μL, 175 μmol) and the mixture was stirred for 20 min at RT. Dimethyl sulphate (18 μL, 192 μmol) was then added at 0° C. and the mixture was stirred overnight at RT. The mixture was then concentrated to dryness at 40° C. under vacuum and the residue was taken up in $CH_2Cl_2$ (40 mL). The organic solution was washed with brine (10 mL), dried over $Na_2SO_4$, filtered and concentrated at 40° C. under vacuum. Purification by column chromatography ($SiO_2$, eluent cyclohexane:EtOAc=100:0 to 86:14) provided 23 mg of 3,6,7-trimethoxy-1-methyl-4-(naphthalen-2-ylmethyl)isoquinoline. This free base was dissolved in MeOH (2 mL) in a 10 mL round-bottomed flask equipped with a magnetic stirrer before addition of a 0.50 M HCl solution in MeOH (0.4 mL). The reaction mixture was stirred for 5 min at RT and concentrated at 40° C. under vacuum to afford 3,6,7-trimethoxy-1-methyl-4-(naphthalen-2-ylmethyl)isoquinoline hydrochloride 18 as a brown solid (25 mg, 38% yield).

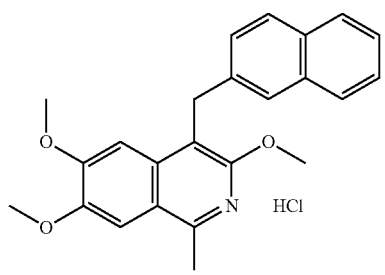

MW: 409.91; Yield: 38%; Brown solid; Mp (° C.): 129.7 (dec.)

$R_f$ (free base): 0.2 (cyclohexane:EtOAc=86:14).

$^1$H-NMR ($CD_3OD$, δ): 3.11 (s, 3H, $CH_3$), 3.83 (s, 3H, $OCH_3$), 4.00 (s, 3H, $OCH_3$), 4.23 (s, 3H, $OCH_3$), 4.62 (s, 2H, $CH_2$), 7.34-7.42 (m, 4H, 4×ArH), 7.52 (s, 1H, ArH), 7.64-7.78 (m, 4H, 4×ArH).

$^{13}$C-NMR ($CD_3OD$, δ): 17.8, 31.6, 56.9, 57.1, 63.4, 104.4, 106.3, 120.2, 121.7, 126.8, 127.4, 127.7 (2×C), 128.4, 128.6, 129.6, 133.7, 135.0, 137.6, 139.9, 152.2, 152.6, 152.7, 159.1.

MS-ESI m/z (rel.int.): 374 ([MH]$^+$, 100).

HPLC: Method A (10 min), XTerra™ column (5 μm, C18, 4.5×50 mm, Model #186000482), detection UV 254 nm, RT=6.25 min, peak area 97.8%.

Preparation of 1-ethyl-6,7-dimethoxy-4-(naphthalen-2-ylmethyl)isoquinolin-3-ol hydrochloride 19

To a solution of 1-ethyl-6,7-dimethoxyisoquinolin-3-ol SLA 28136 (125 mg, 536 μmol) in toluene (10 mL) in a 20 mL microwave vial equipped with a magnetic stirrer was added a 2 N aq. KOH solution (0.30 mL, 0.60 mmol) at RT followed by 2-(bromomethyl)naphthalene (123 mg, 556 μmol) and the mixture was stirred at 150° C. for 1.5 h under microwave irradiation. After cooling to RT, the mixture was diluted with $H_2O$ (10 mL) before extraction with $CH_2Cl_2$ (80 mL). The organic phase was isolated and washed with brine (10 mL), dried over $Na_2SO_4$, filtered and concentrated at 40° C. under vacuum. Purification by column chromatography ($SiO_2$, eluent $CH_2Cl_2$:MeOH=100:0 to 97:3) gave 41 mg of 1-ethyl-6,7-dimethoxy-4-(naphthalen-2-ylmethyl)isoquinolin-3-ol. This free base was dissolved in MeOH (2 mL) in a 10 mL round-bottomed flask equipped with a magnetic stirrer before addition of a 0.42 M HCl solution in MeOH (4.0 mL). The reaction mixture was stirred for 5 min at RT and concentrated at 40° C. under vacuum to afford 1-ethyl-6,7-dimethoxy-4-(naphthalen-2-ylmethyl)isoquinolin-3-ol hydrochloride 19 as a yellow solid (44 mg, 20% yield).

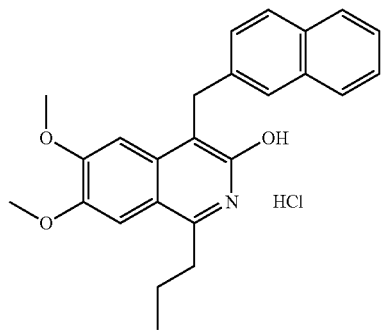

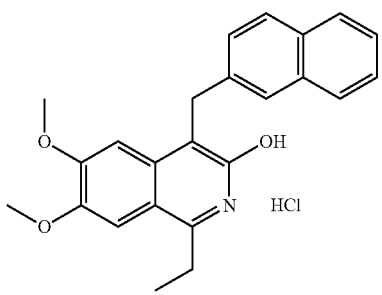

MW: 409.91; Yield: 20%; Brown solid; Mp (° C.): 166.0
$R_f$ (free base): 0.2 (cyclohexane:EtOAc=97:3).
$^1$H-NMR (CD$_3$OD, δ): 1.50 (t, 3H, J=7.6 Hz, CH$_3$), 3.42 (q, 2H, J=7.6 Hz, CH$_2$), 3.80 (s, 3H, OCH$_3$), 3.99 (s, 3H, OCH$_3$), 4.63 (s, 2H, CH$_2$), 7.23 (s, 1H, ArH), 7.39-7.43 (m, 3H, 3×ArH), 7.48 (s, 1H, ArH), 7.63 (s, 1H, ArH), 7.70-7.73 (m, 1H, ArH), 7.78-7.81 (m, 2H, 2×ArH).
$^{13}$C-NMR (CD$_3$OD, δ): 14.6, 25.3, 31.6, 56.8, 56.9, 103.9, 105.4, 114.8, 119.1, 126.8, 127.4, 127.5, 127.6, 128.5, 128.6, 129.6, 133.8, 135.0, 137.2, 141.4, 151.5, 152.1, 155.3, 159.1.
MS-ESI m/z (rel.int.): 374 ([MH]$^+$, 100).
HPLC: Method A (10 min), XTerra™ column (5 µm, C18, 4.5×50 mm, Model #186000482), detection UV 254 nm, RT=5.64 min, peak area 95.0%.

Preparation of 6,7-dimethoxy-4-(naphthalen-2-ylmethyl)-1-propylisoquinolin-3-ol hydrochloride 20

To a solution of 6,7-dimethoxy-1-propylisoquinolin-3-ol RBO 35142 (125 mg, 505 µmol) in toluene (10 mL) in a 20 mL microwave vial equipped with a magnetic stirrer was added a 2 N aq. KOH solution (0.30 mL, 0.60 mmol) at RT followed by 2-(bromomethyl)naphthalene (123 mg, 556 µmol) and the mixture was stirred at 150° C. for 45 min under microwave irradiation. After cooling to RT, the mixture was diluted with H$_2$O (10 mL) before extraction with CH$_2$Cl$_2$ (80 mL). The organic phase was isolated and washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 97:3) gave 57 mg of 6,7-dimethoxy-4-(naphthalen-2-ylmethyl)-1-propylisoquinolin-3-ol. This free base was dissolved in MeOH (2 mL) in a 10 mL round-bottomed flask equipped with a magnetic stirrer before addition of a 0.42 M HCl solution in MeOH (4.0 mL). The reaction mixture was stirred for 5 min at RT and concentrated at 40° C. under vacuum to afford 6,7-dimethoxy-4-(naphthalen-2-ylmethyl)-1-propylisoquinolin-3-ol hydrochloride 20 as a yellow solid (62 mg, 29% yield).

MW: 423.93; Yield: 29%; Brown solid; Mp (° C.): 135.0
$R_f$ (free base): 0.2 (cyclohexane:EtOAc=97:3).
$^1$H-NMR (CD$_3$OD, δ): 1.12 (t, 3H, J=7.3 Hz, CH$_3$), 1.89-1.97 (m, 2H, CH$_2$), 3.38 (t, 2H, J=7.6 Hz, CH$_2$), 3.80 (s, 3H, OCH$_3$), 3.98 (s, 3H, OCH$_3$), 4.63 (s, 2H, CH$_2$), 7.28 (s, 1H, ArH), 7.39-7.46 (m, 4H, 4×ArH), 7.63 (s, 1H, ArH), 7.69-7.81 (m, 3H, 3×ArH).
$^{13}$C-NMR (CD$_3$OD, δ): 14.1, 24.6, 31.6, 33.4, 56.8, 56.9, 103.8, 105.6, 114.9, 119.5, 126.8, 127.4, 127.5, 127.6, 128.5, 128.6, 129.6, 133.7, 135.0, 137.3, 141.3, 151.5, 152.0, 154.0, 159.1.
MS-ESI m/z (rel.int.): 388 ([MH]$^+$, 100).
HPLC: Method A (10 min), XTerra™ column (5 µm, C18, 4.5×50 mm, Model #186000482), detection UV 254 nm, RT=5.80 min, peak area 96.0%.

Preparation of 4-(isoquinolin-6-ylmethyl)-6,7-dimethoxy-1-methylisoquinolin-3-ol dihydrochloride 21

Isoquinolin-6-ylmethanol MDE 32046

To a solution of methyl isoquinoline-6-carboxylate (0.50 g, 2.67 mmol) in absolute EtOH (25 mL) at 0° C. in a 100 mL round-bottomed flask equipped with a magnetic stirrer was added NaBH$_4$ (404 mg, 10.68 mmol) and the mixture was stirred 4 h under reflux. The solution was then cooled down to 0° C. before quenching with 2.0 mL of a 6N aq. HCl solution. The reaction mixture was stirred at RT for 20 min, then basified with 5.3 mL of 2 N aq. NaOH solution. EtOH was removed at 40° C. under vacuum and the residue was extracted with CH$_2$Cl$_2$ (2×50 mL). The organic phase was washed with brine (10 mL), dried over Na$_2$SO$_4$, filtered and concentrated at 40° C. under vacuum. Purification by column chromatography (SiO$_2$, eluent cyclohexane:EtOAc=100:0 to 75:25) gave, after evaporation and drying, isoquinolin-6-ylmethanol MDE 32046 as an off-white solid (263 mg, 62% yield).

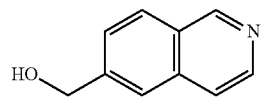

MW: 159.19; Yield: 62%; Off-white solid; Mp (° C.): 78.2
$R_f$: 0.25 (cyclohexane:EtOAc=75:25).
$^1$H-NMR (CDCl$_3$, δ): 4.02 (broad s, 1H, OH), 4.93 (s, 2H, OCH$_2$), 7.61-7.65 (m, 1H, ArH), 7.70-7.76 (m, 2H, 2×ArH), 7.80 (d, 1H, J=8.2 Hz, ArH), 7.95 (d, 1H, J=8.2 Hz, ArH), 9.20 (s, 1H, ArH).

$^{13}$C-NMR (CDCl$_3$, δ): 65.0, 116.8, 126.5, 127.0, 127.6, 127.9, 130.7, 136.4, 152.0, 153.1.

MS-ESI m/z (% rel. Int.): 160 ([MH]$^+$, 100).

HPLC: Method A (10 min), XTerra™ column (5 µm, C18, 4.5×50 mm, Model #186000482), detection UV 254 nm, RT=3.53 min.

6-(Chloromethyl)isoquinoline hydrochloride MDE 32048

To a solution of quinolin-4-ylmethanol MDE 32046 (0.24 g, 1.51 mmol) in dry CH$_2$Cl$_2$ (10 mL) at 0° C. under N$_2$ in a 50 mL round-bottomed flask equipped with a magnetic stirrer was added dropwise SOCl$_2$ (2.3 mL, 31.2 mmol) and the mixture was stirred for 1 h at RT. The volatiles were then removed at 40° C. under vacuum and the residue was taken up in CH$_2$Cl$_2$ (20 mL) before concentration back to dryness at 40° C. under vacuum (done 3 times) to give 6-(chloromethyl)quinoline hydrochloride MDE 32048 as an off-white solid (301 mg, 93% yield).

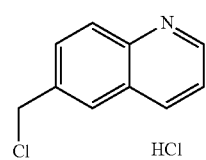

MDE 32048

MW: 214.09; Yield: 93%; Off-white solid; Mp (° C.): 202.4

$^1$H-NMR (CD$_3$OD, δ): 3.55 (s, 2H, CH$_2$), 6.48 (dd, 1H, J=7.0 Hz, ArH), 6.65-6.73 (m, 2H, 2×ArH), 6.95-6.97 (m, 2H, 2×ArH), 8.28 (s, 1H, ArH).

$^{13}$C-NMR (CD$_3$OD, δ): 41.7, 126.3, 128.3, 129.0, 131.9, 132.7, 138.7, 140.5, 142.0, 150.0.

MS-ESI m/z (% rel. Int.): 178 ([MH]$^+$, $^{35}$Cl, 100), 180 ([MH]$^+$, $^{37}$Cl, 32).

HPLC: Method A (10 min), XTerra™ column (5 µm, C18, 4.5×50 mm, Model #186000482), detection UV 254 nm, RT=4.30 min.

4-(Isoquinolin-6-ylmethyl)-6,7-dimethoxy-1-methylisoquinolin-3-ol dihydrochloride 21

To a solution of 6,7-dimethoxy-1-methylisoquinolin-3-ol CCH 18060 (158 mg, 721 µmol) in toluene (15 mL) in a 20 mL microwave vial equipped with a magnetic stirrer was added a 2 N aq. KOH solution (0.70 mL, 1.40 mmol) at RT followed by MDE 32048 (185 mg, 864 µmol) and the mixture was stirred at 160° C. for 1.5 h under microwave irradiation. After cooling to RT, the mixture was diluted with H$_2$O (10 mL) before extraction with EtOAc (50 mL). The organic phase was isolated and the aqueous phase was further extracted with CH$_2$Cl$_2$ (50 mL). Both organic phases were washed with brine (10 mL), combined, dried over Na$_2$SO$_4$, filtered and concentrated at 40° C. under vacuum. Purification by column chromatography (SiO$_2$, eluent CH$_2$Cl$_2$:MeOH=100:0 to 94:6) gave 56 mg of 4-(isoquinolin-6-ylmethyl)-6,7-dimethoxy-1-methylisoquinolin-3-ol. This free base was dissolved in MeOH (3 mL) in a 25 mL round-bottomed flask equipped with a magnetic stirrer before addition of a 0.09 M HCl solution in MeOH (5.0 mL). The reaction mixture was stirred for 5 min at RT and concentrated at 40° C. under vacuum to afford 4-(isoquinolin-6-ylmethyl)-6,7-dimethoxy-1-methylisoquinolin-3-ol dihydrochloride 21 as a brown solid (67 mg, 21% yield).

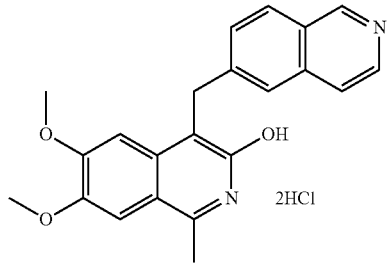

21

MW: 433.33; Yield: 21%; Brown solid; Mp (° C.)>250 (dec.).

R$_f$ (free base): 0.2 (CH$_2$Cl$_2$:MeOH=94:6).

$^1$H-NMR (CD$_3$OD, δ): 3.05 (s, 3H, CH$_3$), 3.94 (s, 3H, OCH$_3$), 4.02 (s, 3H, OCH$_3$), 4.96 (s, 2H, CH$_2$), 7.21 (s, 1H, ArH), 7.49 (s, 1H, ArH), 7.97-8.13 (m, 4H, 4×ArH), 8.48 (d, 1H, J=8.2 Hz, ArH), 9.79 (s, 1H, ArH).

$^{13}$C-NMR (CD$_3$OD, δ): 16.2, 28.0, 56.9, 57.5, 102.2, 106.0, 119.4, 124.2, 127.6, 128.3, 131.4, 131.7, 138.1, 140.6, 140.7, 114.6, 148.6, 151.1, 151.6, 159.6 (2×C not observed).

MS-ESI m/z (rel.int.): 361 ([MH]$^+$, 100).

HPLC: Method A (10 min), XTerra™ column (5 µm, C18, 4.5×50 mm, Model #186000482), detection UV 254 nm, RT=4.38 min, peak area 96.7%.

Preparation of 4-(isoquinolin-5-ylmethyl)-6,7-dimethoxy-1-methylisoquinolin-3-ol 22

Isoquinolin-5-ylmethanol MDE 32040

To a solution of isoquinoline-5-carboxaldehyde (0.65 g, 4.14 mmol) in absolute EtOH (20 mL) at 0° C. in a 100 mL round-bottomed flask equipped with a magnetic stirrer was added NaBH$_4$ (156 mg, 4.14 mmol) and the mixture was stirred overnight at RT. The solution was then cooled down to 0° C. before quenching with 2.8 mL of a 6 N aq. HCl solution. The reaction mixture was stirred at RT for 15 min then basified with a 2 N aq. NaOH solution (8.3 mL). EtOH was removed at 40° C. under vacuum and the residue was extracted with CH$_2$Cl$_2$ (2×50 mL). The organic phase was washed with brine (10 mL), dried over Na$_2$SO$_4$, filtered and concentrated at 40° C. under vacuum. Purification by column chromatography (SiO$_2$, eluent cyclohexane:EtOAc= 100:0 to 75:25) gave, after evaporation and drying, isoquinolin-5-ylmethanol MDE 32040 as an off-white solid (536 mg, 81% yield).

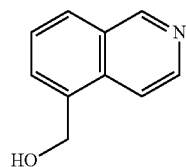

MDE 32040

MW: 159.19; Yield: 81%; Off-white solid; Mp (° C.): 101.2

R$_f$: 0.25 (cyclohexane:EtOAc=75:25).

$^1$H-NMR (CDCl$_3$, δ): 3.23 (broad s, 1H, OH), 5.13 (s, 2H, OCH$_2$), 7.55 (dd, 1H, J=7.7 Hz, ArH), 7.76 (d, 1H, J=7.0 Hz, ArH), 7.86-7.88 (m, 2H, 2×ArH), 8.48 (d, 1H, J=6.0 Hz, ArH), 9.17 (s, 1H, ArH).

$^{13}$C-NMR (CDCl$_3$, δ): 62.5, 116.8, 126.9, 127.7, 128.8, 129.2, 134.0, 136.0, 143.1, 152.9.

MS-ESI m/z (% rel. Int.): 160 ([MH]$^+$, 100).

HPLC: Method A (10 min), XTerra™ column (5 μm, C18, 4.5×50 mm, Model #186000482), detection UV 254 nm, RT=3.41 min.

5-(Chloromethyl)isoquinoline hydrochloride MDE 32044

To a solution of isoquinolin-5-ylmethanol MDE 32040 (0.53 g, 3.33 mmol) in dry CH$_2$Cl$_2$ (10 mL) at 0° C. under N$_2$ in a 50 mL round-bottomed flask equipped with a magnetic stirrer was added dropwise SOCl$_2$ (4.9 mL, 67.4 mmol) and the mixture was stirred for 1 h at RT. The volatiles were then removed at 40° C. under vacuum and the residue was taken up in CH$_2$Cl$_2$ (20 mL) before concentration back to dryness at 40° C. under vacuum (done 3 times) to give 5-(chloromethyl)quinoline hydrochloride MDE 32044 as an off-white solid (301 mg, 42% yield).

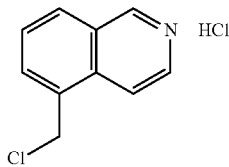

MDE 32044

MW: 214.09; Yield: 42%; Off-white solid; Mp (° C.): 207.3

$^1$H-NMR (CD$_3$OD, δ): 3.71 (s, 2H, CH$_2$), 6.45 (dd, 1H, J=7.7 Hz, ArH), 6.76 (d, 1H, J=7.1 Hz, ArH), 6.97 (d, 1H, J=8.3 Hz, ArH), 7.12-7.19 (m, 2H, 2×ArH), 8.29 (s, 1H, ArH).

$^{13}$C-NMR (CD$_3$OD, δ): 42.9, 123.6, 129.7, 132.2, 132.8, 132.9, 136.3, 138.7, 139.1, 149.1.

MS-ESI m/z (% rel. Int.): 178 ([MH]$^+$, $^{35}$Cl, 100), 180 ([MH]$^+$, $^{37}$Cl, 32).

HPLC: Method A (10 min), XTerra™ column (5 μm, C18, 4.5×50 mm, Model #186000482), detection UV 254 nm, RT=3.96 min, peak area %.

4-(Isoquinolin-5-ylmethyl)-6,7-dimethoxy-1-methylisoquinolin-3-ol dihydrochloride 22

To a solution of 6,7-dimethoxy-1-methylisoquinolin-3-ol CCH 18060 (158 mg, 721 μmol) in toluene (15 mL) in a 20 mL microwave vial equipped with a magnetic stirrer was added a 2 N aq. KOH solution (0.86 mL, 1.72 mmol) at RT followed by MDE 32016 (185 mg, 864 μmol) and the mixture was stirred at 160° C. for 1.5 h under microwave irradiation. After cooling to RT, the mixture was diluted with H$_2$O (10 mL) before extraction with EtOAc (50 mL). The organic phase was isolated and the aqueous phase was further extracted with CH$_2$Cl$_2$ (50 mL). Both organic phases were washed with brine (10 mL), combined, dried over Na$_2$SO$_4$, filtered and concentrated at 40° C. under vacuum. Purification by column chromatography (SiO$_2$, eluent CH$_2$Cl$_2$:MeOH=100:0 to 94:6) gave 48 mg of 4-(isoquinolin-5-ylmethyl)-6,7-dimethoxy-1-methylisoquinolin-3-ol. The free base was dissolved in MeOH (3 mL) in a 25 mL round-bottomed flask equipped with a magnetic stirrer before addition of a 0.09 M HCl solution in MeOH (4.5 mL). The reaction mixture solution was stirred for 5 min at RT and concentrated at 40° C. under vacuum to afford 4-(isoquinolin-5-ylmethyl)-6,7-dimethoxy-1-methylisoquinolin-3-ol dihydrochloride 22 as a brown solid (58 mg, 19% yield).

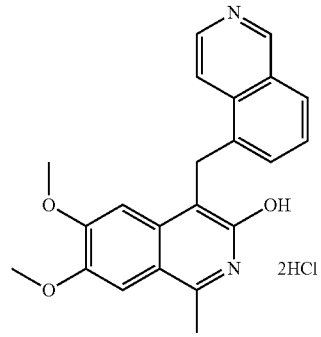

22

MW: 433.33; Yield: 19%; Brown solid; Mp (° C.)>250 (dec.).

R$_f$ (free base): 0.2 (CH$_2$Cl$_2$:MeOH=94:6).

$^1$H-NMR (CD$_3$OD, δ): 3.09 (s, 3H, CH$_3$), 3.73 (s, 3H, OCH$_3$), 4.03 (s, 3H, OCH$_3$), 5.06 (s, 2H, CH$_2$), 7.02 (s, 1H, ArH), 7.50-7.54 (m, 2H, 2×ArH), 7.84 (dd, 1H, J=7.3 Hz, ArH), 8.42 (d, 1H, J=8.0 Hz, ArH), 8.78 (d, 1H, J=4.5 Hz, ArH), 9.00-9.02 (m, 1H, ArH), 9.87 (s, 1H, ArH).

$^{13}$C-NMR (CD$_3$OD, δ): 17.5, 28.2, 56.9, 57.1, 103.0, 106.3, 112.0, 120.0, 123.6, 129.7, 130.7, 132.2, 132.7, 136.2, 136.7, 139.5, 141.0, 148.8, 151.4, 152.1, 159.6 (1×C not observed).

MS-ESI m/z (rel.int.): 361 ([MH]$^+$, 100).

HPLC: Method A (10 min), XTerra™ column (5 μm, C18, 4.5×50 mm, Model #186000482), detection UV 254 nm, RT=4.11 min, peak area 99.5%.

Preparation of 6,7-dimethoxy-1-methyl-4-(quinolin-2-ylmethyl)isoquinolin-3-ol dihydrochloride 23

To a solution of 6,7-dimethoxy-1-methylisoquinolin-3-ol CCH 18060 (147 mg, 0.67 mmol) in toluene (3 mL) in a 10 mL microwave vial equipped with a magnetic stirrer was added a 2 N aq. KOH solution (0.70 mL, 1.40 mmol) at RT followed by 2-(chloromethyl)quinoline hydrochloride (158 mg, 0.74 mmol) and the mixture was stirred at 115° C. for 25 min under microwave irradiation. Another portion of a 2 N aq. KOH solution (0.30 mL, 0.60 mmol) was then added at RT followed by 2-(chloromethyl)quinoline hydrochloride (70 mg, 0.33 mmol) and the mixture was stirred at 115° C. for 10 min under microwave irradiation. After cooling to RT, the mixture was diluted with H$_2$O (5 mL) and neutralised with a 10% aqueous citric acid solution before extraction with CH$_2$Cl$_2$ (50 mL). The organic phase was washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 100:7) gave 49 mg of 6,7-dimethoxy-1-methyl-4-(quinolin-2-ylmethyl)isoquinolin-3-ol as a yellow solid. The free base (45 mg) was dissolved in MeOH (10 mL) in a 25 mL round-bottomed flask equipped with a magnetic stirrer before addition of a 0.09 M HCl solution in MeOH (5.5 mL). The reaction mixture was stirred for 5 min at RT and concentrated at 40° C. under vacuum to afford 6,7-dimethoxy-1-methyl-4-(quinolin-2-ylmethyl)isoquinolin-3-ol hydrochloride 23 as a yellow solid (54 mg, 19% yield).

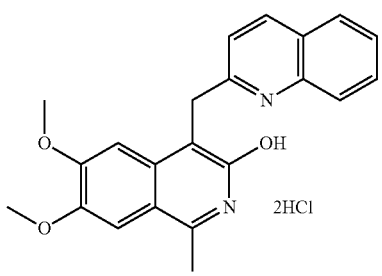

23

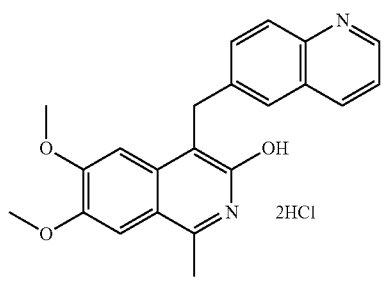

24

MW: 433.33; Yield: 19%; Brown solid; Mp (° C.): 196.7 (dec.).

$R_f$ (free base): 0.25 (CH$_2$Cl$_2$:MeOH=100:7).

$^1$H-NMR (CD$_3$OD, δ): 3.07 (s, 3H, CH$_3$), 4.00 (s, 3H, OCH$_3$), 4.04 (s, 3H, OCH$_3$), 5.17 (s, 2H, CH$_2$), 7.29 (s, 1H, ArH), 7.52 (s, 1H, ArH),), 7.65 (d, 1H, J=8.6 Hz, ArH), 7.97 (dd, 1H, J=7.6 Hz, ArH), 8.18-8.23 (m, 1H, ArH), 8.30 (d, 1H, J=8.3 Hz, ArH), 8.41 (d, 1H, J=8.6 Hz, ArH), 9.00 (d, 1H, J=8.6 Hz, ArH).

$^{13}$C-NMR (CD$_3$OD, δ): 17.6, 31.1, 56.9, 57.7, 102.3, 106.3, 109.4, 119.6, 121.2, 122.8, 129.2, 130.4, 131.0, 136.5, 139.5, 140.8, 148.5, 151.8, 151.9, 153.2, 159.4, 160.1.

MS-ESI m/z (rel.int.): 361 ([MH]$^+$, 100).

HPLC: Method A (10 min), XTerra™ column (5 μm, C18, 4.5×50 mm, Model #186000482), detection UV 254 nm, RT=4.09 min, peak area 99.6%.

Preparation of 6,7-dimethoxy-1-methyl-4-(quinolin-6-ylmethyl)isoquinolin-3-ol dihydrochloride 24

To a solution of 6,7-dimethoxy-1-methylisoquinolin-3-ol CCH 18060 (200 mg, 0.912 mmol) in DME (5 mL) in a 10 mL microwave vial equipped with a magnetic stirrer was added a 2 N aq. KOH solution (0.95 mL, 1.90 mmol) at RT followed by 6-(chloromethyl)quinoline hydrochloride (234 mg, 1.093 mmol, prepared by stirring quinolin-6-yl methanol (330 mg) in SOCl$_2$ (1 mL) for 1 h at RT, then concentration under vacuum and repeated coevaporation with CH$_2$Cl$_2$ and the mixture was stirred at 115° C. for 25 min under microwave irradiation. After cooling to RT, the mixture was diluted with H$_2$O (5 mL) before extraction with EtOAc (50 mL). The organic phase was washed with brine (10 mL) and the aqueous phase was further extracted with CH$_2$Cl$_2$ (50 mL). The dichloromethane phase was washed with brine (10 mL), combined with the first organic phase, dried over Na$_2$SO$_4$, filtered and concentrated at 40° C. under vacuum. Purification by column chromatography (SiO$_2$, eluent CH$_2$Cl$_2$:MeOH=100:0 to 92:8) gave 37 mg of 6,7-dimethoxy-1-methyl-4-(quinolin-6-ylmethyl)isoquinolin-3-ol as a yellow solid. This free base was dissolved in MeOH (10 mL) in a 25 mL round-bottomed flask equipped with a magnetic stirrer before addition of a 0.09 M HCl solution in MeOH (4.0 mL). The reaction mixture was stirred for 5 min at RT and concentrated at 40° C. under vacuum to afford 6,7-dimethoxy-1-methyl-4-(quinolin-6-ylmethyl)isoquinolin-3-ol dihydrochloride 24 as a brown solid (44 mg, 11% yield).

MW: 433.33; Yield: 11%; Brown solid; Mp (° C.): 269.9 (dec.).

$R_f$ (free base): 0.2 (CH$_2$Cl$_2$:MeOH=92:8).

$^1$H-NMR (CD$_3$OD, δ): 3.10 (s, 3H, CH$_3$), 3.89 (s, 3H, OCH$_3$), 4.03 (s, 3H, OCH$_3$), 4.85 (s, 2H, CH$_2$), 7.20 (s, 1H, ArH), 7.53 (d, 1H, J=1.6 Hz, ArH), 8.06-8.10 (m, 1H, ArH), 8.11 (s, 1H, ArH), 8.22 (dd, 1H, J=1.6 and 8.9 Hz, ArH), 8.30 (d, 1H, J=8.9 Hz, ArH), 9.12 (d, 1H, J=8.4 Hz, ArH), 9.20 (dd, 1H, J=1.3 and 5.4 Hz, ArH).

$^{13}$C-NMR (CD$_3$OD, δ): 17.5, 31.2, 56.9, 57.2, 103.1, 106.2, 113.1, 120.2, 121.9, 123.4, 128.6, 130.8, 137.6, 138.1, 140.5, 143.1, 145.4, 148.4, 151.4, 151.6, 152.0, 159.5.

MS-ESI m/z (rel.int.): 361 ([MH]$^+$, 100).

HPLC: Method A (10 min), XTerra™ column (5 μm, C18, 4.5×50 mm, Model #186000482), detection UV 254 nm, RT=4.18 min, peak area 99.8%.

Preparation of 6,7-dimethoxy-1-methyl-4-(quinolin-4-ylmethyl)isoquinolin-3-ol dihydrochloride 25

Quinolin-3-ylmethanol MDE 32014

To a solution of 4-quinolinecarboxaldehyde (0.47 g, 3.00 mmol) in a mixture of EtOH:THF=1:1 (40 mL) at 0° C. in a 100 mL round-bottomed flask equipped with a magnetic stirrer was added NaBH$_4$ (0.11 g, 3.01 mmol) and the mixture was stirred overnight at RT. The solution was then cooled down to 0° C. before quenching a 6 N aq. HCl solution (2 mL). The reaction mixture was stirred at RT for 15 min then basified with a 2 N aq. NaOH solution (6 mL). EtOH was removed at 40° C. under vacuum and the residue was extracted with CH$_2$Cl$_2$ (2×50 mL). The organic phase was washed with brine (10 mL), dried over Na$_2$SO$_4$, filtered and concentrated at 40° C. under vacuum. Purification by column chromatography (SiO$_2$, eluent cyclohexane: EtOAc=100:0 to 0:100) gave, after evaporation and drying, quinolin-4-ylmethanol MDE 32014 as an off-white solid (311 mg, 65% yield).

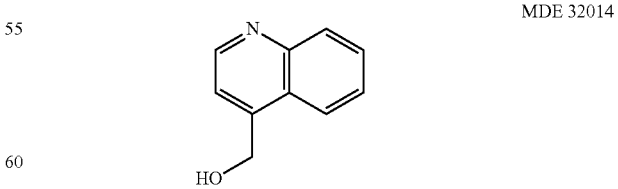

MDE 32014

MW: 159.19; Yield: 65%; Off-white solid; Mp (° C.): 109.3

$R_f$: 0.25 (EtOAc=100%).

$^1$H-NMR (CDCl$_3$, δ): 3.86 (broad s, 1H, OH), 5.23 (s, 2H, OCH$_2$), 7.51-7.56 (m, 2H, 2×ArH), 7.69 (dd, 1H, J=7.6 Hz, ArH), 7.94 (d, 1H, J=8.4 Hz, ArH), 8.09 (d, 1H, J=8.4 Hz, ArH), 8.67-8.77 (m, 1H, ArH).

$^{13}$C-NMR (CDCl$_3$, δ): 61.3, 118.1, 122.9, 125.8, 126.7, 129.3, 129.7, 146.8, 147.6, 150.2.

MS-ESI m/z (% rel. Int.): 160 ([MH]$^+$, 100).

HPLC: Method A (10 min), XTerra™ column (5 µm, C18, 4.5×50 mm, Model #186000482), detection UV 254 nm, RT=4.20 min.

4-(Chloromethyl)quinoline hydrochloride MDE 32016

To a solution of quinolin-4-ylmethanol MDE 32014 (0.28 g, 1.76 mmol) in dry CH$_2$Cl$_2$ (18 mL) at 0° C. under N$_2$ in a 50 mL round-bottomed flask equipped with a magnetic stirrer was added dropwise SOCl$_2$ (2.6 mL, 36.0 mmol) and the mixture was stirred for 1 h at RT. The volatiles were then removed at 40° C. under vacuum and the residue was taken up in CH$_2$Cl$_2$ (20 mL) before concentration back to dryness at 40° C. under vacuum (done 3 times) to give 4-(chloromethyl)quinoline hydrochloride MDE 32016 as an off-white solid (246 mg, 65% yield).

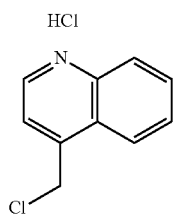

MDE 32016

MW: 214.09; Yield: 65%; Off-white solid; Mp (° C.): 40.1

$^1$H-NMR (CD$_3$OD, δ): 4.91 (s, 2H, CH$_2$), 8.07 (dd, 1H, J=7.7 Hz, ArH), 8.21-8.35 (m, 3H, 3×ArH), 8.59 (d, 1H, J=8.6 Hz, ArH), 9.26 (d, 1H, J=5.6 Hz, ArH).

$^{13}$C-NMR (CD$_3$OD, δ): 42.0, 122.3, 122.9, 126.4, 128.3, 131.7, 136.3, 139.1, 146.0, 156.9.

MS-ESI m/z (% rel. Int.): 178 ([MH]$^+$, $^{35}$Cl, 100), 180 ([MH]$^+$, $^{37}$Cl, 32).

HPLC: Method A (10 min), XTerra™ column (5 µm, C18, 4.5×50 mm, Model #186000482), detection UV 254 nm, RT=4.43 min.

6,7-Dimethoxy-1-methyl-4-(quinolin-4-ylmethyl)isoquinolin-3-ol dihydrochloride 25

To a solution of 6,7-dimethoxy-1-methylisoquinolin-3-ol CCH 18060 (120 mg, 547 µmol) in toluene (15 mL) in a 20 mL microwave vial equipped with a magnetic stirrer was added a 2 N aq. KOH solution (0.58 mL, 1.16 mmol) at RT followed by MDE 32016 (130 mg, 607 µmol) and the mixture was stirred at 160° C. for 1.5 h under microwave irradiation. After cooling to RT, the mixture was diluted with H$_2$O (10 mL) before extraction with EtOAc (50 mL). The organic phase was isolated and the aqueous phase was further extracted with CH$_2$Cl$_2$ (50 mL). Both organic phases were washed with brine (10 mL), combined, dried over Na$_2$SO$_4$, filtered and concentrated at 40° C. under vacuum. Purification by column chromatography (SiO$_2$, eluent CH$_2$Cl$_2$:MeOH=100:0 to 92:8) gave 37 mg of 6,7-dimethoxy-1-methyl-4-(quinolin-3-ylmethyl)isoquinolin-3-ol. This free base was dissolved in MeOH (2 mL) in a 25 mL round-bottomed flask equipped with a magnetic stirrer before addition of a 0.09 M HCl solution in MeOH (4 mL). The reaction mixture was stirred for 5 min at RT and concentrated at 40° C. under vacuum to afford 6,7-dimethoxy-1-methyl-4-(quinolin-4-ylmethyl)isoquinolin-3-ol dihydrochloride 25 as a brown solid (44 mg, 19% yield).

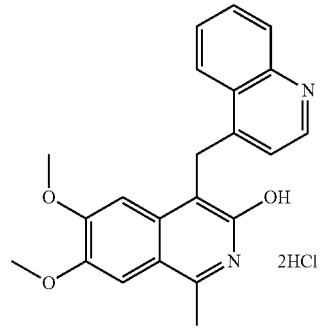

25

MW: 433.33; Yield: 19%; Brown solid; Mp (° C.): 236.6 (dec.).

R$_f$ (free base): 0.2 (CH$_2$Cl$_2$:MeOH=95:5).

$^1$H-NMR (CD$_3$OD, δ): 3.10 (s, 3H, CH$_3$), 3.79 (s, 3H, OCH$_3$), 4.04 (s, 3H, OCH$_3$), 5.31 (s, 2H, CH$_2$), 7.03 (s, 1H, ArH), 7.38-7.40 (m, 1H, ArH), 7.55 (s, 1H, ArH), 8.17-8.36 (m, 3H, 3×ArH), 8.90-8.98 (m, 2H, 2×ArH).

$^{13}$C-NMR (CD$_3$OD, δ): 17.5, 29.7, 56.9, 57.1, 102.6, 106.3, 110.3, 119.7, 121.2, 122.3, 126.8, 129.6, 131.6, 136.3, 138.7, 140.9, 145.4, 151.7, 151.9, 159.8, 160.3 (1×C not observed).

MS-ESI m/z (rel.int.): 361 ([MH]$^+$, 100).

HPLC: Method A (10 min), XTerra™ column (5 µm, C18, 4.5×50 mm, Model #186000482), detection UV 254 nm, RT=4.13 min, peak area 99.4%.

Preparation of 6,7-dimethoxy-1-methyl-4-(quinolin-3-ylmethyl)isoquinolin-3-ol dihydrochloride 26

Quinolin-3-ylmethanol MDE 32002

To a solution of 3-quinolinecarboxaldehyde (0.39 g, 2.48 mmol) in absolute EtOH (25 mL) at 0° C. in a 100 mL round-bottomed flask equipped with a magnetic stirrer was added NaBH$_4$ (48 mg, 1.26 mmol) and the mixture was stirred overnight at RT. Then a second portion of NaBH$_4$ (48 mg, 1.26 mmol) was added at RT and stirring was continued for 1 h at RT. The solution was then cooled down to 0° C. before quenching with a 6 N aq. HCl solution (2 mL). The reaction mixture was stirred at RT for 15 min and then basified with a 2 N aq. NaOH solution (8 mL). EtOH was removed at 40° C. under vacuum and the residue was extracted with CH$_2$Cl$_2$ (2×50 mL). The organic phase was washed with brine (10 mL), dried over Na$_2$SO$_4$, filtered and concentrated at 40° C. under vacuum. Purification by column chromatography (SiO$_2$, eluent cyclohexane:EtOAc=100:0 to 0:100) gave, after evaporation and drying, quinolin-3-ylmethanol MDE 32002 as an off-white solid (280 mg, 71% yield).

MDE 32002

MW: 159.19; Yield: 71%; Off-white solid; Mp (° C.): 87.6 $R_f$: 0.25 (EtOAc=100%).

$^1$H-NMR (CDCl$_3$, δ): 3.80 (broad s, 1H, OH), 4.90 (s, 2H, OCH$_2$), 7.49-7.54 (m, 1H, ArH), 7.64-7.70 (m, 1H, ArH), 7.76 (d, 1H, J=8.1 Hz, ArH), 8.50 (d, 1H, J=8.5 Hz, ArH), 8.15 (s, 1H, ArH), 8.80 (s, 1H, ArH).

$^{13}$C-NMR (CDCl$_3$, δ): 62.6, 126.9, 127.7, 127.9, 128.9, 129.4, 133.8, 147.3, 150.1 (1×C not observed).

MS-ESI m/z (% rel. Int.): 160 ([MH]$^+$, 100).

HPLC: Method A (10 min), XTerra™ column (5 μm, C18, 4.5×50 mm, Model #186000482), detection UV 254 nm, RT=4.62 min.

3-(Chloromethyl)quinoline hydrochloride MDE 32004

To a solution of quinolin-3-ylmethanol MDE 32002 (0.26 g, 1.63 mmol) in dry CH$_2$Cl$_2$ (10 mL) at 0° C. under N$_2$ in a 25 mL round-bottomed flask equipped with a magnetic stirrer was added dropwise SOCl$_2$ (2.4 mL, 33.1 mmol) and the mixture was stirred for 1 h at RT. The volatiles were then removed at 40° C. under vacuum and the residue was taken up in CH$_2$Cl$_2$ (20 mL) before concentration back to dryness at 40° C. under vacuum (done 3 times) to give 3-(chloromethyl)quinoline hydrochloride MDE 32004 as an off-white solid (301 mg, 85% yield).

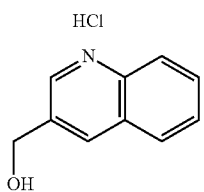

MDE 32004

MW: 214.09; Yield: 85%; Off-white solid; Mp (° C.): 192.1

$^1$H-NMR (CD$_3$OD, δ): 5.10 (s, 2H, CH$_2$), 8.01-8.06 (m, 1H, ArH), 8.24-8.26 (m, 1H, ArH), 8.31 (d, 1H, J=8.4 Hz, ArH), 8.39 (d, 1H, J=8.4 Hz, ArH), 9.32 (s, 1H, ArH), 9.41-9.42 (m, 1H, ArH).

$^{13}$C-NMR (CD$_3$OD, δ): 42.3, 121.5, 130.3, 130.7, 131.9, 134.5, 136.8, 138.6, 146.5, 147.8.

MS-ESI m/z (% rel. Int.): 178 ([MH]$^+$, $^{35}$Cl, 100), 180 ([MH]$^+$, $^{37}$Cl, 32).

HPLC: Method A (10 min), XTerra™ column (5 μm, C18, 4.5×50 mm, Model #186000482), detection UV 254 nm, RT=4.55 min.

6,7-Dimethoxy-1-methyl-4-(quinolin-3-ylmethyl) isoquinolin-3-ol dihydrochloride 26

To a solution of 6,7-dimethoxy-1-methylisoquinolin-3-ol CCH 18060 (120 mg, 547 μmol) in toluene (15 mL) in a 20 mL microwave vial equipped with a magnetic stirrer was added a 2 N aq. KOH solution (0.58 mL, 1.16 mmol) at RT followed by MDE 32004 (130 mg, 607 μmol) and the mixture was stirred at 160° C. for 1.5 h under microwave irradiation. After cooling to RT, the mixture was diluted with H$_2$O (10 mL) before extraction with CH$_2$Cl$_2$ (50 mL). The organic phase was washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 92:8) gave 67 mg of 6,7-dimethoxy-1-methyl-4-(quinolin-3-ylmethyl)isoquinolin-3-ol.

The free base was dissolved in MeOH (2 mL) in a 25 mL round-bottomed flask equipped with a magnetic stirrer before addition of a 0.09 M HCl solution in MeOH (6 mL). The reaction mixture was stirred for 5 min at RT and concentrated at 40° C. under vacuum to afford 6,7-dimethoxy-1-methyl-4-(quinolin-3-ylmethyl)isoquinolin-3-ol dihydrochloride 26 as a brown solid (80 mg, 31% yield).

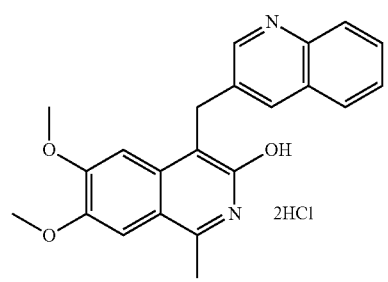

26

MW: 433.33; Yield: 31%; Brown solid; Mp (° C.): 229.7 (dec.).

$R_f$ (free base): 0.2 (CH$_2$Cl$_2$:MeOH=95:5).

$^1$H-NMR (CD$_3$OD, δ): 3.06 (s, 3H, CH$_3$), 3.95 (s, 3H, OCH$_3$), 4.02 (s, 3H, OCH$_3$), 4.88 (s, 2H, CH$_2$), 7.22 (s, 1H, ArH), 7.52 (s, 1H, ArH), 7.93 (dd, 1H, J=7.6 Hz, ArH), 8.11-8.26 (m, 3H, 3×ArH), 8.88 (s, 1H, ArH), 9.25 (s, 1H, ArH).

$^{13}$C-NMR (CD$_3$OD, δ): 17.6, 28.6, 56.9, 57.5, 102.8, 106.4, 111.7, 120.2, 121.3, 130.2, 130.4, 131.6, 135.1, 136.0, 137.9, 140.5, 146.5, 146.5, 151.8, 152.1, 159.9 (1×C not observed).

MS-ESI m/z (rel.int.): 361 ([MH]$^+$, 100).

HPLC: Method A (10 min), XTerra™ column (5 μm, C18, 4.5×50 mm, Model #186000482), detection UV 254 nm, RT=4.24 min, peak area 98.9%.

Preparation of 6,7-dimethoxy-4-((5-methoxyquinolin-3-yl)methyl)-1-methylisoquinolin-3-ol dihydrochloride 27

5-Methoxyquinoline-3-carbaldehyde RBO 35110

Two 20 mL microwave vials were equipped with a magnetic stirrer and charged with a solution of 3-methoxyaniline (0.625 mL, 5.6 mmol) in absolute EtOH (10 mL) before addition of vinamidinium bis-tetrafluoroborate RW/EXH 001-AB (6.0 g, 16.8 mmol) and each vial was heated with stirring at 150° C. for 15 min under microwave irradiation. After cooling to RT, AcOH (10 mL) was then added in each vial before stirring at 150° C. for 15 min under microwave irradiation. The mixture was then cooled down to RT and combined into a 250 mL round-bottomed flask before addition of a mixture of THF:1 N aq. HCl=1:1 (40 mL) and stirring was continued at RT for 2 h. The mixture was then neutralised with saturated aqueous NaHCO$_3$ solution. THF and EtOH were then removed at 40° C. under vacuum and the residue was extracted with CH$_2$Cl$_2$ (100 mL). The organic phase was washed with brine (20 mL), dried over Na$_2$SO$_4$, filtered, and concentrated under vacuum. Purification by column chromatography (SiO$_2$, eluent cyclohexane:EtOAc=75:25) gave, after evaporation and drying, 5-methoxyquinoline-3-carbaldehyde RBO 35110A as a yellow solid (90 mg, 4% yield).

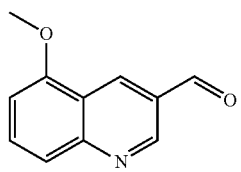

RBO 35110A

MW: 187.20; Yield: 4%; Yellow solid.
R$_f$: 0.18 (cyclohexane:EtOAc=75:25).
$^1$H-NMR (CDCl$_3$, δ): 4.02 (s, 3H, OCH$_3$), 6.92-6.98 (m, 1H, ArH), 7.75-7.83 (m, 2H, 2×ArH), 9.00 (s, 1H, ArH), 9.32 (s, 1H, ArH), 10.21 (s, 1H, HC=O).
$^{13}$C-NMR (CDCl$_3$, δ): 56.0, 105.5, 119.7, 121.6, 127.8, 133.1, 135.7, 149.3, 151.2, 156.3, 190.9.

(5-Methoxyquinolin-3-yl)methanol CCH 34144-3

To a stirred solution of 5-methoxyquinoline-3-carbaldehyde RBO 35110A (98 mg, 524 µmol) in THF (20 mL) at 0° C. in a 100 mL round-bottomed flask equipped with a magnetic stirrer was added NaBH$_4$ (20 mg, 529 µmol) and the mixture was stirred overnight at RT then cooled in an ice bath before quenching by addition of a 1 N aq. HCl solution (10 mL). After stirring for 20 min at that temperature, the mixture was basified with a 2 N aq. NaOH solution (8 mL). THF was then removed at 40° C. under vacuum and the solution was extracted with CH$_2$Cl$_2$ (60 mL), and the organic layer was washed with brine (10 mL), dried over Na$_2$SO$_4$, filtered, and concentrated under vacuum. Purification by column chromatography (SiO$_2$, eluent cyclohexane:EtOAc=100:0 to 0:100) provided, after evaporation and drying, (5-methoxyquinolin-3-yl)methanol CCH 34144-3 as a pale brown solid (80 mg, 81% yield).

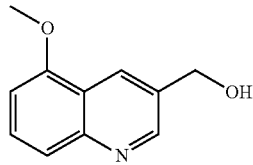

CCH 34144-3

MW: 189.21; Yield: 81%; Pale brown solid.
R$_f$: 0.20 (EtOAc 100%).
$^1$H-NMR (CDCl$_3$, δ): 2.25 (broad s, 1H, OH), 4.01 (s, 3H, OCH$_3$), 4.90 (s, 2H, OCH$_2$), 6.86 (dd, 1H, J=0.7 & 7.6 Hz, ArH), 7.57-7.70 (m, 2H, 2×ArH), 8.54-8.55 (m, 1H, ArH), 8.88 (d, 1H, J=2.2 Hz, ArH).
$^{13}$C-NMR (CDCl$_3$, δ): 55.8, 63.2, 104.5, 120.3, 121.2, 128.8, 129.4, 132.6, 148.4, 150.4, 155.2.
MS-ESI m/z (% rel. Int.): 190 ([MH]$^+$, 100).
HPLC: Method A (10 min), XTerra™ column (5 µm, C18, 4.5×50 mm, Model #186000482), detection UV 254 nm, RT=3.57 min.

3-(Chloromethyl)-5-methoxyquinoline hydrochloride CCH 34144B

To a solution of (5-methoxyquinolin-3-yl)methanol CCH 34144-3 (80 mg, 423 µmol) in dry CH$_2$Cl$_2$ (12 mL) at 0° C. under N$_2$ in a 25 mL round-bottomed flask equipped with a magnetic stirrer was added dropwise SOCl$_2$ (0.60 mL, 8.27 mmol) and the mixture was stirred for 2 h at RT. The volatiles were then removed at 40° C. under vacuum and the residue was taken up in CH$_2$Cl$_2$ (20 mL) before concentration back to dryness at 40° C. under vacuum (done 3 times) to give 3-(chloromethyl)-5-methoxyquinoline hydrochloride CCH 34144B as an off-white solid (87 mg, 84% yield).

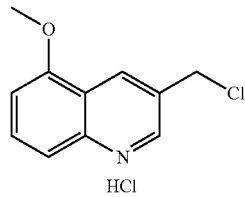

CCH 34144B

MW: 244.12; Yield: 84%.; Off-white solid; Mp (° C.): 50.3
$^1$H-NMR (CDCl$_3$, δ): 4.19 (s, 3H, OCH$_3$), 4.80 (broad s, 1H, NH), 5.04 (s, 2H, CH$_2$), 7.36 (d, 1H, J=8.0 Hz, ArH), 7.87 (d, 1H, J=8.6 Hz, ArH), 8.13 (dd, 1H, J=8.3 Hz, ArH), 9.31 (s, 1H, ArH), 9.44 (s, 1H, ArH).
$^{13}$C-NMR (CDCl$_3$, δ): 42.8, 58.2, 110.1, 113.3, 123.5, 133.4, 138.7, 139.7, 143.2, 146.3, 157.8.
MS-ESI m/z (% rel. Int.): 208 ([MH]$^+$, $^{35}$Cl, 100), 210 ([MH]$^+$, $^{37}$Cl, 35).
HPLC:: Method A (10 min), XTerra™ column (5 µm, C18, 4.5×50 mm, Model #186000482), detection UV 254 nm, RT=3.61 min.

Methyl 2-(3,4-dimethoxyphenyl)-3-(5-methoxyquinolin-3-yl)propanoate CCH 34144-5

To a solution of methyl 2-(3,4-dimethoxyphenyl)acetate SLA 28134 (73 mg, 347 µmol) in dry THF (10 mL) at −66° C. in a 25 mL round-bottomed flask equipped with a magnetic stirrer was added LiHMDS (1.0 N in TBME, 0.70 mL, 700 µmol) and the mixture was stirred for 20 min at that temperature. 3-(Chloromethyl)-5-methoxyquinoline hydrochloride CCH 34144B (84 mg, 344 µmol) was then added and the mixture was stirred for 2 h allowing the temperature to reach RT. The mixture was then quenched by carefully adding H$_2$O (4 mL) and diluted with EtOAc (30 mL). The organic phase was isolated and the aqueous phase was further extracted with CH$_2$Cl$_2$ (40 mL). Both organic phases were washed with brine (10 mL), then combined, dried over Na$_2$SO$_4$, filtered and concentrated at 40° C. under vacuum. Purification by column chromatography (SiO$_2$, eluent cyclohexane:EtOAc=100:0 to 50:50) provided methyl 2-(3,4-dimethoxyphenyl)-3-(5-methoxyquinolin-3-yl)propanoate 34144-5 as a pale yellow oil (46 mg, 35% yield).

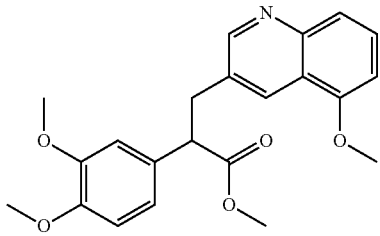

CCH 34144-5

MW: 381.42; Yield: 35%; Pale yellow oil.

¹H-NMR (CDCl₃, δ): 3.20 (dd, 1H, J=7.1 & 13.9 Hz, CHH), 3.56 (dd, 1H, J=8.5 & 13.9 Hz, CHH), 3.62 (s, 3H, OCH₃), 3.85 (s, 6H, 2×OCH₃), 3.85-3.91 (m, 1H, CH), 3.99 (s, 3H, OCH₃), 6.81-6.87 (m, 4H, 4×ArH), 7.52-7.65 (m, 2H, 2×ArH), 8.33 (s, 1H, ArH), 8.66 (d, 1H, J=2.2 Hz, ArH).

¹³C-NMR (CDCl₃, δ): 37.3, 52.2, 52.8, 55.7, 55.9, 55.9, 104.3, 110.9, 111.3, 120.2, 120.4, 121.3, 128.8, 130.1, 130.4, 130.9, 147.8, 148.5, 149.1, 152.1, 154.9, 173.6.

MS-ESI m/z (% rel. Int.): 382 ([MH]⁺, 100).

HPLC: Method A (10 min), XTerra™ column (5 μm, C18, 4.5×50 mm, Model #186000482), detection UV 254 nm, RT=3.99 min.

Methyl 2-(2-acetyl-4,5-dimethoxyphenyl)-3-(5-methoxyquinolin-3-yl)propanoate CCH 34154

To a solution of methyl 2-(3,4-dimethoxyphenyl)-3-(5-methoxyquinolin-3-yl)propanoate CCH 34144-5 (46 mg, 121 μmol) in acetic anhydride (2.0 mL, 21.2 mmol) at 0° C. in a 50 mL round-bottomed flask equipped with a magnetic stirrer was added HClO₄ (ca. 70% solution in water, 0.1 mL, 1.2 mmol). The reaction mixture was then allowed to warm up to RT, stirred for 45 min and diluted with Et₂O (40 mL). The solid was filtered and washed several times with Et₂O giving a brown residue. The residue was then suspended in CH₂Cl₂ (40 mL) before neutralisation with saturated aqueous NaHCO₃ solution. The organic phase was isolated, washed with brine (10 mL), dried over Na₂SO₄, filtered and concentrated at 40° C. under vacuum. Purification by column chromatography (SiO₂, eluent cyclohexane:EtOAc=100:0 to 0:100) gave methyl 2-(2-acetyl-4,5-dimethoxyphenyl)-3-(5-methoxyquinolin-3-yl)propanoate CCH 34154 as a yellow solid (30 mg, 59% yield).

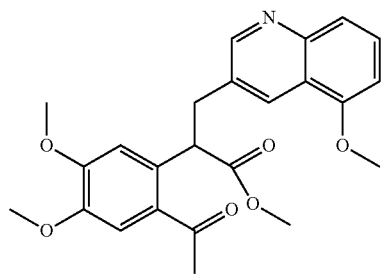

CCH 34154

MW: 423.46; Yield: 59%; Yellow solid.

¹H-NMR (CDCl₃, δ): 2.46 (s, 3H, CH₃), 3.23 (d, 1H, J=13.8 Hz, CHH), 3.52 (d, 1H, J=13.8 Hz, CHH), 3.61 (s, 3H, OCH₃), 3.85-3.89 (m, 1H, CH), 3.86 (s, 3H, OCH₃), 3.91 (s, 3H, OCH₃), 4.00 (s, 3H, OCH₃), 6.82 (d, 1H, J=7.5 Hz, ArH), 6.89-6.91 (m, 1H, ArH), 7.18 (s, 1H, ArH), 7.51-7.64 (m, 2H, 2×ArH), 8.41 (s, 1H, ArH), 8.70 (d, 1H, J=2.0 Hz, ArH).

¹³C-NMR (CDCl₃, δ): 29.3, 37.1, 48.3, 52.1, 55.7, 56.0, 56.1, 104.2, 111.7, 113.0, 120.4, 121.2, 128.7, 129.6, 130.4, 131.2, 132.3, 147.3, 147.7, 151.8, 152.4, 154.9, 173.8, 199.9.

MS-ESI m/z (% rel. Int.): 424 ([MH]⁺, 100).

HPLC: Method A (10 min), XTerra™ column (5 μm, C18, 4.5×50 mm, Model #186000482), detection UV 214 nm, RT=3.90 min.

6,7-Dimethoxy-4-((5-methoxyquinolin-3-yl)methyl)-1-methylisoquinolin-3-ol dihydrochloride 27

A mixture of methyl 2-(2-acetyl-4,5-dimethoxyphenyl)-3-(5-methoxyquinolin-3-yl)propanoate CCH 34154 (30 mg, 71 μmol) and NH₄OAc (0.50 g, 6.49 mmol) in a 2 mL microwave vial equipped with a magnetic stirrer was stirred at 160° C. for 7 min under microwave irradiation. After cooling to RT, the mixture was taken up in CH₂Cl₂:MeOH=9:1 (50 mL) and H₂O (10 mL). The organic layer was isolated and the aqueous layer was further extracted with CH₂Cl₂ (25 mL). The organics were combined, washed with brine (10 mL), dried over Na₂SO₄, filtered and concentrated at 40° C. under vacuum. Purification by column chromatography (SiO₂, eluent CH₂Cl₂:MeOH=100:0 to 93:7) gave 21 mg of 6,7-dimethoxy-4-((5-methoxyquinolin-3-yl)methyl)-1-methylisoquinolin-3-ol. This free base was dissolved in MeOH (2 mL) in a 10 mL round-bottomed flask equipped with a magnetic stirrer before addition of a 0.09 M HCl solution in MeOH (2 mL). The reaction mixture was stirred for 5 min at RT and concentrated at 40° C. under vacuum to afford 6,7-dimethoxy-4-((5-methoxyquinolin-3-yl)methyl)-1-methylisoquinolin-3-ol dihydrochloride 27 as a brown solid (25 mg, 76% yield).

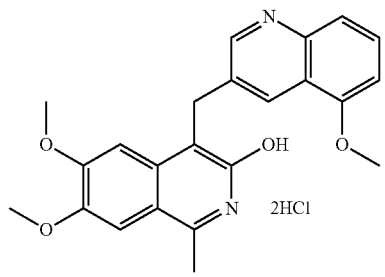

27

MW: 463.35; Yield: 76%; Brown solid; Mp (° C.)>250 (dec.).

Rf: 0.20 (CH₂Cl₂:MeOH=93:7).

¹H-NMR (CD₃OD, δ): 3.08 (s, 3H, CH₃), 4.01 (s, 3H, OCH₃), 4.04 (s, 3H, OCH₃), 4.10 (s, 3H, OCH₃), CH₂ hidden by H₂O peak, 7.29 (s, 1H, ArH), 7.38 (d, 1H, J=7.7 Hz, ArH), 7.53 (s, 1H, ArH), 7.77 (d, 1H, J=8.2 Hz, ArH), 8.06-8.11 (m, 1H, ArH), 9.16-9.19 (m, 2H, 2×ArH).

¹³C-NMR (CD₃OD, δ): 17.5, 28.6, 56.9, 57.4, 57.4, 102.6, 106.3, 109.4, 112.5, 119.9, 123.1, 134.1, 137.1, 138.8, 140.3, 141.4, 146.1, 151.6, 152.0, 152.2, 157.0, 159.8, (1×C not observed).

MS-ESI m/z (rel.int.): 391 ([MH]⁺, 100), 413 ([M+Na]⁺, 8).

HPLC: Method A (10 min), XTerra™ column (5 µm, C18, 4.5×50 mm, Model #186000482), detection UV 214 nm, RT=3.49 min, peak area 98.4%.

Preparation of 4-((5-ethoxyquinolin-3-yl)methyl)-6,7-dimethoxy-1-methylisoquinolin-3-ol dihydrochloride 28

7-Ethoxyquinoline-3-carbaldehyde CCH 29158A & 5-ethoxyquinoline-3-carbaldehyde CCH 29158B To a solution of 3-aminophenol (0.78 g, 7.15 mmol) in absolute EtOH (60 mL) in a 250 mL round-bottomed flask equipped with a magnetic stirrer was added vinamidinium bis-tetrafluoroborate (prepared according the method of Tom, N.; Ruel, E., Synthesis, 2001, 9, 135) (18.00 g, 21.45 mmol) and the reaction mixture was stirred overnight under reflux, then concentrated at 40° C. under vacuum. The residue was taken up in a mixture of THF:1 N aq. HCl=1:1 (80 mL) and stirred for 1 h at 50° C. before neutralisation with saturated $NaHCO_3$ aqueous solution. THF was then removed at 40° C. under vacuum and the residue was extracted with $CH_2Cl_2$ (100 mL). The organic phase was washed with brine (20 mL), dried over $Na_2SO_4$, filtered, and concentrated under vacuum. The residue was purified by column chromatography ($SiO_2$, eluent $CH_2Cl_2$:MeOH=100:0 to 96:4) to give a mixture of two regioisomers MDE 32056-2 (300 mg, 24% yield).

To a suspension of MDE 32056-2 (300 mg, 1.73 mmol) in DMF (10 mL) in a 50 mL round-bottomed flask equipped with a magnetic stirrer was added $Cs_2CO_3$ (1.13 g, 3.47 mmol) followed by bromoethane (0.273 mL, 3.66 mmol). The reaction mixture was stirred overnight at RT and then DMF was removed at 60° C. under vacuum. The residue was taken up in $CH_2Cl_2$ (50 mL) and the organic solution was washed with brine (10 mL), dried over $Na_2SO_4$, filtered, and concentrated at 40° C. under vacuum. Purification by column chromatography ($SiO_2$, eluent cyclohexane:EtOAc=100:0 to 75:25) provided, after evaporation and drying, 7-ethoxyquinoline-3-carbaldehyde CCH 29158A as a pale yellow solid (195 mg, 56% yield, 14% yield over 2 steps) and of 5-ethoxyquinoline-3-carbaldehyde CCH 29158B as a pale yellow solid (106 mg, 30% yield, 7% yield over 2 steps).

7-ethoxyquinoline-3-carbaldehyde CCH 29158A

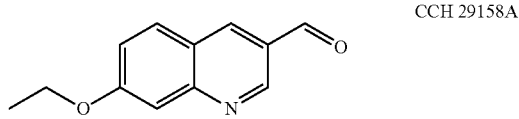

CCH 29158A

MW: 201.22; Yield: 14% over 2 steps; Pale yellow solid; Mp (° C.): 152.6

$R_f$: 0.25 (cyclohexane:EtOAc=75:25).

$^1$H-NMR (CDCl$_3$, δ): 1.52 (t, 3H, J=7.5 Hz, CH$_3$), 4.23 (q, 2H, J=7.5 Hz, CH$_2$), 7.26-7.30 (m, 1H, ArH), 7.44-7.47 (m, 1H, ArH), 7.84 (dd, 1H, J=1.6 & 9.0 Hz, ArH), 8.51 (s, 1H, ArH), 9.26 (s, 1H, ArH), 10.17 (s, 1H, HC=O).

$^{13}$C-NMR (CDCl$_3$, δ): 14.5, 64.1, 108.3, 121.5, 122.1, 127.0, 130.5, 139.0, 150.0, 152.8, 162.7, 190.5.

MS-ESI m/z (% rel. Int.): 202 ([MH]$^+$, 100).

HPLC: Method A (10 min), XTerra™ column (5 µm, C18, 4.5×50 mm, Model #186000482), detection UV 254 nm, RT=5.04 min.

5-ethoxyquinoline-3-carbaldehyde CCH 29158B

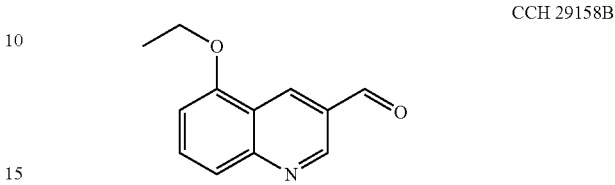

CCH 29158B

MW: 201.22; Yield: 7% over 2 steps; Pale yellow solid; Mp (° C.): 78.9

$R_f$: 0.18 (cyclohexane:EtOAc=75:25).

$^1$H-NMR (CDCl$_3$, δ): 1.59 (t, 3H, J=8.4 Hz, CH$_3$), 4.25 (q, 2H, J=8.4 Hz, CH$_2$), 6.91 (d, 1H, J=7.0 Hz, ArH), 7.70-7.79 (m, 2H, 2×ArH), 9.02-9.07 (m, 1H, ArH), 9.32 (d, 1H, J=2.0 Hz, ArH), 10.22 (s, 1H, HC=O).

$^{13}$C-NMR (CDCl$_3$, δ): 14.7, 64.4, 106.1, 119.7, 121.3, 127.7, 133.2, 135.7, 149.3, 151.2, 155.7, 190.9.

MS-ESI m/z (% rel. Int.): 202 ([MH]$^+$, 100).

HPLC: Method A (10 min), XTerra™ column (5 µm, C18, 4.5×50 mm, Model #186000482), detection UV 254 nm, RT=5.04 min.

(5-Ethoxyquinolin-3-yl)methanol MDE 32076

To a stirred solution of 5-ethoxyquinoline-3-carbaldehyde CCH 29158B (98 mg, 487 µmol) in THF (10 mL) at 0° C. in a 50 mL round-bottomed flask equipped with a magnetic stirrer was added NaBH$_4$ (18 mg, 476 µmol) and the mixture was stirred overnight at RT then cooled in an ice bath before quenching by addition of a 6 N aq. HCl solution (0.33 mL). After stirring for 15 min at that temperature, the mixture was basified by a 2 N aq. NaOH solution (1.0 mL). THF was then removed at 40° C. under vacuum and the solution was extracted with CH$_2$Cl$_2$ (50 mL), washed with brine (10 mL), dried over Na$_2$SO$_4$, filtered, and concentrated under vacuum. Purification by column chromatography (SiO$_2$, eluent CH$_2$Cl$_2$:MeOH=100:0 to 97:3) provided 41 mg (5-ethoxyquinolin-3-yl)methanol MDE 32076 as a colorless oil (41 mg, 41% yield).

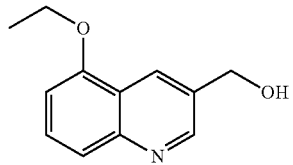

MDE 32076

MW: 203.24; Yield: 41%; Colorless oil.

$^1$H-NMR (CDCl$_3$, δ): 1.50 (t, 3H, J=8.3 Hz, CH$_3$), 3.82-4.52 (broad, s, 1H, OH), 4.14 (q, 2H, J=8.3 Hz, CH$_2$), 4.84 (s, 2H, OCH$_2$), 6.75-6.79 (m, 1H, ArH), 7.47-7.60 (m, 2H, 2×ArH), 8.52 (s, 1H, ArH), 8.74 (s, 1H, ArH).

$^{13}$C-NMR (CDCl$_3$, δ): 14.7, 62.8, 64.0, 105.2, 120.5, 120.7, 129.0, 129.3, 132.9, 148.1, 150.2, 154.4.

MS-ESI m/z (% rel. Int.): 204 ([MH]$^+$, 100).

HPLC: Method A (10 min), XTerra™ column (5 µm, C18, 4.5×50 mm, Model #186000482), detection UV 254 nm, RT=3.65 min.

3-(chloromethyl)-5-ethoxyquinoline hydrochloride CCH 29192

To a solution of (5-ethoxyquinolin-3-yl)methanol MDE 32076 (40 mg, 197 µmol) in dry CH$_2$Cl$_2$ (10 mL) at 0° C. under N$_2$ in a 25 mL round-bottomed flask equipped with a magnetic stirrer was added dropwise SOCl$_2$ (0.30 mL, 4.13 mmol) and the mixture was stirred for 30 min at 0° C. then for 2 h at RT. The volatiles were then removed at 40° C. under vacuum and the residue was taken up in CH$_2$Cl$_2$ (20 mL) before concentration back to dryness at 40° C. under vacuum (done 3 times) to give 3-(chloromethyl)-5-ethoxyquinoline hydrochloride CCH 29192 as a yellow solid (51 mg, 100% yield).

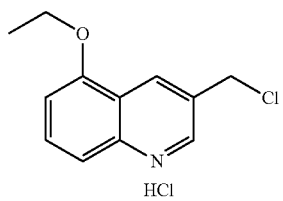

CCH 29192

MW: 258.14; Yield: 100%; Yellow solid; Mp (° C.): 218.5
$^1$H-NMR (CD$_3$OD, δ): 1.62 (t, 3H, J=6.8 Hz, CH$_3$), 4.41 (q, 2H, J=6.8 Hz, CH$_2$), 5.09 (s, 2H, CH$_2$), 7.41 (d, 1H, J=8.1 Hz, ArH), 7.78 (d, 1H, J=8.6 Hz, ArH), 8.09-8.15 (m, 1H, ArH), 9.34 (d, 1H, J=1.5 Hz, ArH), 9.47 (s, 1H, ArH).
$^{13}$C-NMR (CD$_3$OD, δ): 14.8, 42.4, 66.8, 110.3, 112.4, 123.2, 133.2, 138.3, 139.4, 142.7, 146.3, 156.8.
MS-ESI m/z (% rel. Int.): 222 ([MH]$^+$, $^{35}$Cl, 100), 224 ([MH]$^+$, $^{37}$Cl, 35).
HPLC: Method A (10 min), XTerra™ column (5 µm, C18, 4.5×50 mm, Model #186000482), detection UV 254 nm, RT=4.52 min.

4-((5-Ethoxyquinolin-3-yl)methyl)-6,7-dimethoxy-1-methylisoquinolin-3-ol dihydrochloride 28

To a solution of 6,7-dimethoxy-1-methylisoquinolin-3-ol CCH 18060 (51 mg, 233 µmol) in toluene (15 mL) in a 20 mL microwave vial equipped with a magnetic stirrer was added a 2 N aq. KOH solution (0.22 mL, 0.44 mmol) at RT followed by CCH 29192 (50 mg, 194 µmol) and the mixture was stirred at 150° C. for 1.5 h under microwave irradiation. After cooling to RT, the mixture was diluted with H$_2$O (10 mL) before extraction with EtOAc (50 mL). The organic layer was isolated and the aqueous layer was further extracted with CH$_2$Cl$_2$ (50 mL). Both organic layers were washed with brine (10 mL), combined, dried over Na$_2$SO$_4$, filtered and concentrated at 40° C. under vacuum. Purification by column chromatography (SiO$_2$, eluent CH$_2$Cl$_2$:MeOH=100:0 to 94:6) gave 4-((5-ethoxyquinolin-3-yl)methyl)-6,7-dimethoxy-1-methylisoquinolin-3-ol. This free base was dissolved in MeOH (2 mL) in a 10 mL round-bottomed flask equipped with a magnetic stirrer before addition of a 0.09 M HCl solution in MeOH (2 mL). The reaction mixture was stirred for 5 min at RT and concentrated at 40° C. under vacuum to afford 4-((5-ethoxyquinolin-3-yl)methyl)-6,7-dimethoxy-1-methylisoquinolin-3-ol dihydrochloride 28 as a yellow solid (11 mg, 12% yield).

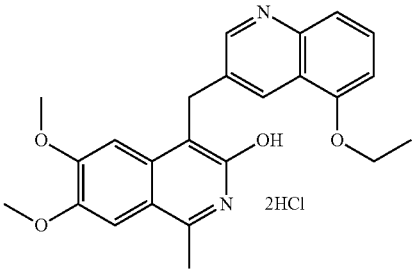

28

MW: 477.38; Yield: 12%; Yellow solid; Mp (° C.): 220.2 (dec.).
R$_f$ (free base): 0.2 (CH$_2$Cl$_2$:MeOH=94:6).
$^1$H-NMR (CD$_3$OD, δ): 1.52 (t, 3H, J=7.0 Hz, CH$_3$), 3.05 (s, 3H, CH$_3$), 4.02 (s, 6H, 2×OCH$_3$), 4.36 (q, 2H, J=7.06 Hz, CH$_2$), 4.87 (s, 2H, CH$_2$), 7.32-7.36 (m, 2H, 2×ArH), 7.50 (s, 1H, ArH), 7.73 (d, 1H, J=8.6 Hz, ArH), 8.01-8.07 (m, 1H, ArH), 9.05 (s, 1H, ArH), 9.31 (s, 1H, ArH).
$^{13}$C-NMR (CD$_3$OD, δ): 14.7, 17.5, 28.6, 56.9, 57.4, 66.6, 102.6, 106.3, 110.0, 112.3, 112.6, 119.8, 123.2, 134.0, 137.5, 138.9, 140.3, 141.8, 145.8, 151.4, 151.9, 152.3, 156.3, 159.8.
MS-ESI m/z (rel.int.): 405 [M+H]$^+$ (100).
HPLC: Method A (10 min), XTerra™ column (5 µm, C18, 4.5×50 mm, Model #186000482), RT=3.80 min, peak area 98.4%.

Preparation of 6,7-dimethoxy-4-((7-methoxyquinolin-3-yl)methyl)-1-methylisoquinolin-3-ol dihydrochloride 29

7-Methoxyquinoline-3-carbaldehyde MDE 32006

To a solution of 3-methoxyaniline (0.40 mL, 3.56 mmol) in absolute EtOH (10 mL) in a 20 mL microwave vial equipped with a magnetic stirrer was added vinamidinium bis-tetrafluoroborate (prepared according to the method of Tom, N.; Ruel, E., *Synthesis*, 2001, 9, 135) (4.12 g, 11.05 mmol) and the reaction mixture was stirred at 150° C. for 8 min under microwave irradiation. After cooling to RT, AcOH (5 mL) was added and the reaction mixture was stirred at 150° C. for 8 min under microwave irradiation. The mixture was then cooled down to RT and transferred into a 250 mL round-bottomed flask before adding a mixture of THF:1 N aq. HCl=1:1 (40 mL) and stirring was continued at RT for 2 h. The mixture was then neutralised with a saturated NaHCO$_3$ aqueous solution. THF and EtOH were then removed at 40° C. under vacuum and the residue was extracted with CH$_2$Cl$_2$ (100 mL). The organic phase was washed with brine (20 mL), dried over Na$_2$SO$_4$, filtered, and concentrated under vacuum. Purification by column chromatography (SiO$_2$, eluent cyclohexane:EtOAc=70:30) gave, after evaporation and drying, 7-methoxyquinoline-3-carbaldehyde MDE 32006 as a yellow solid (352 mg, 53% yield).

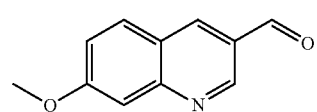

MDE 32006

MW: 187.20; Yield: 53%; Yellow solid; Mp (° C.): 126.5
R$_f$: 0.20 (cyclohexane:EtOAc=70:30).
$^1$H-NMR (CDCl$_3$, δ): 4.00 (s, 3H, OCH$_3$), 7.29 (dd, 1H, J=2.5 & 9.0 Hz, ArH), 7.49 (d, 1H, J=2.5 Hz, ArH), 7.85 (d, 1H, J=9.0 Hz, ArH), 8.53 (d, 1H, J=1.9 Hz, ArH), 9.27 (d, 1H, J=1.9 Hz, ArH), 10.18 (s, 1H, HC=O).
$^{13}$C-NMR (CDCl$_3$, δ): 55.8, 107.7, 121.2, 122.2, 127.1, 130.5, 139.1, 150.0, 152.8, 163.4, 190.5.
MS-ESI m/z (% rel. Int.): 188 ([MH]$^+$, 100).
HPLC: Method A (10 min), XTerra™ column (5 μm, C18, 4.5×50 mm, Model #186000482), detection UV 254 nm, RT=4.42 min.

(7-Methoxyquinolin-3-yl)methanol MDE 32010

To a stirred solution of 7-methoxyquinoline-3-carbaldehyde MDE 32006 (0.328 g, 1.75 mmol) in a mixture of EtOH:THF=18:6 mL at 0° C. in a 50 mL round-bottomed flask equipped with a magnetic stirrer was added sodium borohydride NaBH$_4$ (66 mg, 1.75 mmol) and the mixture was stirred overnight at RT then cooled in an ice bath before quenching by addition of a 6 N aq. HCl solution (1.20 mL). After stirring for 15 min at that temperature, the mixture was basified with 2 N aq. NaOH solution (3.60 mL). THF was then removed at 40° C. under vacuum and the solution was extracted with CH$_2$Cl$_2$ (50 mL), washed with brine (10 mL), dried over Na$_2$SO$_4$, filtered, and concentrated under vacuum. Purification by column chromatography (SiO$_2$, eluent cyclohexane:EtOAc=100:0 to 0:100) provided, after evaporation and drying, (7-methoxyquinolin-3-yl)methanol MDE 32010 as an off-white solid (246 mg, 74% yield).

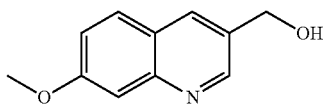

MDE 32010

MW: 189.21; Yield: 74%; Off-white solid; Mp (° C.): 223.0
R$_f$: 0.20 (EtOAc 100%).
$^1$H-NMR (CDCl$_3$, δ): 3.63 (broad s, 1H, OH), 3.89 (s, 3H, OCH$_3$), 4.83 (s, 2H, OCH$_2$), 7.17 (dd, 1H, J=2.5 & 9.0 Hz, ArH), 7.35 (d, 1H, J=2.5 Hz, ArH), 7.63 (d, 1H, J=9.0 Hz, ArH), 8.02 (s, 1H, ArH), 8.74 (s, 1H, ArH).
$^{13}$C-NMR (CDCl$_3$, δ): 55.5, 62.7, 106.9, 120.1, 123.1, 128.7, 131.6, 133.9, 149.1, 150.2, 160.7.
MS-ESI m/z (% rel. Int.): 190 ([MH]$^+$, 100).
HPLC: Method A (10 min), XTerra™ column (5 μm, C18, 4.5×50 mm, Model #186000482), detection UV 254 nm, RT=4.32 min.

3-(Chloromethyl)-7-methoxyquinoline hydrochloride MDE 32012

To a solution of (7-methoxyquinolin-3-yl)methanol MDE 32006 (219 mg, 1.16 mmol) in dry CH$_2$Cl$_2$ (12 mL) at 0° C. under N$_2$ in a 25 mL round-bottomed flask equipped with a magnetic stirrer was added dropwise SOCl$_2$ (1.68 mL, 23.16 mmol) and the mixture was stirred for 1 h at RT. The volatiles were then removed at 40° C. under vacuum and the residue was taken up in CH$_2$Cl$_2$ (20 mL) before concentration back to dryness at 40° C. under vacuum (done 3 times) to give 3-(chloromethyl)-7-methoxyquinoline hydrochloride MDE 32012 as an off-white solid (246 mg, 87% yield).

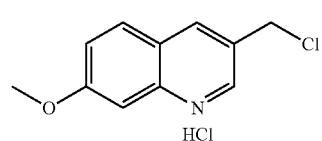

MDE 32012

MW: 244.12; Yield: 87%.; Off-white solid; Mp (° C.): 50.3
$^1$H-NMR (CD$_3$OD, δ): 4.12 (s, 3H, OCH$_3$), 5.04 (s, 2H, CH$_2$), 7.60-7.65 (m, 2H, 2×ArH), 8.28 (d, 1H, J=8.9 Hz, ArH), 9.18 (s, 1H, ArH), 9.23 (s, 1H, ArH).
$^{13}$C-NMR (CD$_3$OD, δ): 42.7, 57.7, 100.1, 125.3, 126.5, 132.0, 132.5, 141.8, 145.2, 147.6, 167.5.
MS-ESI m/z (% rel. Int.): 208 ([MH]$^+$, $^{35}$Cl, 100), 210 ([MH]$^+$, $^{37}$Cl, 35).
HPLC: Method A (10 min), XTerra™ column (5 μm, C18, 4.5×50 mm, Model #186000482), detection UV 254 nm, RT=4.50 min.

6,7-Dimethoxy-4-((7-methoxyquinolin-3-yl)methyl)-1-methylisoquinolin-3-ol dihydrochloride 29

To a solution of 6,7-dimethoxy-1-methylisoquinolin-3-ol CCH 18060 (200 mg, 912 μmol) in toluene (15 mL) in a 20 mL microwave vial equipped with a magnetic stirrer was added a 2 N aq. KOH solution (0.95 mL, 1.90 mmol) at RT followed by 3-(chloromethyl)-7-methoxyquinoline hydrochloride MDE 32012 (245 mg, 1.00 mmol) and the mixture was stirred at 150° C. for 20 min under microwave irradiation. After cooling to RT, another portion of a 2 N aq. KOH solution (0.30 mL, 0.60 mmol) was added and the mixture was stirred at 150° C. for 20 min under microwave irradiation. After cooling to RT, the mixture was diluted with EtOAc (50 mL) and acidified by a 10% aqueous citric acid solution (5 mL) before neutralisation with a saturated aqueous NaHCO$_3$ solution. The organic phase was isolated and the aqueous phase was further extracted with CH$_2$Cl$_2$ (50 mL). Both organic phases were washed with brine (10 mL), combined, dried over Na$_2$SO$_4$, filtered and concentrated at 40° C. under vacuum. Purification by column chromatography (SiO$_2$, eluent CH$_2$Cl$_2$:7N NH$_3$ in MeOH=100:0 to 94:6) gave 23 mg of 6,7-dimethoxy-4-((7-methoxyquinolin-3-yl)methyl)-1-methylisoquinolin-3-ol. This free base was dissolved in MeOH (2 mL) in a 10 mL round-bottomed flask equipped with a magnetic stirrer before addition of a 0.09 M HCl solution in MeOH (4 mL). The reaction mixture was stirred for 5 min at RT and concentrated at 40° C. under vacuum to afford 6,7-dimethoxy-4-((7-methoxyquinolin-3-yl)methyl)-1-methylisoquinolin-3-ol dihydrochloride 29 as a brown solid (27 mg, 6% yield).

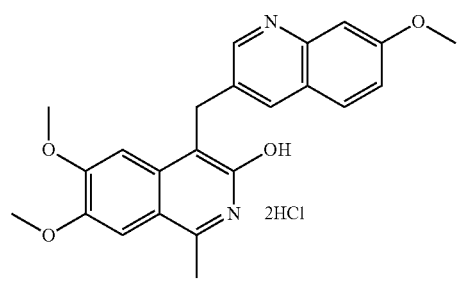

29

MW: 463.35; Yield: 6%; Brown solid; Mp (° C.)>250 (dec.).

$^1$H-NMR (CD$_3$OD, δ): 3.06 (s, 3H, CH$_3$), 3.96 (s, 3H, OCH$_3$), 4.01 (s, 3H, OCH$_3$), 4.06 (s, 3H, OCH$_3$), 7.21 (s, 1H, ArH), 7.50-7.53 (m, 3H, 3×ArH), 8.09-8.12 (m, 1H, ArH), 8.80 (s, 1H, ArH), 9.04 (s, 1H, ArH).

$^{13}$C-NMR (CD$_3$OD, δ): 17.5, 28.2, 56.9, 57.2, 57.4, 99.5, 102.6, 106.3, 112.1, 119.9, 124.8, 126.3, 131.7, 132.4, 140.4, 140.7, 144.5, 146.2, 151.4, 151.9, 152.4, 159.7, 166.5.

MS-ESI m/z (rel.int.): 391 ([MH]$^+$, 100), 413 ([M+Na]$^+$, 8).

HPLC: Method A (10 min), XTerra™ column (5 μm, C18, 4.5×50 mm, Model #186000482), detection UV 254 nm, RT=4.41 min, peak area 98.2%.

Preparation of 4-((7-ethoxyquinolin-3-yl)methyl)-6,7-dimethoxy-1-methylisoquinolin-3-ol dihydrochloride 30

(7-Ethoxyquinolin-3-yl)methanol MDE 32072

To a stirred solution of 7-ethoxyquinoline-3-carbaldehyde CCH 29158A (184 mg, 0.91 mmol) in THF (10 mL) at 0° C. in a 50 mL round-bottomed flask equipped with a magnetic stirrer was added sodium borohydride NaBH$_4$ (34 mg, 0.90 mmol) and the mixture was stirred overnight at RT then cooled in an ice bath before quenching by addition of a 6 N aq. HCl solution (0.60 mL). After stirring for 15 min at that temperature, the mixture was basified with 2 N aq. NaOH solution (1.80 mL). THF was then removed at 40° C. under vacuum and the solution was extracted with CH$_2$Cl$_2$ (50 mL), washed with brine (10 mL), dried over Na$_2$SO$_4$, filtered, and concentrated under vacuum. Purification by column chromatography (SiO$_2$, eluent cyclohexane:EtOAc=100:0 to 25:75) provided, after evaporation and drying, (7-ethoxyquinolin-3-yl)methanol MDE 32072 as an off-white solid (94 mg, 51% yield).

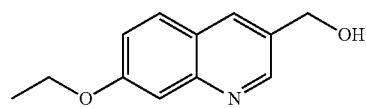

MDE 32072

MW: 203.24; Yield: 51%; Off-white solid; Mp (° C.): 99.5

$^1$H-NMR (CDCl$_3$, δ): 1.43 (t, 3H, J=7.0 Hz, CH$_3$), 4.04 (q, 2H, J=7.0 Hz, CH$_2$), 4.25 (broad s, 1H, OH), 4.79 (s, 2H, OCH$_2$), 7.12 (dd, 1H, J=2.5 and 9.0 Hz, ArH), 7.26 (d, 1H, J=2.5 Hz, ArH), 7.57 (d, 1H, J=9.0 Hz, ArH), 7.97 (s, 1H, ArH), 8.67 (s, 1H, ArH).

$^{13}$C-NMR (CDCl$_3$, δ): 14.6, 62.4, 63.7, 107.2, 119.9, 123.0, 128.6, 131.8, 133.9, 148.9, 150.0, 160.0.

MS-ESI m/z (% rel. Int.): 204 ([MH]$^+$, 100).

HPLC: Method A (10 min), XTerra™ column (5 μm, C18, 4.5×50 mm, Model #186000482), detection UV 254 nm, RT=3.62 min.

3-(Chloromethyl)-7-ethoxyquinoline hydrochloride CCH 29190

To a solution of (7-ethoxyquinolin-3-yl)methanol MDE 32072 (88 mg, 433 μmol) in dry CH$_2$Cl$_2$ (10 mL) at 0° C. under N$_2$ in a 25 mL round-bottomed flask equipped with a magnetic stirrer was added dropwise SOCl$_2$ (0.64 mL, 8.82 mmol) and the mixture was stirred for 30 min at 0° C. then for 2 h at RT. The volatiles were then removed at 40° C. under vacuum and the residue was taken up in CH$_2$Cl$_2$ (20 mL) before concentration back to dryness at 40° C. under vacuum (done 3 times) to give 3-(chloromethyl)-7-ethoxyquinoline hydrochloride CCH 29190 as a brown solid (113 mg, >100% yield).

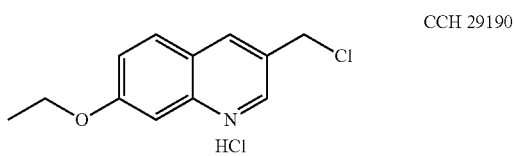

CCH 29190

MW: 258.14; Yield: quant.; Brown solid; Mp (° C.): 235.6

$^1$H-NMR (CD$_3$OD, δ): 1.53 (t, 3H, J=7.0 Hz, CH$_3$), 4.35 (q, 2H, J=7.0 Hz, CH$_2$), 5.03 (s, 2H, CH$_2$), 7.55-7.61 (m, 2H, 2×ArH), 8.25 (d, 1H, J=9.1 Hz, ArH), 9.15 (s, 1H, ArH), 9.20 (s, 1H, ArH).

$^{13}$C-NMR (CD$_3$OD, δ): 14.7, 42.4, 66.7, 100.3, 125.3, 126.1, 131.6, 132.2, 141.4, 144.7, 147.3, 166.4.

MS-ESI m/z (% rel. Int.): 222 ([MH]$^+$, $^{35}$Cl, 100), 224 ([MH]$^+$, $^{37}$Cl, 35).

HPLC: Method A (10 min), XTerra™ column (5 μm, C18, 4.5×50 mm, Model #186000482), detection UV 254 nm, RT=4.15 min.

4-((7-Ethoxyquinolin-3-yl)methyl)-6,7-dimethoxy-1-methylisoquinolin-3-ol dihydrochloride 30

To a solution of 6,7-dimethoxy-1-methylisoquinolin-3-ol CCH 18060 (112 mg, 511 μmol) in toluene (15 mL) in a 20 mL microwave vial equipped with a magnetic stirrer was added a 2 N aq. KOH solution (0.48 mL, 0.96 mmol) at RT followed by CCH 29190 (110 mg, 426 μmol) and the mixture was stirred at 150° C. for 1.5 h under microwave irradiation. After cooling to RT, the mixture was diluted with H$_2$O (10 mL) before extraction with EtOAc (50 mL). The organic phase was isolated and the aqueous phase was further extracted with CH$_2$Cl$_2$ (50 mL). Both organic phases were washed with brine (10 mL), combined, dried over Na$_2$SO$_4$, filtered and concentrated at 40° C. under vacuum. Purification by column chromatography (SiO$_2$, eluent CH$_2$Cl$_2$:MeOH=100:0 to 94:6) gave 47 mg of 4-((7-ethoxyquinolin-3-yl)methyl)-6,7-dimethoxy-1-methylisoquinolin-3-ol. The free base was dissolved in MeOH (2 mL) in a 10 mL round-bottomed flask equipped with a magnetic stirrer before addition of 0.09 M HCl in MeOH (4 mL) and the solution was stirred for 5 min at RT, and concentrated at 40° C. under vacuum to afford 4-((7-ethoxyquinolin-3-yl)methyl)-6,7-dimethoxy-1-methylisoquinolin-3-ol dihydrochloride 30 as a yellow solid (56 mg, 28% yield).

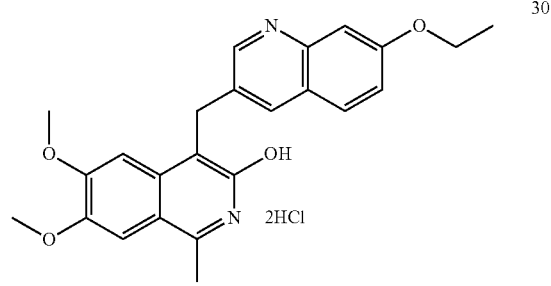 [SMILES: CCOc1ccc2cc(Cc3c(O)nc(C)c4cc(OC)c(OC)cc34)cnc2c1 ; "2HCl"]

30

MW: 477.38; Yield: 28%; Yellow solid; Mp (° C.): 242.6 (dec.).

$^1$H-NMR (CD$_3$OD, δ): 1.51 (t, 3H, J=6.6 Hz, CH$_3$), 3.01 (s, 3H, CH$_3$), 3.95 (s, 3H, OCH$_3$), 4.00 (s, 3H, OCH$_3$), 4.30 (q, 2H, J=6.6 Hz, CH$_2$), 4.76 (s, 2H, CH$_2$), 7.17 (s, 1H, ArH), 7.46-7.53 (m, 3H, 3×ArH), 8.09 (d, 1H, J=8.4 Hz, ArH), 8.78 (s, 1H, ArH), 9.00 (s, 1H, ArH).

$^{13}$C-NMR (CD$_3$OD, δ): 14.6, 17.4, 28.2, 56.8, 57.3, 66.5, 99.9, 102.4, 106.2, 112.2, 119.5, 125.0, 126.3, 131.7, 132.4, 140.4, 140.8, 144.5, 146.1, 151.1, 151.7, 159.6, 165.7.

MS-ESI m/z (rel.int.): 405 ([MH]$^+$, 100).

HPLC: Method A (10 min), XTerra™ column (5 μm, C18, 4.5×50 mm, Model #186000482), detection UV 254 nm, RT=3.81 min, peak area 98.0%.

Preparation of 1-ethyl-6,7-dimethoxy-4-((7-methoxyquinolin-3-yl)methyl)isoquinolin-3-ol dihydrochloride 31

To a solution of 1-ethyl-6,7-dimethoxyisoquinolin-3-ol SLA 28136 (121 mg, 519 μmol) in toluene (10 mL) in a 20 mL microwave vial equipped with a magnetic stirrer was added a 2 N aq. KOH solution (0.57 mL, 1.14 mmol) at RT followed by 3-(chloromethyl)-7-methoxyquinoline hydrochloride MDE 32012 (136 mg, 557 μmol) and the mixture was stirred at 150° C. for 2 h under microwave irradiation. After cooling to RT, the mixture was diluted with CH$_2$Cl$_2$ (50 mL) and H$_2$O (10 mL). The organic phase was isolated and the aqueous phase was further extracted with CH$_2$Cl$_2$ (50 mL). The combined organic phase was washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 95:5) gave 34 mg of 1-ethyl-6,7-dimethoxy-4-((7-methoxyquinolin-3-yl)methyl)isoquinolin-3-ol. This free base was dissolved in MeOH (2 mL) in a 10 mL round-bottomed flask equipped with a magnetic stirrer before addition of a 0.09 M HCl solution in MeOH (3.0 mL). The reaction mixture was stirred for 5 min at RT and concentrated at 40° C. under vacuum to afford 1-ethyl-6,7-dimethoxy-4-((7-methoxyquinolin-3-yl)methyl)isoquinolin-3-ol dihydrochloride 31 as a brown solid (40 mg, 16% yield).

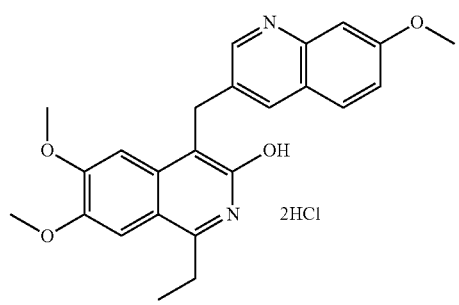

MW: 477.38; Yield: 16%; Brown solid; Mp (° C.): 247.9 (dec.).

$^1$H-NMR (CD$_3$OD, δ): 1.49 (t, 3H, J=7.5 Hz, CH$_3$), 3.40 (q, 2H, J=7.5 Hz, CH$_2$), 3.95 (s, 3H, OCH$_3$), 4.01 (s, 3H, OCH$_3$), 4.06 (s, 3H, OCH$_3$), 4.76 (s, 2H, CH$_2$), 7.20 (s, 1H, ArH), 7.50-7.55 (m, 3H, 3×ArH), 8.11 (d, 1H, J=9.1 Hz, ArH), 8.81 (s, 1H, ArH), 9.04 (s, 1H, ArH).

$^{13}$C-NMR (CD$_3$OD, δ): 14.6, 25.3, 28.1, 56.9, 57.1, 57.4, 99.4, 102.5, 105.5, 112.3, 118.6, 124.8, 126.2, 131.5, 132.2, 140.6, 140.8, 144.2, 146.1, 151.9, 155.6, 159.5, 166.4, (1×C not observed).

MS-ESI m/z (rel.int.): 405 ([MH]$^+$, 100).

HPLC: Method A (10 min), XTerra™ column (5 μm, C18, 4.5×50 mm, Model #186000482), detection UV 254 nm, RT=4.47 min, peak area 95.2%.

Preparation of 6,7-dimethoxy-4-((7-methoxyquinolin-3-yl)methyl)-1-propylisoquinolin-3-ol dihydrochloride 32

To a solution of 1-ethyl-6,7-dimethoxyisoquinolin-3-ol RBO 35142 (117 mg, 473 μmol) in toluene (10 mL) in a 20 mL microwave vial equipped with a magnetic stirrer was added a 2 N aq. KOH solution (0.52 mL, 1.04 mmol) at RT followed by 3-(chloromethyl)-7-methoxyquinoline hydrochloride MDE 32012 (124 mg, 508 μmol) and the mixture was stirred at 150° C. for 2 h under microwave irradiation. After cooling to RT, the mixture was diluted with CH$_2$Cl$_2$ (50 mL) and H$_2$O (10 mL). The organic phase was isolated and the aqueous phase was further extracted with CH$_2$Cl$_2$ (50 mL). The combined organic phase was washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 95:5) gave 26 mg of 6,7-dimethoxy-4-((7-methoxyquinolin-3-yl)methyl)-1-propylisoquinolin-3-ol. This free base was dissolved in MeOH (2 mL) in a 10 mL round-bottomed flask equipped with a magnetic stirrer before addition of a 0.09 M HCl solution in MeOH (2.0 mL). The reaction mixture was stirred for 5 min at RT and concentrated at 40° C. under vacuum to afford 6,7-dimethoxy-4-((7-methoxyquinolin-3-yl)methyl)-1-propylisoquinolin-3-ol dihydrochloride 32 as a brown solid (30 mg, 13% yield).

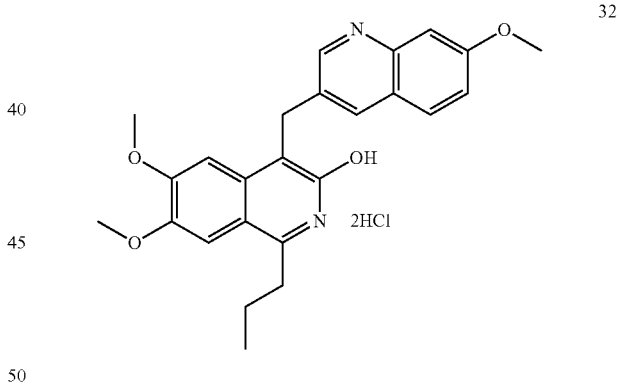

MW: 491.41; Yield: 13%; Brown solid; Mp (° C.): 253.5 (dec.).

$^1$H-NMR (CD$_3$OD, δ): 1.13 (t, 3H, J=6.7 Hz, CH$_3$), 1.90-1.96 (m, 2H, CH$_2$), 3.36-3.40 (m, 2H, CH$_2$), 3.96 (s, 3H, OCH$_3$), 4.02 (s, 3H, OCH$_3$), 4.07 (s, 3H, OCH$_3$), 4.80 (s, 2H, CH$_2$), 7.22 (s, 1H, ArH), 7.52-7.54 (m, 3H, 3×ArH), 8.12 (d, 1H, J=8.8 Hz, ArH), 8.81 (s, 1H, ArH), 9.05 (s, 1H, ArH).

$^{13}$C-NMR (CD$_3$OD, δ): 14.2, 24.5, 28.1, 33.5, 56.9, 57.1, 57.4, 99.3, 102.6, 105.8, 112.3, 119.3, 124.8, 126.2, 131.5, 132.0, 140.6, 140.8, 144.3, 146.1, 151.9, 152.0, 154.6, 159.6, 166.4.

MS-ESI m/z (rel.int.): 419 ([MH]$^+$, 100).

HPLC: Method A (10 min), XTerra™ column (5 μm, C18, 4.5×50 mm, Model #186000482), detection UV 254 nm, RT=4.82 min, peak area 95.1%.

Preparation of 6,7-dimethoxy-1-methyl-4-((6-methyl-2-(methylamino)quinolin-3-yl)methylisoquinolin-3-ol dihydrochloride 33

6-Methyl-2-(methylamino)quinoline-3-carbaldehyde MDE 32036

To a solution of 2-chloro-6-methylquinoline-3-carboxaldehyde (400 mg, 1.95 mmol) in 1,4-dioxan (10 mL) in a 20 mL microwave vial equipped with a magnetic stirrer was added methylamine (40 wt % in $H_2O$, 1.68 mL, 19.5 mmol) and the reaction mixture was stirred for 10 min at 120° C. under microwave irradiation then for an additional 45 min at 160° C. under microwave irradiation. After cooling to RT, the volatiles were removed at 40° C. under vacuum and the resulting yellow oil was taken up in a mixture of THF:1 N aq. HCl=1:1 (50 mL) and stirred for 1 h at RT. The volatiles were removed at 40° C. under vacuum and the residue was neutralised with saturated $NaHCO_3$ aqueous solution before extraction with $CH_2Cl_2$ (100 mL). The organic phase was washed with brine (20 mL), dried over $MgSO_4$, filtered, and concentrated under vacuum. The residue was purified by column chromatography ($SiO_2$, eluent cyclohexane:EtOAc=100:0 to 91:9) to give, after evaporation and drying, 6-methyl-2-(methylamino)quinoline-3-carbaldehyde MDE 32036 as a yellow solid (330 mg, 85% yield).

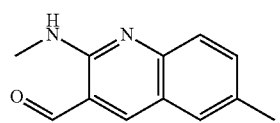

MDE 32036

MW: 200.24; Yield: 85%; Yellow solid; Mp (° C.): 96.9 $R_f$: 0.25 (cyclohexane:EtOAc=91:9).
$^1$H-NMR ($CDCl_3$, δ): 2.43 (s, 3H, $CH_3$), 3.16 (d, 3H, J=4.9 Hz, $NCH_3$), 7.40-7.43 (m, 1H, ArH), 7.48 (dd, 1H, J=4.9 & 8.6 Hz, ArH), 7.61 (d, 1H, J=8.6 Hz, ArH), 7.95-7.99 (broad m, 1H, NH), 8.12 (s, 1H, ArH), 9.95 (s, 1H, HC=O).
$^{13}$C-NMR ($CDCl_3$, δ): 21.0, 27.6, 117.4, 121.7, 126.3, 128.0, 131.9, 135.8, 147.9, 149.7, 155.1, 193.1.
MS-ESI m/z (% rel. Int.): 201 ([MH]$^+$, 100).
HPLC: Method A (10 min), XTerra™ column (5 µm, C18, 4.5×50 mm, Model #186000482), detection UV 254 nm, RT=4.09 min.

(6-Methyl-2-(methylamino)quinolin-3-yl)methanol MDE 32060

To a stirred solution of 6-methyl-2-(methylamino)quinoline-3-carbaldehyde MDE 32036 (134 mg, 0.67 mmol) in THF (10 mL) at 0° C. in a 50 mL round-bottomed flask equipped with a magnetic stirrer was added $NaBH_4$ (25 mg, 0.66 mmol) and the mixture was stirred overnight at RT then cooled in an ice bath before quenching by addition of a 6 N aq. HCl solution (0.45 mL). After stirring for 15 min at +4° C., the mixture was basified with a 2 N aq. NaOH solution (1.35 mL). THF was then removed at 40° C. under vacuum and the solution was extracted with $CH_2Cl_2$ (50 mL), washed with brine (10 mL), dried over $Na_2SO_4$, filtered, and concentrated under vacuum. Purification by column chromatography ($SiO_2$, eluent cyclohexane:EtOAc=100:0 to 50:50) provided, after evaporation and drying, 6-methyl-2-(methylamino)quinolin-3-yl)methanol MDE32060 as a a white solid (73 mg, 55% yield).

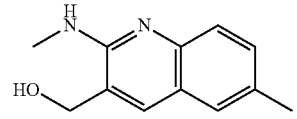

MDE 32060

MW: 202.25; Yield: 55%; White solid; Mp (° C.): 169.8
$^1$H-NMR (DMSO $d_6$, δ): 2.38 (s, 3H, $CH_3$), 2.94 (d, 3H, J=4.7 Hz, $NCH_3$), 4.47-4.49 (m, 2H, $CH_2OH$), 5.37 (t, 1H, J=5.4 Hz, $CH_2OH$), 6.22-6.24 (broad m, 1H, $NHCH_3$), 7.28 (dd, 1H, J=2.0 and 8.4 Hz, ArH), 7.40-7.42 (m, 1H, ArH), 7.46 (d, 1H, J=8.4 Hz, ArH), 7.74 (s, 1H, ArH).
$^{13}$C-NMR (DMSO $d_6$, δ): 20.7, 28.0, 59.9, 122.6, 124.4, 125.2, 126.3, 129.9, 130.2, 131.9, 145.2, 155.0.
MS-ESI m/z (% rel. Int.): 203 ([MH]$^+$, 100).
HPLC: Method B (10 min), XBridge™ column (5 µm, C18, 4.5×50 mm, Model #186003113), detection UV 254 nm, RT=4.21 min.

3-(Chloromethyl)-N,6-dimethylquinolin-2-amine hydrochloride MDE 32062

To a solution of 6-methyl-2-(methylamino)quinolin-3-yl)methanol MDE32060 (56 mg, 0.28 mmol) in dry $CH_2Cl_2$ (10 mL) at 0° C. under $N_2$ in a 25 mL round-bottomed flask equipped with a magnetic stirrer was added dropwise $SOCl_2$ (0.40 mL, 5.51 mmol) and the mixture was stirred for 2 days at RT. The volatiles were then removed at 40° C. under vacuum and the residue was taken up in $CH_2Cl_2$ (20 mL) before concentration back to dryness at 40° C. under vacuum (done 3 times) to give 3-(chloromethyl)-N,6-dimethylquinolin-2-amine hydrochloride MDE 32062 as an off-white solid (56 mg, 78% yield).

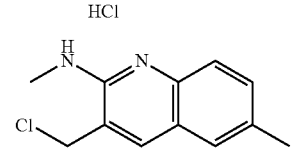

MDE 32062

MW: 257.16; Yield: 78%; Off-white solid; Mp (° C.): 92.4
$^1$H-NMR (DMSO $d_6$, δ): 2.44 (s, 3H, $CH_3$), 3.23 (d, 3H, J=4.7 Hz, $NCH_3$), 3.45-3.56 (broad m, NH), 4.98 (s, 2H, $CH_2$), 7.63 (dd, 1H, J=1.5 & 8.5 Hz, ArH), 7.67-7.71 (m, 1H, ArH), 8.11 (d, 1H, J=8.5 Hz, ArH), 8.45 (s, 1H, ArH), 9.09-9.32 (broad s, 1H, NH).
$^{13}$C-NMR (DMSO $d_6$, δ): 20.5, 30.1, 41.3, 117.9, 120.5, 122.1, 127.8, 134.1, 134.7, 141.8, 151.0, (1×C not observed).
MS-ESI m/z (% rel. Int.): 221 ([MH]$^+$, $^{35}$Cl, 100), 223 ([MH]$^+$, $^{37}$Cl, 32).
HPLC: Method A (10 min), XTerra™ column (5 µm, C18, 4.5×50 mm, Model #186000482), detection UV 254 nm, RT=5.51 min.

6,7-Dimethoxy-1-methyl-4-((6-methyl-2-(methylamino)quinolin-3-yl)methylisoquinolin-3-ol dihydrochloride 33

To a solution of 6,7-dimethoxy-1-methylisoquinolin-3-ol CCH 18060 (40 mg, 182 µmol) in toluene (15 mL) in a 20 mL microwave vial equipped with a magnetic stirrer was added 2 N aq. KOH solution (0.17 mL, 0.34 mmol) at RT followed by 3-(chloromethyl)-N,6-dimethylquinolin-2-amine hydrochloride MDE 32062 (39 mg, 152 µmol) and the mixture was stirred at 150° C. for 1.5 h under microwave irradiation. After cooling to RT, the mixture was diluted with H$_2$O (10 mL) before to be extracted with EtOAc (50 mL). The organic phase was isolated and the aqueous phase was further extracted with CH$_2$Cl$_2$ (50 mL). Both organic phases were washed with brine (10 mL), combined, dried over Na$_2$SO$_4$, filtered and concentrated at 40° C. under vacuum. Purification by column chromatography (SiO$_2$, eluent CH$_2$Cl$_2$:MeOH=100:0 to 94:6 to 90:10) gave 12 mg of 6,7-dimethoxy-1-methyl-4-((6-methyl-2-(methylamino)quinolin-3-yl)methyl)isoquinolin-3-ol. This free base was dissolved in MeOH (2 mL) in a 10 mL round-bottomed flask equipped with a magnetic stirrer before addition of a 0.09 M HCl solution in MeOH (1.0 mL). The reaction mixture was stirred for 5 min at RT and concentrated at 40° C. under vacuum to afford 6,7-dimethoxy-1-methyl-4-((6-methyl-2-(methylamino)quinolin-3-yl)methyl)isoquinolin-3-ol dihydrochloride 33 as a brown solid (14 mg, 19% yield).

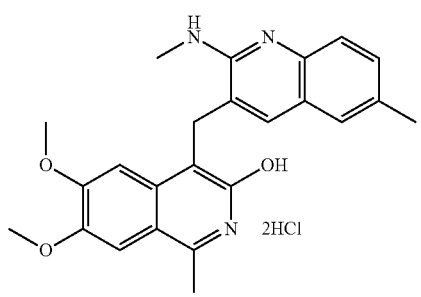

MW: 476.40; Yield: 19%; Brown solid; Mp (° C.)>250 (dec.).

R$_f$ (free base): 0.2 (CH$_2$Cl$_2$:MeOH=90:10).

$^1$H-NMR (CD$_3$OD, δ): 2.39 (s, 3H, CH$_3$), 3.06 (s, 3H, CH$_3$), 3.39 (s, 3H, CH$_3$), 3.94 (s, 3H, OCH$_3$), 4.03 (s, 3H, OCH$_3$), 4.33 (s, 2H, CH$_2$), 7.08 (s, 1H, ArH), 7.43-7.58 (m, 4H, 4×ArH), 7.87 (d, 1H, J=8.5 Hz, ArH).

$^{13}$C-NMR (CD$_3$OD, δ): 17.5, 20.9, 27.0, 30.0, 56.9, 57.3, 102.3, 106.2, 118.1, 119.4, 122.6, 124.1, 128.8, 134.7, 134.8, 137.1, 139.3, 141.1, 151.1, 151.7, 154.2, 159.7 (2×C not observed).

MS-ESI m/z (rel.int.): 404 ([MH]$^+$, 100).

HPLC: Method A (10 min), XTerra™ column (5 µm, C18, 4.5×50 mm, Model #186000482), detection UV 254 nm, RT=4.01 min, peak area 96.6%.

Preparation of 6,7-dimethoxy-4-((6-methyl-2-(methylamino)quinolin-3-yl)methyl)-1-propylisoquinolin-3-ol dihydrochloride 34

To a solution of 6,7-dimethoxy-1-propylisoquinolin-3-ol RBO 35142 (250 mg, 1 mmol) in toluene (15 mL) in a 20 mL microwave vial was added a 2 N KOH solution (1 mL, 2 mmol) following by 3-(chloromethyl)-N,6-dimethylquinolin-2-amine hydrochloride MDE 32062 (352 mg, 1.2 mmol). The reaction mixture was stirred at 160° C. for 1.5 h under microwave irradiation then cooled to RT. The volatiles were removed under vacuum and the residue was taken back in a mixture of CH$_2$Cl$_2$:MeOH=9:1 (50 mL). The organic layer was washed with water (3×20 mL), brine (20 mL), dried over Na$_2$SO$_4$, filtered and evaporated to give yellow solid that was purified by column chromatography (SiO$_2$, eluent CH$_2$Cl$_2$:MeOH=100:0 to 90:10) to give, after evaporation and drying, 6,7-dimethoxy-4-(6-methyl-2-methylamino-quinolin-3-ylmethyl)-1-propyl-isoquinolin-3-ol (26 mg). This free base was dissolved in MeOH (5 mL) and a 0.19 N HCl solution in MeOH (600 µL, 0.11 mmol) was slowly added. The reaction mixture was stirred at 4° C. for 15 min. After evaporation of the solvent and drying under vacuum pump over P$_2$O$_5$, 6,7-dimethoxy-4-((6-methyl-2-(methylamino)quinolin-3-yl)methyl)-1-propylisoquinolin-3-ol hydrochloride 34 was obtained as a yellow solid (28.7 mg, 5% yield).

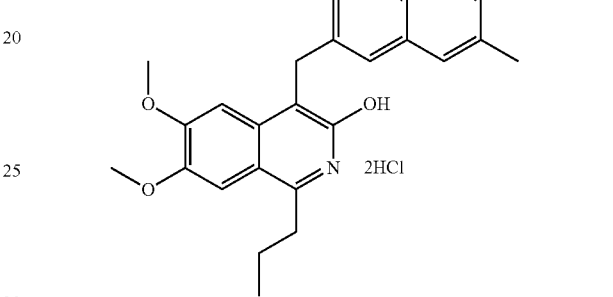

MW: 504.45; Yield: 5%; Yellow Solid; Mp (° C.): 264.2° C.

R$_f$: 0.20 (CH$_2$Cl$_2$:MeOH=9:1, free base).

$^1$H-NMR (CD$_3$OD, δ): 1.15 (t, 3H, J=6 Hz, CH$_3$), 2.00 (m, 2H, CH$_2$), 2.40 (s, 3H, CH$_3$), 3.30 (s, 2H, CH$_2$), 3.40 (s, 3H, NCH$_3$), 3.93 (s, 6H, O—CH$_3$), 4.04 (s, 3H, 0-CH$_3$), 4.36 (s, 2H, CH$_2$), 7.10 (s, 1H, ArH), 7.33-7.78 (m, 2H, ArH), 7.53-7.59 (m, 2H, ArH), 7.92 (d, 1H, J=9 Hz, ArH), 8.04 (s, 1H, ArH).

$^{13}$H-NMR (CD$_3$OD, δ): 14.3, 21.0, 24.7, 27.1, 30.2, 33.7, 57.0, 57.5, 102.7, 106.0, 109.9, 118.1, 119.3, 122.6, 123.8, 128.8, 134.7, 134.8, 137.1, 139.1, 141.6, 152.1, 152.6, 154.2, 155.0, 159.9.

MS-ESI m/z (% rel. Int.): 432 ([MH]$^+$, 100).

HPLC: Method A, XTerra™ column (5 µm, C18, 4.5×50 mm, Model #186000482), detection UV 254 nm, RT=4.14 min, peak area 99.0%.

Preparation of 4-((2-(ethylamino)-6-methylquinolin-3-yl)methyl)-6,7-dimethoxy-1-propylisoquinolin-3-ol dihydrochloride 35

2-(Ethylamino)-6-methylquinoline-3-carbaldehyde RBO 35156

To a solution of 2-chloro-6-methylquinoline-3-carbaldehyde (1.0 g, 4.86 mmol) in dioxane (10 mL) in a 20 mL microwave vial was added ethylamine (4 mL, 70% in water) and the resulting mixture was heated at 160° C. under microwave irradiation for 45 min. After cooling to RT, the mixture was poured into a solution THF:1 N HCl=1:1 (25 mL) and stirred for 25 min at RT. The mixture was neutralized until pH=7 with a satured solution of NaHCO$_3$ and extracted with CH$_2$Cl$_2$ (50 mL). The organic layer was washed with H$_2$O (3×30 mL), brine (30 mL), dried over Na₂SO₄, filtered and evaporated to give 2-(ethylamino)-6-methylquinoline-3-carbaldehyde RBO 35156 as a yellow solid (566 mg, 54% yield).

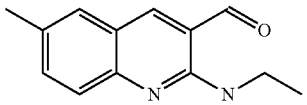

RBO 35156

MW: 214.27; Yield: 54%; Yellow Solid.
¹H-NMR (CDCl₃, δ): 1.33 (t, 3H, J=7.5 Hz, CH₃), 2.45 (s, 3H, CH₃), 3.67 (m, 2H, CH₂CH₃), 6.93 (s, 1H, ArH), 7.43 (s, 1H, ArH), 7.48 (d, 1H, J=9.0 Hz, ArH), 7.58 (d, 1H, J=9.0 Hz, ArH), 8.13 (s, 1H, ArH), 9.95 (s, 1H, HC=O).

(2-(Ethylamino)-6-methylquinolin-3-yl)methanol RBO 35160

To a solution of 2-(ethylamino)-6-methylquinoline-3-carbaldehyde RBO 35156 (500 mg, 2.33 mmol) in a mixture EtOH:THF=7:3 (35 mL) at 0° C. was added NaBH₄ (88 mg, 2.33 mmol) by small portions. The reaction mixture was stirred overnight at RT, cooled at 0° C. and treated by a 6 N HCl solution (6 mL). The solution was then neutralized with 2 N NaOH solution until pH=7 and concentrated under vacuum at 45° C. The crude residue was diluted in CH₂Cl₂ (50 mL), washed with brine (3×50 mL), dried over Na₂SO₄, filtered to give, after evaporation, (2-(ethylamino)-6-methylquinolin-3-yl)methanol RBO 35160 as a yellow solid (460 mg, 91% yield).

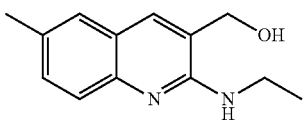

RBO 35160

MW: 216.29; Yield: 91%; Yellow Solid.
¹H-NMR (CDCl₃, δ): 1.29 (t, 3H, J=7.5 Hz, CH₃), 2.45 (s, 3H, CH₃), 3.57 (m, 2H, CH₂CH₃), 4.46 (s, 2H, CH₂OH), 6.86 (s, 1H, ArH), 7.13 (s, 1H, ArH), 7.35 (d, 1H, J=6.0 Hz, ArH), 7.57 (d, 1H, J=6.0 Hz, ArH).
MS-ESI m/z (rel.int.): 217 ([MH]⁺, 100).
HPLC: Method A, XTerra™ column (5 μm, C18, 4.5×50 mm, Model #186000482), detection UV 254 nm, RT=3.28 min, peak area 99.9%.

3-(Chloromethyl)-N-ethyl-6-methylquinolin-2-amine hydrochloride RBO 35162

To a solution of (2-(ethylamino)-6-methylquinolin-3-yl)methanol RBO 35160 (460 mg, 2.13 mmol) in CH₂Cl₂ (30 mL) in a round-bottomed flask equipped with a magnetic stirrer was added thionyl chloride (1.55 mL, 21.3 mmol). The mixture was stirred for 2 h at RT, evaporated under vacuum at 45° C., coevaporated twice with CH₂Cl₂ to remove SOCl₂ to afford 3-(chloromethyl)-N-ethyl-6-methylquinolin-2-amine hydrochloride RBO 35162 as a yellow solid (520 mg, 90% yield).

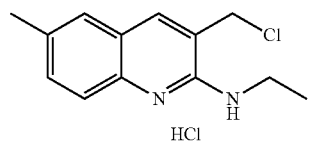 [SMILES: CCNc1nc2ccc(C)cc2cc1CCl ; Cl]

MW: 301.17; Yield: 90%; Mp (° C.): 253.5
¹H-NMR (CD₃OD, δ): 1.43 (t, 3H, J=7.5 Hz, CH₃CH₂), 2.50 (s, 3H, CH₃), 3.73 (q, 2H, J=7.5 Hz, CH₂CH₃), 4.89 (s, 2H, CH₂), 7.67 (m, 2H, 2×ArH), 7.86 (d, 1H J=6 Hz, ArH), 8.39 (s, 1H, ArH).

4-((2-(Ethylamino)-6-methylquinolin-3-yl)methyl)-6,7-dimethoxy-1-propylisoquinolin-3-ol dihydrochloride 35

To a solution of 6,7-dimethoxy-1-propylisoquinolin-3-ol RBO 34142 (250 mg, 1.0 mmol) in toluene (15 mL) in a 20 mL microwave vial with magnetic stirrer was added a 2 N LiOH solution (1 mL, 2.0 mmol) followed with 3-(chloromethyl)-N-ethyl-6-methylquinolin-2-amine hydrochloride RBO 35162 (271.2 mg, 1.0 mmol). The mixture was heated for 1.5 h at 150° C. under microwave irradiation. The vial was cooled to RT and the solution was extracted with CH₂Cl₂ (30 mL). The organic layer was washed with H₂O (3×30 mL), brine (30 mL), dried over Na₂SO₄ and filtered to give, after evaporation under reduced pressure, a yellow solid. Purification by column chromatography (SiO₂, eluent CH₂Cl₂:7 N NH₃ solution in MeOH=95:5) gave, after evaporation, 4-(6-ethylamino-[1,3]dioxolo[4,5-g]quinolin-7-ylmethyl)-6,7-dimethoxy-1-propyl-isoquinolin-3-ol. This free base was treated by a 0.49 N HCl solution in MeOH (5 mL) for 5 min at RT to give, after evaporation and drying, 4-((2-(ethylamino)-6-methylquinolin-3-yl)methyl)-6,7-dimethoxy-1-propylisoquinolin-3-ol dihydrochloride as yellow solid 35 (21.5 mg, 4% yield).

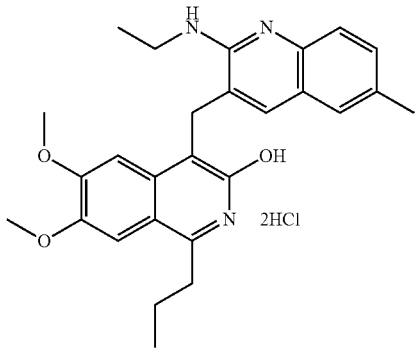

35

MW: 518.48; Yield: 4%; Yellow Solid; Mp (° C.): 252.6° C.
¹H-NMR (CD₃OD, δ): 1.13 (t, 3H, J=9 Hz, CH₃), 1.53 (t, 3H J=7.5 Hz, CH₃), 1.93 (m, 2H, CH₂), 2.41 (s, 3H, CH₃), 3.33 (shoulder behind MeOD, CH₂N), 3.78 (q, 2H, J=9 Hz, CH₂), 3.96 (s, 3H, OCH₃), 4.01 (s, 3H, OCH₃), 4.35 (s, 2H₂OCH₂O), 7.10 (s, 1H, ArH), 7.47 (s, 2H, 2×ArH), 7.57 (d, 1H, J=9 Hz, ArH), 7.70 (broad s, 1H, ArH), 7.85 (d, 1H, J=9 Hz, ArH).
¹³C-NMR (CD₃OD, δ): 13.8, 14.1, 20.9, 24.6, 27.5, 33.5, 39.1, 56.7, 57.2, 102.0, 105.7, 110.0, 118.0 (2×C), 122.5, 124.6, 128.7, 134.7 (2×C), 137.1, 140.0, 141.7, 151.3, 153.2, 159.4, (2×C not observed).

MS-ESI m/z (rel.int.): 446 ([MH]⁺, 100).

HPLC: Method B (10 min), XBridge™ column (5 μm, C18, 4.5×50 mm, Model #186003113), detection UV 254 nm, RT=4.58 min, peak area 95.0%.

Preparation of 4-((2-(dimethylamino)-6-methylquinolin-3-yl)methyl)-6,7-dimethoxy-1-propylisoquinolin-3-ol dihydrochloride 36

2-(Dimethylamino)-6-methylquinoline-3-carbaldehyde RBO 35148

To a stirred solution of 2-chloro-6-methoxyquinoline-3-carbaldehyde (1.0 g, 4.86 mmol) in dioxane (10 mL) in a 20 mL microwave vial equipped with a magnetic stirrer was added dimethylamine (40% in water, 6.1 mL, 48.6 mmol) and the reaction mixture was stirred for 45 min at 160° C. under microwave irradiation. After cooling to RT, the volatiles were removed at 40° C. under vacuum and the resulting yellow oil was taken back in CH₂Cl₂ (30 mL). The organic layer was washed with water (3×20 mL), brine (20 mL), dried over Na₂SO₄, filtered and concentrated under vacuum to give 2-(dimethylamino)-6-methylquinoline-3-carbaldehyde RBO 35148 as a yellow oil (988 mg, 95% yield).

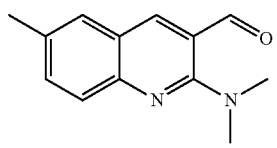

RBO 35148

MW: 214.26; Yield: 95%; Yellow oil.

¹H-NMR (CDCl₃, δ): 2.5 (s, 3H, CH₃), 3.20 (s, 6H, 2×NCH₃), 7.50 (m, 1H, 2×ArH), 7.69 (d, 1H, J=10 Hz, ArH), 8.35 (s, 1H, ArH), 10.15 (s, 1H, HC=O).

MS-ESI m/z (% rel. Int.): 215 ([MH]⁺, 100).

HPLC: Method A, XTerra™ column (5 μm, C18, 4.5×50 mm, Model #186000482), detection UV 254 nm, RT=3.33 min, peak area 98%.

(2-(Dimethylamino)-6-methylquinolin-3-yl)methanol RBO 40152

To a stirred solution of 2-(dimethylamino)-6-methylquinoline-3-carbaldehyde RBO 35148 (988 mg, 4.61 mmol) in a mixture EtOH:THF=50 mL:20 mL in a 250 mL round-bottomed flask equipped with a magnetic stirrer was added NaBH₄ (174 mg, 4.61 mmol) and the mixture was stirred overnight at RT, cooled in an ice bath and treated by a 6 N aq. HCl solution (2 mL). After stirring for 1 h at 4° C., the mixture was brought to pH=9 with a 2N aq. NaOH solution (6 mL). Volatiles were removed at 40° C. under vacuum and the solution was extracted with CH₂Cl₂ (50 mL). The organic layer was washed with water (3×20 mL), brine (20 mL), dried over Na₂SO₄, filtered, and concentrated under vacuum to give (2-(dimethylamino)-6-methylquinolin-3-yl)methanol RBO 40152 as yellow oil (900 mg, 90% yield).

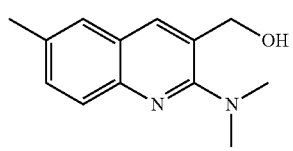

RBO 40152

MW: 216.29; Yield: 90%; Yellow oil.

¹H-NMR (CDCl₃, δ): 2.48 (s, 3H, CH₃), 2.94 (s, 6H, 2×NCH₃), 4.85 (s, 2H, CH₂), 7.44 (m, 2H, 2×ArH), 7.76 (d, 1H, J=9 Hz, ArH), 7.88 (s, 1H, ArH), OH not observed.

MS-ESI m/z (% rel. Int.): 217.0 ([MH]⁺, 100).

HPLC: Method A, XTerra™ column (5 μm, C18, 4.5×50 mm, Model #186000482), detection UV 254 nm, RT=3.18 min, peak area 98%.

3-(chloromethyl)-N,N,6-trimethylquinolin-2-amine hydrochloride RBO 35154

To a stirred solution of 2-(dimethylamino)-6-methylquinolin-3-yl)methanol RBO 40152 (900 mg, 4.16 mmol) in dry CH₂Cl₂ (30 mL) in a 100 mL round-bottomed flask equipped with a magnetic stirrer was added dropwise SOCl₂ (3 mL, 42 mmol). The mixture was stirred for 3 h at RT then concentrated to dryness at 40° C. under vacuum. The residue was coevaporated twice with CH₂Cl₂ (20 mL) at 40° C. under vacuum to give of 3-(chloromethyl)-N,N,6-trimethylquinolin-2-amine hydrochloride RBO 35154 as a yellow solid (558 mg, 50% yield).

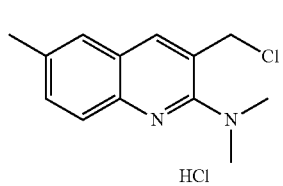

RBO 35154

MW: 271.19; Yield: 50%; Yellow solid.

¹H-NMR (MeOD, δ): 2.52 (s, 3H, CH₃), 3.53 (s, 6H, 2×OCH₃), 5.00 (s, 2H, CH₂), 7.73 (m, 2H, 2×ArH), 7.90 (d, 1H, J=9 Hz, ArH), 8.58 (s, 1H, ArH).

MS-ESI m/z (% rel. Int.): 231.1 ([MH]⁺, 100).

HPLC: Method A, XTerra™ column (5 μm, C18, 4.5×50 mm, Model #186000482), detection UV 254 nm, RT=3.43 min, peak area 65%. [RT=3.11 min, peak area 35% (m/z=217.1)]

4-((2-(Dimethylamino)-6-methylquinolin-3-yl)methyl)-6,7-dimethoxy-1-propylisoquinolin-3-ol dihydrochloride 36

To a stirred solution of 6,7-dimethoxy-1-propylisoquinolin-3-ol RBO 35142 (173 mg, 0.638 mmol) in toluene (10 mL) in a 100 mL round-bottomed flask equipped with a magnetic stirrer was added 3-(chloromethyl)-N,N,6-trimethylquinolin-2-amine hydrochloride RBO 35154 (158 mg, 0.638 mmol) and the mixture was stirred at 150° C. for 1.5 h. After cooling to RT, the volatiles were removed and the residue was taken back in CH₂Cl₂ (20 mL). This solution was washed with water (3×10 mL), brine (10 mL), dried over Na₂SO₄, filtered, and concentrated at 40° C. under vacuum. Purification by column chromatography (SiO₂, eluent CH₂Cl₂:7 N NH₃ solution in MeOH=100:0 to 95:5) gave after evaporation 20.2 mg of 4-((2-(dimethylamino)-6-methylquinolin-3-yl)methyl)-6,7-dimethoxy-1-propylisoquinolin-3-ol as a yellow solid. The free base was dissolved in MeOH (2 mL) and converted into salt by addition of a 0.19 M HCl solution in MeOH (0.525 mL). The reaction mixture was stirred for 5 min at RT then concentrated at 40° C. under vacuum to afford 4-(2-dimethylamino-6-methylquinolin-3-ylmethyl)-6,7-dimethoxy-1-propyl-soquinolin-3-ol dihydrochloride 36 as a yellow solid (22.2 mg, 6.7% yield).

36

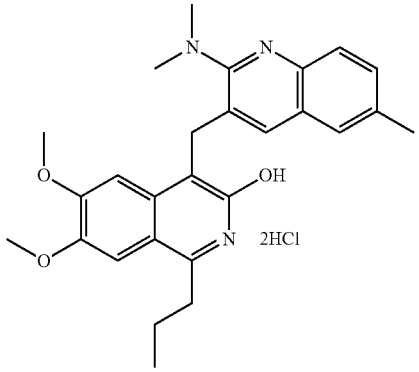

MW: 504.45; Yield: 6.7%; Yellow solid; Mp (° C.): 68.5

$^1$H-NMR (CD$_3$OD, δ): 1.10 (t, 3H, J=9 Hz, CH$_3$), 1.91 (q, 2H J=9 Hz, CH$_2$), 2.35 (s, 3H, CH$_3$), 3.35 (m, 2H, CH$_2$), 3.59 (s, 6H, 2×NCH$_3$), 3.89 (s, 3H, OCH$_3$), 3.99 (s, 3H, OCH$_3$), 4.60 (s, 2H, CH$_2$), 6.99 (s, 1H, ArH), 7.40 (s, 1H, ArH), 7.52 (s, 1H, ArH), 7.61 (m, 2H, 2×ArH), 7.90 (d, 1H, J=9 Hz, ArH).

$^{13}$C-NMR (CD$_3$OD, δ): 14.2, 21.0, 24.7, 29.5, 33.6, 43.4 (2×C), 56.9, 57.2, 102.7, 106.0, 112.3, 118.5 (2×C), 119.6, 123.8, 126.9, 128.5, 131.5, 135.8, 138.2, 141.2, 143.8, 152.2, 155.2, 157.4, 159.9, (2×C not observed).

MS-ESI m/z (% rel. Int.): 446.3 ([MH]$^+$, 100).

HPLC: Method A, XTerra™ column (5 μm, C18, 4.5×50 mm, Model #186000482), detection UV 254 nm, detection UV 254 nm, RT=4.27 min, peak area 97%.

Preparation of 6,7-dimethoxy-4-((6-methoxy-2-(methylamino)quinolin-3-yl)methyl)-1-methyl-isoquinolin-3-ol dihydrochloride 37

6-Methoxy-2-(methylamino)quinoline-3-carbaldehyde SLA 28150

To a stirred solution of 2-chloro-6-methoxyquinoline-3-carbaldehyde (1.50 g, 6.77 mmol) in 1,4-dioxan (10 mL) in a 20 mL microwave vial equipped with a magnetic stirrer was added methylamine (40 wt % solution in water, 2.10 mL, 24.3 mmol) and the reaction mixture was stirred for 6 h at 160° C. under microwave irradiation. After cooling to RT, the volatiles were removed at 40° C. under vacuum and the resulting yellow oil was taken up in a mixture of THF:1 N aq. HCl=1:1 (50 mL) and stirred for 1 h at RT. THF was removed at 40° C. under vacuum and the residue was then neutralised with a saturated NaHCO$_3$ aqueous solution before to be extracted with CH$_2$Cl$_2$ (100 mL). The organic phase was washed with brine (20 mL), dried over MgSO$_4$, filtered, and concentrated under vacuum, to give 6-methoxy-2-(methylamino)quinoline-3-carbaldehyde SLA 28150 as an orange oil (1.44 g, 98% yield).

SLA 28150

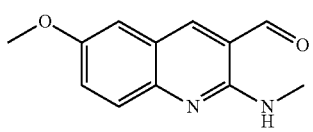

MW: 216.24; Yield: 98%; Orange oil.

$^1$H-NMR (CDCl$_3$, δ): 3.15 (d, 3H, J=4.9 Hz, NCH$_3$), 3.85 (s, 3H, OCH$_3$), 6.97 (d, 1H, J=2.9 Hz, ArH), 7.33 (dd, 1H, J=2.9 & 9.2 Hz, ArH), 7.64 (d, 1H, J=9.2 Hz, ArH), 7.84 (broad s, 1H, NH), 8.14 (s, 1H, ArH), 9.97 (s, 1H, HC=O).

$^{13}$C-NMR (CDCl$_3$, δ): 27.6, 55.5, 106.8, 117.4, 121.9, 125.9, 127.9, 147.1, 147.2, 154.5, 154.8, 193.1.

MS-ESI m/z (% rel. Int.): 217.1 ([MH]$^+$, 100).

HPLC: Method B (10 min), XBridge™ column (5 μm, C18, 4.5×50 mm, Model #186003113), detection UV 254 nm, RT=3.99 min.

((6-Methoxy-2-(methylamino)quinolin-3-yl)methanol SLA 28152

To a stirred solution of 6-methoxy-2-(methylamino) quinoline-3-carbaldehyde SLA 28150 (1.006 g, 4.65 mmol) in THF (80 mL) in a 250 mL round-bottomed flask equipped with a magnetic stirrer was added sodium borohydride NaBH$_4$ (0.176 g, 4.65 mmol) and the mixture was stirred for 4 h at RT then cooled in an ice bath before quenching by addition of a 1 N aq. HCl solution (40 mL). After stirring for 15 min at RT, the mixture was basified to pH=9 with a 2 N aq. NaOH solution. THF was then removed at 40° C. under vacuum and the solution was extracted with CH$_2$Cl$_2$ (200 mL), washed with brine (20 mL), dried over Na$_2$SO$_4$, filtered, and concentrated under vacuum to give (6-methoxy-2-(methylamino)quinolin-3-yl)methanol SLA 28152 as an orange oil (0.907 g, 89% yield).

SLA 28152

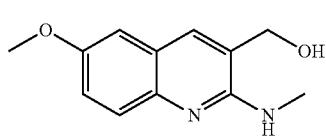

MW: 218.25; Yield: 89%; Orange oil.

$^1$H-NMR (CDCl$_3$, δ): 3.09 (s, 3H, NCH$_3$), 3.87 (s, 3H, OCH$_3$), 4.64 (s, 2H, CH$_2$), 6.97 (d, 1H, J=2.9 Hz, ArH), 7.19 (dd, 1H, J=2.9 Hz & 9.1 Hz, ArH), 7.62 (s, 1H, ArH), 7.69 (d, 1H, J=9.1 Hz, ArH), OH & NH not seen.

$^{13}$C-NMR (DMSO, δ): 28.1, 55.2, 59.9, 106.8, 119.2, 123.1, 124.7, 126.7, 131.7, 142.2, 153.8, 154.2.

MS-ESI m/z (% rel. Int.): 219.1 ([MH]$^+$, 100).

HPLC: Method A (10 min), XBridge™ column (5 μm, C18, 4.5×50 mm, Model #186003113), detection UV 214 nm, RT=5.01 min.

3-(Chloromethyl)-6-methoxy-N-methylquinolin-2-amine hydrochloride SLA 28154

To a stirred solution of (6-methoxy-2-(methylamino)quinolin-3-yl)methanol SLA 28152 (0.906 g, 4.15 mmol) in dry CH$_2$Cl$_2$ (100 mL) in a 250 mL round-bottomed flask equipped with a magnetic stirrer was added dropwise SOCl$_2$ (6.03 mL, 83.1 mmol). The mixture was stirred for 1 h at RT then concentrated to dryness at 40° C. under vacuum. The residue was then taken up in CH$_2$Cl$_2$ (20 mL) before concentration back to dryness at 40° C. under vacuum (done 3 times) to give 3-(chloromethyl)-6-methoxy-N-methylquinolin-2-amine hydrochloride SLA 28154 (1.20 g, >100%) as a yellow solid.

SLA 28154

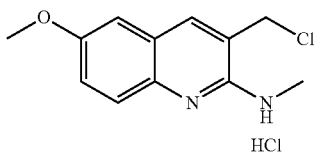

MW: 273.16; Yield: Quantitative; Yellow solid.

$^1$H-NMR (CDCl$_3$, exchange with CD$_3$OD, δ): 3.37 (s, 3H, NCH$_3$), 3.90 (s, 3H, OCH$_3$), 4.80 (s, 2H, CH$_2$), 7.09 (d, 1H, J=2.7 Hz, ArH), 7.35 (dd, 1H, J=2.7 & 9.2 Hz, ArH), 8.10 (s, 1H, ArH), 8.32 (d, 1H, J=9.2 Hz, ArH).

$^{13}$C-NMR (CDCl$_3$, exchange with CD$_3$OD, δ): 30.3, 40.9, 55.7, 108.4, 119.6, 121.6, 122.0, 123.2, 131.1, 141.3, 150.5, 157.2.

MS-ESI m/z (% rel. Int.): 237.3 ([MH]$^+$, $^{35}$Cl, 100), 239.3 ([MH]$^+$, $^{37}$Cl, 33).

HPLC: Method A (10 min), XBridge™ column (5 μm, C18, 4.5×50 mm, Model #186003113), detection UV 214 nm, RT=4.65 min.

6,7-Dimethoxy-4-((6-methoxy-2-(methylamino) quinolin-3-yl)methyl)-1-methyl-isoquinolin-3-ol dihydrochloride 37

To a solution of 6,7-dimethoxy-1-methylisoquinolin-3-ol CCH 18060 (77 mg, 351 μmol) in toluene (15 mL) in a 20 mL microwave vial equipped with a magnetic stirrer was added a 2 N aq. KOH solution (0.35 mL, 0.70 mmol) at RT followed by 3-(chloromethyl)-6-methoxy-N-methylquinolin-2-amine hydrochloride SLA 28154 (90 mg, 350 μmol) and the mixture was stirred at 160° C. for 1.5 h under microwave irradiation. After cooling to RT, the mixture was diluted with H$_2$O (10 mL) before extraction with EtOAc (50 mL). The organic phase was isolated and the aqueous phase was further extracted with CH$_2$Cl$_2$ (50 mL). Both organic phases were washed with brine (10 mL), combined, dried over Na$_2$SO$_4$, filtered and concentrated at 40° C. under vacuum. Purification by column chromatography (SiO$_2$, eluent CH$_2$Cl$_2$:MeOH=100:0 to 94:6 to 90:10) gave 19 mg of 6,7-dimethoxy-4-((6-methoxy-2-(methylamino)quinolin-3-yl)methyl)-1-methylisoquinolin-3-ol. This free base was dissolved in MeOH (2 mL) in a 10 mL round-bottomed flask equipped with a magnetic stirrer before addition of a 0.09 M HCl solution in MeOH (2 mL). The reaction mixture was stirred for 5 min at RT and concentrated at 40° C. under vacuum to afford 6,7-dimethoxy-4-((6-methoxy-2-(methylamino)quinolin-3-yl)methyl)-1-methylisoquinolin-3-ol dihydrochloride 37 as a brown solid (22 mg, 13% yield).

37

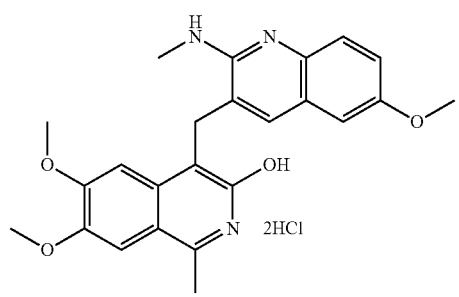

MW: 492.39; Yield: 13%; Brown solid; Mp (° C.)>250 (dec.).

$^1$H-NMR (CD$_3$OD, δ): 3.09 (s, 3H, CH$_3$), 3.39 (s, 3H, CH$_3$), 3.82 (s, 3H, OCH$_3$), 4.01 (s, 3H, OCH$_3$), 4.07 (s, 3H, OCH$_3$), 4.39 (s, 2H, CH$_2$), 7.03 (s, 2H, 2×ArH), 7.32 (d, 1H, J=9.1 Hz, ArH), 7.40-7.44 (m, 2H, 2×ArH), 7.98 (d, 1H, J=9.1 Hz, ArH).

$^{13}$C-NMR (CD$_3$OD, δ): 17.5, 26.6, 30.0, 56.1, 56.8, 57.3, 101.7, 105.3, 109.0, 109.6, 118.7, 119.3, 122.8, 123.0, 123.7, 130.7, 138.7, 140.4, 149.8, 151.0, 152.6, 158.0, 159.0, (1×C not observed).

MS-ESI m/z (rel.int.): 420 ([MH]$^+$, 100).

HPLC: Method B (10 min), XBridge™ column (5 μm, C18, 4.5×50 mm, Model #186003113), detection UV 254 nm, RT=4.30 min, peak area 96.4%.

Preparation of 6,7-dimethoxy-4-((6-methoxy-2-(propylamino)quinolin-3-yl)methyl)-1-propylisoquinolin-3-ol dihydrochloride 38

6-Methoxy-2-(propylamino)quinoline-3-carbaldehyde SLA 28172

To a stirred solution of 2-chloro-6-methoxyquinoline-3-carbaldehyde (1.50 g, 6.77 mmol) in THF (10 mL) in a 20 mL microwave vial equipped with a magnetic stirrer was added propan-1-amine (5.6 mL, 67.7 mmol) and the reaction mixture was stirred for 1.5 h at 160° C. under microwave irradiation. After cooling to RT, the volatiles were removed at 40° C. under vacuum and the resulting yellow oil was taken up in a mixture of THF:1 N aq. HCl=1:1 (50 mL) and stirred for 1 h at RT. The volatiles were then removed at 40° C. under vacuum and the residue was then neutralised with a saturated NaHCO$_3$ aqueous solution before extraction with CH$_2$Cl$_2$ (100 mL). The organic phase was washed with brine (20 mL), dried over MgSO$_4$, filtered, and concentrated under vacuum to give 6-methoxy-2-(propylamino)quinoline-3-carbaldehyde SLA 28172 as an orange solid (1.68 g, 99% yield).

SLA 28172

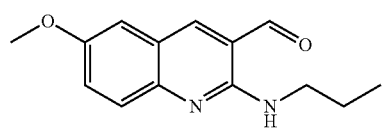

MW: 244.29; Yield: 99%; Orange solid; Mp (° C.): 110.0

$^1$H-NMR (CDCl$_3$, δ): 1.04 (t, 3H, J=7.4 Hz, CH$_3$), 1.66-1.77 (m, 2H, CH$_2$), 3.56-3.62 (m, 2H, NHCH$_2$), 3.87 (s, 3H, OCH$_3$), 6.97 (d, 1H, J=2.8 Hz, ArH), 7.33 (dd, 1H, J=2.8 & 9.2 Hz, ArH), 7.60 (d, 1H, J=9.2 Hz, ArH), 7.89 (broad s, 1H, NH), 8.12 (s, 1H, ArH), 9.97 (s, 1H, HC=O).

$^{13}$C-NMR (CDCl$_3$, δ): 11.7, 22.6, 42.5, 55.5, 106.7, 117.2, 121.9, 125.9, 128.0, 147.2, 147.3, 154.0, 154.8, 193.2.

HPLC: Method B (10 min), XBridge™ column (5 μm, C18, 4.5×50 mm, Model #186003113), detection UV 254 nm, RT=3.68 min.

(6-Methoxy-2-(propylamino)quinolin-3-yl)methanol SLA 28174

To a stirred solution of 6-methoxy-2-(propylamino)quinoline-3-carbaldehyde SLA 28172 (1.565 g, 6.41 mmol) in THF (120 mL) in a 250 mL round-bottomed flask equipped with a magnetic stirrer was added sodium borohydride NaBH₄ (0.242 g, 6.41 mmol) and the mixture was stirred overnight at RT then cooled in an ice bath before quenching by addition of a 1 N aq. HCl solution (40 mL). After stirring for 15 min at that temperature, the mixture was basified to pH=9 with a 2 N aq. NaOH solution. THF was then removed at 40° C. under vacuum and the solution was extracted with CH₂Cl₂ (200 mL), washed with brine (20 mL), dried over Na₂SO₄, filtered, and concentrated under vacuum to give (6-methoxy-2-(propylamino)quinolin-3-yl)methanol SLA 28174 as an orange solid (1.55 g, 98% yield).

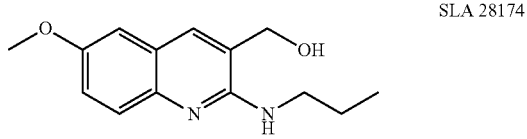 [SMILES: CCCNc1nc2ccc(OC)cc2cc1CO]

SLA 28174

MW: 246.30; Yield: 98%; Orange solid; Mp (° C.): 113.5
¹H-NMR (CDCl₃, δ): 1.02 (t, 3H, J=7.4 Hz, CH₃), 1.21 (s, 1H, OH), 1.62-1.75 (m, 2H, CH₂), 3.45-3.55 (m, 2H, NCH₂), 3.87 (s, 3H, OCH₃), 4.44 (s, 2H, OCH₂), 5.74 (broad s, 1H, NH), 6.74 (d, 1H, J=2.9 Hz, ArH), 6.80 (s, 1H, ArH), 7.19 (dd, 1H, J=2.9 Hz & 9.1 Hz, ArH), 7.59 (d, 1H, J=9.1 Hz, ArH).
¹³C-NMR (CDCl₃, δ): 11.8, 22.8, 42.9, 55.5, 63.9, 106.7, 120.3, 122.1, 123.3, 126.7, 134.1, 142.9, 154.5, 155.3.
MS-ESI m/z (% rel. Int.): 245 ([MH]⁺, 100),
HPLC: Method B (5 min), XBridge™ column (5 μm, C18, 4.5×50 mm, Model #186003113), detection UV 214 nm, RT=2.22 min.

3-(Chloromethyl)-6-methoxy-N-propylquinolin-2-amine hydrochloride SLA 28178

To a stirred solution of (6-methoxy-2-(propylamino)quinolin-3-yl)methanol SLA 28174 (1.45 g, 5.88 mmol) in dry CH₂Cl₂ (115 mL) in a 250 mL round-bottomed flask equipped with a magnetic stirrer was added dropwise SOCl₂ (8.53 mL, 118 mmol). The mixture was stirred for 2 h at RT then concentrated to dryness at 40° C. under vacuum. The residue was then taken up in CH₂Cl₂ (20 mL) before concentration back to dryness at 40° C. under vacuum (done 3 times), to give 3-(chloromethyl)-6-methoxy-N-propylquinolin-2-amine hydrochloride SLA 28178 (1.28 g, 82% yield) as a yellow solid.

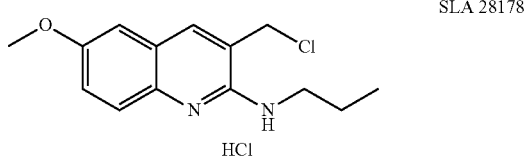 [SMILES: CCCNc1nc2ccc(OC)cc2cc1CCl ; Cl]

SLA 28178

MW: 301.21; Yield: 82%; Yellow solid; Mp (° C.): 118.8
¹H-NMR (CDCl₃, δ): 1.02 (t, 3H, J=6.5 Hz, CH₃), 1.82-1.90 (m, 2H, CH₂), 3.86 (s, 3H, OCH₃), 4.04-4.08 (m, 2H, CH₂), 5.02 (s, 2H, CH₂), 6.98 (s, 1H, ArH), 7.24-7.28 (m, 1H, ArH), 8.02 (s, 1H, ArH), 8.17 (broad s, 1H, NH), 8.82 (d, 1H, J=9.0 Hz, ArH), 13.6 (broad s, 1H, NH).
¹³C-NMR (CDCl₃, δ): 11.2, 21.9, 42.2, 45.7, 55.8, 108.0, 120.7, 121.6, 122.0, 123.1, 131.6, 141.4, 149.7, 157.1.
MS-ESI m/z (% rel. Int.): 265.0 ([MH]⁺, ³⁵Cl, 100), 267.0 ([MH]⁺, ³⁷Cl, 34).

HPLC: HPLC: Method B (10 min), XBridge™ column (5 μm, C18, 4.5×50 mm, Model #186003113), detection UV 214 nm, RT=4.10 min.

6,7-Dimethoxy-4-((6-methoxy-2-(propylamino)quinolin-3-yl)methyl)-1-propylisoquinolin-3-ol dihydrochloride 38

To a stirred solution of 3-(chloromethyl)-6-methoxy-N-propylquinolin-2-amine hydrochloride SLA 28178 (308 mg, 1.16 mmol) in toluene (10 mL) in a 20 mL microwave vial equipped with a magnetic stirrer was added 6,7-dimethoxy-1-methylisoquinolin-3-ol CCH 18060 (255 mg, 1.16 mmol) followed by a 2.0 N aq. LiOH solution (1.17 mL, 2.34 mmol) and the mixture was stirred at 150° C. for 1.5 h under microwave irradiation. After cooling to RT, the mixture was diluted with CH₂Cl₂:MeOH=9:1 (150 mL) and washed with brine (20 mL), dried over Na₂SO₄, filtered, and concentrated at 40° C. under vacuum. Purification by column chromatography (SiO₂, eluent EtOAc:MeOH=100:0 to 92:8) followed by a new purification by column chromatography (SiO₂, eluent CH₂Cl₂:MeOH=100:0 to 94:6) provided 37.6 mg of a brown solid. This free base was dissolved in CH₂Cl₂ (2 mL) in a 10 mL round-bottomed flask equipped with a magnetic stirrer before addition of a 0.49 M HCl solution in MeOH (0.70 mL). The reaction mixture was stirred for 5 min at RT and concentrated at 40° C. under vacuum to afford 6,7-dimethoxy-4-((6-methoxy-2-(propylamino)quinolin-3-yl)methyl)-1-methylisoquinolin-3-ol dihydrochloride 38 as a yellow solid (36.7 mg, 6% yield).

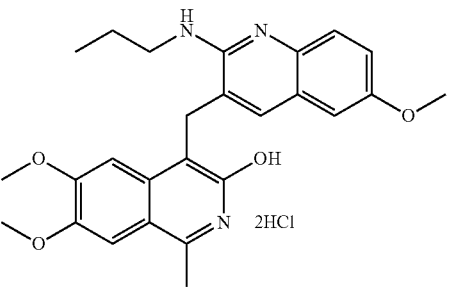

38

MW: 520.45; Yield: 6%; Yellow solid; Mp (° C.): 148.3
¹H-NMR (CD₃OD, δ): 1.14 (t, 3H, J=7.2 Hz, CH₃), 1.90-1.95 (m, 2H, CH₂), 2.97 (s, 3H, CH₃), 3.62-3.71 (m, 2H, CH₂), 3.83 (s, 3H, OCH₃), 4.00 (s, 6H, 2×OCH₃), 4.36 (s, 2H, CH₂), 7.08 (s, 1H, ArH), 7.21 (s, 1H, ArH), 7.34-7.38 (m, 2H, 2×ArH), 7.87 (d, 1H, J=9.0 Hz, ArH), 7.91 (s, 1H, ArH).
MS-ESI m/z (% rel. Int.): 448 ([MH]⁺, 100).
HPLC: Method B (10 min), X Bridge™ column (5 μm, C18, 4.5×50 mm, Model #186003113), detection UV 254 nm, RT=4.26 min, peak area 96.2%.

Preparation of 1-ethyl-6,7-dimethoxy-4-((6-methoxy-2-(methylamino)quinolin-3-yl)methyl)isoquinolin-3-ol 39

To a stirred solution of 1-ethyl-6,7-dimethoxyisoquinolin-3-ol SLA 28136 (200 mg, 0.86 mmol) in toluene (10 mL) in a 20 mL microwave vial equipped with a magnetic stirrer was added 3-(chloromethyl)-6-methoxy-N-methylquinolin-2-amine hydrochloride SLA 28154 (234 mg, 0.86 mmol) at RT followed by a 2 N aq. LiOH solution (0.86 mL, 1.72 mmol) and the mixture was stirred at 150° C. for 1.5 h under microwave irradiation. After cooling to RT, the mixture was diluted with a mixture CH₂Cl₂:MeOH=9:1 (150 mL), washed with brine (20 mL), dried over Na₂SO₄, filtered, and concentrated at 40° C. under vacuum. Purification by column chromatography (SiO₂, eluent CH₂Cl₂:MeOH=100:0 to 92:8) provided 21 mg of 1-ethyl-6,7-dimethoxy-4-((6-methoxy-2-(methylamino)quinolin-3-yl)methyl)isoquinolin-3-ol as a brown solid. This free base was dissolved in CH₂Cl₂ (2 mL) in a 10 mL round-bottomed flask equipped with a magnetic stirrer before addition of a 0.49 M HCl solution in MeOH (0.40 mL). The reaction mixture was stirred for 5 min at RT then concentrated at 40° C. under vacuum to afford 1-ethyl-6,7-dimethoxy-4-((6-methoxy-2-(methylamino)quinolin-3-yl)methyl)isoquinolin-3-ol dihydrochloride 39 as a yellow solid (20.0 mg, 5% yield).

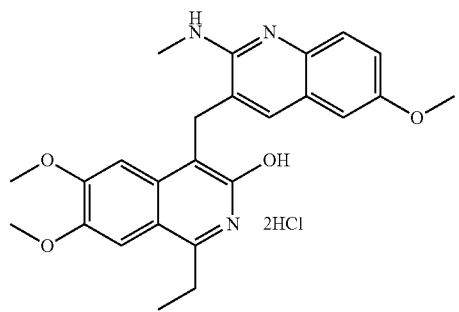

39

MW: 506.42; Yield: 5%; Yellow solid; Mp (° C.): 198.0
¹H-NMR (CD₃OD, δ): 1.54 (t, 3H, J=7.4 Hz, CH₃), 3.38 (s, 3H, NCH₃), 3.43 (q, 2H, J=7.4 Hz, CH₂CH₃), 3.76 (s, 3H, OCH₃), 3.92 (s, 3H, OCH₃), 4.05 (s, 3H, OCH₃), 4.34 (s, 2H, CH₂), 7.08 (s, 1H, ArH), 7.13 (s, 1H, ArH), 7.32 (dd, 1H, J=1.6 & 9.2 Hz, ArH), 7.53 (s, 1H, ArH), 7.56 (s, 1H, ArH), 7.92 (d, 1H, J=9.2 Hz, ArH).
¹³C-NMR (CD₃OD, δ): 14.7, 25.5, 27.0, 30.0, 56.3, 56.9, 57.4, 102.6, 105.8, 109.5, 109.8, 118.7, 119.6, 123.3, 123.7, 124.3, 131.2, 138.9, 141.7, 152.1, 152.9, 153.5, 156.1, 158.7, 159.9.
MS-ESI m/z (% rel. Int.): 434 ([MH]⁺, 100).
HPLC: Method B (10 min), X Bridge™ column (5 μm, C18, 4.5×50 mm, Model #186003113), detection UV 254 nm, RT=4.11 min, peak area 95.8%.

Preparation of 1-ethyl-6,7-dimethoxy-4-((6-methoxy-2-(ethylamino)quinolin-3-yl)methyl)isoquinolin-3-ol dihydrochloride 40

2-(Ethylamino)-6-methoxyquinoline-3-carbaldehyde SLA 28162

To a stirred solution of 2-chloro-6-methoxyquinoline-3-carbaldehyde (1.51 g, 6.80 mmol) in THF (10 mL) in a 20 mL microwave vial equipped with a magnetic stirrer was added ethylamine (2 M in THF, 33.8 mL, 67.6 mmol) and the mixture was stirred at 160° C. for 6 h under microwave irradiation. After cooling to RT, the volatiles were removed under vacuum at 40° C. and the resulting yellow oil was taken up in a mixture of THF:1 N aq. HCl=1:1 (50 mL) and stirred for 15 min at RT. THF was removed at 40° C. under vacuum and the residue was then neutralised with a saturated NaHCO₃ aqueous solution before to be extracted with CH₂Cl₂ (100 mL). The organic phase was washed with brine (20 mL), dried over MgSO₄, filtered, and concentrated at 40° C. under vacuum to give 2-(ethylamino)-6-methoxyquinoline-3-carbaldehyde SLA 28162 as an orange oil (1.19 g, 76% yield).

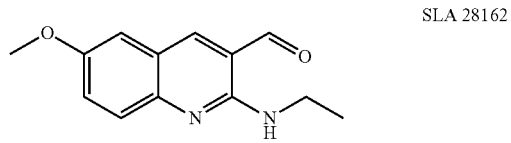 [SMILES: CCNc1nc2ccc(OC)cc2cc1C=O]

SLA 28162

MW: 230.26; Yield: 76%; Orange oil.
¹H-NMR (CDCl₃, δ): 1.33 (t, 3H, J=7.2 Hz, CH₂CH₃), 3.60-3.70 (m, 2H, CH₂), 3.95 (s, 3H, OCH₃), 6.96 (d, 1H, J=2.9 Hz, ArH), 7.33 (dd, 1H, J=2.9 & 9.2 Hz, ArH), 7.60 (d, 1H, J=9.2 Hz, ArH), 7.82 (broad s, 1H, NH), 8.13 (s, 1H, ArH), 9.97 (s, 1H, HC=O).
¹³C-NMR (CDCl₃, δ): 14.8, 35.4, 55.5, 106.4, 117.2, 121.9, 125.8, 128.0, 147.1, 147.3, 153.8, 154.8, 193.1.
MS-ESI m/z (% rel. Int.): 231 ([MH]⁺, 100)
HPLC: Method B (10 min), XBridge™ column (5 μm, C18, 4.5×50 mm, Model #186003113), detection UV 254 nm, RT=3.47 min.

(2-(Ethylamino)-6-methoxyquinolin-3-yl)methanol SLA 28164

To a stirred solution of SLA 28162 (1.495 g, 6.49 mmol) in THF (120 mL) in a 250 mL round-bottomed flask equipped with a magnetic stirrer was added sodium borohydride NaBH₄ (0.246 g, 6.50 mmol) and the mixture was stirred overnight at RT then cooled in an ice bath before quenching by addition of a 1 N aq. HCl solution (40 mL). After stirring for 15 min at RT, the mixture was basified to pH=9 with a 2 N aq. NaOH solution. THF was then removed at 40° C. under vacuum and the solution was extracted with CH₂Cl₂ (200 mL), washed with brine (20 mL), dried over Na₂SO₄, filtered, and concentrated under at 40° C. under vacuum to give (2-(ethylamino)-6-methoxyquinolin-3-yl)methanol SLA 28164 as an orange oil (1.17 g, 78% yield).

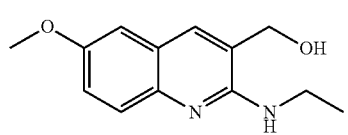

SLA 28164

MW: 232.28; Yield: 78%; Orange oil.
¹H-NMR (CDCl₃, δ): 1.29 (t, 3H, J=7.3 Hz, CH₂CH₃), 3.30 (broad s, 1H, OH), 3.52-3.61 (m, 2H, CH₂CH₃), 3.92 (s, 3H, OCH₃), 4.46 (s, 2H, CH₂OH), 5.64 (broad s, 1H, NH), 6.74 (d, 1H, J=2.8 Hz, ArH), 6.86 (s, 1H, ArH), 7.19 (dd, 1H, J=2.8 & 9.1 Hz, ArH), 7.60 (d, 1H, J=9.1 Hz, ArH).
¹³C-NMR (CDCl₃, δ): 14.9, 35.9, 55.5, 63.9, 106.7, 120.4, 122.1, 123.0, 126.8, 134.2, 143.0, 154.6, 155.2.
MS-ESI m/z (% rel. Int.): 233.2 ([MH]⁺, 100).
HPLC: Method B (10 min), XBridge™ column (5 μm, C18, 4.5×50 mm, Model #186003113), detection UV 254 nm, RT=3.33 min.

3-(Chloromethyl)-N-ethyl-6-methoxyquinolin-2-amine SLA 28166

To a stirred solution of (2-(ethylamino)-6-methoxyquinolin-3-yl)methanol SLA 28164 (1.150 g, 4.95 mmol) in dry CH$_2$Cl$_2$ (127 mL) a 250 mL round-bottomed flask equipped with a magnetic stirrer was added dropwise SOCl$_2$ (7.18 mL, 99.0 mmol). The mixture was stirred for 2 h at RT then concentrated to dryness at 40° C. under vacuum. The residue was taken up in CH$_2$Cl$_2$ (20 mL) before concentration back to dryness at 40° C. under vacuum (done 3 times) to give 3-(chloromethyl)-N-ethyl-6-methoxyquinolin-2-amine hydrochloride SLA 28166 as a yellow solid (1.43 g, 100% yield) that was used immediately in the next step.

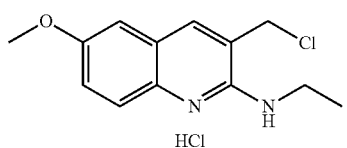

SLA 28166

MW: 287.18; Yield: 100%; Yellow solid; Mp (° C.): 168.7
$^1$H NMR (CDCl$_3$, δ): 1.44 (t, 3H, J=7.1 Hz, CH$_2$CH$_3$), 3.86 (s, 3H, OCH$_3$), 4.10-4.17 (m, 2H, CH$_2$CH$_3$), 5.05 (s, 2H, CH$_2$Cl), 7.00 (d, 1H, J=2.2 Hz, ArH), 7.25-7.29 (m, 1H, ArH), 8.05 (s, 1H, ArH), 8.42-8.50 (broad m, 1H, NH), 8.83 (d, 1H, J=9.2 Hz, ArH), 13.51 (broad s, 1H, NH).
$^{13}$C-NMR (CDCl$_3$, δ): 14.0, 39.2, 42.0, 55.8, 108.1, 120.3, 121.6, 122.4, 122.9, 131.5, 141.3, 149.5, 157.0.
MS-ESI m/z (rel.int.): 251 ([MH]$^+$, $^{35}$Cl, 100), 253 ([MH]$^+$, $^{37}$Cl, 35).
HPLC: Method B (10 min), XBridge™ column (5 μm, C18, 4.5×50 mm, Model #186003113), detection UV 254 nm, RT=3.92 min.

1-Ethyl-6,7-dimethoxy-4-((6-methoxy-2-(ethyl-amino)quinolin-3-yl)methylisoquinolin-3-ol dihydrochloride 40

To a stirred solution of 1-ethyl-6,7-dimethoxyisoquinolin-3-ol SLA 28136 (250 mg, 1.07 mmol) in toluene (10 mL) in a 20 mL microwave vial equipped with a magnetic stirrer was added 3-(chloromethyl)-N-ethyl-6-methoxyquinolin-2-amine hydrochloride SLA 28166 (308 mg, 1.07 mmol) followed by 2N aq. LiOH solution (1.07 ml, 2.14 mmol) and the mixture was stirred for 1.5 h at 150° C. under microwave irradiation. After cooling to RT, the mixture was diluted with CH$_2$Cl$_2$:MeOH=9:1 (150 mL) and washed with brine (20 mL), dried over Na$_2$SO$_4$, filtered, and concentrated at 40° C. under vacuum. Purification by column chromatography (SiO$_2$, eluent EtOAc:MeOH=100:0 to 95:5) followed by a new purification by column chromatography (SiO$_2$, eluent CH$_2$Cl$_2$:MeOH=100:0 to 92:8) provided 29 mg of 1-ethyl-4-((2-(ethylamino)-6-methoxyquinolin-3-yl)methyl)-6,7-dimethoxyisoquinolin-3-ol as a brown solid. This product was dissolved in CH$_2$Cl$_2$ (2 mL) in a 10 mL round-bottomed flask equipped with a magnetic stirrer before addition of a 0.49 M HCl solution in MeOH (0.55 mL). The reaction mixture was stirred for 5 min at RT then concentrated at 40° C. under vacuum to afford 1-ethyl-4-((2-(ethylamino)-6-methoxyquinolin-3-yl)methyl)-6,7-dimethoxyisoquinolin-3-ol dihydrochloride 40 as a yellow solid (20 mg, 4% yield).

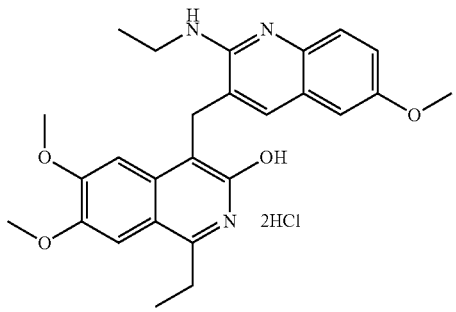

40

MW: 520.45; Yield: 4%; Yellow solid; Mp (° C.): 218.4 (dec.)
$^1$H NMR (CD$_3$OD, δ): 1.40-1.44 (m, 6H, 2×CH$_3$), 3.30 (q, 2H, J=6.9 Hz, CH$_2$CH$_3$), 3.67 (q, 2H, J=7.0 Hz, CH$_2$CH$_3$), 3.70 (s, 3H, OCH$_3$), 3.87 (s, 3H, OCH$_3$), 3.92 (s, 3H, OCH$_3$), 4.26 (s, 2H, CH$_2$), 6.99 (s, 1H, ArH), 7.08 (s, 1H, ArH), 7.25 (d, 1H, J=9.1 Hz, ArH), 7.39 (s, 1H, ArH), 7.63 (s, 1H, ArH), 7.80 (d, 1H, J=9.1 Hz, ArH).
$^{13}$C-NMR (CD$_3$OD, δ): 13.8, 14.7, 25.4, 27.4, 39.0, 56.3, 56.8, 57.3, 102.2, 105.5, 109.5, 110.0, 117.8, 119.6, 123.3, 123.6, 124.9, 131.2, 139.8, 141.7, 151.6, 152.5, 155.3, 158.8, 159.5.
MS-ESI m/z (% rel. Int.): 462 ([MH]$^+$, 100).
HPLC: Method B (10 min), X Bridge™ column (5 μm, C18, 4.5×50 mm, Model #186003113), detection UV 254 nm, RT=4.46 min, peak area 99.4%.

Preparation of 1-ethyl-6,7-dimethoxy-4-((6-ethoxy-2-(ethylamino)quinolin-3-yl)methyl)isoquinolin-3-ol dihydrochloride 41

2-Chloro-6-hydroxyquinoline-3-carbaldehyde SLA 41026

To a solution of 2-chloro-6-methoxyquinoline-3-carbaldehyde (1.01 g, 4.54 mmol) in dry CH$_2$Cl$_2$ (36 mL) in a 100 mL round-bottomed flask equipped with a magnetic stirrer at 0° C. under N$_2$ was added dropwise BBr$_3$ (1.0 N solution in CH$_2$Cl$_2$, 13.60 mL, 13.60 mmol). After complete addition, the bath was removed and stirring was continued overnight at RT. The reaction mixture was then added dropwise to a mixture of water and ice (50 mL) under stirring. After complete addition, the mixture was stirred for 30 min at RT and then filtered to give, after drying, 2-chloro-6-hydroxyquinoline-3-carbaldehyde as a yellow solid (0.77 g, 82% yield).

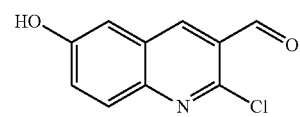

SLA 41026

MW: 207.61; Yield: 82%; Yellow solid; Mp (° C.): 205.0
$^1$H-NMR (DMSO, δ): 7.43 (d, 1H, J=2.7 Hz, ArH), 7.52 (dd, 1H, J=2.7 & 9.1 Hz, ArH), 7.90 (d, 1H, J=9.1 Hz, ArH), 8.77 (s, 1H, ArH), 10.35 (s, 1H, HC=O), 10.46 (broad s, 1H, OH).
$^{13}$C-NMR (DMSO, δ): 110.2, 126.1, 126.2, 127.8, 129.3, 139.5, 143.7, 145.4, 156.7, 189.6.

MS-ESI m/z (% rel. Int.): 208 ([MH]+, 35Cl, 100), 210 ([MH]+, 37Cl, 36).

HPLC: Method B (5 min), XBridge™ column (5 μm, C18, 4.5×50 mm, Model #186003113), detection UV 254 nm, RT=2.55 min.

2-Chloro-6-ethoxyquinoline-3-carbaldehyde SLA 41028

To a solution of 2-chloro-6-hydroxyquinoline-3-carbaldehyde SLA 41026 (0.70 g, 3.37 mmol) in dry DMF (15 mL) in a 50 mL round-bottomed flask equipped with a magnetic stirrer was added $Cs_2CO_3$ (1.21 g, 3.71 mmol) and the reaction mixture was stirred at RT for 10 min before adding bromoethane (0.30 mL, 4.05 mmol). The reaction mixture was stirred overnight at RT, then diluted with $Et_2O$ (100 mL) and $H_2O$ (10 mL). The organic phase was isolated and further washed with $H_2O$ (2×10 mL), brine (20 mL), dried over $Na_2SO_4$, filtered, and concentrated at 40° C. under vacuum. Purification by column chromatography ($SiO_2$, eluent cyclohexane:EtOAc:=100:0 to 75:25) provided, after evaporation and drying, 2-chloro-6-ethoxyquinoline-3-carbaldehyde SLA 41028 as a yellow solid (544 mg, 68% yield).

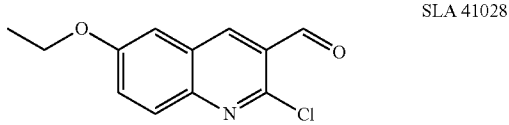 [SMILES: CCOc1ccc2nc(Cl)c(C=O)cc2c1]

SLA 41028

MW: 235.67; Yield: 68%; Yellow solid; Mp (° C.): 165.7

$^1$H-NMR (CDCl$_3$, δ): 1.53 (t, 3H, J=7.0 Hz, CH$_3$), 4.17 (q, 2H, J=7.0 Hz, CH$_2$), 7.17 (d, 1H, J=2.7 Hz, ArH), 7.51 (dd, 1H, J=2.7 & 9.2 Hz, ArH), 7.95 (d, 1H, J=9.2 Hz, ArH), 8.62 (s, 1H, ArH), 10.55 (s, 1H, HC=O).

$^{13}$C-NMR (CDCl$_3$, δ): 14.6, 64.2, 107.1, 126.4, 126.8, 127.8, 129.9, 138.6, 145.8, 147.6, 158.2, 189.5.

MS-ESI m/z (% rel. Int.): 236 ([MH]+, 100).

HPLC: Method B (5 min), XBridge™ column (5 μm, C18, 4.5×50 mm, Model #186003113), detection UV 254 nm, RT=3.32 min.

6-Ethoxy-2-(ethylamino)quinoline-3-carbaldehyde SLA 41034

To a stirred solution of 2-chloro-6-ethoxyquinoline-3-carbaldehyde (298 mg, 1.26 mmol) in a 20 mL microwave vial equipped with a magnetic stirrer was added ethylamine (2.0 N in THF, 13.0 mL, 26.0 mmol) and the reaction mixture was stirred for 10 h at 140° C. under microwave irradiation then for 13 h at 130° C. still under microwave irradiation. After cooling to RT, the reaction mixture was concentrated to dryness at 40° C. under vacuum and the resulting yellow oil was taken up in a mixture of THF:1 N aq. HCl=1:1 (50 mL) and stirred for 1 h at RT. The volatiles were then removed at 40° C. under vacuum and the residue was then neutralised with saturated NaHCO$_3$ aqueous solution before extraction with CH$_2$Cl$_2$ (100 mL). The organic phase was washed with brine (20 mL), dried over MgSO$_4$, filtered, and concentrated under vacuum, which gave 6-ethoxy-2-(ethylamino)quinoline-3-carbaldehyde SLA 41034 as an orange solid (313 mg, >100% yield).

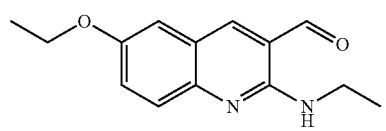

SLA 41034

MW: 244.29; Yield: quantitative; Orange solid.

$^1$H-NMR (CDCl$_3$, δ): 1.33 (t, 3H, J=7.2 Hz, CH$_3$), 1.47 (t, 3H, J=7.0 Hz, CH$_3$), 3.61-3.70 (m, 2H, NCH$_2$), 4.09 (q, 2H, J=7.0 Hz, OCH$_2$), 6.95 (d, 1H, J=2.6 Hz, ArH), 7.33 (dd, 1H, J=2.6 & 9.1 Hz, ArH), 7.60 (d, 1H, J=9.1 Hz, ArH), 7.81 (broad s, 1H, NH), 8.12 (s, 1H, ArH), 9.96 (s, 1H, HC=O).

$^{13}$C-NMR (CD$_3$OD, δ): 14.8, 14.8, 35.4, 63.8, 107.5, 117.2, 121.9, 126.2, 127.9, 147.2, 153.8, 154.1, 193.1, (1×C not observed).

MS-ESI m/z (% rel. Int.): 245 ([MH]+, 100).

HPLC: Method B (5 min), X Bridge™ column (5 μm, C18, 4.5×50 mm, Model #186003113), detection UV 254 nm, RT=2.13 min.

(6-Ethoxy-2-(ethylamino)quinolin-3-yl)methanol SLA 41040

To a stirred solution of 6-ethoxy-2-(ethylamino)quinoline-3-carbaldehyde SLA 41034 (0.605 g, 2.48 mmol) in THF (50 mL) in a 250 mL round-bottomed flask equipped with a magnetic stirrer was added NaBH$_4$ (0.094 g, 2.48 mmol) and the mixture was stirred overnight at RT then cooled in an ice bath before quenching by addition of a 1 N aq. HCl solution (40 mL). After stirring for 15 min at that temperature, the mixture was basified to pH=9 with a 2 N aq. NaOH solution. THF was then removed at 40° C. under vacuum and the solution was extracted with CH$_2$Cl$_2$ (200 mL), washed with brine (20 mL), dried over Na$_2$SO$_4$, filtered, and concentrated under vacuum to give (6-ethoxy-2-(ethylamino)quinolin-3-yl)methanol SLA 41040 as an orange solid (481 mg, 79% yield).

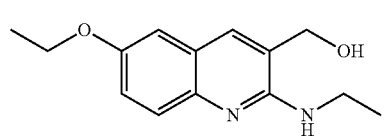

SLA 41040

MW: 246.30; Yield: 79%; Orange solid, Mp (° C.): 133.8

$^1$H-NMR (CDCl$_3$, δ): 1.32 (t, 3H, J=9.0 Hz, CH$_3$), 1.43-1.51 (m, 3H, CH$_3$), 3.52-3.58 (m, 2H, CH$_2$), 4.07 (q, 2H, J=6.9 Hz, CH$_2$), 4.48 (s, 2H, CH$_2$), 5.64 (broad s, 1H, NH), 6.75 (d, 1H, J=2.6 Hz, ArH), 6.92 (s, 1H, ArH), 7.17-7.23 (m, 1H, ArH), 7.61 (d, 1H, J=9.0 Hz, ArH).

$^{13}$C-NMR (CDCl$_3$, δ): 14.9, 14.9, 36.0, 63.8, 63.9, 107.7, 120.8, 122.1, 123.3, 126.8, 134.2, 142.9, 153.9, 155.1.

MS-ESI m/z (% rel. Int.): 247 ([MH]+, 100).

HPLC: Method B (5 min), XBridge™ column (5 μm, C18, 4.5×50 mm, Model #186003113), detection UV 254 nm, RT=2.17 min.

3-(Chloromethyl)-6-ethoxy-N-ethylquinolin-2-amine hydrochloride SLA 41042

To a stirred solution of (6-ethoxy-2-(ethylamino)quinolin-3-yl)methanol SLA 41040 (0.457 g, 1.86 mmol) in dry CH$_2$Cl$_2$ (40 mL) in a 100 mL round-bottomed flask equipped with a magnetic stirrer was added dropwise SOCl₂ (2.63 mL, 37.1 mmol). The mixture was stirred for 4 h at RT then concentrated to dryness at 40° C. under vacuum. The residue was then taken up in CH₂Cl₂ (20 mL) before concentration back to dryness at 40° C. under vacuum (done 3 times) to give 3-(chloromethyl)-6-ethoxy-N-ethylquinolin-2-amine hydrochloride SLA 41042 as a yellow solid (552 mg, 99% yield).

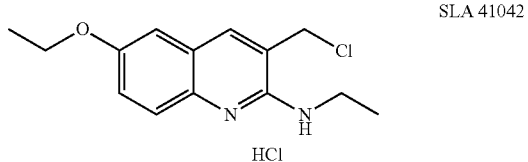 [SMILES: CCNc1nc2ccc(OCC)cc2cc1CCl ; Cl]

SLA 41042

MW: 301.21; Yield: 99%; Yellow solid; Mp (° C.): 118.7

¹H-NMR (CD₃OD, δ): 1.38-1.50 (m, 6H, 2×CH₃), 3.73 (q, 2H, J=8.4 Hz, CH₂), 4.16 (q, 2H, J=7.0 Hz, CH₂), 4.91 (s, 2H, CH₂), 7.36 (s, 1H, ArH), 7.43-7.47 (m, 1H, ArH), 7.92 (d, 1H, J=9.3 Hz, ArH), 8.41 (s, 1H, ArH).

¹³C-NMR (CD₃OD, δ): 13.7, 15.0, 38.8, 42.0, 65.4, 110.7, 119.8, 123.5, 123.8, 124.9, 132.0, 143.7, 151.2, 158.2.

MS-ESI m/z (% rel. Int.): 265 ([MH]⁺, ³⁵Cl, 100), 267 ([MH]⁺, ³⁷Cl, 38).

HPLC: Method B (5 min), XBridge™ column (5 μm, C18, 4.5×50 mm, Model #186003113), detection UV 254 nm, RT=2.44 min.

4-((6-Ethoxy-2-(ethylamino)quinolin-3-yl)methyl)-1-ethyl-6,7-dimethoxyisoquinolin-3-ol dihydrochloride 41

To a stirred solution of 1-ethyl-6,7-dimethoxyisoquinolin-3-ol SLA 28136 (140 mg, 0.60 mmol) in THF (10 mL) in a 20 mL microwave vial equipped with a magnetic stirrer was added 3-(chloromethyl)-6-ethoxy-N-ethylquinolin-2-amine hydrochloride SLA 41042 (181 mg, 0.60 mmol) at RT followed by a 2 N aq. LiOH solution (0.60 mL, 1.20 mmol) and the mixture was stirred at 150° C. for 1.5 h under microwave irradiation. After cooling to RT, the mixture was diluted with CH₂Cl₂:MeOH=9:1 (150 mL), washed with brine (20 mL), dried over Na₂SO₄, filtered, and concentrated at 40° C. under vacuum. Purification by column chromatography (SiO₂, eluent EtOAc:MeOH=100:0 to 95:5) followed by a second purification by column chromatography (SiO₂, eluent CH₂Cl₂:MeOH=100:0 to 97:3) provided after evaporation 33 mg of 4-((6-ethoxy-2-(ethylamino)quinolin-3-yl)methyl)-1-ethyl-6,7-dimethoxyisoquinolin-3-ol as a brown solid. This free base was dissolved in CH₂Cl₂ (2 mL) in a 10 mL round-bottomed flask equipped with a magnetic stirrer before addition of a 0.49 M HCl solution in MeOH (1.05 mL). The reaction mixture was stirred for 5 min at RT then concentrated at 40° C. under vacuum to afford 4-((6-ethoxy-2-(ethylamino)quinolin-3-yl)methyl)-1-ethyl-6,7-dimethoxyisoquinolin-3-ol dihydrochloride 41 as a yellow solid (31.4 mg, 10% yield).

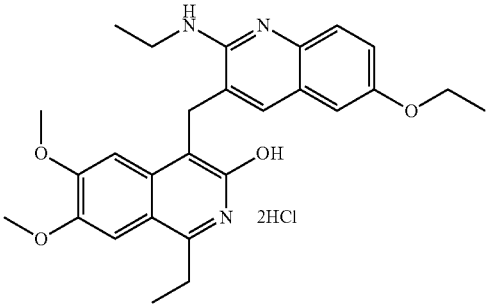

41

MW: 534.47; Yield: 10%; Yellow solid; Mp (° C.): 242.2

¹H-NMR (CD₃OD, δ): 1.28 (t, 3H, J=6.7 Hz, CH₃), 1.35-1.45 (s, 6H, 2×CH₃), 3.28 (q, 2H, J=7.2 Hz, CH₂), 3.65 (q, 2H, J=7.1 Hz, CH₂), 3.88 (s, 3H, OCH₃), 3.91 (s, 3H, OCH₃), 3.88-3.99 (m, 2H, CH₂), 4.25 (s, 2H, CH₂), 6.99 (s, 1H, ArH), 7.07 (s, 1H, ArH), 7.26 (d, 1H, J=9.2 Hz, ArH), 7.36 (s, 1H, ArH), 7.68 (s, 1H, ArH), 7.77 (d, 1H, J=9.2 Hz, ArH).

¹³C-NMR (CD₃OD, δ): 14.0, 14.7, 15.0, 25.6, 27.2, 39.2, 57.1, 57.5, 65.3, 102.7, 105.8, 110.2, 118.7, 119.6, 123.7, 124.4, 131.1, 139.5, 141.7, 152.0, 152.5, 153.1, 156.0, 158.0, 159.8, (2×C not observed).

MS-ESI m/z (% rel. Int.): 462 ([MH]⁺, 100).

HPLC: Method B (10 min), XBridge™ column (5 μm, C18, 4.5×50 mm, Model #186003113), detection UV 254 nm, RT=4.57 min, peak area 96.2%

Preparation of 1-ethyl-6,7-dimethoxy-4-((6-methoxy-2-(propylamino)quinolin-3-yl)methyl)isoquinolin-3-ol dihydrochloride 42

To a stirred solution of 1-ethyl-6,7-dimethoxyisoquinolin-3-ol SLA 28136 (250 mg, 1.07 mmol) in p-cymene (11 mL) in a 100 mL round-bottomed flask equipped with a magnetic stirrer was added 3-(chloromethyl)-6-methoxy-N-propylquinolin-2-amine hydrochloride SLA 28178 (323 mg, 1.07 mmol) at RT followed by a 2 N aq. LiOH solution (1.07 mL, 2.14 mmol) and the mixture was stirred at 150° C. for 1 h before addition of a new portion of SLA 28178 (323 mg, 1.07 mmol, done 3 times). After cooling to RT, the mixture was diluted with CH₂Cl₂:MeOH=9:1 (150 mL) and washed with brine (20 mL), dried over Na₂SO₄, filtered, and concentrated at 40° C. under vacuum. Purification by column chromatography (SiO₂, eluent EtOAc:MeOH=100:0 to 92:8) followed by a second purification by column chromatography (SiO₂, eluent CH₂Cl₂:MeOH=100:0 to 95:5) provided, after evaporation, 14.8 mg of 1-ethyl-6,7-dimethoxy-4-((6-methoxy-2-(propylamino)quinolin-3-yl)methyl)isoquinolin-3-ol as a brown solid. This free base was dissolved in CH₂Cl₂ (2 mL) in a 10 mL round-bottomed flask equipped with a magnetic stirrer before addition of a 0.49 M HCl solution in MeOH (0.26 mL). The reaction mixture was stirred for 5 min at RT then concentrated at 40° C. under vacuum, to afford 1-ethyl-6,7-dimethoxy-4-((6-methoxy-2-(propylamino)quinolin-3-yl)methyl)isoquinolin-3-ol dihydrochloride 42 as a yellow solid (6 mg, 10% yield).

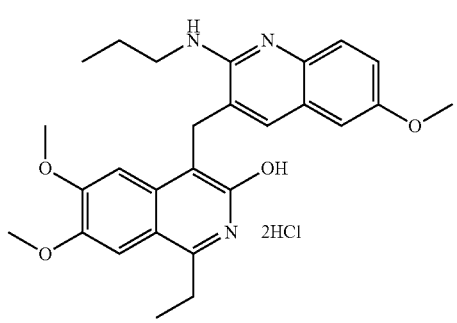

MW: 534.47; Yield: 10%; Yellow solid; Mp (° C.): 160.0

$^1$H-NMR (CD$_3$OD, δ): 1.05 (t, 3H, J=9.0 Hz, CH$_3$), 1.42 (t, 3H, J=9.0 Hz, CH$_3$), 1.80-1.89 (m, 2H, CH$_2$), 3.30-3.33 (m, 2H, CH$_2$), 3.58-3.63 (m, 2H, CH$_2$), 3.69 (s, 3H, OCH$_3$), 3.86 (s, 3H, OCH$_3$), 3.92 (s, 3H, OCH$_3$), 4.27 (s, 2H, CH$_2$), 6.98 (s, 1H, ArH), 7.07 (s, 1H, ArH), 7.23 (d, 1H, J=9.2 Hz, ArH), 7.41 (s, 1H, ArH), 7.60 (s, 1H, ArH), 7.80 (d, 1H, J=9.2 Hz, ArH).

$^{13}$C-NMR (CD$_3$OD, δ): 11.7, 14.7, 22.6, 25.4, 27.3, 45.7, 56.3, 56.9, 57.3, 102.3, 105.6, 109.5, 109.9, 118.1, 119.6, 123.4, 123.6, 124.7, 131.2, 139.7, 141.7, 151.7, 152.6, 155.7, 158.8, 159.6, (1×C not observed).

MS-ESI m/z (% rel. Int.): 462 ([MH]$^+$, 100).

HPLC: Method B (10 min), XBridge™ column (5 μm, C18, 4.5×50 mm, Model #186003113), detection UV 214 nm, RT=4.51 min.

Preparation of 1-ethyl-4-((2-(isopropylamino)-6-methoxyquinolin-3-yl)methyl)-6,7-dimethoxyisoquinolin-3-ol dihydrochloride 43

2-(Isopropylamino)-6-methoxyquinoline-3-carbaldehyde SLA 28186

To a stirred solution of 2-chloro-6-methoxyquinoline-3-carbaldehyde (1.50 g, 6.77 mmol) in THF (10 mL) in a 20 mL microwave vial equipped with a magnetic stirrer was added propan-2-amine (5.76 mL, 67.7 mmol) and the reaction mixture was stirred for 12.5 h at 160° C. and finally 45 min at 180° C. under microwave irradiation. After cooling to RT, the volatiles were removed at 40° C. under vacuum and the resulting yellow oil was taken up in a mixture of THF:1 N aq. HCl=1:1 (50 mL) and stirred for 1 h at RT. The volatiles were then removed at 40° C. under vacuum and the residue was then neutralised with saturated NaHCO$_3$ aqueous solution before extraction with CH$_2$Cl$_2$ (100 mL). The organic phase was washed with brine (20 mL), dried over MgSO$_4$, filtered, and concentrated under vacuum to give 2-(isopropylamino)-6-methoxyquinoline-3-carbaldehyde SLA 28186 as an orange solid (1.64 g, 99% yield).

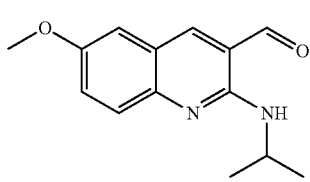

SLA 28186

MW: 244.29; Yield: 99%; Orange solid; Mp (° C.): 160.0

$^1$H-NMR (CDCl$_3$, δ): 1.32 (d, 6H, J=6.0 Hz, 2×CH$_3$), 3.77 (s, 3H, OCH$_3$), 4.44-4.57 (m, 1H, CH), 6.96 (d, 1H, J=2.8 Hz, ArH), 7.32 (dd, 1H, J=2.8 & 9.2 Hz, ArH), 7.58 (d, 1H, J=9.2 Hz, ArH), 7.75 (broad d, 1H, J=9.0 Hz, CHNH), 8.12 (s, 1H, ArH), 9.96 (s, 1H, HC=O).

$^{13}$C-NMR (CDCl$_3$, δ): 22.9, 41.8, 55.5, 106.6, 117.1, 121.8, 125.8, 128.1, 147.2, 147.4, 153.2, 154.7, 193.2, (1×C not observed).

MS-ESI m/z (% rel. Int.): 245 ([MH]$^+$, 100).

HPLC: Method B (5 min), XBridge™ column (5 μm, C18, 4.5×50 mm, Model #186003113), detection UV 254 nm, RT=2.76 min.

(2-(Isopropylamino)-6-methoxyquinolin-3-yl)methanol SLA 28188

To a stirred solution of 2-(isopropylamino)-6-methoxyquinoline-3-carbaldehyde SLA 28186 (1.55 g, 6.35 mmol) in THF (100 mL) in a 250 mL round-bottomed flask equipped with a magnetic stirrer was added sodium borohydride NaBH$_4$ (0.24 g, 6.35 mmol) and the mixture was stirred for overnight at RT then cooled in an ice bath before quenching by addition of a 1 N aq. HCl solution (40 mL). After stirring for 15 min at that temperature, the mixture was basified to pH=9 with a 2 N aq. NaOH solution. THF was then removed at 40° C. under vacuum and the solution was extracted with CH$_2$Cl$_2$ (200 mL), washed with brine (20 mL), dried over Na$_2$SO$_4$, filtered and concentrated under vacuum to give (2-(isopropylamino)-6-methoxyquinolin-3-yl)methanol SLA 28188 as an orange solid (1.45 g, 93% yield).

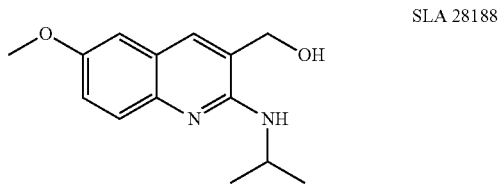 [SMILES: COc1ccc2nc(NC(C)C)c(CO)cc2c1]

SLA 28188

MW: 246.30; Yield: 93%; orange solid; Mp (° C.): 150.0

$^1$H-NMR (CDCl$_3$, δ): 1.28 (d, 6H, J=6.0 Hz, 2×CH$_3$), 2.46 (broad, s, 1H, OH), 3.87 (s, 3H, OCH$_3$), 4.36-4.45 (m, 1H, CH), 4.56 (s, 2H, OCH$_2$), 5.37 (broad d, 1H, J=6.0 Hz, CHNH), 6.82 (d, 1H, J=2.8 Hz, ArH), 7.18 (dd, 1H, J=2.8 & 9.1 Hz, ArH), 7.26 (s, 1H, ArH), 7.60 (d, 1H, J=9.1 Hz, ArH).

$^{13}$C-NMR (CDCl$_3$, δ): 23.0 (2×C), 42.2, 55.4, 63.8, 106.6, 120.3, 122.2, 122.9, 127.1, 134.3 143.1, 154.2, 154.5.

MS-ESI m/z (% rel. Int.): 247 ([MH]$^+$, 100).

HPLC: Method B (5 min), XBridge™ column (5 μm, C18, 4.5×50 mm, Model #186003113), detection UV 214 nm, RT=2.13 min.

3-(Chloromethyl)-N-isopropyl-6-methoxyquinolin-2-amine hydrochloride SLA 28190

To a stirred solution of (2-(isopropylamino)-6-methoxyquinolin-3-yl)methanol SLA 28188 (1.41 g, 5.72 mmol) in dry CH$_2$Cl$_2$ (115 mL) in a 250 mL round-bottomed flask equipped with a magnetic stirrer was added dropwise SOCl$_2$ (8.30 mL, 114 mmol). The mixture was stirred for 1 h at RT then concentrated to dryness at 40° C. under vacuum. The residue was then taken up in CH$_2$Cl$_2$ (20 mL) before concentration back to dryness at 40° C. under vacuum (done 3 times) to give 3-(chloromethyl)-N-isopropyl-6-methoxyquinolin-2-amine hydrochloride SLA 28190 as a yellow solid (1.79 g, >100% yield).

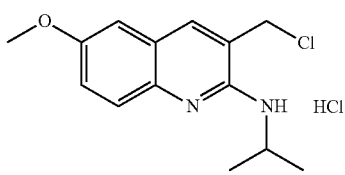

SLA 28190

MW: 301.21; Yield: Quantitative; yellow solid; Mp (° C.): 145.0

¹H-NMR (CDCl₃, δ): 1.49 (d, 6H, J=6.3 Hz, 2×CH₃), 3.87 (s, 3H, OCH₃), 5.01 (s, 2H, CH₂), 5.28-5.38 (m, 1H, CH), 7.02 (d, 1H, J=2.7 Hz, ArH), 7.20 (broad d, 1H, J=8.6 Hz, NH), 7.29 (dd, 1H, J=2.7 & 9.2 Hz, ArH), 8.07 (s, 1H, ArH), 9.00 (d, 1H, J=9.2 Hz, ArH), 14.11 (s, 1H, NH).

¹³C-NMR (CD₃OD, δ): 22.0, 42.2, 46.7, 56.4, 109.9, 120.0, 123.4, 123.9, 124.5, 132.2, 143.9, 150.3, 158.9, (1×C not observed).

MS-ESI m/z (% rel. Int.): 265 ([MH]⁺, ³⁵Cl, 100), 267 ([MH]⁺, ³⁷Cl, 38)

HPLC: Method B (5 min), XBridge™ column (5 μm, C18, 4.5×50 mm, Model #186003113), detection UV 254 nm, RT=2.40 min.

1-Ethyl-4-((2-(isopropylamino)-6-methoxyquinolin-3-yl)methyl)-6,7-dimethoxyisoquinolin-3-ol dihydrochloride 43

To a stirred solution of 3-(chloromethyl)-N-isopropyl-6-methoxyquinolin-2-amine hydrochloride SLA 28190 (323 mg, 1.07 mmol) in THF (10 mL) in a 20 mL microwave vial equipped with a magnetic stirrer was added 1-ethyl-6,7-dimethoxyisoquinolin-3-ol SLA 28136 (250 mg, 1.07 mmol) followed by a 2 N aq. LiOH solution (1.07 mL, 2.14 mmol) and the mixture was stirred at 150° C. for 1.5 h under microwave irradiation. After cooling to RT, the mixture was diluted with CH₂Cl₂:MeOH=9:1 (150 mL), washed with brine (20 mL), dried over Na₂SO₄, filtered, and concentrated at 40° C. under vacuum. Purification by column chromatography (SiO₂, eluent EtOAc:MeOH=100:0 to 94:6) followed by a second purification by column chromatography (SiO₂, eluent CH₂Cl₂:MeOH=100:0 to 93:7) provided, after evaporation, 60 mg of 1-ethyl-4-((2-(isopropylamino)-6-methoxyquinolin-3-yl)methyl)-6,7-dimethoxyisoquinolin-3-ol as a brown solid. This free base was dissolved in CH₂Cl₂ (2 mL) in a 10 mL round-bottomed flask equipped with a magnetic stirrer before addition of a 0.49 M HCl solution in MeOH (1.04 mL). The reaction mixture was stirred for 5 min at RT then concentrated at 40° C. under vacuum to afford 1-ethyl-4-((2-(isopropylamino)-6-methoxyquinolin-3-yl)methyl)-6,7-dimethoxyisoquinolin-3-ol dihydrochloride 43 as a yellow solid (69 mg, 12% yield).

MW: 534.47; Yield: 12%; Yellow solid; Mp (° C.): 257.6

¹H-NMR (CD₃OD, δ): 1.52-1.59 (m, 9H, 3×CH₃), 3.48 (q, 2H, J=9.0 Hz, CH₂), 3.79 (s, 3H, OCH₃), 3.98 (s, 3H, OCH₃), 4.06 (s, 3H, OCH₃), 4.44 (s, 2H, CH₂), 4.50-4.59 (m, 1H, CH), 7.15-7.16 (m, 2H, 2×ArH), 7.33 (d, 1H, J=9.0 Hz, ArH), 7.58 (s, 1H, ArH), 7.62 (s, 1H, ArH), 8.00 (d, 1H, J=9.0 Hz, ArH).

¹³C-NMR (CD₃OD, δ): 14.7, 22.3, 25.5, 27.3, 46.6, 56.3, 57.0, 57.4, 102.6, 105.8, 109.4, 110.0, 118.7, 119.7, 123.4, 123.6, 124.4, 131.2, 139.6, 141.7, 151.6, 152.0, 152.9, 156.1, 158.7, 159.9, (1×C not observed).

MS-ESI m/z (% rel. Int.): 462 ([MH]⁺, 100).

HPLC: Method B (10 min), XBridge™ column (5 μm, C18, 4.5×50 mm, Model #186003113), detection UV 254 nm, RT=4.50 min, peak area 97.2%.

Preparation of 4-((2-(benzylamino)-6-methoxyquinolin-3-yl)methyl)-1-ethyl-6,7-dimethoxyisoquinolin-3-ol dihydrochloride 44

2-(Benzylamino)-6-methoxyquinoline-3-carbaldehyde SLA 41002

To a stirred solution of 2-chloro-6-methoxyquinoline-3-carbaldehyde (2.00 g, 9.02 mmol) in THF (10 mL) in a 20 mL microwave vial equipped with a magnetic stirrer was added benzylamine (4.88 mL, 90.20 mmol) and the reaction mixture was stirred for 1.5 h at 160° C. then 45 min at 180° C. under microwave irradiation. After cooling to RT, the volatiles were removed at 40° C. under vacuum and the resulting yellow oil was taken up in a mixture of THF:1 N aq. HCl=1:1 (50 mL) and stirred for 1 h at RT. The volatiles were then removed at 40° C. under vacuum and the residue was then neutralised with a saturated NaHCO₃ aqueous solution before extraction with CH₂Cl₂ (100 mL). The organic phase was washed with brine (20 mL), dried over MgSO₄, filtered and concentrated at 40° C. under vacuum. Purification by column chromatography (SiO₂, eluent cyclohexane:EtOAc=100:0 to 75:25) provided a mixture of the desired product and its benzyl imine derivative. This mixture was taken up in a mixture of THF:1 N aq. HCl=1:1 (20 mL) and stirred for 2 h at RT. The volatiles were then removed at 40° C. under vacuum and the residue was then neutralised with a saturated NaHCO₃ aqueous solution before extraction with CH₂Cl₂ (100 mL). The organic phase was washed with brine (20 mL), dried over MgSO₄, filtered and concentrated at 40° C. under vacuum. Purification by column chromatography (SiO₂, eluent cyclohexane:EtOAc=100:0 to 75:25) gave, after evaporation and drying, 2-(benzylamino)-6-methoxyquinoline-3-carbaldehyde SLA 41002 as a yellow solid (0.431 g, 16% yield).

43

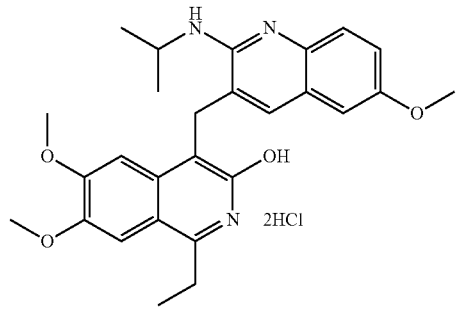

SLA 41002

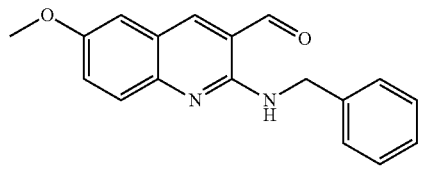

MW: 292.33; Yield: 16%; Yellow solid; Mp (° C.): 131.7

¹H-NMR (CDCl₃, δ): 3.88 (s, 3H, OCH₃), 4.86 (d, 2H, J=6.0 Hz, CH₂), 6.99-7.00 (m, 1H, ArH), 7.23-7.44 (m, 6H, 6×ArH), 7.62 (d, 1H, J=7.9 Hz, ArH), 8.17 (s, 1H, ArH), 8.20 (broad s, 1H, NH), 9.99 (s, 1H, HC=O).

$^{13}$C-NMR (CDCl$_3$, δ): 44.5, 55.6, 106.7, 117.3, 122.2, 125.9, 127.1, 127.8 (2×C), 128.1, 128.4, 128.5 (2×C), 139.5, 147.1, 153.6, 155.0, 193.0.

MS-ESI m/z (% rel. Int.): 293 ([MH]$^+$, 100).

HPLC: Method B (5 min), XBridge™ column (5 μm, C18, 4.5×50 mm, Model #186003113), detection UV 254 nm, RT=2.51 min.

(2-(Benzylamino)-6-methoxyquinolin-3-yl)methanol SLA 41006

To a stirred solution of 2-(benzylamino)-6-methoxyquinoline-3-carbaldehyde SLA 41002 (0.40 g, 1.37 mmol) in THF (50 mL) in a 100 mL round-bottomed flask equipped with a magnetic stirrer was added sodium borohydride NaBH$_4$ (0.24 g, 6.35 mmol) and the mixture was stirred overnight at RT then cooled in an ice bath before quenching by addition of a 1 N aq. HCl solution (15 mL). After stirring for 15 min at that temperature, the mixture was basified to pH=9 with a 2 N aq. NaOH solution. THF was then removed at 40° C. under vacuum and the solution was extracted with CH$_2$Cl$_2$ (200 mL), washed with brine (20 mL), dried over Na$_2$SO$_4$, filtered, and concentrated under vacuum to give (2-(benzylamino)-6-methoxyquinolin-3-yl)methanol SLA 41006 as a yellow solid (0.395 g, 98% yield).

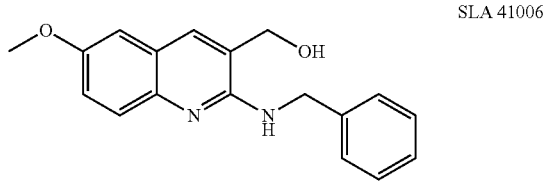 [SMILES: COc1ccc2nc(NCc3ccccc3)c(CO)cc2c1]

SLA 41006

MW: 294.35; Yield: 98%; Yellow solid; Mp (° C.): 132.2

$^1$H-NMR (CDCl$_3$, δ): 3.88 (s, 3H, OCH$_3$), 4.61 (s, 2H, OCH$_2$), 4.76 (d, 2H, J=5.3 Hz, NCH$_2$), 5.90-5.92 (broad m, NH or OH), 6.86 (d, 1H, J=2.8 Hz, ArH), 7.20 (dd, 1H, J=2.8 Hz & 9.0 Hz, ArH), 7.26-7.36 (m, 5H, 4×ArH and NH or OH), 7.39-7.42 (m, 2H, 2×ArH), 7.62 (d, 1H, J=9.0 Hz, ArH).

$^{13}$C-NMR (CDCl$_3$, δ): 45.4, 55.6, 63.9, 106.6, 120.6, 122.1, 123.5, 127.1, 127.4, 128.0 (2×C), 128.5 (2×C), 134.5, 139.9, 143.1, 154.7, 154.9.

MS-ESI m/z (% rel. Int.): 295 ([MH]$^+$, 100).

HPLC: Method B (5 min), XBridge™ column (5 μm, C18, 4.5×50 mm, Model #186003113), detection UV 214 nm, RT=2.34 min.

N-Benzyl-3-(chloromethyl)-6-methoxyquinolin-2-amine hydrochloride SLA 41008

To a stirred solution of (2-(benzylamino)-6-methoxyquinolin-3-yl)methanol SLA 41006 (0.101 g, 0.343 mmol) in dry CH$_2$Cl$_2$ (50 mL) in a 250 mL round-bottomed flask equipped with a magnetic stirrer was added dropwise SOCl$_2$ (0.50 mL, 6.86 mmol). The mixture was stirred for 1 h at RT then concentrated to dryness at 40° C. under vacuum. The residue was then taken up in CH$_2$Cl$_2$ (20 mL) before concentration back to dryness at 40° C. under vacuum (done 3 times) to give N-benzyl-3-(chloromethyl)-6-methoxyquinolin-2-amine hydrochloride SLA 41008 (120 mg, 100% yield) as a yellow solid.

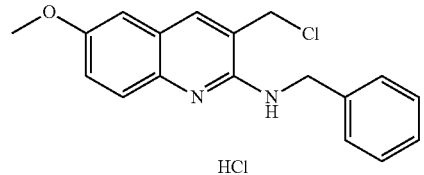

SLA 41008

MW: 349.25; Yield: 100%; Yellow solid; Mp (° C.): 233.2

$^1$H-NMR (CDCl$_3$, δ): 3.93 (s, 3H, OCH$_3$), 4.97-4.98 (m, 4H, 2×CH$_2$), 7.33-7.46 (m, 7H, 7×ArH), 7.83 (d, 1H, J=9.0 Hz, ArH), 8.49 (s, 1H, ArH).

$^{13}$C-NMR (CD$_3$OD, δ): 42.1, 46.9, 56.4, 110.0, 119.8, 123.7, 123.9, 124.9, 128.2 (2×C), 129.2, 130.1 (2×C), 132.0, 136.3, 144.2, 151.6, 159.1.

MS-ESI m/z (% rel. Int.): 313 ([MH]$^+$, $^{35}$Cl, 100), 315 ([MH]$^+$, $^{37}$Cl, 38), HPLC: Method B (5 min), XBridge™ column (5 μm, C18, 4.5×50 mm, Model #186003113), detection UV 254 nm, RT=2.59 min.

4-((2-(Benzylamino)-6-methoxyquinolin-3-yl)methyl)-1-ethyl-6,7-dimethoxyisoquinolin-3-ol dihydrochloride 44

To a stirred solution of 1-ethyl-6,7-dimethoxyisoquinolin-3-ol SLA 28136 (70 mg, 0.30 mmol) in THF (10 mL) in a 20 mL microwave vial equipped with a magnetic stirrer was added N-benzyl-3-(chloromethyl)-6-methoxyquinolin-2-amine hydrochloride SLA 41008 (105 mg, 0.30 mmol) followed by a 2 N aq. LiOH (0.30 mL, 0.60 mmol) and the mixture was stirred at 160° C. for 1.5 h under microwave irradiation. After cooling to RT, the mixture was diluted with CH$_2$Cl$_2$:MeOH=9:1 (150 mL), washed with brine (20 mL), dried over Na$_2$SO$_4$, filtered, and concentrated at 40° C. under vacuum. Purification by column chromatography (SiO$_2$, eluent CH$_2$Cl$_2$:MeOH=100:0 to 97:3) provided, after evaporation, 17.3 mg of 4-((2-(benzylamino)-6-methoxyquinolin-3-yl)methyl)-1-ethyl-6,7-dimethoxyisoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (0.28 mL). The reaction mixture was stirred for 5 min at RT then concentrated at 40° C. under vacuum to afford 4-((2-(benzylamino)-6-methoxyquinolin-3-yl)methyl)-1-ethyl-6,7-dimethoxyisoquinolin-3-ol dihydrochloride 44 as a yellow solid (16 mg, 9% yield).

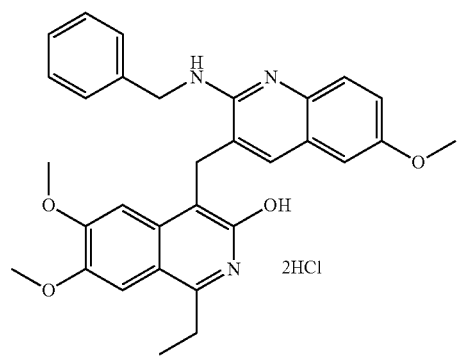

44

MW: 582.52; Yield: 9%; Yellow solid; Mp (° C.): 250.0
1H-NMR (CD3OD, δ): 1.46 (t, 3H, J=7.5 Hz, CH3), 3.23-3.30 (m, 2H, CH2), 3.85 (s, 3H, OCH3), 3.99 (s, 3H, OCH3), 4.01 (s, 3H, OCH3), 4.41 (s, 2H, CH2), 4.98 (s, 2H, CH2), 7.08 (s, 1H, ArH), 7.27 (d, 1H, J=2.6 Hz, ArH), 7.34-7.41 (m, 7H, 7×ArH), 7.79 (d, 1H, J=9.1 Hz, ArH), 8.08 (s, 1H, ArH).
13C-NMR (CD3OD, δ): 14.7, 25.4, 27.4, 47.1, 56.3, 56.8, 57.2, 102.1, 105.6, 109.4, 109.9, 119.6, 123.6, 123.9, 128.4 (2×C), 129.2, 130.1 (2×C), 131.1, 136.6, 140.4, 141.7, 152.7, 155.6, 158.9, 159.5, (4×C not observed).
MS-ESI m/z (% rel. Int.): 510 ([MH]+, 100).
HPLC: Method B (10 min), XBridge™ column (5 μm, C18, 4.5×50 mm, Model #186003113), detection UV 254 nm, RT=4.62 min, peak area 95.3%.

Preparation of 1-ethyl-6,7-dimethoxy-4-((6-methoxy-2-(2,2,2-trifluoroethylamino)quinolin-3-yl)methyl)isoquinolin-3-ol dihydrochloride 45

6-Methoxy-2-(2,2,2-trifluoroethylamino)quinoline-3-carbaldehyde SLA 41066

To a stirred solution of 2-chloro-6-methoxyquinoline-3-carbaldehyde (1.50 g, 6.77 mmol) in THF (10 mL) in a 20 mL microwave vial equipped with a magnetic stirrer was added 2,2,2-trifluoroethanamine (10.06 mL, 102.0 mmol) and the reaction mixture was stirred for 10 h at 160° C. under microwave irradiation. After cooling to RT, the volatiles were removed at 40° C. under vacuum and the resulting yellow oil was taken up in a mixture of THF:1 N aq. HCl=1:1 (50 mL) and stirred for 1 h at RT. The volatiles were then removed at 40° C. under vacuum and the residue was then neutralised with saturated NaHCO3 aqueous solution before extraction with CH2Cl2 (100 mL). The organic phase was washed with brine (20 mL), dried over MgSO4, filtered and concentrated under vacuum to give 6-methoxy-2-(2,2,2-trifluoroethylamino)quinoline-3-carbaldehyde SLA 41066 as an orange solid (2.22 g, >100% yield).

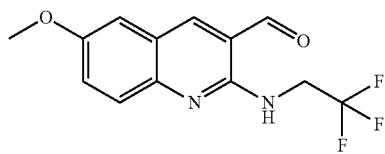

SLA 41066

MW: 284.23; Yield: >100%; Orange solid; Mp (° C.): 129.2
1H-NMR (CDCl3, δ): 3.92 (s, 3H, CH3), 4.37-4.48 (m, 2H, CH2), 7.02 (d, 1H, J=2.8 Hz, ArH), 7.38 (dd, 1H, J=2.8 Hz & 9.1 Hz, ArH), 7.65 (d, 1H, J=9.1 Hz, ArH), 8.24 (s, 1H, ArH), 10.01 (s, 1H, HC=O).
13C-NMR (CDCl3, δ): 41.0 (q, J=34.2 Hz), 55.2, 106.1, 116.8, 122.5, 125.8, 127.9, 145.9, 146.6, 152.3, 155.2, 192.7, (CF3 not seen).
MS-ESI m/z (% rel. Int.): 285 ([MH]+, 100).
HPLC: Method B (5 min), X Bridge™ column (5 μm, C18, 4.5×50 mm, Model #186003113), detection UV 254 nm, RT=3.11 min.

(6-Methoxy-2-(2,2,2-trifluoroethylamino)quinolin-3-yl)methanol SLA 41068

To a stirred solution of 6-methoxy-2-(2,2,2-trifluoroethylamino)quinoline-3-carbaldehyde SLA 41066 (1.98 g, 6.97 mmol) in THF (150 mL) in a 250 mL round-bottomed flask equipped with a magnetic stirrer was added sodium borohydride NaBH4 (0.264 g, 6.98 mmol) and the mixture was stirred overnight at RT then cooled in an ice bath before quenching by addition of a 1 N aq. HCl solution (40 mL). After stirring for 15 min at that temperature, the mixture was basified to pH=9 with a 2 N aq. NaOH solution. THF was then removed at 40° C. under vacuum and the solution was extracted with CH2Cl2 (500 mL), washed with brine (50 mL), dried over Na2SO4, filtered, and concentrated under vacuum. Purification by column chromatography (SiO2, eluent CH2Cl2:MeOH=100:0 to 95:5) provided, after evaporation and drying, (6-methoxy-2-(2,2,2-trifluoroethylamino)quinolin-3-yl)methanol SLA 41068 as an orange solid (1.47 g, 74% yield).

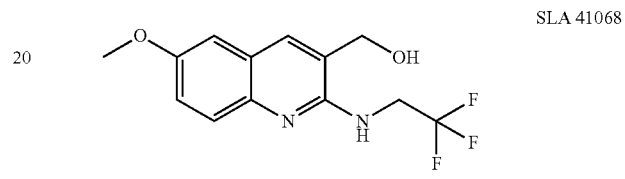

SLA 41068

MW: 286.25; Yield: 74%; Orange solid; Mp (° C.): 171.9
1H-NMR (CD3OD, δ): 3.85 (s, 3H, OCH3), 4.34 (q, 2H, J=9.4 Hz, CH2), 4.70 (s, 2H, CH2), 7.02 (d, 1H, J=2.7 Hz, ArH), 7.21 (dd, 1H, J=2.7 & 9.1 Hz, ArH), 7.65 (d, 1H, J=9.1 Hz, ArH), 7.72 (s, 1H, ArH).
13C-NMR (CD3OD, δ): 43.2 (q, J=33.5 Hz), 56.7, 63.8, 107.8, 122.1, 124.3, 125.5, 128.5, 136.2, 143.6, 155.2, 156.7, (CF3 not seen).
MS-ESI m/z (% rel. Int.): 287 ([MH]+, 100).
HPLC: Method B (5 min), XBridge™ column (5 μm, C18, 4.5×50 mm, Model #186003113), detection UV 254 nm, RT=2.15 min.

3-(Chloromethyl)-6-methoxy-N-(2,2,2-trifluoroethyl)quinolin-2-amine hydrochloride SLA 41070

To a stirred solution of (6-methoxy-2-(2,2,2-trifluoroethylamino)quinolin-3-yl)methanol SLA 41068 (1.45 g, 5.07 mmol) in dry CH2Cl2 (20 mL) in a 100 mL round-bottomed flask equipped with a magnetic stirrer was added dropwise SOCl2 (7.35 mL, 101.3 mmol). The mixture was stirred for 2 h at RT then concentrated to dryness at 40° C. under vacuum. The residue was then taken up in CH2Cl2 (20 mL) before concentration back to dryness at 40° C. under vacuum (done 3 times) to give 3-(chloromethyl)-6-methoxy-N-(2,2,2-trifluoroethyl)quinolin-2-amine hydrochloride SLA 41070 as a yellow solid (1.74 g, >100% yield).

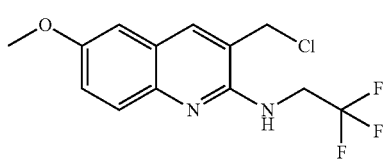

SLA 41070

MW: 341.16; Yield: >100%; Yellow solid; Mp (° C.): 231.2
1H-NMR (CD3OD, δ): 3.94 (s, 3H, OCH3), 4.65 (q, J=8.7 Hz, 2H, CH2), 4.95 (s, 2H, CH2), 7.45 (d, 1H, J=2.4 Hz, ArH), 7.52 (dd, 1H, J=2.4 Hz & 9.2 Hz, ArH), 8.01 (d, 1H, J=9.2 Hz, ArH), 8.60 (s, 1H, ArH).
$^{13}$C-NMR (CD$_3$OD, δ): 41.8, 44.1 (q, J=34.7 Hz), 56.5, 109.7, 120.1, 123.8, 124.3, 125.6 (q, J=279.4 Hz), 125.6, 131.9, 145.3, 151.9, 159.5.
MS-ESI m/z (% rel. Int.): 305 ([MH]$^+$, $^{35}$Cl, 100), 307 ([MH]$^+$, $^{37}$Cl, 38).
HPLC: Method B, XBridge™ column (5 μm, C18, 4.5×50 mm, Model #186003113), detection UV 254 nm, RT=4.50 min.

1-Ethyl-6,7-dimethoxy-4-((6-methoxy-2-(2,2,2-trifluoroethylamino)quinolin-3-yl)methyl)isoquinolin-3-ol dihydrochloride 45

To a stirred solution of 1-ethyl-6,7-dimethoxyisoquinolin-3-ol SLA 28136 (342 mg, 1.47 mmol) in THF (10 mL) in a 20 mL microwave vial equipped with a magnetic stirrer was added 3-(chloromethyl)-6-methoxy-N-(2,2,2-trifluoroethyl)quinolin-2-amine hydrochloride SLA 41070 (500 mg, 1.47 mmol) at RT followed by a 2 N aq. LiOH solution (1.47 mL, 2.94 mmol) and the mixture was stirred at 160° C. for 1.5 h under microwave irradiation. After cooling to RT, the mixture was diluted with CH$_2$Cl$_2$:MeOH=9:1 (150 mL), washed with brine (20 mL), dried over Na$_2$SO$_4$, filtered, and concentrated at 40° C. under vacuum. Purification by column chromatography (SiO$_2$, eluent EtOAc:MeOH=100:0 to 97:3) followed by a second purification by column chromatography (SiO$_2$, eluent CH$_2$Cl$_2$:MeOH=100:0 to 95:5) provided, after evaporation and drying, 233 mg of 1-ethyl-6,7-dimethoxy-4-((6-methoxy-2-(2,2,2-trifluoroethylamino)quinolin-3-yl)methyl)isoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (3.05 mL). The reaction mixture was stirred for 5 min at RT then concentrated at 40° C. under vacuum to afford 1-ethyl-6,7-dimethoxy-4-((6-methoxy-2-(2,2,2-trifluoroethylamino)quinolin-3-yl)methyl)isoquinolin-3-ol dihydrochloride 45 as a yellow solid (200 mg, 24% yield).

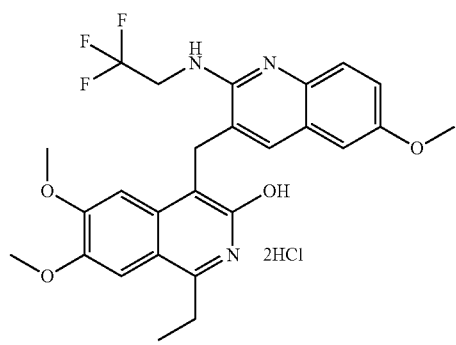

MW: 574.42; Yield: 24%; Yellow solid; Mp (° C.): 118.6
$^1$H-NMR (CD$_3$OD, δ): 1.46-1.58 (m, 3H, CH$_3$), 3.45-3.54 (m, 2H, CH$_2$), 3.79 (s, 3H, OCH$_3$), 3.95 (s, 3H, OCH$_3$), 4.04 (s, 3H, OCH$_3$), 4.47 (s, 2H, CH$_2$), 4.81 (q, 2H, J=8.0 Hz, CH$_2$), 7.11 (s, 1H, ArH), 7.24 (s, 1H, ArH), 7.40 (d, 1H, J=9.1 Hz, ArH), 7.59 (s, 1H, ArH), 7.77 (s, 1H, ArH), 8.05 (d, 1H, J=9.1 Hz, ArH).
$^{13}$C-NMR (CD$_3$OD, δ): 14.7, 25.5, 27.3, 44.5 (q, J=34.9 Hz), 56.4, 57.0, 57.4, 102.6, 105.9, 109.2, 109.6, 118.9, 119.9, 124.2, 124.5, 124.5, 125.8 (q, J=279.3 Hz), 131.0, 141.0, 141.6, 152.1, 152.7, 153.0, 156.4, 159.3, 160.0.
MS-ESI m/z (% rel. Int.): 502 ([MH]$^+$, 100).
HPLC: Method B (10 min), XBridge™ column (5 μm, C18, 4.5×50 mm, Model #186003113), detection UV 254 nm, RT=4.41 min, peak area 99.0%.

Preparation 4-((6-ethoxy-2-(ethylamino)quinolin-3-yl)methyl)-1-isopropyl-6,7-dimethoxyisoquinolin-3-ol dihydrochloride 46

1-Isopropyl-6,7-dimethoxyisoquinolin-3-ol SIL 32164

To a solution of methyl 2-(3,4-dimethoxyphenyl)acetate SLA 28134 (10.09 g, 48.0 mmol) in isobutyric anhydride (60.5 mL, 364.8 mmol) at 0° C. in a 500 mL round-bottomed flask equipped with a magnetic stirrer was added HClO$_4$ (ca. 70% solution in water, 4.91 mL, 56.8 mmol) over a period of 10 min. The reaction mixture was then allowed to warm up to RT, stirred for 2 h and diluted with Et$_2$O (400 mL). The solid was filtered and washed several times with Et$_2$O to give 16.88 g of a brown solid. The solid was then suspended in H$_2$O (70 mL) in a 500 mL round-bottomed flask equipped with a magnetic stirrer and cooled in an ice bath before dropwise addition of concentrated NH$_4$OH (180 mL). After complete addition, the ice bath was removed and the reaction mixture was stirred overnight at RT. The mixture was then extracted with CH$_2$Cl$_2$ (100 mL, the organic layer was isolated and the aqueous layer was further extracted with CH$_2$Cl$_2$ (3×100 mL). The organic layers were combined, washed with brine (50 mL), dried over Na$_2$SO$_4$, filtered and concentrated under vacuum to give 1-isopropyl-6,7-dimethoxyisoquinolin-3-ol SIL 32164 as a yellow solid (9.69 g, 82% yield).

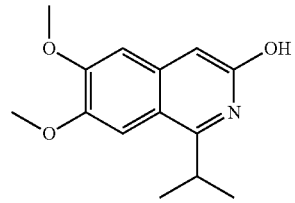

SIL 32164

MW: 247.29; Yield: 82%; Yellow solid; Mp (° C.): 175.0
$^1$H-NMR (CDCl$_3$, δ): 1.52 (d, 6H, J=6.9 Hz, 2×CH$_3$), 3.63-3.70 (m, 1H, CH), 3.93 (s, 3H, OCH$_3$), 3.96 (s, 3H, OCH$_3$), 6.57 (s, 1H, ArH), 6.60 (s, 1H, ArH), 6.94 (s, 1H, ArH), OH not seen.
$^{13}$C-NMR (CDCl$_3$, δ): 21.1 (2×C), 29.4, 55.8, 56.0, 101.8, 102.8, 104.8, 111.8, 142.0, 147.5, 154.5, 154.8, 161.2.
MS-ESI m/z (% rel. Int.): 248 ([MH]$^+$, 100).
HPLC: Method B (5 min), X Bridge™ column (5 μm, C18, 4.5×50 mm, Model #186003113), detection UV 254 nm, RT=2.13 min.

4-((6-Ethoxy-2-(ethylamino)quinolin-3-yl)methyl)-1-isopropyl-6,7-dimethoxyisoquinolin-3-ol dihydrochloride 46

To a stirred solution of 1-isopropyl-6,7-dimethoxyisoquinolin-3-ol SIL 32164 (149 mg, 0.60 mmol) in THF (10 mL) in a 20 mL microwave vial equipped with a magnetic stirrer was added 3-(chloromethyl)-6-ethoxy-N-ethylquinolin-2- amine hydrochloride SLA 41042 (181 mg, 0.68 mmol) at RT followed by a 2 N aq. LiOH solution (0.60 mL, 1.20 mmol) and the mixture was stirred at 160° C. for 1.5 h under microwave irradiation. After cooling to RT, the mixture was diluted with CH$_2$Cl$_2$:MeOH=9:1 (150 mL), washed with brine (20 mL), dried over Na$_2$SO$_4$, filtered, and concentrated at 40° C. under vacuum. Purification by column chromatography (SiO$_2$, eluent EtOAc:MeOH=100:0 to 95:5) followed by a second purification by column chromatography (SiO$_2$, eluent CH$_2$Cl$_2$:MeOH=100:0 to 97:3) provided 16 mg of 4-((6-ethoxy-2-(ethylamino)quinolin-3-yl)methyl)-1-isopropyl-6,7-dimethoxyisoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (1.05 mL) The reaction mixture was stirred for 5 min at RT then concentrated at 40° C. under vacuum to afford 4-((6-ethoxy-2-(ethylamino)quinolin-3-yl)methyl)-1-isopropyl-6,7-dimethoxyisoquinolin-3-ol dihydrochloride 46 as a yellow solid (12 mg, 4% yield).

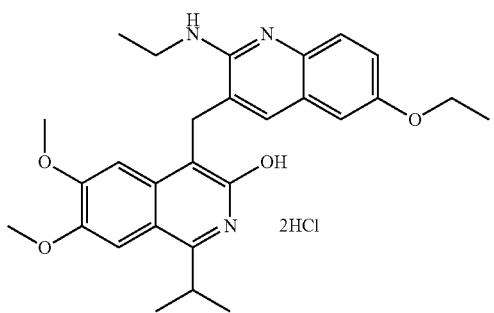

46

MW: 548.50; Yield: 4%; Yellow solid; Mp (° C.): 222.2

$^1$H-NMR (CD$_3$OD, δ): 1.42 (t, 3H, J=6.8 Hz, CH$_3$), 1.46-1.55 (m, 9H, 3×CH$_3$), 3.69 (q, 2H, J=6.8 Hz, CH$_2$), 3.97-4.05 (m, 1H, CH), 3.93 (s, 3H, OCH$_3$), 3.97 (s, 3H, OCH$_3$), 4.10 (q, 2H, J=6.8 Hz, CH$_2$), 4.35 (s, 2H, CH$_2$), 7.07 (s, 1H, ArH), 7.24 (s, 1H, ArH), 7.33 (d, 1H, J=9.1 Hz, ArH), 7.40 (s, 1H, ArH), 7.83 (d, 1H, J=9.1 Hz, ArH), 8.11 (s, 1H, ArH).

$^{13}$C-NMR (CD$_3$OD, δ): 13.7, 15.0, 21.3, 28.0, 30.3, 39.0, 56.6, 57.1, 65.3, 103.3, 104.8, 110.2, 114.7, 115.2, 119.5, 123.4, 123.6, 125.9, 131.1, 140.7, 141.9, 150.3, 152.5, 156.7, 158.0, 158.5, (1×C not observed).

MS-ESI m/z (% rel. Int.): 476 ([MH]$^+$, 100).

HPLC: Method B (10 min), XBridge™ column (5 μm, C18, 4.5×50 mm, Model #186003113), detection UV 254 nm, RT=4.78 min, peak area 98.3%.

Preparation 4-((2-(ethylamino)-6-methoxyquinolin-3-yl)methyl)-1-isopropyl-6,7-dimethoxyisoquinolin-3-ol dihydrochloride 47

To a stirred solution of 3-(chloromethyl)-N-ethyl-6-methoxyquinolin-2-amine hydrochloride (250 mg, 0.87 mmol) in THF (10 mL) in a 20 mL microwave vial equipped with a magnetic stirrer was added 1-isopropyl-6,7-dimethoxyisoquinolin-3-ol SIL 32164 (215 mg, 0.87 mmol) followed by a 2 N aq. LiOH solution (0.87 mL, 1.74 mmol) and the mixture was stirred at 150° C. for 1.5 h under microwave irradiation. After cooling to RT, the mixture was diluted with CH$_2$Cl$_2$:MeOH=9:1 (150 mL), washed with brine (20 mL), dried over Na$_2$SO$_4$, filtered, and concentrated at 40° C. under vacuum. Purification by column chromatography (SiO$_2$, eluent cyclohexane:EtOAc=100:0 to 0:100) followed by a second purification by column chromatography (SiO$_2$, eluent CH$_2$Cl$_2$:MeOH=100:0 to 95:5) provided, after evaporation and drying, 38 mg of 4-((2-(ethylamino)-6-methoxyquinolin-3-yl)methyl)-1-isopropyl-6,7-dimethoxyisoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (0.70 mL). The reaction mixture was stirred for 5 min at RT then concentrated at 40° C. under vacuum to afford 4-((2-(ethylamino)-6-methoxyquinolin-3-yl)methyl)-1-isopropyl-6,7-dimethoxyisoquinolin-3-ol dihydrochloride 47 as a yellow solid (24 mg, 5% yield).

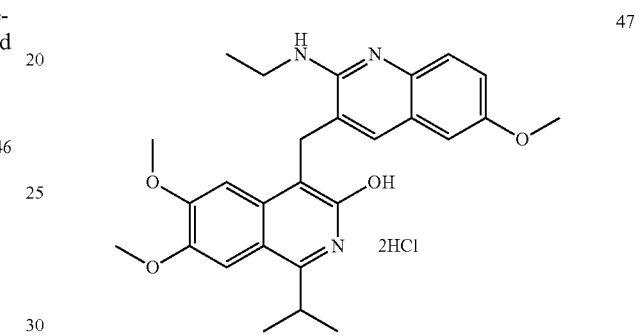

47

MW: 534.47; Yield: 5%; Yellow solid.

$^1$H-NMR (CD$_3$OD, δ): 1.51-1.65 (m, 9H, 3×CH$_3$), 3.72-3.88 (m, 2H, CH$_2$), 3.80 (s, 3H, OCH$_3$), 3.97 (s, 3H, OCH$_3$), 4.04 (s, 3H, OCH$_3$), 4.12-4.30 (m, 1H, CH), 4.38 (s, 2H, CH$_2$), 6.98 (s, 1H, ArH), 7.18 (s, 1H, ArH), 7.34 (d, 1H, J=8.6 Hz, ArH), 7.61 (s, 1H, ArH), 7.73 (s, 1H, ArH), 7.91 (d, 1H, J=8.6 Hz, ArH).

MS-ESI m/z (% rel. Int.): 462 ([MH]$^+$, 100).

HPLC: Method B (10 min), X Bridge™ column (5 μm, C18, 4.5×50 mm, Model #186003113), detection UV 254 nm, RT=4.50 min, peak area 98.4%.

Preparation of 6,7-dimethoxy-4-((6-methoxy-2-(methylamino)quinolin-3-yl)methyl)-1-propylisoquinolin-3-ol dihydrochloride 48

To a stirred solution of 6,7-dimethoxy-1-propylisoquinolin-3-ol RBO 35142 (250 mg, 1.01 mmol) in toluene (15 mL) in a 20 mL microwave vial equipped with a magnetic stirrer was added 3-(chloromethyl)-6-methoxy-N-methylquinolin-2-amine hydrochloride SLA 28154 (276 mg, 1.01 mmol) followed by a 2 N aq. LiOH solution (1.01 mL, 2.02 mmol) and the mixture was stirred at 150° C. for 1.5 h under microwave irradiation. After cooling to RT, the mixture was diluted with a CH$_2$Cl$_2$:MeOH=9:1 mixture (150 mL), washed with brine (20 mL), dried over Na$_2$SO$_4$, filtered and concentrated at 40° C. under vacuum. Purification by column chromatography (SiO$_2$, eluent CH$_2$Cl$_2$:MeOH=100:0 to 92:8) provided, after evaporation and drying, 39 mg of 6,7-dimethoxy-4-((6-methoxy-2-(methylamino)quinolin-3-yl)methyl)-1-propylisoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (0.40 mL). The reaction mixture was stirred for 5 min at RT and concentrated at 40° C. under vacuum to give 6,7-dimethoxy-4-((6-methoxy-2-(methylamino)quinolin-3-yl)methyl)-1-propylisoquinolin-3-ol dihydrochloride 48 as a yellow solid (31 mg, 6% yield).

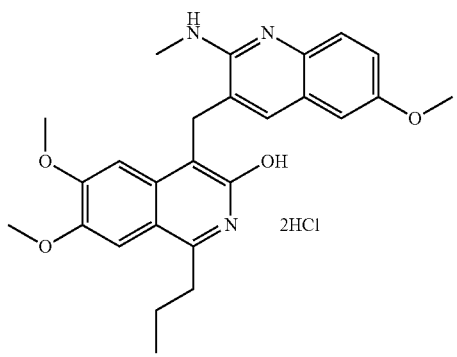

48

MW: 520.45; Yield: 6%; Yellow solid, Mp (° C.): 216.9 (dec.)

$^1$H-NMR (CD$_3$OD, δ): 1.13 (t, 3H, J=7.2 Hz, CH$_3$), 1.93 (t, 2H, J=7.2 Hz, CH$_2$), 3.28 (s, 3H, CH$_3$), 3.35 (s, 2H, CH$_2$), 3.76 (s, 3H, CH$_3$), 3.91 (s, 3H, CH$_3$), 4.01 (s, 3H, CH$_3$), 4.30 (s, 2H, CH$_2$), 7.06 (s, 1H, ArH), 7.11 (s, 1H, ArH), 7.31 (dd, 1H, J=9.1 Hz, J=2.2 Hz, ArH), 7.52 (s, 1H, ArH), 7.88 (d, 1H, J=9.2 Hz, ArH).

$^{13}$C-NMR (CD$_3$OD, δ): 14.2, 24.7, 27.1, 29.9, 33.6, 56.3, 56.9, 57.3, 102.4, 105.9, 109.5, 109.9, 119.0, 119.6, 123.3, 123.7, 124.3, 131.2, 139.0, 141.7, 152.0, 153.2, 153.5, 154.7, 158.8, 159.9.

MS-ESI m/z (% rel. Int.): 448.3 ([MH]$^+$, 100).

HPLC: Method B (10 min), X Bridge™ column (5 μm, C18, 4.5×50 mm, Model #186003113), detection UV 254 nm, RT=4.34 min, peak area 99.6%.

Preparation of 4-((6-ethoxy-2-(ethylamino)quinolin-3-yl)methyl)-6,7-dimethoxy-1-propylisoquinolin-3-ol dihydrochloride 49

To a stirred solution of 6,7-dimethoxy-1-propylisoquinolin-3-ol RBO 35134 (149 mg, 0.60 mmol) in THF (10 mL) in a 20 mL microwave vial equipped with a magnetic stirrer was added 3-(chloromethyl)-6-ethoxy-N-ethylquinolin-2-amine hydrochloride SLA 41042 (181 mg, 0.68 mmol) at RT followed by a 2 N aq. LiOH solution (0.60 mL, 1.20 mmol) and the mixture was stirred at 150° C. for 1.5 h under microwave irradiation. After cooling to RT, the mixture was diluted with CH$_2$Cl$_2$:MeOH=9:1 (150 mL) and washed with brine (20 mL), dried over Na$_2$SO$_4$, filtered, and concentrated at 40° C. under vacuum. Purification by column chromatography (SiO$_2$, eluent EtOAc:MeOH=100:0 to 95:5) followed by a second purification by column chromatography (SiO$_2$, eluent CH$_2$Cl$_2$:MeOH=100:0 to 97:3) provided 35 mg of 4-((6-ethoxy-2-(ethylamino)quinolin-3-yl)methyl)-6,7-dimethoxy-1-propylisoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (1.0 mL). The reaction mixture was stirred for 5 min at RT then concentrated at 40° C. under vacuum to afford 4-((6-ethoxy-2-(ethylamino)quinolin-3-yl)methyl)-6,7-dimethoxy-1-propylisoquinolin-3-ol dihydrochloride 49 as a yellow solid (14 mg, 4% yield).

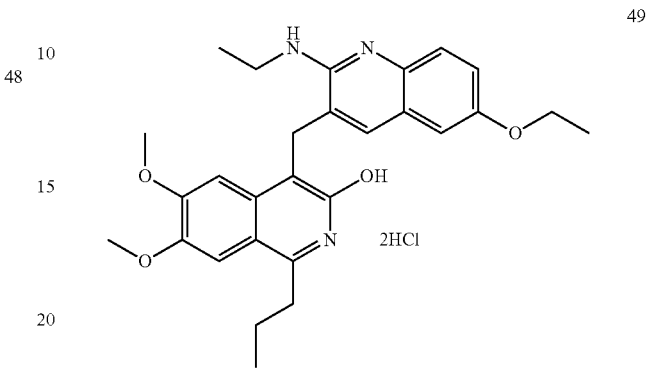

49

MW: 548.50; Yield: 4%; Yellow solid; Mp (° C.): 132.2

$^1$H-NMR (CD$_3$OD, δ): 1.17 (t, 3H, J=7.1 Hz, CH$_3$), 1.49 (t, 3H, J=7.1 Hz, CH$_3$), 1.57 (t, 3H, J=6.8 Hz, CH$_3$), 1.91-2.00 (m, 2H, CH$_2$), 3.30-3.38 (m, 2H, CH$_2$), 3.72-3.78 (m, 2H, CH$_2$), 4.04 (s, 3H, OCH$_3$), 4.06 (s, 3H, OCH$_3$), 4.09-4.20 (m, 2H, CH$_2$), 4.40 (s, 2H, CH$_2$), 7.13-7.20 (m, 1H, ArH), 7.27 (s, 1H, ArH), 7.39-7.43 (m, 2H, 2×ArH), 7.90 (d, 1H, J=9.0 Hz, ArH), 8.06 (s, 1H, ArH).

MS-ESI m/z (% rel. Int.): 476 ([MH]$^+$, 100).

HPLC: Method B (10 min), XBridge™ column (5 μm, C18, 4.5×50 mm, Model #186003113), detection UV 254 nm, RT=4.77 min, peak area 97.8%.

Preparation of 4-((2-(ethylamino)-6-methoxyquinolin-3-yl)methyl)-6,7-dimethoxy-1-propylisoquinolin-3-ol dihydrochloride 50

To a stirred solution of 6,7-dimethoxy-1-propylisoquinolin-3-ol RBO 35142 (250 mg, 1.01 mmol) in toluene (10 mL) in a 20 mL microwave vial equipped with a magnetic stirrer was added 3-(chloromethyl)-N-ethyl-6-methoxyquinolin-2-amine hydrochloride SLA 28166 (290 mg, 1.01 mmol) followed by a 2 N aq. LiOH solution (1.01 mL, 2.02 mmol) and the mixture was stirred at 150° C. for 1.5 h under microwave irradiation. After cooling to RT, the mixture was diluted with CH$_2$Cl$_2$:MeOH=9:1 (150 mL), washed with brine (20 mL), dried over Na$_2$SO$_4$, filtered, and concentrated at 40° C. under vacuum. Purification by column chromatography (SiO$_2$, eluent EtOAc:MeOH=100:0 to 95:5) followed by a second purification by column chromatography (SiO$_2$, eluent EtOAc:MeOH=100:0 to 92:8) provided, after evaporation and drying, 25 mg of 4-((2-(ethylamino)-6-methoxyquinolin-3-yl)methyl)-6,7-dimethoxy-1-propylisoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (0.45 mL). The reaction mixture was stirred for 5 min at RT, concentrated at 40° C. under vacuum, to afford 4-((2-(ethylamino)-6-methoxyquinolin-3-yl)methyl)-6,7-dimethoxy-1-propylisoquinolin-3-ol dihydrochloride 50 as a yellow solid (30 mg, 6% yield).

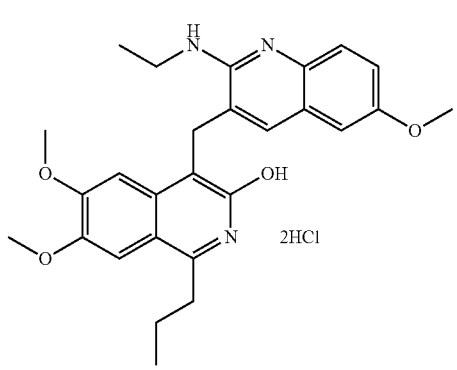

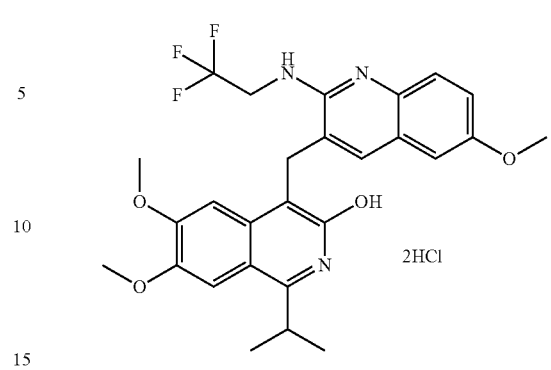

MW: 534.47; Yield: 6%; Yellow solid; Mp (° C.): 218.4 (dec.)

$^1$H-NMR (CD$_3$OD, δ): 1.02 (t, 3H, J=6.8 Hz, CH$_3$), 1.42 (t, 3H, J=6.6 Hz, CH$_3$), 1.79-1.90 (m, 2H, CH$_2$), 3.18-3.28 (m, 2H, CH$_2$), 3.65 (q, 2H, J=6.8 Hz, CH$_2$), 3.70 (s, 3H, OCH$_3$), 3.87 (s, 3H, OCH$_3$), 3.90 (s, 3H, OCH$_3$), 4.26 (s, 2H, CH$_2$), 6.98 (s, 1H, ArH), 7.08 (s, 1H, ArH), 7.23 (d, 1H, J=9.1 Hz, ArH), 7.34 (s, 1H, ArH), 7.68 (s, 1H, ArH), 7.79 (d, 1H, J=9.1 Hz, ArH).

$^{13}$C-NMR (CD$_3$OD, δ): 13.8, 14.2, 24.6, 30.8, 33.5, 39.1, 56.3, 56.8, 57.3, 102.1, 105.7, 109.5, 119.6, 123.3, 123.6, 123.6, 131.2, 139.9, 141.7, 151.3, 152.5, 153.9, 158.8, 159.4, (3×C not observed).

MS-ESI m/z (% rel. Int.): 462.3 ([MH]$^+$, 100).

HPLC: Method B (10 min), XBridge™ column (5 μm, C18, 4.5×50 mm, Model #186003113), detection UV 254 nm, RT=4.50 min, peak area 99.4%.

Preparation of 1-isopropyl-6,7-dimethoxy-4-((6-methoxy-2-(2,2,2-trifluoroethylamino)quinolin-3-yl)methyl)isoquinolin-3-ol dihydrochloride 51

To a stirred solution of 1-isopropyl-6,7-dimethoxyisoquinolin-3-ol SIL 32164 (362 mg, 1.46 mmol) in THF (10 mL) in a 20 mL microwave vial equipped with a magnetic stirrer was added 3-(chloromethyl)-6-methoxy-N-(2,2,2-trifluoroethyl)quinolin-2-amine hydrochloride SLA 41070 (500 mg, 1.47 mmol) at RT followed by a 2 N aq. solution of LiOH (1.47 mL, 2.94 mmol) and the mixture was stirred at 160° C. for 1.5 h under microwave irradiation. After cooling to RT, the mixture was diluted with CH$_2$Cl$_2$:MeOH=9:1 (150 mL), washed with brine (20 mL), dried over Na$_2$SO$_4$, filtered, and concentrated at 40° C. under vacuum. Purification by column chromatography (SiO$_2$, eluent EtOAc:MeOH=100:0 to 95:5) followed by a second purification by column chromatography (SiO$_2$, eluent CH$_2$Cl$_2$:MeOH=100:0 to 97:3) provided, after evaporation, 161 mg of 1-isopropyl-6,7-dimethoxy-4-((6-methoxy-2-(2,2,2-trifluoroethylamino)quinolin-3-yl)methyl)isoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (1.5 mL). The reaction mixture was stirred for 5 min at RT then concentrated at 40° C. under vacuum to afford 1-isopropyl-6,7-dimethoxy-4-((6-methoxy-2-(2,2,2-trifluoroethylamino)quinolin-3-yl)methyl)isoquinolin-3-ol dihydrochloride 51 as a yellow solid (130 mg, 15% yield).

MW: 588.45; Yield: 15%; Yellow solid; Mp (° C.): 210.0

$^1$H-NMR (CD$_3$OD, δ): 1.62 (d, 6H, J=6.9 Hz, 2×CH$_3$), 3.83 (s, 3H, OCH$_3$), 3.98 (s, 3H, OCH$_3$), 4.04 (s, 3H, OCH$_3$), 4.18-4.25 (m, 1H, CH), 4.44 (s, 2H, CH$_2$), 4.73 (q, 2H, J=8.7 Hz, CH$_2$), 7.10 (s, 1H, ArH), 7.27 (d, 1H, J=2.6 Hz, ArH), 7.43 (dd, 1H, J=2.6 Hz & J=9.2 Hz, ArH), 7.63 (s, 1H, ArH), 7.93 (s, 1H, ArH), 7.99 (d, 1H, J=9.2 Hz, ArH).

$^{13}$C-NMR (CD$_3$OD, δ): 21.3 (2×C), 27.4, 30.6, 44.3 (q, J=35.2 Hz), 56.4, 56.9, 57.3, 102.1, 105.5, 109.2, 109.6, 117.6, 119.8, 124.5, 124.5, 125.6 (q, J=281.9 Hz), 131.0, 141.4, 141.9, 151.7, 153.0, 154.5, 158.6, 159.3, 159.8, (1×C not observed).

MS-ESI m/z (% rel. Int.): 516 ([MH]$^+$, 100).

HPLC: Method B (10 min), XBridge™ column (5 μm, C18, 4.5×50 mm, Model #186003113), detection UV 254 nm, RT=4.64 min, peak area 99.1%

Preparation of 6,7-dimethoxy-4-((6-methoxy-2-(propylamino)quinolin-3-yl)methyl)-1-propylisoquinolin-3-ol dihydrochloride 52

To a stirred solution of 6,7-dimethoxy-1-propyl-isoquinolin-3-ol RBO 35134 (250 mg, 1.01 mmol) in THF (10 mL) in a 20 mL microwave vial equipped with a magnetic stirrer was added 3-(chloromethyl)-6-methoxy-N-propylquinolin-2-amine free base SLA 28178 (269 mg, 1.01 mmol) followed by a dropwise addition of n-Buli (1.6 M in hexane, 0.65 mL, 1.04 mmol) and the mixture was stirred at 150° C. for 1.5 h under microwave irradiation. After cooling to RT, the mixture was diluted with CH$_2$Cl$_2$:MeOH=9:1 (150 mL) and washed with brine (20 mL), dried over Na$_2$SO$_4$, filtered and concentrated at 40° C. under vacuum. Purification by column chromatography (SiO$_2$, eluent EtOAc:MeOH=100:0 to 92:8) followed by a second purification by column chromatography (SiO$_2$, eluent CH$_2$Cl$_2$:MeOH=100:0 to 95:5) provided, after evaporation, 70 mg of 6,7-dimethoxy-4-((6-methoxy-2-(propylamino)quinolin-3-yl)methyl)-1-propylisoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (0.40 mL). The reaction mixture was stirred for 5 min at RT then concentrated at 40° C. under vacuum to afford 6,7-dimethoxy-4-((6-methoxy-2-(propylamino)quinolin-3-yl)methyl)-1-propylisoquinolin-3-ol dihydrochloride 52 as a yellow solid (26.6 mg, 5% yield).

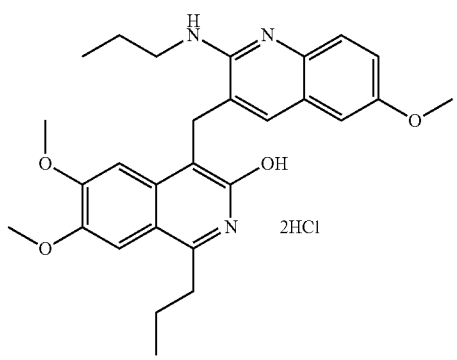

MW: 548.50; Yield: 5%; Yellow solid; Mp (° C.): 148.3

$^1$H-NMR (CD$_3$OD, δ): 1.02-1.18 (m, 6H, 2×CH$_3$), 1.80-1.85 (m, 4H, 2×CH$_2$), 3.20-3.25 (m, 2H, CH$_2$), 3.57-3.87 (m, 2H, CH$_2$), 3.70 (s, 3H, OCH$_3$), 3.87 (s, 3H, OCH$_3$), 3.91 (s, 3H, OCH$_3$), 4.27 (s, 2H, CH$_2$), 6.98 (s, 1H, ArH), 7.08 (s, 1H, ArH), 7.23 (d, 1H, J=9.2 Hz, ArH), 7.36 (s, 1H, ArH), 7.66 (s, 1H, ArH), 7.80 (d, 1H, J=9.2 Hz, ArH).

$^{13}$C-NMR (CD$_3$OD, δ): 11.8, 14.2, 22.6, 24.6, 27.5, 33.5, 45.7, 56.3, 56.8, 57.3, 102.4, 105.7, 109.5, 109.5, 119.6, 119.6, 123.3, 123.3, 123.6, 124.8, 131.2, 139.9, 141.7, 151.4, 152.6, 154.1, 158.8, 159.9.

MS-ESI m/z (% rel. Int.): 476 ([MH]$^+$, 100).

HPLC: Method B (10 min), XBridge™ column (5 μm, C18, 4.5×50 mm, Model #186003113), detection UV 214 nm, RT=4.72 min, peak area 95.1%.

Preparation of 4-((2-(isopropylamino)-6-methoxy-quinolin-3-yl)methyl)-6,7-dimethoxy-1-propyliso-quinolin-3-ol dihydrochloride 53

2-(Isopropylamino)-6-methoxyquinoline-3-carbalde-hyde SLA 28186

To a stirred solution of 2-chloro-6-methoxyquinoline-3-carbaldehyde (1.50 g, 6.77 mmol) in THF (10 mL) in a 20 mL microwave vial equipped with a magnetic stirrer was added propan-2-amine (5.76 mL, 67.7 mmol) and the reaction mixture was stirred for 12.5 h at 160° C. and finally 45 min at 180° C. under microwave irradiation. After cooling to RT, the volatiles were removed at 40° C. under vacuum and the resulting yellow oil was taken up in a mixture of THF:1 N aq. HCl=1:1 (50 mL) and stirred for 1 h at RT. The volatiles were then removed at 40° C. under vacuum and the residue was then neutralised with a saturated NaHCO$_3$ aqueous solution before extraction with CH$_2$Cl$_2$ (100 mL). The organic layer was washed with brine (20 mL), dried over MgSO$_4$, filtered, and concentrated under vacuum to give 2-(isopropylamino)-6-methoxyquinoline-3-carbalde-hyde SLA 28186 as an orange solid (1.64 g, 99% yield).

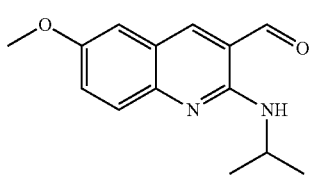

MW: 244.29; Yield: 99%; Orange solid; Mp (° C.): 160.0

$^1$H-NMR (CDCl$_3$, δ): 1.32 (d, 6H, J=6.0 Hz, 2×CH$_3$), 3.77 (s, 3H, OCH$_3$), 4.44-4.57 (m, 1H, CH), 6.96 (d, 1H, J=2.8 Hz, ArH), 7.32 (dd, 1H, J=2.8 & 9.2 Hz, ArH), 7.58 (d, 1H, J=9.2 Hz, ArH), 7.75 (broad d, 1H, J=9.0 Hz, CHNH), 8.12 (s, 1H, ArH), 9.96 (s, 1H, HC=O).

$^{13}$C-NMR (CDCl$_3$, δ): 22.9, 41.8, 55.5, 106.6, 117.1, 121.8, 125.8, 128.1, 147.2, 147.4, 153.2, 154.7, 193.2, (1×C not observed).

MS-ESI m/z (% rel. Int.): 245 ([M+H]$^+$, 100).

HPLC: Method B (5 min), XBridge™ column (5 μm, C18, 4.5×50 mm, Model #186003113), detection UV 254 nm, RT=2.76 min.

(2-(Isopropylamino)-6-methoxyquinolin-3-yl)metha-nol SLA 28188

To a stirred solution of 2-(isopropylamino)-6-methoxy-quinoline-3-carbaldehyde SLA 28186 (1.55 g, 6.35 mmol) in THF (100 mL) in a 250 mL round-bottomed flask equipped with a magnetic stirrer was added NaBH$_4$ (0.24 g, 6.35 mmol) and the mixture was stirred for overnight at RT then cooled in an ice bath before quenching by addition of a 1 N aq. HCl solution (40 mL). After stirring for 15 min at that temperature, the mixture was basified to pH=9 with a 2 N aq. NaOH solution. THF was removed at 40° C. under vacuum and the solution was extracted with CH$_2$Cl$_2$ (200 mL). The organic layer was washed with brine (20 mL), dried over Na$_2$SO$_4$, filtered, and concentrated under vacuum to give (2-(isopropylamino)-6-methoxyquinolin-3-yl) methanol SLA 28188 as an orange solid (1.45 g, 93% yield).

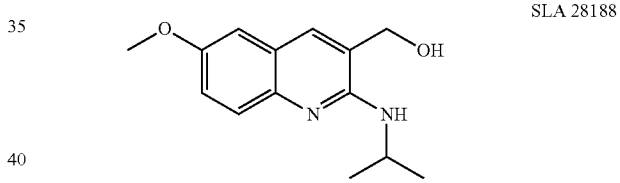

MW: 246.30; Yield: 93%; Orange solid; Mp (° C.): 150.0

$^1$H-NMR (CDCl$_3$, δ): 1.28 (d, 6H, J=6.0 Hz, 2×CH$_3$), 2.46 (broad s, 1H, OH), 3.87 (s, 3H, OCH$_3$), 4.36-4.45 (m, 1H, CH), 4.56 (s, 2H, OCH$_2$), 5.37 (broad d, 1H, J=6.0 Hz, NH), 6.82 (d, 1H, J=2.8 Hz, ArH), 7.18 (dd, 1H, J=2.8 & 9.1 Hz, ArH), 7.26 (s, 1H, ArH), 7.60 (d, 1H, J=9.1 Hz, ArH).

$^{13}$C-NMR (CDCl$_3$, δ): 23.0, 42.2, 55.4, 63.8, 106.6, 120.3, 122.2, 122.9, 127.1, 134.3 143.1, 154.2, 154.5, (1×C not observed).

MS-ESI m/z (% rel. Int.): 247 ([M+H]$^+$, 100).

HPLC: Method B (5 min), XBridge™ column (5 μm, C18, 4.5×50 mm, Model #186003113), detection UV 214 nm, RT=2.13 min.

3-(Chloromethyl)-N-isopropyl-6-methoxyquinolin-2-amine hydrochloride SLA 28190

To a stirred solution of (6-methoxy-2-(propylamino)qui-nolin-3-yl)methanol SLA 28188 (1.41 g, 5.72 mmol) in dry CH$_2$Cl$_2$ (115 mL) in a 250 mL round-bottomed flask equipped with a magnetic stirrer was added dropwise SOCl$_2$ (8.30 mL, 114 mmol). The mixture was stirred for 1 h at RT then concentrated to dryness at 40° C. under vacuum. The residue was then taken up in CH₂Cl₂ (20 mL) before concentration back to dryness at 40° C. under vacuum (done 3 times) to give of 3-(chloromethyl)-N-isopropyl-6-methoxyquinolin-2-amine hydrochloride SLA 28190 as a yellow solid (1.79 g, >100% yield).

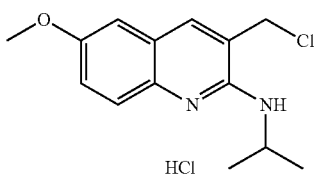

SLA 28190

MW: 301.21; Yield: Quantitative; Yellow solid; Mp (° C.): 145.0

¹H-NMR (CDCl₃, δ): 1.49 (d, 6H, J=6.3 Hz, 2×CH₃), 3.87 (s, 3H, OCH₃), 5.01 (s, 2H, CH₂), 5.28-5.38 (m, 1H, CH), 7.02 (d, 1H, J=2.7 Hz, ArH), 7.20 (broad d, 1H, J=8.6 Hz, NH), 7.29 (dd, 1H, J=2.7 & 9.2 Hz, ArH), 8.07 (s, 1H, ArH), 9.00 (d, 1H, J=9.2 Hz, ArH).

¹³C-NMR (CD₃OD, δ): 22.0, 42.2, 46.7, 56.4, 109.9, 120.0, 123.4, 123.9, 124.5, 132.2, 143.9, 150.3, 158.9, (1×C not observed).

MS-ESI m/z (% rel. Int.): 265 ([MH]⁺, ³⁵Cl, 100), 267 ([MH]⁺, ³⁷Cl, 38)

HPLC: Method B (5 min), XBridge™ column (5 μm, C18, 4.5×50 mm, Model #186003113), detection UV 254 nm, RT=2.40 min.

4-((2-(Isopropylamino)-6-methoxyquinolin-3-yl)methyl)-6,7-dimethoxy-1-propylisoquinolin-3-ol dihydrochloride 53

To a stirred solution of 3-(chloromethyl)-N-isopropyl-6-methoxyquinolin-2-amine hydrochloride SLA 28190 (305 mg, 1.01 mmol) in toluene (10 mL) in a 20 mL microwave vial equipped with a magnetic stirrer was added 6,7-dimethoxy-1-propylisoquinolin-3-ol RBO 35134 (250 mg, 1.01 mmol) followed by a 2 N aq. LiOH solution (1.01 mL, 2.02 mmol) and the mixture was stirred at 150° C. for 1.5 h under microwave irradiation. After cooling to RT, the mixture was diluted with CH₂Cl₂:MeOH=9:1 (150 mL), washed with brine (20 mL), dried over Na₂SO₄, filtered and concentrated at 40° C. under vacuum. Purification by column chromatography (SiO₂, eluent EtOAc:MeOH=100:0 to 94:6) followed by a second purification by column chromatography (SiO₂, eluent CH₂Cl₂:MeOH=100:0 to 95:5) provided 61 mg of 4-((2-(isopropylamino)-6-methoxyquinolin-3-yl)methyl)-6,7-dimethoxy-1-propylisoquinolin-3-ol as a brown solid. This free base was dissolved in CH₂Cl₂ (2 mL) in a 10 mL round-bottomed flask equipped with a magnetic stirrer before addition of a 0.49 M HCl solution in MeOH (1.05 mL). The reaction mixture was stirred for 5 min at RT then concentrated at 40° C. under vacuum to afford 4-((2-(isopropylamino)-6-methoxyquinolin-3-yl)methyl)-6,7-dimethoxy-1-propylisoquinolin-3-ol dihydrochloride 53 as a yellow solid (68 mg, 12% yield).

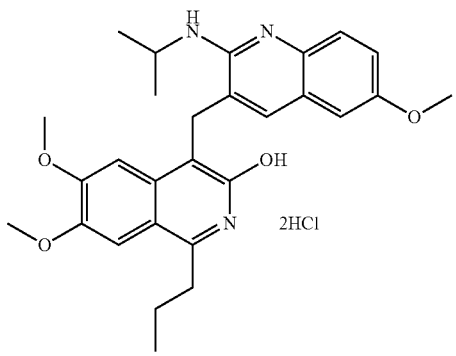

53

2HCl

MW: 548.50; Yield: 12%; Yellow solid; Mp (° C.): 148.3

¹H-NMR (CD₃OD, δ): 1.10 (t, 3H, J=6.5 Hz, CH₃), 1.47 (d, 6H, J=5.4 Hz, 2×CH₃), 1.85-1.90 (m, 2H, CH₂), 3.22-3.31 (m, 2H, CH₂), 3.85 (s, 3H, OCH₃), 3.96 (s, 3H, OCH₃), 4.01 (s, 3H, OCH₃), 4.29-4.40 (m, 3H, CH & CH₂), 7.06 (s, 1H, 1×ArH), 7.24 (s, 1H, 1×ArH), 7.32-7.36 (m, 2H, 2×ArH), 7.84 (d, 1H, J=9.1 Hz, 1×ArH), 8.08 (s, 1H, 1×ArH).

MS-ESI m/z (% rel. Int.): 476 ([MH]⁺, 100).

HPLC: method B (10 min) XBridge™ column (5 μm, C18, 4.5×50 mm, Model #186003113), detection UV 254 nm, RT=4.57 min, peak area 95.2%.

Preparation of 6,7-dimethoxy-4-((6-methoxy-2-((2,2,2-trifluoroethyl)amino)quinolin-3-yl)methyl)-1-propylisoquinolin-3-ol dihydrochloride 54

To a stirred solution of 6,7-dimethoxy-1-propylisoquinolin-3-ol RBO 35134 (116 mg, 0.47 mmol) in THF (10 mL) in a 20 mL microwave vial equipped with a magnetic stirrer was added 3-(chloromethyl)-6-methoxy-N-(2,2,2-trifluoroethyl)quinolin-2-amine hydrochloride SLA 41062 (160 mg, 0.47 mmol) at RT followed by a 2 N aq. solution of LiOH (0.47 mL, 0.94 mmol) and the mixture was stirred at 160° C. for 1.5 h under microwave irradiation. After cooling to RT, the mixture was diluted with CH₂Cl₂:MeOH=9:1 (150 mL), washed with brine (20 mL), dried over Na₂SO₄, filtered and concentrated at 40° C. under vacuum. Purification by column chromatography (SiO₂, eluent EtOAc:MeOH=100:0 to 97:3) followed by a second purification by column chromatography (SiO₂, eluent CH₂Cl₂:MeOH=100:0 to 95:5) provided, after evaporation, 30 mg of 6,7-dimethoxy-4-((6-methoxy-2-((2,2,2-trifluoroethyl)amino)quinolin-3-yl)methyl)-1-propylisoquinolin-3-ol as a brown solid. This free base was dissolved in CH₂Cl₂ (2 mL) in a 10 mL round-bottomed flask equipped with a magnetic stirrer before addition of a 0.49 M HCl solution in MeOH (1.05 mL). The reaction mixture was stirred for 5 min at RT then concentrated at 40° C. under vacuum to give 6,7-dimethoxy-4-((6-methoxy-2-((2,2,2-trifluoroethyl)amino)quinolin-3-yl)methyl)-1-propylisoquinolin-3-ol dihydrochloride SLA 41064 as a yellow solid (31 mg, 11% yield).

54

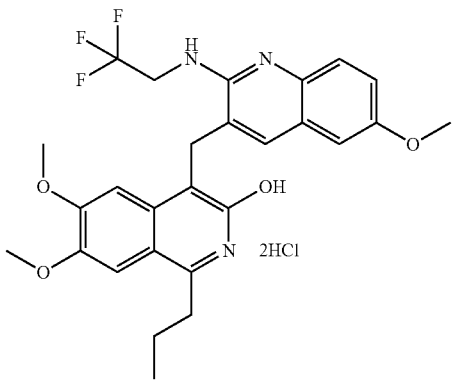

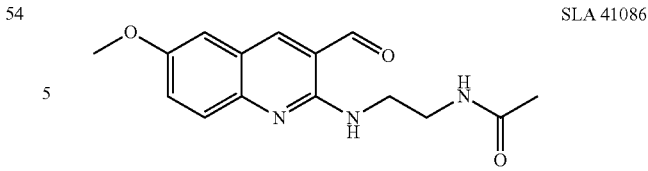

SLA 41086

MW: 588.45; Yield: 11%; Yellow solid; Mp (° C.): 245.5
¹H-NMR (CD₃OD, δ): 1.13 (t, 3H, J=7.0 Hz, CH₃), 1.90-1.97 (m, 2H, CH₂), 3.31-3.35 (m, 2H, CH₂), 3.86 (s, 3H, OCH₃), 4.00 (s, 6H, 2×OCH₃), 4.43 (s, 2H, CH₂), 4.65 (q, 2H, J=8.7 Hz, CH₂), 7.08 (s, 1H, ArH), 7.31 (s, 1H, ArH), 7.42-7.45 (m, 2H, 2×ArH), 7.95 (d, 1H, J=9.2 Hz, ArH), 8.09 (s, 1H, ArH).
¹³C-NMR (CD₃OD, δ): 14.1, 24.6, 27.8, 33.5, 44.3 (q, J=34.4 Hz), 56.4, 56.8, 57.3, 101.8, 105.6, 109.2, 117.7, 119.8, 124.3, 124.4, 125.2, 127.5, 131.0, 141.6, 141.8, 151.1, 153.1, 153.7, 155.8, 159.3, 159.3, CF₃ not seen.
MS-ESI m/z (% rel. Int.): 516 ([MH]⁺, 100).
HPLC: Method B (10 min), XBridge™ column (5 μm, C18, 4.5×50 mm, Model #186003113), detection UV 254 nm, RT=4.70 min, peak area 95.1%.

Preparation of N-(2-((3-((3-hydroxy-6,7-dimethoxy-1-propylisoquinolin-4-yl)methyl)-6-methoxyquinolin-2-yl)amino)ethyl)acetamide dihydrochloride 55

N-(2-((3-Formyl-6-methoxyquinolin-2-yl)amino)ethyl)acetamide SLA 41086

To a stirred solution of 2-chloro-6-methoxyquinoline-3-carbaldehyde (1.00 g, 4.51 mmol) in THF (10 mL) in a 20 mL microwave vial equipped with a magnetic stirrer was added ethylenediamine (2.71 g, 45.09 mmol) and the reaction mixture was stirred for 2 h at 160° C. under microwave irradiation then for 45 min at 180° C. under microwave irradiation. After cooling to RT, the volatiles were removed at 40° C. under vacuum and the residue was taken up in a mixture of THF:1 N aq. HCl=1:1 (50 mL) and stirred for 1 h at RT. THF was then removed at 40° C. under vacuum and the residue was neutralised with a saturated NaHCO₃ aqueous solution before extraction with CH₂Cl₂ (200 mL). The organic layer was isolated, washed with brine (20 mL), dried over MgSO₄, filtered and concentrated under vacuum to give 1.22 g of a brown solid. This solid (600 mg, 2.45 mmol) was then dissolved in dry CH₂Cl₂ (100 mL) in a 250 mL round-bottomed flask equipped with a magnetic stirrer before addition of triethylamine (0.481 mL, 3.46 mmol) and acetic anhydride (0.28 mL, 2.96 mmol) and the reaction mixture was stirred overnight at RT. The organic solution was then washed with brine (20 mL), dried over Na₂SO₄, filtered, and concentrated at 40° C. under vacuum. Purification by column chromatography (SiO₂, eluent cyclohexane:EtOAc=100:0 to 50:50) gave N-(2-((3-formyl-6-methoxyquinolin-2-yl)amino)ethyl)acetamide SLA 41086 as a brown solid (150 mg, 21% yield).

MW: 287.31; Yield: 21%; Brown solid; Mp (° C.): 147.2
¹H-NMR (CDCl₃, δ): 1.93 (s, 3H, CH₃CO), 3.51-3.56 (m, 2H, CH₂N), 3.77-3.83 (m, 2H, CH₂N), 3.90 (s, 3H, OCH₃), 7.02 (d, 1H, J=2.8 Hz, ArH), 7.38 (dd, 1H, J=2.8 Hz and 9.2 Hz, ArH), 7.46 (broad s, 1H, NH), 7.58 (d, 1H, J=9.2 Hz, ArH), 8.17-8.22 (broad m, 1H, NH), 8.21 (s, 1H, ArH), 9.99 (s, 1H, HC=O).
¹³C-NMR (CDCl₃, δ): 23.3, 40.1, 42.2, 55.6, 106.9, 117.4, 122.4, 126.3, 127.3, 146.2, 147.4, 154.5, 155.3, 170.3, 192.9.
MS-ESI m/z (% rel. Int.): 288 ([MH]⁺, 100).
HPLC: Method B (5 min), XBridge™ column (5 μm, C18, 4.5×50 mm, Model #186003113), detection UV 254 nm, RT=1.98 min.

N-(2-(3-(Hydroxymethyl)-6-methoxyquinolin-2-ylamino)ethyl)acetamide SLA 41088

To a stirred solution of N-(2-((3-formyl-6-methoxyquinolin-2-yl)amino)ethyl)acetamide SLA 41086 (147 mg, 512 μmol) in THF (20 mL) in a 100 mL round-bottomed flask equipped with a magnetic stirrer was added sodium borohydride NaBH₄ (19 mg, 502 μmol) and the mixture was stirred overnight at RT then cooled in an ice bath before quenching by addition of a 1 N aq. HCl solution (40 mL). After stirring for 15 min at that temperature, the mixture was basified to pH=9 with a 2 N aq. NaOH solution. THF was then removed at 40° C. under vacuum and the solution was extracted with CH₂Cl₂ (100 mL). The organic layer was washed with brine (20 mL), dried over Na₂SO₄, filtered and concentrated under vacuum to give N-(2-((3-(hydroxymethyl)-6-methoxyquinolin-2-ylamino)ethyl)acetamide SLA 41088 as an orange solid (113 mg, 76% yield).

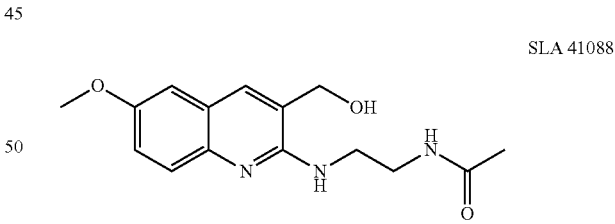

SLA 41088

MW: 289.33; Yield: 76%; Orange solid; Mp (° C.): 168.5
¹H-NMR (CDCl₃, δ): 1.84 (s, 3H, CH₃CO), 3.39-3.44 (m, 2H, CH₂), 3.64-3.68 (m, 2H, CH₂), 3.85 (s, 3H, OCH₃), 4.62 (s, 2H, CH₂), 6.88 (d, 1H, J=2.6 Hz, ArH), 7.18 (dd, 1H, J=2.6 & 9.1 Hz, ArH), 7.46 (s, 1H, ArH), 7.55 (d, 1H, J=9.1 Hz, ArH), OH not seen.
¹³C-NMR (CDCl₃, δ): 23.1, 40.7, 42.4, 55.5, 63.2, 106.7, 120.8, 122.8, 123.5, 126.6, 134.8, 142.4, 154.9, 155.5, 171.1.
MS-ESI m/z (% rel. Int.): 290 ([MH]⁺, 100).
HPLC: Method B (5 min), XBridge™ column (5 μm, C18, 4.5×50 mm, Model #186003113), detection UV 214 nm, RT=2.03 min.

N-(2-((3-(Chloromethyl)-6-methoxyquinolin-2-yl)amino)ethyl)acetamide hydrochloride SLA 41090

To a stirred solution of N-(2-((3-(hydroxymethyl)-6-methoxyquinolin-2-yl)amino)ethyl)acetamide SLA 41088 (113 mg, 391 μmol) in dry CH$_2$Cl$_2$ (20 mL) in a 100 mL round-bottomed flask equipped with a magnetic stirrer was added dropwise SOCl$_2$ (0.28 mL, 3.86 mmol). The mixture was stirred for 1.5 h at RT then concentrated to dryness at 40° C. under vacuum. The residue was then taken up in CH$_2$Cl$_2$ (20 mL) before concentration back to dryness at 40° C. under vacuum (done 3 times) to give N-(2-((3-(chloromethyl)-6-methoxyquinolin-2-yl)amino)ethyl)acetamide hydrochloride SLA 41090 as a yellow solid (135 mg, 100% yield).

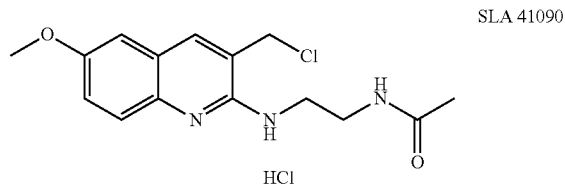 [SMILES: COc1ccc2nc(NCCNC(C)=O)c(CCl)cc2c1 ; Cl]

SLA 41090

MW: 344.24; Yield: 100%; Yellow solid; Mp (° C.): 197.5
$^1$H-NMR (CD$_3$OD, δ): 2.10 (s, 3H, CH$_3$CO), 3.50-3.60 (m, 2H, CH$_2$), 3.72-3.83 (m, 2H, CH$_2$), 3.96 (s, 3H, OCH$_3$), 4.90-4.91 (m, 2H, CH$_2$), 7.42 (s, 1H, ArH), 7.48 (d, 1H, J=8.8 Hz, ArH), 8.05 (d, 1H, J=8.8 Hz, ArH), 8.47 (s, 1H, ArH).
$^{13}$C-NMR (CD$_3$OD, δ): 22.4, 38.7, 41.9, 42.9, 56.5, 109.8, 120.3, 123.7, 123.8, 124.8, 132.3, 143.8, 151.7, 159.1, 175.8.
MS-ESI m/z (% rel. Int.): 308 ([MH]$^+$, $^{35}$Cl, 100), 310 ([MH]$^+$, $^{37}$Cl, 38).
HPLC: Method B (5 min), XBridge™ column (5 μm, C18, 4.5×50 mm, Model #186003113), detection UV 254 nm, RT=2.18 min.

N-(2-((3-((3-hydroxy-6,7-dimethoxy-1-propylisoquinolin-4-yl)methyl)-6-methoxyquinolin-2-yl)amino)ethyl)acetamide 55

To a stirred solution of N-(2-((3-(chloromethyl)-6-methoxyquinolin-2-yl)amino)ethyl)acetamide hydrochloride SLA 41090 (128 mg, 0.372 mmol) in THF (10 mL) in a 20 mL microwave vial equipped with a magnetic stirrer was added 6,7-dimethoxy-1-propylisoquinolin-3-ol RBO 35134 (103 mg, 0.417 mmol) followed by a 2 N aq. LiOH solution (0.21 mL, 0.42 mmol) and the mixture was stirred at 150° C. for 1.5 h under microwave irradiation. After cooling to RT, the mixture was diluted with CH$_2$Cl$_2$:MeOH=9:1 (150 mL) and washed with brine (20 mL), dried over Na$_2$SO$_4$, filtered and concentrated at 40° C. under vacuum. Purification by column chromatography (SiO$_2$, eluent CH$_2$Cl$_2$:MeOH=100:0 to 92:8) provided 19.4 mg of N-(2-(3-((3-hydroxy-6,7-dimethoxy-1-propylisoquinolin-4-yl)methyl)-6-methoxyquinolin-2-ylamino)ethyl)acetamide. This free base was dissolved in CH$_2$Cl$_2$ (2 mL) in a 10 mL round-bottomed flask equipped with a magnetic stirrer before addition of a 0.49 M HCl solution in MeOH (1.0 mL). The reaction mixture was stirred for 5 min at RT then concentrated at 40° C. under vacuum to afforded N-(2-((3-((3-hydroxy-6,7-dimethoxy-1-propylisoquinolin-4-yl)methyl)-6-methoxyquinolin-2-yl)amino)ethyl)acetamide dihydrochloride 55 as a yellow solid (20 mg, 9% yield).

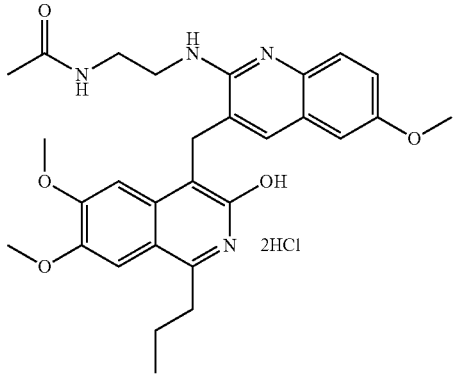

55

MW: 591.53; Yield: 9%; Yellow solid; Mp (° C.): 165.8
$^1$H NMR (CD$_3$OD, δ): 1.21-1.29 (m, 3H, CH$_3$), 1.92-1.98 (m, 2H, CH$_2$), 2.06 (s, 3H, CH$_3$CO), 3.34-3.55 (m, 4H, 2×CH$_2$), 3.70-3.98 (m, 8H, 2×OCH$_3$ and CH$_2$), 4.03 (s, 3H, OCH$_3$), 4.34 (s, 2H, CH$_2$), 7.07-7.18 (m, 2H, 2×ArH), 7.33 (d, 1H, J=8.3 Hz, ArH), 7.45-7.61 (m, 2H, 2×ArH), 8.01 (d, 1H, J=8.3 Hz, ArH).
$^{13}$C-NMR (CD$_3$OD, δ): 14.3, 22.5, 24.8, 27.2, 33.7, 37.9, 39.0, 43.5, 56.5, 57.1, 57.6, 102.9, 106.0, 109.4, 119.3, 120.0, 123.6, 123.9, 124.4, 131.3, 139.5, 141.7, 152.2, 152.9, 154.9, 158.8, 160.0, 175.7, (1×C not observed).
MS-ESI m/z (% rel. Int.): 519 ([MH]$^+$, 100).
HPLC: Method B (10 min), XBridge™ column (5 μm, C18, 4.5×50 mm, Model #186003113), detection UV 254 nm, RT=4.28 min, peak area 98.2%.

Preparation of 4-((2-((2-acetamidoethyl)amino)-6-methoxyquinolin-3-yl)methyl)-6,7-dimethoxy-1-propylisoquinolin-3-yl acetate 56

6,7-Dimethoxy-1-methylisoquinolin-3-yl acetate SIL 32158

To a solution of 6,7-dimethoxy-1-methylisoquinolin-3-ol CCH 18060 (3.11 g, 14.19 mmol) in dry CH$_2$Cl$_2$ (230 mL) in a 500 mL round-bottomed flask equipped with a magnetic stirrer was added DIEA (2.46 mL, 14.88 mmol), DMAP (173 mg, 1.42 mmol) and acetic anhydride (1.39 mL, 14.80 mmol) and the reaction mixture was stirred overnight at RT. The organic solution was then washed with brine (50 mL), dried over Na$_2$SO$_4$, filtered and concentrated under vacuum. The residue was finally purified by column chromatography (SiO$_2$, eluent cyclohexane:EtOAc=100:0 to 50:50) to give 6,7-dimethoxy-1-methylisoquinolin-3-yl acetate SIL 32158 as an off-white solid (3.26 g, 88% yield).

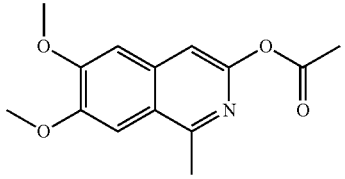

SIL 32158

MW: 261.27; Yield: 88%; Off-white solid; Mp (° C.): 139.4

$R_f$ (free base): 0.2 (cyclohexane:EtOAc=50:50).

$^1$H-NMR (CDCl$_3$, δ): 2.38 (s, 3H, CH$_3$), 2.86 (s, 3H, CH$_3$CO), 4.01 (s, 3H, OCH$_3$), 4.03 (s, 3H, OCH$_3$), 7.03 (s, 1H, ArH), 7.18 (s, 1H, ArH), 7.23 (s, 1H, ArH).

$^{13}$C-NMR (CDCl$_3$, δ): 21.4, 22.1, 56.0 (2×C), 103.7, 105.2, 108.2, 122.2, 135.4, 149.7, 151.9, 153.2, 155.9, 169.7.

MS-ESI m/z (% rel. Int.): 262 ([MH]$^+$, 100).

HPLC: Method B (10 min), XBridge™ column (5 μm, C18, 4.5×50 mm, Model #186003113), detection UV 254 nm, RT=4.04 min.

1-(Bromomethyl)-6,7-dimethoxyisoquinolin-3-yl acetate SIL 32162

To a solution of 6,7-dimethoxy-1-methylisoquinolin-3-yl acetate SIL 32158 (261 mg, 1.00 mmol) in dry CCl$_4$ (5 mL) in a 10 mL microwave vial equipped with a magnetic stirrer was added benzoyl peroxide (12 mg, 0.05 mmol) followed by NBS (178 mg, 1.00 mmol) and the mixture was stirred for 15 min at 130° C. under microwave irradiation. After cooling to RT, the mixture was diluted with CH$_2$Cl$_2$ (20 mL), washed with brine (5 mL), dried over Na$_2$SO$_4$, filtered and concentrated under vacuum. Purification by column chromatography (SiO$_2$, eluent cyclohexane:EtOAc=100:0 to 75:25) gave 1-(bromomethyl)-6,7-dimethoxyisoquinolin-3-yl acetate SIL 32162 as a yellow solid (140 mg, 41% yield).

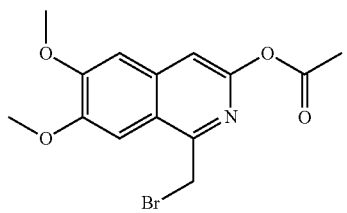

SIL 32162

MW: 340.17; Yield: 41%; Yellow solid; Mp (° C.): 164.9

$R_f$: 0.2 (cyclohexane:EtOAc=75:25).

$^1$H-NMR (CDCl$_3$, δ): 2.39 (s, 3H, CH$_3$), 4.03 (s, 3H, CH$_3$O), 4.07 (s, 3H, CH$_3$O), 4.92 (s, 2H, CH$_2$Br), 7.07 (s, 1H, ArH), 7.32 (s, 1H, ArH), 7.38 (s, 1H, ArH).

$^{13}$C-NMR (CDCl$_3$, δ): 21.4, 31.2, 56.2 (2×C), 103.2, 105.2, 111.0, 121.5, 136.6, 150.3, 151.6, 152.4, 153.7, 169.5.

MS-ESI m/z (rel. int.): 340 ([MH]$^+$, $^{79}$Br, 63), 342 ([MH]$^+$, $^{81}$Br, 68).

HPLC: Method B (5 min), XBridge™ column (5 μm, C18, 4.5×50 mm, Model #186003113), detection UV 254 nm, RT=2.77 min.

1-((1,3-Dioxoisoindolin-2-yl)methyl)-6,7-dimethoxyisoquinolin-3-yl acetate SIL 32166

To a stirred solution of 1-(bromomethyl)-6,7-dimethoxyisoquinolin-3-yl acetate SIL 32162 (2.57 g, 7.56 mmol) in dry DMF (60 mL) in a 250 mL round-bottomed flask equipped with a magnetic stirrer was added potassium phthalimide (2.43 g, 13.12 mmol) and the mixture was stirred overnight at RT and then diluted with Et$_2$O (150 mL) and H$_2$O (40 mL). A solid appeared and was isolated by filtration. The aqueous phase was isolated and diluted with Et$_2$O (100 mL) before vigorous stirring for 15 min, which gave a new amount of solid that was isolated by filtration (done 3 times). The solids were then combined, further washed with Et$_2$O (100 mL) and dried overnight under vacuum in presence of P$_2$O$_5$, which gave 2.10 g of 1-((1,3-dioxoisoindolin-2-yl)methyl)-6,7-dimethoxyisoquinolin-3-yl acetate SIL 32166 as an off-white solid (68%).

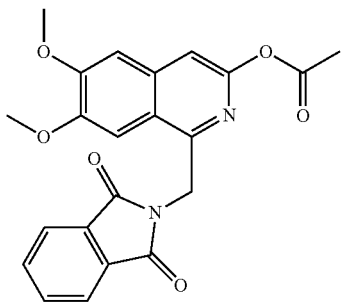

SIL 32166

MW: 406.39; Yield: 68%; Off-white solid; Mp (° C.): 247.0 (dec.).

$R_f$: 0.25 (cyclohexane:EtOAc=50:50).

$^1$H-NMR (CDCl$_3$, δ): 2.26 (s, 3H, CH$_3$), 4.00 (s, 3H, CH$_3$O), 4.05 (s, 3H, CH$_3$O), 5.39 (s, 2H, CH$_2$), 7.04 (s, 1H, ArH), 7.25 (s, 1H, ArH), 7.49 (s, 1H, ArH), 7.69-7.75 (m, 2H, 2×ArH), 7.85-7.91 (m, 2H, 2×ArH).

$^{13}$C-NMR (CDCl$_3$, δ): 21.4, 41.2, 56.1, 56.2, 102.4, 105.1, 109.8, 120.9, 123.4 (2×C), 132.3, 134.0 (2×C), 136.1, 150.2, 150.8, 151.9, 153.3, 168.2 (2×C), 169.3, (1×C not observed).

MS-ESI m/z (% rel. Int.): 407 ([MH]$^+$, 100).

HPLC: Method B (5 min), XBridge™ column (5 mm, C18, 4.5×50 mm, Model #186003113), detection UV 254 nm, RT=2.92 min.

2-((4-((2-(Ethylamino)-6-methoxyquinolin-3-yl)methyl)-3-hydroxy-6,7-dimethoxyisoquinolin-1-yl)methyl)isoindoline-1,3-dione CCH 42006-1 and 2-((3-hydroxy-6,7-dimethoxyisoquinolin-1-yl)methyl)isoindoline-1,3-dione hydrochloride CCH 42006B To a solution of 1-((1,3-dioxoisoindolin-2-yl)methyl)-6,7-dimethoxyisoquinolin-3-yl acetate SIL 32166 (297 mg, 0.73 mmol) in dry CH$_2$Cl$_2$ (9 mL) in a 25 mL round-bottomed flask equipped with a magnetic stirrer was added a 7 N NH$_3$ solution in MeOH (1 mL) and the reaction mixture was stirred for 4 h at RT then concentrated to dryness at 40° C. under vacuum. The solid was taken up in THF (7 mL) and transferred in a 20 mL microwave vial equipped with a magnetic stirrer before addition of a 2 N aq. LiOH solution (0.37 mL, 0.74 mmol) and 3-(chloromethyl)-N-ethyl-6-methoxyquinolin-2-amine SLA 28166 free base (240 mg, 0.96 mmol) and the mixture was stirred at 150° C. for 1.5 h under microwave irradiation. After cooling to RT, the mixture was diluted with CH$_2$Cl$_2$:MeOH=9:1 (80 mL)

and the organic solution was washed with brine (10 mL), dried over $Na_2SO_4$, filtered and concentrated at 40° C. under vacuum. Purification by column chromatography ($SiO_2$, eluent $CH_2Cl_2$:MeOH=100:0 to 97:3) followed by a second purification by column chromatography ($SiO_2$, eluent cyclohexane:EtOAc=100:0 to 0:100) gave 2-((4-((2-(ethylamino)-6-methoxyquinolin-3-yl)methyl)-3-hydroxy-6,7-dimethoxyisoquinolin-1-yl)methyl)isoindoline-1,3-dione CCH 42006-1 as a yellow oil (75 mg, 32%).

During the purification, 2-((3-hydroxy-6,7-dimethoxyisoquinolin-1-yl)methyl)isoindoline-1,3-dione was also isolated. The free base (23 mg) was dissolved in MeOH (2 mL) in a 10 mL round-bottomed flask equipped with a magnetic stirrer before addition of a 0.49 M HCl solution in MeOH (0.5 mL). The reaction mixture was stirred for 5 min at RT then concentrated at 40° C. under vacuum to afford 2-((3-hydroxy-6,7-dimethoxyisoquinolin-1-yl)methyl)isoindoline-1,3-dione hydrochloride CCH 42006B as a yellow solid (25 mg, 9% yield).

2-((4-((2-(Ethylamino)-6-methoxyquinolin-3-yl)methyl)-3-hydroxy-6,7-dimethoxyisoquinolin-1-yl)methyl)isoindoline-1,3-dione CCH 42006-1

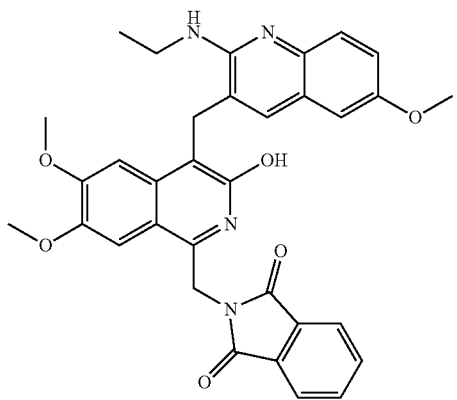

CCH 42006-1

MW: 578.61; Yield: 32%; Yellow oil.

$R_f$ (free base): 0.2 ($CH_2Cl_2$:MeOH=97:3).

$^1$H-NMR ($CDCl_3$, δ): 1.23 (t, 3H, J=7.0 Hz, $CH_2CH_3$), 3.51 (q, 2H, J=7.0 Hz, $CH_2CH_3$), 3.79 (s, 3H, $OCH_3$), 3.86 (s, 3H, $OCH_3$), 3.96 (s, 3H, $OCH_3$), 4.08 (s, 2H, $CH_2$), 5.26 (s, 2H, $CH_2$), 6.76 (d, 1H, J=2.5 Hz, ArH), 6.88 (s, 1H, ArH), 7.07 (dd, 1H, J=2.5 and 9.0 Hz, ArH), 7.24-7.28 (m, 1H, ArH), 7.46 (s, 1H, ArH), 7.55-7.63 (m, 3H, 3×ArH), 7.72-7.76 (m, 2H, 2×ArH).

$^{13}$C-NMR ($CDCl_3$, δ): 14.6, 28.2, 36.6, 38.4, 55.5, 56.0, 56.1, 62.1, 100.6, 102.3, 106.3, 112.4, 115.2, 119.5, 122.5, 123.2, 123.5 (2×C), 127.0, 131.8 (2×C), 134.2 (2×C), 134.8, 138.9, 141.5, 148.0, 154.4, 158.6, 168.0 (2×C), (3×C not observed).

MS-ESI m/z (% rel. Int.): 579 ([MH]$^+$, 100).

HPLC: method B (5 min), XBridge™ column (5 µm, C18, 4.5×50 mm, Model #186003113), detection UV 254 nm, RT=2.53 min.

2-((3-Hydroxy-6,7-dimethoxyisoquinolin-1-yl)methyl)isoindoline-1,3-dione hydrochloride CCH 42006B

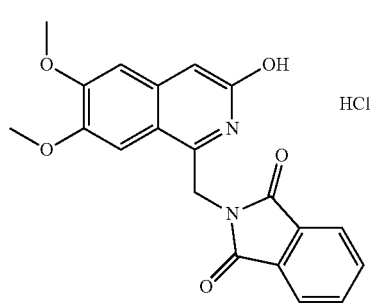

CCH 42006B

MW: 400.81; Yield: 9%; Yellow solid; Mp (° C.): 274.1

$^1$H-NMR ($CDCl_3$:$CD_3OD$=1:1, δ): 4.01 (s, 3H, $OCH_3$), 4.03 (s, 3H, $OCH_3$), 5.41 (s, 2H, $CH_2$), 7.16-7.20 (m, 2H, 2×ArH), 7.58 (s, 1H, ArH), 7.81-7.91 (m, 4H, 4×ArH).

$^{13}$C-NMR ($CDCl_3$:$CD_3OD$=1:1, δ): 38.6, 57.2, 57.4, 103.7, 105.2, 105.4, 118.7, 124.9 (2×C), 133.0 (2×C), 136.1 (2×C), 143.4, 145.7, 152.3, 155.5, 158.8, 169.3 (2×C).

MS-ESI m/z (% rel. Int.): 365 ([MH]$^+$, 100).

HPLC: Method B (10 min), XBridge™ column (5 µm, C18, 4.5×50 mm, Model #186003113), detection UV 254 nm, RT=4.02 min, peak area 98.9%.

1-(Acetamidomethyl)-4-((2-(ethylamino)-6-methoxyquinolin-3-yl)methyl)-6,7-dimethoxyisoquinolin-3-yl acetate 56

To a solution of 2-((4-((2-(ethylamino)-6-methoxyquinolin-3-yl)methyl)-3-hydroxy-6,7-dimethoxyisoquinolin-1-yl)methyl)isoindoline-1,3-dione CCH 42006-1 (75 mg, 130 µmol) in EtOH (5 mL) in a 10 mL microwave vial equipped with a magnetic stirrer was added hydrazine monohydrate (26 µL, 536 µmol) and the mixture was stirred for 10 min at 130° C. under microwave irradiation. After cooling to RT, the reaction mixture was concentrated to dryness at 40° C. under vacuum. The residue CCH 42006-2 was dissolved in dry $CH_2Cl_2$ (4 mL) and half of the solution (around 65 µmol) was transferred in a 5 mL microwave vial equipped with a magnetic stirrer before addition of diisopropylaminomethyl-polystyrene resin (3 mmol/g, 86 mg, 258 µmol), DMAP (2 mg, 16 µmol) and acetic anhydride (34.5 µL, 365 µmol) and the reaction mixture was stirred for 20 min at 100° C. under microwave irradiation. After cooling to RT, the mixture was diluted with $CH_2Cl_2$ (30 mL), filtered through cotton wool, then washed with brine (5 mL), dried over $Na_2SO_4$, filtered, and concentrated under vacuum. Purification by column chromatography ($SiO_2$, eluent cyclohexane:EtOAc=100:0 to 0:100) gave 1-(acetamidomethyl)-4-((2-(ethylamino)-6-methoxyquinolin-3-yl)methyl)-6,7-dimethoxyisoquinolin-3-yl acetate 56 as an off-white solid (25 mg, 72% yield).

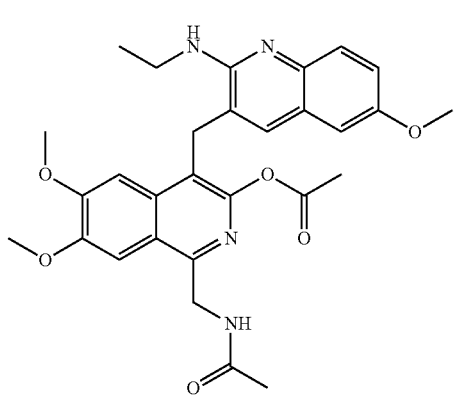

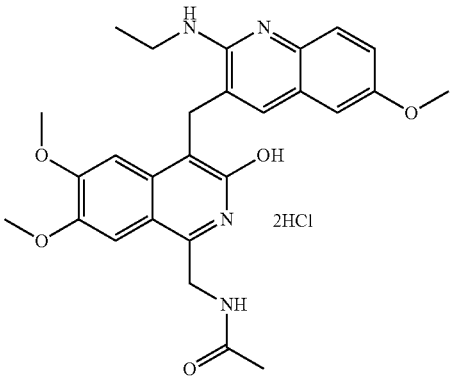

MW: 532.59; Yield: 72%; Off-white solid; Mp (° C.): 262.5

$^1$H-NMR (CDCl$_3$, δ): 1.36 (t, 3H, J=7.1 Hz, CH$_2$CH$_3$), 2.15 (s, 3H, CH$_3$), 2.32 (s, 3H, CH$_3$), 3.67-3.76 (m, 2H, CH$_2$CH$_3$), 3.74 (s, 3H, OCH$_3$), 3.76 (s, 3H, OCH$_3$), 4.03-4.04 (m, 5H, OCH$_3$ & CH$_2$), 4.58-4.62 (broad m, 1H, NH), 5.01-5.02 (m, 2H, CH$_2$), 6.67 (d, 1H, J=2.6 Hz, ArH), 6.94 (s, 1H, ArH), 7.08-7.16 (m, 3H, 2×ArH & NH), 7.38 (s, 1H, ArH), 7.64 (d, 1H, J=9.1 Hz, ArH).

$^{13}$C-NMR (CDCl$_3$, δ): 15.1, 21.1, 23.3, 27.1, 36.7, 42.1, 55.4, 56.0, 56.4, 102.6, 102.9, 106.0, 115.7, 120.2, 120.5, 121.3, 123.6, 127.4, 134.2, 134.9, 142.3, 150.2, 150.6, 151.4, 153.6, 153.7, 154.8, 169.6, 170.1.

MS-ESI m/z (% rel. Int.): 533 ([MH]$^+$, 100), 555 ([M+Na]$^+$, 16).

HPLC: Method B (10 min), XBridge™ column (5 mm, C18, 4.5×50 mm, Model #186003113), detection UV 254 nm, RT=3.85 min, peak area 96.2%.

Preparation of N-(2-((3-((3-hydroxy-6,7-dimethoxy-1-propylisoquinolin-4-yl)methyl)-6-methoxyquinolin-2-yl)amino)ethyl)acetamide dihydrochloride 57

To a solution of 1-(acetamidomethyl)-4-((2-(ethylamino)-6-methoxyquinolin-3-yl)methyl)-6,7-dimethoxyisoquinolin-3-yl acetate 56 (20 mg, 38 µmol) in CH$_2$Cl$_2$ (9 mL) in a 25 mL round-bottomed flask equipped with a magnetic stirrer was added a 7 N NH$_3$ solution in MeOH (1 mL) and the reaction mixture was stirred overnight at RT then diluted with CH$_2$Cl$_2$:MeOH=9:1 (50 mL) and the organic solution was washed with brine (10 mL), dried over Na$_2$SO$_4$, filtered and concentrated at 40° C. under vacuum. Purification by column chromatography (SiO$_2$, eluent CH$_2$Cl$_2$:MeOH=100:0 to 90:10) gave N-((4-((2-(ethylamino)-6-methoxyquinolin-3-yl)methyl)-3-hydroxy-6,7-dimethoxyisoquinolin-1-yl)methyl)acetamide. The free base was dissolved in MeOH (3 mL) in a 10 mL round-bottomed flask equipped with a magnetic stirrer before addition of a 0.4 M HCl solution in MeOH (1 mL). The reaction mixture was stirred for 5 min at RT and concentrated at 40° C. under vacuum to afford N-((4-((2-(ethylamino)-6-methoxyquinolin-3-yl)methyl)-3-hydroxy-6,7-dimethoxyisoquinolin-1-yl)methyl)acetamide dihydrochloride 57 as a pale yellow solid (17 mg, 79% yield).

MW: 563.47; Yield: 79%; Pale yellow solid; Mp (° C.): 210.3

$^1$H-NMR (CD$_3$OD, δ): 1.51-1.56 (m, 3H, CH$_2$CH$_3$), 2.13 (s, 3H, CH$_3$), 3.75 (s, 3H, OCH$_3$), 3.83-3.88 (m, 2H, CH$_2$CH$_3$), 3.95 (s, 3H, OCH$_3$), 4.03 (s, 3H, OCH$_3$), 4.41-4.43 (m, 2H, CH$_2$), 5.12 (s, 2H, CH$_2$), 7.12-7.19 (m, 2H, 2×ArH), 7.28-7.38 (m, 1H, ArH), 7.50 (s, 1H, ArH), 7.66-7.72 (m, 1H, ArH), 7.93-8.01 (m, 1H, ArH).

$^{13}$C-NMR (CD$_3$OD, δ): 14.0, 22.7, 27.0, 39.2, 40.2, 56.3, 57.2, 57.5, 102.5, 105.5, 109.5, 111.6, 119.0, 119.7, 123.4, 123.7, 124.1, 131.2, 139.2, 142.0, 149.1, 152.3, 152.4, 158.7, 160.1, 174.3, (1×C not observed).

MS-ESI m/z (% rel. Int.): 533 ([MH]$^+$, 100), 555 ([M+Na]$^+$, 16).

HPLC: Method B (10 min), XBridge™ column (5 µm, C18, 4.5×50 mm, Model #186003113), detection UV 254 nm, RT=3.85 min, peak area 96.2%.

Preparation of N-((4-((2-(ethylamino)-6-methoxyquinolin-3-yl)methyl)-3-hydroxy-6,7-dimethoxyisoquinolin-1-yl)methyl)methanesulfonamide dihydrochloride 58

The other portion of the residue CCH 42006-2 (see preparation of compound 56) was transferred in a 5 mL microwave vial equipped with a magnetic stirrer before addition of diisopropylaminomethyl-polystyrene resin (3 mmol/g, 86 mg, 258 µmol), DMAP (2 mg, 16 µmol) and methanesulfonyl chloride (25 µL, 323 µmol) and the reaction mixture was stirred for 20 min at 100° C. under microwave irradiation. After cooling to RT, the mixture was diluted with CH$_2$Cl$_2$ (30 mL), filtered through cotton wool, then washed with brine (5 mL), dried over Na$_2$SO$_4$, filtered, and concentrated under vacuum. Purification by column chromatography (SiO$_2$, eluent cyclohexane:EtOAc=100:0 to 0:100) gave 4-((2-(ethylamino)-6-methoxyquinolin-3-yl)methyl)-6,7-dimethoxy-1-(methylsulfonamidomethyl)isoquinolin-3-yl methanesulfonate as a pale yellow solid.

This solid (21 mg, 35 µmol) was then dissolved in dry THF (10 mL) in a 20 mL microwave vial equipped with a magnetic stirrer before addition of phenylmagnesium bromide (1.0 N in THF, 0.25 mL, 0.25 mmol) and the reaction mixture was stirred for 20 min at 140° C. under microwave irradiation. After cooling to RT, another portion of phenylmagnesium bromide (1.0 N in THF, 0.10 mL, 0.10 mmol) was added and the reaction mixture was stirred for 20 min at 150° C. under microwave irradiation. After cooling to RT, the mixture was carefully quenched with H$_2$O (5 mL), then THF was removed at 40° C. under vacuum and the residue was acidified with 1 mL of a 1 N aqueous HCl solution then neutralised with a saturated aqueous NaHCO$_3$ solution before to be extracted by a mixture CH$_2$Cl$_2$:MeOH=9:1 (30 mL). The organic layer was isolated, washed with brine (5 mL), dried over Na$_2$SO$_4$, filtered and concentrated under vacuum. Purification by column chromatography (SiO$_2$, eluent CH$_2$Cl$_2$:MeOH=100:0 to 90:10) gave N-((4-((2-(ethylamino)-6-methoxyquinolin-3-yl)methyl)-3-hydroxy-6,7-dimethoxyisoquinolin-1-yl)methyl)methanesulfonamide. This free base was dissolved in MeOH (3 mL) in a 10 mL round-bottomed flask equipped with a magnetic stirrer before addition of a 0.4 M HCl solution in MeOH (1 mL). The reaction mixture was stirred for 5 min at RT, and concentrated at 40° C. under vacuum to afford N-((4-((2-(ethylamino)-6-methoxyquinolin-3-yl)methyl)-3-hydroxy-6,7-dimethoxyisoquinolin-1-yl)methyl)methanesulfonamide dihydrochloride 58 as a pale yellow solid (12 mg, 31% yield over 2 steps).

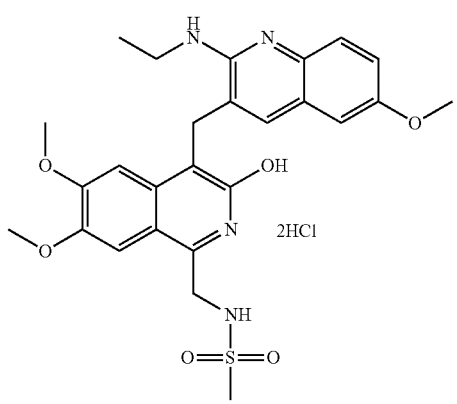

58

MW: 599.53; Yield: 31%; Pale yellow solid; Mp (° C.): 205.7 (dec.)

$^1$H-NMR (CD$_3$OD, δ): 1.55 (t, 3H, J=6.5 Hz, CH$_2$CH$_3$), 3.22 (s, 3H, CH$_3$), 3.78 (s, 3H, OCH$_3$), 3.83-3.88 (m, 2H, CH$_2$CH$_3$), 3.98 (s, 3H, OCH$_3$), 4.05 (s, 3H, OCH$_3$), 4.42 (s, 2H, CH$_2$), 5.07 (s, 2H, CH$_2$), 7.08-7.22 (m, 2H, 2×ArH), 7.34 (d, 1H, J=8.9 Hz, ArH), 7.52-7.65 (m, 1H, ArH), 7.72 (s, 1H, ArH), 7.94 (d, 1H, J=8.9 Hz, ArH).

$^{13}$C-NMR (CD$_3$OD, δ): 13.9, 27.1, 39.1, 40.0, 43.3, 56.4, 57.2, 57.5, 102.3, 105.4, 109.5, 111.8, 118.7, 119.6, 123.4, 123.6, 124.3, 131.2, 139.6, 142.0, 148.1, 152.1, 152.5, 158.7, 159.9, (1×C not observed).

MS-ESI m/z (% rel. Int.): 527 ([MH]$^+$, 100).

HPLC: Method B (10 min), XBridge™ column (5 μm, C18, 4.5×50 mm, Model #186003113), detection UV 254 nm, RT=4.00 min, peak area 99.4%.

Preparation of 3-((3-hydroxy-6,7-dimethoxy-1-methylisoquinolin-4-yl)methyl)-2-(methylamino) quinoline-6,7-diol dihydrochloride 59

To a solution of 6,7-dimethoxy-1-methyl-4-((6-(methylamino)-[1,3]dioxolo[4,5-g]quinolin-7-yl)methyl)isoquinolin-3-ol 60 free base (28 mg, 65 μmol) in dry CH$_2$Cl$_2$ (5 mL) at 0° C. in a 25 mL round-bottomed flask equipped with a magnetic stirrer under N$_2$ was added dropwise BCl$_3$ (1.0 N solution in CH$_2$Cl$_2$, 0.30 mL, 0.30 mmol). After complete addition, the bath was immediately removed and stirring was continued overnight at RT. The reaction mixture was then carefully quenched with MeOH (3 mL) and the mixture was concentrated to dryness at 40° C. under vacuum before purification by prep. HPLC (eluent H$_2$O:CH$_3$CN:TFA=100:0:0.05 to 60:40:0.05 in 10 min) and lyophilisation. The residue was then dissolved in a 0.19 N HCl solution in MeOH (5 mL) before concentration at 40° C. under vacuum. Ion exchange on Amberlite IRA-400 (chloride form, 50 eq.) finally afforded 3-((3-hydroxy-6,7-dimethoxy-1-methylisoquinolin-4-yl)methyl)-2-(methylamino)quinoline-6,7-diol dihydrochloride 59 as a brown solid (10 mg, 31% yield).

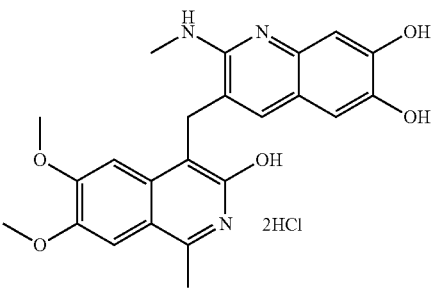

59

MW: 494.37; Yield: 31%; Brown solid; Mp (° C.)>295.0 (dec.)

$^1$H-NMR (CD$_3$OD, δ): 3.04 (s, 3H, CH$_3$), 3.35 (s, 3H, CH$_3$), 3.93 (s, 3H, OCH$_3$), 4.02 (s, 3H, OCH$_3$), 4.25 (s, 2H, CH$_2$), 6.90 (s, 1H, ArH), 7.03 (s, 1H, ArH), 7.37-7.38 (m, 2H, 2×ArH), 7.48 (s, 1H, ArH).

$^{13}$C-NMR (CD$_3$OD, δ): 17.4, 26.6, 29.7, 56.8, 57.2, 102.2, 102.8, 106.1, 110.0, 111.9, 116.7, 119.4, 119.5, 132.2, 138.8, 141.0, 146.4, 151.0, 151.6, 153.0, 153.1, 159.6, (1×C not observed).

MS-ESI m/z (rel.int.): 422 ([MH]$^+$, 100).

HPLC: Method B (10 min), XBridge™ column (5 μm, C18, 4.5×50 mm, Model #186003113), detection UV 254 nm, RT=3.38 min, peak area 98.7%.

Preparation of 6,7-dimethoxy-1-methyl-4-((6-(methylamino)-[1,3]dioxolo[4,5-d]quinolin-7-yl)methyl) isoquinolin-3-ol dihydrochloride 60

6-(Methylamino)-[1,3]dioxolo[4,5-g]quinoline-7-carbaldehyde CCH 34158-1

To a stirred solution of 6-chloro[1,3]dioxolo[4,5-g]quinoline-7-carboxaldehyde (1.14 g, 4.84 mmol) in 1,4-dioxane (10 mL) in a 20 mL microwave vial equipped with a magnetic stirrer was added methylamine (40 wt. %, 4.0 mL, 46.2 mmol) and the reaction mixture was stirred for 25 min at 160° C. under microwave irradiation. After cooling to RT, the volatiles were removed at 40° C. under vacuum and the resulting yellow oil was taken up in a mixture of THF:2 N aq. HCl=1:1 (10 mL) and stirred for 20 min at RT. The volatiles were then removed at 40° C. under vacuum and the residue was then neutralised with a 10 N aqueous NaOH solution before extraction with CH$_2$Cl$_2$ (100 mL). The organic phase was washed with brine (20 mL), dried over MgSO$_4$, filtered, and concentrated under vacuum to give 6-(methylamino)-[1,3]dioxolo[4,5-g]quinoline-7-carbaldehyde CCH 34158-1 as a yellow solid (1.10 g, 99% yield).

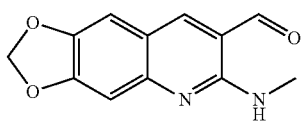

CCH 34158-1

MW: 230.22; Yield: 99%; Orange solid; Mp (° C.): 177.6
$R_f$ (free base)=0.2 (cyclohexane:EtOAc=84:16).
$^1$H-NMR (CDCl$_3$, δ): 3.14 (d, 3H, J=4.8 Hz, NHCH$_3$), 6.09 (s, 2H, OCH$_2$O), 6.94 (s, 1H, ArH), 7.06 (s, 1H, ArH), 7.92-8.00 (broad m, 1H, NH), 8.01 (s, 1H, ArH), 9.90 (s, 1H, HC=O).
MS-ESI m/z (% rel. Int.): 231 ([MH]$^+$, 100).
HPLC: Method A (10 min), XTerra™ column (5 μm, C18, 4.5×50 mm, Model #186000482), detection UV 254 nm, RT=3.10 min.

(6-(Methylamino)-[1,3]dioxolo[4,5-]quinolin-7-yl) methanol CCH 34158-2

To a stirred solution of 6-(methylamino)-[1,3]dioxolo[4, 5-g]quinoline-7-carbaldehyde CCH 34158-1 (1.10 g, 4.78 mmol) in THF (50 mL) in a 100 mL round-bottomed flask equipped with a magnetic stirrer was added NaBH$_4$ (184 mg, 4.86 mmol) and the mixture was stirred for 2 h at RT then quenched by addition of a 2 N aq. HCl solution (10 mL). After stirring for 10 min at RT, THF was removed at 40° C. under vacuum and the mixture was then neutralised with a 2 N aq. NaOH solution, extracted with CH$_2$Cl$_2$ (100 mL). The organic layer was washed with brine (20 mL), dried over Na$_2$SO$_4$, filtered, and concentrated under vacuum. Purification by column chromatography (SiO$_2$, eluent cyclohexane:EtOAc=100:0 to 33:67) gave, after evaporation, (6-(methylamino)-[1,3]dioxolo[4,5-g]quinolin-7-yl)methanol CCH 34158-2 as an off-white solid (1.03 g, 93% yield).

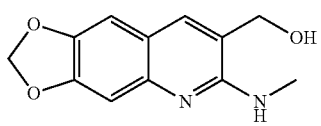

CCH 34158-2

MW: 232.24; Yield: 93%; Off-white solid; Mp (° C.): 191.6 (dec.).
$R_f$ (free base)=0.2 (cyclohexane:EtOAc=33:67).
$^1$H-NMR (CDCl$_3$ exchang. with CD$_3$OD, δ): 3.05 (s, 3H, CH$_3$), 4.59 (s, 2H, CH$_2$O), 6.01 (s, 2H, OCH$_2$O), 6.87 (s, 1H, ArH), 7.15 (s, 1H, ArH), 7.48 (s, 1H, ArH).
$^{13}$C-NMR (CDCl$_3$ exchang. with CD$_3$OD, δ): 29.8, 64.5, 102.9, 105.0, 105.3, 119.8, 122.0, 136.4, 146.0, 146.8, 152.1, 158.0.
MS-ESI m/z (% rel. Int.): 233 ([MH]$^+$, 100).
HPLC: Method B (10 min), XBridge™ column (5 μm, C18, 4.5×50 mm, Model #186003113), detection UV 254 nm, RT=3.08 min.

7-(Chloromethyl)-N-methyl-[1,3]dioxolo[4,5-g]quinolin-6-amine hydrochloride CCH 341588

To a stirred solution of (6-(methylamino)-[1,3]dioxolo[4, 5-g]quinolin-7-yl)methanol CCH 34158-2 (1.00 g, 4.31 mmol) in dry CH$_2$Cl$_2$ (20 mL) in a 50 mL round-bottomed flask equipped with a magnetic stirrer was added dropwise SOCl$_2$ (5.0 mL, 68.9 mmol). The mixture was stirred for 2 h at RT then concentrated to dryness at 40° C. under vacuum. The residue was then taken up in CH$_2$Cl$_2$ (15 mL) before concentration back to dryness at 40° C. under vacuum (done 3 times) to give 7-(chloromethyl)-N-methyl-[1,3] dioxolo[4,5-g]quinolin-6-amine hydrochloride CCH 34158B as a yellow solid (1.24 g, 100% yield).

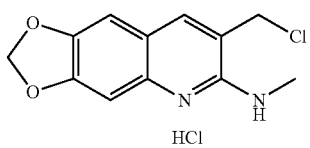

CCH 34158B

MW: 287.14; Yield: 100%; Yellow solid.
$^1$H-NMR (CD$_3$OD, δ): 3.26 (s, 3H, CH$_3$), 4.81 (s, 2H, CH$_2$), 6.19 (s, 2H, OCH$_2$O), 7.23 (s, 1H, ArH), 7.45 (s, 1H, ArH), 8.27 (s, 1H, ArH).
$^{13}$C-NMR (CD$_3$OD, δ): 29.8, 42.0, 97.9, 104.6, 106.2, 118.0, 120.5, 135.5, 143.4, 148.4, 152.4, 154.8.

6,7-Dimethoxy-1-methyl-4-((6-(methylamino)-[1,3] dioxolo[4,5-g]quinolin-7-yl)methyl)isoquinolin-3-ol dihydrochloride 60

To a solution of 6,7-dimethoxy-1-methylisoquinolin-3-ol CCH 18060 (147 mg, 670 μmol) in toluene (10 mL) in a 20 mL microwave vial equipped with a magnetic stirrer was added a 2 N aq. KOH solution (0.70 mL, 1.40 mmol) at RT followed by 7-(chloromethyl)-N-methyl-[1,3]dioxolo[4,5-g] quinolin-6-amine hydrochloride CCH 34158B (200 mg, 697 μmol) and the mixture was stirred at 150° C. for 1.5 h under microwave irradiation. After cooling to RT, the mixture was diluted with CH$_2$Cl$_2$:MeOH=9:1 (80 mL) and the organic solution was washed with brine (10 mL), dried over Na$_2$SO$_4$, filtered and concentrated at 40° C. under vacuum. Purification by column chromatography (SiO$_2$, eluent CH$_2$Cl$_2$:7 N NH$_3$ solution in MeOH=100:0 to 95:5) gave 6,7-dimethoxy-1-methyl-4-((6-(methylamino)-[1,3]dioxolo [4,5-g]quinolin-7-yl)methyl)isoquinolin-3-ol. This free base was dissolved in MeOH (2 mL) in a 10 mL round-bottomed flask equipped with a magnetic stirrer before addition of a 0.19 M HCl solution in MeOH (1 mL). The reaction mixture was stirred for 5 min at RT and concentrated at 40° C. under vacuum to afford 6,7-dimethoxy-1-methyl-4-((6-(methylamino)-[1,3]dioxolo[4,5-g]quinolin-7-yl)methyl)isoquinolin-3-ol dihydrochloride 60 as a brown solid (30 mg, 6% yield).

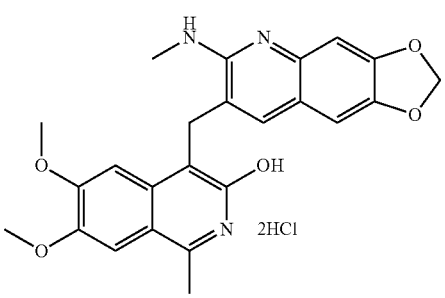

60

MW: 506.38; Yield: 6%; Brown solid; Mp (° C.)>295 (dec.)

$R_f$ (free base)=0.3 ($CH_2Cl_2$:MeOH=95:5).

$^1$H-NMR ($CDCl_3$, δ): 3.09 (s, 3H, $CH_3$), 3.37 (s, 3H, $NCH_3$), 3.93 (s, 3H, $OCH_3$), 4.04 (s, 3H, $OCH_3$), 4.29 (s, 2H, $CH_2$), 6.11 (s, 2H, $OCH_2O$), 6.99 (s, 1H, ArH), 7.06 (s, 1H, ArH), 7.38 (s, 1H, ArH), 7.47 (s, 1H, ArH), 7.55 (s, 1H, ArH).

$^{13}$C-NMR ($CDCl_3$, δ): 17.6, 26.6, 30.0, 57.0, 57.4, 97.7, 102.5, 104.3, 105.9, 106.3, 109.8, 118.3, 120.0, 120.9, 134.1, 139.0, 141.0, 148.1, 151.6, 152.0, 153.5, 153.8, 159.9, (1×C not observed).

MS-ESI m/z (% rel. Int.): 434 ([MH]$^+$, 100).

HPLC: Method B (10 min), XBridge™ column (5 μm, C18, 4.5×50 mm, Model #186003113), detection UV 254 nm, RT=3.83 min, peak area 97.9%.

Preparation of 1-ethyl-6,7-dimethoxy-4-((6-(methyl-amino)-[1,3]dioxolo[4,5-g]quinolin-7-yl)methyliso-quinolin-3-ol dihydrochloride 61

To a solution of 1-ethyl-6,7-dimethoxyisoquinolin-3-ol SLA 28136 (284 mg, 1.22 mmol) in toluene (10 mL) in a 20 mL microwave vial equipped with a magnetic stirrer was added a 2 N aq. LiOH solution (1.20 mL, 2.40 mmol) at RT followed by 7-(chloromethyl)-N-methyl-[1,3]dioxolo[4,5-g]quinolin-6-amine hydrochloride CCH 34158B (350 mg, 1.22 mmol) and the mixture was stirred at 150° C. for 1.5 h under microwave irradiation. After cooling to RT, the mixture was diluted with $CH_2Cl_2$:MeOH=9:1 (80 mL) and the organic solution was washed with brine (10 mL), dried over $Na_2SO_4$, filtered and concentrated at 40° C. under vacuum. Purification by column chromatography ($SiO_2$, eluent $CH_2Cl_2$:7 N $NH_3$ solution in MeOH=100:0 to 95:5) gave 1-ethyl-6,7-dimethoxy-4-((6-(methylamino)-[1,3]dioxolo[4,5-g]quinolin-7-yl)methyl)isoquinolin-3-ol. This free base was dissolved in MeOH (6 mL) in a 25 mL round-bottomed flask equipped with a magnetic stirrer before addition of a 0.19 M HCl solution in MeOH (5 mL). The reaction mixture was stirred for 5 min at RT and concentrated at 40° C. under vacuum. Recrystallization from a mixture of MeOH:$Et_2O$ afforded 1-ethyl-6,7-dimethoxy-4-((6-(methylamino)-[1,3]dioxolo[4,5-g]quinolin-7-yl)methyl)isoquinolin-3-ol dihydrochloride 61 as a pale brown solid (104 mg, 16% yield).

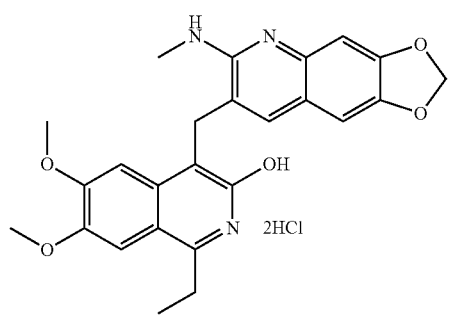

61

MW: 520.40; Yield: 16%; Pale brown solid; Mp (° C.): 263.4

$R_f$ (free base): 0.25 ($CH_2Cl_2$:7 N $NH_3$ in MeOH=95:5).

$^1$H-NMR ($CD_3OD$:$CDCl_3$=1:1, δ): 1.41 (t, 3H, J=7.6 Hz, $CH_3$), 3.14 (q, 2H, J=7.6 Hz, $CH_2$), 3.20 (s, 3H, $NCH_3$), 3.93 (s, 3H, $OCH_3$), 4.09 (s, 3H, $OCH_3$), 4.26 (s, 2H, $CH_2$), 6.16 (s, 2H, $OCH_2O$), 7.00 (s, 1H, ArH), 7.06 (s, 1H, ArH), 7.17 (s, 1H, ArH), 7.38 (s, 1H, ArH), 8.30 (s, 1H, ArH).

$^{13}$C-NMR ($CD_3OD$:$CDCl_3$=1:1, δ): 17.5, 27.9, 31.2, 32.5, 59.4, 59.8, 100.5, 103.4, 106.7, 107.1, 108.4, 113.3, 116.9, 120.5, 126.1, 136.6, 144.1, 144.5, 150.7, 151.8, 156.2, 156.3, 160.2 (2×C not observed).

MS-ESI m/z (% rel. Int.): 448 ([MH]$^+$, 100).

HPLC: Method B (10 min), XBridge™ column (5 μm, C18, 4.5×50 mm, Model #186003113), detection UV 254 nm, RT=3.99 min, peak area 98.7%.

Preparation of 6,7-dimethoxy-4-((6-(methylamino)-[1,3]dioxolo[4,5-g]quinolin-7-yl)methyl)-1-propylisoquinolin-3-ol dihydrochloride 62

To a solution of 6,7-dimethoxy-1-propylisoquinolin-3-ol RBO 35142 (245 mg, 0.99 mmol) in toluene (10 mL) in a 20 mL microwave vial equipped with a magnetic stirrer was added a 2 N aq. LiOH solution (1.00 mL, 2.00 mmol) at RT followed by 7-(chloromethyl)-N-methyl-[1,3]dioxolo[4,5-g]quinolin-6-amine hydrochloride CCH 34158B (284 mg, 0.99 mmol) and the mixture was stirred at 150° C. for 1.5 h under microwave irradiation. After cooling to RT, the mixture was diluted with $CH_2Cl_2$:MeOH=9:1 (80 mL) and the organic solution was washed with brine (10 mL), dried over $Na_2SO_4$, filtered and concentrated at 40° C. under vacuum. Purification by column chromatography ($SiO_2$, eluent $CH_2Cl_2$:7 N $NH_3$ solution in MeOH=100:0 to 95:5) gave, after evaporation, 6,7-dimethoxy-4-((6-(methylamino)-[1,3]dioxolo[4,5-g]quinolin-7-yl)methyl)-1-propylisoquinolin-3-ol. This free base was dissolved in MeOH (3 mL) in a 10 mL round-bottomed flask equipped with a magnetic stirrer before addition of a 0.19 M HCl solution in MeOH (2 mL). The reaction mixture was stirred for 5 min at RT and concentrated at 40° C. under vacuum to afford 6,7-dimethoxy-4-((6-(methylamino)-[1,3]dioxolo[4,5-g]quinolin-7-yl)methyl)-1-propylisoquinolin-3-ol dihydrochloride 62 as a beige solid (46 mg, 9% yield).

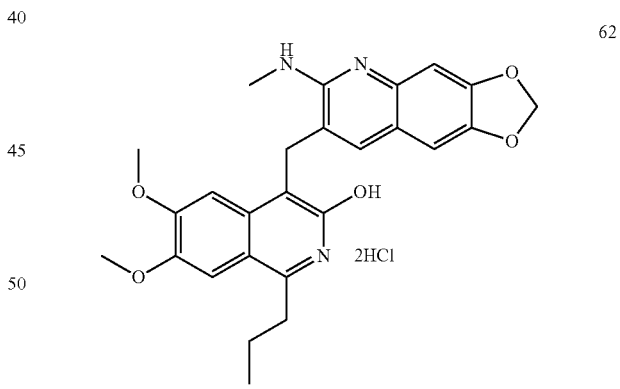

62

MW: 534.43; Yield: 9%; Beige solid; Mp (° C.)>295 (dec.)

$R_f$ (free base)=0.3 ($CH_2Cl_2$:7N $NH_3$ in MeOH=95:5).

$^1$H-NMR ($CD_3OD$, δ): 1.13 (t, 3H, J=7.1 Hz, $CH_3$), 1.90-1.97 (m, 2H, $CH_2$), 3.25-3.38 (m, 5H, $NCH_3$ & $CH_2$), 3.94 (s, 3H, $OCH_3$), 4.01 (s, 3H, $OCH_3$), 4.27 (s, 2H, $CH_2$), 6.12 (s, 2H, $OCH_2O$), 7.03-7.05 (m, 2H, 2×ArH), 7.42-7.52 (m, 3H, 3×ArH).

$^{13}$C-NMR ($CD_3OD$, δ): 14.2, 24.7, 26.8, 29.9, 33.5, 56.8, 57.7, 97.6, 102.3, 104.3, 105.8, 110.1, 118.2, 118.8, 121.2, 134.1, 139.2, 141.6, 148.1, 151.8, 153.5, 153.8, 154.5, 159.7 (2×C not observed).

MS-ESI m/z (% rel. Int.): 462 ([MH]⁺, 100).
HPLC: Method B (10 min), XBridge™ column (5 μm, C18, 4.5×50 mm, Model #186003113), detection UV 254 nm, RT=4.21 min, peak area 97.6%.

Preparation of 4-((6-(dimethylamino)-[1,3]dioxolo [4,5-g]quinolin-7-yl)methyl)-6,7-dimethoxy-1-propylisoquinolin-3-ol dihydrochloride 63

6-(Dimethylamino)-[1,3]dioxolo[4,5-g]quinoline-7-carbaldehyde RBO 35166

To a stirred solution of 6-chloro-[1,3]dioxolo[4,5-g]quinoline-7-carbaldehyde (1.0 g, 4.07 mmol) in dioxane (10 mL) in a 20 mL microwave vial equipped with a magnetic stirrer was added dimethylamine (40% in water, 5.1 mL, 40.7 mmol) and the reaction mixture was stirred for 45 min at 160° C. under microwave irradiation. After cooling to RT, the volatiles were removed at 40° C. under vacuum and the resulting yellow oil was taken back in water (30 mL). The precipitate formed was filtered through a fritted glass filter (porosity 3) to give after evaporation 6-(dimethylamino)-[1,3]dioxolo[4,5-g]quinoline-7-carbaldehyde RBO 35166 (960 mg, 97%).

RBO 35166

MW: 244.25; Yield: 97%; Green solid.
¹H-NMR (CDCl₃, δ): 3.12 (s, 6H, 2×NCH₃), 6.10 (s, 2H, CH₂), 7.00 (s, 1H, ArH), 7.15 (s, 1H, ArH), 8.26 (s, 1H, ArH), 10.10 (s, 1H, HC=O).
MS-ESI m/z (% rel. Int.): 245.2 ([MH]⁺, 100).
HPLC: Method B (10 min), XBridge™ column (5 μm, C18, 4.5×50 mm, Model #186003113), detection UV 254 nm, RT=3.30 min, peak area 98.0%.

(6-(Dimethylamino)-[1,3]dioxolo[4,5-g]quinolin-7-yl)methanol RBO 35168

To a stirred solution of 6-dimethylamino-[1,3]dioxolo[4,5-g]quinoline-7-carbaldehyde RBO 35166 (960 mg, 3.93 mmol) in a mixture EtOH:THF=50 mL:20 mL in a 250 mL round-bottomed flask equipped with a magnetic stirrer at 0° C. was added NaBH₄ (149 mg, 3.93 mmol) and the mixture was stirred overnight at RT. After cooling with an ice bath, a 6 N aq. HCl solution (2 mL) was added. After stirring for 1 h at 0° C., the mixture was brought to pH=9 with a 2 N aq. NaOH solution (6 mL). The volatiles were removed at 40° C. under vacuum until precipitation of a solid.
This solid was filtered, washed with water (315 mL) to give after drying (6-(dimethylamino)-[1,3]dioxolo[4,5-g]quinolin-7-yl)methanol RBO 35168 as a green solid (775 mg, 80% yield).

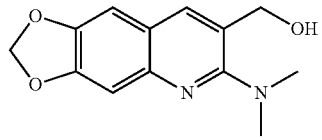
RBO 35168

MW: 246.27; Yield: 80%; Green solid.
¹H-NMR (MeOD, δ): 2.85 (s, 6H, 2×NCH₃), 4.62 (s, 2H, CH₂), 5.93 (s, 2H, CH₂), 6.95 (s, 1H, ArH), 7.05 (s, 1H, ArH), 7.90 (s, 1H, ArH).
MS-ESI m/z (% rel. Int.): 247.0 ([MH]⁺, 100).
HPLC: Method B (10 min), XBridge™ column (5 μm, C18, 4.5×50 mm, Model #186003113), detection UV 254 nm, RT=3.17 min, peak area 90%.

7-(Chloromethyl)-N,N-dimethyl-[1,3]dioxolo[4,5-g] quinolin-6-amine hydrochloride RBO 35172

To a stirred solution of (6-(dimethylamino)-[1,3]dioxolo [4,5-g]quinolin-7-yl)methanol RBO 35168 (775 mg, 3.15 mmol) in dry CH₂Cl₂ (30 mL) in a 100 mL round-bottomed flask equipped with a magnetic stirrer was added dropwise SOCl₂ (2.3 mL, 31.5 mmol). The mixture was stirred for 1.5 h at RT then concentrated to dryness at 40° C. under vacuum. The residue was coevaporated twice with CH₂Cl₂ (20 mL) at 40° C. under vacuum to give after further drying 7-(chloromethyl)-N,N-dimethyl-[1,3]dioxolo[4,5-g]quinolin-6-amine hydrochloride RBO 35172 as a green solid (850 mg, 90% yield).

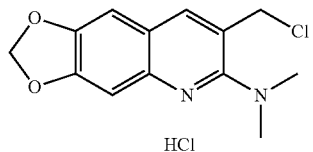
RBO 35172

MW: 301.19; Yield: 90%; green solid; Mp (° C.)>360.0
¹H-NMR (MeOD, δ): 3.29 (s, 6H, 2×NCH₃), 4.80 (s, 2H, CH₂), 6.05 (s, 2H, CH₂), 7.10 (s, 1H, ArH), 7.22 (s, 1H, ArH), 8.30 (s, 1H, ArH).
HPLC: Method B (10 min), XBridge™ column (5 μm, C18, 4.5×50 mm, Model #186003113), detection UV 254 nm, RT=3.22 min, peak area 92%.

4-((6-(Dimethylamino)-[1,3]dioxolo[4,5-g]quinolin-7-yl)methyl)-6,7-dimethoxy-1-propylisoquinolin-3-ol dihydrochloride 63

To a solution of 6,7-dimethoxy-1-propylisoquinolin-3-ol RBO 35142 (250 mg, 1.0 mmol) in toluene in a 20 mL microwave vial was added LiOH.H₂O (84 mg, 2.0 mmol) and 7-(chloromethyl)-N,N-dimethyl-[1,3]dioxolo[4,5-g] quinolin-6-amine hydrochloride RBO 35172 (301 mg, 1.0 mmol). The mixture was stirred at 150° C. for 1.5 h under microwave irradiation then cooled to RT. The volatiles were removed under vacuum and the residue was taken back in dichloromethane (30 mL), washed with water (3×10 mL), brine (10 mL), dried over Na₂SO₄, filtered and evaporated to give an orange solid. This solid was purified by column chromatography (SiO₂, eluent CH₂Cl₂:7 N NH₃ solution in MeOH=100:0 to 95:5) to give after evaporation and drying 4-((6-(dimethylamino)-[1,3]dioxolo[4,5-g]quinolin-7-yl) methyl)-6,7-dimethoxy-1-propylisoquinolin-3-ol (142 mg). This free base was dissolved in MeOH (5 mL) and a HCl 0.19 N solution in MeOH (1.35 mL, 0.26 mmol) was slowly added. The reaction mixture was stirred at 4° C. for 15 min. After evaporation and drying under vacuum pump under P₂O₅, 4-((6-(dimethylamino)-[1,3]dioxolo[4,5-g]quinolin- 7-yl)methyl)-6,7-dimethoxy-1-propylisoquinolin-3-ol dihydrochloride 63 was obtained as a yellow solid (148 mg, 55% yield).

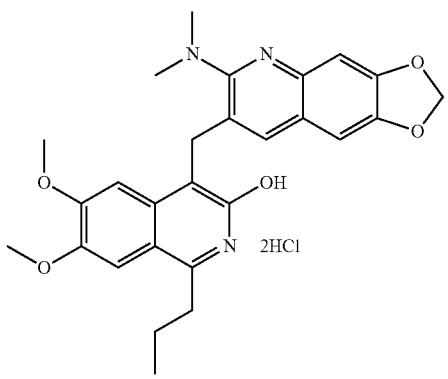

MW: 548.46; Yield: 13%; Yellow Solid; Mp (° C.): 169.6
$R_f$ (free base)=0.10 (CH$_2$Cl$_2$: 7 N NH$_3$ solution in MeOH=95:5).
$^1$H-NMR (CD$_3$OD, δ): 1.15 (t, 3H, J=9 Hz, CH$_3$), 1.95 (q, 2H, J=9 Hz, CH$_2$), 3.39 (2H, CH$_2$, peak under solvent signal), 3.55 (s, 6H, 2×CH$_3$N), 3.95 (s, 3H, CH$_3$O), 4.03 (s, 3H, CH$_3$O), 4.55 (s, 2H, CH$_2$), 6.13 (s, 2H, CH$_2$), 6.96 (s, 1H, ArH), 7.04 (s, 1H, ArH), 7.44 (s, 1H, ArH), 7.50 (s, 1H, ArH), 7.72 (s, 1H, ArH).
$^{13}$C-NMR (CD$_3$OD, δ): 14.2, 24.7, 28.8, 33.6, 43.4, 56.9, 57.3, 98.0, 102.6, 104.6 (2×C), 105.1, 106.0, 112.8, 119.2, 121.0, 124.6, 135.6, 141.1, 143.5, 149.3, 152.0, 152.7, 154.7, 156.4, 159.7.
MS-ESI m/z (% rel. Int.): 476 ([MH]$^+$, 100).
HPLC: Method B (10 min), XBridge™ column (5 μm, C18, 4.5×50 mm, Model #186003113), detection UV 254 nm, RT=4.23 min, peak area 99.0%.

Preparation of 4-((6-(ethylamino)-[1,3]dioxolo[4,5-g]quinolin-7-yl)methyl)-6,7-dimethoxy-1-propylisoquinolin-3-ol dihydrochloride 64

6-(Ethylamino)-[1,3]dioxolo[4,5-g]quinoline-7-carbaldehyde RBO 35180

To a solution of 6-chloro-[1,3]dioxolo[4,5-g]quinoline-7-carbaldehyde (1.0 g, 4.24 mmol) in dioxane (10 mL) was added ethylamine (3.58 mL, 70% in water) and the mixture was heated at 160° C. under microwave irradiation for 45 min. After cooling to RT, the mixture was poured into a mixture of THF:1 N HCl aq. solution=1:1 (25 mL) and stirred for 25 min at RT. The mixture was brought to pH=7 with a satured aq. solution of NaHCO$_3$ and extracted with CH$_2$Cl$_2$ (50 mL). The organic layer was washed with H$_2$O (3×30 mL), brine (30 mL), dried over Na$_2$SO$_4$, filtered and evaporated to give 6-(ethylamino)-[1,3]dioxolo[4,5-g]quinoline-7-carbaldehyde RBO 35180 as a yellow solid (941 mg, 91% yield).

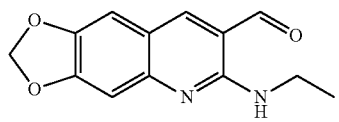

MW: 244.25; Yield: 91%; Yellow solid.
$^1$H-NMR (CDCl$_3$, δ): 1.32 (t, 3H, J=7.5 Hz, CH$_3$), 3.59-3.69 (m, 2H, CH$_2$CH$_3$), 6.06 (s, 2H, OCH$_2$O), 6.93 (s, 1H, ArH), 7.03 (s, 1H, ArH), 7.95 (broad s, 1H, NH), 8.00 (s, 1H, ArH), 9.89 (s, 1H, HC=O).
MS-ESI m/z (rel.int.): 245 ([M+H]$^+$, 100).
HPLC: Method (5 min), XBridge™ column (5 μm, C18, 4.5×50 mm, Model #186003113), detection UV 254 nm, RT=2.08 min, peak area 98%.

(6-(Ethylamino)-[1,3]dioxolo[4,5-g]quinolin-7-yl) methanol RBO 40002

To a solution of 6-(ethylamino)-[1,3]dioxolo[4,5-g]quinoline-7-carbaldehyde RBO 35180 (941 mg, 3.85 mmol) in a mixture EtOH:THF=5:2 (70 mL) at 0° C. was added NaBH$_4$ (146 mg, 3.85 mmol) by small portions. The mixture was stirred for 2 h at RT, cooled at 0° C. and treated with a 1 N HCl solution (6 mL). The solution was neutralized with a concentrated NaHCO$_3$ aq. solution and evaporated under vacuum at 45° C. The crude residue was diluted with CH$_2$Cl$_2$ (50 mL), washed with brine (3×50 mL) and the separated organic layer was dried over Na$_2$SO$_4$ and filtered to give, after evaporation and drying, (6-(ethylamino)-[1,3]dioxolo[4,5-g]quinolin-7-30 yl)methanol RBO 40002 as a brown solid (901 mg, 95% yield).

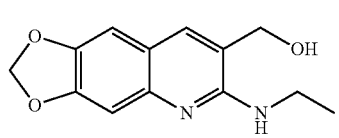

MW: 246.26; Yield: 95%; Brown Solid.
MS-ESI m/z (rel.int.): 247 ([M+H]$^+$, (100).
HPLC: Method B (5 min), XBridge™ column (5 μm, C18, 4.5×50 mm, Model #186003113), detection UV 254 nm, RT=2.03 min, peak area 98%.

7-(Chloromethyl)-N-ethyl-[1,3]dioxolo[4,5-g]quinolin-6-amine hydrochloride RBO 40004

To a solution of (6-(ethylamino)-[1,3]dioxolo[4,5-g]quinolin-7-yl)methanol RBO 40002 (901 mg, 3.66 mmol) in CH$_2$Cl$_2$ (30 mL) in a round-bottomed flask equipped with a magnetic stirrer was added thionyl chloride (2.65 mL, 36.6 mmol). The mixture was stirring for 3 h at RT, evaporated under vacuum at 45° C. and coevaporated twice with CH$_2$Cl$_2$ (to remove SOCl$_2$) to afford 7-(chloromethyl)-N-ethyl-[1,3]dioxolo[4,5-g]quinolin-6-amine hydrochloride RBO 40004 as a yellow solid (1.01 g, 92% yield).

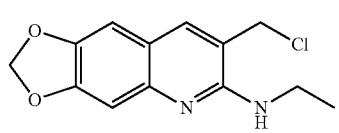

MW: 301.17; Yield: 92%; Yellow Solid; Mp (° C.): 71.4
$^1$H-NMR (CD$_3$OD, δ): 1.43 (t, 3H, J=7.5 Hz, CH$_3$), 3.71 (q, 2H, J=6.9 Hz, CH$_2$CH$_3$), 4.85 (s, 2H, OCH$_2$O), 6.20 (2H, s, CH$_2$Cl), 7.25 (s, 1H, ArH), 7.45 (s, 1H, ArH), 8.30 (s, 1H, ArH).

MS-ESI m/z (rel.int.): 265 ([MH]$^+$, $^{35}$Cl, 100), 267 ([MH]$^+$, $^{37}$Cl, 36).

HPLC: Method B (10 min), XBridge™ column (5 mm, C18, 4.5×50 mm, Model #186003113), detection UV 254 nm, RT=3.77 min, peak area %.

4-((6-(Ethylamino)-[1,3]dioxolo[4,5-g]quinolin-7-yl)methyl)-6,7-dimethoxy-1-propylisoquinolin-3-ol dihydrochloride 64

To a solution of 6,7-dimethoxy-1-propylisoquinolin-3-ol RBO 35142 (305 mg, 1.0 mmol) in toluene (12 mL) in a 20 mL microwave vial equipped with a magnetic stirrer was added LiOH.H$_2$O (56% LiOH solution) (84 mg, 2.0 mmol) followed by 7-(chloromethyl)-N-ethyl-[1,3]dioxolo[4,5-g]quinolin-6-amine hydrochloride RBO 40004 (250 mg, 1.0 mmol). The mixture was heated for 1.5 h at 150° C. under microwave irradiation. The vial was cooled to RT and the reaction mixture was extracted with CH$_2$Cl$_2$ (30 mL). The organic layer was washed with H$_2$O (3×30 mL), brine (30 mL), dried over Na$_2$SO$_4$ and filtered to give, after evaporation, a yellow solid. This crude solid was purified by column chromatography (SiO$_2$, eluent CH$_2$Cl$_2$:7 N NH$_3$ solution in MeOH=100:0 to 95:5) to give after evaporation 4-((6-(ethylamino)-[1,3]dioxolo[4,5-g]quinolin-7-yl)methyl)-6,7-dimethoxy-1-propylisoquinolin-3-ol. This free base was treated for 5 min by a 0.49 N HCl solution in MeOH (5 mL). The reaction mixture was evaporated to give, after further drying, 4-((6-(ethylamino)-[1,3]dioxolo[4,5-g]quinolin-7-yl)methyl)-6,7-dimethoxy-1-propylisoquinolin-3-ol dihydrochloride as a yellow solid 64 (20 mg, 3.6% yield).

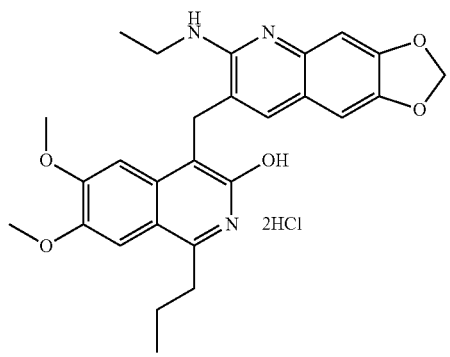

64

MW: 548.46; Yield: 3.6%; Yellow Solid.

$^1$H-NMR (CD$_3$OD, δ): 1.11 (t, 3H, J=7.5 Hz, CH$_3$), 1.50 (t, 3H J=6 Hz, CH$_3$), 1.90 (m, 2H, CH$_2$), 3.28 (shoulder behind CD$_3$OD, 2H, CH$_2$N), 3.70 (q, 2H, J=6 Hz, CH$_2$), 4.00 (s, 6H, 2OCH$_3$), 4.30 (s, 2H,OCH$_2$O), 6.13 (s, 2H, CH$_2$), 7.04 (s, 1H, ArH), 7.09 (s, 1H, ArH), 7.39 (s, 2H, 2×ArH), 7.81 (s, 1H, ArH).

MS-ESI m/z (rel.int.): 476 ([M+H]$^+$, 100).

HPLC: Method B (10 min), XBridge™ column (5 μm, C18, 4.5×50 mm, Model #186003113), detection UV 254 nm, RT=4.47 min, peak area 94.0%.

Preparation of 4-(dibenzo[b,d]furan-2-ylmethyl)-6,7-dimethoxy-1-propylisoquinolin-3-amine hydrochloride 65

4-(Dibenzo[b,d]furan-2-ylmethyl)-6,7-dimethoxy-1-propylisoquinolin-3-yl trifluoromethanesulfonate CCH 42040-1

To a solution of 4-(dibenzo[b,d]furan-2-ylmethyl)-6,7-dimethoxy-1-propylisoquinolin-3-ol hydrochloride 7 (15 mg, 32 μmol) in DMF (2 mL) in a 5 mL round-bottomed flask equipped with a magnetic stirrer were added triethylamine (16 μl, 114 μmol) and N-phenyl-bis(trifluoromethanesulfonimide) (30 mg, 84 μmol). The mixture was stirred for 5 h at RT, then for 1 h at 65° C. After cooling to RT, the mixture was diluted with Et$_2$O (30 mL) and washed with brine (10 mL). The organic phase was dried over Na$_2$SO$_4$, filtered and concentrated under vacuum. Purification by column chromatography (SiO$_2$, eluent cyclohexane:EtOAc=100:0 to 75:25) gave 4-(dibenzo[b,d]furan-2-ylmethyl)-6,7-dimethoxy-1-propylisoquinolin-3-yl trifluoromethanesulfonate CCH 42040-1 as a pale yellow oil (13 mg, 72% yield).

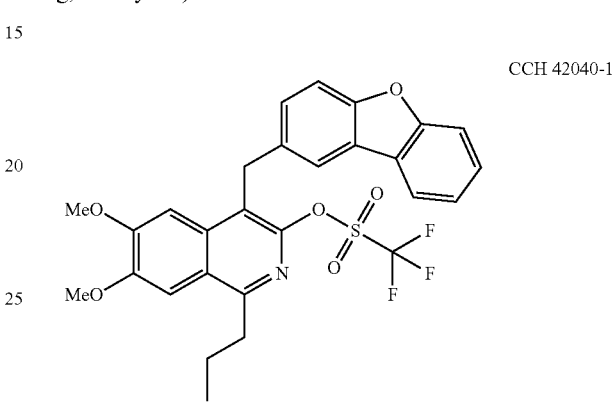

CCH 42040-1

MW: 559.55; Yield: 72%; Pale Yellow Oil.

R$_f$: 0.2 (cyclohexane:EtOAc=75:25).

$^1$H-NMR (CDCl$_3$, δ): 1.09 (t, 3H, J=7.4 Hz, CH$_3$), 1.94-2.05 (m, 2H, CH$_2$), 3.17 (t, 2H, J=7.5 Hz, CH$_2$), 3.80 (s, 3H, OCH$_3$), 4.01 (s, 3H, OCH$_3$), 4.55 (s, 2H, CH$_2$), 7.18 (s, 1H, ArH), 7.28-7.34 (m, 2H, 2×ArH), 7.39-7.54 (m, 4H, 4×ArH), 7.71-7.73 (m, 1H, ArH), 7.80-7.86 (m, 1H, ArH).

$^{13}$C-NMR (CD$_3$OD, δ): 14.1, 21.0, 31.7, 36.3, 55.9, 56.0, 103.5, 104.0, 111.7 (2×C), 116.3, 120.0, 120.7, 122.7, 123.4, 123.9, 124.7, 127.2, 127.3, 133.2, 134.8, 149.9, 150.1, 153.2, 155.0, 156.5, 158.2, CF$_3$ not seen.

4-(Dibenzo[b,d]furan-2-ylmethyl)-6,7-dimethoxy-1-propylisoquinolin-3-amine hydrochloride 65

A 2 mL microwave vial equipped with a magnetic stirrer was charged under N$_2$ with 4-(dibenzo[b,d]furan-2-ylmethyl)-6,7-dimethoxy-1-propylisoquinolin-3-yl trifluoromethanesulfonate CCH 42040-1 (13 mg, 23 μmol), t-butyl carbamate (5 mg, 43 μmol), dry powdered cesium carbonate (15 mg, 46 μmol), 9,9-dimethyl-4,5-bis(diphenylphosphino)xanthene (4 mg, 7 μmol) and tris(dibenzylideneacetone)dipalladium(0) (4 mg, 4 μmol). Dry THF (1.5 mL) was then added and the mixture was stirred for 45 min at 140° C. under microwave irradiation. After cooling to RT, the mixture was diluted with EtOAc (30 mL), then filtered through celite. The solution was washed with brine (10 mL), dried over Na$_2$SO$_4$, filtered and and concentrated at 40° C. under vacuum. The residue was then dissolved in CH$_2$Cl$_2$ (10 mL) in a 25 mL round-bottomed flask equipped with a magnetic stirrer before addition of TFA (1 mL) and the mixture was stirred overnight at RT then concentrated to dryness under vacuum. The residue was basified with a saturated NaHCO$_3$ solution (10 mL) before extraction with CH$_2$Cl$_2$ (40 mL). The organic phase was isolated, washed with brine (10 mL), dried over Na$_2$SO$_4$, filtered and and concentrated at 40° C. under vacuum. Purification by column chromatography (SiO₂, eluent cyclohexane:EtOAc=100:0 to 50:50) gave 4 mg of 4-(dibenzo[b,d]furan-2-ylmethyl)-6,7-dimethoxy-1-propylisoquinolin-3-amine. This free base was dissolved in MeOH (2 mL) in a 10 mL round-bottomed flask equipped with a magnetic stirrer before addition of a 0.49 M HCl solution in MeOH (0.5 mL) and the solution was stirred for 5 min at RT, and concentrated at 40° C. under vacuum to afford 4-(dibenzo[b,d]furan-2-ylmethyl)-6,7-dimethoxy-1-propylisoquinolin-3-amine hydrochloride 65 as a pale brown solid (4 mg, 38% yield).

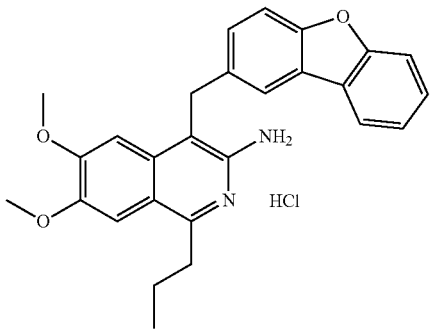

MW: 462.97; Yield: 38%; Pale Brown Solid.

$R_f$: 0.2 (cyclohexane:EtOAc=50:50, free base).

¹H-NMR (CD₃OD, δ): 1.13 (t, 3H, J=7.3 Hz, CH₃), 1.94 (sextuplet, 2H, J=7.3 Hz, CH₂), 3.25-3.35 (m, 2H, CH₂), 3.86 (s, 3H, OCH₃), 3.97 (s, 3H, OCH₃), 4.52 (s, 2H, CH₂), 7.15 (s, 1H, ArH), 7.30-7.36 (m, 3H, 3×ArH), 7.44-7.56 (m, 3H, 3×ArH), 7.88-7.94 (m, 2H, 2×ArH).

¹³C-NMR (CD₃OD, δ): 14.2, 24.3, 31.6, 33.7, 56.6, 56.8, 102.3, 104.9, 112.2, 112.6, 112.8, 117.7, 121.0, 121.6, 124.0, 125.1, 125.9, 128.4, 128.6, 134.2, 140.9, 147.1, 151.2, 151.5, 156.4, 158.0, 159.1.

MS-ESI m/z (rel. int.): 427 ([MH]⁺, 100).

HPLC: Method B (10 min), XBridge™ column (5 mm, C18, 4.5×50 mm, Model #186003113), detection UV 254 nm, RT=5.57 min, peak area 95.8%.

Preparation of 4-((2-ethyl-6-methoxyquinolin-3-yl)methyl)-6,7-dimethoxy-1-propylisoquinolin-3-ol dihydrochloride 66

2-Chloro-3-(1,3-dioxolan-2-yl)-6-methoxyquinoline SMA 44002

To a solution of 2-chloro-6-methoxyquinoline-3-carbaldehyde (4.01 g, 18.10 mmol) in toluene (200 mL) in a 500 mL round-bottomed flask equipped with a magnetic stirrer under N₂ was added ethylene glycol (1.20 mL, 21.52 mmol) followed by p-toluenesulfonic acid monohydrate (348 mg, 1.83 mmol). The mixture was stirred overnight under reflux using a Dean-Stark apparatus. After cooling to RT, the mixture was concentrated at 40° C. under vacuum, then the residue was diluted with saturated aqueous NaHCO₃ solution (40 mL) before extraction with CH₂Cl₂ (100 mL). The organic phase was isolated, washed with brine (20 mL), dried over Na₂SO₄, filtered and concentrated at 40° C. under vacuum. Purification by column chromatography (SiO₂, eluent cyclohexane:EtOAc=100:0 to 92:8 to 75:25) gave 2-chloro-3-(1,3-dioxolan-2-yl)-6-methoxyquinoline SMA 44002 as a white solid (4.39 g, 91% yield).

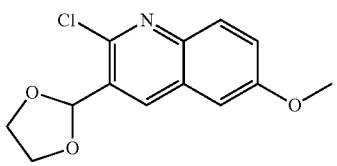

SMA 44002

MW: 265.69; Yield: 91%; White Solid; Mp (° C.): 93.6

Rf: 0.2 (cyclohexane:EtOAc=75:25).

¹H NMR (CDCl₃, δ): 3.93 (s, 3H, OCH₃), 4.11-4.23 (m, 4H, 2×CH₂), 6.22 (s, 1H, CH), 7.11 (d, 1H, J=2.7 Hz, ArH), 7.40 (dd, 1H, J=2.7 & 9.2 Hz, ArH), 7.92 (d, 1H, J=9.2 Hz, ArH), 8.31 (s, 1H, ArH).

MS-ESI m/z (% rel. Int.): 268 ([MH]⁺, ³⁷Cl, 38), 266 ([MH]⁺, ³⁵Cl, 100).

HPLC: Method B (5 min), XBridge™ column(5 mm, C18, 4.5×50 mm, Model #186003113), detection UV 214 nm, RT=3.01 min.

2-Ethyl-6-methoxyquinoline-3-carbaldehyde SMA 44004

To a solution of 3-[1,3]dioxolan-2-yl-2-ethyl-6-methoxyquinoline SMA 44002 (400 mg, 1.54 mmol) in THF (10 mL) in a 50 mL round-bottomed flask equipped with a magnetic stirrer was added a 1 N aqueous HCl solution (5 mL) and the mixture was stirred overnight at RT, then for 1 h at 70° C. A 6 N aqueous HCl solution (2.5 mL) was then added and the mixture was stirred for 26 h at 70° C. THF was removed at 40° C. under vacuum before addition of a conc. NH₄OH solution (5 mL). The solution was extracted with CH₂Cl₂ (50 mL) and the organic phase was isolated, washed with brine (10 mL), dried over Na₂SO₄, filtered and concentrated at 40° C. under vacuum to give 2-ethyl-6-methoxyquinoline-3-carbaldehyde SMA 44004 as a brown oil (269 mg, 81% yield).

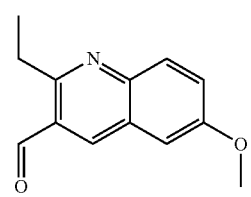

SMA 44004

MW: 215.25; Yield: 81%; Brown Oil.

Rf: 0.25 (cyclohexane:EtOAc=75:25, free base).

¹H NMR (CDCl₃, δ): 1.38 (t, 3H, J=7.5 Hz, CH₃), 3.35 (q, 2H, J=7.5 Hz, CH₂), 3.95 (s, 3H, OCH₃), 7.16 (d, 1H, J=2.7 Hz, ArH), 7.48 (dd, 1H, J=2.7 & 9.2 Hz, ArH), 7.99 (d, 1H, J=9.2 Hz, ArH), 8.50 (s, 1H, ArH), 10.38 (s, 1H, CHO).

¹³C-NMR (CDCl₃, δ): 14.3, 29.3, 55.6, 106.0, 125.4, 127.1, 127.4, 130.1, 140.6, 145.7, 157.9, 160.8, 191.4.

MS-ESI m/z (% rel. Int.): 216 ([MH]⁺, 100).

HPLC: Method B (5 min), XBridge™ column (5 mm, C18, 4.5×50 mm, Model #186003113), detection UV 214 nm, RT=2.05 min.

(2-Ethyl-6-methoxyquinolin-3-yl)-methanol SMA 44008

To a solution of 2-ethyl-6-methoxyquinoline-3-carbaldehyde SMA 44004 (256 mg, 1.19 mmol) in THF (12 mL) in a 25 mL round-bottomed flask equipped with a magnetic stirrer was added NaBH$_4$ (48 mg, 1.25 mmol) and the mixture was stirred for 2 h at RT, then quenched by careful addition of 2 N aqueous HCl (2.6 mL). After stirring for 30 min at RT, the mixture was basified with 2 N aqueous NaOH (2.6 mL) and THF was removed at 40° C. under vacuum. The residue was diluted with CH$_2$Cl$_2$ (50 mL) and the organic phase was isolated, washed with brine (10 mL), dried over Na$_2$SO$_4$, filtered and concentrated at 40° C. under vacuum. Purification by column chromatography (SiO$_2$, eluent cyclohexane:EtOAc=100:0 to 50:50) gave (2-ethyl-6-methoxyquinolin-3-yl)-methanol SMA 44008 as a white solid (173 mg, 67% yield).

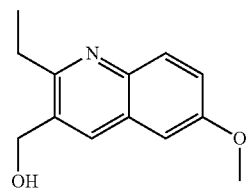

SMA 44008

MW: 217.26; Yield: 67%; White Solid.

Rf 0.25 (cyclohexane:EtOAc=50:50, free base).

$^1$H NMR (CDCl$_3$, δ): 1.31 (t, 3H, J=7.5 Hz, CH$_3$), 2.90 (q, 2H, J=7.5 Hz, CH$_2$), 3.46 (br, s, 1H, OH), 3.88 (s, 3H, OCH$_3$), 4.86 (s, 2H, CH$_2$), 6.96 (d, 1H, J=2.5 Hz, ArH), 7.28 (dd, 1H, J=2.5 & 9.1 Hz, ArH), 7.90 (d, 1H, J=9.1 Hz, ArH), 8.00 (s, 1H, ArH).

$^{13}$C-NMR (CDCl$_3$, δ): 13.5, 28.3, 55.5, 61.9, 105.2, 121.6, 127.8, 129.6, 132.5, 133.1, 143.0, 157.3, 159.3.

MS-ESI m/z (% rel. Int.): 218 ([MH]$^+$, 100).

HPLC: Method B (5 min), XBridge™ column (5 mm, C18, 4.5×50 mm, Model #186003113), detection UV 214 nm, RT=1.93 min.

3-Chloromethyl-2-ethyl-6-methoxyquinoline hydrochloride SMA 44014

To a solution of (2-ethyl-6-methoxyquinolin-3-yl)-methanol SMA 44008 (150 mg, 0.69 mmol) in dry CH$_2$Cl$_2$ (20 mL) at 0° C. under N$_2$ in a 50 mL round-bottomed flask equipped with a magnetic stirrer was added dropwise SOCl$_2$ (1.0 mL, 13.8 mmol) and the mixture was stirred for 2 h at RT. The volatiles were then removed at 40° C. under vacuum and the residue was taken up in CH$_2$Cl$_2$ (20 mL) before concentration back to dryness at 40° C. under vacuum (done 3 times) to give 3-chloromethyl-2-ethyl-6-methoxyquinoline hydrochloride SMA 44014 as a brown solid (197 mg, >100% yield).

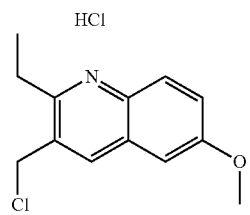

SMA 44014

MW: 272.17; Yield: >100%; Brown Solid.

$^1$H NMR (CD$_3$OD, δ): 1.44 (t, 3H, J=7.6 Hz, CH$_3$), 3.27 (q, 2H, J=7.6 Hz, CH$_2$), 3.94 (s, 3H, OCH$_3$), 4.99 (s, 2H, CH$_2$), 7.58 (d, 1H, J=1.7 Hz, 1×ArH), 7.67 (dd, 1H, J=1.7 and 9.3 Hz, 1×ArH), 8.10 (d, 1H, J=9.3 Hz, 1×ArH), 8.99 (s, 1H, 1×ArH).

$^{13}$C-NMR (CD$_3$OD, δ): 14.3, 26.1, 42.0, 56.9, 107.6, 122.3, 129.4, 130.9, 133.2, 134.9, 147.0, 159.5, 161.7.

MS-ESI m/z (% rel. Int.): 238 ([MH]$^+$, $^{37}$Cl, 38), 236 ([MH]$^+$, $^{35}$Cl, 100).

HPLC: Method B (5 min), XBridge™ column (5 mm, C18, 4.5×50 mm, Model #186003113), detection UV 214 nm, RT=2.26 min.

4-((2-Ethyl-6-methoxyquinolin-3-yl)methyl)-6,7-dimethoxy-1-propylisoquinolin-3-ol dihydrochloride SLA 41122

To a stirred solution of 3-(chloromethyl)-2-ethyl-6-methoxyquinoline hydrochloride SMA 44014 (183 mg, 0.67 mmol) in THF (10 mL) in a 20 mL microwave vial equipped with a magnetic stirrer was added 6,7-dimethoxy-1-propylisoquinolin-3-ol RBO 35134 (166 mg, 0.67 mmol) followed by a 2 N aq. LiOH solution (0.67 mL, 1.34 mmol) and the mixture was stirred at 160° C. for 1.5 h under microwave irradiation. After cooling to room temperature, the mixture was diluted with CH$_2$Cl$_2$:MeOH=9:1 (150 mL), washed with brine (20 mL), dried over Na$_2$SO$_4$, filtered, and concentrated at 40° C. under vacuum. Purification by column chromatography (SiO$_2$, eluent EtOAc:MeOH=100:0 to 95:5) followed by a new purification by column chromatography (SiO$_2$, eluent CH$_2$Cl$_2$:MeOH=100:0 to 95:5) provided after evaporation 4-((2-ethyl-6-methoxyquinolin-3-yl) methyl)-6,7-dimethoxy-1-propylisoquinolin-3-ol. This free base was dissolved in CH$_2$Cl$_2$ (2 mL) in a 10 mL round-bottomed flask equipped with a magnetic stirrer before addition of a 0.49 M HCl solution in MeOH (0.32 mL) and the mixture was stirred for 5 min at RT then concentrated at 40° C. under vacuum to afford 4-((2-ethyl-6-methoxyquinolin-3-yl)methyl)-6,7-dimethoxy-1-propylisoquinolin-3-ol dihydrochloride 66 as a yellow solid (17 mg, 5% yield).

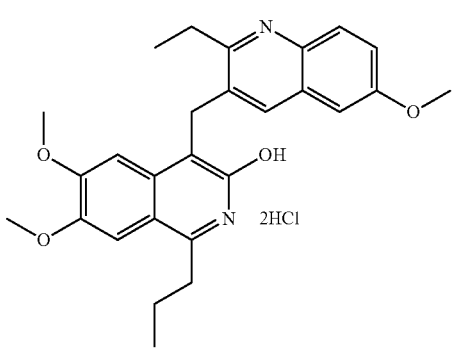

66

MW: 519.46; Yield: 5%; Yellow Solid; Mp (° C.): 200.9.

$^1$H NMR (CD$_3$OD, δ): 1.14 (t, 3H, J=9.0 Hz, CH$_3$), 1.61 (t, 3H, J=9.0 Hz, CH$_3$), 1.94-1.97 (m, 2H, CH$_2$), 3.39-3.44 (m, 2H, CH$_2$), 3.48-3.55 (m, 2H, CH$_2$), 3.84 (s, 3H, OCH$_3$), 3.86 (s, 3H, OCH$_3$), 4.02 (s, 3H, OCH$_3$), 4.75 (s, 2H, CH$_2$), 7.04 (s, 1H, ArH), 7.39 (s, 1H, ArH), 7.57 (s, 1H, ArH), 7.64 (d, 1H, J=9.2 Hz, ArH), 8.13-8.17 (m, 2H, 2×ArH).

$^{13}$C-NMR (CD$_3$OD, δ): 13.3, 14.2, 24.7, 26.7, 27.7, 33.6, 56.7, 56.9, 57.3, 102.8, 106.1, 107.2, 111.2, 119.6, 122.1, 128.3, 130.9, 133.5, 133.9, 141.4, 143.3, 152.2, 152.4, 155.2, 159.6, 159.9, 161.5.

MS-ESI m/z (% rel. Int.): 447 ([MH]+, 100).

HPLC: Method B (10 min), XBridge™ column (5 mm, C18, 4.5×50 mm, Model #186003113), detection UV 254 nm, RT=4.07 min, peak area 99.1%.

Preparation of 4-((2-(ethylamino)-6-methoxyquinolin-3-yl)methyl)-6,7-dimethoxy-1-(methoxymethyl)isoquinolin-3-ol dihydrochloride 67

6,7-Dimethoxy-1-methoxymethyl-isoquinolin-3-ol SMA 44012

A mixture of methoxyacetic acid (21.9 g, 242.67 mmol) and acetic anhydride (24.80 g, 242.67 mmol) in a 250 mL round-bottomed flask equipped with a magnetic stirrer and a distillation assembly was heated with stirring for 2 h at 100° C. and then distilled under reduced pressure. Methoxyacetic anhydride (13.5 g, 34% yield) was collected at 108° C. at around 20 mb.

To a solution of methyl 2-(3,4-dimethoxy-phenyl)acetate SLA 28134 (3.36 g, 15.98 mmol) in methoxyacetic anhydride SMA 44010 (10.19 g, 62.85 mmol) at 0° C. in a 250 mL round-bottomed flask equipped with a magnetic stirrer was added dropwise $HClO_4$ (ca. 70% solution in water, 1.64 mL, 18.98 mmol). The mixture was then stirred for 45 min at RT then diluted with $Et_2O$ (151 mL). The organic solution was removed to give a viscous residue that was suspended in $H_2O$ (30 mL) at 5° C. before dropwise addition of a conc. $NH_4OH$ solution (38 mL). After complete addition, the mixture was stirred overnight at RT and extracted with $CH_2Cl_2$ (50 mL) then with $CH_2Cl_2$:MeOH=95:5 (100 mL). The organic phase was combined, washed with brine (30 mL), dried over $Na_2SO_4$, filtered and concentrated at 40° C. under vacuum. Purification by column chromatography ($SiO_2$, eluent $CH_2Cl_2$:MeOH=100:0 to 93:7) gave 6,7-dimethoxy-1-methoxymethyl-isoquinolin-3-ol SMA 44012 as a yellow solid (96 mg, 2% yield).

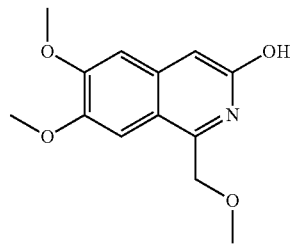

SMA 44012

MW: 249.27; Yield: 2%; Yellow Solid. Mp (° C.): 214.1 (dec.)

Rf (free base)=0.2 ($CH_2Cl_2$:MeOH=95:5).

$^1$H NMR ($CDCl_3$:$CD_3OD$=2:1, δ): 3.57 (s, 3H, $OCH_3$), 3.95 (s, 3H, $OCH_3$), 4.00 (s, 3H, $OCH_3$), 4.88 (s, 2H, $CH_2$), 6.65 (s, 1H, ArH), 6.74 (s, 1H, ArH), 6.87 (s, 1H, ArH).

$^{13}$C-NMR ($CDCl_3$:$CD_3OD$=2:1, δ): 57.4, 57.6, 60.5, 70.3, 102.3, 104.2, 107.9, 114.5, 143.9, 145.2, 150.0, 156.9, 161.8.

MS-ESI m/z (% rel. Int.): 250 ([MH]+, 100).

HPLC: Method B (5 min), XBridge™ column (5 mm, C18, 4.5×50 mm, Model #186003113), detection UV 214 nm, RT=2.00 min.

4-((2-(Ethylamino)-6-methoxyquinolin-3-yl)methyl)-6,7-dimethoxy-1-(methoxymethyl)isoquinolin-3-ol dihydrochloride 67

To a stirred solution of 3-(chloromethyl)-N-ethyl-6-methoxyquinolin-2-amine hydrochloride SLA 28166 (84 mg, 0.29 mmol) in THF (10 mL) in a 20 mL microwave vial equipped with a magnetic stirrer was added 6,7-dimethoxy-1-(methoxymethyl)isoquinolin-3-ol SMA 44012 (73 mg, 0.29 mmol) followed by a 2 N aq. LiOH solution (0.29 mL, 0.58 mmol) and the mixture was stirred at 160° C. for 1.5 h under microwave irradiation. After cooling to RT, the mixture was diluted with $CH_2Cl_2$:MeOH=9:1 (150 mL), washed with brine (20 mL), dried over $Na_2SO_4$, filtered and concentrated at 40° C. under vacuum. Purification by column chromatography ($SiO_2$, eluent EtOAc:MeOH=100:0 to 95:5) followed by a new purification by column chromatography ($SiO_2$, eluent $CH_2Cl_2$:MeOH=100:0 to 95:5) provided 4-((2-(ethylamino)-6-methoxyquinolin-3-yl)methyl)-6,7-dimethoxy-1-(methoxymethyl)isoquinolin-3-ol. This free base was dissolved in $CH_2Cl_2$ (2 mL) in a 10 mL round-bottomed flask equipped with a magnetic stirrer before addition of a 0.49 M HCl solution in MeOH (0.28 mL) and the mixture was stirred for 5 min at room temperature and concentrated at 40° C. under vacuum to afford 4-((2-(ethylamino)-6-methoxyquinolin-3-yl)methyl)-6,7-dimethoxy-1-(methoxymethyl)isoquinolin-3-ol dihydrochloride 67 as a yellow solid (9 mg, 6% yield).

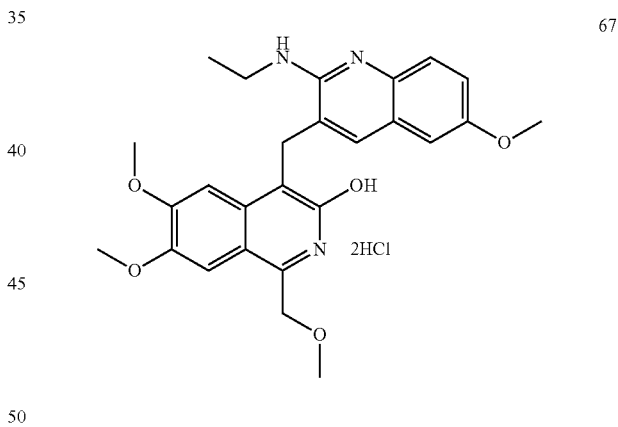

67

MW: 536.45; Yield: 6%; Yellow Solid; Mp (° C.): 199.9.

$^1$H NMR ($CD_3OD$, δ): 1.51 (t, 3H, J=7.0 Hz, $CH_3$), 3.63 (s, 3H, $OCH_3$), 3.68 (s, 3H, $OCH_3$), 3.68-3.76 (m, 2H, $NCH_2$), 3.95 (s, 3H, $OCH_3$), 4.00 (s, 3H, $OCH_3$), 4.37 (s, 2H, $CH_2$), 5.24 (s, 2H, $CH_2$), 7.11 (s, 2H, 2×ArH), 7.32 (d, 1H, J=9.1 Hz, ArH), 7.43 (s, 1H, ArH), 7.57 (s, 1H, ArH), 7.89 (d, 1H, J=9.1 Hz, ArH).

$^{13}$C-NMR ($CD_3OD$, δ): 13.9, 27.0, 39.1, 56.3, 56.9, 57.4, 60.0, 69.0, 102.2, 104.6, 109.5, 111.4, 117.8, 119.6, 123.4, 123.7, 124.4, 131.2, 139.5, 141.7, 148.6, 152.0, 152.5, 153.4, 158.7, 160.0.

MS-ESI m/z (% rel. Int.): 464 ([MH]+, 100).

HPLC: Method B (10 min), XBridge™ column (5 mm, C18, 4.5×50 mm, Model #186003113), detection UV 254 nm, RT=4.08 min, peak area 99.5%.

Preparation of 4-((2-azido-6-methoxyquinolin-3-yl)methyl)-1-ethyl-6,7-dimethoxyisoquinolin-3-ol dihydrochloride 68

2-Azido-3-(chloromethyl)-6-methoxyquinoline hydrochloride SLA 41152

To a stirred solution of 2-chloro-6-methoxyquinoline-3-carbaldehyde (0.94 g, 4.24 mmol) in DMF (10 mL) in a 25 mL round-bottomed flask equipped with a magnetic stirrer was added sodium azide (303 mg, 4.66 mmol) and the mixture was stirred overnight at 80° C. After cooling to RT, the mixture was diluted with Et$_2$O (50 mL) and the solid was filtered, washed with more Et$_2$O (50 mL) then with H$_2$O (10 mL) and dried under vacuum to give 0.88 g of a beige solid (91%). This solid (446 mg, 1.95 mmol) was then dissolved in MeOH (30 mL) in a 100 mL round-bottomed flask equipped with a magnetic stirrer before addition of NaBH$_4$ (150 mg, 3.97 mmol) and the reaction mixture was stirred for 1.5 h at RT. MeOH was then removed at 40° C. under vacuum and the residue was taken up in CH$_2$Cl$_2$:MeOH=7:1 (40 mL) and the solution was washed with H$_2$O (10 mL), brine (10 mL), dried over Na$_2$SO$_4$, filtered and concentrated at 40° C. under vacuum to give 435 mg of an off-white solid (97% yield). This solid (200 mg, 0.87 mmol) was then dissolved in dry CH$_2$Cl$_2$ (20 mL) in a 100 mL round-bottomed flask equipped with a magnetic stirrer before dropwise addition of SOCl$_2$ (1.26 mL, 17.37 mmol). The mixture was stirred for 2 h at RT then concentrated to dryness at 40° C. under vacuum. The residue was then taken up in CH$_2$Cl$_2$ (20 mL) before concentration back to dryness at 40° C. under vacuum (done 3 times) to give 2-azido-3-(chloromethyl)-6-methoxyquinoline hydrochloride SLA 41152 as a yellow solid (200 mg, 92% yield).

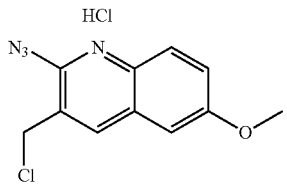

SLA 44152

MW: 285.13; Yield: 81% (3 steps); Yellow Solid; Mp (° C.): 145.1.
$^1$H NMR ((CD$_3$)$_2$SO, δ): 3.95 (s, 3H, CH$_3$), 5.22 (s, 2H, CH$_2$), 7.59 (dd, 1H, J=2.7 & 9.2 Hz, ArH), 7.76 (d, 1H, J=2.7 Hz, ArH), 8.33 (s, 1H, ArH), 8.53 (d, 1H, J=9.2 Hz, ArH).
$^{13}$C-NMR ((CD$_3$)$_2$SO, δ): 41.0, 55.9, 110.7, 117.7, 120.9, 122.8, 124.3, 125.1, 132.6, 145.7, 158.6.
MS-ESI m/z (% rel. Int.): 251 ([MH]$^+$, $^{37}$Cl, 14), 249 ([MH]$^+$, $^{35}$Cl, 45), 221 (100).
HPLC: Method B (5 min), XBridge™ column(5 mm, C18, 4.5×50 mm, Model #186003113), detection UV 254 nm, RT=2.89 min.

4-((2-Azido-6-methoxyquinolin-3-yl)methyl)-1-ethyl-6,7-dimethoxyisoquinolin-3-ol dihydrochloride 68

To a solution of 1-ethyl-6,7-dimethoxyisoquinolin-3-ol SLA 28136 (161 mg, 0.69 mmol) in THF (13 mL) in a 20 mL microwave vial equipped with a magnetic stirrer was added 2-azido-3-(chloromethyl)-6-methoxyquinoline hydrochloride SLA 41152 (197 mg, 0.69 mmol) followed by a 2 N aq. LiOH solution (0.69 mL, 1.38 mmol) and the mixture was stirred at 160° C. for 1.5 h under microwave irradiation. After cooling to RT, THF was removed at 40° C. under vacuum and the residue was taken up in CH$_2$Cl$_2$ (50 mL), washed with brine (10 mL), dried over Na$_2$SO$_4$, filtered, and concentrated under vacuum. Purification by column chromatography (SiO$_2$, eluent EtOAc:MeOH=100:0 to 95:5) followed by a new purification by column chromatography (SiO$_2$, eluent CH$_2$Cl$_2$:MeOH=100:0 to 95:5) gave 4-((2-azido-6-methoxyquinolin-3-yl)methyl)-1-ethyl-6,7-dimethoxyisoquinolin-3-ol (10 mg). This free base was dissolved in MeOH (2 mL) in a 10 mL round-bottomed flask equipped with a magnetic stirrer before addition of a 0.149 M HCl solution in MeOH (2.0 mL). The reaction mixture was stirred for 5 min at RT and concentrated at 40° C. under vacuum to afford 4-((2-azido-6-methoxyquinolin-3-yl)methyl)-1-ethyl-6,7-dimethoxyisoquinolin-3-ol dihydrochloride 68 as a yellow solid (11 mg, 3% yield).

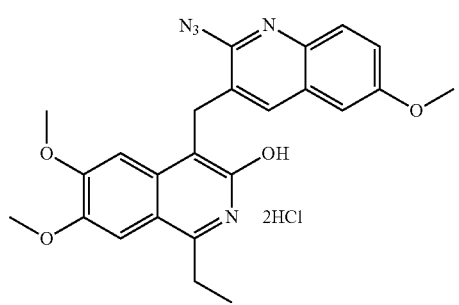

MW: 518.39; Yield: 3%; Yellow Solid; Mp (° C.): 168.4.
$^1$H-NMR (CD$_3$OD, δ): 1.55 (t, 3H, J=7.5 Hz, CH$_3$), 3.28-3.44 (m, 2H, CH$_2$), 3.96 (s, 3H, OCH$_3$), 4.04 (s, 6H, 2×OCH$_3$), 4.89 (s, 2H, CH$_2$), 7.38-7.51 (m, 4H, 4×ArH), 7.95 (s, 1H, ArH), 8.52 (d, 1H, J=9.0 Hz, ArH).
$^{13}$C-NMR (CD$_3$OD, δ): 13.8, 24.3, 25.9, 55.6, 56.0, 56.6, 102.1, 104.1, 109.7, 112.0, 117.7, 120.7, 123.4, 124.2, 125.9, 131.8, 139.9, 147.0, 150.7, 150.9, 154.2, 158.3, 159.6, 1×C not observed.
MS-ESI m/z (rel.int.): 446 ([MH]$^+$, 100).
HPLC: Method B (10 min), XBridge™ column (5 mm, C18, 4.5×50 mm, Model #186003113), detection UV 254 nm, RT=4.68 min, peak area 96.6%.

Preparation of N-(2-(3-((1-ethyl-3-hydroxy-6,7-dimethoxyisoquinolin-4-yl)methyl)-6-methoxyquinolin-2-ylamino)ethyl)acetamide dihydrochloride 69

N-(2-(3-Formyl-6-methoxyquinolin-2-ylamino)ethyl)acetamide SLA 41168

To a stirred solution of 2-chloro-6-methoxyquinoline-3-carbaldehyde (2.00 g, 9.0 mmol) in THF (10 mL) in a 20 mL microwave vial equipped with a magnetic stirrer was added N-(2-aminoethyl)acetamide (2.76 g, 27.1 mmol) and the reaction mixture was stirred for 1 h at 160° C. under microwave irradiation. After cooling to RT, the volatiles were removed at 40° C. under vacuum and the resulting yellow oil was taken up with CH$_2$Cl$_2$ (100 mL). This organic solution was washed with brine (2×10 mL), dried over MgSO$_4$, filtered, and concentrated under vacuum. The residue was finally purified by column chromatography (SiO$_2$, eluent cyclohexane:EtOAc=100:0 to 0:100) to give N-(2-(3-formyl-6-methoxyquinolin-2-ylamino)ethyl)acetamide SLA 41168 as an orange solid (601 mg, 23% yield).

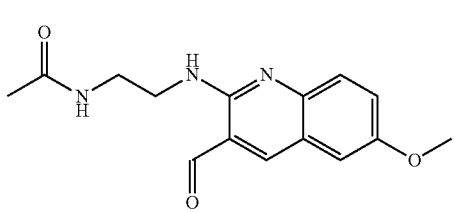

SLA 44168

MW: 287.31; Yield: 23%; Brown Solid; Mp (° C.): 150.0.

$^1$H NMR (CDCl$_3$, δ): 1.93 (s, 3H, CH$_3$C=O), 3.53 (q, 2H, J=5.7 Hz, CH$_2$N), 3.80 (q, 2H, J=5.7 Hz, CH$_2$N), 3.90 (s, 3H, OCH$_3$), 7.02 (d, 1H, J=2.8 Hz, ArH), 7.38 (dd, 1H, J=2.8 & 9.2 Hz, ArH), 7.46 (broad s, 1H, NH), 7.58 (d, 1H, J=9.2 Hz, ArH), 8.18 (broad s, 1H, NH), 8.21 (s, 1H, ArH).

$^{13}$C-NMR (CDCl$_3$, δ): 23.3, 40.1, 42.2, 55.6, 106.9, 117.4, 122.4, 126.3, 127.3, 146.2, 147.4, 154.5, 155.3, 170.3, 192.9.

MS-ESI m/z (% rel. Int.): 288 ([MH]$^+$, 100).

HPLC: Method B (5 min), XBridge™ column (5 mm, C18, 4.5×50 mm, Model #186003113), detection UV 254 nm, RT=1.98 min.

N-(2-(3-(Hydroxymethyl)-6-methoxyquinolin-2-ylamino)ethyl)acetamide SLA 41174

To a stirred solution of N-(2-(3-formyl-6-methoxyquinolin-2-ylamino)ethyl)acetamide SLA 41168 (0.70 g, 2.43 mmol) in THF (30 mL) in a 100 mL round-bottomed flask equipped with a magnetic stirrer was added NaBH$_4$ (0.09 g, 2.43 mmol) and the mixture was stirred overnight at RT then cooled in an ice bath before quenching by addition of a 1 N aq. HCl solution (40 mL). After stirring for 15 min, the mixture was basified to pH=9 using a 2 N aq. NaOH solution. THF was removed at 40° C. under vacuum and the solution was extracted with CH$_2$Cl$_2$ (200 mL), washed with brine (20 mL), dried over Na$_2$SO$_4$, filtered and concentrated to give N-(2-(3-(hydroxymethyl)-6-methoxyquinolin-2-ylamino)ethyl)acetamide SLA 41174 as an orange solid (0.65 g, 93% yield).

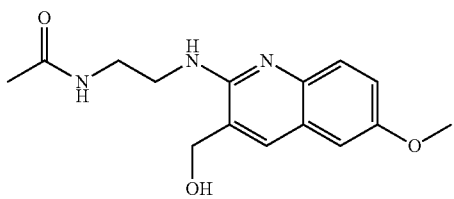

SLA 41174

MW: 289.33; Yield: 93%; Orange Solid; Mp (° C.): 168.5.

$^1$H NMR (CDCl$_3$, δ): 1.84 (s, 3H, CH$_3$C=O), 3.39-3.44 (m, 2H, CH$_2$), 3.64-3.68 (m, 2H, CH$_2$), 3.85 (s, 3H, OCH$_3$), 4.62 (s, 2H, CH$_2$), 6.88 (d, 1H, J=2.6 Hz, ArH), 7.18 (dd, 1H, J=2.6 & 9.1 Hz, ArH), 7.46 (s, 1H, ArH), 7.55 (d, 1H, J=9.1 Hz, ArH).

$^{13}$C-NMR (CDCl$_3$, δ): 23.1, 40.7, 42.4, 55.5, 63.2, 106.7, 120.8, 122.8, 123.5, 126.6, 134.8, 142.4, 154.9, 155.5, 171.1.

MS-ESI m/z (% rel. Int.): 290 ([MH]$^+$, 100).

HPLC: Method B (5 min), XBridge™ column (5 mm, C18, 4.5×50 mm, Model #186003113), detection UV 214 nm, RT=2.03 min.

N-(2-(3-((1-Ethyl-3-hydroxy-6,7-dimethoxyisoquinolin-4-yl)methyl)-6-methoxyquinolin-2-ylamino)ethyl)acetamide dihydrochloride 69

To a stirred solution of N-(2-(3-(chloromethyl)-6-methoxyquinolin-2-ylamino)ethyl)acetamide hydrochloride SLA 41174 (350 mg, 1.02 mmol) in THF (10 mL) in a 20 mL microwave vial equipped with a magnetic stirrer was added 1-ethyl-6,7-dimethoxyisoquinolin-3-ol SLA 28136 (237 mg, 1.02 mmol) followed by a 2 N aq. LiOH solution (1.02 mL, 2.0 mmol) and the mixture was stirred at 160° C. for 1.5 h under microwave irradiation. After cooling to RT, the mixture was diluted with CH$_2$Cl$_2$:MeOH=9:1 (150 mL), washed with brine (20 mL), dried over Na$_2$SO$_4$, filtered and concentrated at 40° C. under vacuum. Purification by column chromatography (SiO$_2$, eluent CH$_2$Cl$_2$:MeOH=100:0 to 90:10) provided N-(2-(3-((1-ethyl-3-hydroxy-6,7-dimethoxyisoquinolin-4-yl)methyl)-6-methoxyquinolin-2-ylamino)ethyl)acetamide. The product was dissolved in CH$_2$Cl$_2$ (2 mL) in a 10 mL round-bottomed flask equipped with a magnetic stirrer before addition of a 0.49 M HCl solution in MeOH (2 mL) and the solution was stirred for 5 min at RT then concentrated at 40° C. under vacuum to give N-(2-(3-((1-ethyl-3-hydroxy-6,7-dimethoxyisoquinolin-4-yl)methyl)-6-methoxyquinolin-2-ylamino)ethyl)acetamide dihydrochloride 69 as a yellow solid (83.5 mg, 17% yield).

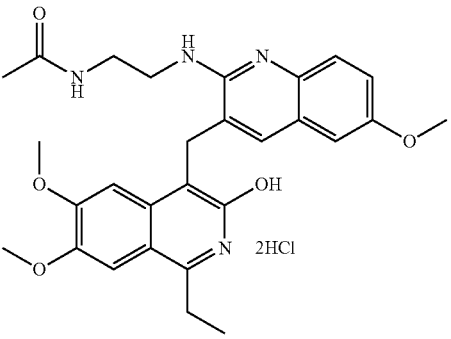

MW: 577.50; Yield: 17%; Yellow Solid; Mp (° C.): 244.8.

$^1$H NMR (CD$_3$OD, δ): 1.50-1.65 (m, 3H, CH$_3$), 2.10 (s, 3H, CH$_3$O), 3.40-3.50 (m, 2H, CH$_2$), 3.52-3.65 (m, 2H, CH$_2$), 3.79 (s, 3H, OCH$_3$), 3.82-3.90 (m, 2H, CH$_2$), 3.96 (s, 3H, OCH$_3$), 4.07 (s, 3H, OCH$_3$), 4.35 (s, 2H, CH$_2$), 7.15 (s, 2H, 2×ArH), 7.39 (d, 1H, J=9.0 Hz, ArH), 7.54 (s, 1H, ArH), 7.61 (s, 1H, ArH), 8.02 (d, 1H, J=9.0 Hz, ArH).

$^{13}$C-NMR (CD$_3$OD, δ): 14.7, 22.5, 25.6, 27.1, 39.0, 43.6, 56.4, 57.1, 57.6, 102.2, 103.0, 105.8, 109.4, 112.3, 119.9, 123.7, 123.9, 126.8, 131.3, 139.5, 141.8, 144.7, 145.7, 152.2, 152.9, 158.1, 158.9, 175.8.

MS-ESI m/z (% rel. Int.): 505 ([MH]$^+$, 100).

HPLC: Method B (10 min), XBridge™ column (5 mm, C18, 4.5×50 mm, Model #186003113), detection UV 254 nm, RT=4.77 min, peak area 96.2%.

Preparation of 4-((2-(ethylamino)-7-fluoro-6-methoxyquinolin-3-yl)methyl)-6,7-dimethoxy-1-propylisoquinolin-3-ol dihydrochloride 70

N-(3-Fluoro-4-methoxyphenyl)acetamide SMA 44032

To a solution of 3-fluoro-4-methoxyaniline (1.15 g, 8.15 mmol) in dry CH$_2$Cl$_2$ (81 mL) in a 250 mL round-bottomed flask equipped with a magnetic stirrer were added DIEA (5.4 mL, 32.7 mmol), DMAP (221 mg, 1.81 mmol) and acetic anhydride (4.4 mL, 46.5 mmol) and the mixture was stirred overnight at RT. The solution was washed with brine (10 mL), dried over Na$_2$SO$_4$, filtered and concentrated at 40° C. under vacuum. Purification by column chromatography (SiO$_2$, eluent cyclohexane:EtOAc=100:0 to 50:50) gave N-(3-fluoro-4-methoxyphenyl)acetamide SMA 44032 as a brown solid (1.08 g, 72% yield).

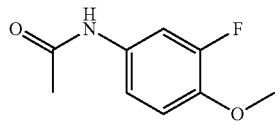

SMA 44032

MW: 183.18; Yield: 72%; Brown solid; Mp (° C.): 112.4.
Rf: 0.25 (cyclohexane:EtOAc=50:50).
$^1$H NMR (CDCl$_3$, δ): 2.15 (s, 3H, CH$_3$), 3.86 (s, 3H, OCH$_3$), 6.88 (dd, 1H, J=9.0 Hz & 9.0 Hz, ArH), 7.08-7.16 (m, 1H, ArH), 7.40 (dd, J=2.4 Hz & 12.8 Hz, 1H, ArH), 7.51 (broad s, 1H, NH).
$^{13}$C-NMR (CDCl$_3$, δ): 24.3, 56.6, 109.4 (d, J=22.6 Hz), 113.7 (d, J=2.4 Hz), 115.7 (d, J=3.5 Hz), 131.4 (d, J=9.3 Hz), 144.4 (d, J=10.9 Hz), 152.1 (d, J=245.3 Hz), 168.3.
MS-ESI m/z (% rel. Int.): 184 ([MH]$^+$, 100).
HPLC: Method B (5 min), XBridge™ column (5 mm, C18, 4.5×50 mm, Model #186003113), detection UV 214 nm, RT=2.32 min.

2-Chloro-7-fluoro-6-methoxyquinoline-3-carbaldehyde SMA 44034

POCl$_3$ (3.6 mL, 39.3 mmol) was added dropwise under N$_2$ to DMF (0.7 mL, 9.04 mmol) at 0° C. in a 2 mL microwave vial equipped with a magnetic stirrer. The mixture was then stirred for 15 min at 0° C. before addition of N-(3-fluoro-4-methoxyphenyl)acetamide SMA 44032 (1.00 g, 5.46 mmol) and the mixture was stirred overnight at RT then for 30 min at 160° C. under microwave irradiation. After cooling to RT, the mixture was poured on a mixture of ice-water (20 mL) then neutralized with a 10 N aqueous NaOH solution (to pH=7) before extraction with CH$_2$Cl$_2$ (80 mL). The separated organic layer was washed with brine (10 mL), dried over Na$_2$SO$_4$, filtered and concentrated at 40° C. under vacuum. Purification by column chromatography (SiO$_2$, eluent cyclohexane:EtOAc=100:0 to 83:17) gave 2-chloro-7-fluoro-6-methoxyquinoline-3-carbaldehyde SMA 44034 as a yellow solid (233 mg, 18% yield).

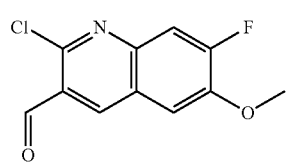

SMA 44034

MW: 239.64; Yield: 18%; Yellow Solid; Mp (° C.): 290.0.
Rf: 0.30 (cyclohexane:EtOAc=83:17).
$^1$H NMR (DMSO d$_6$, δ): 4.01 (s, 3H, OCH$_3$), 7.89-7.95 (m, 2H, 2×ArH), 8.86 (s, 1H, ArH), 10.36 (s, 1H, CHO).
$^{13}$C-NMR (DMSO d$_6$, δ): 56.4, 110.0 (d, J=3.0 Hz), 112.8 (d, J=18.9 Hz), 124.5, 125.9 (d, J=3.0 Hz), 139.3, 144.8 (d, J=12.8 Hz), 147.6, 148.4 (d, J=13.6 Hz), 156.3 (d, J=258.0 Hz), 189.2.
MS-ESI m/z (% rel. Int.): 242 ([MH]$^+$, $^{37}$Cl, 38), 240 ([MH]$^+$, $^{35}$Cl, 100).
HPLC: Method B (5 min), XBridge™ column (5 mm, C18, 4.5×50 mm, Model #186003113), detection UV 214 nm, RT=5.43 min.

2-(Ethylamino)-7-fluoro-6-methoxyquinoline-3-carbaldehyde CCH 42068

To a stirred solution of 2-chloro-7-fluoro-6-methoxyquinoline-3-carbaldehyde SMA 44034 (219 mg, 0.91 mmol) in THF (10 mL) in a 20 mL microwave vial equipped with a magnetic stirrer was added ethylamine (2 M in THF, 4.50 mL, 9.00 mmol) and the mixture was stirred at 150° C. for 2 h under microwave irradiation. After cooling to RT, the volatiles were removed under vacuum at 40° C. and the resulting yellow oil was taken up in a 2 N aq. HCl solution (15 mL) and stirred for 15 min at RT then neutralised with a 2 N aq. NaOH solution (15 mL). The mixture was extracted with CH$_2$Cl$_2$:MeOH=9:1 (50 mL) and the organic phase was washed with brine (10 mL), dried over Na$_2$SO$_4$, filtered, and concentrated at 40° C. under vacuum. Purification by column chromatography (SiO$_2$, eluent cyclohexane:EtOAc=100:0 to 75:25) gave 2-(ethylamino)-7-fluoro-6-methoxyquinoline-3-carbaldehyde CCH 42068 as a yellow oil (105 mg, 46% yield).

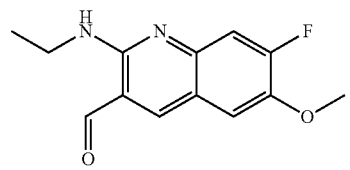

CCH 42068

MW: 248.25; Yield: 46%; Yellow Oil.
Rf: 0.45 (cyclohexane:EtOAc=75:25).
$^1$H NMR (CDCl$_3$, δ): 1.29 (t, 3H, J=7.2 Hz, CH$_3$), 3.59-3.68 (m, 2H, CH$_2$), 3.96 (s, 3H, OCH$_3$), 7.04 (d, J=9.2 Hz, 1H, ArH), 7.34 (d, J=12.8 Hz, 1H, ArH), 7.93 (broad s, 1H, NH), 8.10 (s, 1H, ArH), 9.94 (s, 1H, CHO).
$^{13}$C-NMR (CDCl$_3$, δ): 14.7, 35.5, 56.2, 108.9 (d, J=3.8 Hz), 111.9 (d, J=18.2 Hz), 116.5 (d, J=2.3 Hz), 118.4, 145.2 (d, J=3.8 Hz), 146.5, 147.9 (d, J=13.1 Hz), 154.3, 157.8 (d, J=257.6 Hz), 192.7.
MS-ESI m/z (% rel. Int.): 249 ([MH]$^+$, 100).
HPLC: Method B (5 min), XBridge™ column (5 mm, C18, 4.5×50 mm, Model #186003113), detection UV 214 nm, RT=2.17 min.

(2-Ethylamino-7-fluoro-6-methoxyquinolin-3-yl) methanol SMA 44090

To a solution of 2-(ethylamino)-7-fluoro-6-methoxyquinoline-3-carbaldehyde CCH 42068 (500 mg, 2.01 mmol) in THF (50 mL) in a 100 mL round-bottomed flask equipped with a magnetic stirrer was added NaBH$_4$ (80 mg, 2.11 mmol) and the reaction mixture was stirred overnight at RT, then cooled in an ice bath and quenched by addition of a 6 N aqueous HCl solution (10 mL). The mixture was then basified with a 10 N aqueous NaOH solution (to pH=12). THF was then removed at 40° C. under vacuum and the residue was taken up in $CH_2Cl_2$ (50 mL) and the organic phase was isolated, washed with brine (10 mL), dried over $Na_2SO_4$, filtered and concentrated at 40° C. under vacuum. Purification by column chromatography ($SiO_2$, eluent cyclohexane:EtOAc=100:0 to 50:50) followed by a new purification by column chromatography ($SiO_2$, eluent $CH_2Cl_2$:EtOAc=100:0 to 90:10) gave (2-ethylamino-7-fluoro-6-methoxyquinolin-3-yl)methanol SMA 44090 as a white solid (290 mg, 58% yield).

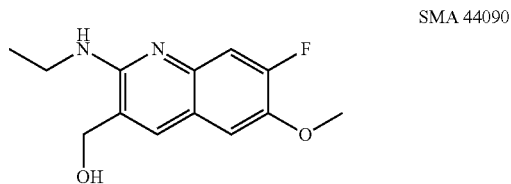 [SMILES: CCNc1nc2cc(F)c(OC)cc2cc1CO]

SMA 44090

MW: 250.27; Yield: 58%; White Solid; Mp (° C.): 154.6.

$^1$H NMR ($CDCl_3$, δ): 1.29 (t, 3H, J=7.2 Hz, $CH_3$), 2.78 (br, 1H, OH), 3.51-3.60 (m, 2H, $CH_2$), 3.93 (s, 3H, $OCH_3$), 4.55 (s, 2H, $CH_2$), 5.61-5.65 (br, m, 1H, NH), 6.83 (d, 1H, J=9.2 Hz, ArH), 7.09 (s, 1H, ArH), 7.30 (d, 1H, J=12.9 Hz, ArH).

$^{13}$C-NMR ($CDCl_3$, δ): 14.8, 35.9, 56.3, 63.8, 108.4, 111.3 (d, J=18.1 Hz), 119.3 (d, J=1.5 Hz), 121.1 (d, J=2.2 Hz), 133.7, 143.3 (d, J=12.1 Hz), 144.3 (d, J=12.8 Hz), 154.7 (d, J=249.8 Hz), 155.5.

MS-ESI m/z (% rel. Int.): 251 $[MH]^+$, 100).

HPLC: Method B (5 min), XBridge™ column (5 mm, C18, 4.5×50 mm, Model #186003113), detection UV 214 nm, RT=3.25 min.

3-(Chloromethyl)-N-ethyl-7-fluoro-6-methoxyquinolin-2-amine hydrochloride SMA 44096

To a solution of (2-ethylamino-7-fluoro-6-methoxyquinolin-3-yl)methanol SMA 44090 (278 mg, 1.11 mmol) in dry $CH_2Cl_2$ (30 mL) at 0° C. under $N_2$ in a 100 mL round-bottomed flask equipped with a magnetic stirrer was added dropwise $SOCl_2$ (1.60 mL, 22.1 mmol) and the mixture was stirred for 3 h at RT then concentrated to dryness at 40° C. under vacuum. The residue was then diluted with $CH_2Cl_2$ (30 mL) and concentrated back to dryness at 40° C. under vacuum (done 3 times) to give 3-(chloromethyl)-N-ethyl-7-fluoro-6-methoxyquinolin-2-amine hydrochloride SMA 44096 as a yellow solid (348 mg, quantitative yield).

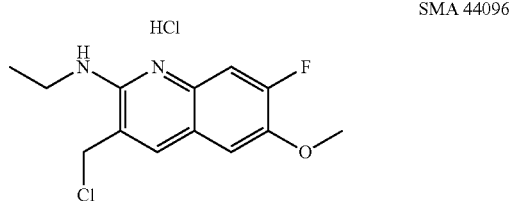 [SMILES: Cl ; CCNc1nc2cc(F)c(OC)cc2cc1CCl]

SMA 44096

MW: 305.22; Yield: quantitative; Yellow Solid; Mp (° C.): 226.6 (dec.).

$^1$H NMR ($CD_3OD$, δ): 1.45 (t, 3H, J=7.2 Hz, $CH_3$), 3.75 (q, 2H, J=7.2 Hz, $CH_3$), 4.01 (s, 3H, $OCH_3$), 4.91 (s, 2H, $CH_2$), 7.58 (d, 1H, J=8.7 Hz, ArH), 7.82 (d, 1H, J=11.6 Hz, ArH), 8.43 (s, 1H, ArH).

$^{13}$C-NMR ($CD_3OD$, δ): 13.7, 39.0, 41.9, 57.2, 105.9 (d, J=24.9 Hz), 112.1 (d, J=3.0 Hz), 119.5 (d, J=2.2 Hz), 123.0 (d, J=3.0 Hz), 132.4 (d, J=11.3 Hz), 143.3, 148.3 (d, J=12.0 Hz), 151.67, 157.2 (d, J=257.3 Hz).

MS-ESI m/z (% rel. Int.): 271 ($[MH]^+$, $^{37}$Cl, 38), 269 ($[MH]^+$, $^{35}$Cl, 100).

HPLC: XBridge™ column(5 mm, C18, 4.5×50 mm, Model #186003113), detection UV 214 nm, RT=2.19 min.

4-((2-(Ethylamino)-7-fluoro-6-methoxyquinolin-3-yl)methyl)-6,7-dimethoxy-1-propylisoquinolin-3-ol dihydrochloride 70

To a stirred solution of 6,7-dimethoxy-1-propylisoquinolin-3-ol RBO 35142 (184 mg, 0.744 mmol) in THF (15 mL) in a 20 mL microwave vial equipped with a magnetic stirrer was added 3-(chloromethyl)-N-ethyl-7-fluoro-6-methoxyquinolin-2-amine hydrochloride SMA 44096 (227 mg, 0.744 mmol) at RT followed by a 2 N aq. LiOH solution (0.75 mL, 1.50 mmol) and the mixture was stirred at 155° C. for 1.5 h under microwave irradiation. The microwave vial was then cooled in an ice bath and the solid was filtered, washed with cold THF (20 mL) and taken up in $CH_2Cl_2$:MeOH=9:1 (50 mL). The organic solution was washed with brine (10 mL), dried over $Na_2SO_4$, filtered and concentrated at 40° C. under vacuum. Purification by column chromatography ($SiO_2$, eluent $CH_2Cl_2$:MeOH=100:0 to 95:5) followed by a second purification by column chromatography ($SiO_2$, eluent EtOAc:MeOH=100:0 to 95:5) gave 83 mg of 4-((2-(ethylamino)-7-fluoro-6-methoxyquinolin-3-yl)methyl)-6,7-dimethoxy-1-propylisoquinolin-3-ol as a brown solid. This free base was dissolved in $CH_2Cl_2$ (5 mL) in a 10 mL round-bottomed flask equipped with a magnetic stirrer before addition of a 0.49 M HCl solution in MeOH (1.0 mL). The reaction mixture was stirred for 5 min at RT then concentrated at 40° C. under vacuum to afford 4-((2-(ethylamino)-7-fluoro-6-methoxyquinolin-3-yl)methyl)-6,7-dimethoxy-1-propylisoquinolin-3-ol dihydrochloride 70 as a yellow solid (96 mg, 23% yield).

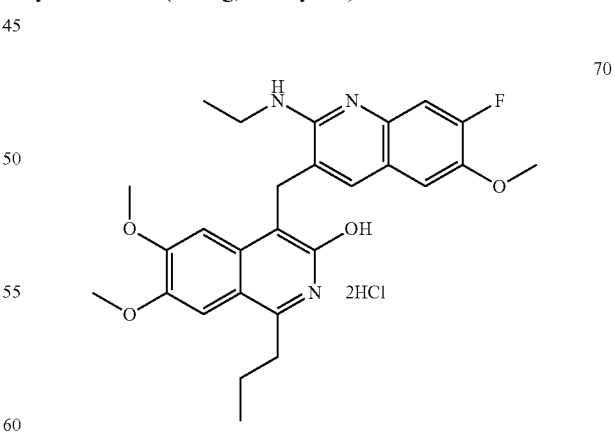

MW: 552.47; Yield: 23%; Yellow Solid; Mp (° C.): 215.8 (dec.).

$R_f$: 0.25 ($CH_2Cl_2$:MeOH=95:5, free base).

$^1$H-NMR ($CD_3OD$, δ): 1.15 (t, 3H, J=7.2 Hz, $CH_3$), 1.54 (t, 3H, J=7.1 Hz, $CH_3$), 1.91-1.98 (m, 2H, $CH_2$), 3.30-3.36 (m, 2H, $CH_2$), 3.78 (q, 2H, J=6.9 Hz, $CH_2$), 3.88 (s, 3H,

OCH₃), 3.99 (s, 3H, OCH₃), 4.02 (s, 3H, OCH₃), 4.37 (s, 2H, CH₂), 7.09 (s, 1H, ArH), 7.40 (d, 1H, J=8.1 Hz, ArH), 7.47 (s, 1H, ArH), 7.75-7.80 (m, 2H, 2×ArH).

¹³C-NMR (CD₃OD, δ): 13.9, 14.2, 24.7, 27.0, 33.6, 39.2, 56.9, 57.0, 57.4, 102.6, 105.6 (d, J=24.2 Hz), 106.0, 109.9, 111.6 (d, J=3.1 Hz), 119.3, 119.7, 123.4, 131.3 (d, J=11.3 Hz), 138.8, 141.6, 148.0 (d, J=12.0 Hz), 152.18, 152.5, 152.9, 155.0, 156.4 (d, J=255.5 Hz), 160.04.

MS-ESI m/z (rel. int.): 480 ([MH]⁺, 100).

HPLC: Method B (10 min), XBridge™ column (5 mm, C18, 4.5×50 mm, Model #186003113), detection UV 254 nm, RT=4.47 min, peak area 99.6%.

Preparation of 4-((2-butyl-6-methoxyquinolin-3-yl)methyl)-6,7-dimethoxy-1-propylisoquinolin-3-ol dihydrochloride 71

4-Iodo-6,7-dimethoxy-1-propylisoquinolin-3-ol CCH 42098-1

A mixture of 6,7-dimethoxy-1-propylisoquinolin-3-ol RBO 35142 (2.00 g, 8.09 mmol) and p-toluenesulfonic acid monohydrate (1.50 g, 7.89 mmol) in dry CH₃CN (20 mL) in a 100 mL round-bottomed flask equipped with a magnetic stirrer was stirred for 10 min at RT before portionwise addition of N-iodosuccinimide (1.82 g, 8.09 mmol) under vigorous stirring. After 2.5 h, the mixture was slowly poured into a cold solution of NaHCO₃ (2.0 g) in 50 mL of water and the solid was filtered, washed with water (50 mL) and dried overnight under vacuum to yield 4-iodo-6,7-dimethoxy-1-propylisoquinolin-3-ol CCH 42098-1 as a brown solid (2.35 g, 78% yield).

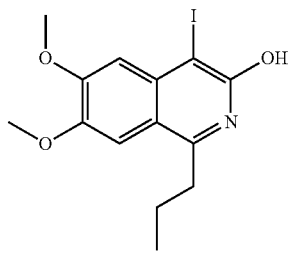

CCH 42098-1

MW: 373.19; Yield: 78%; Brown Solid.

¹H-NMR (CDCl₃, δ): 1.10 (t, 3H, J=7.3 Hz, CH₃), 1.84-1.92 (m, 2H, CH₂), 3.14 (t, 2H, J=7.6 Hz, CH₂), 3.99 (s, 3H, OCH₃), 4.06 (s, 3H, OCH₃), 6.90 (s, 1H, ArH), 7.07 (s, 1H, ArH), OH not seen.

¹³C-NMR (CDCl₃, δ): 14.0, 23.2, 32.7, 56.0, 56.2, 103.0, 108.4, 112.5, 143.1, 147.6, 150.5, 156.6, 159.4, 1×C not observed.

MS-ESI m/z (rel. int.): 374 ([MH]⁺, 100).

HPLC: Method B (10 min), XBridge™ column (5 mm, C18, 4.5×50 mm, Model #186003113), detection UV 254 nm, RT=4.29 min.

3-(tert-Butyldimethylsilyloxy)-4-iodo-6,7-dimethoxy-1-propylisoquinoline CCH 42098-2

To a mixture of 4-iodo-6,7-dimethoxy-1-propylisoquinolin-3-ol CCH 42098-1 (0.60 g, 1.61 mmol) and diisopropylaminomethyl-polystyrene resin (3 mmol/g, 0.80 g, 2.40 mmol) in dry CH₂Cl₂ (16 mL) in a 50 mL round-bottomed flask equipped with a magnetic stirrer was added tert-butylchlorodimethylsilane (267 mg, 1.77 mmol) and the reaction mixture was stirred for 15 min at RT then for 1 h under reflux. After cooling to RT, the reaction mixture was filtered and the filtrate was washed with brine (5 mL), dried over Na₂SO₄, filtered and concentrated at 40° C. under vacuum. Purification by column chromatography (SiO₂, eluent cyclohexane:EtOAc=100:0 to 95:5) gave 3-(tert-butyldimethylsilyloxy)-4-iodo-6,7-dimethoxy-1-propylisoquinoline CCH 42098-2 as an off-white solid (0.65 g, 83% yield).

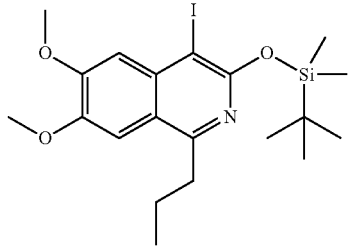

CCH 42098-2

MW: 487.45; Yield: 83%; Off-White Solid; Mp (° C.): 193.1 (dec.).

R_f: 0.3 (cyclohexane:EtOAc=95:5).

¹H-NMR (CDCl₃, δ): 0.38 (s, 6H, 2×CH₃), 1.08 (s, 9H, 3×CH₃), 1.02-1.09 (m, 3H, CH₃), 1.89-1.91 (m, 2H, CH₂), 3.02-3.09 (m, 2H, CH₂), 4.00 (s, 3H, OCH₃), 4.06 (s, 3H, OCH₃), 7.20 (s, 1H, ArH), 7.30 (s, 1H, ArH).

¹³C-NMR (CDCl₃, δ): −4.1 (2×C), 14.2, 18.2, 21.5, 25.9 (3×C), 36.1, 56.0 (2×C), 103.7, 109.7, 119.1, 138.0, 148.1, 153.8, 157.0, 157.7, 1×C not observed.

2-Butyl-3-(1,3-dioxolan-2-yl)-6-methoxyquinoline SMA 44042

To a solution of 2-chloro-3-(1,3-dioxolan-2-yl)-6-methoxyquinoline SMA 44002 (1.41 g, 5.31 mmol) in dry THF (27 mL) at 0° C. under N₂ in a 100 mL round-bottomed flask equipped with a magnetic stirrer was added Fe(acac)₃ (197 mg, 0.547 mmol) followed by dropwise addition of n-butylmagnesium chloride (2.0 M in THF, 12.4 mL, 24.8 mmol). After complete addition, the mixture was stirred for 5 h at 70° C. then cooled to RT and quenched with water (10 mL). THF was then removed at 40° C. under vacuum and the resulting mixture was extracted with CH₂Cl₂ (50 mL). The organic phase was isolated, washed with brine (10 mL), dried over Na₂SO₄, filtered and concentrated at 40° C. under vacuum. Purification by column chromatography (SiO₂, eluent CH₂Cl₂:EtOAc=100:0 to 95:5) gave 2-butyl-3-(1,3-dioxolan-2-yl)-6-methoxyquinoline SMA 44042 as an orange oil (867 mg, 57% yield).

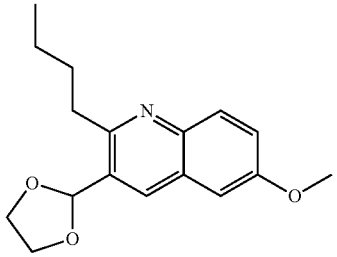

SMA 44042

MW: 287.35; Yield: 57%; Orange Oil.
Rf=0.3 (CH$_2$Cl$_2$:EtOAc=95:5).

$^1$H NMR (CDCl$_3$, δ): 0.94-0.96 (m, 3H, CH$_3$), 1.45-1.52 (m, 2H, CH$_2$), 1.78-1.81 (m, 2H, CH$_2$), 3.00-3.06 (m, 2H, CH$_2$), 3.91 (s, 3H, OCH$_3$), 4.11-4.19 (m, 4H, 2×OCH$_2$), 6.13 (s, 1H, CH), 7.07 (s, 1H, ArH), 7.33-7.36 (m, 1H, ArH), 7.91-7.95 (m, 1H, ArH), 8.21-8.22 (m, 1H, ArH).

$^{13}$C-NMR (CDCl$_3$, δ): 14.0, 23.0, 31.9, 35.3, 55.4, 65.3 (2×C), 101.2, 105.5, 122.3, 127.2, 129.4, 130.0, 132.7, 144.0, 157.3, 158.7.

MS-ESI m/z (% rel. Int.): 288 [MH]$^+$ (100).

HPLC: Method B (5 min), XBridge™ column (5 mm, C18, 4.5×50 mm, Model #186003113), detection UV 214 nm, RT=4.11 min.

2-Butyl-6-methoxyquinoline-3-carbaldehyde SMA 44044

To a solution of 2-butyl-3-(1,3-dioxolan-2-yl)-6-methoxyquinoline SMA 44042 (847 mg, 2.95 mmol) in THF (20 mL) in a 100 mL round-bottomed flask equipped with a magnetic stirrer was added a 12 N aqueous HCl solution (5.0 mL, 60.0 mmol) and the mixture was stirred overnight at RT then for 3 h at 70° C. After cooling to RT, THF was removed at 40° C. under vacuum before addition of a 10 N aqueous NaOH solution until neutral pH. The residue was then taken up in CH$_2$Cl$_2$ (50 mL) and the organic layer was isolated, washed with brine (10 mL), dried over Na$_2$SO$_4$, filtered and concentrated at 40° C. under vacuum. Purification by column chromatography (SiO$_2$, eluent CH$_2$Cl$_2$:EtOAc=100:0 to 98:2) gave 2-butyl-6-methoxyquinoline-3-carbaldehyde SMA 44044 as an orange solid (583 mg, 81% yield).

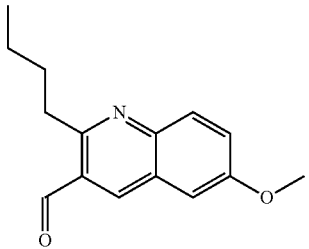

SMA 44044

MW: 243.30; Yield: 81%; Orange Solid; Mp (° C.): 86.5.
Rf: 0.35 (CH$_2$Cl$_2$:EtOAc=98:2).

$^1$H NMR (CDCl$_3$, δ): 0.96-1.01 (m, 3H, CH$_3$), 1.45-1.51 (m, 2H, CH$_2$), 1.72-1.80 (m, 2H, CH$_2$), 3.30-3.34 (m, 2H, CH$_2$), 3.95 (s, 3H, OCH$_3$), 7.16-7.17 (m, 1H, ArH), 7.46 (d, 1H, J=9.3 Hz, ArH), 7.98 (d, 1H, J=9.3 Hz, ArH), 8.51 (s, 1H, ArH), 10.39 (s, 1H, CHO).

$^{13}$C-NMR (CDCl$_3$, δ): 13.9, 22.8, 32.6, 35.7, 55.6, 106.0, 125.3, 127.0, 127.7, 130.3, 140.1, 145.7, 157.9, 160.0, 191.2.

MS-ESI m/z (% rel. Int.): 244 [MH]$^+$ (100).

HPLC: Method B (5 min), XBridge™ column (5 mm, C18, 4.5×50 mm, Model #186003113), detection UV 214 nm, RT=2.49 min.

4-((2-Butyl-6-methoxyquinolin-3-yl)methyl)-6,7-dimethoxy-1-propylisoquinolin-3-ol dihydrochloride 71

To a stirred solution of 3-(tert-butyldimethylsilyloxy)-4-iodo-6,7-dimethoxy-1-propylisoquinoline CCH 42098-2 (200 mg, 0.41 mmol) in freshly distilled dry THF (4 mL) at −105° C. in a 25 mL round-bottomed flask equipped with a magnetic stirrer was added dropwise n-BuLi (1.6 M in hexanes, 0.40 mL, 0.64 mmol) and the reaction mixture was stirred for 15 min at −105° C. before quick addition of a solution of 2-butyl-6-methoxyquinoline-3-carbaldehyde SMA 44044 (100 mg, 0.41 mmol) in dry THF (1 mL). The reaction mixture was stirred for 1 h at −105° C. then quenched by addition of a 5% aqueous NH$_4$Cl solution (5 mL), allowing the medium to warm up to RT. THF was then removed at 40° C. under vacuum and the residue was extracted with CH$_2$Cl$_2$ (50 mL). The organic solution was washed with brine (10 mL), dried over Na$_2$SO$_4$, filtered, and concentrated at 40° C. under vacuum. Purification by column chromatography (SiO$_2$, eluent cyclohexane:EtOAc=100:0 to 66:34) gave 120 mg of a yellow solid. This solid (120 mg, 245 μmol) was dissolved in CH$_2$Cl$_2$ (3 mL) in a 10 mL round-bottomed flask equipped with a magnetic stirrer before addition of TFA (0.6 mL) and triethylsilane (60 μl, 372 μmol). The mixture was stirred overnight at RT, concentrated to dryness at 40° C. under vacuum. The residue was neutralised with a saturated aqueous NaHCO$_3$ solution (5 mL) before to be extracted with CH$_2$Cl$_2$ (30 mL). The organic phase was isolated, washed with brine (5 mL), dried over Na$_2$SO$_4$, filtered and concentrated at 40° C. under vacuum. Purification by column chromatography (SiO$_2$, eluent EtOAc:MeOH=100:0 to 95:5) gave 4-((2-butyl-6-methoxyquinolin-3-yl)methyl)-6,7-dimethoxy-1-propylisoquinolin-3-ol as a yellow solid. This free base was dissolved in CH$_2$Cl$_2$ (2 mL) in a 10 mL round-bottomed flask equipped with a magnetic stirrer before addition of a 0.49 M HCl solution in MeOH (0.5 mL). The reaction mixture was stirred for 5 min at RT then concentrated at 40° C. under vacuum to afford 4-((2-butyl-6-methoxyquinolin-3-yl)methyl)-6,7-dimethoxy-1-propylisoquinolin-3-ol dihydrochloride 71 as a pale brown solid (54 mg, 24% yield).

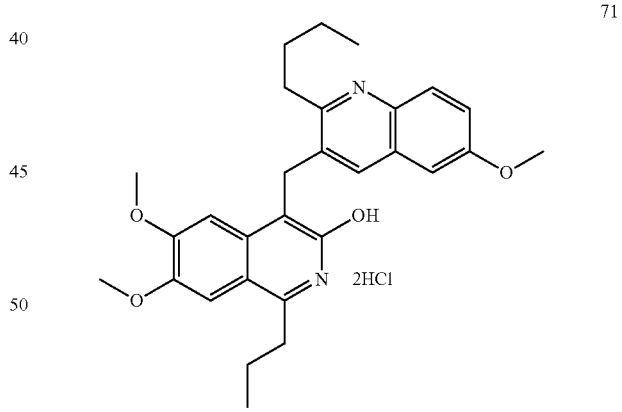

71

MW: 547.51; Yield: 24%; Pale Brown Solid; Mp (° C.): 227.4 (dec.)

R$_f$: 0.2 (EtOAc:MeOH=95:5, free base).

$^1$H-NMR (CD$_3$OD, δ): 1.08 (t, 3H, J=7.3 Hz, CH$_3$), 1.19 (t, 3H, J=7.3 Hz, CH$_3$), 1.69 (sextuplet, 2H, J=7.3 Hz, CH$_2$), 1.95-2.05 (m, 4H, 2×CH$_2$), 3.32-3.33 (m, 2H, CH$_2$), 3.46-3.58 (m, 2H, CH$_2$), 3.88 (s, 3H, OCH$_3$), 3.92 (s, 3H, OCH$_3$), 4.06 (s, 3H, OCH$_3$), 4.83 (s, 2H, CH$_2$), 7.13 (s, 1H, ArH), 7.47 (d, 1H, J=1.8 Hz, ArH), 7.62-7.67 (m, 2H, 2×ArH), 7.75 (d, 1H, J=9.6 Hz, ArH), 8.26 (s, 1H, ArH).

$^{13}$C-NMR (CD$_3$OD, δ): 14.1, 14.3, 24.0, 24.7, 27.9, 32.2, 33.0, 33.6, 56.8, 57.0, 57.4, 103.0, 106.2, 107.2, 111.6, 119.8, 122.0, 128.2, 130.9, 133.6, 133.8, 141.3, 143.5, 151.9, 152.3, 155.3, 158.6, 159.9, 161.4.

MS-ESI m/z (rel. int.): 475 ([MH]+, 100).

HPLC: Method B (10 min), XBridge™ column (5 mm, C18, 4.5×50 mm, Model #186003113), detection UV 254 nm, RT=4.68 min, peak area 99.5%.

Preparation of 6,7-dimethoxy-4-((6-methoxy-2-(trifluoromethyl)quinolin-3-yl)methyl)-1-propylisoquinolin-3-ol hydrochloride 72

6-Methoxy-2-(trifluoromethyl)quinoline-3-carbaldehyde SLA 47010

To a solution of 2-chloro-6-methoxyquinoline-3-carbaldehyde (1.50 g, 6.77 mmol) in N,N-dimethylacetamide (13.6 mL) in a 50 mL round-bottomed flask equipped with a magnetic stirrer were added dibromodifluoromethane (1.30 mL, 14.23 mmol) and Cu (2.58 g, 40.60 mmol) and the mixture was stirred for 1 h at 100° C. then overnight at 150° C. After cooling to RT, the mixture was stirred through celite and the celite plug was washed with EtOAc (50 mL). The organic solution was washed with brine (10 mL), dried over MgSO4, filtered and concentrated at 40° C. under vacuum. Purification by column chromatography (SiO2, eluent cyclohexane:EtOAc=100:0 to 75:25) gave 6-methoxy-2-(trifluoromethyl)quinoline-3-carbaldehyde SLA 47010 as a brown solid (536 mg, 31% yield).

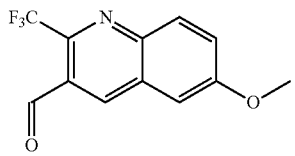

SLA 47010

MW: 255.19; Yield: 31%; Brown Solid; Mp (° C.): 114.9

Rf: 0.2 (cyclohexane:EtOAc=75:25).

1H NMR (CDCl3, δ): 3.99 (s, 3H, OCH3), 7.25 (d, 1H, J=2.7 Hz, ArH), 7.59 (dd, J=9.3 & 2.7 Hz, ArH), 8.16 (d, 1H, J=9.3 Hz, ArH), 8.82 (s, 1H, ArH), 10.50-10.52 (m, 1H, CHO).

13C-NMR (CDCl3, δ): 53.8, 106.0, 121.8 (q, J=273.3 Hz), 126.4, 126.7, 129.5, 131.5, 137.8, 143.8 (q, J=273.3 Hz), 144.0, 160.16, 187.9-188.0 (m).

MS-ESI m/z (% rel. Int.): 256 ([MH]+, 100).

HPLC: Method B (10 min), XBridge™ column(5 mm, C18, 4.5×50 mm, Model #186003113), detection UV 214 nm, RT=5.76 min.

6,7-Dimethoxy-4-((6-methoxy-2-(trifluoromethyl)quinolin-3-yl)methyl)-1-propylisoquinolin-3-ol hydrochloride 72

To a stirred solution of 3-(tert-butyldimethylsilyloxy)-4-iodo-6,7-dimethoxy-1-propylisoquinoline CCH 42098-2 (200 mg, 0.41 mmol) in freshly distilled dry THF (4 mL) at −105° C. in a 25 mL round-bottomed flask equipped with a magnetic stirrer was added dropwise n-BuLi (1.6 M in hexanes, 0.30 mL, 0.48 mmol) and the reaction mixture was stirred for 15 min at −105° C. before quick addition of a solution of 6-methoxy-2-(trifluoromethyl)quinoline-3-carbaldehyde SLA 47010 (105 mg, 0.41 mmol) in dry THF (1 mL). The reaction mixture was stirred for 1 h at −105° C. then quenched by addition of a 5% aqueous NH4Cl solution (5 mL), allowing the medium to warm up to RT. THF was then removed at 40° C. under vacuum and the residue was extracted with CH2Cl2 (50 mL). The organic solution was washed with brine (10 mL), dried over Na2SO4, filtered, and concentrated at 40° C. under vacuum. Purification by column chromatography (SiO2, eluent cyclohexane: EtOAc=100:0 to 66:34) gave 187 mg of a yellow solid. This solid (120 mg, around 200 μmol) was then dissolved in CH2Cl2 (3 mL) in a 10 mL round-bottomed flask equipped with a magnetic stirrer before addition of TFA (0.6 mL) and triethylsilane (60 μL, 372 μmol). The mixture was stirred overnight at RT, then concentrated to dryness at 40° C. under vacuum. The residue was neutralised with saturated aqueous NaHCO3 solution (5 mL) before extraction with CH2Cl2 (30 mL). The organic phase was isolated, washed with brine (5 mL), dried over Na2SO4, filtered and concentrated at 40° C. under vacuum. Purification by column chromatography (SiO2, eluent EtOAc:MeOH=100:0 to 95:5) gave 6,7-dimethoxy-4-((6-methoxy-2-(trifluoromethyl)quinolin-3-yl) methyl)-1-propylisoquinolin-3-ol. This free base was dissolved in CH2Cl2 (2 mL) in a 10 mL round-bottomed flask equipped with a magnetic stirrer before addition of a 0.49 M HCl solution in MeOH (0.5 mL). The reaction mixture was stirred for 5 min at RT then concentrated at 40° C. under vacuum to afford a pale brown solid. This solid was purified by column chromatography (RP18, eluent H2O: CH3CN=100:0 to 40:60), then concentrated to dryness at 40° C. under vacuum. The residue was dissolved in 0.5 M HCl in MeOH (2 mL) and concentrated back to dryness. Finally, recrystallization from MeOH/Et2O gave 6,7-dimethoxy-4-((6-methoxy-2-(trifluoromethyl)quinolin-3-yl) methyl)-1-propylisoquinolin-3-ol hydrochloride 72 as a pale brown solid (9 mg, 4% yield).

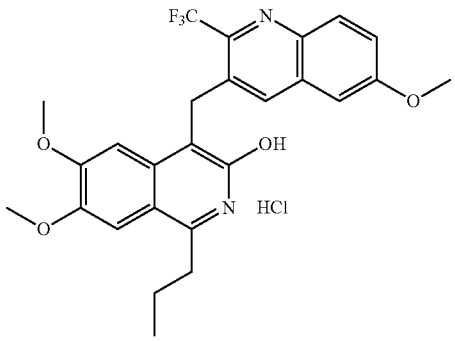

72

MW: 522.94; Yield: 4%; Pale Brown Solid; Mp (° C.): 258.7 (dec.).

Rf: 0.2 (EtOAc:MeOH=95:5, free base).

1H-NMR (CD3OD:CDCl3=1:1, δ): 1.17 (t, 3H, J=7.2 Hz, CH3), 1.96-2.04 (m, 2H, CH2), 3.43 (t, 2H, J=7.4 Hz, CH2), 3.78 (s, 3H, OCH3), 3.86 (s, 3H, OCH3), 4.04 (s, 3H, OCH3), 4.70 (s, 2H, CH2), 6.84 (s, 1H, ArH), 7.02 (s, 1H, ArH), 7.40-7.44 (m, 2H, 2×ArH), 7.60 (s, 1H, ArH), 8.05 (d, 1H, J=9.2 Hz, ArH).

13C-NMR (CD3OD:CDCl3=1:1, δ): 13.8, 22.6, 25.8, 33.0, 55.5, 55.7, 55.8, 100.4, 104.7, 105.1, 108.2, 122.5 (q, J=251.1 Hz), 123.3, 130.2, 130.5, 135.2, 137.7, 140.2, 142.0, 142.4, 147.8, 153.1, 155.1, 155.4, 159.1, 1×C not seen.

MS-ESI m/z (rel. int.): 475 ([MH]+, 100).

HPLC: Method B (10 min), XBridge™ column (5 mm, C18, 4.5×50 mm, Model #186003113), detection UV 254 nm, RT=5.60 min, peak area 95.1%.

Preparation of N-(2-(3-((3-hydroxy-6,7-dimethoxy-1-methylisoquinolin-4-yl)methyl)-6-methoxyquinolin-2-ylamino)ethyl)acetamide dihydrochloride 73

To a stirred solution of N-(2-(3-(chloromethyl)-6-methoxyquinolin-2-ylamino)ethyl)acetamide hydrochloride SLA41176 (115 mg, 0.33 mmol) in THF (10 mL) in a 20 mL microwave vial equipped with a magnetic stirrer was added 6,7-dimethoxy-1-methylisoquinolin-3-ol CCH18060 (73 mg, 0.33 mmol) followed by a 2 N aq. LiOH solution (0.33 mL, 0.66 mmol) and the mixture was stirred at 160° C. for 1.5 h under microwave irradiation. After cooling to RT, the mixture was diluted with $CH_2Cl_2$:MeOH=9:1 (150 mL), washed with brine (20 mL), dried over $Na_2SO_4$, filtered and concentrated at 40° C. under vacuum. Purification by column chromatography ($SiO_2$, eluent $CH_2Cl_2$:MeOH=100:0 to 90:10) provided N-(2-(3-((3-hydroxy-6,7-dimethoxy-1-methylisoquinolin-4-yl)methyl)-6-methoxyquinolin-2-ylamino)ethyl)acetamide. This free base was dissolved in $CH_2Cl_2$ (2 mL) in a 10 mL round-bottomed flask equipped with a magnetic stirrer before addition of 0.49 M HCl in MeOH (2 mL) and the solution was stirred for 5 min at RT then concentrated at 40° C. under vacuum to afforded N-(2-(3-((3-hydroxy-6,7-dimethoxy-1-methylisoquinolin-4-yl)methyl)-6-methoxyquinolin-2-ylamino)ethyl)acetamide dihydrochloride 73 as a yellow solid (19.5 mg, 10% yield).

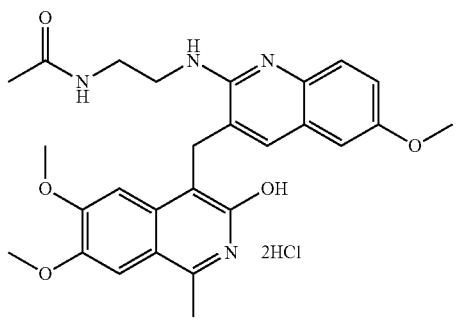

73

MW: 563.47; Yield: 10%; Yellow Solid; Mp (° C.): 160.4.

$^1$H NMR ($CD_3OD$, δ): 2.09 (s, 3H, $CH_3$), 3.08 (s, 3H, $CH_3$), 3.59-3.64 (m, 2H, $CH_2$), 3.80 (s, 3H, $OCH_3$), 3.83-3.88 (m, 2H, $CH_2$), 3.97 (s, 3H, $OCH_3$), 4.05 (s, 3H, $OCH_3$), 4.33 (s, 2H, $CH_2$), 7.14 (s, 1H, ArH), 7.15 (d, 1H, J=2.7 Hz, ArH), 7.39 (dd, 1H, J=2.7 & 9.2 Hz, ArH), 7.53 (s, 1H, ArH), 7.61 (s, 1H, ArH), 8.00 (d, 1H, J=9.2 Hz, ArH).

$^{13}$C-NMR ($CD_3OD$, δ): 17.4, 22.4, 27.0, 39.0, 43.5, 56.3, 56.9, 57.4, 102.4, 106.2, 109.4, 109.4, 119.9, 123.6, 123.9, 124.4, 131.3, 139.4, 141.2, 152.0, 152.9, 158.9, 159.9, 175.8, 3×C not observed.

MS-ESI m/z (% rel. Int.): 491 ([MH]$^+$, 100).

HPLC: Method B (10 min), XBridge™ column (5 mm, C18, 4.5×50 mm, Model #186003113), detection UV 254 nm, RT=4.63 min, peak area 98.6%.

Preparation of 6,7-dimethoxy-1-propyl-4-(quinolin-3-ylmethyl)isoquinolin-3-ol dihydrochloride 74

To a stirred solution of 3-(tert-butyldimethylsilyloxy)-4-iodo-6,7-dimethoxy-1-propylisoquinoline CCH 42098-2 (497 mg, 1.02 mmol) in freshly distilled dry THF (4 mL) at −105° C. in a 25 mL round-bottomed flask equipped with a magnetic stirrer was added dropwise n-BuLi (1.6 M in hexanes, 0.79 mL, 1.26 mmol) and the reaction mixture was stirred for 10 min at −105° C. then another portion of n-BuLi (1.6 M in hexanes, 0.79 mL, 1.26 mmol) was added dropwise and stirring was continued for 5 min at −105° C. before quick addition of a solution of 3-quinolinecarboxaldehyde (165 mg, 1.05 mmol) in dry THF (1 mL). The reaction mixture was stirred for 1 h at −105° C. then quenched by addition of a 5% aqueous $NH_4Cl$ solution (5 mL), allowing the medium to warm up to RT. THF was then removed at 40° C. under vacuum and the residue was extracted with $CH_2Cl_2$ (50 mL). The organic solution was washed with brine (10 mL), dried over $Na_2SO_4$, filtered, and concentrated at 40° C. under vacuum. Purification by column chromatography ($SiO_2$, eluent cyclohexane:EtOAc=100:0 to 75:25) gave 45 mg of a yellow solid. This solid (45 mg, 111 μmol) was dissolved in $CH_2Cl_2$ (2 mL) in a 10 mL round-bottomed flask equipped with a magnetic stirrer before addition of TFA (0.29 mL) and triethylsilane (21 μL, 130 μmol). The mixture was stirred for 2 h at RT, then another portion of triethylsilane (160 μL, 0.99 mmol) was added and stirring was continued for 1 h at RT, then for 1.5 h under reflux. After concentration to dryness at 40° C. under vacuum, the residue was neutralised with a saturated aqueous $NaHCO_3$ solution (5 mL) before extraction with $CH_2Cl_2$ (30 mL). The organic phase was isolated, washed with brine (5 mL), dried over $Na_2SO_4$, filtered and concentrated at 40° C. under vacuum. Purification by column chromatography ($SiO_2$, eluent EtOAc:MeOH=100:0 to 95:5) followed by a new purification by column chromatography ($SiO_2$, eluent $CH_2Cl_2$:MeOH=100:0 to 95:5) gave 6,7-dimethoxy-1-propyl-4-(quinolin-3-ylmethyl)isoquinolin-3-ol. This free base was dissolved in $CH_2Cl_2$ (2 mL) in a 10 mL round-bottomed flask equipped with a magnetic stirrer before addition of a 0.4 M HCl solution in MeOH (0.5 mL). The reaction mixture was stirred for 5 min at RT then concentrated at 40° C. under vacuum to give 6,7-dimethoxy-1-propyl-4-(quinolin-3-ylmethyl)isoquinolin-3-ol hydrochloride 74 as a pale yellow solid (10 mg, 21% yield).

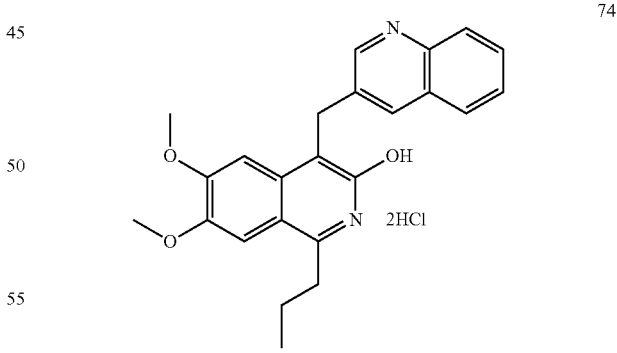

74

MW: 461.38; Yield: 21%; Pale Yellow Solid; Mp (° C.): 239.8 (dec.).

$^1$H-NMR ($CD_3OD$:$CDCl_3$=1:1, δ): 1.14 (t, 3H, J=7.3 Hz, $CH_3$), 1.92-2.00 (m, 2H, $CH_2$), 3.38 (t, 2H, J=7.7 Hz, $CH_2$), 4.03 (s, 3H, $OCH_3$), 4.04 (s, 3H, $OCH_3$), 4.90 (s, 2H, $CH_2$), 7.27 (s, 1H, ArH), 7.43 (s, 1H, ArH), 7.92-7.97 (m, 1H, ArH), 8.10-8.15 (m, 1H, ArH), 8.24 (d, 1H, J=8.2 Hz, ArH), 8.32 (d, 1H, J=8.5 Hz, ArH), 8.95 (s, 1H, ArH), 9.27 (s, 1H, ArH).

$^{13}$C-NMR (CD$_3$OD:CDCl$_3$=1:1, δ): 14.6, 24.7, 28.9, 33.8, 57.3, 58.0, 102.7, 105.9, 119.1, 121.6, 130.3, 130.4, 131.8, 135.3, 136.2, 138.0, 141.0, 146.2, 146.7, 152.0, 154.3, 159.9, 2×C not observed.

MS-ESI m/z (rel. int.): 389 ([MH]$^+$, 100).

HPLC: Method B (10 min), XBridge™ column (5 mm, C18, 4.5×50 mm, Model #186003113), detection UV 254 nm, RT=3.85 min, peak area 96.8%.

Preparation of (2-(ethylamino)-6-methoxyquinolin-3-yl)(3-hydroxy-6,7-dimethoxy-1-methylisoquinolin-4-yl)methanone dihydrochloride 75

4-Bromo-3,6,7-trimethoxy-1-methylisoquinoline SMA 44070

To a solution of 6,7-dimethoxy-1-methylisoquinolin-3-ol CCH 18060 (603 mg, 2.75 mmol) in acetic acid (27 mL) in a 100 mL round-bottomed flask equipped with a magnetic stirrer was added dropwise bromine (0.15 mL, 2.92 mmol) and the mixture was stirred for 2 h at RT. The solid was then filtered and washed with acetic acid (20 mL), EtOAc (30 mL), Et$_2$O (4×7 mL), CH$_2$Cl$_2$ (55 mL), saturated NaHCO$_3$ (15 mL) and finally with H$_2$O (10 mL). After drying under vacuum, a yellow solid was obtained (718 mg). This solid (500 mg, 1.68 mmol) was dissolved in acetone (20 mL) in a 100 mL round-bottomed flask equipped with a magnetic stirrer before addition of Cs$_2$CO$_3$ (550 mg, 1.69 mmol). The mixture was stirred for 20 min at RT, MeI (1.0 mL, 16.06 mmol) was added and the mixture was stirred for 4.5 h at RT. After addition of SiO$_2$ (3.0 g), the residue was filtered and washed several times with a mixture of cyclohexane:EtOAc=90:10 (until all the desired product was eluted). The filtrate was then concentrated to dryness at 40° C. under vacuum to give 4-bromo-3,6,7-trimethoxy-1-methylisoquinoline SMA 44070 as a yellow solid (139 mg, 23% yield).

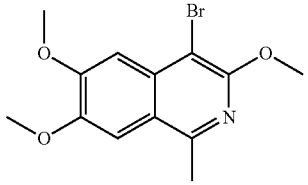

SMA 44070

MW: 312.16; Yield: 23%; Yellow Solid; Mp (° C.): 202.3.

$^1$H NMR (CDCl$_3$, δ): 2.79 (s, 3H, CH$_3$), 4.01 (s, 3H, OCH$_3$), 4.06 (s, 3H, OCH$_3$), 4.09 (s, 3H, OCH$_3$), 7.13 (s, 1H, ArH), 7.33 (s, 1H, ArH).

$^{13}$C-NMR (CDCl$_3$, δ): 21.9, 54.4, 56.0, 56.1, 98.0, 103.8, 104.0, 120.1, 134.8, 148.2, 152.7, 153.8, 155.0.

MS-ESI m/z (% rel. Int.): 314 ([MH]$^+$, $^{81}$Br, 50), 312 ([MH]$^+$, $^{79}$Br, 50).

HPLC: Method B (5 min), XBridge™ column (5 mm, C18, 4.5×50 mm, Model #186003113), detection UV 214 nm, RT=3.54 min.

(2-(Ethylamino)-6-methoxyquinolin-3-yl)(3-hydroxy-6,7-dimethoxy-1-methylisoquinolin-4-yl) methanone 75

To a stirred solution of 4-bromo-3,6,7-trimethoxy-1-methylisoquinoline SMA 44070 (242 mg, 775 µmol) in freshly distilled dry THF (10 mL) at −105° C. in a 25 mL round-bottomed flask equipped with a magnetic stirrer was added dropwise n-BuLi (1.6 M in hexanes, 0.56 mL, 0.90 mmol) and the reaction mixture was stirred for 15 min at −105° C. then another portion of n-BuLi (1.6 M in hexanes, 0.60 mL, 0.96 mmol) was added dropwise and stirring was continued for 10 min at −105° C. before quick addition of 2-chloro-6-methoxyquinoline-3-carbaldehyde (172 mg, 776 µmol). The reaction mixture was stirred for 1 h at −105° C. then quenched by addition of 5% aqueous NH$_4$Cl solution (5 mL), allowing the medium to warm up to RT. THF was removed at 40° C. under vacuum and the residue was extracted with CH$_2$Cl$_2$ (50 mL). The organic solution was washed with brine (10 mL), dried over Na$_2$SO$_4$, filtered, and concentrated at 40° C. under vacuum. Purification by column chromatography (SiO$_2$, eluent cyclohexane:EtOAc=100:0 to 50:50) gave 51 mg of a yellow solid (14%).

This solid (51 mg, 112 µmol) was then dissolved in dry CH$_2$Cl$_2$ (5 mL) at 0° C. in a 25 mL round-bottomed flask equipped with a magnetic stirrer before addition of Dess Martin periodinane (57 mg, 134 µmol). After addition, the reaction mixture was stirred for 2 h, allowing the medium to reach RT. The mixture was then diluted with CH$_2$Cl$_2$ (20 mL), filtered through celite and the organic solution was washed with a saturated aq. NaHCO$_3$ solution (10 mL), brine (10 mL), dried over Na$_2$SO$_4$, filtered and concentrated at 40° C. under vacuum. Purification by column chromatography (SiO$_2$, eluent cyclohexane:EtOAc=100:0 to 75:25) gave 32 mg of a pale yellow solid (63%).

This solid (32 mg, 71 µmol) was then dissolved in THF (3 mL) in a 10 mL microwave vial equipped with a magnetic stirrer before adding ethylamine (2.0 M in THF, 1.0 mL, 2.0 mmol) and the mixture was stirred for 30 min at 160° C. under microwave irradiation. After cooling to RT, the volatiles were removed under vacuum at 40° C. and the residue was then taken up in 6N aq. HCl solution and the solution was stirred for 1 h at 110° C., then cooled to RT and neutralised with a saturated aq. NaHCO$_3$ solution before extraction with CH$_2$Cl$_2$:MeOH=95:5 (30 mL). The organic phase was washed with brine (10 mL), dried over MgSO$_4$, filtered, and concentrated at 40° C. under vacuum. Purification by column chromatography (SiO$_2$, eluent CH$_2$Cl$_2$:MeOH=100:0 to 95:5) gave (2-(ethylamino)-6-methoxyquinolin-3-yl)(3-hydroxy-6,7-dimethoxy-1-methylisoquinolin-4-yl)methanone. This free base was dissolved in CH$_2$Cl$_2$ (2 mL) in a 10 mL round-bottomed flask equipped with a magnetic stirrer before addition of a 0.4 M HCl solution in MeOH (0.5 mL). The reaction mixture was stirred for 5 min at RT then concentrated at 40° C. under vacuum to give (2-(ethylamino)-6-methoxyquinolin-3-yl)(3-hydroxy-6,7-dimethoxy-1-methylisoquinolin-4-yl)methanone dihydrochloride 75 as a pale orange solid (10 mg, 2% overall yield).

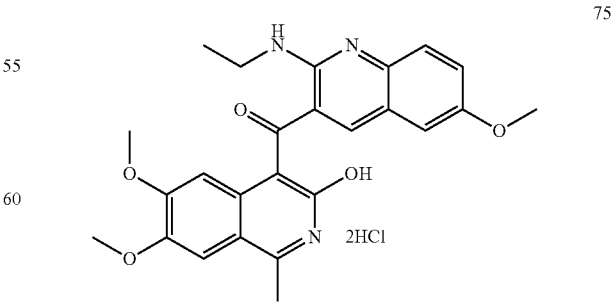

75

MW: 520.40; Yield: 2%; Pale Orange Solid; Mp (° C.): 240.9 (dec.).

¹H-NMR (CD₃OD, δ): 1.51 (t, 3H, J=7.2 Hz, CH₃), 2.96 (s, 3H, CH₃), 3.80 (q, 2H, J=7.2 Hz, CH₂), 3.86 (s, 3H, OCH₃), 3.93 (s, 3H, OCH₃), 4.00 (s, 3H, OCH₃), 7.22 (s, 1H, ArH), 7.34 (s, 1H, ArH), 7.43 (d, 1H, J=2.5 Hz, ArH), 7.55 (dd, 1H, J=2.5 & 9.2 Hz, ArH), 7.99 (d, 1H, J=9.2 Hz, ArH), 8.80 (s, 1H, ArH).
¹³C-NMR (CD₃OD, δ): 13.9, 17.8, 38.8, 56.5, 56.7, 56.9, 102.3, 105.9, 111.4, 112.3, 116.4, 119.9, 122.3, 123.1, 127.5, 133.9, 141.0, 149.5, 150.2, 152.1, 155.0, 158.9, 159.8, 195.8, 1×C not observed.
MS-ESI m/z (rel. int.): 448 ([MH]⁺, 100).
HPLC: Method B (10 min), XBridge™ column (5 mm, C18, 4.5×50 mm, Model #186003113), detection UV 254 nm, RT=3.86 min, peak area 98.1%.

Preparation of 6,7-dimethoxy-4-((6-methoxy-2-(2-methoxyethylamino)quinolin-3-yl)methyl)-1-propylisoquinolin-3-ol dihydrochloride 76

To a solution of 6,7-dimethoxy-1-propylisoquinolin-3-ol RBO 35134 (312 mg, 1.3 mmol) in THF (13 mL) in a 20 mL microwave vial equipped with a magnetic stirrer were added 3-(chloromethyl)-6-methoxy-N-(2-methoxyethyl)quinolin-2-amine hydrochloride SLA 47064B (400 mg, 1.3 mmol) and a 2 N aq. LiOH solution (1.26 mL, 2.52 mmol) and the mixture was stirred at 160° C. for 1.5 h under microwave irradiation. After cooling to room temperature, THF was removed at 40° C. under vacuum and the residue was then taken up in CH₂Cl₂ (50 mL), washed with brine (10 mL), dried over Na₂SO₄, filtered, and concentrated under vacuum. Purification by column chromatography (SiO₂, eluent CH₃CN:H₂O:TFA=100:0:0.05 to 50:50:0.05) gave 6,7-dimethoxy-4-((6-methoxy-2-(2-methoxyethylamino) quinolin-3-yl)methyl)-1-propylisoquinolin-3-ol. This free base was dissolved in MeOH (2 mL) in a 10 mL round-bottomed flask equipped with a magnetic stirrer before addition of a 0.149 M HCl solution in MeOH (2.0 mL). The reaction mixture was stirred for 5 min at room temperature and concentrated at 40° C. under vacuum to afford 6,7-dimethoxy-4-((6-methoxy-2-(2-methoxyethylamino)quinolin-3-yl)methyl)-1-propylisoquinolin-3-ol dihydrochloride 76 as a brown solid (39.5 mg, 5% yield).

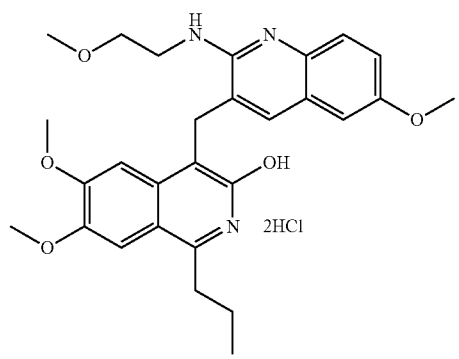

76

MW: 564.50; Yield: 5%; Brown Solid; Mp (° C.): 204.1.
¹H-NMR (CD₃OD, δ): 1.17 (t, 3H, J=7.2 Hz, CH₃), 1.95-2.03 (m, 2H, CH₂), 3.41-3.46 (m, 2H, CH₂), 3.50 (s, 3H, OCH₃), 3.80 (s, 3H, OCH₃), 3.86-3.90 (m, 2H, CH₂), 3.96 (s, 3H, OCH₃), 4.02-4.04 (m, 2H, CH₂), 4.06 (s, 3H, OCH₃), 4.36 (s, 2H, CH₂), 7.03 (s, 1H, ArH), 7.20 (s, 1H, ArH), 7.32 (s, 1H, ArH), 7.36 (d, 1H, J=9.3 Hz, ArH), 7.75 (d, 1H, J=9.3 Hz, ArH), 8.34 (s, 1H, ArH).
¹³C-NMR (CD₃OD, δ): 14.2, 24.7, 27.4, 33.6, 44.2, 56.4, 56.9, 57.3, 59.5, 72.3, 102.3, 105.8, 109.5, 119.7, 123.6, 123.8, 124.6, 130.9, 140.0, 141.6, 151.7, 153.2, 154.5, 158.9, 159.6, 3×C not observed.
MS-ESI m/z (rel.int.): 492 ([MH]⁺, 100).
HPLC: Method B (10 min), XBridge™ column (5 mm, C18, 4.5×50 mm, Model #186003113), detection UV 254 nm, RT=4.47 min, peak area 99.9%.

Preparation of 1-ethyl-6,7-dimethoxy-4-((6-methoxy-2-(2-methoxyethylamino)quinolin-3-yl)methylisoquinolin-3-ol dihydrochloride 77

6-Methoxy-2-(2-methoxyethylamino)quinoline-3-carbaldehyde SLA 47060

To a stirred solution of 2-chloro-6-methoxyquinoline-3-carbaldehyde (1.5 g, 6.8 mmol) in THF (8 mL) in a 20 mL microwave vial equipped with a magnetic stirrer was added 2-methoxyethylamine (11.82 mL, 135.0 mmol) and the mixture was stirred at 160° C. for 1.5 h under microwave irradiation. After cooling to room temperature, THF was removed at 40° C. under vacuum and the residue was taken up in THF (8 mL) before addition of a 6 N aq. HCl solution until pH=2. After stirring for 3 h at RT, the mixture was basified to pH=9 with a 2 N aq. NaOH solution and further stirred for 1 h at RT. THF was then removed at 40° C. under vacuum and the solution was extracted with CH₂Cl₂ (200 mL), washed with brine (20 mL), dried over Na₂SO₄, filtered, and concentrated under vacuum. Purification by column chromatography (SiO₂, eluent cyclohexane:EtOAc=100:0 to 50:50) gave, after evaporation and drying, 6-methoxy-2-(2-methoxyethylamino)quinoline-3-carbaldehyde SLA 47060 as a yellow solid (1.30 g, 73% yield).

SLA 47060

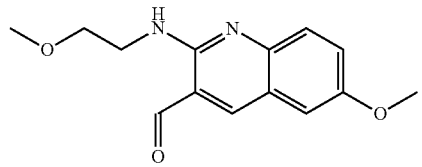

MW: 260.29; Yield: 73%; Yellow Solid; Mp (° C.): 88.0.
¹H NMR (CD₃OD, δ): 3.43 (s, 3H, OCH₃), 3.64-3.69 (m, 2H, CH₂), 3.75-3.79 (m, 2H, CH₂), 3.89 (s, 3H, OCH₃), 7.16 (d, 1H, J=3.0 Hz, ArH), 7.33 (dd, 1H, J=3.0 & 9.3 Hz, ArH), 7.55 (d, 1H, J=9.3 Hz, ArH), 8.40 (s, 1H, ArH), 9.97 (s, 1H, CHO).
¹³C-NMR (CD₃OD, δ): 41.3, 56.1, 59.0, 72.2, 108.2, 119.0, 123.8, 126.8, 128.2, 147.7, 149.1, 155.0, 156.6, 194.9.
MS-ESI m/z (% rel. Int.): 261 ([MH]⁺, 100).
HPLC: Method B (10 min), XBridge™ column (5 mm, C18, 4.5×50 mm, Model #186003113), detection UV 254 nm, RT=3.43 min.

(6-Methoxy-2 (2-methoxyethylamino)quinolin-3-yl)methanol SLA 47064A

To a stirred solution of 6-methoxy-2-(2-methoxyethylamino)quinoline-3-carbaldehyde SLA 47060 (0.895 g, 3.4 mmol) in THF (34 mL) in a 100 mL round-bottomed flask equipped with a magnetic stirrer was added NaBH$_4$ (0.13 g, 3.4 mmol) and the mixture was stirred overnight at RT then cooled in an ice bath before quenching by addition of a 1 N aq. HCl solution (10 mL). After stirring for 15 min at that temperature, the mixture was basified to pH=9 with a 2 N aq. NaOH solution. THF was then removed at 40° C. under vacuum and the solution was extracted with CH$_2$Cl$_2$ (200 mL), washed with brine (20 mL), dried over Na$_2$SO$_4$, filtered, and concentrated under vacuum to give (6-methoxy-2-(2-methoxyethylamino)quinolin-3-yl)methanol SLA 47064A as a yellow oil (0.90 g, 100% yield).

SLA 47064A

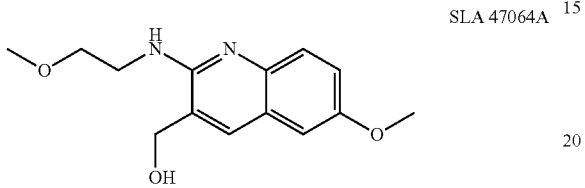

MW: 262.30; Yield: 100%; Yellow Oil.

$^1$H NMR (CDCl$_3$, δ): 2.05 (broad s, 1H, NH or OH), 3.41 (s, 3H, OCH$_3$), 3.65-3.69 (m, 2H, CH$_2$), 3.76-3.82 (m, 2H, CH$_2$), 3.87 (s, 3H, OCH$_3$), 4.69 (s, 2H, CH$_2$), 5.82 (broad s, 1H, NH or OH), 6.90 (d, 1H, J=2.7 Hz, ArH), 7.20 (dd, 1H, J=2.7 & 9.1 Hz, ArH), 7.46 (s, 1H, ArH), 7.63 (d, 1H, J=9.1 Hz, ArH).

$^{13}$C-NMR (CDCl$_3$, δ): 40.9, 55.5, 58.8, 63.8, 71.6, 106.6, 120.6, 122.3, 123.3, 127.5, 134.4, 143.0, 154.7, 154.8.

MS-ESI m/z (% rel. Int.): 263 ([MH]$^+$, 100).

HPLC: Method B (10 min), XBridge™ column(5 mm, C18, 4.5×50 mm, Model #186003113), detection UV 214 nm, RT=3.33 min.

3-(Chloromethyl)-6-methoxy-N-(2-methoxyethyl)quinolin-2-amine hydrochloride SLA 47064B To a stirred solution of (6-methoxy-2-(2-methoxyethylamino)quinolin-3-yl)methanol SLA 47064A (0.90 g, 3.43 mmol) in dry CH$_2$Cl$_2$ (30 mL) in a 100 mL round-bottomed flask equipped with a magnetic stirrer was added dropwise SOCl$_2$ (4.98 mL, 68.6 mmol). The mixture was stirred for 1.5 h at RT then concentrated to dryness at 40° C. under vacuum. The residue was then taken up in CH$_2$Cl$_2$ (20 mL) before concentration back to dryness at 40° C. under vacuum (done 3 times) to give 3-(chloromethyl)-6-methoxy-N-(2-methoxyethyl)quinolin-2-amine hydrochloride SLA 47064 as a yellow solid (1.13 g, 100%).

SLA 47064B

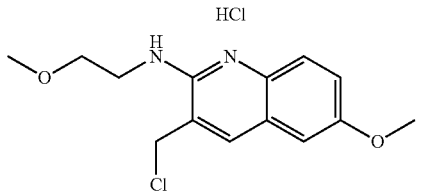

MW: 317.21; Yield: 100%; Yellow Solid; Mp (° C.): 170.6.

$^1$H NMR (CD$_3$OD, δ): 3.42 (s, 3H, OCH$_3$), 3.66-3.76 (m, 4H, 2×CH$_2$), 3.87 (s, 3H, OCH$_3$), 4.65 (s, 2H, CH$_2$), 7.09 (d, 1H, J=3.0 Hz, ArH), 7.17 (dd, 1H, J=3.0 & 9.0 Hz, ArH), 7.60 (d, 1H, J=9.0 Hz, ArH), 7.77 (s, 1H, ArH).

$^{13}$C-NMR (CD$_3$OD, δ): 41.9, 56.0, 59.0, 63.1, 72.4, 107.9, 121.4, 125.0, 125.1, 127.4, 135.4, 143.8, 156.3, 156.4.

MS-ESI m/z (% rel. Int.): 283 ([MH]$^+$, $^{37}$Cl, 38), 281 ([MH]$^+$, $^{35}$Cl, 100).

HPLC: Method B (10 min), XBridge™ column (5 mm, C18, 4.5×50 mm, Model #186003113), detection UV 214 nm, RT=3.38 min.

1-Ethyl-6,7-dimethoxy-4-((6-methoxy-2-(2-methoxyethylamino)quinolin-3-yl)methyl)isoquinolin-3-ol dihydrochloride 77

To a solution of 1-ethyl-6,7-dimethoxyisoquinolin-3-ol SLA 47022 (215 mg, 0.92 mmol) in THF (13 mL) in a 20 mL microwave vial equipped with a magnetic stirrer was added a 3-(chloromethyl)-6-methoxy-N-(2-methoxyethyl)quinolin-2-amine hydrochloride SLA 47064B (292 mg, 0.92 mmol) and a 2 N aq. LiOH solution (0.92 mL, 1.84 mmol) and the mixture was stirred at 160° C. for 1.5 h under microwave irradiation. After cooling to room temperature, THF was then removed at 40° C. under vacuum and the solution was extracted with CH$_2$Cl$_2$ (50 mL), washed with brine (10 mL), dried over Na$_2$SO$_4$, filtered, and concentrated under vacuum. Purification by column chromatography (RP 18, eluent CH$_3$CN:H$_2$O:TFA=100:0:0.05 to 50:50:0.05) followed by a new purification by column chromatography (RP 18, eluent CH$_3$CN:H$_2$O:TFA=100:0:0.05 to 66:34:0.05) gave 6,7-dimethoxy-4-((6-methoxy-2-(2-methoxyethylamino)quinolin-3-yl)methyl)-1-propylisoquinolin-3-ol (mg). This free base was dissolved in MeOH (2 mL) in a 10 mL round-bottomed flask equipped with a magnetic stirrer before addition of a 0.149 M HCl solution in MeOH (2.0 mL). The reaction mixture was stirred for 5 min at RT and concentrated at 40° C. under vacuum to afford 6,7-dimethoxy-4-((6-methoxy-2-(2-methoxyethylamino)quinolin-3-yl)methyl)-1-propylisoquinolin-3-ol dihydrochloride 77 as a brown solid (61 mg, 12% yield).

77

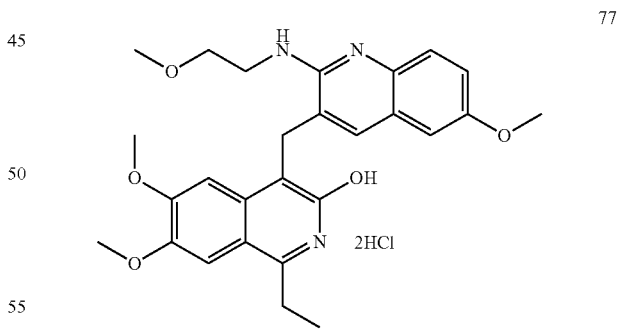

MW: 550.47; Yield: 12%; Brown Solid; Mp (° C.): 212.3.

$^1$H-NMR (CD$_3$OD, δ): 1.53 (t, 3H, J=7.5 Hz, CH$_3$), 3.39-3.45 (m, 2H, CH$_2$), 3.46 (s, 3H, OCH$_3$), 3.82 (s, 3H, OCH$_3$), 3.83-3.88 (m, 2H, CH$_2$), 3.92 (s, 3H, OCH$_3$), 3.93-3.98 (m, 2H, CH$_2$), 4.03 (s, 3H, OCH$_3$), 4.40 (s, 2H, CH$_2$), 7.10 (s, 1H, ArH), 7.20-7.22 (m, 1H, ArH), 7.37 (dd, 1H, J=2.5 & 9.2 Hz, ArH), 7.51 (s, 1H, ArH), 7.76 (s, 1H, ArH), 7.85 (d, 1H, J=9.2 Hz, ArH).

$^{13}$C-NMR (CD$_3$OD, δ): 14.6, 25.4, 27.4, 44.3, 56.4, 56.9, 57.3, 59.5, 72.0, 102.3, 105.7, 109.5, 117.9, 119.7, 123.6, 123.8, 124.8, 130.9, 140.0, 141.7, 151.6, 153.2, 154.4, 155.5, 158.9, 159.6, 1×C not observed.

MS-ESI m/z (rel.int.): 478 ([MH]$^+$, 100).

HPLC: Method B (10 min), XBridge™ column (5 mm, C18, 4.5×50 mm, Model #186003113), detection UV 254 nm, RT=4.16 min, peak area 99.0%.

Preparation of 1-ethyl-6,7-dimethoxy-4-(quinolin-3-ylmethyl)isoquinolin-3-ol dihydrochloride 78

To a solution of 1-ethyl-6,7-dimethoxyisoquinolin-3-ol SLA 47022 (436 mg, 1.9 mmol) in THF (13 mL) in a 20 mL microwave vial equipped with a magnetic stirrer was added 3-(chloromethyl)quinoline hydrochloride SLA 47064B (400 mg, 1.9 mmol) and a 2 N aq. LiOH solution (1.90 mL, 3.80 mmol) and the mixture was stirred at 160° C. for 1.5 h under microwave irradiation. After cooling to RT, THF was removed at 40° C. under vacuum and the residue was taken up in CH$_2$Cl$_2$ (50 mL), washed with brine (10 mL), dried over Na$_2$SO$_4$, filtered, and concentrated under vacuum. Purification by column chromatography (SiO$_2$, eluent CH$_2$Cl$_2$:MeOH=100:0 to 94:6) provided 1-ethyl-6,7-dimethoxy-4-(quinolin-3-ylmethyl)isoquinolin-3-ol. This free base was dissolved in MeOH (2 mL) in a 10 mL round-bottomed flask equipped with a magnetic stirrer before addition of 0.149 M HCl solution in MeOH (2.0 mL). The reaction mixture was stirred for 5 min at RT and concentrated at 40° C. under vacuum to afford 1-ethyl-6,7-dimethoxy-4-(quinolin-3-ylmethyl)isoquinolin-3-ol dihydrochloride 78 as a yellow solid (87.5 mg, 10% yield).

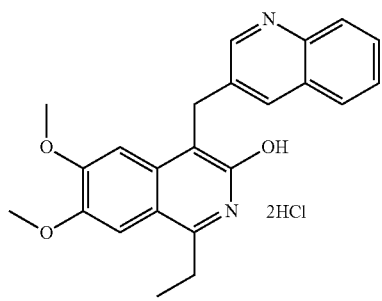

78

MW: 447.35; Yield: 10%; Yellow Solid; Mp (° C.): 268.2.

$^1$H-NMR (CD$_3$OD, δ): 1.52 (t, 3H, J=7.5 Hz, CH$_3$), 3.31-3.34 (m, 2H, CH$_2$), 3.40-3.48 (m, 2H, CH$_2$), 3.97 (s, 3H, OCH$_3$), 4.04 (s, 3H, OCH$_3$), 4.88 (s, 2H, CH$_2$), 7.23 (s, 1H, ArH), 7.54 (s, 1H, ArH), 7.95 (dd, 1H, J=7.5 & 7.5 Hz, ArH), 8.16 (dd, 1H, J=8.2 & 8.2 Hz, ArH), 8.23-8.27 (m, 2H, 2×ArH), 8.93 (s, 1H, ArH), 9.28 (s, 1H, ArH).

$^{13}$C-NMR (CD$_3$OD, δ): 14.6, 25.5, 28.5, 56.9, 57.3, 102.8, 105.7, 118.1, 121.4, 130.2, 130.5, 131.5, 133.2, 135.9, 138.1, 140.9, 146.4, 146.6, 152.0, 159.9, (3×C not observed).

MS-ESI m/z (rel.int.): 375 ([MH]$^+$, 100).

HPLC: Method B (10 min), XBridge™ column (5 mm, C18, 4.5×50 mm, Model #186003113), detection UV 254 nm, RT=3.53 min, peak area 99.9%.

Preparation of 1-isopropyl-6,7-dimethoxy-4-(quinolin-3-ylmethyl)isoquinolin-3-ol dihydrochloride 79

3-(Chloromethyl)quinoline hydrochloride SLA 47074B

To a stirred solution of quinoline-3-carbaldehyde (1.00 g, 6.36 mmol) in THF (60 mL) in a 100 mL round-bottomed flask equipped with a magnetic stirrer was added NaBH$_4$ (0.24 g, 6.36 mmol) and the mixture was stirred overnight at RT then cooled in an ice bath before quenching by addition of a 1 N aq. HCl solution. After stirring for 15 min at RT, the mixture was basified to pH=9 with a 2 N aq. NaOH solution. THF was removed at 40° C. under vacuum and the solution was extracted with CH$_2$Cl$_2$ (200 mL), washed with brine (20 mL), dried over Na$_2$SO$_4$, filtered, and concentrated under vacuum to give quinolin-3-ylmethanol SLA 47074A as a yellow oil (1.06 g, >100%). This oil (1.056 g, 6.6 mmol) was dissolved in dry CH$_2$Cl$_2$ (40 mL) in a 100 mL round-bottomed flask equipped with a magnetic stirrer before dropwise addition of SOCl$_2$ (9.62 mL, 133.3 mmol). The mixture was stirred for 2 h at RT and concentrated to dryness at 40° C. under vacuum. The residue was then taken up in CH$_2$Cl$_2$ (20 mL) before concentration back to dryness at 40° C. under vacuum (done 3 times) to give 3-(chloromethyl)quinoline hydrochloride SLA 47074B as a yellow solid (1.20 g, 85% yield).

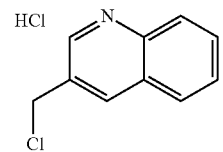

SLA 47074B

MW: 214.09; Yield: 85%; Yellow Solid; Mp (° C.): 155.2.

$^1$H NMR (CD$_3$OD, δ): 5.08 (s, 2H, CH$_2$), 7.99-8.05 (m, 1H, ArH), 8.18-8.24 (m, 1H, ArH), 8.28 (d, 1H, J=8.3 Hz, ArH), 8.37 (d, 1H, J=8.3 Hz, ArH), 9.30 (d, 1H, J=1.5 Hz, ArH), 9.39 (d, 1H, J=1.5 Hz, ArH).

MS-ESI m/z (% rel. Int.): 180 ([MH]$^+$, $^{37}$Cl, 32), 178 ([MH]$^+$, $^{35}$Cl, 100).

HPLC: Method B (10 min), XBridge™ column (5 mm, C18, 4.5×50 mm, Model #186003113), detection UV 214 nm, RT=3.38 min.

1-Isopropyl-6,7-dimethoxy-4-(quinolin-3-ylmethyl)isoquinolin-3-ol dihydrochloride 79

To a solution of 1-isopropyl-6,7-dimethoxyisoquinolin-3-ol SIL 32164 (462 mg, 1.87 mmol) in THF (13 mL) in a 20 mL microwave vial equipped with a magnetic stirrer was added a 3-(chloromethyl)quinoline hydrochloride SLA 47064B (400 mg, 1.87 mmol) and a 2 N aq. LiOH solution (1.87 mL, 3.74 mmol) and the mixture was stirred at 160° C. for 1.5 h under microwave irradiation. After cooling to RT, THF was removed at 40° C. under vacuum and the residue was taken up in CH$_2$Cl$_2$ (50 mL), washed with brine (10 mL), dried over Na$_2$SO$_4$, filtered, and concentrated under vacuum. Purification by column chromatography (SiO$_2$, eluent CH$_2$Cl$_2$:MeOH=100:0 to 94:6) provided 1-isopropyl-6,7-dimethoxy-4-(quinolin-3-ylmethyl)isoquinolin-3-ol. This free base was dissolved in MeOH (2 mL) in a 10 mL round-bottomed flask equipped with a magnetic stirrer before addition of 0.149 M HCl solution in MeOH (2.0 mL). The reaction mixture was stirred for 5 min at RT and concentrated at 40° C. under vacuum to afford 1-isopropyl- 6,7-dimethoxy-4-(quinolin-3-ylmethyl)isoquinolin-3-ol dihydrochloride 79 as a yellow solid (76 mg, 9% yield).

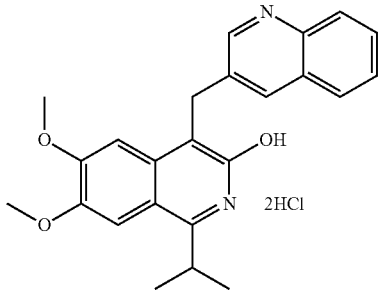

MW: 461.38; Yield: 9%; Yellow Solid; Mp (° C.): 200.2.

$^1$H-NMR (CD$_3$OD, δ): 1.63 (d, 6H, J=6.9 Hz, 2×CH$_3$), 4.00 (s, 3H, OCH$_3$), 4.05 (s, 3H, OCH$_3$), 4.24-4.29 (m, 1H, CH), 4.92-4.99 (m, 2H, CH$_2$), 7.32 (s, 1H, ArH), 7.68 (s, 1H, ArH), 7.95 (dd, 1H, J=7.5 & 7.0 Hz, ArH), 8.15 (dd, 1H, J=7.5 & 8.1 Hz, ArH), 8.28 (dd, 2H, J=7.0 & 8.1 Hz, 2×ArH), 9.00 (s, 1H, ArH), 9.30 (s, 1H, ArH).

$^{13}$C-NMR (CD$_3$OD, δ): 21.4 (2×C), 28.6, 30.8, 57.0, 57.6, 102.9, 105.6, 105.8, 111.9, 118.6, 121.3, 130.3, 130.5, 131.6, 135.1, 136.0, 137.9, 141.4, 146.5, 146.7, 152.3, 158.9, 160.1.

MS-ESI m/z (rel.int.): 389 ([MH]$^+$, 100).

HPLC: Method B (10 min), XBridge™ column (5 mm, C18, 4.5×50 mm, Model #186003113), detection UV 254 nm, RT=3.70 min, peak area 99.9%.

Preparation of 6,7-dimethoxy-4-((2-methylquinolin-6-yl)methyl)-1-propylisoquinolin-3-ol dihydrochloride 80

To a solution of 6,7-dimethoxy-1-propylisoquinolin-3-ol RBO 35134 (434 mg, 1.75 mmol) in THF (13 mL) in a 20 mL microwave vial equipped with a magnetic stirrer was added a 6-(chloromethyl)-2-methylquinolinehydrochloride SLA 47080B (400 mg, 1.75 mmol) and a 2 N aq. LiOH solution (1.75 mL, 3.50 mmol) and the mixture was stirred at 160° C. for 1.5 h under microwave irradiation. After cooling to RT, THF was removed at 40° C. under vacuum and the residue was taken up in CH$_2$Cl$_2$ (50 mL), washed with brine (10 mL), dried over Na$_2$SO$_4$, filtered, and concentrated under vacuum. Purification by column chromatography (SiO$_2$, eluent EtOAc:MeOH=100:0 to 95:5) followed by a new purification by column chromatography (SiO$_2$, eluent CH$_2$Cl$_2$:MeOH=100:0 to 95:5) provided 6,7-dimethoxy-4-((2-methylquinolin-6-yl)methyl)-1-propylisoquinolin-3-ol. This free base was dissolved in MeOH (2 mL) in a 10 mL round-bottomed flask equipped with a magnetic stirrer before addition of a 0.49 M HCl solution in MeOH (2.0 mL). The reaction mixture was stirred for 5 min at RT and concentrated at 40° C. under vacuum to afford 6,7-dimethoxy-4-((2-methylquinolin-6-yl)methyl)-1-propylisoquinolin-3-ol dihydrochloride 80 as a yellow solid (28 mg, 3% yield).

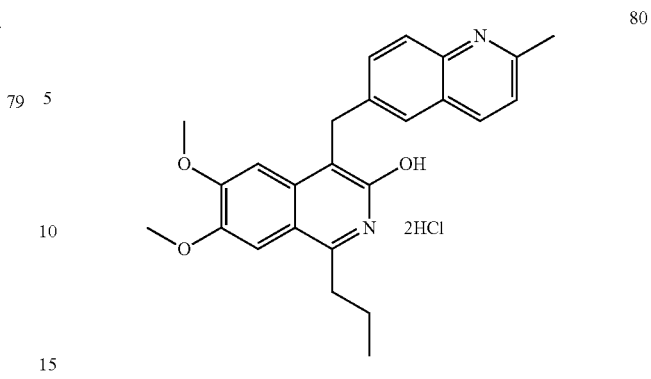

MW: 475.41; Yield: 3%; Yellow Solid; Mp (° C.): 201.0.

$^1$H-NMR (CD$_3$OD, δ): 1.14 (t, 3H, J=7.3 Hz, CH$_3$), 1.92-2.00 (m, 2H, CH$_2$), 3.01 (s, 3H, CH$_3$), 3.39 (t, 2H, J=7.3 Hz, CH$_2$), 3.89 (s, 3H, OCH$_3$), 4.02 (s, 3H, OCH$_3$), 4.80 (s, 2H, CH$_2$), 7.18 (s, 1H, ArH), 7.52 (s, 1H, ArH), 7.90 (d, 1H, J=8.8 Hz, ArH), 8.07 (s, 1H, ArH), 8.12 (d, 1H, J=8.8 Hz, ArH), 8.20 (d, 1H, J=8.7 Hz, ArH), 8.92 (d, 1H, J=8.7 Hz, ArH).

$^{13}$C-NMR (CD$_3$OD, δ): 14.2, 20.8, 24.6, 31.3, 33.5, 56.9, 57.2, 103.3, 105.9, 113.9, 119.4, 121.4, 125.1, 128.5, 128.9, 136.9, 138.0, 141.1, 142.3, 147.3, 152.0, 152.2, 154.5, 158.9, 159.5.

MS-ESI m/z (rel.int.): 403 ([MH]$^+$, 82), 202 (100).

HPLC: Method B (10 min), XBridge™ column (5 mm, C18, 4.5×50 mm, Model #186003113), detection UV 254 nm, RT=3.78 min, peak area 97.2%.

Preparation of 1-ethyl-6,7-dimethoxy-4-((2-methylquinolin-6-yl)methyl)isoquinolin-3-ol dihydrochloride 81

(2-Methylquinolin-6-yl)methanol SLA 47080A

To a stirred solution of 2-methylquinoline-6-carbaldehyde (1.00 g, 5.8 mmol) in THF (60 mL) in a 100 mL round-bottomed flask equipped with a magnetic stirrer was added NaBH$_4$ (0.221 g, 5.8 mmol) and the mixture was stirred overnight at RT then cooled in an ice bath before quenching by addition of a 1 N aq. HCl solution (10 mL). After stirring for 15 min at RT, the mixture was basified to pH=9 with a 2 N aq. NaOH solution. THF was then removed at 40° C. under vacuum and the solution was extracted with CH$_2$Cl$_2$ (200 mL), washed with brine (20 mL), dried over Na$_2$SO$_4$, filtered and concentrated under vacuum to give (2-methylquinolin-6-yl)methanol SLA 47080A as a yellow oil (1.056 g, quant.).

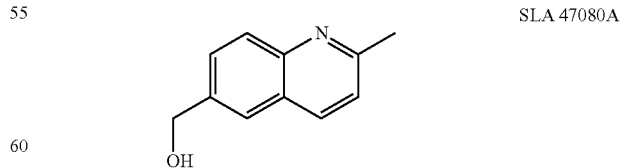

MW: 173.21; Yield: 100%; Yellow Oil.

$^1$H NMR (CDCl$_3$, δ): 2.60 (broad s, 1H, OH), 2.70 (s, 3H, CH$_3$), 4.87 (s, 2H, CH$_2$), 7.27 (d, 1H, J=8.5 Hz, ArH), 7.63 (dd, 1H, J=2.1 & 8.7 Hz, ArH), 7.72-7.74 (m, 1H, ArH), 7.96-8.02 (m, 2H, 2×ArH).

¹³C-NMR (CDCl₃, δ): 25.2, 64.9, 122.2, 124.8, 126.3, 128.7, 128.8, 136.1, 138.4, 147.4, 158.9.

MS-ESI m/z (% rel. Int.): 174 ([MH]⁺, 100).

HPLC: Method B (10 min), XBridge™ column (5 mm, C18, 4.5×50 mm, Model #186003113), detection UV 214 nm, RT=2.39 min.

6-(Chloromethyl)-2-methylquinoline hydrochloride SLA 47080B

To a stirred solution of (2-methylquinolin-6-yl)methanol SLA 47080A (0.973 g, 5.62 mmol) in dry CH₂Cl₂ (40 mL) in a 100 mL round-bottomed flask equipped with a magnetic stirrer was added dropwise SOCl₂ (8.15 mL, 112 mmol). The mixture was stirred for 2 h at RT then concentrated to dryness at 40° C. under vacuum. The residue was then taken up in CH₂Cl₂ (20 mL) before concentration back to dryness at 40° C. under vacuum (done 3 times) to give 6-(chloromethyl)-2-methylquinoline hydrochloride SLA 47080B as a yellow solid (1.30 g, quant).

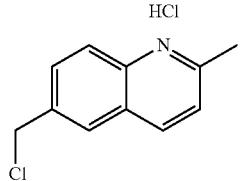

SLA 47080B

MW: 228.12; Yield: 100%; Yellow Solid; Mp (° C.): 134.0.

MS-ESI m/z (% rel. Int.): 194 ([MH]⁺, ³⁷Cl, 34), 192 ([MH]⁺, ³⁵Cl, 100).

HPLC: Method B (10 min), XBridge™ column (5 mm, C18, 4.5×50 mm, Model #186003113), detection UV 214 nm, RT=3.30 min.

1-Ethyl-6,7-dimethoxy-4-((2-methylquinolin-6-yl)methyl)isoquinolin-3-ol dihydrochloride 81

To a solution of 1-ethyl-6,7-dimethoxyisoquinolin-3-ol SLA 47022 (409 mg, 1.7 mmol) in THF (13 mL) in a 20 mL microwave vial equipped with a magnetic stirrer was added a 6-(chloromethyl)-2-methylquinolinehydrochloride SLA 47080B (400 mg, 1.7 mmol) and a 2 N aq. LiOH solution (1.75 mL, 3.5 mmol) and the mixture was stirred at 160° C. for 1.5 h under microwave irradiation. After cooling to RT, THF was removed at 40° C. under vacuum and the residue was taken up in CH₂Cl₂ (50 mL), washed with brine (10 mL), dried over Na₂SO₄, filtered, and concentrated under vacuum. Purification by column chromatography (SiO₂, eluent EtOAc:MeOH=100:0 to 93:7) followed by a new purification by column chromatography (SiO₂, eluent CH₂Cl₂:MeOH=100:0 to 93:7) provided 1-ethyl-6,7-dimethoxy-4-((2-methylquinolin-6-yl)methyl)isoquinolin-3-ol. This free base was dissolved in MeOH (2 mL) in a 10 mL round-bottomed flask equipped with a magnetic stirrer before addition of a 0.149 M HCl solution in MeOH (2.0 mL). The reaction mixture was stirred for 5 min at RT and concentrated at 40° C. under vacuum to afford 1-ethyl-6,7-dimethoxy-4-((2-methylquinolin-6-yl)methyl)isoquinolin-3-ol dihydrochloride 81 as a yellow solid (66 mg, 8% yield).

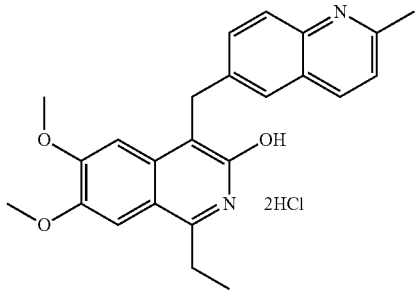

81

MW: 461.38; Yield: 8%; Yellow Solid; Mp (° C.): 198.1.

¹H-NMR (CD₃OD, δ): 1.53 (t, 3H, J=7.6 Hz, CH₃), 3.01 (s, 3H, CH₃), 3.46 (q, 2H, J=7.6 Hz, CH₂), 3.88 (s, 3H, OCH₃), 4.03 (s, 3H, OCH₃), 4.81 (s, 2H, CH₂), 7.19 (s, 1H, ArH), 7.55 (s, 1H, ArH), 7.90 (d, 1H, J=8.4 Hz, ArH), 8.05 (s, 1H, ArH), 8.13 (s, 1H, J=8.4 Hz, ArH), 8.19 (d, 1H, J=8.7 Hz, ArH), 8.92 (d, 1H, J=8.7 Hz, ArH).

¹³C-NMR (CD₃OD, δ): 14.6, 20.8, 25.4, 31.2, 56.9, 57.2, 103.4, 105.8, 113.6, 119.2, 121.4, 125.1, 128.5, 128.9, 136.9, 138.0, 141.2, 142.2, 147.3, 151.9, 152.2, 155.9, 159.0, 159.6.

MS-ESI m/z (rel.int.): 389 ([MH]⁺, 56), 195 (100).

HPLC: Method B (10 min), XBridge™ column (5 mm, C18, 4.5×50 mm, Model #186003113), detection UV 254 nm, RT=3.43 min, peak area 97.3%.

1-Ethyl-4-((2-(ethylamino)-7-fluoro-6-methoxyquinolin-3-yl)methyl)-6,7-dimethoxyisoquinolin-3-ol dihydrochloride 82

To a stirred solution of 1-ethyl-6,7-dimethoxyisoquinolin-3-ol SLA 28136 (114 mg, 0.49 mmol) in THF (10 mL) in a 20 mL microwave vial equipped with a magnetic stirrer was added 3-(chloromethyl)-N-ethyl-7-fluoro-6-methoxyquinolin-2-amine hydrochloride SMA 44096 (149 mg, 0.49 mmol) at RT followed by a 2 N aq. LiOH solution (0.49 mL, 0.98 mmol) and the mixture was stirred at 155° C. for 1.5 h under microwave irradiation. After cooling to RT, THF was removed at 40° C. under vacuum and the residue was taken up in CH₂Cl₂ (50 mL). The organic solution was washed with brine (10 mL), dried over Na₂SO₄, filtered, and concentrated at 40° C. under vacuum. Purification by column chromatography (SiO₂, eluent EtOAc:MeOH=100:0 to 95:5) gave 16 mg of 1-ethyl-4-((2-(ethylamino)-7-fluoro-6-methoxyquinolin-3-yl)methyl)-6,7-dimethoxyisoquinolin-3-ol as a brown solid. This free base was dissolved in CH₂Cl₂ (2 mL) in a 10 mL round-bottomed flask equipped with a magnetic stirrer before addition of a 0.49 M HCl solution in MeOH (0.5 mL). The reaction mixture was stirred for 5 min at RT then concentrated at 40° C. under vacuum to afford 1-ethyl-4-((2-(ethylamino)-7-fluoro-6-methoxyquinolin-3-yl)methyl)-6,7-dimethoxyisoquinolin-3-ol dihydrochloride 82 as a yellow solid (19 mg, 7% yield).

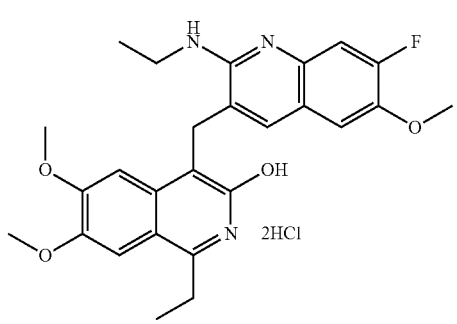

MW: 538.44; Yield: 7%; Yellow Solid; Mp (° C.): 178.1 (dec.)

R$_f$: 0.2 (CH$_2$Cl$_2$:MeOH=95:5, free base).

$^1$H-NMR (CD$_3$OD, δ): 1.51-1.56 (m, 6H, 2×CH$_3$), 3.33-3.40 (m, 2H, CH$_2$), 3.76 (q, 2H, J=6.8 Hz, CH$_2$), 3.89 (s, 3H, OCH$_3$), 3.99 (s, 3H, OCH$_3$), 4.02 (s, 3H, OCH$_3$), 4.36 (s, 2H, CH$_2$), 7.08 (s, 1H, ArH), 7.40 (d, 1H, J=7.2 Hz, ArH), 7.47 (s, 1H, ArH), 7.75 (d, 1H, J=11.6 Hz, ArH), 7.73-7.84 (m, 1H, ArH).

$^{13}$C-NMR (CD$_3$OD, δ): 13.9, 14.7, 25.5, 27.1, 39.3, 57.0, 57.1, 57.5, 102.7, 105.5, 105.8, 110.1, 111.7, 118.7, 119.7, 123.6, 131.3 (d, J=11.4 Hz), 139.2, 141.7, 148.0 (d, J=12.0 Hz), 152.0, 152.9, 156.0, 156.4 (d, J=255.3 Hz), 159.9, 1×C not seen.

MS-ESI m/z (rel. int.): 466 ([MH]$^+$, 100).

HPLC: Method B (10 min), XBridge™ column (5 mm, C18, 4.5×50 mm, Model #186003113), detection UV 254 nm, RT=4.26 min, peak area 96.1%.

Preparation of N-(2-(6-(cyclopropylmethoxy)-3-((3-hydroxy-6,7-dimethoxy-1-propylisoquinolin-4-yl)methyl)quinolin-2-ylamino)ethyl)acetamide dihydrochloride 83

To a solution of 6,7-dimethoxy-1-propylisoquinolin-3-ol RBO 35134 (151 mg, 0.6 mmol) in THF (13 mL) in a 20 mL microwave vial equipped with a magnetic stirrer was added N-(2-(3-(chloromethyl)-6-(cyclopropylmethoxy)quinolin-2-ylamino)ethyl)-acetamide hydrochloride SLA 47096B (235 mg, 0.6 mmol) followed by a 2 N aq. LiOH solution (0.612 mL, 1.2 mmol) and the mixture was stirred at 160° C. for 1.5 h under microwave irradiation. After cooling to RT, THF was removed at 40° C. under vacuum and the residue was taken up in CH$_2$Cl$_2$ (50 mL). The organic solution was washed with brine (10 mL), dried over Na$_2$SO$_4$, filtered, and concentrated under vacuum. Purification by column chromatography (SiO$_2$, eluent CH$_2$Cl$_2$:MeOH=100:0 to 94:6) provided N-(2-(6-(cyclopropylmethoxy)-3-((3-hydroxy-6,7-dimethoxy-1-propylisoquinolin-4-yl)methyl)quinolin-2-ylamino)ethyl)acetamide. The free base was dissolved in MeOH (2 mL) in a 10 mL round-bottomed flask equipped with a magnetic stirrer before addition of a 0.149 M HCl solution in MeOH (2.0 mL). The reaction mixture was stirred for 5 min at RT and concentrated at 40° C. under vacuum to afford N-(2-(6-(cyclopropylmethoxy)-3-((3-hydroxy-6,7-dimethoxy-1-propylisoquinolin-4-yl)methyl)quinolin-2-ylamino)ethyl)acetamide dihydrochloride 83 as a brown solid (41 mg, 11% yield).

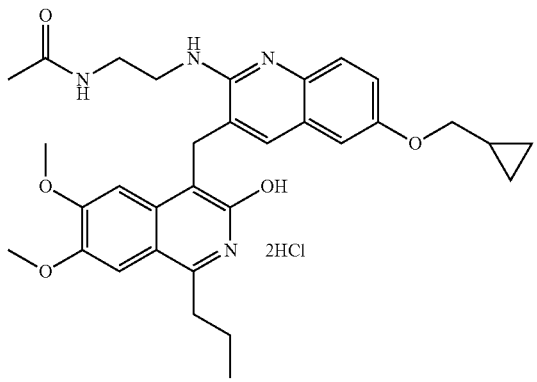

MW: 631.59; Yield: 11%; Brown Solid; Mp (° C.): 210.6.

$^1$H-NMR (CD$_3$OD, δ): 0.29-0.34 (m, 2H, CH$_2$), 0.56-0.63 (m, 2H, CH$_2$), 1.18 (t, 3H, J=6.7 Hz, CH$_3$), 1.28-1.35 (m, 1H, CH), 1.96-2.03 (m, 2H, CH$_2$), 2.09 (s, 3H, CH$_3$), 3.41-3.46 (m, 2H, CH$_2$), 3.60-3.66 (m, 2H, CH$_2$), 3.81 (t, 2H, J=6.7 Hz, CH$_2$), 3.86-3.91 (m, 2H, CH$_2$), 3.96 (s, 3H, OCH$_3$), 4.02 (s, 3H, OCH$_3$), 4.26 (s, 2H, CH$_2$), 7.11-7.15 (m, 2H, 2×ArH), 7.38 (d, 1H, J=9.1 Hz, ArH), 7.52 (s, 1H, ArH), 7.58 (s, 1H, ArH), 8.02 (d, 1H, J=9.1 Hz, ArH).

$^{13}$C-NMR (CD$_3$OD, δ): 3.5, 3.5, 10.9, 14.2, 22.5, 24.7, 27.1, 33.6, 39.0, 43.5, 56.9, 57.5, 74.4, 102.7, 106.0, 109.9, 110.2, 119.2, 119.9, 123.9, 124.0, 124.3, 124.5, 131.2, 139.4, 141.7, 152.1, 152.9, 154.9, 158.3, 160.0, 175.7.

MS-ESI m/z (rel.int.): 559 ([MH]$^+$, 100).

HPLC: Method B (10 min), XBridge™ column (5 mm, C18, 4.5×50 mm, Model #186003113), detection UV 254 nm, RT=4.68 min, peak area 95.5%.

Preparation of 6,7-dimethoxy-4-((6-methoxyquinolin-3-yl)methyl)-1-propylisoquinolin-3-ol dihydrochloride 84

(6-Methoxyquinolin-3-yl)methanol SLA 47088A

To a stirred solution of 6-methoxyquinoline-3-carbaldehyde (1.00 g, 5.3 mmol) in THF (50 mL) in a 100 mL round-bottomed flask equipped with a magnetic stirrer was added NaBH$_4$ (0.20 g, 5.3 mmol) and the mixture was stirred overnight at RT then cooled in an ice bath before quenching by addition of a 1 N aq. HCl solution (12 mL). After stirring for 15 min at RT, the mixture was basified to pH=9 with a 2 N aq. NaOH solution. THF was removed at 40° C. under vacuum and the solution was extracted with CH$_2$Cl$_2$ (200 mL), washed with brine (20 mL), dried over Na$_2$SO$_4$, filtered, and concentrated under vacuum. Purification by column chromatography (SiO$_2$, eluent cyclohexane:EtOAc=100:0 to 0:100) gave (6-methoxyquinolin-3-yl)methanol SLA 47088A as a yellow solid (0.49 g, 49% yield).

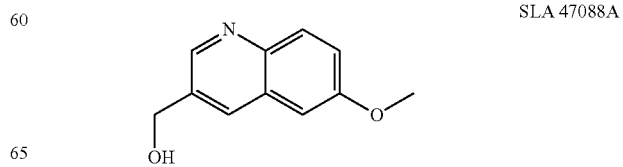

SLA 47088A

MW: 189.21; Yield: 49%; Yellow Solid; Mp (° C.): 169.1.

$^1$H NMR (CDCl$_3$, δ): 3.48 (broad s, 1H, OH), 3.90 (s, 3H, OCH$_3$), 4.85 (s, 2H, CH$_2$), 6.99 (d, 1H, J=2.7 Hz, ArH), 7.30 (dd, 1H, J=2.7 & 9.0 Hz, ArH), 7.93 (d, 1H, J=9.0 Hz, ArH), 7.98 (d, 1H, J=1.5 Hz, ArH), 8.64 (d, 1H, J=1.5 Hz, ArH).

$^{13}$C-NMR (CDCl$_3$, δ): 55.5, 62.8, 105.2, 122.1, 129.0, 130.3, 132.6, 134.1, 143.6, 147.5, 158.0.

MS-ESI m/z (% rel. Int.): 190 ([MH]$^+$, 100).

HPLC: Method B (10 min), XBridge™ column (5 mm, C18, 4.5×50 mm, Model #186003113), detection UV 214 nm, RT=2.83 min.

3-(Chloromethyl)-6-methoxyquinoline hydrochloride SLA 47088B

To a stirred solution of (6-methoxyquinolin-3-yl)methanol SLA 47088A (0.476 g, 2.5 mmol) in dry CH$_2$Cl$_2$ (25 mL) in a 100 mL round-bottomed flask equipped with a magnetic stirrer was added dropwise SOCl$_2$ (3.65 mL, 50.4 mmol). The mixture was stirred for 2 h at RT then concentrated to dryness at 40° C. under vacuum. The residue was then taken up in CH$_2$Cl$_2$ (20 mL) before concentration back to dryness at 40° C. under vacuum (done 3 times) to give 3-(chloromethyl)-6-methoxyquinoline hydrochloride SLA 47088B as a yellow solid (0.60 g, 98% yield).

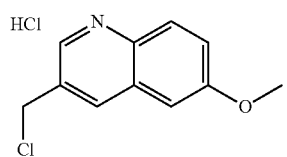

SLA 47088B

MW: 244.12; Yield: 98%; Yellow Solid; Mp (° C.): 178.5.

$^1$H NMR (CD$_3$OD, δ): 4.07 (s, 3H, OCH$_3$), 5.08 (s, 2H, CH$_2$), 7.75 (d, 1H, J=2.7 Hz, ArH), 7.83 (dd, 1H, J=2.7 & 9.3 Hz, ArH), 8.22 (d, 1H, J=9.3 Hz, ArH), 9.17 (s, 1H, ArH), 9.19 (s, 1H, ArH).

$^{13}$C-NMR (CD$_3$OD, δ): 42.4, 57.0, 107.7, 122.9, 130.0, 132.5, 134.5, 134.7, 142.9, 145.8, 162.3.

MS-ESI m/z (% rel. Int.): 210 ([MH]$^+$, $^{37}$Cl, 34), 208 ([MH]$^+$, $^{35}$Cl, 100).

HPLC: Method B (10 min), XBridge™ column (5 mm, C18, 4.5×50 mm, Model #186003113), detection UV 214 nm, RT=3.55 min.

6,7-Dimethoxy-4-((6-methoxyquinolin-3-yl)methyl)-1-propylisoquinolin-3-ol dihydrochloride 84

To a solution of 6,7-dimethoxy-1-propylisoquinolin-3-ol RBO 35134 (316 mg, 1.3 mmol) in THF (13 mL) in a 20 mL microwave vial equipped with a magnetic stirrer was added a 3-(chloromethyl)-6-methoxyquinoline hydrochloride SLA 47088B (265 mg, 1.1 mmol) and a 2 N aq. LiOH solution (1.3 mL, 2.6 mmol) and the mixture was stirred at 160° C. for 1.5 h under microwave irradiation. After cooling to RT, THF was then removed at 40° C. under vacuum and the residue was then taken up in CH$_2$Cl$_2$ (50 mL), washed with brine (10 mL), dried over Na$_2$SO$_4$, filtered, and concentrated under vacuum. Purification by column chromatography (SiO$_2$, eluent CH$_2$Cl$_2$:MeOH=100:0 to 94:6) gave 89 mg of 6,7-dimethoxy-4-((6-methoxyquinolin-3-yl)methyl)-1-propylisoquinolin-3-ol. This free base was dissolved in MeOH (2 mL) in a 10 mL round-bottomed flask equipped with a magnetic stirrer before addition of a 0.149 M HCl solution in MeOH (3.0 mL). The reaction mixture was stirred for 5 min at RT and concentrated at 40° C. under vacuum to afford 6,7-dimethoxy-4-((6-methoxyquinolin-3-yl)methyl)-1-propylisoquinolin-3-ol dihydrochloride 84 as a brown solid (93 mg, 17% yield).

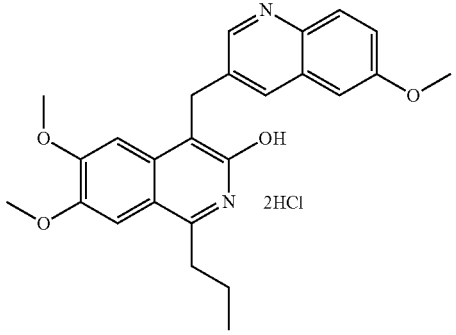

84

MW: 491.41; Yield: 17%; Brown Solid; Mp (° C.): 220.0.

$^1$H-NMR (CD$_3$OD, δ): 1.13 (t, 3H, J=6.7 Hz, CH$_3$), 1.90-1.96 (m, 2H, CH$_2$), 3.36-3.40 (m, 2H, CH$_2$), 3.97 (s, 6H, 2×OCH$_3$), 4.04 (s, 3H, OCH$_3$), 4.89 (s, 2H, CH$_2$), 7.23 (s, 1H, ArH), 7.54 (s, 1H, ArH), 7.61 (s, 1H, ArH), 7.75 (d, 1H, J=9.7 Hz, ArH), 8.15 (d, 1H, J=9.7 Hz, ArH), 8.75 (s, 1H, ArH), 9.07 (s, 1H, ArH).

$^{13}$C-NMR (CD$_3$OD, δ): 14.0, 24.6, 28.8, 33.3, 56.9, 56.9, 57.3, 102.4, 105.9, 107.2, 112.4, 118.8, 122.7, 129.1, 132.6, 133.9, 135.8, 141.1, 142.9, 144.5, 149.9, 151.6, 154.2, 159.2, 162.1.

MS-ESI m/z (rel.int.): 419 ([MH]$^+$, 100).

HPLC: Method B (10 min), XBridge™ column (5 mm, C18, 4.5×50 mm, Model #186003113), detection UV 254 nm, RT=4.85 min, peak area 96.2%.

Preparation of 1-ethyl-6,7-dimethoxy-4-((6-methoxyquinolin-3-yl)methyl)isoquinolin-3-ol dihydrochloride 85

To a solution of 1-ethyl-6,7-dimethoxyisoquinolin-3-ol SLA 28136 (288 mg, 1.18 mmol) in THF (13 mL) in a 20 mL microwave vial equipped with a magnetic stirrer was added 3-(chloromethyl)-6-methoxyquinoline hydrochloride SLA 47088B (275 mg, 1.18 mmol) and a 2 N aq. LiOH solution (1.20 mL, 2.40 mmol) and the mixture was stirred at 160° C. for 1.5 h under microwave irradiation. After cooling to RT, THF was then removed at 40° C. under vacuum and the solution was extracted with CH$_2$Cl$_2$ (50 mL), washed with brine (10 mL), dried over Na$_2$SO$_4$, filtered, and concentrated under vacuum. Purification by column chromatography (SiO$_2$, eluent CH$_2$Cl$_2$:MeOH=100:0 to 94:6) followed by a new purification by column chromatography (RP 18, eluent CH$_3$CN:H$_2$O=100:0 to 34:66) gave 1-ethyl-6,7-dimethoxy-4-((6-methoxyquinolin-3-yl)methyl)isoquinolin-3-ol. This free base was dissolved in MeOH (2 mL) in a 10 mL round-bottomed flask equipped with a magnetic stirrer before addition of a 0.149 M HCl solution in MeOH (3.0 mL). The reaction mixture was stirred for 5 min at RT and concentrated at 40° C. under vacuum to afford 1-ethyl-6,7-dimethoxy-4-((6-methoxyquinolin-3-yl)methyl)isoquinolin-3-ol dihydrochloride 85 as a brown solid (46.5 mg, 8% yield).

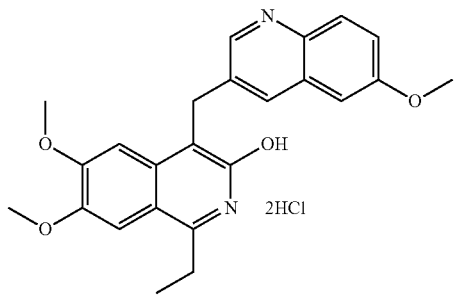

MW: 477.38; Yield: 8%; Brown Solid; Mp (° C.): 220.2 (dec.).

$^1$H-NMR (CD$_3$OD, δ): 1.53 (t, 3H, J=7.5 Hz, CH$_3$), 3.46 (q, 2H, J=7.5 Hz, CH$_2$), 3.98 (s, 6H, 2×OCH$_3$), 4.05 (s, 3H, OCH$_3$), 4.76 (s, 2H, CH$_2$), 7.24 (s, 1H, ArH), 7.55 (s, 1H, ArH), 7.61 (s, 1H, ArH), 7.77 (d, 1H, J=9.4 Hz, ArH), 8.16 (d, 1H, J=9.4 Hz, ArH), 8.75 (s, 1H, ArH), 9.08 (s, 1H, ArH).

$^{13}$C-NMR (CD$_3$OD, δ): 14.6, 25.5, 28.6, 56.9, 56.9, 57.4, 102.8, 105.8, 107.2, 118.9, 122.7, 129.2, 132.1, 132.6, 133.9, 135.5, 140.2, 141.1, 143.0, 152.2, 152.7, 156.1, 159.9, 162.1.

MS-ESI m/z (rel.int.): 405 ([MH]$^+$, 100).

HPLC: Method B (10 min), XBridge™ column (5 mm, C18, 4.5×50 mm, Model #186003113), detection UV 254 nm, RT=3.58 min, peak area 99.6%.

Preparation of 4-((6-Ethoxy-2-(ethylamino)-7-fluoroquinolin-3-yl)methyl)-6,7-dimethoxy-1-propylisoquinolin-3-ol dihydrochloride 86

4-Ethoxy-3-fluoroaniline SMA 44094

To a solution of 4-amino-2-fluorophenol (2.15 g, 16.9 mmol) in dry DMF (60 mL) in a 100 mL round-bottomed flask equipped with a magnetic stirrer was added Cs$_2$CO$_3$ (10.6 g, 25.4 mmol) and the mixture was stirred for 10 min at RT before addition of bromoethane (1.5 mL, 20.3 mmol). The reaction mixture was then stirred for 7 h at RT, concentrated to dryness, and the residue was partitioned between CH$_2$Cl$_2$ (100 mL) and water (20 mL). The organic layer was washed with brine (20 mL), dried over Na$_2$SO$_4$, filtered and concentrated at 40° C. under vacuum. Purification by column chromatography (SiO$_2$, eluent cyclohexane:EtOAc=100:0 to 88:12) gave 4-ethoxy-3-fluoroaniline SMA 44094 as a brown oil (480 mg, 18% yield).

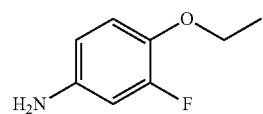
SMA 44094

MW: 155.17; Yield: 18%; Brown Oil.

$^1$H-NMR (CDCl$_3$, δ): 1.38 (t, 3H, J=7.0 Hz, CH$_3$), 3.45 (broad s, 2H, NH$_2$), 4.01 (q, 2H, J=7.0 Hz, CH$_2$), 6.33-6.37 (m, 1H, ArH), 6.46 (dd, 1H, J=2.7 & 12.7 Hz, ArH), 6.79 (dd, 1H, J=8.9 & 8.9 Hz, ArH).

$^{13}$C-NMR (CDCl$_3$, δ): 15.0, 66.5, 104.1 (d, J=21.8 Hz), 110.4 (d, J=3.0 Hz), 118.0 (d, J=3.8 Hz), 139.2 (d, J=11.3 Hz), 141.3 (d, J=9.8 Hz), 153.9 (d, J=244.5 Hz).

MS-ESI m/z (% rel. Int.): 156 ([MH]$^+$, 100).

HPLC: Method B (5 min), XBridge™ column (5 mm, C18, 4.5×50 mm, Model #186003113), detection UV 214 nm, RT=1.83 min.

N-(4-ethoxy-3-fluorophenyl)acetamide SMA 44098

To a solution of 4-ethoxy-3-fluoroaniline SMA 44094 (464 mg, 2.99 mmol) in dry CH$_2$Cl$_2$ (15 mL) in a 50 mL round-bottomed flask equipped with a magnetic stirrer were added DIEA (2.0 mL, 12 mmol), DMAP (87 mg, 0.7 mmol) and acetic anhydride (1.7 mL, 18 mmol) and the mixture was stirred for 5 h at RT. The solution was then diluted with more CH$_2$Cl$_2$ (30 mL), washed with brine (10 mL), dried over Na$_2$SO$_4$, filtered and concentrated at 40° C. under vacuum. Purification by column chromatography (SiO$_2$, eluent cyclohexane:EtOAc=100:0 to 50:50) gave N-(4-ethoxy-3-fluorophenyl)acetamide SMA 44098 as a beige solid (242 mg, 41% yield).

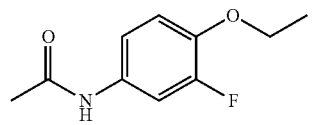
SMA 44098

MW: 197.21; Yield: 41%; Beige Solid; Mp (° C.): 127.4.

$^1$H NMR (CDCl$_3$, δ): 1.42 (t, 3H, J=7.0 Hz, CH$_3$), 2.15 (s, 3H, CH$_3$), 4.08 (q, 2H, J=7.0 Hz, CH$_2$), 6.88 (dd, 1H, J=8.9 & 8.9 Hz, ArH), 7.07-7.10 (m, 1H, ArH), 7.29 (broad s, 1H, NH), 7.40 (dd, 1H, J=2.5 & 12.8 Hz, ArH).

$^{13}$C-NMR (CDCl$_3$, δ): 14.0, 23.5, 64.6, 108.5 (d, J=22.6 Hz), 114.6, 114.8 (d, J=3.8 Hz), 130.6 (d, J=9.1 Hz), 142.8 (d, J=10.6 Hz), 151.7 (d, J=245.3 Hz), 167.3.

MS-ESI m/z (% rel. Int.): 198 ([MH]$^+$, 100).

HPLC: Method B (5 min), XBridge™ column (5 mm, C18, 4.5×50 mm, Model #186003113), detection UV 214 nm, RT=2.37 min.

2-Chloro-6-ethoxy-7-fluoroquinoline-3-carbaldehyde SMA 44100

POCl$_3$ (0.77 mL, 8.32 mmol) was added dropwise under N$_2$ to DMF (0.23 mL, 2.95 mmol) at 0° C. in a 2 mL microwave vial equipped with a magnetic stirrer. The mixture was stirred for 15 min at 0° C. before addition of N-(4-ethoxy-3-fluorophenyl)acetamide SMA 44098 (232 mg, 1.18 mmol) and the mixture was stirred for 45 min at 120° C. under microwave irradiation. After cooling to RT, the mixture was poured on a mixture of ice-water (10 mL) and basified with a 10 N aqueous NaOH solution (pH=12) before extraction with CH$_2$Cl$_2$ (80 mL). The separated organic layer was washed with brine (10 mL), dried over Na$_2$SO$_4$, filtered and concentrated at 40° C. under vacuum. Purification by column chromatography (SiO$_2$, eluent cyclohexane:EtOAc=100:0 to 90:10) gave 2-chloro-6-ethoxy-7-fluoro-quinoline-3-carbaldehyde SMA 44100 as a yellow solid (119 mg, 40% yield).

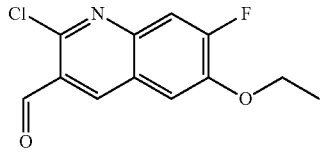
SMA 44100

MW: 253.66; Yield: 40%; Yellow Solid.

$^{1}$H NMR (CDCl$_{3}$, δ): 1.56 (t, 3H, J=7.0 Hz, CH$_{3}$), 4.25 (q, 2H, J=7.0 Hz, CH$_{2}$), 7.28 (d, 1H, J=8.7 Hz, ArH), 7.70 (d, 1H, J=11.4 Hz, ArH), 8.61 (s, 1H, ArH), 10.53 (s, 1H, CHO).

$^{13}$C-NMR (CDCl$_{3}$, δ): 14.4, 65.2, 109.1 (d, J=3.8 Hz), 113.6 (d, J=18.9 Hz), 124.5, 125.9 (d, J=2.2 Hz), 138.1, 145.9 (d, J=12.8 Hz), 148.9 (d, J=13.6 Hz), 157.4 (d, J=261.9 Hz), 189.1, 1×C not observed.

MS-ESI m/z (% rel. Int.): 256 ([MH]$^{+}$, $^{37}$Cl, 38), 254 ([MH]$^{+}$, $^{35}$Cl, 100).

HPLC: Method B (5 min), XBridge™ column (5 mm, C18, 4.5×50 mm, Model #186003113), detection UV 214 nm, RT=3.22 min.

6-Ethoxy-2-(ethylamino)-7-fluoroquinoline-3-carbaldehyde SMA 44102

A solution of 2-chloro-6-ethoxy-7-fluoroquinoline-3-carbaldehyde SMA 44100 (110 mg, 0.43 mmol) in ethylamine (2.0 M in THF, 2.20 mL, 4.40 mmol) in a 10 mL microwave vial equipped with a magnetic stirrer was stirred for 3.5 h at 150° C. under microwave irradiation. After cooling to RT, the volatiles were removed at 40° C. under vacuum and the resulting yellow oil was taken up in a mixture of THF:1 N aq. HCl=50:50 (10 mL) and the mixture was stirred for 30 min at RT. THF was then removed at 40° C. under vacuum and the residue was basified with a 10 N aq. NaOH solution (pH=8) before extraction with CH$_{2}$Cl$_{2}$ (40 mL). The separated organic layer was washed with brine (10 mL), dried over Na$_{2}$SO$_{4}$, filtered and concentrated at 40° C. under vacuum. Purification by column chromatography (SiO$_{2}$, eluent cyclohexane:EtOAc=100:0 to 90:10) gave 6-ethoxy-2-(ethylamino)-7-fluoroquinoline-3-carbaldehyde SMA 44102 as a yellow solid (63 mg, 56% yield).

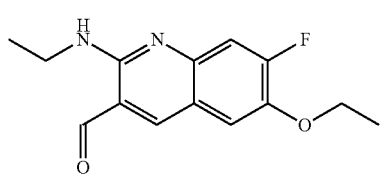

SMA 44102

MW: 262.28; Yield: 56%; Yellow Solid.

$^{1}$H NMR (CDCl$_{3}$, δ): 1.31 (t, 3H, J=7.2 Hz, CH$_{3}$), 1.53 (t, 3H, J=7.0 Hz, CH$_{3}$), 3.58-3.67 (m, 2H, CH$_{2}$), 4.14 (q, 2H, J=7.0 Hz, CH$_{2}$), 7.01 (d, 1H, J=9.1 Hz, ArH), 7.32 (d, 1H, J=12.7 Hz, ArH), 7.91 (br, s, 1H, NH), 8.05 (s, 1H, ArH), 9.92 (s, 1H, CHO).

$^{13}$C-NMR (CDCl$_{3}$, δ): 14.6, 14.7, 35.4, 64.9, 110.2 (d, J=4.5 Hz), 111.8 (d, J=18.9 Hz), 116.4 (d, J=2.2 Hz), 118.4, 144.4 (d, J=13.6 Hz), 146.5, 147.8 (d, J=12.8 Hz), 154.3, 158.0 (d, J=258.1 Hz), 192.7.

MS-ESI m/z (% rel. Int.): 263 ([MH]$^{+}$, 100).

HPLC: Method B (5 min), XBridge™ column (5 mm, C18, 4.5×50 mm, Model #186003113), detection UV 214 nm, RT=2.22 min.

((6-Ethoxy-2-(ethylamino)-7-fluoroquinolin-3-yl)methanol SMA 44104

To a solution of 6-ethoxy-2-(ethylamino)-7-fluoroquinoline-3-carbaldehyde SMA 44102 (63 mg, 0.24 mmol) in THF (10 mL) in a 25 mL round-bottomed flask equipped with a magnetic stirrer was added NaBH$_{4}$ (11 mg, 0.29 mmol) and the reaction mixture was stirred for 3 h at RT, then cooled down to 0° C. and quenched with a 6 N aq. HCl solution (5 mL). The mixture was stirred for 10 min at RT before basification to pH=12 with a 10 N aq. NaOH. THF was then removed at 40° C. and the residue was extracted with CH$_{2}$Cl$_{2}$ (30 mL). The organic phase was isolated, washed with brine (10 mL), dried over Na$_{2}$SO$_{4}$, filtered and concentrated at 40° C. under vacuum to give (6-ethoxy-2-(ethylamino)-7-fluoroquinolin-3-yl)methanol SMA 44104 as a pink solid (61 mg, 96% yield).

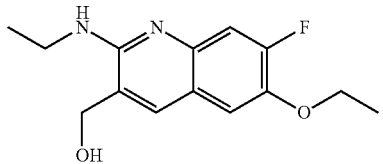

SMA 44104

MW: 264.30; Yield: 96%; Pink Solid.

$^{1}$H NMR (CDCl$_{3}$, δ): 1.27 (t, 3H, J=7.2 Hz, CH$_{3}$), 1.49 (t, 3H, J=7.0 Hz, CH$_{3}$), 3.49-3.53 (m, 3H, OH & CH$_{2}$), 4.08 (q, 2H, J=7.0 Hz, CH$_{2}$), 4.42 (s, 2H, CH$_{2}$), 5.71 (broad s, 1H, NH), 6.69 (d, 1H, J=9.1 Hz, ArH), 6.77 (s, 1H, ArH), 7.31 (d, 1H, J=12.8 Hz, ArH).

$^{13}$C-NMR (CDCl$_{3}$, δ): 14.7, 14.8, 35.9, 63.7, 65.1, 109.8 (d, J=2.2 Hz), 111.1 (d, J=18.9 Hz), 119.3 (d, J=1.5 Hz), 121.2 (d, J=3.0 Hz), 133.7, 143.1 (d, J=12.1 Hz), 143.4 (d, J=12.8 Hz), 154.9 (d, J=250.5 Hz), 155.6.

MS-ESI m/z (% rel. Int.): 265 [MH]$^{+}$ (100).

HPLC: Method B (5 min), XBridge™ column (5 mm, C18, 4.5×50 mm, Model #186003113), detection UV 214 nm, RT=2.09 min.

3-(Chloromethyl)-6-ethoxy-N-ethyl-7-fluoroquinolin-2-amine hydrochloride SMA 44106

To a solution of (6-ethoxy-2-(ethylamino)-7-fluoroquinolin-3-yl)methanol SMA 44104 (61 mg, 0.23 mmol) in dry CH$_{2}$Cl$_{2}$ (10 mL) at 0° C. under N$_{2}$ in a 25 mL round-bottomed flask equipped with a magnetic stirrer was added dropwise SOCl$_{2}$ (0.33 mL, 4.56 mmol) and the mixture was stirred for 3 h at RT. The mixture was then concentrated to dryness at 40° C. under vacuum and the residue was taken up in CH$_{2}$Cl$_{2}$ (20 mL) before concentration back to dryness (done 3 times) to give 3-(chloromethyl)-6-ethoxy-N-ethyl-7-fluoroquinolin-2-amine hydrochloride SMA 44106 as a brown solid (88 mg, >100% yield).

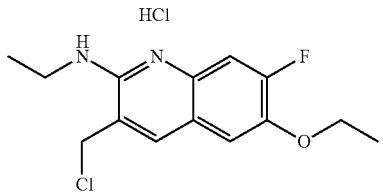

SMA 44106

MW: 319.20; Yield: >100%; Brown solid.

$^{1}$H NMR (CD$_{3}$OD, δ): 1.45 (t, 3H, J=7.2 Hz, CH$_{3}$), 1.50 (t, 3H, J=7.0 Hz, CH$_{3}$), 3.74 (q, 2H, J=7.2 Hz, CH$_{2}$), 4.25 (q, 2H, J=7.0 Hz, CH$_{2}$), 4.90 (s, 2H, CH$_{2}$), 7.57 (d, 1H, J=8.6 Hz, ArH), 7.77 (d, 1H, J=11.6 Hz, ArH), 8.40 (s, 1H, ArH).

$^{13}$C-NMR (CD$_3$OD, δ): 13.7, 14.8, 38.9, 41.9, 66.5, 105.9 (d, J=24.9 Hz), 112.9 (d, J=3.8 Hz), 119.5 (d, J=2.2 Hz), 123.0 (d, J=3.0 Hz), 132.4 (d, J=12.1 Hz), 143.3, 147.6 (d, J=12.8 Hz), 151.7, 157.4 (d, J=256.6 Hz).

MS-ESI m/z (% rel. Int.): 285 ([MH]$^+$, $^{37}$Cl, 38), 283 ([MH]$^+$, $^{35}$Cl, 100).

HPLC: Method B (5 min), XBridge™ column (5 mm, C18, 4.5×50 mm, Model #186003113), detection UV 214 nm, RT=2.35 min.

4-((6-Ethoxy-2-(ethylamino)-7-fluoroquinolin-3-yl)methyl)-6,7-dimethoxy-1-propylisoquinolin-3-ol 86

To a stirred solution of 6,7-dimethoxy-1-propylisoquinolin-3-ol RBO 35142 (55 mg, 222 μmol) in THF (5 mL) in a 10 mL microwave vial equipped with a magnetic stirrer was added a solution of 3-(chloromethyl)-6-ethoxy-N-ethyl-7-fluoroquinolin-2-amine hydrochloride SMA 44106 (76 mg, 238 μmol) in MeOH (0.5 mL) at RT followed by a 2 N aq. LiOH solution (240 μL, 480 μmol) and the mixture was stirred at 155° C. for 1.5 h under microwave irradiation. After cooling to RT, THF and MeOH were removed at 40° C. under vacuum and the residue was taken up in CH$_2$Cl$_2$ (50 mL). The organic solution was washed with brine (10 mL), dried over Na$_2$SO$_4$, filtered, and concentrated at 40° C. under vacuum. Purification by column chromatography (SiO$_2$, eluent EtOAc:MeOH=100:0 to 95:5) followed by a new purification by column chromatography (SiO$_2$, eluent CH$_2$Cl$_2$:MeOH=100:0 to 96:4) gave 4-((6-ethoxy-2-(ethylamino)-7-fluoroquinolin-3-yl)methyl)-6,7-dimethoxy-1-propylisoquinolin-3-ol as a brown solid. This free base was dissolved in CH$_2$Cl$_2$ (2 mL) in a 10 mL round-bottomed flask equipped with a magnetic stirrer before addition of a 0.49 M HCl solution in MeOH (0.5 mL). The reaction mixture was stirred for 5 min at RT then concentrated at 40° C. under vacuum to afford 4-((6-ethoxy-2-(ethylamino)-7-fluoroquinolin-3-yl)methyl)-6,7-dimethoxy-1-propylisoquinolin-3-ol 86 as a brown solid (15 mg, 12% yield).

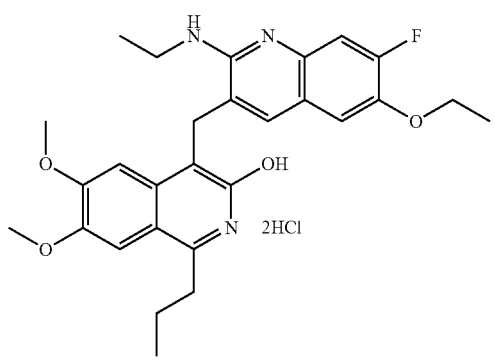

86

MW: 566.49; Yield: 12%; Brown Solid; Mp (° C.): 180.3 (dec.)

R$_f$: 0.35 (CH$_2$Cl$_2$:MeOH=95:5, free base).

$^1$H-NMR (CD$_3$OD, δ): 1.15 (t, 3H, J=7.1 Hz, CH$_3$), 1.41 (t, 3H, J=6.3 Hz, CH$_3$), 1.54 (t, 3H, J=7.1 Hz, CH$_3$), 1.91-2.00 (m, 2H, CH$_2$), 3.36 (t, 2H, J=7.1 Hz, CH$_2$), 3.79 (q, 2H, J=7.1 Hz, CH$_2$), 3.99 (s, 3H, OCH$_3$), 4.02 (s, 3H, OCH$_3$), 4.05-4.11 (m, 2H, CH$_2$), 4.38 (s, 2H, CH$_2$), 7.09 (s, 1H, ArH), 7.38 (d, 1H, J=8.0 Hz, ArH), 7.47 (s, 1H, ArH), 7.74 (s, 1H, ArH), 7.79 (d, 1H, J=11.6 Hz, ArH).

$^{13}$C-NMR (CD$_3$OD, δ): 13.8, 14.2, 14.8, 24.6, 27.4, 33.5, 39.2, 56.8, 57.3, 66.4, 102.1, 105.6 (d, J=24.3 Hz), 105.8, 110.1, 112.5, 118.1, 119.7 (d, J=12.2 Hz), 124.0, 131.2 (d, J=11.2 Hz), 139.4, 141.7, 147.2 (d, J=12.2 Hz), 151.4, 152.9, 154.0, 154.7, 156.6 (d, J=254.7 Hz), 159.5.

MS-ESI m/z (rel. int.): 494 ([MH]$^+$, 100).

HPLC: Method B (10 min), XBridge™ column (5 mm, C18, 4.5×50 mm, Model #186003113), detection UV 254 nm, RT=4.75 min, peak area 97.6%.

Preparation of N-(2-(6-(cyclopropylmethoxy)-3-((1-ethyl-3-hydroxy-6,7-dimethoxyisoquinolin-4-yl)methyl)quinolin-2-ylamino)ethyl)acetamide dihydrochloride 87

2-Chloro-6-hydroxyquinoline-3-carbaldehyde SLA 47016

To a stirred solution of 2-chloro-6-methoxyquinoline-3-carbaldehyde (5.27 g, 23.8 mmol) in anhydrous CH$_2$Cl$_2$ (180 mL) in a 500 mL round-bottomed flask equipped with a magnetic stirrer was added dropwise BBr$_3$ (71.3 mL, 71.3 mmol) at 0° C. and the mixture was stirred at RT overnight. The mixture was then added dropwise to a water/ice mixture, and the solid was filtered and dried under vacuum to give 2-chloro-6-hydroxyquinoline-3-carbaldehyde SLA 47016 as a yellow solid (3.14 g, 64% yield).

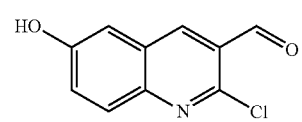

SLA 47016

MW: 207.61; Yield: 64%; Yellow Solid; Mp (° C.):170.0.

$^1$H NMR ((CD$_3$)$_2$SO, δ): 4.50 (br s, 1H, OH), 7.43 (s, 1H, ArH), 7.51 (d, 1H, J=8.2 Hz, ArH), 7.89 (d, 1H, J=8.2 Hz, ArH), 8.77 (s, 1H, ArH), 10.34 (s, 1H, CHO).

$^{13}$C-NMR ((CD$_3$)$_2$SO, δ): 110.3, 126.2, 128.0, 128.6, 139.5, 143.7, 145.4, 156.8, 189.6, 1×C not observed.

MS-ESI m/z (% rel. Int.): 208 ([MH]$^+$, 100).

HPLC: Method B (10 min), XBridge™ column (5 mm, C18, 4.5×50 mm, Model #186003113), detection UV 254 nm, RT=4.28 min.

2-Chloro-6-(cyclopropylmethoxy)quinoline-3-carbaldehyde SLA 47086

A mixture of 2-chloro-6-hydroxyquinoline-3-carbaldehyde SLA 47016 (1.00 g, 4.8 mmol), cesium carbonate (3.14 g, 9.6 mmol) and (bromomethyl)cyclopropane (0.94 mL, 9.6 mmol) in dry DMF (30 mL) in a 50 mL round-bottomed flask equipped with a magnetic stirrer was stirred overnight at RT. DMF was removed at 40° C. under vacuum and the residue was taken up in CH$_2$Cl$_2$ (50 mL), washed with brine (10 mL), dried over Na$_2$SO$_4$, filtered, and concentrated under vacuum. Purification by column chromatography (SiO$_2$, eluent cyclohexane:EtOAc=100:0 to 95:5) followed by a new purification by column chromatography (SiO$_2$, eluent CH$_2$Cl$_2$:MeOH=100:0 to 95:5) gave 2-chloro-6-(cyclopropylmethoxy)quinoline-3-carbaldehyde SLA 47086 as a pale brown solid (513 mg, 41% yield).

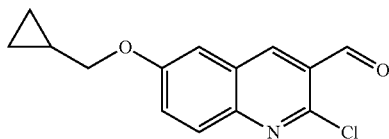

SLA 47086

MW: 261.70; Yield: 41%; Brown Solid; Mp (° C.): 182.1.
MS-ESI m/z (rel.int.): 262 ([MH]+, 100).
HPLC: Method B (10 min), XBridge™ column (5 mm, C18, 4.5×50 mm, Model #186003113), detection UV 254 nm, RT=3.39 min, peak area 99.9%.

N-(2-(6-(cyclopropylmethoxy)-3-formylquinolin-2-ylamino)ethyl)acetamide SLA 47092

To a stirred solution of 2-chloro-6-(cyclopropylmethoxy)quinoline-3-carbaldehyde SLA 47086 (770 mg, 2.94 mmol) in THF (15 mL) in a 20 mL microwave vial equipped with a magnetic stirrer was added N-(2-aminoethyl)acetamide (1.202 g, 11.8 mmol) and the reaction mixture was stirred for 6 h at 160° C. under microwave irradiation. After cooling to RT, the volatiles were removed at 40° C. under vacuum and the resulting yellow oil was taken up in a mixture of THF:1 N aq. HCl=1:1 (50 mL) and stirred for 20 min at RT. The volatiles were then removed at 40° C. under vacuum and the residue was then neutralised with a 10 N aqueous NaOH solution. THF was then evaporated before extraction with $CH_2Cl_2$ (100 mL). The separated organic layer was washed with brine (20 mL), dried over $MgSO_4$, filtered, and concentrated under vacuum to give N-(2-(6-(cyclopropylmethoxy)-3-formylquinolin-2-ylamino)ethyl)acetamide SLA 47092 as a yellow solid (365 mg, 38% yield).

SLA 47092

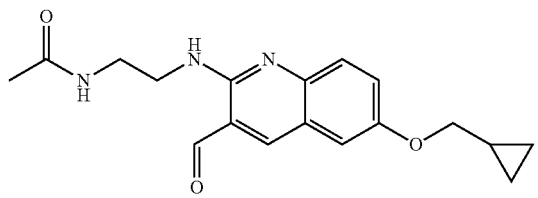

MW: 327.38; Yield: 38%; Yellow Solid; Mp (° C.): 185.4.
$^1$H NMR (CDCl$_3$, δ): 0.39-0.43 (m, 2H, CH$_2$), 0.66-0.73 (m, 2H, CH$_2$), 1.25-1.36 (m, 1H, CH), 1.92 (s, 3H, CH$_3$), 3.50-3.56 (m, 2H, CH$_2$), 3.76-3.82 (m, 2H, CH$_2$), 3.88 (d, 2H, J=6.9 Hz, OCH$_2$), 7.00 (d, 1H, J=2.8 Hz, ArH), 7.41 (dd, 1H, J=2.8 & 9.2 Hz, ArH), 7.45 (s, 1H, NH), 7.57 (d, 1H, J=9.2 Hz, ArH), 8.15 (s, 1H, NH), 8.17 (s, 1H, ArH), 9.97 (s, 1H, CHO).
MS-ESI m/z (% rel. Int.): 328 ([MH]+, 100).
HPLC: Method B (5 min), XBridge™ column (5 mm, C18, 4.5×50 mm, Model #186003113), detection UV 254 nm, RT=2.18 min.

N-(2-(6-(Cyclopropylmethoxy)-3-(hydroxymethyl)quinolin-2-ylamino)ethyl)acetamide SLA 47096A To a stirred solution of N-(2-(6-(cyclopropylmethoxy)-3-formylquinolin-2-ylamino)ethyl)acetamide SLA 47092 (0.35 g, 1.1 mmol) in THF (10 mL) in a 50 mL round-bottomed flask equipped with a magnetic stirrer was added NaBH$_4$ (0.04 g, 1.1 mmol) and the mixture was stirred overnight at RT then cooled in an ice bath before quenching by addition of a 1 N aq. HCl solution. After stirring for 15 min at RT, the mixture was basified to pH=9 with a 2 N aq. NaOH solution. THF was removed at 40° C. under vacuum and the residue was extracted with $CH_2Cl_2$ (200 mL), washed with brine (20 mL), dried over $Na_2SO_4$, filtered, and concentrated under vacuum, to give N-(2-(6-(cyclopropylmethoxy)-3-(hydroxymethyl)quinolin-2-ylamino)ethyl)acetamide SLA 47096A as a yellow oil (0.39 g, quant. yield).

SLA 47096A

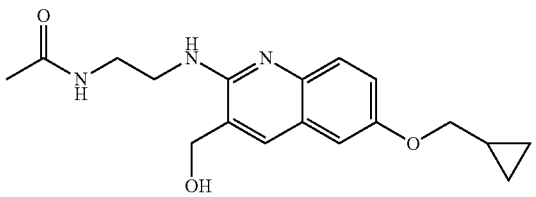

MW: 329.39; Yield: 100%; Yellow Oil.
$^1$H NMR (CDCl$_3$, δ): 0.34-0.40 (m, 2H, CH$_2$), 0.63-0.69 (m, 2H, CH$_2$), 1.25-1.43 (m, 1H, CH), 1.84 (s, 3H, CH$_3$), 3.41-3.44 (m, 2H, CH$_2$), 3.65-3.67 (m, 2H, CH$_2$), 3.83 (d, 2H, J=6.9 Hz, OCH$_2$), 4.63 (s, 2H, CH$_2$), 6.87 (d, 1H, J=2.7 Hz, ArH), 7.21 (dd, 1H, J=2.7 & 9.1 Hz, ArH), 7.45 (s, 1H, ArH), 7.55 (d, 1H, J=9.1 Hz, ArH) (NH & OH not seen).
$^{13}$C-NMR (CDCl$_3$, δ): 3.2, 3.2, 10.1, 23.1, 40.8, 42.4, 63.3, 73.2, 107.9, 121.3, 122.6, 123.6, 126.6, 134.8, 142.5, 154.4, 155.5, 170.9.
MS-ESI m/z (% rel. Int.): 330 ([MH]+, 100).
HPLC: Method B (10 min), XBridge™ column (5 mm, C18, 4.5×50 mm, Model #186003113), detection UV 214 nm, RT=3.79 min.

N-(2-(3-(Chloromethyl)-6-(cyclopropylmethoxy)quinolin-2-ylamino)ethyl)acetamide hydrochloride SLA 47096B To a stirred solution of N-(2-(6-(cyclopropylmethoxy)-3-(hydroxymethyl)quinolin-2-ylamino)ethyl)acetamide SLA 47096A (0.374 g, 1.1 mmol) in dry $CH_2Cl_2$ (11 mL) in a 25 mL round-bottomed flask equipped with a magnetic stirrer was added dropwise SOCl$_2$ (1.65 mL, 22.7 mmol). The mixture was stirred for 2 h at RT then concentrated to dryness at 40° C. under vacuum. The residue was then taken up in $CH_2Cl_2$ (20 mL) before concentration back to dryness at 40° C. under vacuum (done 3 times) to give N-(2-(3-(chloromethyl)-6-(cyclopropylmethoxy)quinolin-2-ylamino)ethyl)acetamide hydrochloride SLA 47096B as a yellow solid (0.475 g, 100% yield).

SLA 47096B

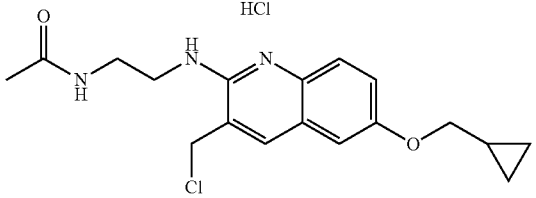

MW: 384.30; Yield: 100%; Yellow Solid; Mp (° C.): 162.5.
$^1$H NMR (CD$_3$OD, δ): 0.40-0.44 (m, 2H, CH$_2$), 0.64-0.71 (m, 2H, CH$_2$), 1.30-1.33 (m, 1H, CH), 2.08 (s, 3H, CH$_3$), 3.53 (t, 2H, J=6.8 Hz, CH$_2$), 3.77 (t, 2H, J=6.8 Hz, CH$_2$), 3.96 (d, 2H, J=6.7 Hz, OCH$_2$), 4.86 (s, 2H, CH$_2$), 7.37 (d, 1H, J=2.7 Hz, ArH), 7.47 (dd, 1H, J=2.7 & 9.0 Hz, ArH), 8.04 (d, 1H, J=9.0 Hz, ArH), 8.43 (s, 1H, ArH).
$^{13}$C-NMR (CD$_3$OD, δ): 3.6, 3.6, 11.0, 22.4, 38.7, 41.8, 43.0, 74.5, 110.7, 120.3, 123.7, 123.7, 125.2, 132.2, 143.8, 151.7, 158.5, 175.8.
MS-ESI m/z (% rel. Int.): 350 ([MH]$^+$, $^{37}$Cl, 36), 348 ([MH]$^+$, $^{35}$Cl, 100).
HPLC: Method B (10 min), XBridge™ column (5 mm, C18, 4.5×50 mm, Model #186003113), detection UV 214 nm, RT=4.25 min.

N-(2-(6-(Cyclopropylmethoxy)-3-((1-ethyl-3-hydroxy-6,7-dimethoxyisoquinolin-4-yl)methyl)quinolin-2-ylamino)ethyl)acetamide dihydrochloride 87

To a solution of 1-ethyl-6,7-dimethoxyisoquinolin-3-ol SLA 47022 (128 mg, 0.55 mmol) in THF (13 mL) in a 20 mL microwave vial equipped with a magnetic stirrer was added N-(2-(3-(chloromethyl)-6-(cyclopropylmethoxy)quinolin-2-ylamino)ethyl)acetamide hydrochloride SLA 47096B (211 mg, 0.55 mmol) and 2 N aq. LiOH solution (0.55 mL, 1.10 mmol) and the mixture was stirred at 160° C. for 1.5 h under microwave irradiation. After cooling to RT, THF was then removed at 40° C. under vacuum and the residue was taken up in CH$_2$Cl$_2$ (50 mL), washed with brine (10 mL), dried over Na$_2$SO$_4$, filtered, and concentrated under vacuum. Purification by column chromatography (SiO$_2$, eluent CH$_2$Cl$_2$:MeOH=100:0 to 93:7) followed by a new purification by column chromatography (SiO$_2$, eluent CH$_2$Cl$_2$:MeOH=100:0 to 95:5) gave 27 mg of N-(2-(6-(cyclopropylmethoxy)-3-((1-ethyl-3-hydroxy-6,7-dimethoxyisoquinolin-4-yl)methyl)quinolin-2-ylamino)ethyl)acetamide. This free base was dissolved in MeOH (2 mL) in a 10 mL round-bottomed flask equipped with a magnetic stirrer before addition of a 0.149 M HCl solution in MeOH (2.0 mL). The reaction mixture was stirred for 5 min at RT and concentrated at 40° C. under vacuum to give N-(2-(6-(cyclopropylmethoxy)-3-((1-ethyl-3-hydroxy-6,7-dimethoxyisoquinolin-4-yl)methyl)quinolin-2-ylamino)ethyl)acetamide dihydrochloride 87 as a brown solid (28.9 mg, 8% yield).

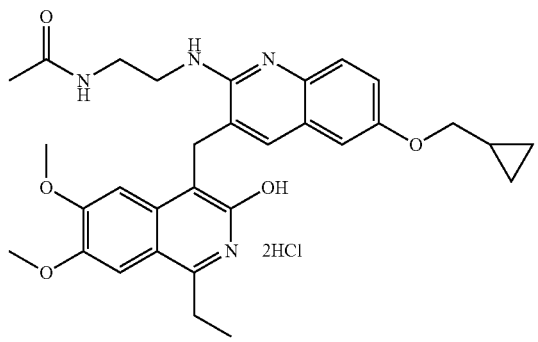

87

MW: 617.56; Yield: 8%; Brown Solid; Mp (° C.): 201.2.
$^1$H-NMR (CD$_3$OD, δ): 0.29-0.34 (m, 2H, CH$_2$), 0.56-0.63 (m, 2H, CH$_2$), 1.20-1.25 (m, 1H, CH), 1.56 (t, 3H, J=6.9 Hz, CH$_3$), 2.09 (s, 3H, CH$_3$), 3.44-3.49 (m, 2H, CH$_2$), 3.60-3.66 (m, 2H, CH$_2$), 3.80 (d, 2H, J=7.0 Hz, OCH$_2$), 3.86-3.91 (m, 2H, CH$_2$), 3.96 (s, 3H, OCH$_3$), 4.06 (s, 3H, OCH$_3$), 4.35 (s, 2H, CH$_2$), 7.12 (s, 1H, ArH), 7.15 (s, 1H, ArH), 7.38 (d, 1H, J=9.2 Hz, ArH), 7.53 (s, 1H, ArH), 7.60 (s, 1H, ArH), 8.03 (d, 1H, J=9.2 Hz, ArH).
$^{13}$C-NMR (CD$_3$OD, δ): 3.5, 3.5, 10.9, 14.6, 22.5, 25.5, 27.1, 39.0, 43.5, 57.0, 57.5, 74.4, 102.7, 105.8, 110.0, 110.6, 117.5, 119.9, 123.9, 124.0, 124.3, 131.2, 139.4, 141.8, 152.2, 152.9, 156.1, 158.3, 160.0, 175.7, 1×C not observed.
MS-ESI m/z (rel.int.): 545 ([MH]$^+$, 100).
HPLC: Method B (10 min), XBridge™ column (5 mm, C18, 4.5×50 mm, Model #186003113), detection UV 254 nm, RT=4.61 min, peak area 97.4%.

Preparation of N-(2-(6-ethoxy-3-((3-hydroxy-6,7-dimethoxy-1-propylisoquinolin-4-yl)methyl)quinolin-2-ylamino)ethyl)acetamide dihydrochloride 88

To a stirred solution of N-(2-(3-(chloromethyl)-6-ethoxyquinolin-2-ylamino)ethyl)acetamide hydrochloride SMA 44092 (231 mg, 0.65 mmol) in THF (10 mL) in a 20 mL microwave vial equipped with a magnetic stirrer was added 6,7-dimethoxy-1-propylisoquinolin-3-ol RBO 35134 (159 mg, 0.65 mmol) followed by a 2 N aq. LiOH solution (0.65 mL, 1.29 mmol) and the mixture was stirred at 160° C. for 1.5 h under microwave irradiation. After cooling to RT, the mixture was diluted with CH$_2$Cl$_2$:MeOH=9:1 (150 mL) and washed with brine (20 mL), dried over Na$_2$SO$_4$, filtered, and concentrated at 40° C. under vacuum. Purification by column chromatography (SiO$_2$, eluent CH$_2$Cl$_2$:MeOH=100:0 to 93:7) provided N-(2-(6-ethoxy-3-((3-hydroxy-6,7-dimethoxy-1-propylisoquinolin-4-yl)methyl)quinolin-2-ylamino)ethyl)acetamide. This free base was dissolved in CH$_2$Cl$_2$ (2 mL) in a 10 mL round-bottomed flask equipped with a magnetic stirrer before addition of 0.49 M HCl in MeOH (2 mL) and the solution was stirred for 5 min at RT then concentrated at 40° C. under vacuum to afford N-(2-(6-ethoxy-3-((3-hydroxy-6,7-dimethoxy-1-propylisoquinolin-4-yl)methyl)quinolin-2-ylamino)ethyl)acetamide dihydrochloride 88 as a yellow solid (25 mg, 6% yield).

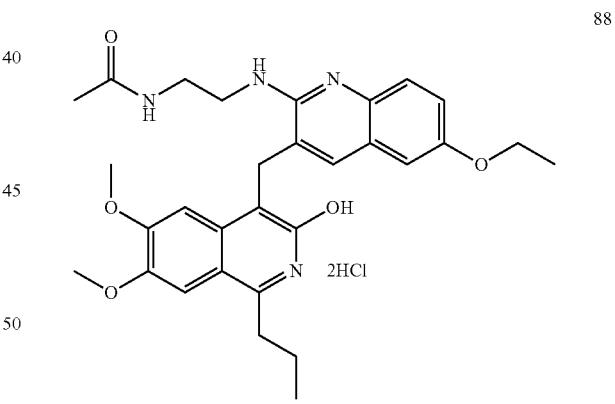

88

MW: 605.55; Yield: 6%; Yellow Solid; Mp (° C.): 164.7.
$^1$H NMR (CD$_3$OD, δ): 1.18 (t, 3H, J=7.3 Hz, CH$_3$), 1.36 (t, 3H, J=6.5 Hz, CH$_3$), 1.96-2.04 (m, 2H, CH$_2$), 2.10 (s, 3H, CH$_3$), 3.43-3.49 (m, 2H, CH$_2$), 3.61-3.67 (m, 2H, CH$_2$), 3.89-3.92 (m, 2H, CH$_2$), 3.94 (s, 3H, OCH$_3$), 3.94-3.97 (m, 2H, CH$_2$), 4.00 (s, 3H, OCH$_3$), 4.38 (s, 2H, CH$_2$), 7.13 (s, 1H, ArH), 7.17 (s, 1H, ArH), 7.35 (d, 1H, J=9.2 Hz, ArH), 7.49 (s, 1H, ArH), 7.61 (s, 1H, ArH), 8.05 (d, 1H, J=9.2 Hz, ArH).
$^{13}$C-NMR (CD$_3$OD, δ): 14.2, 14.9, 22.5, 24.7, 27.10, 33.7, 39.1, 43.5, 57.0, 57.6, 65.2, 102.9, 106.1, 109.9, 110.1, 119.5, 119.9, 123.9, 123.9, 124.1, 131.2, 139.2, 141.7, 152.2, 152.3, 152.8, 155.2, 158.14, 160.2, 175.8.

MS-ESI m/z (% rel. Int.): 533 ([MH]$^+$, 100).

HPLC: Method B (10 min), XBridge™ column (5 mm, C18, 4.5×50 mm, Model #186003113), detection UV 254 nm, RT=4.43 min, peak area 95.8%.

Example 2

PDE10A Inhibitory Activity of Compounds According to the Invention

Phosphodiesterase Assay

The PDE assay is based on the homogenous time-resolved fluorescence resonance energy transfer (TR-FRET) technology (LANCE® from Perkin Elmer). This competition based assay is formatted using a cAMP specific antibody labeled with the dye, Alexa Fluor® 647, biotin-cAMP and streptavidin labeled with Europium (Eu-SA). As the complex of Eu-SA/biotin-cAMP/Alexa Fluor 647 labeled antibody is formed, an increase in signal is generated. When there is PDE activity, resulting in the degradation of the cyclic nucleotide, the complex is not formed and a decrease in signal is observed.

The phosphodiesterase assay was developed using the LANCE® cAMP kit (PerkinElmer). The assay buffer contained HBSS with 5 mM HEPES, 0.1% BSA, and 1.5 mM MgCl$_2$, pH 7.4. PDE10A (BPS Bioscience) was used at 200 pg/well (with a specific activity of 3200 μmole/min/μg with assay conditions: 10 mM Tris-HCl, pH7.4, 10 mM MgCl$_2$, 1 mM MnCl$_2$, 200 μM cAMP, 2.5 kU 5' nucleotidase, 37° C., 20 min). The Biotin-cAMP tracer, supplied in 10 mmol/L Tris-HCl buffered (pH 8.0) salt solution with 1 mmol/L ethylenediaminetetraacetic acid (EDTA), 0.1% bovine serum albumin (BSA), and 0.05% sodium azide, is used at a dilution of 1/375. The assay detection mixture contained the LANCE Eu-W8044 labeled streptavidin 1/2250 (supplied in 50 mmol/L Tris-HCl buffered (pH 7.8) salt solution with 0.9% sodium chloride (NaCl), 0.1% BSA, and 0.05% sodium azide) and the Alexa Fluor® 647-anti cAMP antibody 1/200 (supplied in 50 mmol/L Tris-HCl buffered (pH 7.8) salt solution with 0.9% NaCl, 0.1% BSA, and 0.05% sodium azide). Chemical compounds were dissolved in DMSO (final concentration 2% (v/v)).

In a 384-well plate, 2 μL inhibitor and 3 μL PDE were added to the well, followed by the addition of 5 μl substrate biotinylated cAMP (1:5). After 60 min incubation at room temperature, 10 μL of assay detection mixture was added to the assay plate. After 1 h at room temperature, the signal was measured on EnVision™ (Perkin Elmer).

The results are summarized in table 1.

TABLE 1

PDE10A inhibitory activity for compounds of the invention

| Compd No. | Structure | Name | PDE10A IC$_{50}$ |
|---|---|---|---|
| 1 | 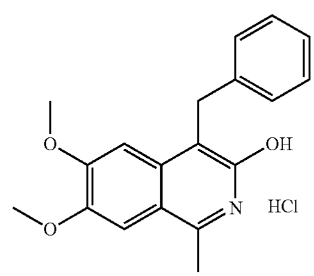 [SMILES: COc1cc2c(C)nc(O)c(Cc3ccccc3)c2cc1OC ; Cl] | 4-benzyl-6,7-dimethoxy-1-methylisoquinolin-3-ol hydrochloride | — |
| 2 | 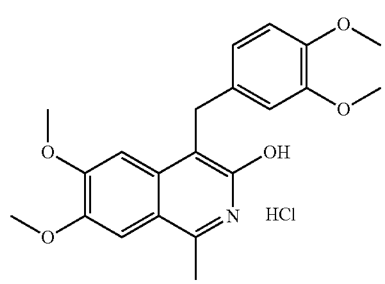 | 4-(3,4-dimethoxybenzyl)-6,7-dimethoxy-1-methylisoquinolin-3-ol hydrochloride | — |
| 3 | 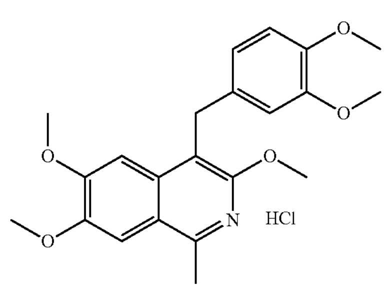 | 4-(3,4-dimethoxybenzyl)-3,6,7-trimethoxy-1-methylisoquinoline hydrochloride | — |

TABLE 1-continued

PDE10A inhibitory activity for compounds of the invention

| Compd No. | Structure | Name | PDE10A IC$_{50}$ |
|---|---|---|---|
| 4 | 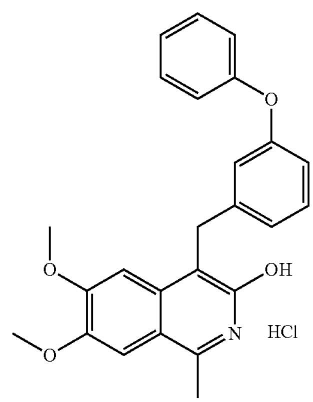 [SMILES: COc1cc2c(C)nc(O)c(Cc3cccc(Oc4ccccc4)c3)c2cc1OC ; Cl] | 6,7-dimethoxy-1-methyl-4-(3-phenoxybenzyl)isoquinolin-3-ol hydrochloride | 140 nM |
| 5 | 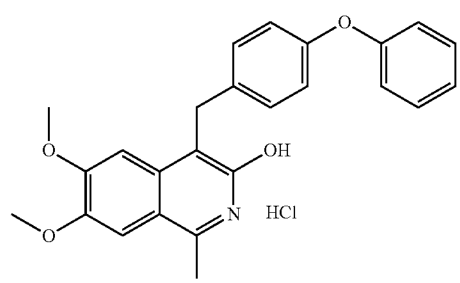 [SMILES: COc1cc2c(C)nc(O)c(Cc3ccc(Oc4ccccc4)cc3)c2cc1OC ; Cl] | 6,7-dimethoxy-1-methyl-4-(4-phenoxybenzyl)isoquinolin-3-ol hydrochloride | — |
| 6 | 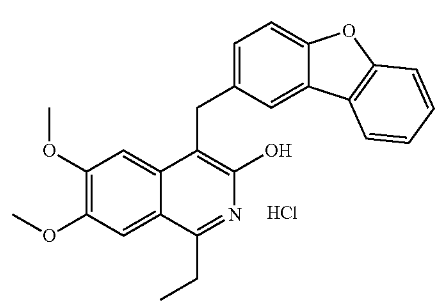 [SMILES: CCc1nc(O)c(Cc2ccc3oc4ccccc4c3c2)c2cc(OC)c(OC)cc12 ; Cl] | 4-(dibenzo[b,d]furan-2-ylmethyl)-1-ethyl-6,7-dimethoxyisoquinolin-3-ol hydrochloride | 0.12 nM |
| 7 | 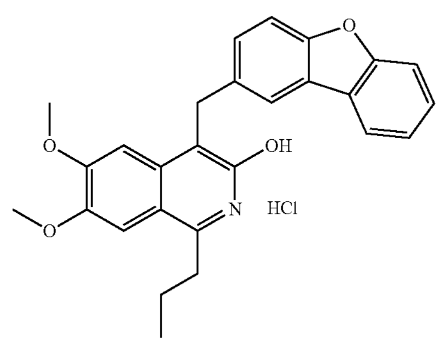 [SMILES: CCCc1nc(O)c(Cc2ccc3oc4ccccc4c3c2)c2cc(OC)c(OC)cc12 ; Cl] | 4-(dibenzo[b,d]furan-2-ylmethyl)-6,7-dimethoxy-1-propylisoquinolin-3-ol hydrochloride | 0.5 nM |

TABLE 1-continued

PDE10A inhibitory activity for compounds of the invention

| Compd No. | Structure | Name | PDE10A IC$_{50}$ |
|---|---|---|---|
| 8 | 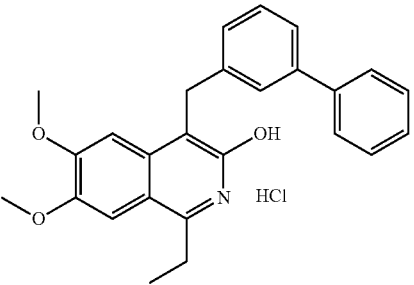 [SMILES: CCc1nc(O)c(Cc2cccc(-c3ccccc3)c2)c2cc(OC)c(OC)cc12 ; Cl] | 4-([1,1'-biphenyl]-3-ylmethyl)-1-ethyl-6,7-dimethoxyisoquinolin-3-ol hydrochloride | 6710 nM |
| 9 | 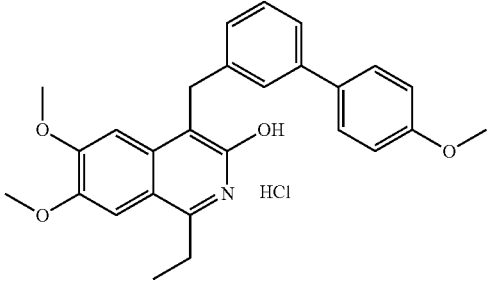 | 1-ethyl-6,7-dimethoxy-4-((4'-methoxy-[1,1'-biphenyl]-3-yl)methyl)isoquinolin-3-ol hydrochloride | 10600 nM |
| 10 | 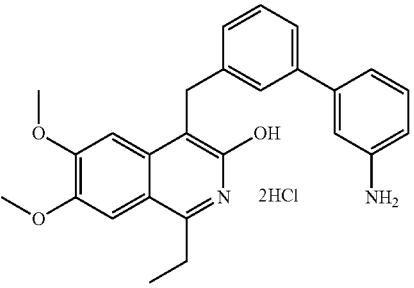 [SMILES: CCc1nc(O)c(Cc2cccc(-c3cccc(N)c3)c2)c2cc(OC)c(OC)cc12 ; "2HCl"] | 4-((3'-amino-[1,1'-biphenyl]-3-yl)methyl)-1-ethyl-6,7-dimethoxyisoquinolin-3-ol dihydrochloride | 52 nM |
| 11 | 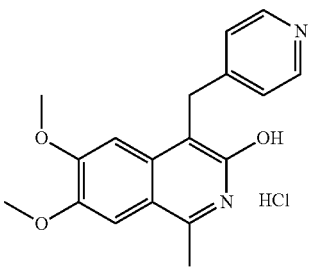 [SMILES: COc1cc2c(C)nc(O)c(Cc3ccncc3)c2cc1OC ; Cl] | 6,7-dimethoxy-1-methyl-4-(pyridin-4-ylmethyl)isoquinolin-3-ol hydrochloride | 223 nM |
| 12 | 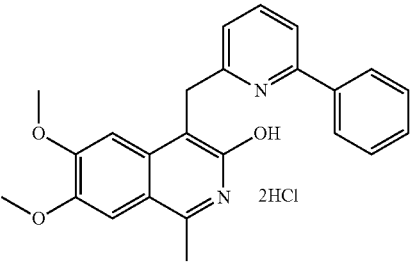 [SMILES: COc1cc2c(C)nc(O)c(Cc3cccc(-c4ccccc4)n3)c2cc1OC ; "2HCl"] | 6,7-dimethoxy-1-methyl-4-((6-phenylpyridin-2-yl)methyl)isoquinolin-3-ol dihydrochloride | 94 nM |

TABLE 1-continued

PDE10A inhibitory activity for compounds of the invention

| Compd No. | Structure | Name | PDE10A IC$_{50}$ |
|---|---|---|---|
| 13 | 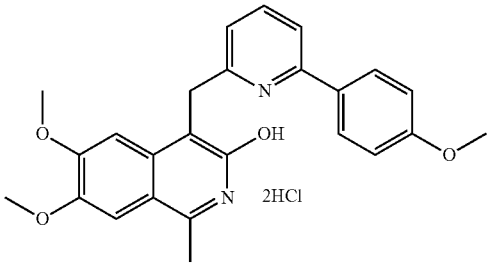 | 6,7-dimethoxy-4-((6-(4-methoxyphenyl)pyridin-2-yl)methyl)-1-methylisoquinolin-3-ol dihydrochloride | 50 nM |
| 14 | 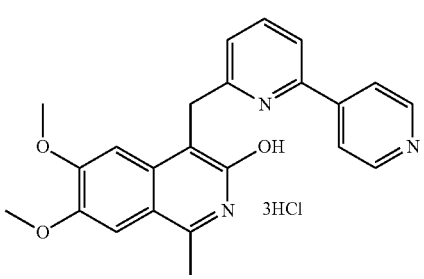 [SMILES: COc1cc2c(C)nc(O)c(Cc3cccc(-c4ccncc4)n3)c2cc1OC ; "3HCl"] | 4-(2,4'-bipyridin-6-ylmethyl)-6,7-dimethoxy-1-methylisoquinolin-3-ol trihydrochloride trihydrochloride | 100 nM |
| 15 | 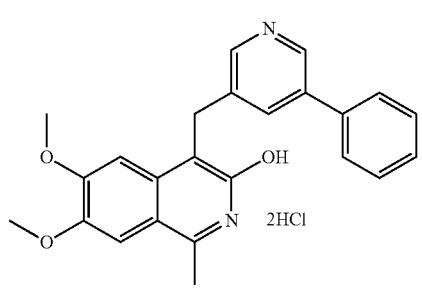 [SMILES: COc1cc2c(C)nc(O)c(Cc3cncc(-c4ccccc4)c3)c2cc1OC ; "2HCl"] | 6,7-dimethoxy-1-methyl-4-((5-phenylpyridin-3-yl)methyl)isoquinolin-3-ol dihydrochloride | 97 nM |
| 16 | 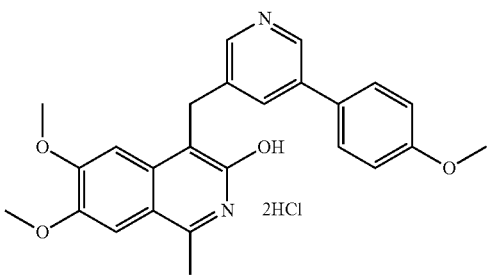 | 6,7-dimethoxy-4-((5-(4-methoxyphenyl)pyridin-3-yl)methyl)-1-methylisoquinolin-dihydrochloride | 69 nM |
| 17 | 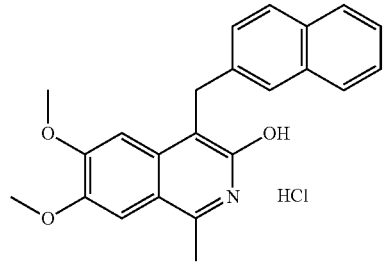 [SMILES: COc1cc2c(C)nc(O)c(Cc3ccc4ccccc4c3)c2cc1OC ; Cl] | 6,7-dimethoxy-1-methyl-4-(naphthalen-2-ylmethyl)isoquinolin-3-ol hydrochloride | 14 nM |

TABLE 1-continued

PDE10A inhibitory activity for compounds of the invention

| Compd No. | Structure | Name | PDE10A IC$_{50}$ |
|---|---|---|---|
| 18 | 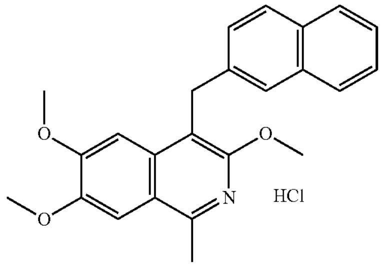 [SMILES: COc1cc2c(C)nc(OC)c(Cc3ccc4ccccc4c3)c2cc1OC ; Cl] | 3,6,7-trimethoxy-1-methyl-4-(naphthalen-2-ylmethyl)isoquinoline hydrochloride | 1410 nM |
| 19 | 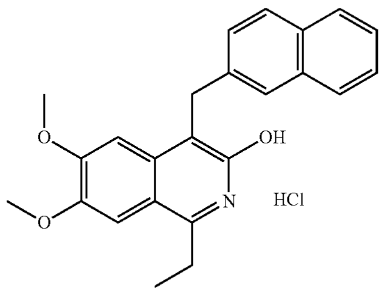 [SMILES: CCc1nc(O)c(Cc2ccc3ccccc3c2)c2cc(OC)c(OC)cc12 ; Cl] | 1-ethyl-6,7-dimethoxy-4-(naphthalen-2-ylmethyl)isoquinolin-3-ol hydrochloride | 11 nM |
| 20 | 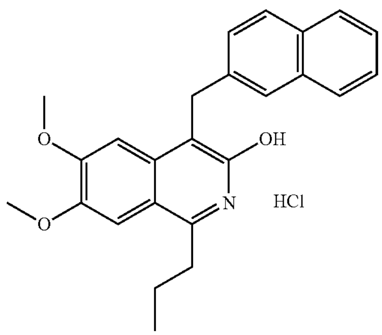 [SMILES: CCCc1nc(O)c(Cc2ccc3ccccc3c2)c2cc(OC)c(OC)cc12 ; Cl] | 6,7-dimethoxy-4-(naphthalen-2-ylmethyl)-1-propylisoquinolin-3-ol hydrochloride | 34 nM |
| 21 | 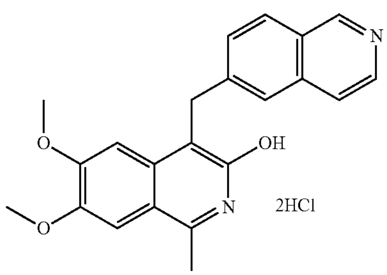 [SMILES: COc1cc2c(C)nc(O)c(Cc3ccc4cnccc4c3)c2cc1OC ; "2HCl"] | 4-(isoquinolin-6-ylmethyl)-6,7-dimethoxy-1-methylisoquinolin-3-ol dihydrochloride | 333 nM |
| 22 | 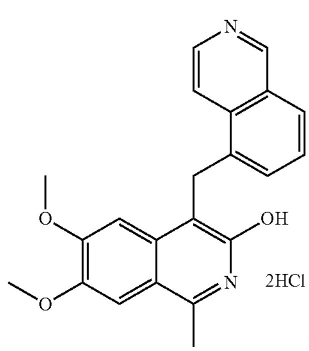 [SMILES: COc1cc2c(C)nc(O)c(Cc3cccc4cnccc34)c2cc1OC ; "2HCl"] | 4-(isoquinolin-5-ylmethyl)-6,7-dimethoxy-1-methylisoquinolin-3-ol dihydrochloride | 333 nM |

TABLE 1-continued

PDE10A inhibitory activity for compounds of the invention

| Compd No. | Structure | Name | PDE10A IC$_{50}$ |
|---|---|---|---|
| 23 | 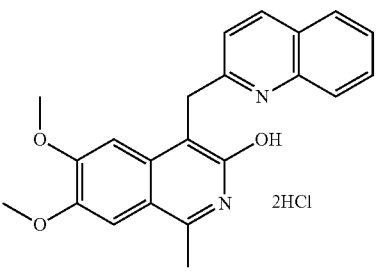 [SMILES: COc1cc2c(C)nc(O)c(Cc3ccc4ccccc4n3)c2cc1OC ; "2HCl"] | 6,7-dimethoxy-1-methyl-4-(quinolin-2-ylmethyl)isoquinolin-3-ol hydrochloride | 130 nM |
| 24 | 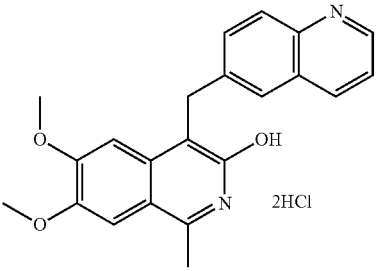 [SMILES: COc1cc2c(C)nc(O)c(Cc3ccc4ncccc4c3)c2cc1OC ; "2HCl"] | 6,7-dimethoxy-1-methyl-4-(quinolin-6-ylmethyl)isoquinolin-3-ol dihydrochloride | 86 nM |
| 25 | 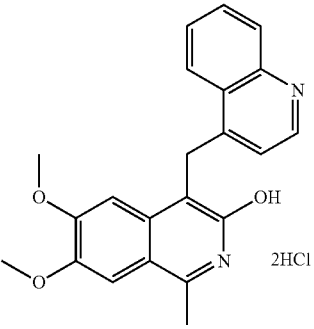 [SMILES: COc1cc2c(C)nc(O)c(Cc3ccnc4ccccc34)c2cc1OC ; "2HCl"] | 6,7-dimethoxy-1-methyl-4-(quinolin-4-ylmethyl)isoquinolin-3-ol dihydrochloride | 265 nM |
| 26 | 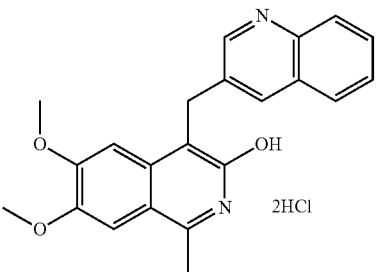 [SMILES: COc1cc2c(C)nc(O)c(Cc3cnc4ccccc4c3)c2cc1OC ; "2HCl"] | 6,7-dimethoxy-1-methyl-4-(quinolin-3-ylmethyl)isoquinolin-3-ol dihydrochloride | 24 nM |
| 27 | 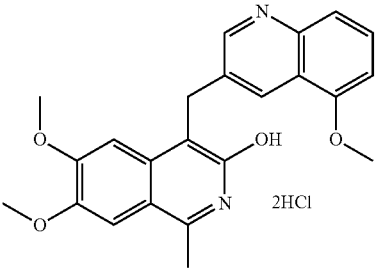 | 6,7-dimethoxy-4-((5-methoxyquinolin-3-yl)methyl)-1-methylisoquinolin-3-ol dihydrochloride | 17 nM |

TABLE 1-continued

PDE10A inhibitory activity for compounds of the invention

| Compd No. | Structure | Name | PDE10A IC$_{50}$ |
|---|---|---|---|
| 28 | 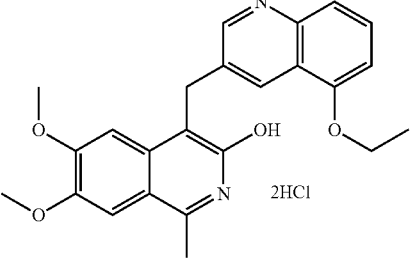 | 4-((5-ethoxyquinolin-3-yl)methyl)-6,7-dimethoxy-1-methylisoquinolin-3-ol dihydrochloride | 6 nM |
| 29 | 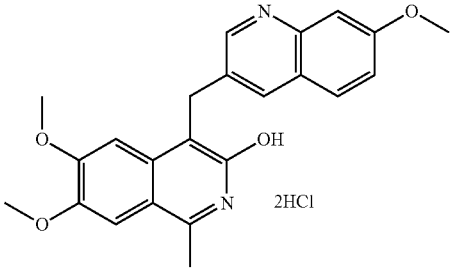 | 6,7-dimethoxy-4-((7-methoxyquinolin-3-yl)methyl)-1-methylisoquinolin-3-ol dihydrochloride | 29 nM |
| 30 | 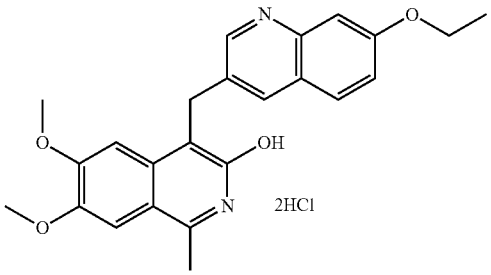 [SMILES: CCOc1ccc2cc(Cc3c(O)nc(C)c4cc(OC)c(OC)cc34)cnc2c1 ; "2HCl"] | 4-((7-ethoxyquinolin-3-yl)methyl)-6,7-dimethoxy-1-methylisoquinolin-3-ol dihydrochloride | 21 nM |
| 31 | 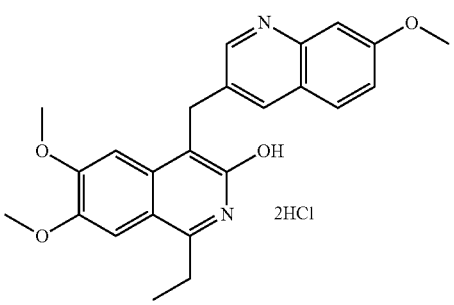 | 1-ethyl-6,7-dimethoxy-4-((7-methoxyquinolin-3-yl)methyl)isoquinolin-3-ol dihydrochloride | 13 nM |
| 32 | 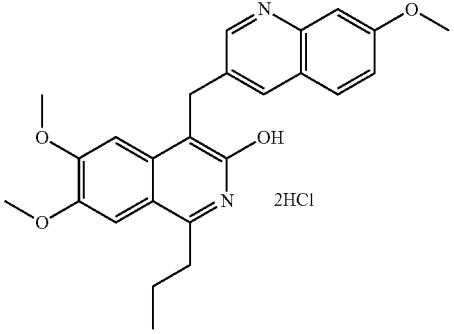 | 6,7-dimethoxy-4-((7-methoxyquinolin-3-yl)methyl)-1-propylisoquinolin-3-ol dihydrochloride | 4 nM |

TABLE 1-continued

PDE10A inhibitory activity for compounds of the invention

| Compd No. | Structure | Name | PDE10A IC$_{50}$ |
|---|---|---|---|
| 33 | 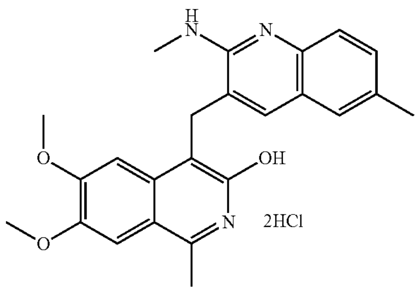 | 6,7-dimethoxy-1-methyl-4-((6-methyl-2-(methylamino)quinolin-3-yl)methyl)isoquinolin-3-ol dihydrochloride | 13 nM |
| 34 | 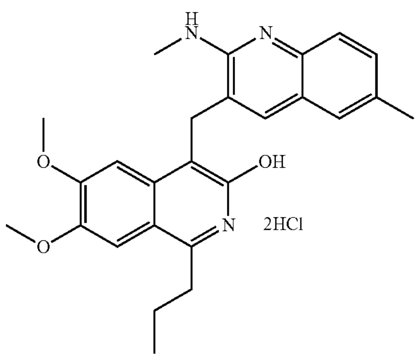 | 6,7-dimethoxy-4-((6-methyl-2-(methylamino)quinolin-3-yl)methyl)-1-propylisoquinolin-3-hydrochloride | 1.9 nM |
| 35 | 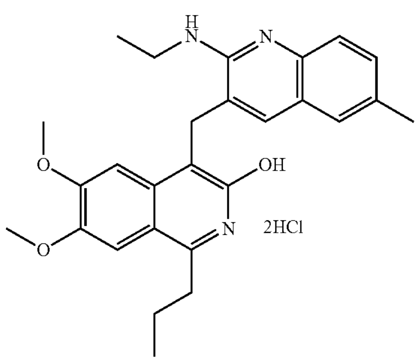 | 4-((2-(ethylamino)-6-methylquinolin-3-yl)methyl)-6,7-dimethoxy-1-propylisoquinolin-3-dihydrochloride | 1.5 nM |
| 36 | 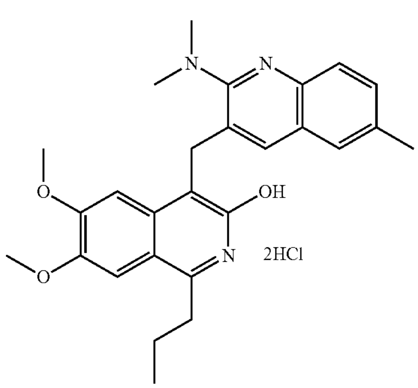 | 4-(2-dimethylamino-6-methyl-quinolin-3-ylmethyl)-6,7-dimethoxy-1-propyl-soquinolin-3-ol dihydrochloride | 698 nM |

TABLE 1-continued

PDE10A inhibitory activity for compounds of the invention

| Compd No. | Structure | Name | PDE10A IC$_{50}$ |
|---|---|---|---|
| 37 | 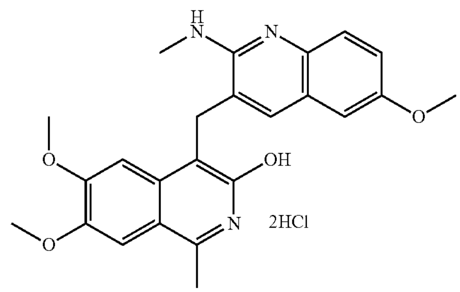 | 6,7-dimethoxy-4-((6-methoxy-2-(methylamino)quinolin-3-yl)methyl)-1-methylisoquinolin-3-ol dihydrochloride | 6 nM |
| 38 | 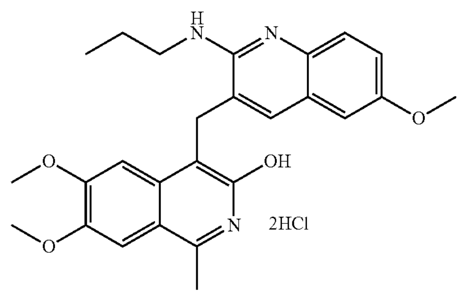 | 6,7-dimethoxy-4-((6-methoxy-2-(propylamino)quinolin-3-yl)methyl)-1-methylisoquinolin-3-ol dihydrochloride | 2.7 nM |
| 39 | 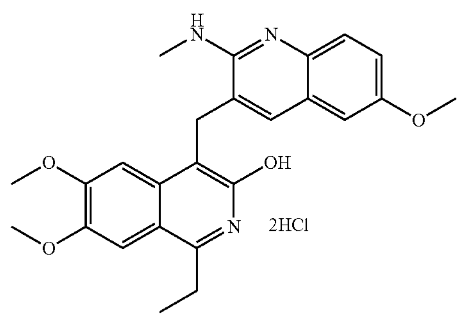 | 1-ethyl-6,7-dimethoxy-4-((6-methoxy-2-(methylamino)quinolin-3-yl)methyl)isoquinolin-3-ol dihydrochloride | 1.6 nM |
| 40 | 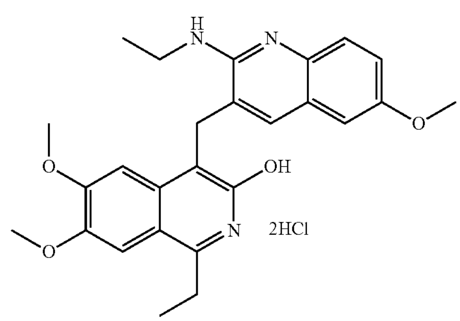 | 1-ethyl-4-((2-(ethylamino)-6-methoxyquinolin-3-yl)methyl)-6,7-dimethoxyisoquinolin-3-ol dihydrochloride | 0.4 nM |
| 41 | 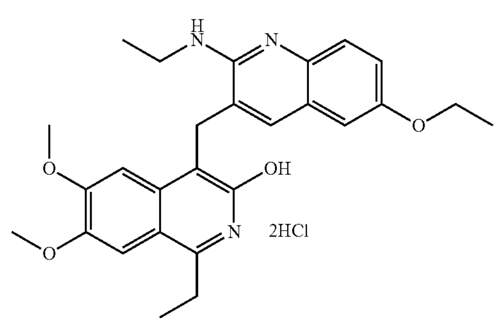 [SMILES: CCNc1nc2ccc(OCC)cc2cc1Cc1c(O)nc(CC)c2cc(OC)c(OC)cc12 ; "2HCl"] | 4-((6-ethoxy-2-(ethylamino)quinolin-3-yl)methyl)-1-ethyl-6,7-dimethoxyisoquinolin-3-ol dihydrochloride | 5 nM |

TABLE 1-continued

PDE10A inhibitory activity for compounds of the invention

| Compd No. | Structure | Name | PDE10A IC$_{50}$ |
|---|---|---|---|
| 42 | 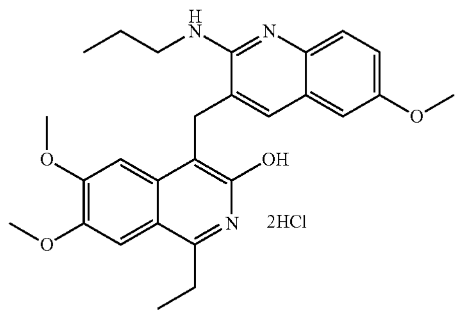 | 1-ethyl-6,7-dimethoxy-4-((6-methoxy-2-(propylamino)quinolin-3-yl)methyl)isoquinolin-3-ol dihydrochloride | 0.5 nM |
| 43 | 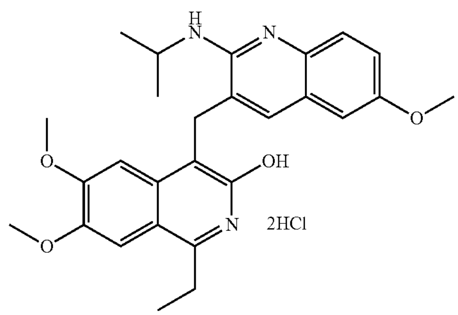 | 1-ethyl-4-((2-(isopropylamino)-6-methoxyquinolin-3-yl)methyl)-6,7-dimethoxyisoquinolin-3-ol dihydrochloride | 3.5 nM |
| 44 | 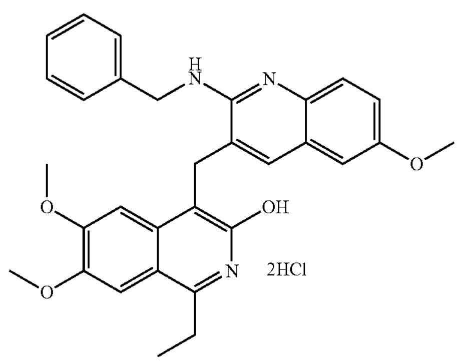 | 4-((2-(benzylamino)-6-methoxyquinolin-3-yl)methyl)-1-ethyl-6,7-dimethoxyisoquinolin-3-ol dihydrochloride | 8 nM |
| 45 | 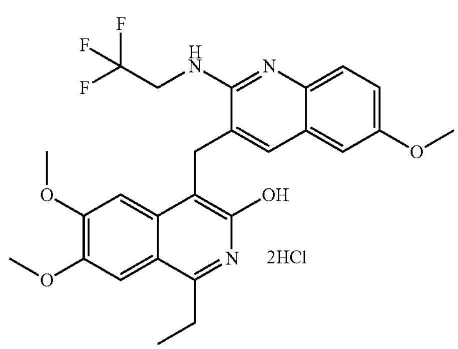 | 1-ethyl-6,7-dimethoxy-4-((6-methoxy-2-(2,2,2-trifluoroethylamino)quinolin-3-yl)methyl)isoquinolin-3-ol dihydrochloride | 30 nM |

TABLE 1-continued

PDE10A inhibitory activity for compounds of the invention

| Compd No. | Structure | Name | PDE10A IC$_{50}$ |
|---|---|---|---|
| 46 | 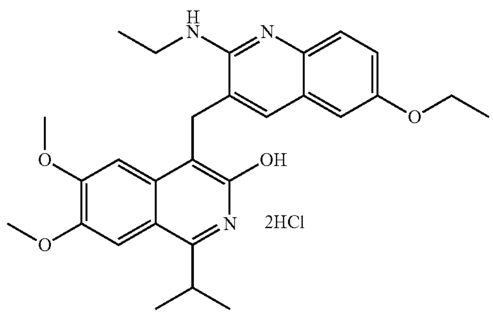 [SMILES: CCNc1nc2ccc(OCC)cc2cc1Cc1c(O)nc(C(C)C)c2cc(OC)c(OC)cc12 ; "2HCl"] | 4-((6-ethoxy-2-(ethylamino)quinolin-3-yl)methyl)-1-isopropyl-6,7-dimethoxyisoquinolin-3-ol dihydrochloride | 29 nM |
| 47 | 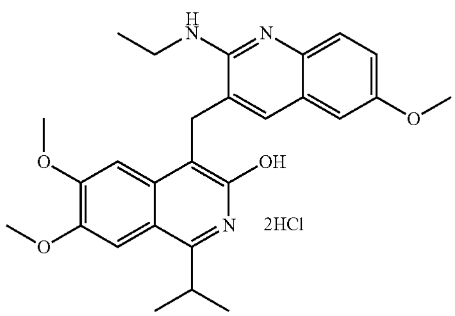 | 4-((2-(ethylamino)-6-methoxyquinolin-3-yl)methyl)-1-isopropyl-6,7-dimethoxyisoquinolin-3-ol dihydrochloride | 11 nM |
| 48 | 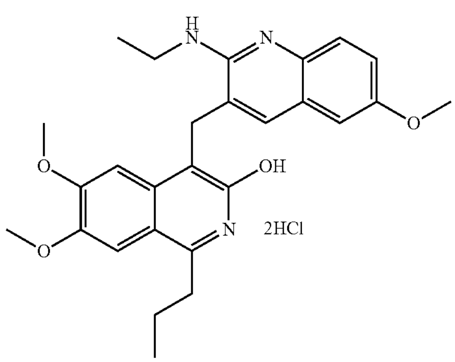 | 6,7-dimethoxy-4-((6-methoxy-2-(methylamino)quinolin-3-yl)methyl)-1-propylisoquinolin-3-ol dihydrochloride | 0.34 nM |
| 49 | 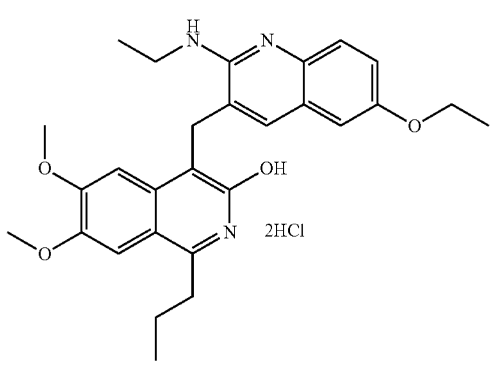 [SMILES: CCCc1nc(O)c(Cc2cc3cc(OCC)ccc3nc2NCC)c2cc(OC)c(OC)cc12 ; "2HCl"] | 4-((6-ethoxy-2-(ethylamino)quinolin-3-yl)methyl)-6,7-dimethoxy-1-propylisoquinolin-3-ol dihydrochloride | 4.6 nM |

TABLE 1-continued

PDE10A inhibitory activity for compounds of the invention

| Compd No. | Structure | Name | PDE10A IC$_{50}$ |
|---|---|---|---|
| 50 | 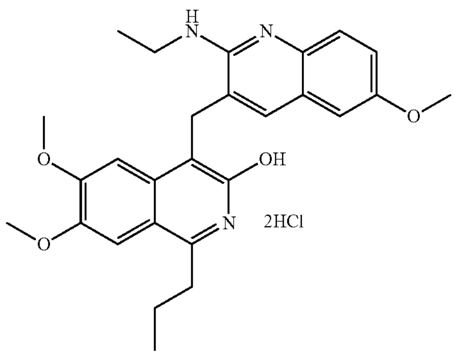 | 4-((2-(ethylamino)-6-methoxyquinolin-3-yl)methyl)-6,7-dimethoxy-1-propylisoquinolin-3-ol dihydrochloride | 0.28 nM |
| 51 | 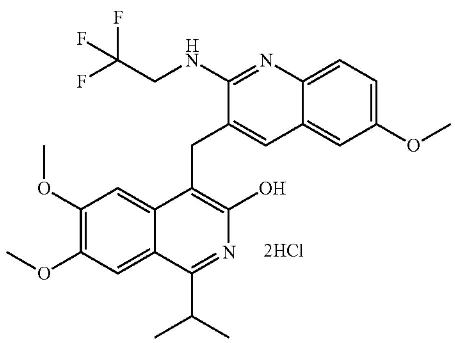 | 1-isopropyl-6,7-dimethoxy-4-((6-methoxy-2-(2,2,2-trifluoroethylamino)quinolin-3-yl)methyl)isoquinolin-3-ol dihydrochloride | 55 nM |
| 52 | 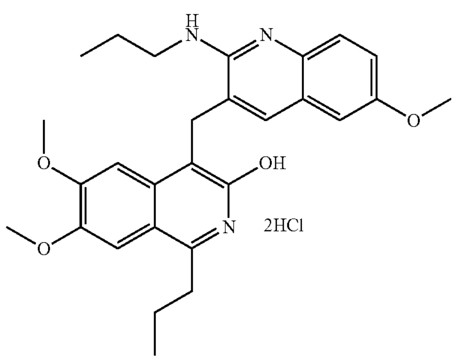 | 6,7-dimethoxy-4-((6-methoxy-2-(propylamino)quinolin-3-yl)methyl)-1-propylisoquinolin-3-ol dihydrochloride | 1.5 nM |
| 53 | 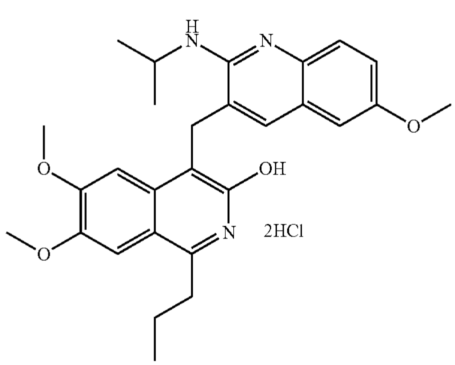 | 4-((2-(isopropylamino)-6-methoxyquinolin-3-yl)methyl)-6,7-dimethoxy-1-propylisoquinolin-3-ol dihydrochloride | 0.8 nM |

TABLE 1-continued

PDE10A inhibitory activity for compounds of the invention

| Compd No. | Structure | Name | PDE10A IC$_{50}$ |
|---|---|---|---|
| 54 | 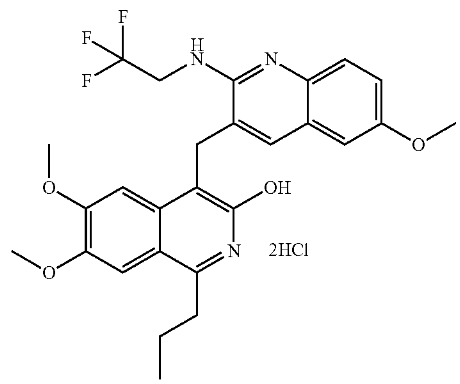 | 6,7-dimethoxy-4-((6-methoxy-2-((2,2,2-trifluoroethyl)amino)quinolin-3-yl)methyl)-1-propylisoquinolin-3-ol dihydrochloride | 23 nM |
| 55 | 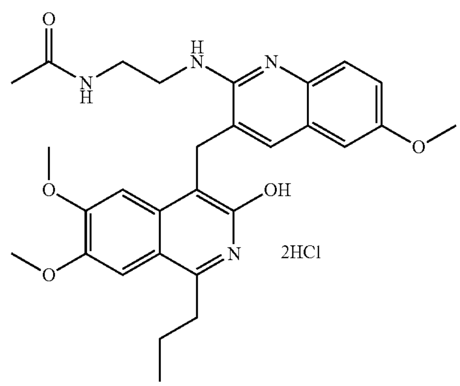 | N-(2-((3-((3-hydroxy-6,7-dimethoxy-1-propylisoquinolin-4-yl)methyl)-6-methoxyquinolin-2-yl)amino)ethyl)acetamide dihydrochloride | 4.4 nM |
| 56 | 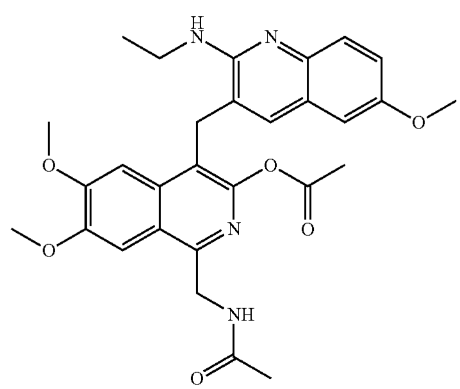 | 1-(acetamidomethyl)-4-((2-(ethylamino)-6-methoxyquinolin-3-yl)methyl)-6,7-dimethoxyisoquinolin-3-yl acetate | 175 nM |
| 57 | 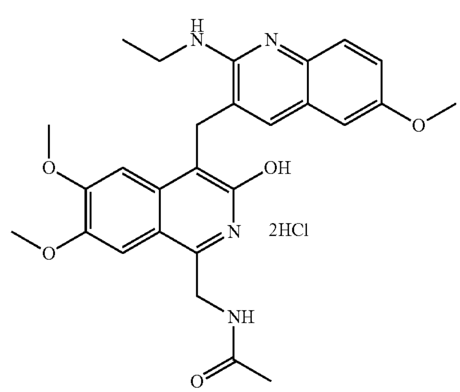 | N-((4-((2-(ethylamino)-6-methoxyquinolin-3-yl)methyl)-3-hydroxy-6,7-dimethoxyisoquinolin-1-yl)methyl)acetamide dihydrochloride | 47 nM |

TABLE 1-continued

PDE10A inhibitory activity for compounds of the invention

| Compd No. | Structure | Name | PDE10A IC$_{50}$ |
|---|---|---|---|
| 58 | 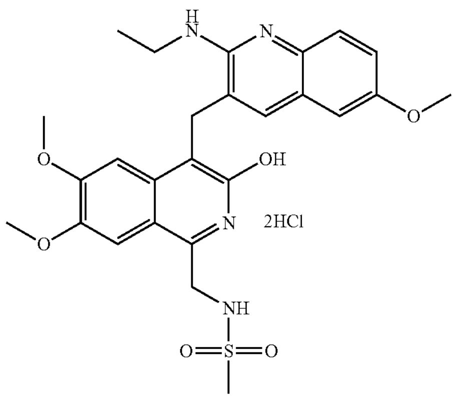 | N-((4-((2-(ethylamino)-6-methoxyquinolin-3-yl)methyl)-3-hydroxy-6,7-dimethoxyisoquinolin-1-yl)methyl)methanesulfonamide dihydrochloride | 221 nM |
| 59 | 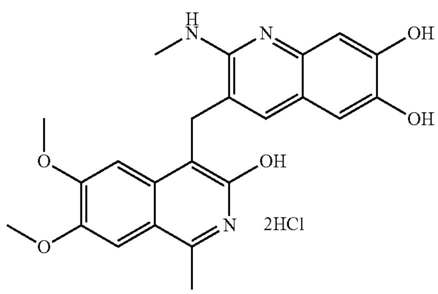 [SMILES: CNc1nc2cc(O)c(O)cc2cc1Cc1c(O)nc(C)c2cc(OC)c(OC)cc12 ; "2HCl"] | 3-((3-hydroxy-6,7-dimethoxy-1-methylisoquinolin-4-yl)methyl)-2-(methylamino)quinoline-6,7-diol dihydrochloride | 27 nM |
| 60 | 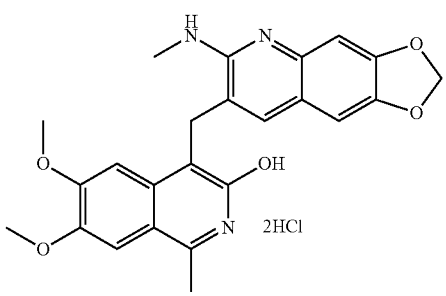 [SMILES: CNc1nc2cc3c(cc2cc1Cc1c(O)nc(C)c2cc(OC)c(OC)cc12)OCO3 ; "2HCl"] | 6,7-dimethoxy-1-methyl-4-((6-(methylamino)-[1,3]dioxolo[4,5-g]quinolin-7-yl)methyl)isoquinolin-3-ol dihydrochloride | 2.7 nM |
| 61 | 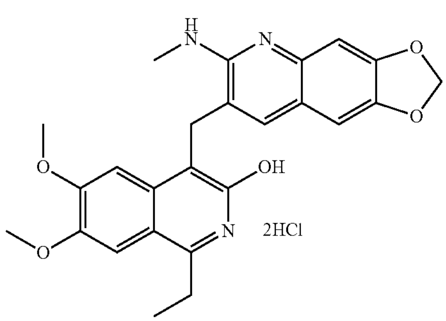 [SMILES: CCc1nc(O)c(Cc2cc3cc4c(cc3nc2NC)OCO4)c2cc(OC)c(OC)cc12 ; "2HCl"] | 1-ethyl-6,7-dimethoxy-4-((6-(methylamino)-[1,3]dioxolo[4,5-g]quinolin-7-yl)methyl)isoquinolin-3-ol dihydrochloride | 2.2 nM |

TABLE 1-continued

PDE10A inhibitory activity for compounds of the invention

| Compd No. | Structure | Name | PDE10A IC$_{50}$ |
|---|---|---|---|
| 62 | 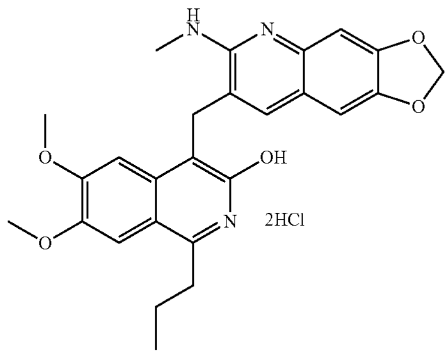 [SMILES: CCCc1nc(O)c(Cc2cc3cc4c(cc3nc2NC)OCO4)c2cc(OC)c(OC)cc12 ; "2HCl"] | 6,7-dimethoxy-4-((6-(methylamino)-[1,3]dioxolo[4,5-g]quinolin-7-yl)methyl)-1-propylisoquinolin-3-ol dihydrochloride | 1.1 nM |
| 63 | 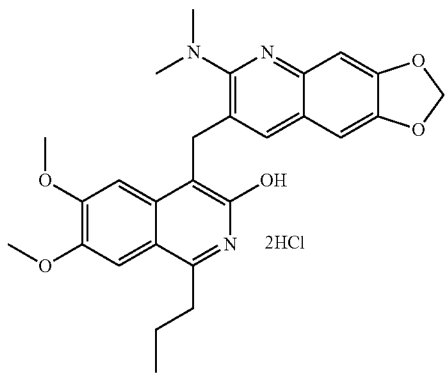 [SMILES: CCCc1nc(O)c(Cc2cc3cc4c(cc3nc2N(C)C)OCO4)c2cc(OC)c(OC)cc12 ; "2HCl"] | 4-((6-(dimethylamino)-[1,3]dioxolo[4,5-g]quinolin-7-yl)methyl)-6,7-dimethoxy-1-propylisoquinolin-3-ol dihydrochloride | 560 nM |
| 64 | 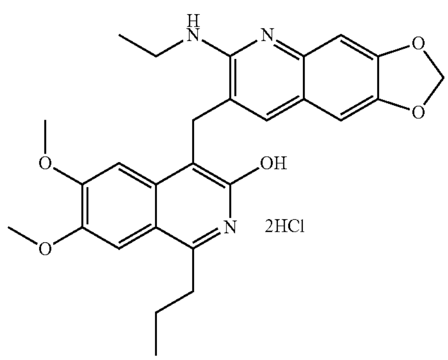 [SMILES: CCCc1nc(O)c(Cc2cc3cc4c(cc3nc2NCC)OCO4)c2cc(OC)c(OC)cc12 ; "2HCl"] | 4-((6-(ethylamino)-[1,3]dioxolo[4,5-g]quinolin-7-yl)methyl)-6,7-dimethoxy-1-propylisoquinolin-3-ol dihydrochloride | 1.2 nM |
| 65 | 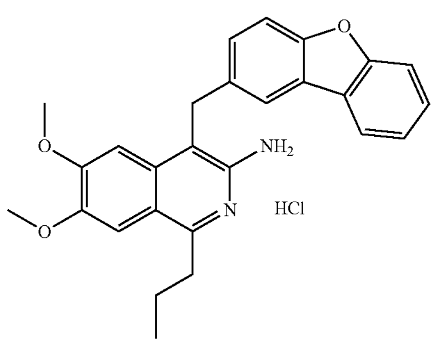 [SMILES: CCCc1nc(N)c(Cc2ccc3oc4ccccc4c3c2)c2cc(OC)c(OC)cc12 ; Cl] | 4-(dibenzo[b,d]furan-2-ylmethyl)-6,7-dimethoxy-1-propylisoquinolin-3-amine hydrochloride | 967 nM |

TABLE 1-continued

PDE10A inhibitory activity for compounds of the invention

| Compd No. | Structure | Name | PDE10A IC$_{50}$ |
|---|---|---|---|
| 66 | 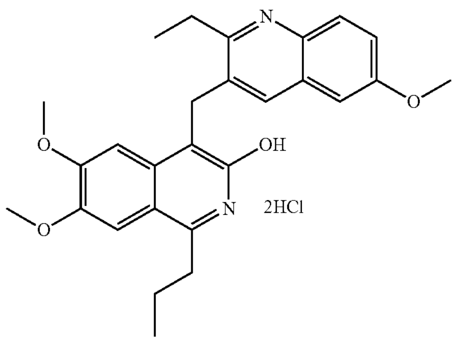 | 4-((2-ethyl-6-methoxyquinolin-3-yl)methyl)-6,7-dimethoxy-1-propylisoquinolin-3-ol dihydrochloride | 16 nM |
| 67 | 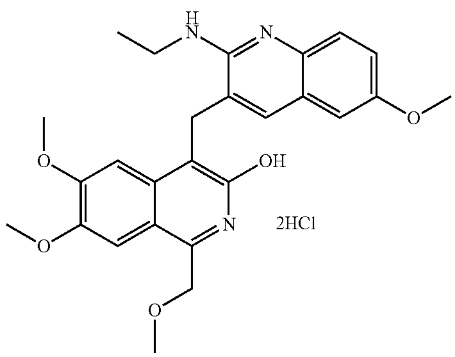 | 4-((2-(ethylamino)-6-methoxyquinolin-3-yl)methyl)-6,7-dimethoxy-1-(methoxymethyl)isoquinolin-3-ol dihydrochloride | 1.8 nM |
| 68 | 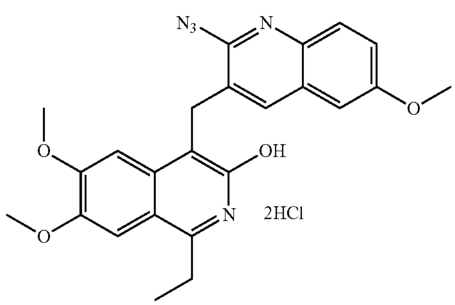 | 4-((2-azido-6-methoxyquinolin-3-yl)methyl)-1-ethyl-6,7-dimethoxyisoquinolin-3-ol dihydrochloride | 200 nM |
| 69 | 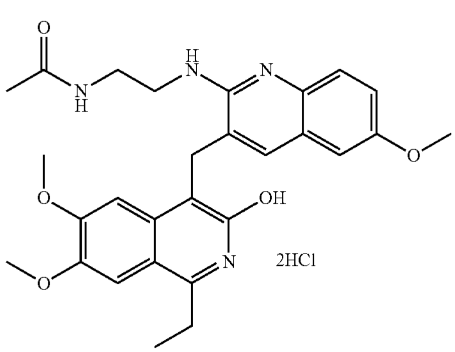 | N-(2-((3-((1-ethyl-3-hydroxy-6,7-dimethoxyisoquinolin-4-yl)methyl)-6-methoxyquinolin-2-yl)amino)ethyl)acetamide dihydrochloride | 1.5 nM |

TABLE 1-continued

PDE10A inhibitory activity for compounds of the invention

| Compd No. | Structure | Name | PDE10A IC$_{50}$ |
|---|---|---|---|
| 70 | 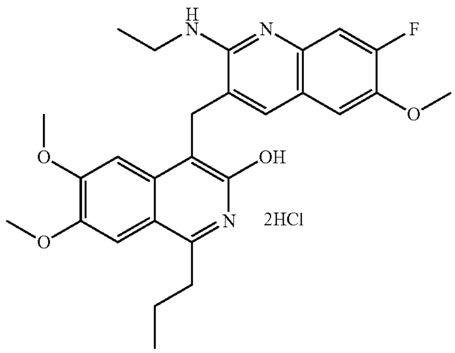 | 4-((2-(ethylamino)-7-fluoro-6-methoxyquinolin-3-yl)methyl)-6,7-dimethoxy-1-propylisoquinolin-3-ol dihydrochloride | 2.4 nM |
| 71 | 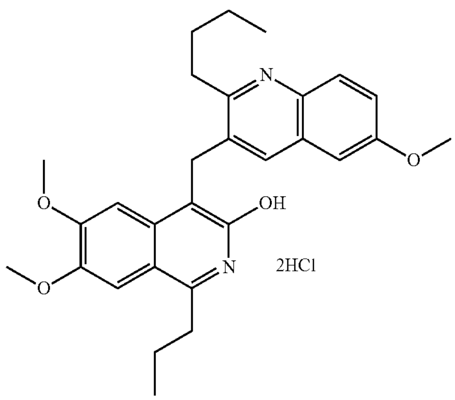 | 4-((2-butyl-6-methoxyquinolin-3-yl)methyl)-6,7-dimethoxy-1-propylisoquinolin-3-ol dihydrochloride | 93 nM |
| 72 | 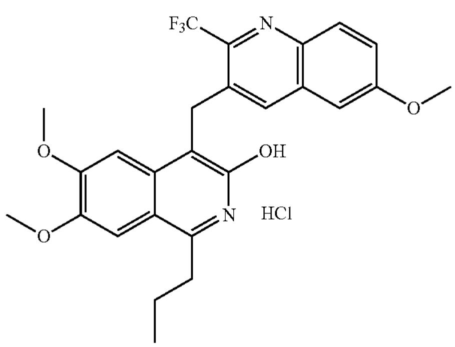 | 6,7-dimethoxy-4-((6-methoxy-2-(trifluoromethyl)quinolin-3-yl)methyl)-1-propylisoquinolin-3-ol hydrochloride | 445 nM |
| 73 | 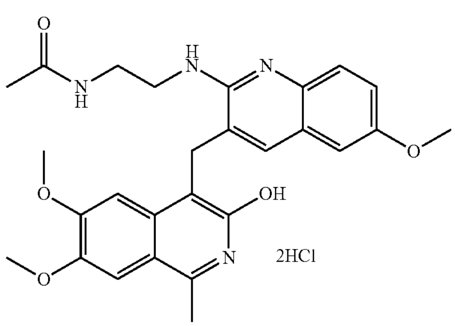 | N-(2-((3-((3-hydroxy-6,7-dimethoxy-1-methylisoquinolin-4-yl)methyl)-6-methoxyquinolin-2-yl)amino)ethyl)acetamide dihydrochloride | 2.7 nM |

TABLE 1-continued

PDE10A inhibitory activity for compounds of the invention

| Compd No. | Structure | Name | PDE10A IC$_{50}$ |
|---|---|---|---|
| 74 | 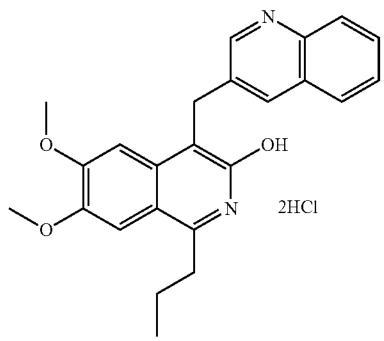 [SMILES: CCCc1nc(O)c(Cc2cnc3ccccc3c2)c2cc(OC)c(OC)cc12 ; "2HCl"] | 6,7-dimethoxy-1-propyl-4-(quinolin-3-ylmethyl)isoquinolin-3-ol dihydrochloride | 6.1 nM |
| 75 | 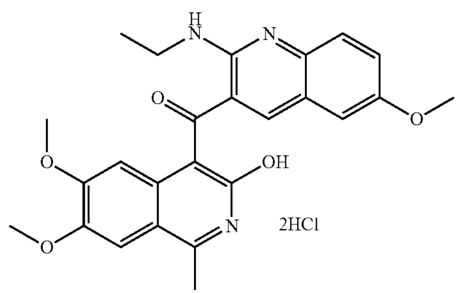 | (2-(ethylamino)-6-methoxyquinolin-3-yl)(3-hydroxy-6,7-dimethoxy-1-methylisoquinolin-4-yl)methanone dihydrochloride | >1000 nM |
| 76 | 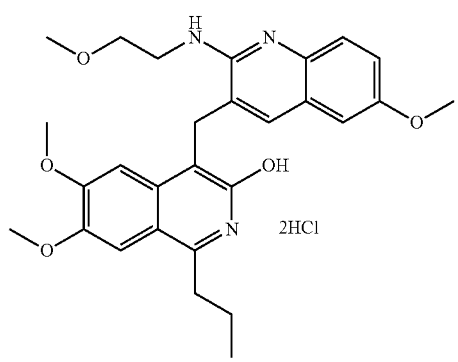 | 6,7-dimethoxy-4-((6-methoxy-2-((2-methoxyethyl)amino)quinolin-3-yl)methyl)-1-propylisoquinolin-3-ol dihydrochloride | 2.3 nM |
| 77 | 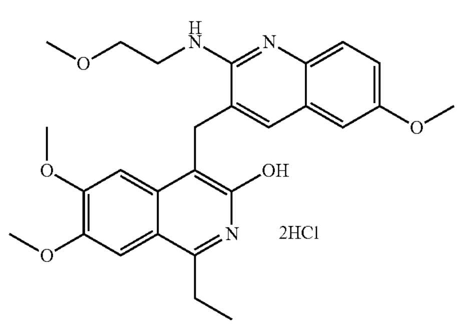 | 1-ethyl-6,7-dimethoxy-4-((6-methoxy-2-((2-methoxyethyl)amino)quinolin-3-yl)methyl)isoquinolin-3-ol dihydrochloride | 2.0 nM |

TABLE 1-continued

PDE10A inhibitory activity for compounds of the invention

| Compd No. | Structure | Name | PDE10A IC$_{50}$ |
|---|---|---|---|
| 78 | 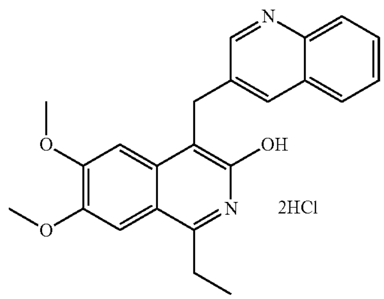 [SMILES: CCc1nc(O)c(Cc2cnc3ccccc3c2)c2cc(OC)c(OC)cc12 ; "2HCl"] | 1-ethyl-6,7-dimethoxy-4-(quinolin-3-ylmethyl)isoquinolin-3-ol dihydrochloride | 27 nM |
| 79 | 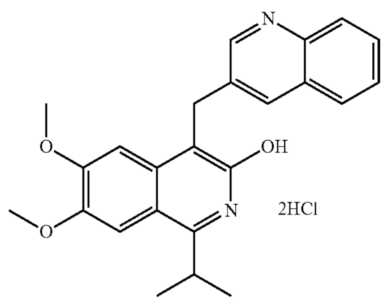 [SMILES: COc1cc2c(C(C)C)nc(O)c(Cc3cnc4ccccc4c3)c2cc1OC ; "2HCl"] | 1-isopropyl-6,7-dimethoxy-4-(quinolin-3-ylmethyl)isoquinolin-3-ol dihydrochloride | 88 nM |
| 80 | 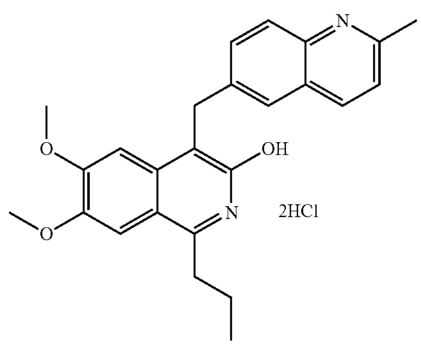 | 6,7-dimethoxy-4-((2-methylquinolin-6-yl)methyl)-1-propylisoquinolin-3-ol dihydrochloride | 3.2 nM |
| 81 | 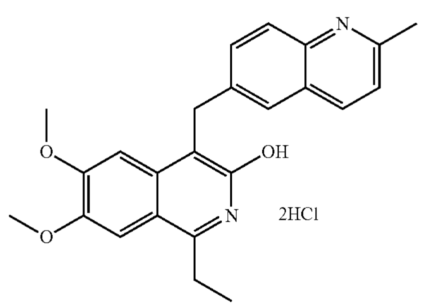 | 1-ethyl-6,7-dimethoxy-4-((2-methylquinolin-6-yl)methyl)isoquinolin-3-ol dihydrochloride | 7.5 nM |
| 82 | 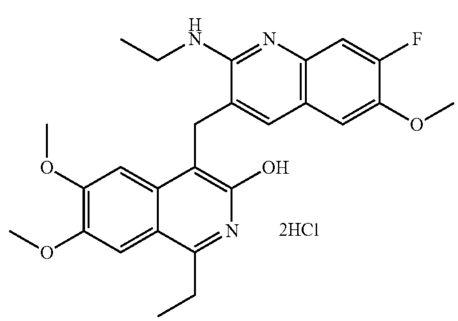 | 1-ethyl-4-((2-(ethylamino)-7-fluoro-6-methoxyquinolin-3-yl)methyl)-6,7-dimethoxyisoquinolin-3-ol dihydrochloride | 1.4 nM |

TABLE 1-continued

PDE10A inhibitory activity for compounds of the invention

| Compd No. | Structure | Name | PDE10A IC$_{50}$ |
|---|---|---|---|
| 83 | 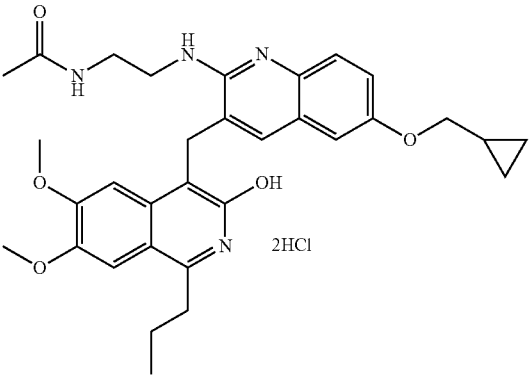 [SMILES: CCCc1nc(O)c(Cc2cc3cc(OCC4CC4)ccc3nc2NCCNC(C)=O)c2cc(OC)c(OC)cc12 ; "2HCl"] | N-(2-((6-(cyclopropylmethoxy)-3-((3-hydroxy-6,7-dimethoxy-1-propylisoquinolin-4-yl)methyl)quinolin-2-yl)amino)ethyl)acetamide dihydrochloride | 10 nM |
| 84 | 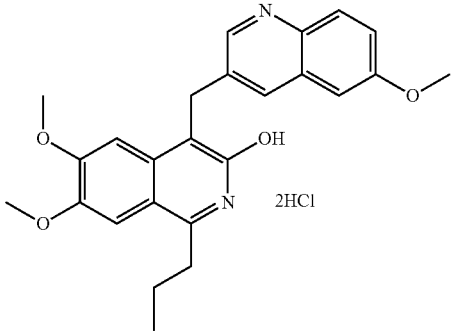 | 6,7-dimethoxy-4-((6-methoxyquinolin-3-yl)methyl)-1-propylisoquinolin-3-ol dihydrochloride | 1.6 nM |
| 85 | 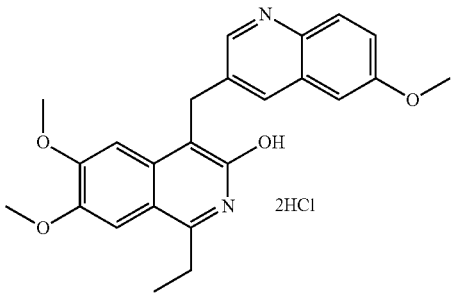 | 1-ethyl-6,7-dimethoxy-4-((6-methoxyquinolin-3-yl)methyl)isoquinolin-3-ol dihydrochloride | 0.4 nM |
| 86 | 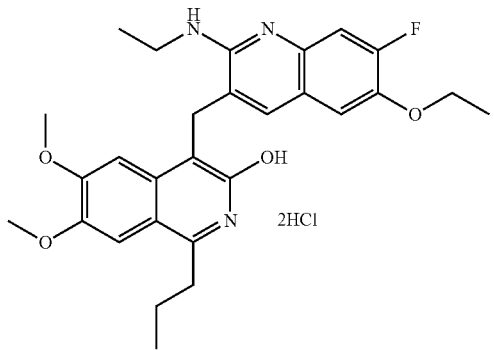 [SMILES: CCCc1nc(O)c(Cc2cc3cc(OCC)c(F)cc3nc2NCC)c2cc(OC)c(OC)cc12 ; "2HCl"] | 4-((6-ethoxy-2-(ethylamino)-7-fluoroquinolin-3-yl)methyl)-6,7-dimethoxy-1-propylisoquinolin-3-ol dihydrochloride | 0.3 nM |

TABLE 1-continued

PDE10A inhibitory activity for compounds of the invention

| Compd No. | Structure | Name | PDE10A IC$_{50}$ |
|---|---|---|---|
| 87 | 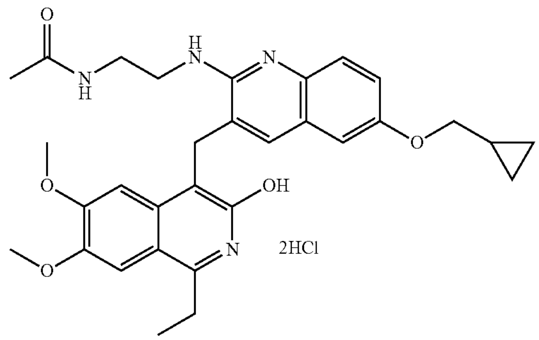 [SMILES: CCc1nc(O)c(Cc2cc3cc(OCC4CC4)ccc3nc2NCCNC(C)=O)c2cc(OC)c(OC)cc12 ; "2HCl"] | N-(2-((6-(cyclopropylmethoxy)-3-((1-ethyl-3-hydroxy-6,7-dimethoxyisoquinolin-4-yl)methyl)quinolin-2-yl)amino)ethyl)acetamide dihydrochloride | 3.9 nM |
| 88 | 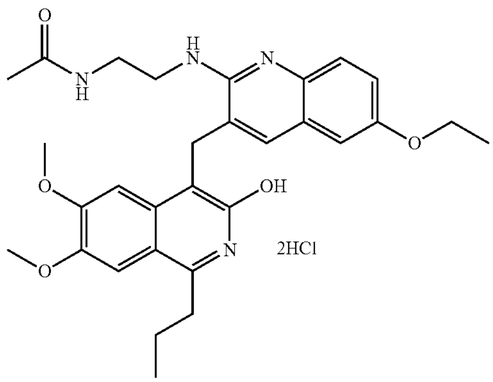 [SMILES: CCCc1nc(O)c(Cc2cc3cc(OCC)ccc3nc2NCCNC(C)=O)c2cc(OC)c(OC)cc12 ; "2HCl"] | N-(2-((6-ethoxy-3-((3-hydroxy-6,7-dimethoxy-1-propylisoquinolin-4-yl)methyl)quinolin-2-yl)amino)ethyl)acetamide dihydrochloride | 1.8 nM |

The compounds have also been tested for their activities on PDEs1-9 and PDE11. The most active PDE10A inhibitors are all selective (at least 100 to 10000-fold) vs PDEs1-3, PDEs5-9 and PDE11. They are also selective (at least 15-fold) for PDE10A vs PDE4D3 (excepted the compound 6 that inhibits PDE4D3 with an IC$_{50}$ of 0.9 nM, compound 31 that inhibits PDE4D3 with an IC$_{50}$ of 82 nM, and compound 51 that inhibits PDE4D3 with an IC$_{50}$ of 280 nM).

Each and every reference (whether patent publication or a scientific/journal publication) disclosed herein is incorporated by reference herein for all purposes.

The details of specific embodiments described in this invention are not be construed as limitations. Various equivalents and modifications may be made without departure from the essence and scope of this invention, and it is understood that such equivalent embodiments are part of this invention.

What is claimed is:

1. A compound of Formula (I)

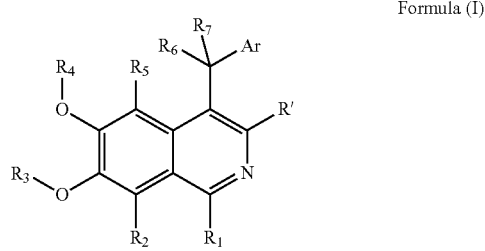

Formula (I)

a pharmaceutically acceptable salt, or a tautomer form thereof; wherein:

$R_1$ is methyl, ethyl, n-propyl, isopropyl;

$R_2$ is a hydrogen atom;

$R_3$ and $R_4$ independently represent a $(C_1$-$C_3)$alkyl group;

$R_5$ is a hydrogen atom;

$R_6$ and $R_7$ independently represent a hydrogen atom, a halogen atom, or $R_6$ and $R_7$ together with the carbon atom to which they are shown attached form a —C(=O)— group;

R' is —NH$_2$ or —OR, wherein R is a hydrogen atom, a $(C_1$-$C_3)$alkyl group or a $(C_1$-$C_3)$alkyl-C(=O)— group;

Ar is an aryl or heteroaryl group which can optionally be substituted with one to four substituents independently selected from the group consisting of halogen, azido, hydroxy, $(C_1$-$C_4)$alkyl, halogenoalkyl, $(C_1$-$C_4)$alkoxy, —O—$(C_1$-$C_4)$alkyl-$(C_1C_6)$cycloalkyl, aryl, $(C_1$-$C_4)$alkyl-aryl-, $(C_1$-$C_4)$alkoxy-aryl-, amino-substituted aryl, N(($C_1$-$C_4)$alkyl)$_2$-substituted aryl, aryloxy, heteroaryl, $(C_1$-$C_4)$alkyl-heteroaryl-, and R$_b$R$_c$N, or wherein two substituents at adjacent positions of the aryl or heteroaryl together with the atoms to which they are attached form a heterocyclic ring; and R$_b$ and R$_c$ are independently selected from the group consisting of hydrogen, $(C_1$-$C_4)$alkyl, halogeno$(C_1$-$C_4)$alkyl-, $(C_1$-$C_4)$alkoxy$(C_1$-$C_4)$alkyl-, aryl$(C_1$-$C_4)$alkyl- and acetylamino$(C_1$-$C_4)$alkyl-.

2. The compound according to claim 1, wherein $R_3$ and $R_4$ both represent a methyl group.

3. The compound according to claim 1, wherein R' is selected from the group consisting of —NH$_2$, —OH, —OCH$_3$, and —OC(=O)CH$_3$.

4. The compound according to claim 1, wherein Ar represents
- a pyridinyl group optionally substituted with one or two substituents independently selected from the group consisting of aryl, ($C_1$-$C_4$)alkylaryl, heteroaryl, ($C_1$-$C_4$)heteroaryl and ($C_1$-$C_4$)alkoxy-aryl-;
- a phenyl group optionally substituted with one or two substituents selected from the group consisting of ($C_1$-$C_4$)alkyloxy, aryloxy, ($C_1$-$C_4$)alkoxy-aryl-, and amino-aryl;
- a naphthyl group optionally substituted with one or two substituents selected from the group consisting of ($C_1$-$C_4$)alkyloxy, arloxy, ($C_1$-$C_4$)alkoxy-aryl and amino-aryl;
- a quinolinyl group optionally substituted with one or more substituents, in particular one or two substituents, selected from the group consisting of ($C_1$-$C_4$)alkyl, ($C_1$-$C_4$)alkyloxy and $R_bR_cN$;
- [1,3]dioxolo[4,5-g]quinolyn group, optionally substituted with a $R_bR_cN$-substituent;
- an isoquinolinyl group; or
- a dibenzofuran group.

5. The compound of claim 1, wherein Ar is an aryl or heteroaryl group which can optionally be substituted with one to four substituents independently selected from the group consisting of fluoro, azido, hydroxyl, methyl, ethyl, hydroxy, methoxy, ethoxy, —O—$CH_2$-cyclopropyl, phenyl, methoxyphenyl, aminophenyl, phenoxy, pyridinyl, methylamino, ethylamino, N,N-dimethylamino, ethylamino, n-propylamino, n-butylamino, isopropylamino, trifluoromethyl, 2,2,2-trifluoroethylamino, benzylamino, and acetyl-2-aminoethylamino.

6. The compound according to claim 1, selected from the group consisting of:

4-([1,1'-biphenyl]-3-ylmethyl)-1-ethyl-6,7-dimethoxy-isoquinolin-3-ol hydrochloride 8,
1-ethyl-6,7-dimethoxy-4-((4'-methoxy-[1,1'-biphenyl]-3-yl)methyl)isoquinolin-3-ol hydrochloride 9,
3,6,7-trimethoxy-1-methyl-4-(naphthalen-2-ylmethyl) isoquinoline hydrochloride 18,
4-(dibenzo[b,d]furan-2-ylmethyl)-6,7-dimethoxy-1-propylisoquinolin-3-amine hydrochloride 65,
and
(2-(ethylamino)-6-methoxyquinolin-3-yl)(3-hydroxy-6,7-dimethoxy-1-methylisoquinolin-4-yl)methanone dihydrochloride 75,
or any other pharmaceutically acceptable salt, or a tautomer form thereof.

7. A pharmaceutical composition comprising at least one compound of claim 1, a pharmaceutically acceptable salt thereof, or tautomer form thereof, and at least one pharmaceutically acceptable carrier.

8. A method of treating a disease selected from the group consisting of wet Age Related Macular Degeneration (ARMD) and dry ARMD in a mammal, comprising administering to said mammal, a therapeutically effective amount of at least one compound of claim 1, any pharmaceutically acceptable salt, or a tautomer form thereof.

9. A method of treating a disease selected from the group consisting of wet Age Related Macular Degeneration (ARMD) and dry ARMD in a mammal, comprising administering to said mammal, a therapeutically effective amount of at least one compound of claim 6, a pharmaceutically acceptable salt, or a tautomer form thereof.

10. A pharmaceutical composition comprising at least one compound of claim 6, a pharmaceutically acceptable salt thereof, or tautomer form thereof and at least one pharmaceutically acceptable carrier.

* * * * *

UNITED STATES PATENT AND TRADEMARK OFFICE
CERTIFICATE OF CORRECTION

PATENT NO. : 9,670,181 B2
APPLICATION NO. : 14/314930
DATED : June 6, 2017
INVENTOR(S) : Bertrand Leblond et al.

It is certified that error appears in the above-identified patent and that said Letters Patent is hereby corrected as shown below:

In the Specification

In Column 3, Lines 7-8, delete "heteroarylamid" and insert -- heteroarylamide --, therefor.

In Column 4, Line 47, delete "NS)" and insert -- A/S) --, therefor.

In Column 4, Line 61, delete "Huntigton's" and insert -- Huntington's --, therefor.

In Column 5, Line 6, delete "NS)" and insert -- A/S) --, therefor.

In Column 5, Line 39, delete "NS)" and insert -- A/S) --, therefor.

In Column 6, Line 47, delete "hetero-cyclically" and insert -- heterocyclically --, therefor.

In Column 7, Line 40, after "wherein" insert -- : --.

In Column 8, Line 29, after "group" insert -- ; --.

In Column 9, Line 9, delete "antracenyl," and insert -- anthracenyl, --, therefor.

In Column 9, Line 15, delete "antracenyl." and insert -- anthracenyl. --, therefor.

In Column 9, Line 39, delete "quinolyn," and insert -- quinoline, --, therefor.

In Column 9, Line 65, delete "quinolyn" and insert -- quinoline --, therefor.

In Column 10, Line 26, after "propyl" insert -- ; --.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)

In Column 10, Line 47, delete "dibenzoburan" and insert -- dibenzofuran --, therefor.

In Column 15, Line 44, delete "fonic" and insert -- folic --, therefor.

In Column 21, Line 4, after "3)" insert -- . --.

In Column 38, Line 19, after "human" insert -- . --.

In Column 38, Line 64, delete "temperal" and insert -- temporal --, therefor.

In Column 39, Line 55, delete "temperal" and insert -- temporal --, therefor.

In Column 40, Line 60, delete "Stargard's" and insert -- Stargardt's --, therefor.

In Column 41, Line 23, delete "Stargard's" and insert -- Stargardt's --, therefor.

In Column 41, Line 55, delete "Stargard's" and insert -- Stargardt's --, therefor.

In Column 59, Line 66, delete "trihydrochloride trihydrochloride" and insert -- trihydrochloride --, therefor.

In Column 60, Line 30, delete "methylisoquinolin" and insert -- methyl)isoquinolin- --, therefor.

In Column 63, Line 45, delete "exchang." and insert -- exchange --, therefor.

In Column 71, Line 20, delete "ArH),),"  and insert -- ArH), --, therefor.

In Column 75, Lines 36-45, delete " 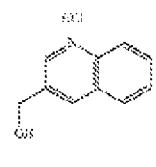 " and insert -- 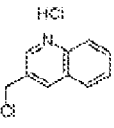 --, therefor.

In Column 78, Line 28, delete "84%.;" and insert -- 84%; --, therefor.

In Column 78, Line 38, delete "HPLC::" and insert -- HPLC: --, therefor.

In Column 81, Line 45, delete "291588" and insert -- 29158B --, therefor.

In Column 86, Line 9, delete "87%.;" and insert -- 87%; --, therefor.

In Column 91, Lines 2-3, delete "methylisoquinolin" and insert -- methyl)isoquinolin- --, therefor.

In Column 92, Line 1, delete "MDE32060" and insert -- MDE 32060 --, therefor.

In Column 92, Line 1, delete "a a" and insert -- a --, therefor.

In Column 92, Line 27, delete "MDE32060" and insert -- MDE 32060 --, therefor.

In Column 92, Line 63, delete "methylisoquinolin" and insert -- methyl)isoquinolin- --, therefor.

In Column 94, Line 37, delete "0-" and insert -- O- --, therefor.

In Column 94, Line 65, delete "satured" and insert -- saturated --, therefor.

In Column 96, Line 61, delete "2H$_2$OCH$_2$O)," and insert -- 2H, OCH$_2$O), --, therefor.

In Column 98, Line 42, after "217.1)]" insert -- . --.

In Column 103, Line 29, delete "100)," and insert -- 100). --, therefor.

In Column 104, Line 54, delete "X Bridge™" and insert -- XBridge™ --, therefor.

In Column 105, Line 45, delete "X Bridge™" and insert -- XBridge™ --, therefor.

In Column 106, Line 21, after "100)" insert -- . --.

In Column 107, Line 40, delete "methylisoquinolin" and insert -- methyl)isoquinolin- --, therefor.

In Column 108, Line 30, delete "X Bridge™" and insert -- XBridge™ --, therefor.

In Column 110, Line 19, delete "X Bridge™" and insert -- XBridge™ --, therefor.

In Column 112, Line 33, after "96.2%" insert -- . --.

In Column 115, Line 20, after "38)" insert -- . --.

In Column 118, Line 19, delete "38)," and insert -- 38). --, therefor.

In Column 119, Line 59, delete "X Bridge™" and insert -- XBridge™ --, therefor.

In Column 122, Line 56, delete "X Bridge™" and insert -- XBridge™ --, therefor.

In Column 123, Line 16, after "mL)" insert -- . --.

In Column 124, Line 41, delete "X Bridge™" and insert -- XBridge™ --, therefor

In Column 125, Line 39, delete "X Bridge™" and insert -- XBridge™ --, therefor.
In Column 128, Line 35, after "99.1%" insert -- . --.

In Column 131, Line 30, after "38)" insert -- . --.

In Column 144, Line 44, delete "[4,5-d]" and insert -- [4,5-g] --, therefor.

In Column 145, Line 20, delete "[4,5-]" and insert -- [4,5-g] --, therefor.

In Column 145, Line 50, delete "exchang." and insert -- exchange --, therefor.

In Column 145, Line 53, delete "exchang." and insert -- exchange --, therefor.

In Column 145, Line 62, delete "341588" and insert -- 34158B --, therefor.

In Column 147, Lines 20-21, delete "methylisoquinolin" and insert -- methyl)isoquinolin- --, therefor.

In Column 151, Line 53, delete "satured" and insert -- saturated --, therefor.

In Column 152, Line 26, delete "-7-30 yl)" and insert -- -7-yl) --, therefor.

In Column 154, Line 58, delete "and and" and insert -- and --, therefor.

In Column 154, Line 66, delete "and and" and insert -- and --, therefor.

In Column 156, Line 18, delete "Column(5" and insert -- Column (5 --, therefor.

In Column 157, Line 26, after "Rf" insert -- : --.

In Column 159, Line 56, after "Rf" insert -- : --.

In Column 161, Line 56, delete "Column(5" and insert -- Column (5 --, therefor.

In Column 163, Line 6, delete "44168" and insert -- 41168 --, therefor.

In Column 168, Line 12, delete "Column(5" and insert -- Column (5 --, therefor.

In Column 173, Line 49, delete "Column(5" and insert -- Column (5 --, therefor.

In Column 180, Line 14, delete "methylisoquinolin" and insert -- methyl)isoquinolin- --, therefor.

In Column 180, Line 62, delete "-2" and insert -- -2- --, therefor.

In Column 181, Line 34, delete "Column(5" and insert -- Column (5 --, therefor.
In Column 186, Line 35, delete "methylisoquinolin" and insert -- methyl)isoquinolin- --, therefor.

CERTIFICATE OF CORRECTION (continued)

In Column 199, Line 16, delete "-(cyclopropylmethoxy)-" and insert -- -(Cyclopropylmethoxy)- --, therefor.

In Column 204, Line 2, delete "μmole/" and insert -- pmole/ --, therefor.

In Column 204, Line 3, delete "pH7.4," and insert -- pH=7.4, --, therefor.

In Columns 209-210, Line 4, in TABLE 1-continued, (Compd. No. 14), delete "trihydrochloride trihydrochloride" and insert -- trihydrochloride --, therefor.

In Columns 209-210, Lines 3-4, in TABLE 1-continued, (Compd. No. 16), delete "-methylisoquinolin- dihydrochloride" and insert -- -methylisoquinolin-3-ol dihydrochloride --, therefor.

In Columns 217-218, Lines 3-4, in TABLE 1-continued, (Compd. No. 34), delete "-3- hydrochloride" and insert -- -3-ol hydrochloride --, therefor.

In Columns 217-218, Lines 3-4, in TABLE 1-continued, (Compd. No. 35), delete "-3- hydrochloride" and insert -- -3-ol hydrochloride --, therefor.

In Columns 223-224, Line 1, in TABLE 1-continued, (Compd. No. 48),

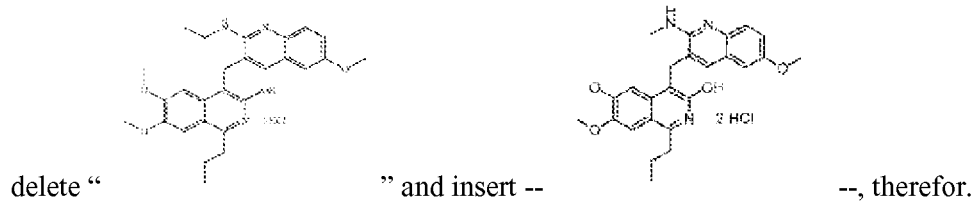

delete "                    " and insert --                    --, therefor.

In Column 233-234, Lines 4-5, in TABLE 1-continued, (Compd. No. 67), delete "-3- hydrochloride" and insert -- -3-ol hydrochloride --, therefor.

In Column 243-244, Line 1, in TABLE 1-continued, (Compd. No. 87),

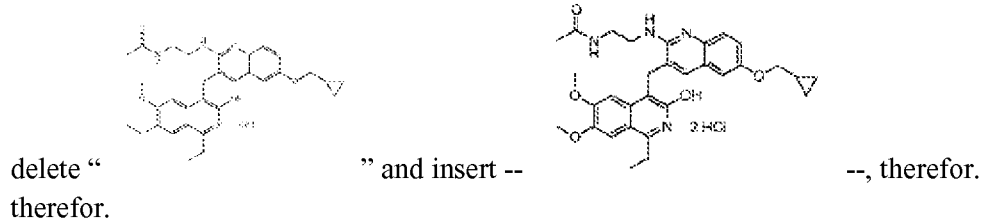

delete "                    " and insert --                    --, therefor.
therefor.

In the Claims

In Column 244, Line 48, in Claim 1, after "group" delete "which can".
In Column 244, Line 48, in Claim 1, after "optionally" delete "be".

CERTIFICATE OF CORRECTION (continued)
U.S. Pat. No. 9,670,181 B2

In Column 244, Line 52, in Claim 1, delete "-($C_1C_6$)" and insert -- -($C_1$-$C_6$) --, therefor.

In Column 245, Line 13, in Claim 4, delete "arloxy," and insert -- aryloxy, --, therefor.

In Column 245, Line 20, in Claim 4, delete "quinolyn," and insert -- quinoline, --, therefor.

In Column 246, Line 22, in Claim 8, after "any" insert -- other --.